US011623002B2

(12) United States Patent
Li et al.

(10) Patent No.: US 11,623,002 B2
(45) Date of Patent: Apr. 11, 2023

(54) ALK POLYPEPTIDES AND METHODS OF USE THEREOF

(71) Applicant: Elicio Therapeutics, Inc., Cambridge, MA (US)

(72) Inventors: Adrienne Li, Cambridge, MA (US); Jackson Eby, Arlington, MA (US); Peter C. Demuth, Medford, MA (US)

(73) Assignee: Elicio Therapeutics, Inc., Boston, MA (US)

(*) Notice: Subject to any disclaimer, the term of this patent is extended or adjusted under 35 U.S.C. 154(b) by 269 days.

(21) Appl. No.: 16/072,699

(22) PCT Filed: Jan. 27, 2017

(86) PCT No.: PCT/US2017/015422
§ 371 (c)(1),
(2) Date: Jul. 25, 2018

(87) PCT Pub. No.: WO2017/132555
PCT Pub. Date: Aug. 3, 2017

(65) Prior Publication Data
US 2020/0405834 A1    Dec. 31, 2020

Related U.S. Application Data

(60) Provisional application No. 62/288,972, filed on Jan. 29, 2016.

(51) Int. Cl.
| | | |
|---|---|---|
| *A61K 39/00* | (2006.01) | |
| *A61K 47/69* | (2017.01) | |
| *A61K 47/54* | (2017.01) | |
| *A61K 31/4545* | (2006.01) | |
| *A61K 31/506* | (2006.01) | |
| *A61K 31/5377* | (2006.01) | |
| *A61K 31/675* | (2006.01) | |
| *A61K 38/45* | (2006.01) | |
| *A61K 47/10* | (2017.01) | |
| *A61P 37/04* | (2006.01) | |
| *C12N 9/12* | (2006.01) | |
| *C12N 9/00* | (2006.01) | |
| *C07K 14/705* | (2006.01) | |
| *C07K 14/00* | (2006.01) | |
| *A61K 38/00* | (2006.01) | |

(52) U.S. Cl.
CPC ......... *A61K 39/001162* (2018.08); *A61K 31/4545* (2013.01); *A61K 31/506* (2013.01); *A61K 31/5377* (2013.01); *A61K 31/675* (2013.01); *A61K 38/45* (2013.01); *A61K 47/10* (2013.01); *A61K 47/543* (2017.08); *A61K 47/6911* (2017.08); *A61P 37/04* (2018.01); *C07K 14/00* (2013.01); *C07K 14/705* (2013.01); *C12N 9/00* (2013.01); *C12N 9/1205* (2013.01); *A61K 38/00* (2013.01); *A61K 2039/55555* (2013.01); *A61K 2039/6031* (2013.01); *A61K 2039/627* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,485,045 A | 11/1984 | Regen | |
| 8,980,287 B2 | 3/2015 | Chiarle et al. | |
| 9,650,614 B2 | 5/2017 | Chiarle et al. | |
| 2003/0157101 A1 | 8/2003 | Gambacorti-Passerini et al. | |
| 2007/0128633 A1* | 6/2007 | Zozulya | C12P 21/02 435/6.14 |
| 2009/0118216 A1* | 5/2009 | Chiarle | A61K 31/704 514/44 R |
| 2013/0295129 A1* | 11/2013 | Irvine | A61K 39/21 424/194.1 |

FOREIGN PATENT DOCUMENTS

| | | |
|---|---|---|
| WO | WO-2016/115480 A1 | 7/2016 |
| WO | WO-2021/055580 A2 | 3/2021 |

OTHER PUBLICATIONS

Aubry et al., "Peptides derived from the dependence receptor ALK are proapoptotic for ALK-positive tumors." Cell Death Dis 6:e1736 (2015).
Blasco, "Abstract A021: Development of an ALK vaccines to treat ALK-rearranged non-small cell lung cancers," <http://cancerimmunolres.aacrjournals.org/content/4/11_Supplement/A021 >, retrieved on Jul. 30, 2019 (5 pages).
Dennis et al., "Albumin binding as a general strategy for improving the pharmacokinetics of proteins," J Biol Chem. 277(38):35035-43 (2002).
Extended European Search Report for European Patent Application No. 17745002.0 dated Nov. 18, 2019 (10 pages).
International Preliminary Report on Patentability for International Patent Application No. PCT/US17/15422, dated Jul. 30, 2018 (10 pages).
International Search Report and Written Opinion for International Application No. PCT/US17/15422, dated Jul. 3, 2017 (21 pages).
Passoni et al., "In vivo T-cell immune response against anaplastic lymphoma kinase in patients with anaplastic large cell lymphomas," Haematologica91(1):48-55 (2006).
Voena et al., "Efficacy of a Cancer Vaccine against ALK-Rearranged Lung Tumors," Cancer Immunol Res 3(12):1333-1343 (2015).

* cited by examiner

*Primary Examiner* — Sergio Coffa
(74) *Attorney, Agent, or Firm* — Clark & Elbing LLP

(57) ABSTRACT

The invention features immunogenic compositions containing anaplastic lymphoma kinase (ALK) polypeptides and methods of use thereof. The immunogenic compositions and methods of the invention may be used to treat a disease associated with ALK in a subject, such as cancer (e.g., a solid tumor cancer or an ALK+ cancer).

5 Claims, 9 Drawing Sheets

Specification includes a Sequence Listing.

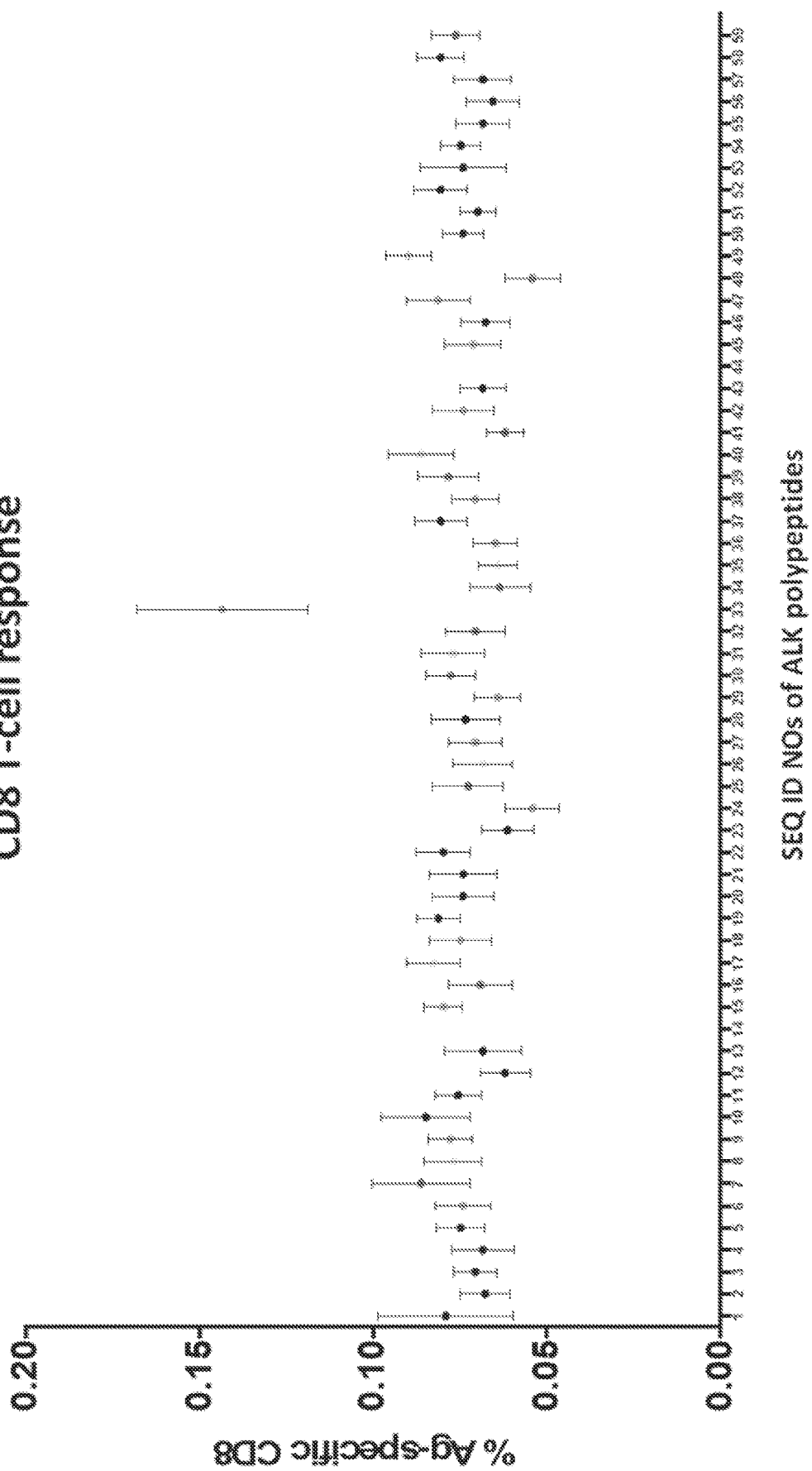

FIG. 4-1

SEQ ID NO: 67

```
         10         20         30         40         50
MGAIGLLWLL PLLLSTAAVG SGMGTGQRAG SPAAGPPLQP REPLSYSRLQ
         60         70         80         90        100
RKSLAVDFVV PSLFRVYARD LLLPPSSSEL KAGRPEARGS LALDCAPLLR
        110        120        130        140        150
LLGPAPGVSW TAGSPAPAEA RTLSRVLKGG SVRKLRRAKQ LVLELGEEAI
        160        170        180        190        200
LEGCVGPPGE AAVGLLQFNL SELFSWWIRQ GEGRLRIRLM PEKKASEVGR
        210        220        230        240        250
EGRLSAAIRA SQPRLLFQIF GTGHSSLESP TNMPSPSPDY FTWNLTWIMK
        260        270        280        290        300
DSFPFLSHRS RYGLECSFDF PCELEYSPPL HDLRNQSWSW RRIPSEEASQ
        310        320        330        340        350
MDLLDGPGAE RSKEMPRGSF LLLNTSADSK HTILSPWMRS SSEHCTLAVS
        360        370        380        390        400
VHRHLQPSGR YIAQLLPHNE AAREILLMPT PGKHGWTVLQ GRIGRPDNPF
        410        420        430        440        450
RVALEYISSG NRSLSAVDFF ALKNCSEGTS PGSKMALQSS FTCWNGTVLQ
        460        470        480        490        500
LGQACDFHQD CAQGEDESQM CRKLPVGFYC NFEDGFCGWT QGTLSPHTPQ
        510        520        530        540        550
WQVRTLKDAR FQDHQDHALL LSTTDVPASE SATVTSATFP APIKSSPCEL
        560        570        580        590        600
RMSWLIRGVL RGNVSLVLVE NKTGKEQGRM VWHVAAYEGL SLWQWMVLPL
        610        620        630        640        650
LDVSDRFWLQ MVAWWGQGSR AIVAFDNISI SLDCYLTISG EDKILQNTAP
        660        670        680        690        700
KSRNLFERNP NKELKPGENS PRQTPIFDPT VEWLFTTCGA SGPHGPTQAQ
        710        720        730        740        750
CNNAYQNSNL SVEVGSEGPL KGIQIWKVPA TDTYSISGYG AAGGKGGKNT
        760        770        780        790        800
MMRSHGVSVL GIFNLEKDDM LYILVGQQGE DACPSTNQLI QKVCIGENNV
        810        820        830        840        850
IEEEIRVNRS VHEWAGGGGG GGGATYVFKM KDGVPVPLII AAGGGGRAYG
        860        870        880        890        900
AKTDTFHPER LENNSSVLGL NGNSGAAGGG GGWNDNTSLL WAGKSLQEGA
        910        920        930        940        950
TGGHSCPQAM KKWGWETRGG FGGGGGGCSS GGGGGGYIGG NAASNNDPEM
        960        970        980        990       1000
DGEDGVSFIS PLGILYTPAL KVMEGHGEVN IKHYLNCSHC EVDECHMDPE
       1010       1020       1030       1040       1050
SHKVICFCDH GTVLAEDGVS CIVSPTPEPH LPLSLILSVV TSALVAALVL
       1060       1070       1080       1090       1100
AFSGIMIVYR RKHQELQAMQ MELQSPEYKL SKLRTSIIMT DYNPNYCFAG
       1110       1120       1130       1140       1150
KTSSISDLKE VPRKNITLIR GLGHGAFGEV YEGQVSGMPN DPSPLQVAVK
       1160       1170       1180       1190       1200
TLPEVCSEQD ELDFLMEALI ISKFNHQNIV RCIGVSLQSL PRFILLELMA
       1210       1220       1230       1240       1250
GGDLKSFLRE TRPRPSQPSS LAMLDLLHVA RDIACGCQYL EENHFIHRDI
       1260       1270       1280       1290       1300
AARNCLLTCP GPGRVAKIGD FGMARDIYRA SYYRKGGCAM LPVKWMPPEA
       1310       1320       1330       1340       1350
FMEGIFTSKT DTWSFGVLLW EIFSLGYMPY PSKSNQEVLE FVTSGGRMDP
       1360       1370       1380       1390       1400
PKNCPGPVYR IMTQCWQHQP EDRPNFAIIL ERIEYCTQDP DVINTALPIE
       1410       1420       1430       1440       1450
YGPLVEEEEK VPVRPKDPEG VPPLLVSQQA KREEERSPAA PPPLPTTSSG
       1460       1470       1480       1490       1500
KAAKKPTAAE ISVRVPRGPA VEGGHVNMAF SQSNPPSELH KVHGSRNKPT
       1510       1520       1530       1540       1550
SLWNPTYGSW FTEKPTKKNN PIAKKEPHDR GNLGLEGSCT VPPNVATGRL
       1560       1570       1580       1590       1600
PGASLLLEPS SLTANMKEVP LFRLRHFPCG NVNYGYQQQG LPLEAATAPG
       1610       1620
AGHYEDTILK SKNSMNQPGP
```

FIG. 4-2

SEQ ID NO: 68

```
         10         20         30         40         50
MGAIGLLWLL PLLLSTAAVG SGMGTGQRAG SPAAGPPLQP REPLSYSRLQ
         60         70         80         90        100
RKSLAVDFVV PSLFRVYARD LLLPPSSSEL KAGRPEARGS LALDCAPLLR
        110        120        130        140        150
LLGPAPGVSW TAGSPAPAEA RTLSRVLKGG SVRKLRRAKQ LVLELGEEAI
        160        170        180        190        200
LEGCVGPPGE AAVGLLQFNL SELFSWWIRQ GEGRLRIRLM PEKKASEVGR
        210        220        230        240        250
EGRLSAAIRA SQPRLLFQIF GTGESSLESP TNMPSPSPDY FTWNLTWIMK
        260        270        280        290        300
DSFPFLSHRS RYGLECSFDF PCELEYSPPL HDLRNQSWSW RRIPSEEASQ
        310        320        330        340        350
MDLLDGPGAE RSKEMPRGSF LLLNTSADSK HTILSPWMRS SSEHCTLAVS
        360        370        380        390        400
VHRLQPSGR  YIAQLLPHNE AAREILLMPT PGKHGWTVLQ GRIGRPDNPF
        410        420        430        440        450
RVALEYISSG NRSLSAVDFF ALKNCSEGTS PGSKMALQSS FTCWNGTVLQ
        460        470        480        490        500
LGQACDFHQD CAQGEDESQM CRKLPVGFYC NFEDGFCGWT QGTLSPHTPQ
        510        520        530        540        550
WQVRTLKDAR FQDHQDHALL LSTTDVPASE SATVTSATFP APIKSSPCEL
        560        570        580        590        600
RMSWLIRGVL RGNVSLVLVE NKTGKEQGRM VWHVAAYEGL SLWQWMVLPL
        610        620        630        640        650
LDVSDRFWLQ MVAWWGQGSR AIVAFDNISI SLDCYLTISG EDKILQNTAP
        660        670        680        690        700
KSRNLFERNP NKELKPGENS PRQTPIFDPT VHWLFTTCGA SGPHGPTQAQ
        710        720        730        740        750
CNNAYQNSNL SVEVGSEGPL KGIQIWKVPA TDTYSISGYG AAGGKGGKNT
        760        770        780        790        800
MMRSHGVSVL GIFNLEKDDM LYILVGQQGE DACPSTNQLI QKVCIGENNV
        810        820        830        840        850
IEEEIRVNRS VHEWAGGGGG GGGATYVFKM KDGVPVPLII AAGGGGRAYG
        860        870        880        890        900
AKTDTFHPER LENNSSVLGL NGNSGAAGGG GGWNDNTSLL WAGKSLQEGA
        910        920        930        940        950
TGGHSCPQAM KKWGWETRGG FGGGGGGCSS GGGGGGYIGG NAASNNDPEM
        960        970        980        990       1000
DGEDGVSFIS PLGILYTPAL KVMEGHGEVN IKHYLNCSHC EVDECHMDPE
       1010       1020       1030       1040       1050
SHKVICFCDH GTVLAEDGVS CIVSPTPEPH LPLSLILSVV TSALVAALVL
       1060       1070       1080       1090       1100
AFSGIMIVYR RKHQELQAMQ MELQSPEYKL SKLRTSIIMT DYNPNYCFAG
       1110       1120       1130       1140       1150
KTSSISDLKE VPRKNITLIR GLGHGAFGEV YEGQVSGMPN DPSPLQVAVR
       1160       1170       1180       1190       1200
TLPEVCSEQD ELDFLMEALI ISKFNHQNIV RCIGVSLQSL PRFILLELMA
       1210       1220       1230       1240       1250
GGDLKSFLRE TRPRPSQPSS LAMLDLLHVA RDIACGCQYL EENHFIHRDI
       1260       1270       1280       1290       1300
AARNCLLTCP GPGRVAKIGD FGMARDIYRA SYYRKGGCAM LPVKWMPPEA
       1310       1320       1330       1340       1350
FMEGIFTSKT DTWSFGVLLW EIFSLGYMPY PSKSNQEVLE FVTSGGRMDP
       1360       1370       1380       1390       1400
PKNCPGPVYR IMTQCWQHQP EDRPNFAIIL ERIEYCTQDP DVINTALPIE
       1410       1420       1430       1440       1450
YGPLVEEEEK VPVRPKDPEG VPPLLVSQQA KREEERSPAA PPPLPTTSSG
       1460       1470       1480       1490       1500
KAAKKPTAAE ISVRVPRGPA VEGGHVNMAF SQSNPPSELH KVHGSRNKPT
       1510       1520       1530       1540       1550
SLWNPTYGSW FTEKPTKKNN PIAKKEPHDR GNLGLEGSCT VPPNVATGRL
       1560       1570       1580       1590       1600
PGASLLLEPS SLTANMKEVP LFRLRHFPCG NVNYGYQQQG LPLEAATAPG
       1610       1620
AGHYEDTILK SKNSMNQPGP
```

FIG. 4-3

SEQ ID NO: 69

```
  1 VYRKRQELQ AMQMELQSPE YKLSKLRTST IMTDYNPNYC FAGKTSSISD LKEVPRKNIT
 61 LIPGLGHGAF GEVYEGQVSG MPNDPSPLQV AVRTLPEVCS EQDELDFLME ALIISKFNHQ
121 NIVRCIGVSL QSLPRFILLE LMAGGDLKSF LRETRPRPSQ PSSLAMLDLL HVARDIACGC
181 QYLEENHFIH RDIAARNCLL TCPGPGRVAK IGDFGMARDI YRASYYRKGG CAMLPVKWMP
241 PEAFMEGIFT SKTDIWSFGV LLWEIFSLGY MPYPSKSNQE VLEFVTSGGR MDPPKNCPGP
301 VYRIMTQCWQ HQPEDRPNFA IILERIEYCT QDPDVINTAL PIEYGPLVEE EEKVPVRPKD
361 PEGVPPLLVS QQAKREEERS PAAPPPLPTT SSGKAAKKPT AAEVSVRVPR GPAVEGGHVN
421 MAFSQSNPPS ELHRVHGSRN KPTSLWNPTY GSWFTERPTK KNNPIAKKEP HERGNLGLEG
481 SCTVPPNVAT GRLPGASLLL EPSSLTANMK EVPLFRLRHF PCGNVNYGYQ QQGLPLEAAT
541 APGAGHYEDT ILKSKNSMNQ PGP
```

SEQ ID NO: 70

```
  1 VYRKRQELQ AMQMELQSPE YKLSKLRTST IMTDYNPNYC FAGKTSSISD LKEVPRKNIT
 61 LIPGLGHGAF GEVYEGQVSG MPNDPSPLQV AVRTLPEVCS EQDELDFLME ALIISKFNHQ
121 NIVRCIGVSL QSLPRFILLE LMAGGDLKSF LRETRPRPSQ PSSLAMLDLL HVARDIACGC
181 QYLEENHFIH RDIAARNCLL TCPGPGRVAK IGDFGMARDI YRASYYRKGG CAMLPVKWMP
241 PEAFMEGIFT SKTDIWSFGV LLWEIFSLGY MPYPSKSNQE VLEFVTSGGR MDPPKNCPGP
301 VYRIMTQCWQ HQPEDRPNFA IILERIEYCT QDPDVINTAL PIEYGPLVEE EEKVPVRPKD
361 PEGVPPLLVS QQAKREEERS PAAPPPLPTT SSGKAAKKPT AAEVSVRVPR GPAVEGGHVN
421 MAFSQSNPPS ELHRVHGSRN KPTSLWNPTY GSWFTERPTK KNNPIAKKEP HERGNLGLEG
481 SCTVPPNVAT GRLPGASLLL EPSSLTANMK EVPLFRLRHF PCGNVNYGYQ QQGLPLEAAT
541 APGAGHYEDT ILKSKNSMNQ PGP
```

ALK POLYPEPTIDES AND METHODS OF USE THEREOF

BACKGROUND OF THE INVENTION

Anaplastic lymphoma kinase (ALK) is a receptor tyrosine kinase first identified in a chromosomal translocation associated with anaplastic large cell lymphomas (ALCL), a subset of T-cell non-Hodgkin lymphomas. Within ALCLs, nearly 70% of the cases carry the t(2;5)(p23;q35) chromosomal translocation that juxtaposes the ALK locus to the nucleophosmin (NPM) gene locus, generating a fusion protein of NPM and the cytoplasmic domain of ALK. Other ALK fusion proteins have been identified, including tropomyosin (TMP3), 5-Aminoimidazole-4-carboxamide ribonucleotide formyltransferase/IMP cyclohydrolase (ATIC), transforming growth factor (TGF), and echinoderm microtubule-associated protein-like 4 (EML4), in different types of solid tumors, such as non-small-cell lung cancers, neuroblastoma, rhabdomyosarcoma, neuroectodermal tumors, and glioblastomas. Data from human patients carrying ALK-positive ALCL show that the ALK protein is immunogenic. The ALK-elicited immune response involves $CD8^+$ CTL cells, $CD4^+$ T helper cells, and the production of anti-ALK antibodies, and influences the outcome of the disease. There exists a need for novel and effective immunotherapies against cancers, such as immunotherapies using an ALK protein or a portion thereof.

SUMMARY OF THE INVENTION

The invention features immunogenic compositions and constructs containing anaplastic lymphoma kinase (ALK) polypeptides and methods of use thereof. The immunogenic compositions and methods of the invention may be used to treat a disease associated with ALK in a subject, such as cancer (e.g., a solid tumor cancer or a cancer that expresses ALK or a portion thereof (e.g., an ALK+ cancer)).

In a first aspect, the invention features an immunogenic composition including an anaplastic lymphoma kinase (ALK) polypeptide, wherein the ALK polypeptide includes at least 6 contiguous amino acids from a sequence of any one of SEQ ID NOs: 1-66 and 93-139 and wherein the ALK polypeptide does not consist of a sequence of any one of SEQ ID NOs: 67-70 and 140-145. In some embodiments, the ALK polypeptide does not include a sequence of any one of SEQ ID NOs: 67-70 and 140-145.

In some embodiments, the ALK polypeptide is 8 to 230 amino acids in length. In some embodiments, the ALK polypeptide is 8 to 60 amino acids in length. In some embodiments, the ALK polypeptide is 8 to 30 amino acids in length. In some embodiments, the ALK polypeptide is 8 to 15 amino acids in length. In some embodiments, the ALK polypeptide is 8 to 11 amino acids in length.

In some embodiments, the ALK polypeptide includes at least 9 contiguous amino acids from a sequence of any one of SEQ ID NOs: 1-66 and 93-139. In some embodiments, the ALK polypeptide is 9 to 40 amino acids in length. In some embodiments, the ALK polypeptide is 15 to 40 amino acids in length. In some embodiments, the ALK polypeptide is 20 to 40 amino acids in length. In some embodiments, the ALK polypeptide is 25 to 40 amino acids in length. In some embodiments, the ALK polypeptide is 30 to 40 amino acids in length.

In some embodiments, the ALK polypeptide includes at least 11 contiguous amino acids from a sequence of any one of SEQ ID NOs: 1-59 and 93-139.

In some embodiments, the ALK polypeptide includes a sequence of any one of SEQ ID NOs: 1-66 and 93-139.

In some embodiments, the ALK polypeptide includes 9 contiguous amino acids from a sequence of any one of SEQ ID NOs: 1-66 and 93-139 and wherein the ALK polypeptide is 9 amino acids in length. In some embodiments, the ALK polypeptide includes 11 contiguous amino acids from a sequence of any one of SEQ ID NOs: 1-59 and 93-139 and wherein the ALK polypeptide is 11 amino acids in length.

In some embodiments of the first aspect of the invention, the sequence is selected from any one of SEQ ID NOs: 93, 96, 100, 106, 111-116, and 121-139. In some embodiments, the sequence is SEQ ID NO: 93. In some embodiments, the sequence is SEQ ID NO: 96. In some embodiments, the sequence is SEQ ID NO: 100. In some embodiments, the sequence is SEQ ID NO: 106. In some embodiments, the sequence is SEQ ID NO: 111. In some embodiments, the sequence is SEQ ID NO: 112. In some embodiments, the sequence is SEQ ID NO: 113. In some embodiments, the sequence is SEQ ID NO: 114. In some embodiments, the sequence is SEQ ID NO: 115. In some embodiments, the sequence is SEQ ID NO: 116. In some embodiments, the sequence is SEQ ID NO: 121. In some embodiments, the sequence is SEQ ID NO: 122. In some embodiments, the sequence is SEQ ID NO: 123. In some embodiments, the sequence is SEQ ID NO: 124. In some embodiments, the sequence is SEQ ID NO: 125. In some embodiments, the sequence is SEQ ID NO: 126. In some embodiments, the sequence is SEQ ID NO: 127. In some embodiments, the sequence is SEQ ID NO: 128. In some embodiments, the sequence is SEQ ID NO: 129. In some embodiments, the sequence is SEQ ID NO: 130. In some embodiments, the sequence is SEQ ID NO: 131. In some embodiments, the sequence is SEQ ID NO: 132. In some embodiments, the sequence is SEQ ID NO: 133. In some embodiments, the sequence is SEQ ID NO: 134. In some embodiments, the sequence is SEQ ID NO: 135. In some embodiments, the sequence is SEQ ID NO: 136. In some embodiments, the sequence is SEQ ID NO: 137. In some embodiments, the sequence is SEQ ID NO: 138. In some embodiments, the sequence is SEQ ID NO: 139.

In some embodiments of the first aspect of the invention, the sequence is selected from any one of SEQ ID NOs: 10, 14, 17, 22, 33, 52, and 53. In some embodiments, the sequence is SEQ ID NO: 10. In some embodiments, the sequence is SEQ ID NO: 14. In some embodiments, the sequence is SEQ ID NO: 17. In some embodiments, the sequence is SEQ ID NO: 22. In some embodiments, the sequence is SEQ ID NO: 33. In some embodiments, the sequence is SEQ ID NO: 52. In some embodiments, the sequence is SEQ ID NO: 53.

In some embodiments of the first aspect of the invention, the immunogenic composition is formulated for administration as a vaccine or an immunotherapy. A "vaccine" refers to an agent (i.e., a biological agent) that provides immunity to a particular disease or pathogen. A vaccine can be a prophylactic vaccine (i.e., a vaccine used to prevent or ameliorate the effects of a future infection by a pathogen) or a therapeutic vaccine (i.e., a vaccine use for treatment of, e.g., an infection). An "immunotherapy" refers to a type of treatment designed to boost the body's immune system to fight against one or more diseases and/or to suppress the body's negative reactions towards one or more diseases and/or drugs used in the treatment of one or more diseases. An immunotherapy can improve, target, and/or restore functions of the immune system.

In some embodiments, the immunogenic composition further includes an adjuvant. In some embodiments, the immunogenic composition is in a unit dosage form.

In a second aspect, the invention features an immunogenic composition including an ALK polypeptide, wherein the ALK polypeptide includes a first sequence including at least 6 contiguous amino acids from a sequence selected from any one of SEQ ID NOs: 1-66 (e.g., SEQ ID NOs: 10, 14, 17, 22, 33, 52, and 53) and a second sequence including at least 6 contiguous amino acids from a sequence selected from any one of SEQ ID NOs: 1-66 (e.g., SEQ ID NOs: 10, 14, 17, 22, 33, 52, and 53), wherein the first and second sequences are different, wherein the first and second sequences include a pair of sequences of SEQ ID NOs recited in Table 2A, and wherein the ALK polypeptide does not include a sequence of any one of SEQ ID NOs: 67-70 and 140-145.

In some embodiments of the second aspect of the invention, the first and second sequences include one of the following pairs of sequences: SEQ ID NOs: 10 and 14, SEQ ID NOs: 10 and 17, SEQ ID NOs: 10 and 22, SEQ ID NOs: 10 and 33, SEQ ID NOs: 10 and 52, SEQ ID NOs: 10 and 53, SEQ ID NOs: 14 and 17, SEQ ID NOs: 14 and 22, SEQ ID NOs: 14 and 33, SEQ ID NOs: 14 and 52, SEQ ID NOs: 14 and 53, SEQ ID NOs: 17 and 22, SEQ ID NOs: 17 and 33, SEQ ID NOs: 17 and 52, SEQ ID NOs: 17 and 53, SEQ ID NOs: 22 and 33, SEQ ID NOs: 22 and 52, SEQ ID NOs: 22 and 53, SEQ ID NOs: 33 and 52, SEQ ID NOs: 33 and 53, and SEQ ID NOs: 52 and 53.

In a third aspect, the invention features an immunogenic composition including an ALK polypeptide, wherein the ALK polypeptide includes a first sequence including at least 6 contiguous amino acids from a sequence selected from any one of SEQ ID NOs: 93, 96, 100, 106, 111-116, and 121-139 and a second sequence including at least 6 contiguous amino acids from a sequence selected from any one of SEQ ID NOs: 93, 96, 100, 106, 111-116, and 121-139, wherein the first and second sequences are different, wherein the first and second sequences include a pair of sequences of SEQ ID NOs recited in Table 2B, and wherein the ALK polypeptide does not include a sequence of any one of SEQ ID NOs: 67-70 and 140-145. In some embodiments of the second and third aspects of the invention, the first and/or second sequence in the ALK polypeptide is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the second and third aspects of the invention, the first and/or second sequence in the ALK polypeptide includes at least 9 contiguous amino acids from a sequence of any one of SEQ ID NOs: 1-66 and 93-139. In some embodiments of the second and third aspects of the invention, the first and/or second sequence in the ALK polypeptide includes at least 11 contiguous amino acids from a sequence of any one of SEQ ID NOs: 1-59 and 93-139. In some embodiments of the second and third aspects of the invention, the first and/or second sequence in the ALK polypeptide includes a sequence of any one of SEQ ID NOs: 1-58 and 93-139. In some embodiments of the second and third aspects of the invention, the first and/or second sequence in the ALK polypeptide includes 9 contiguous amino acids from a sequence of any one of SEQ ID NOs: 1-66 and 93-139 and wherein the first and/or second sequence in the ALK polypeptide is 9 amino acids in length. In some embodiments, the first and/or second sequence in the ALK polypeptide includes 11 contiguous amino acids from a sequence of any one of SEQ ID NOs: 1-59 and 93-139 and wherein the first and/or second sequence in the ALK polypeptide is 11 amino acids in length. In some embodiments, the first and/or second sequence in the ALK polypeptide includes 15 contiguous amino acids from a sequence of any one of SEQ ID NOs: 1-58 and 93-139 and wherein the first and/or second sequence in the ALK polypeptide is 11 amino acids in length.

In some embodiments of the second and third aspects of the invention, the first and/or second sequence in the ALK polypeptide is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the second and third aspects of the invention, the first and/or second sequence in the ALK polypeptide includes at least 9 contiguous amino acids from a sequence of any one of SEQ ID NOs: 93, 96, 100, 106, 111-116, and 121-139. In some embodiments of the second and third aspects of the invention, the first and/or second sequence in the ALK polypeptide includes at least 11 contiguous amino acids from a sequence of any one of SEQ ID NOs: 93, 96, 100, 106, 111-116, and 121-139. In some embodiments of the second and third aspects of the invention, the first and/or second sequence in the ALK polypeptide includes a sequence of any one of SEQ ID NOs: 93, 96, 100, 106, 111-116, and 121-139. In some embodiments of the second and third aspects of the invention, the first and/or second sequence in the ALK polypeptide includes 9 contiguous amino acids from a sequence of any one of SEQ ID NOs: 93, 96, 100, 106, 111-116, and 121-139 and wherein the first and/or second sequence in the ALK polypeptide is 9 amino acids in length. In some embodiments, the first and/or second sequence in the ALK polypeptide includes 11 contiguous amino acids from a sequence of any one of SEQ ID NOs: 93, 96, 100, 106, 111-116, and 121-139 and wherein the first and/or second sequence in the ALK polypeptide is 11 amino acids in length. In some embodiments, the first and/or second sequence in the ALK polypeptide includes 15 contiguous amino acids from a sequence of any one of SEQ ID NOs: 93, 96, 100, 106, 111-116, and 121-139 and wherein the first and/or second sequence in the ALK polypeptide is 15 amino acids in length.

In a fourth aspect, the invention features an immunogenic composition including an ALK polypeptide, wherein the ALK polypeptide includes a first sequence including at least 6 contiguous amino acids from a sequence selected from any one of SEQ ID NOs: 1-66 (e.g., SEQ ID NOs: 10, 14, 17, 22, 33, 52, and 53), a second sequence including at least 6 contiguous amino acids from a sequence selected from any one of SEQ ID NOs: 1-66 (e.g., SEQ ID NOs: 10, 14, 17, 22, 33, 52, and 53), and a third sequence including at least 6 contiguous amino acids from a sequence selected from any one of SEQ ID NOs: 1-66 (e.g., SEQ ID NOs: 10, 14, 17, 22, 33, 52, and 53), wherein the first, second, and third sequences are different, wherein the first, second, and third sequences include a set of sequences of SEQ ID NOs recited in Table 3A, and wherein the ALK polypeptide does not include a sequence of any one of SEQ ID NOs: 67-70 and 140-145. In some embodiments of the fourth aspect of the invention, the first, second, and third sequences include one of the following sets of sequences: SEQ ID NOs: 10, 14, and 17, SEQ ID NOs; 10, 14, and 22, SEQ ID NOs: 10, 14, and 33, SEQ ID NOs:10, 14, and 52, SEQ ID NOs:10, 14, and 53, SEQ ID NOs:10, 17, and 22, SEQ ID NOs:10, 17, and 33, SEQ ID NOs:10, 17, and 52, SEQ ID NOs:10, 17, and 53, SEQ ID NOs:10, 22, and 33, SEQ ID NOs:10, 22, and 52, SEQ ID NOs:10, 22, and 53, SEQ ID NOs:10, 33, and 52, SEQ ID NOs:10, 33, and 53, SEQ ID NOs:10, 52, and 53, SEQ ID NOs:14, 17, and 22, SEQ ID NOs:14, 17, and 33, SEQ ID NOs:14, 17, and 52, SEQ ID NOs:14, 17, and 53, SEQ ID NOs:14, 22, and 33, SEQ ID NOs:14, 22, and 52, SEQ ID NOs:14, 22, and 53, SEQ ID NOs:14, 33, and 52, SEQ ID NOs:14, 33, and 53, SEQ ID NOs:14, 52, and 53, SEQ ID NOs:17, 22, and 33, SEQ ID NOs:17, 22, and 52, SEQ ID NOs:17, 22, and 53, SEQ ID NOs:17, 33, and 52, SEQ ID NOs:17, 33, and 53, SEQ ID NOs:17, 52, and 53, SEQ ID NOs:22, 33, and 52, SEQ ID NOs:22, 33, and 53, SEQ ID NOs:22, 52, and 53, and SEQ ID NOs: 33, 52, and 53.

In a fifth aspect, the invention features an immunogenic composition including an ALK polypeptide, wherein the ALK polypeptide includes a first sequence including at least 6 contiguous amino acids from a sequence selected from any one of SEQ ID NOs: 93, 96, 100, 106, 111-116, and 121-139, a second sequence including at least 6 contiguous amino acids from a sequence selected from any one of SEQ ID NOs: 93, 96, 100, 106, 111-116, and 121-139, and a third sequence including at least 6 contiguous amino acids from a sequence selected from any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, and wherein the ALK polypeptide does not include a sequence of any one of SEQ ID NOs: 67-70 and 140-145.

In some embodiments of the fourth and fifth aspects of the invention, the first, second, and/or third sequence in the ALK polypeptide is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the fourth and fifth aspects of the invention, the first, second, and/or third sequence in the ALK polypeptide includes at least 9 contiguous amino acids from a sequence of any one of SEQ ID NOs: 1-66 and 93-139. In some embodiments of the fourth and fifth aspects of the invention, the first, second, and/or third sequence in the ALK polypeptide includes at least 11 contiguous amino acids from a sequence of any one of SEQ ID NOs: 1-59 and 93-139. In some embodiments of the fourth and fifth aspects of the invention, the first, second, and/or third sequence in the ALK polypeptide includes a sequence of any one of SEQ ID NOs: 1-58 and 93-139. In some embodiments of the fourth and fifth aspects of the invention, the first, second, and/or third sequence in the ALK polypeptide includes 9 contiguous amino acids from a sequence of any one of SEQ ID NOs: 1-66 and 93-139 and wherein the first, second, and/or third sequence in the ALK polypeptide is 9 amino acids in length. In some embodiments, the first, second, and/or third sequence in the ALK polypeptide includes 11 contiguous amino acids from a sequence of any one of SEQ ID NOs: 1-59 and 93-139 and wherein the first, second, and/or third sequence in the ALK polypeptide is 11 amino acids in length. In some embodiments, the first, second, and/or third sequence in the ALK polypeptide includes 15 contiguous amino acids from a sequence of any one of SEQ ID NOs: 1-58 and 93-139 and wherein the first, second, and/or third sequence in the ALK polypeptide is 15 amino acids in length.

In some embodiments of the fourth and fifth aspects of the invention, the first, second, and/or third sequence in the ALK polypeptide is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the fourth and fifth aspects of the invention, the first, second, and/or third sequence in the ALK polypeptide includes at least 9 contiguous amino acids from a sequence of any one of SEQ ID NOs: 93, 96, 100, 106, 111-116, and 121-139. In some embodiments of the fourth and fifth aspects of the invention, the first, second, and/or third sequence in the ALK polypeptide includes at least 11 contiguous amino acids from a sequence of any one of SEQ ID NOs: 93, 96, 100, 106, 111-116, and 121-139. In some embodiments of the fourth and fifth aspects of the invention, the first, second, and/or third sequence in the ALK polypeptide includes a sequence of any one of SEQ ID NOs: 93, 96, 100, 106, 111-116, and 121-139. In some embodiments of the fourth and fifth aspects of the invention, the first, second, and/or third sequence in the ALK polypeptide includes 9 contiguous amino acids from a sequence of any one of SEQ ID NOs: 93, 96, 100, 106, 111-116, and 121-139 and wherein the first, second, and/or third sequence in the ALK polypeptide is 9 amino acids in length. In some embodiments, the first, second, and/or third sequence in the ALK polypeptide includes 11 contiguous amino acids from a sequence of any one of SEQ ID NOs: 93, 96, 100, 106, 111-116, and 121-139 and wherein the first, second, and/or third sequence in the ALK polypeptide is 11 amino acids in length. In some embodiments, the first, second, and/or third sequence in the ALK polypeptide includes 15 contiguous amino acids from a sequence of any one of SEQ ID NOs: 93, 96, 100, 106, 111-116, and 121-139 and wherein the first, second, and/or third sequence in the ALK polypeptide is 15 amino acids in length.

In a sixth aspect, the invention features an immunogenic composition including an ALK polypeptide, wherein the ALK polypeptide consists of a sequence selected from any one of SEQ ID NOs: 1-66 and 93-139.

In a seventh aspect, the invention features an immunogenic composition including an ALK polypeptide, wherein the ALK polypeptide consists of a sequence selected from any one of SEQ ID NOs: 93, 96, 100, 106, 111-116, and 121-139.

In some embodiments of the first to the seventh aspects of the invention, a partner protein or a fragment thereof is fused to a N- or C-terminus of the ALK polypeptide. In some embodiments, the partner protein is selected from the group consisting of a nucleophosmin (NPM) protein, a tropomyosin 3 (TPM3) protein, a tropomyosin 4 (TPM4) protein, a TRK-fused gene (TFG) protein, a 5-Aminoimidazole-4-carboxamide ribonucleotide formyltransferase/IMP cyclohydrolase (ATIC) protein, a clathrin heavy chain-like 1 (CLTC1) protein, a moesin (MSN) protein, an ALK lymphoma oligomerization partner on chromosome 17 (ALO17) protein, a RAN binding protein 2 (RANBP2), a non-muscle myosin heavy chain (MYH9) protein, a cysteinyl-tRNA synthetase (CARS) protein, a SEC31 homologue A (SEC31 L1) protein, a transforming growth factor (TGF) protein, and an echinoderm microtubule-associated protein-like 4 (EML4) protein. In some embodiments, the fragment is an extracellular domain of the partner protein or a fragment of such extracellular domain.

In an eighth aspect, the invention features an immunogenic composition including a first ALK polypeptide including a first sequence including at least 6 contiguous amino acids from a sequence of any one of SEQ ID NOs: 1-66 (e.g., SEQ ID NOs: 10, 14, 17, 22, 33, 52, and 53) and a second ALK polypeptide including a second sequence including at least 6 contiguous amino acids from a sequence of any one of SEQ ID NOs: 1-66 (e.g., SEQ ID NOs: 10, 14, 17, 22, 33, 52, and 53), wherein the first and second sequences are different, wherein the first and second sequences include a pair of sequences of SEQ ID NOs recited in Table 2A, and wherein neither the first ALK polypeptide nor the second ALK polypeptide includes a sequence of any one of SEQ ID NOs: 67-70 and 140-145.

In some embodiments of the eighth aspect of the invention, the first and second sequences include one of the following pairs of sequences: SEQ ID NOs: 10 and 14, SEQ ID NOs: 10 and 17, SEQ ID NOs: 10 and 22, SEQ ID NOs: 10 and 33, SEQ ID NOs: 10 and 52, SEQ ID NOs: 10 and 53, SEQ ID NOs: 14 and 17, SEQ ID NOs: 14 and 22, SEQ ID NOs: 14 and 33, SEQ ID NOs: 14 and 52, SEQ ID NOs: 14 and 53, SEQ ID NOs: 17 and 22, SEQ ID NOs: 17 and 33, SEQ ID NOs: 17 and 52, SEQ ID NOs: 17 and 53, SEQ ID NOs: 22 and 33, SEQ ID NOs: 22 and 52, SEQ ID NOs: 22 and 53, SEQ ID NOs: 33 and 52, SEQ ID NOs: 33 and 53, and SEQ ID NOs: 52 and 53.

In a ninth aspect, the invention features an immunogenic composition including a first ALK polypeptide including a first sequence including at least 6 contiguous amino acids from a sequence of any one of SEQ ID NOs: 93, 96, 100, 106, 111-116, and 121-139 and a second ALK polypeptide including a second sequence including at least 6 contiguous amino acids from a sequence of any one of SEQ ID NOs: 93, 96, 100, 106, 111-116, and 121-139, wherein the first and second sequences are different, wherein the first and second sequences include a pair of sequences of SEQ ID NOs recited in Table 2B, and wherein neither the first ALK polypeptide nor the second ALK polypeptide includes a sequence of any one of SEQ ID NOs: 67-70 and 140-145.

In some embodiments of the eight and ninth aspects of the invention, the first and/or second sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the eighth and ninth aspects of the invention, the first and/or second sequence includes at least 9 contiguous amino acids from a sequence of any one of SEQ ID NOs: 1-66 and 93-139. In some embodiments of the eighth and ninth aspects of the invention, the first and/or second sequence includes at least 11 contiguous amino acids from a sequence of any one of SEQ ID NOs: 1-59 and 93-139.

In some embodiments of the eighth and ninth aspects of the invention, the first and/or second sequence includes a sequence of any one of SEQ ID NOs: 1-58 and 93-139. In some embodiments of the eighth and ninth aspects of the invention, the first and/or second sequence includes 9 contiguous amino acids from a sequence of any one of SEQ ID NOs: 1-66 and 93-139 and wherein the first and/or second sequence is 9 amino acids in length. In some embodiments, the first and/or second sequence includes 11 contiguous amino acids from a sequence of any one of SEQ ID NOs: 1-59 and 93-139 and wherein the first and/or second sequence is 11 amino acids in length. In some embodiments, the first and/or second sequence includes 15 contiguous amino acids from a sequence of any one of SEQ ID NOs: 1-58 and 93-139 and wherein the first and/or second sequence is 15 amino acids in length.

In some embodiments of the eighth and ninth aspects of the invention, the first and/or second sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the eighth and ninth aspects of the invention, the first and/or second sequence includes at least 9 contiguous amino acids from a sequence of any one of SEQ ID NOs: 93, 96, 100, 106, 111-116, and 121-139. In some embodiments of the eighth and ninth aspects of the invention, the first and/or second sequence includes at least 11 contiguous amino acids from a sequence of any one of SEQ ID NOs: 93, 96, 100, 106, 111-116, and 121-139. In some embodiments of the eighth and ninth aspects of the invention, the first and/or second sequence includes a sequence of any one of SEQ ID NOs: 93, 96, 100, 106, 111-116, and 121-139. In some embodiments of the eighth and ninth aspects of the invention, the first and/or second sequence includes 9 contiguous amino acids from a sequence of any one of SEQ ID NOs: 93, 96, 100, 106, 111-116, and 121-139 and wherein the first and/or second sequence is 9 amino acids in length. In some embodiments, the first and/or second sequence includes 11 contiguous amino acids from a sequence of any one of SEQ ID NOs: 93, 96, 100, 106, 111-116, and 121-139 and wherein the first and/or second sequence is 11 amino acids in length. In some embodiments, the first and/or second sequence includes 15 contiguous amino acids from a sequence of any one of SEQ ID NOs: 93, 96, 100, 106, 111-116, and 121-139 and wherein the first and/or second sequence is 15 amino acids in length.

In some embodiments of the eighth and ninth aspects of the invention, a first partner protein or a fragment thereof is fused to a N- or C-terminus of the first ALK polypeptide, and/or wherein a second partner protein or a fragment thereof is fused to a N- or C-terminus of the second ALK polypeptide. In some embodiments, the first or second partner protein is selected from the group consisting of a nucleophosmin (NPM) protein, a tropomyosin 3 (TPM3) protein, a tropomyosin 4 (TPM4) protein, a TRK-fused gene (TFG) protein, a 5-Aminoimidazole-4-carboxamide ribonucleotide formyltransferase/IMP cyclohydrolase (ATIC) protein, a clathrin heavy chain-like 1 (CLTC1) protein, a moesin (MSN) protein, an ALK lymphoma oligomerization partner on chromosome 17 (ALO17) protein, a RAN binding protein 2 (RANBP2), a non-muscle myosin heavy chain (MYH9) protein, a cysteinyl-tRNA synthetase (CARS) protein, a SEC31 homologue A (SEC31 L1) protein, a transforming growth factor (TGF) protein, and an echinoderm microtubule-associated protein-like 4 (EML4) protein. In some embodiments the fragment is an extracellular domain of the first and/or second partner protein or a fragment of the extracellular domain of the first and/or second partner protein.

In a tenth aspect, the invention features an immunogenic composition including a first ALK polypeptide including a first sequence including at least 6 contiguous amino acids from a sequence of any one of SEQ ID NOs: 1-66 (e.g., SEQ ID NOs: 10, 14, 17, 22, 33, 52, and 53), a second ALK polypeptide including a second sequence including at least 6 contiguous amino acids from a sequence of any one of SEQ ID NOs: 1-66 (e.g., SEQ ID NOs: 10, 14, 17, 22, 33, 52, and 53), and a third ALK polypeptide including a third sequence including at least 6 contiguous amino acids from a sequence of any one of SEQ ID NOs: 1-66 (e.g., SEQ ID NOs: 10, 14, 17, 22, 33, 52, and 53), wherein the first, second, and third sequences are different, wherein the first, second, and third sequences include a set of sequences of SEQ ID NOs recited in Table 3A, and wherein none of the first, second, and third ALK polypeptides includes a sequence of any one of SEQ ID NOs: 67-70 and 140-145.

In some embodiments of the tenth aspect of the invention, the first, second, and third sequences include one of the following sets of sequences: SEQ ID NOs: 10, 14, and 17, SEQ ID NOs; 10, 14, and 22, SEQ ID NOs: 10, 14, and 33, SEQ ID NOs:10, 14, and 52, SEQ ID NOs:10, 14, and 53, SEQ ID NOs:10, 17, and 22, SEQ ID NOs:10, 17, and 33, SEQ ID NOs:10, 17, and 52, SEQ ID NOs:10, 17, and 53, SEQ ID NOs:10, 22, and 33, SEQ ID NOs:10, 22, and 52, SEQ ID NOs:10, 22, and 53, SEQ ID NOs:10, 33, and 52, SEQ ID NOs:10, 33, and 53, SEQ ID NOs:10, 52, and 53, SEQ ID NOs:14, 17, and 22, SEQ ID NOs:14, 17, and 33, SEQ ID NOs:14, 17, and 52, SEQ ID NOs:14, 17, and 53, SEQ ID NOs:14, 22, and 33, SEQ ID NOs:14, 22, and 52, SEQ ID NOs:14, 22, and 53, SEQ ID NOs:14, 33, and 52, SEQ ID NOs:14, 33, and 53, SEQ ID NOs:14, 52, and 53, SEQ ID NOs:17, 22, and 33, SEQ ID NOs:17, 22, and 52, SEQ ID NOs:17, 22, and 53, SEQ ID NOs:17, 33, and 52, SEQ ID NOs:17, 33, and 53, SEQ ID NOs:17, 52, and 53, SEQ ID NOs:22, 33, and 52, SEQ ID NOs:22, 33, and 53, SEQ ID NOs:22, 52, and 53, and SEQ ID NOs: 33, 52, and 53.

In an eleventh aspect, the invention features an immunogenic composition including a first ALK polypeptide including a first sequence including at least 6 contiguous amino acids from a sequence of any one of SEQ ID NOs: 93, 96, 100, 106, 111-116, and 121-139, a second ALK polypeptide including a second sequence including at least 6 contiguous amino acids from a sequence of any one of SEQ ID NOs: 93, 96, 100, 106, 111-116, and 121-139, and a third ALK polypeptide including a third sequence including at least 6 contiguous amino acids from a sequence of any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, and wherein none of the first, second, and third ALK polypeptides includes a sequence of any one of SEQ ID NOs: 67-70 and 140-145.

In some embodiments of the tenth and eleventh aspects of the invention, the first, second, and/or third sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the tenth and eleventh aspects of the invention, the first, second, and/or third sequence includes at least 9 contiguous amino acids from a sequence of any one of SEQ ID NOs: 1-66 and 93-139. In some embodiments of the tenth and eleventh aspects of the invention, the first, second, and/or third sequence includes at least 11 contiguous amino acids from a sequence of any one of SEQ ID NOs: 1-59 and 93-139. In some embodiments of the tenth and eleventh aspects of the invention, the first, second, and/or third sequence includes a sequence of any one of SEQ ID NOs: 1-58 and 93-139. In some embodiments of the tenth and eleventh aspects of the invention, the first, second, and/or third sequence includes 9 contiguous amino acids from a sequence of any one of SEQ ID NOs: 1-66 and 93-139 and wherein the first, second, and/or third sequence is 9 amino acids in length. In some embodiments, the first, second, and/or third sequence includes 11 contiguous amino acids from a sequence of any one of SEQ ID NOs: 1-59 and 93-139 and wherein the first, second, and/or third sequence is 11 amino acids in length. In some embodiments, the first, second, and/or third sequence includes 15 contiguous amino acids from a sequence of any one of SEQ ID NOs: 1-58 and 93-139 and wherein the first, second, and/or third sequence is 15 amino acids in length.

In some embodiments of the tenth and eleventh aspects of the invention, the first, second, and/or third sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the tenth and eleventh aspects of the invention, the first, second, and/or third sequence includes at least 9 contiguous amino acids from a sequence of any one of SEQ ID NOs: 93, 96, 100, 106, 111-116, and 121-139. In some embodiments of the tenth and eleventh aspects of the invention, the first, second, and/or third sequence includes at least 11 contiguous amino acids from a sequence of any one of SEQ ID NOs: 93, 96, 100, 106, 111-116, and 121-139. In some embodiments of the tenth and eleventh aspects of the invention, the first, second, and/or third sequence includes a sequence of any one of SEQ ID NOs: 93, 96, 100, 106, 111-116, and 121-139. In some embodiments of the tenth and eleventh aspects of the invention, the first, second, and/or third sequence includes 9 contiguous amino acids from a sequence of any one of SEQ ID NOs: 93, 96, 100, 106, 111-116, and 121-139 and wherein the first, second, and/or third sequence is 9 amino acids in length. In some embodiments, the first, second, and/or third sequence includes 11 contiguous amino acids from a sequence of any one of SEQ ID NOs: 93, 96, 100, 106, 111-116, and 121-139 and wherein the first, second, and/or third sequence is 11 amino acids in length. In some embodiments, the first, second, and/or third sequence includes 15 contiguous amino acids from a sequence of any one of SEQ ID NOs: 93, 96, 100, 106, 111-116, and 121-139 and wherein the first, second, and/or third sequence is 15 amino acids in length.

In some embodiments of the tenth and eleventh aspects of the invention, a first partner protein or a fragment thereof is fused to a N- or C-terminus of the first ALK polypeptide, and/or wherein a second partner protein or a fragment thereof is fused to a N- or C-terminus of the second ALK polypeptide, and/or wherein a third partner protein or a fragment thereof is fused to a N- or C-terminus of the third ALK polypeptide. In some embodiments of the tenth and eleventh aspects of the invention, the first, second, or third partner protein is selected from the group consisting of a nucleophosmin (NPM) protein, a tropomyosin 3 (TPM3) protein, a tropomyosin 4 (TPM4) protein, a TRK-fused gene (TFG) protein, a 5-Aminoimidazole-4-carboxamide ribonucleotide formyltransferase/IMP cyclohydrolase (ATIC) protein, a clathrin heavy chain-like 1 (CLTC1) protein, a moesin (MSN) protein, an ALK lymphoma oligomerization partner on chromosome 17 (ALO17) protein, a RAN binding protein 2 (RANBP2), a non-muscle myosin heavy chain (MYH9) protein, a cysteinyl-tRNA synthetase (CARS) protein, a SEC31 homologue A (SEC31 L1) protein, a transforming growth factor (TGF) protein, and an echinoderm microtubule-associated protein-like 4 (EML4) protein. In some embodiments, the fragment is an extracellular domain of the first, second, and/or third partner protein or a fragment of the extracellular domain of the first, second, and/or third partner protein.

In a thirteenth aspect, the invention features an immunogenic composition including: (a) a multilamellar lipid vesicle having crosslinks between lipid bilayers; and (b) at least one ALK polypeptide, wherein the ALK polypeptide includes at least 6 contiguous amino acids from a sequence of any one of SEQ ID NOs: 1-66 and 93-139 and wherein the ALK polypeptide does not include a sequence of any one of SEQ ID NOs: 67-70 and 140-145.

In a fourteenth aspect, the invention features an immunogenic composition including: (a) a multilamellar lipid vesicle having crosslinks between lipid bilayers; and (b) at least one ALK polypeptide, wherein the ALK polypeptide includes at least 6 contiguous amino acids from a sequence of any one of SEQ ID NOs: 93, 96, 100, 106, 111-116, and 121-139 and wherein the ALK polypeptide does not include a sequence of any one of SEQ ID NOs: 67-70 and 140-145.

In a fifteenth aspect, the invention features an immunogenic composition including: (a) a multilamellar lipid vesicle having crosslinks between lipid bilayers; and (b) an ALK polypeptide, wherein the ALK polypeptide includes a first sequence including at least 6 contiguous amino acids from a sequence selected from any one of SEQ ID NOs: 1-66 and a second sequence including at least 6 contiguous amino acids from a sequence selected from any one of SEQ ID NOs: 1-66, wherein the first and second sequences are different, wherein the first and second sequences include a pair of sequences of SEQ ID NOs recited in Table 2A, and wherein the ALK polypeptide does not include a sequence of any one of SEQ ID NOs: 67-70 and 140-145.

In a sixteenth aspect, the invention features, an immunogenic composition including: (a) a multilamellar lipid vesicle having crosslinks between lipid bilayers; and (b) an ALK polypeptide, wherein the ALK polypeptide includes a first sequence including at least 6 contiguous amino acids from a sequence selected from any one of SEQ ID NOs: 93, 96, 100, 106, 111-116, and 121-139 and a second sequence including at least 6 contiguous amino acids from a sequence selected from any one of SEQ ID NOs: 93, 96, 100, 106, 111-116, and 121-139, wherein the first and second sequences are different, wherein the first and second sequences include a pair of sequences of SEQ ID NOs recited in Table 2B, and wherein the ALK polypeptide does not include a sequence of any one of SEQ ID NOs: 67-70 and 140-145.

In some embodiments of the fifteenth and sixteenth aspects of the invention, the first and/or second sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the fifteenth and sixteenth aspects of the invention, the first and/or second sequence includes at least 9 contiguous amino acids from a sequence of any one of SEQ ID NOs: 1-66 and 93-139. In some embodiments of the fifteenth and sixteenth aspects of the invention, the first and/or second sequence includes at least 11 contiguous amino acids from a sequence of any one of SEQ ID NOs: 1-59 and 93-139. In some embodiments of the fifteenth and sixteenth aspects of the invention, the first and/or second sequence includes a sequence of any one of SEQ ID NOs: 1-58 and 93-139. In some embodiments of the fifteenth and sixteenth aspects of the invention, the first and/or second sequence includes 9 contiguous amino acids from a sequence of any one of SEQ ID NOs: 1-66 and 93-139 and wherein the first and/or second sequence is 9 amino acids in length. In some embodiments, the first and/or second sequence includes 11 contiguous amino acids from a sequence of any one of SEQ ID NOs: 1-59 and 93-139 and wherein the first and/or second sequence is 11 amino acids in length. In some embodiments, the first and/or second sequence includes 15 contiguous amino acids from a sequence of any one of SEQ ID NOs: 1-58 and 93-139 and wherein the first and/or second sequence is 15 amino acids in length.

In some embodiments of the fifteenth and sixteenth aspects of the invention, the first and/or second sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the fifteenth and sixteenth aspects of the invention, the first and/or second sequence includes at least 9 contiguous amino acids from a sequence of any one of SEQ ID NOs: 93, 96, 100, 106, 111-116, and 121-139. In some embodiments of the fifteenth and sixteenth aspects of the invention, the first and/or second sequence includes at least 11 contiguous amino acids from a sequence of any one of SEQ ID NOs: 93, 96, 100, 106, 111-116, and 121-139. In some embodiments of the fifteenth and sixteenth aspects of the invention, the first and/or second sequence includes a sequence of any one of SEQ ID NOs: 93, 96, 100, 106, 111-116, and 121-139. In some embodiments of the fifteenth and sixteenth aspects of the invention, the first and/or second sequence includes 9 contiguous amino acids from a sequence of any one of SEQ ID NOs: 93, 96, 100, 106, 111-116, and 121-139 and wherein the first and/or second sequence is 9 amino acids in length. In some embodiments, the first and/or second sequence includes 11 contiguous amino acids from a sequence of any one of SEQ ID NOs: 93, 96, 100, 106, 111-116, and 121-139 and wherein the first and/or second sequence is 11 amino acids in length. In some embodiments, the first and/or second sequence includes 15 contiguous amino acids from a sequence of any one of SEQ ID NOs: 93, 96, 100, 106, 111-116, and 121-139 and wherein the first and/or second sequence is 15 amino acids in length.

In a seventeenth aspect, the invention features an immunogenic composition including: (a) a multilamellar lipid vesicle having crosslinks between lipid bilayers; and (b) an ALK polypeptide, wherein the ALK polypeptide includes a first sequence including at least 6 contiguous amino acids from a sequence selected from any one of SEQ ID NOs: 1-66, a second sequence including at least 6 contiguous amino acids from a sequence selected from any one of SEQ ID NOs: 1-66, and a third sequence including at least 6 contiguous amino acids from a sequence selected from any one of SEQ ID NOs: 1-66, wherein the first, second, and third sequences are different, wherein the first, second, and third sequences include a set of sequences of SEQ ID NOs recited in Table 3A, and wherein the ALK polypeptide does not include a sequence of any one of SEQ ID NOs: 67-70 and 140-145.

In an eighteenth aspect, the invention features an immunogenic composition including: (a) a multilamellar lipid vesicle having crosslinks between lipid bilayers; and (b) an ALK polypeptide, wherein the ALK polypeptide includes a first sequence including at least 6 contiguous amino acids from a sequence selected from any one of SEQ ID NOs: 93, 96, 100, 106, 111-116, and 121-139, a second sequence including at least 6 contiguous amino acids from a sequence selected from any one of SEQ ID NOs: 93, 96, 100, 106, 111-116, and 121-139, and a third sequence including at least 6 contiguous amino acids from a sequence selected from any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, and wherein the ALK polypeptide does not include a sequence of any one of SEQ ID NOs: 67-70 and 140-145.

In some embodiments of the seventeenth and eighteenth aspects of the invention, the first, second, and/or third sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the seventeenth and eighteenth aspects of the invention, the first, second, and/or third sequence includes at least 9 contiguous amino acids from a sequence of any one of SEQ ID NOs: 1-66 and 93-139. In some embodiments of the seventeenth and eighteenth aspects of the invention, the first, second, and/or third sequence includes at least 11 contiguous amino acids from a sequence of any one of SEQ ID NOs: 1-59 and 93-139. In some embodiments of the seventeenth and eighteenth aspects of the invention, the first, second, and/or third sequence includes a sequence of any one of SEQ ID NOs: 1-58 and 93-139. In some embodiments of the seventeenth and eighteenth aspects of the invention, the first, second, and/or third sequence includes 9 contiguous amino acids from a sequence of any one of SEQ ID NOs: 1-66 and 93-139 and wherein the first, second, and/or third sequence is 9 amino acids in length. In some embodiments, the first, second, and/or third sequence includes 11 contiguous amino acids from a sequence of any one of SEQ ID NOs: 1-59 and 93-139 and wherein the first, second, and/or third sequence is 11 amino acids in length. In some embodiments, the first, second, and/or third sequence includes 15 contiguous amino acids from a sequence of any one of SEQ ID NOs: 1-58 and 93-139 and wherein the first, second, and/or third sequence is 15 amino acids in length.

In some embodiments of the seventeenth and eighteenth aspects of the invention, the first, second, and/or third sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the seventeenth and eighteenth aspects of the invention, the first, second, and/or third sequence includes at least 9 contiguous amino acids from a sequence of any one of SEQ ID NOs: 93, 96, 100, 106, 111-116, and 121-139. In some embodiments of the seventeenth and eighteenth aspects of the invention, the first, second, and/or third sequence includes at least 11 contiguous amino acids from a sequence of any one of SEQ ID NOs: 93, 96, 100, 106, 111-116, and 121-139. In some embodiments of the seventeenth and eighteenth aspects of the invention, the first, second, and/or third sequence includes a sequence of any one of SEQ ID NOs: 93, 96, 100, 106, 111-116, and 121-139. In some embodiments of the seventeenth and eighteenth aspects of the invention, the first, second, and/or third sequence includes 9 contiguous amino acids from a sequence of any one of SEQ ID NOs: 93, 96, 100, 106, 111-116, and 121-139 and wherein the first, second, and/or third sequence is 9 amino acids in length. In some embodiments, the first, second, and/or third sequence includes 11 contiguous amino acids from a sequence of any one of SEQ ID NOs: 93, 96, 100, 106, 111-116, and 121-139 and wherein the first, second, and/or third sequence is 11 amino acids in length. In some embodiments, the first, second, and/or third sequence includes 15 contiguous amino acids from a sequence of any one of SEQ ID NOs: 93, 96, 100, 106, 111-116, and 121-139 and wherein the first, second, and/or third sequence is 15 amino acids in length.

In a nineteenth aspect, the invention features an immunogenic composition including: (a) a multilamellar lipid vesicle having crosslinks between lipid bilayers; and (b) an ALK polypeptide, wherein the ALK polypeptide consists of a sequence selected from any one of SEQ ID NOs: 1-66 and 93-139.

In a twentieth aspect, the invention features an immunogenic composition including: (a) a multilamellar lipid vesicle having crosslinks between lipid bilayers; and (b) an ALK polypeptide, wherein the ALK polypeptide consists of a sequence selected from any one of SEQ ID NOs: 93, 96, 100, 106, 111-116, and 121-139.

In some embodiments of the thirteenth to the twentieth aspects of the invention, the ALK polypeptide is covalently conjugated to a lipid in the multilamellar lipid vesicle. In some embodiments, the ALK polypeptide and/or the multilamellar lipid vesicle is functionalized with a reactive group. In some embodiments, the multilamellar lipid vesicle is functionalized with a maleimide reactive group, which reacts with a cysteine in the ALK polypeptide to form a covalent attachment between the ALK polypeptide and the multilamellar lipid vesicle. In some embodiments, the cysteine in the ALK polypeptide is a naturally occurring cysteine or a non-naturally occurring cysteine. In some embodiments, the cysteine in the ALK polypeptide is a terminal-cysteine. In some embodiments, the ALK polypeptide is functionalized with a thiol reactive group and the multilamellar lipid vesicle is functionalized with a maleimide reactive group, and the thiol reactive group reacts with the maleimide reactive group to form a covalent attachment between the ALK polypeptide and the multilamellar lipid vesicle.

In a twenty-first aspect, the invention features an immunogenic composition including: (a) a multilamellar lipid vesicle having crosslinks between lipid bilayers; (b) a first ALK polypeptide including a first sequence including at least 6 contiguous amino acids from a sequence of any one of SEQ ID NOs: 1-66; and (c) a second ALK polypeptide including a second sequence including at least 6 contiguous amino acids from a sequence of any one of SEQ ID NOs: 1-66, wherein the first and second sequences are different, wherein the first and second sequences include a pair of sequences of SEQ ID NOs recited in Table 2A, and wherein neither the first ALK polypeptide nor the second ALK polypeptide includes a sequence of any one of SEQ ID NOs: 67-70 and 140-145.

In a twenty-second aspect, the invention features an immunogenic composition including: (a) a multilamellar lipid vesicle having crosslinks between lipid bilayers; (b) a first ALK polypeptide including a first sequence including at least 6 contiguous amino acids from a sequence of any one of SEQ ID NOs: 93, 96, 100, 106, 111-116, and 121-139; and (c) a second ALK polypeptide including a second sequence including at least 6 contiguous amino acids from a sequence of any one of SEQ ID NOs: 93, 96, 100, 106, 111-116, and 121-139, wherein the first and second sequences are different, wherein the first and second sequences include a pair of sequences of SEQ ID NOs recited in Table 2B, and wherein neither the first ALK polypeptide nor the second ALK polypeptide includes a sequence of any one of SEQ ID NOs: 67-70 and 140-145.

In some embodiments of the twenty-first and twenty-second aspects of the invention, the first and/or second sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the twenty-first and twenty-second aspects of the invention, the first and/or second sequence includes at least 9 contiguous amino acids from a sequence of any one of SEQ ID NOs: 1-66 and 93-139. In some embodiments of the twenty-first and twenty-second aspects of the invention, the first and/or second sequence includes at least 11 contiguous amino acids from a sequence of any one of SEQ ID NOs: 1-59 and 93-139. In some embodiments of the twenty-first and twenty-second aspects of the invention, the first and/or second sequence includes a sequence of any one of SEQ ID NOs: 1-58 and 93-139. In some embodiments of the twenty-first and twenty-second aspects of the invention, the first and/or second sequence includes 9 contiguous amino acids from a sequence of any one of SEQ ID NOs: 1-66 and 93-139 and wherein the first and/or second sequence is 9 amino acids in length. In some embodiments, the first and/or second sequence includes 11 contiguous amino acids from a sequence of any one of SEQ ID NOs: 1-59 and 93-139 and wherein the first and/or second sequence is 11 amino acids in length. In some embodiments, the first and/or second sequence includes 15 contiguous amino acids from a sequence of any one of SEQ ID NOs: 1-58 and 93-139 and wherein the first and/or second sequence is 15 amino acids in length.

In some embodiments of the twenty-first and twenty-second aspects of the invention, the first and/or second sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length).

In some embodiments of the twenty-first and twenty-second aspects of the invention, the first and/or second sequence includes at least 9 contiguous amino acids from a sequence of any one of SEQ ID NOs: 93, 96, 100, 106, 111-116, and 121-139. In some embodiments of the twenty-first and twenty-second aspects of the invention, the first and/or second sequence includes at least 11 contiguous amino acids from a sequence of any one of SEQ ID NOs: 93, 96, 100, 106, 111-116, and 121-139. In some embodiments of the twenty-first and twenty-second aspects of the invention, the first and/or second sequence includes a sequence of any one of SEQ ID NOs: 93, 96, 100, 106, 111-116, and 121-139. In some embodiments of the twenty-first and twenty-second aspects of the invention, the first and/or second sequence includes 9 contiguous amino acids from a sequence of any one of SEQ ID NOs: 93, 96, 100, 106, 111-116, and 121-139 and wherein the first and/or second sequence is 9 amino acids in length. In some embodiments, the first and/or second sequence includes 11 contiguous amino acids from a sequence of any one of SEQ ID NOs: 93, 96, 100, 106, 111-116, and 121-139 and wherein the first and/or second sequence is 11 amino acids in length. In some embodiments, the first and/or second sequence includes 15 contiguous amino acids from a sequence of any one of SEQ ID NOs: 93, 96, 100, 106, 111-116, and 121-139 and wherein the first and/or second sequence is 15 amino acids in length.

In some embodiments of the twenty-first and twenty-second aspects of the invention, each of the first and second ALK polypeptides is covalently conjugated to a lipid in the multilamellar lipid vesicle. In some embodiments, each of the first and second ALK polypeptides is functionalized with a reactive group and/or the multilamellar lipid vesicle is functionalized with a reactive group. In some embodiments, the multilamellar lipid vesicle is functionalized with a maleimide reactive group, which reacts with a cysteine in each of the first and second ALK polypeptides to form covalent attachments between the ALK polypeptides and the multilamellar lipid vesicle. In some embodiments, the cysteine in the first or second ALK polypeptide is a naturally occurring cysteine or a non-naturally occurring cysteine. In some embodiments, the cysteine in the first or second ALK polypeptide is a terminal-cysteine. In some embodiments, each of the first and second ALK polypeptides is functionalized with a thiol reactive group and the multilamellar lipid vesicle is functionalized with a maleimide reactive group, and the thiol reactive group in each of the first and second ALK polypeptides reacts with the maleimide reactive group to form covalent attachments between the ALK polypeptides and the multilamellar lipid vesicle.

In a twenty-third aspect, the invention features an immunogenic composition including: (a) a multilamellar lipid vesicle having crosslinks between lipid bilayers; (b) a first ALK polypeptide including a first sequence including at least 6 contiguous amino acids from a sequence of any one of SEQ ID NOs: 1-66; (c) a second ALK polypeptide including a second sequence including at least 6 contiguous amino acids from a sequence of any one of SEQ ID NOs: 1-66; and (d) a third ALK polypeptide including a third sequence including at least 6 contiguous amino acids from a sequence of any one of SEQ ID NOs: 1-66, wherein the first, second, and third sequences are different, wherein the first, second, and third sequences include a set of sequences of SEQ ID NOs recited in Table 3A, and wherein none of the first, second, and third ALK polypeptides includes a sequence of any one of SEQ ID NOs: 67-70 and 140-145.

In a twenty-fourth aspect, the invention features an immunogenic composition including: (a) a multilamellar lipid vesicle having crosslinks between lipid bilayers; (b) a first ALK polypeptide including a first sequence including at least 6 contiguous amino acids from a sequence of any one of SEQ ID NOs: 93, 96, 100, 106, 111-116, and 121-139; (c) a second ALK polypeptide including a second sequence including at least 6 contiguous amino acids from a sequence of any one of SEQ ID NOs: 93, 96, 100, 106, 111-116, and 121-139; and (d) a third ALK polypeptide including a third sequence including at least 6 contiguous amino acids from a sequence of any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, and wherein none of the first, second, and third ALK polypeptides includes a sequence of any one of SEQ ID NOs: 67-70 and 140-145.

In some embodiments of the twenty-third and twenty-fourth aspects of the invention, the first, second, and/or third sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the twenty-third and twenty-fourth aspects of the invention, the first, second, and/or third sequence includes at least 9 contiguous amino acids from a sequence of any one of SEQ ID NOs: 1-66 and 93-139. In some embodiments of the twenty-third and twenty-fourth aspects of the invention, the first, second, and/or third sequence includes at least 11 contiguous amino acids from a sequence of any one of SEQ ID NOs: 1-59 and 93-139. In some embodiments of the twenty-third and twenty-fourth aspects of the invention, the first, second, and/or third sequence includes a sequence of any one of SEQ ID NOs: 1-58 and 93-139. In some embodiments of the twenty-third and twenty-fourth aspects of the invention, the first, second, and/or third sequence includes 9 contiguous amino acids from a sequence of any one of SEQ ID NOs: 1-66 and 93-139 and wherein the first, second, and/or third sequence is 9 amino acids in length. In some embodiments, the first, second, and/or third sequence includes 11 contiguous amino acids from a sequence of any one of SEQ ID NOs: 1-59 and 93-139 and wherein the first, second, and/or third sequence is 11 amino acids in length. In some embodiments, the first, second, and/or third sequence includes 15 contiguous amino acids from a sequence of any one of SEQ ID NOs: 1-58 and 93-139 and wherein the first, second, and/or third sequence is 15 amino acids in length.

In some embodiments of the twenty-third and twenty-fourth aspects of the invention, the first, second, and/or third sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the twenty-third and twenty-fourth aspects of the invention, the first, second, and/or third sequence includes at least 9 contiguous amino acids from a sequence of any one of SEQ ID NOs: 93, 96, 100, 106, 111-116, and 121-139. In some embodiments of the twenty-third and twenty-fourth aspects of the invention, the first, second, and/or third sequence includes at least 11 contiguous amino acids from a sequence of any one of SEQ ID NOs: 93, 96, 100, 106, 111-116, and 121-139. In some embodiments of the twenty-third and twenty-fourth aspects of the invention, the first, second, and/or third sequence includes a sequence of any one of SEQ ID NOs: 93, 96, 100, 106, 111-116, and 121-139. In some embodiments of the twenty-third and twenty-fourth aspects of the invention, the first, second, and/or third sequence includes 9 contiguous amino acids from a sequence of any one of SEQ ID NOs: 93, 96, 100, 106, 111-116, and 121-139 and wherein the first, second, and/or third sequence is 9 amino acids in length. In some embodiments, the first, second, and/or third sequence includes 11 contiguous amino acids from a sequence of any one of SEQ ID NOs: 93, 96, 100, 106, 111-116, and 121-139 and wherein the first, second, and/or third sequence is 11 amino acids in length. In some embodiments, the first, second, and/or third sequence includes 15 contiguous amino acids from a sequence of any one of SEQ ID NOs: 93, 96, 100, 106, 111-116, and 121-139 and wherein the first, second, and/or third sequence is 15 amino acids in length.

In some embodiments of the twenty-third and twenty-fourth aspects of the invention, each of the first, second, and third ALK polypeptides is covalently conjugated to a lipid in the multilamellar lipid vesicle. In some embodiments, the each of the first, second, and third ALK polypeptides is functionalized with a reactive group and/or the multilamellar lipid vesicle is functionalized with a reactive group. In some embodiments, the multilamellar lipid vesicle is functionalized with a maleimide reactive group, which reacts with a cysteine in each of the first, second, and third ALK polypeptides to form covalent attachments between the ALK polypeptides and the multilamellar lipid vesicle. In some embodiments, the cysteine in the first, second, or third ALK polypeptide is a naturally occurring cysteine or a non-naturally occurring cysteine. In some embodiments, the cysteine in the first, second, or third ALK polypeptide is a terminal-cysteine. In some embodiments, each of the first, second, and third ALK polypeptides is functionalized with a thiol reactive group and the multilamellar lipid vesicle is functionalized with a maleimide reactive group, and the thiol reactive group in each of the first, second, and third ALK polypeptides reacts with the maleimide reactive group to form covalent attachments between the ALK polypeptides and the multilamellar lipid vesicle.

In some embodiments of the first to the twenty-fourth aspects of the invention, the immunogenic composition described therein further includes an immunomodulator. In some embodiments, the immunogenic composition further includes an adjuvant. In some embodiments, the immunogenic composition further includes an anti-cancer agent. In some embodiments, the anti-cancer agent is a tyrosine kinase inhibitor. In some embodiments, the tyrosine kinase inhibitor is Crizotinib. In some embodiments, the tyrosine kinase inhibitor is Ceritinib. In some embodiments, the tyrosine kinase inhibitor is Alectinib. In some embodiments, the tyrosine kinase inhibitor is Brigatinib.

In a twenty-fifth aspect, the invention features an amphiphilic conjugate including: (a) an albumin-binding domain; (b) an ALK polypeptide; and (c) an optional linker, wherein the ALK polypeptide includes at least 6 contiguous amino acids from a sequence of any one of SEQ ID NOs: 1-66 and 93-139 and does not include a sequence of any one of SEQ ID NOs: 67-70 and 140-145, and wherein the ALK polypeptide is conjugated directly to the albumin-binding domain or is conjugated to the albumin-binding domain through the linker.

In a twenty-fifth aspect, the invention features an amphiphilic conjugate including: (a) an albumin-binding domain; (b) an ALK polypeptide; and (c) an optional linker, wherein the ALK polypeptide includes at least 6 contiguous amino acids from a sequence of any one of SEQ ID NOs: 93, 96, 100, 106, 111-116, and 121-139 and does not includ a sequence of any one of SEQ ID NOs: 67-70 and 140-145, and wherein the ALK polypeptide is conjugated directly to the albumin-binding domain or is conjugated to the albumin-binding domain through the linker.

In a twenty-sixth aspect, the invention features an amphiphilic conjugate including: (a) an albumin-binding domain; (b) an ALK polypeptide; and (c) an optional linker, wherein the ALK polypeptide includes a first sequence including at least 6 contiguous amino acids from a sequence selected from any one of SEQ ID NOs: 1-66 and a second sequence including at least 6 contiguous amino acids from a sequence selected from any one of SEQ ID NOs: 1-66, wherein the first and second sequences are different, wherein the first and second sequences include a pair of sequences of SEQ ID NOs recited in Table 2A, wherein the ALK polypeptide does not include a sequence of any one of SEQ ID NOs: 67-70 and 140-145, and wherein the ALK polypeptide is conjugated directly to the albumin-binding domain or is conjugated to the albumin-binding domain through the linker.

In a twenty-seventh aspect, the invention features an amphiphilic conjugate including: (a) an albumin-binding domain; (b) an ALK polypeptide; and (c) an optional linker, wherein the ALK polypeptide includes a first sequence including at least 6 contiguous amino acids from a sequence selected from any one of SEQ ID NOs: 93, 96, 100, 106, 111-116, and 121-139 and a second sequence including at least 6 contiguous amino acids from a sequence selected from any one of SEQ ID NOs: 93, 96, 100, 106, 111-116, and 121-139, wherein the first and second sequences are different, wherein the first and second sequences include a pair of sequences of SEQ ID NOs recited in Table 2B, wherein the ALK polypeptide does not include a sequence of any one of SEQ ID NOs: 67-70 and 140-145, and wherein the ALK polypeptide is conjugated directly to the albumin-binding domain or is conjugated to the albumin-binding domain through the linker.

In some embodiments of the twenty-sixth and twenty-seventh aspects of the invention, the first and/or second sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the twenty-sixth and twenty-seventh aspects of the invention, the first and/or second sequence includes at least 9 contiguous amino acids from a sequence of any one of SEQ ID NOs: 1-66 and 93-139. In some embodiments of the twenty-sixth and twenty-seventh aspects of the invention, the first and/or second sequence includes at least 11 contiguous amino acids from a sequence of any one of SEQ ID NOs: 1-59 and 93-139. In some embodiments of the twenty-sixth and twenty-seventh aspects of the invention, the first and/or second sequence includes a sequence of any one of SEQ ID NOs: 1-58 and 93-139. In some embodiments of the twenty-sixth and twenty-seventh aspects of the invention, the first and/or second sequence includes 9 contiguous amino acids from a sequence of any one of SEQ ID NOs: 1-66 and 93-139 and wherein the first and/or second sequence is 9 amino acids in length. In some embodiments, the first and/or second sequence includes 11 contiguous amino acids from a sequence of any one of SEQ ID NOs: 1-59 and 93-139 and wherein the first and/or second sequence is 11 amino acids in length. In some embodiments, the first and/or second sequence includes 15 contiguous amino acids from a sequence of any one of SEQ ID NOs: 1-58 and 93-139 and wherein the first and/or second sequence is 15 amino acids in length.

In some embodiments of the twenty-sixth and twenty-seventh aspects of the invention, the first and/or second sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the twenty-sixth and twenty-seventh aspects of the invention, the first and/or second sequence includes at least 9 contiguous amino acids from a sequence of any one of SEQ ID NOs: 93, 96, 100, 106, 111-116, and 121-139. In some embodiments of the twenty-sixth and twenty-seventh aspects of the invention, the first and/or second sequence includes at least 11 contiguous amino acids from a sequence of any one of SEQ ID NOs: 93, 96, 100, 106, 111-116, and 121-139. In some embodiments of the twenty-sixth and twenty-seventh aspects of the invention, the first and/or second sequence includes a sequence of any one of SEQ ID NOs: 93, 96, 100, 106, 111-116, and 121-139. In some embodiments of the twenty-sixth and twenty-seventh aspects of the invention, the first and/or second sequence includes 9 contiguous amino acids from a sequence of any one of SEQ ID NOs: 93, 96, 100, 106, 111-116, and 121-139 and wherein the first and/or second sequence is 9 amino acids in length. In some embodiments, the first and/or second sequence includes 11 contiguous amino acids from a sequence of any one of SEQ ID NOs: 93, 96, 100, 106, 111-116, and 121-139 and wherein the first and/or second sequence is 11 amino acids in length. In some embodiments, the first and/or second sequence includes 15 contiguous amino acids from a sequence of any one of SEQ ID NOs: 93, 96, 100, 106, 111-116, and 121-139 and wherein the first and/or second sequence is 15 amino acids in length.

In a twenty-eighth aspect, the invention features an amphiphilic conjugate including: (a) an albumin-binding domain; (b) an ALK polypeptide; and (c) an optional linker, wherein the ALK polypeptide includes a first sequence including at least 6 contiguous amino acids from a sequence selected from any one of SEQ ID NOs: 1-66, a second sequence including at least 6 contiguous amino acids from a sequence selected from any one of SEQ ID NOs: 1-66, and a third sequence including at least 6 contiguous amino acids from a sequence selected from any one of SEQ ID NOs: 1-66, wherein the first, second, and third sequences are different, wherein the first, second, and third sequences include a set of sequences of SEQ ID NOs recited in Table 3A, wherein the ALK polypeptide does not include a sequence of any one of SEQ ID NOs: 67-70 and 140-145, and wherein the ALK polypeptide is conjugated directly to the albumin-binding domain or is conjugated to the albumin-binding domain through the linker.

In a twenty-ninth aspect, the invention features an amphiphilic conjugate including: (a) an albumin-binding domain; (b) an ALK polypeptide; and (c) an optional linker, wherein the ALK polypeptide includes a first sequence including at least 6 contiguous amino acids from a sequence selected from any one of SEQ ID NOs: 93, 96, 100, 106, 111-116, and 121-139, a second sequence including at least 6 contiguous amino acids from a sequence selected from any one of SEQ ID NOs: 93, 96, 100, 106, 111-116, and 121-139, and a third sequence including at least 6 contiguous amino acids from a sequence selected from any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, wherein the ALK polypeptide does not include a sequence of any one of SEQ ID NOs: 67-70 and 140-145, and wherein the ALK polypeptide conjugated directly to the albumin-binding domain or is conjugated to the albumin-binding domain through the linker.

In some embodiments of the twenty-eighth and twenty-ninth aspects of the invention, the first, second, and/or third sequence is 8 to 230 amino acids in length (e.g., 8 to 230 amino acids in length, 8 to 60 amino acids in length, 8 to 30 amino acids in length, 8 to 15 amino acids in length, or 8 to 11 amino acids in length). In some embodiments of the twenty-eighth and twenty-ninth aspects of the invention, the first, second, and/or third sequence includes at least 9 contiguous amino acids from a sequence of any one of SEQ ID NOs: 1-66 and 93-139. In some embodiments of the twenty-eighth and twenty-ninth aspects of the invention, the first, second, and/or third sequence includes at least 11 contiguous amino acids from a sequence of any one of SEQ ID NOs: 1-59 and 93-139. In some embodiments of the twenty-eighth and twenty-ninth aspects of the invention, the first, second, and/or third sequence includes a sequence of any one of SEQ ID NOs: 1-58 and 93-139. In some embodiments of the twenty-eighth and twenty-ninth aspects of the invention, the first, second, and/or third sequence includes 9 contiguous amino acids from a sequence of any one of SEQ ID NOs: 1-66 and 93-139 and wherein the first, second, and/or third sequence is 9 amino acids in length. In some embodiments, the first, second, and/or third sequence includes 11 contiguous amino acids from a sequence of any one of SEQ ID NOs: 1-59 and 93-139 and wherein the first, second, and/or third sequence is 11 amino acids in length. In some embodiments, the first, second, and/or third sequence includes 15 contiguous amino acids from a sequence of any one of SEQ ID NOs: 1-58 and 93-139 and wherein the first, second, and/or third sequence is 15 amino acids in length.

In some embodiments of the twenty-eighth and twenty-ninth aspects of the invention, the first, second, and/or third sequence is 9 to 40 amino acids in length (e.g., 9 to 40 amino acids in length, 15 to 40 amino acids in length, 20 to 40 amino acids in length, 25 to 40 amino acids in length, or 30 to 40 amino acids in length). In some embodiments of the twenty-eighth and twenty-ninth aspects of the invention, the first, second, and/or third sequence includes at least 9 contiguous amino acids from a sequence of any one of SEQ ID NOs: 93, 96, 100, 106, 111-116, and 121-139. In some embodiments of the twenty-eighth and twenty-ninth aspects of the invention, the first, second, and/or third sequence includes at least 11 contiguous amino acids from a sequence of any one of SEQ ID NOs: 93, 96, 100, 106, 111-116, and 121-139. In some embodiments of the twenty-eighth and twenty-ninth aspects of the invention, the first, second, and/or third sequence includes a sequence of any one of SEQ ID NOs: 93, 96, 100, 106, 111-116, and 121-139. In some embodiments of the twenty-eighth and twenty-ninth aspects of the invention, the first, second, and/or third sequence includes 9 contiguous amino acids from a sequence of any one of SEQ ID NOs: 93, 96, 100, 106, 111-116, and 121-139 and wherein the first, second, and/or third sequence is 9 amino acids in length. In some embodiments, the first, second, and/or third sequence includes 11 contiguous amino acids from a sequence of any one of SEQ ID NOs: 93, 96, 100, 106, 111-116, and 121-139 and wherein the first, second, and/or third sequence is 11 amino acids in length. In some embodiments, the first, second, and/or third sequence includes 15 contiguous amino acids from a sequence of any one of SEQ ID NOs: 93, 96, 100, 106, 111-116, and 121-139 and wherein the first, second, and/or third sequence is 15 amino acids in length. In some embodiments of the twenty-fifth to the twenty-ninth aspects of the invention, the albumin-binding domain is a lipid.

In some embodiments of the twenty-fifth to the twenty-ninth aspects of the invention, the linker is selected from the group consisting of polymers, a string of amino acids, nucleic acids, polysaccharides, or a combination thereof. In some embodiments, the linker includes consecutive polyethylene glycol units. In some embodiments, the linker includes "N" consecutive polyethylene glycol units, wherein N is between 20 and 80. In some embodiments, the linker includes "N" consecutive polyethylene glycol units, wherein N is between 30 and 80. In some embodiments, the linker includes "N" consecutive polyethylene glycol units, wherein N is between 40 and 60. In some embodiments, the linker includes "N" consecutive polyethylene glycol units, wherein N is between 45 and 55. In some embodiments, the linker includes 48 consecutive polyethylene glycol units.

In some embodiments of the twenty-fifth to the twenty-ninth aspects of the invention, the conjugate spontaneously inserts itself into lipid bilayers of a multilamellar lipid vesicle having crosslinks between lipid bilayers.

In a thirtieth aspect, the invention features an immunogenic composition including an amphiphilic conjugate described in any one of twenty-fifth to the twenty-ninth aspects of the invention.

In some embodiments of the thirtieth aspect of the invention, the immunogenic composition described therein further includes an immunomodulator. In some embodiments, the immunogenic composition further includes an adjuvant. In some embodiments, the immunogenic composition further includes an anti-cancer agent. In some embodiments, the anti-cancer agent is a tyrosine kinase inhibitor. In some embodiments, the tyrosine kinase inhibitor is Crizotinib. In some embodiments, the tyrosine kinase inhibitor is Ceritinib. In some embodiments, the tyrosine kinase inhibitor is Alectinib. In some embodiments, the tyrosine kinase inhibitor is Brigatinib.

In a thirty-first aspect, the invention features a pharmaceutical composition including a therapeutically effective amount of an immunogenic composition described in any one of the first to twenty-third and thirtieth aspects of the invention and one or more pharmaceutically acceptable carriers or excipients.

In a thirty-second aspect, the invention features a method of treating a disease associated with ALK in a subject, wherein the method includes administering to the subject a therapeutically effective amount of an immunogenic composition described in any one of the first to twenty-third and thirtieth aspects of the invention or the pharmaceutical composition described in the thirty-first aspect of the invention.

In some embodiments of the thirty-second aspect of the invention, the pharmaceutical composition is administered without an immunomodulator, an adjuvant, and/or an anti-cancer agent.

In a thirty-third aspect, the invention features a method of treating a disease associated with ALK in a subject, wherein the method includes administering to the subject 1) a therapeutically effective amount of an immunogenic composition described in any one of the first to twenty-third and thirtieth aspects of the invention or the pharmaceutical composition described in the thirty-first aspect of the invention, and 2) at least one immunomodulator.

In a thirty-fourth aspect, the invention features method of treating a disease associated with ALK in a subject, wherein the method includes administering to the subject 1) a therapeutically effective amount of an immunogenic composition described in any one of the first to twenty-third and thirtieth aspects of the invention or the pharmaceutical composition described in the thirty-first aspect of the invention, and 2) at least one tyrosine kinase inhibitor.

In some embodiments of the thirty-third and thirty-fourth aspects of the invention, 1) and 2) are administered substantially simultaneously. In some embodiments, 1) and 2) are administered separately. In some embodiments, 1) is administered first, followed by administering of 2). In some embodiments, 2) is administered first, followed by administering of 1).

In some embodiments of the thirty-third aspect of the invention, the immunomodulator is selected from the group consisting of a PD-1 inhibitor, an anti-PD-L1 antibody, an anti-CTLA-4 antibody, an anti-CD40 antibody, a cyclophosphamide (CPM), an AMD3100, an anti-LAG-3/CD223 antibody, an anti-B7-H5 antibody, an anti-OX40 antibody, an anti-CD28 antibody, an anti-GITR antibody, an anti-4-1 BB/CD137 antibody, a 4-1 BB ligand, an anti-BTLA antibody, an anti-TIM-3/HAVCR2 antibody, an anti-KIR antibody, an anti-Flt3/CD135 antibody, an anti-FasL antibody, an anti-CD25 antibody, an GM-CSF, an anti-GM-CSF-receptor (R) antibody, an IL-2, an anti-IL-2-R antibody, an IL-7, an anti-IL-7-R antibody, an IL-21, an anti-IL-21-R antibody, an IL-12, an anti-IL-12-R antibody, an IL-15, an anti-IL-15-R antibody, an IL-18, an anti-IL-18-R antibody, an anti-IDO antibody, an ipilimumab, a crizotinib, a ceritinib, an alectinib, a brigatinib, a celecoxib, a SOCS-1 inhibitor, a heat shock protein (HSP), a HSP inhibitor, a polyinosinic:polycytidylic acid (poly I:C), and an anti-galectin-1 antibody.

In some embodiments of the thirty-fourth aspect of the invention, the tyrosine kinase inhibitor is Crizotinib. In some embodiments, the tyrosine kinase inhibitor is Ceritinib. In some embodiments, the tyrosine kinase inhibitor is Alectinib. In some embodiments, the tyrosine kinase inhibitor is Brigatinib. In some embodiments, the disease is cancer. In some embodiments, the cancer is a solid tumor cancer. In some embodiments, the cancer is an ALK+ cancer (i.e., a cancer that expresses ALK). In some embodiments, the cancer is anaplastic large cell lymphoma, non-small-cell lung cancer, neuroblastoma, rhabdomyosarcoma, neuroectodermal cancer, glioblastoma, breast carcinoma, melanoma, inflammatory myofibroblastic tumor, soft tissue tumor, ALK expressing lymphoma, or ALK expressing lung, colon, or prostate carcinoma.

In some embodiments, the cancer is selected from the group consisting of bladder cancer, pancreatic cancer, lung cancer, liver cancer, ovarian cancer, colon cancer, stomach cancer, breast cancer, prostate cancer, renal cancer, testicular cancer, thyroid cancer, uterine cancer, rectal cancer, a cancer of the respiratory system, a cancer of the urinary system, oral cavity cancer, skin cancer, leukemia, sarcoma, carcinoma, basal cell carcinoma, non-Hodgkin's lymphoma, acute myeloid leukemia (AML), chronic lymphocytic leukemia (CLL), B-cells chronic lymphocytic leukemia (B-CLL), multiple myeloma (MM), erythroleukemia, renal cell carcinoma, astrocytoma, oligoastrocytoma, biliary tract cancer, choriocarcinoma, CNS cancer, larynx cancer, small cell lung cancer, adenocarcinoma, giant (or oat) cell carcinoma, and squamous cell carcinoma.

In some embodiments, the immunogenic composition is administered before or after surgery to remove at least some of a solid tumor in the solid tumor cancer.

In some embodiments, the subject is a mammal (e.g., a human).

DESCRIPTION OF THE DRAWINGS

FIGS. 2C and 2D show the CD8 T-cell response stimulated by ALK polypeptides each having the sequence of any one of SEQ ID NOs: 1-59 listed in Table 1A.

FIGS. 4-1 to 4-3 show the sequence of wild-type, full-length ALK (SEQ ID NO: 67; UniProt ID NO: B6D4Y2), the sequence of full-length ALK having K1150R substitution (SEQ ID No: 68), the sequence of wild-type, cytoplasmic domain of ALK (SEQ ID NO: 69), and the sequence of cytoplasmic domain of ALK having K93R substitution (SEQ ID NO: 70).

DETAILED DESCRIPTION OF THE INVENTION

The present invention features immunogenic compositions containing anaplastic lymphoma kinase (ALK) polypeptides and methods of use thereof. In some embodiments, the immunogenic compositions may include one or more ALK polypeptides. The immunogenic compositions and methods of the invention may be used to treat a disease associated with ALK in a subject, such as cancer (e.g., a solid tumor cancer or a cancer that expresses ALK or a portion thereof (e.g., an ALK+ cancer)).

Anaplastic Lymphoma Kinase (ALK) Polypeptides and Immunogenic Compositions

Figure 1:
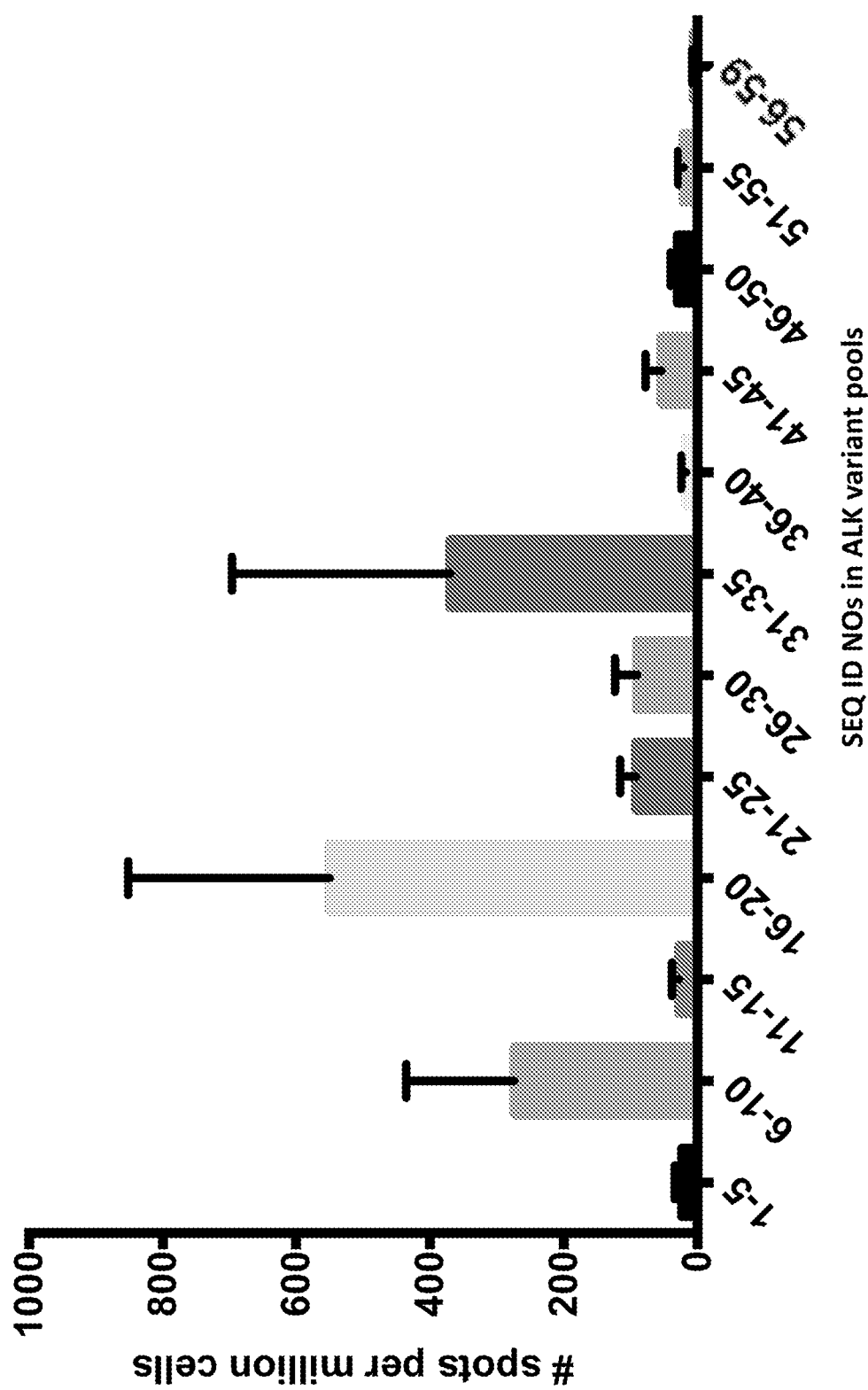
FIG. 1 shows the overall T-cell response stimulated by various ALK polypeptide pools each containing 5 ALK polypeptides having the sequences of SEQ ID NOs listed in Table 1A.
Figure 3:
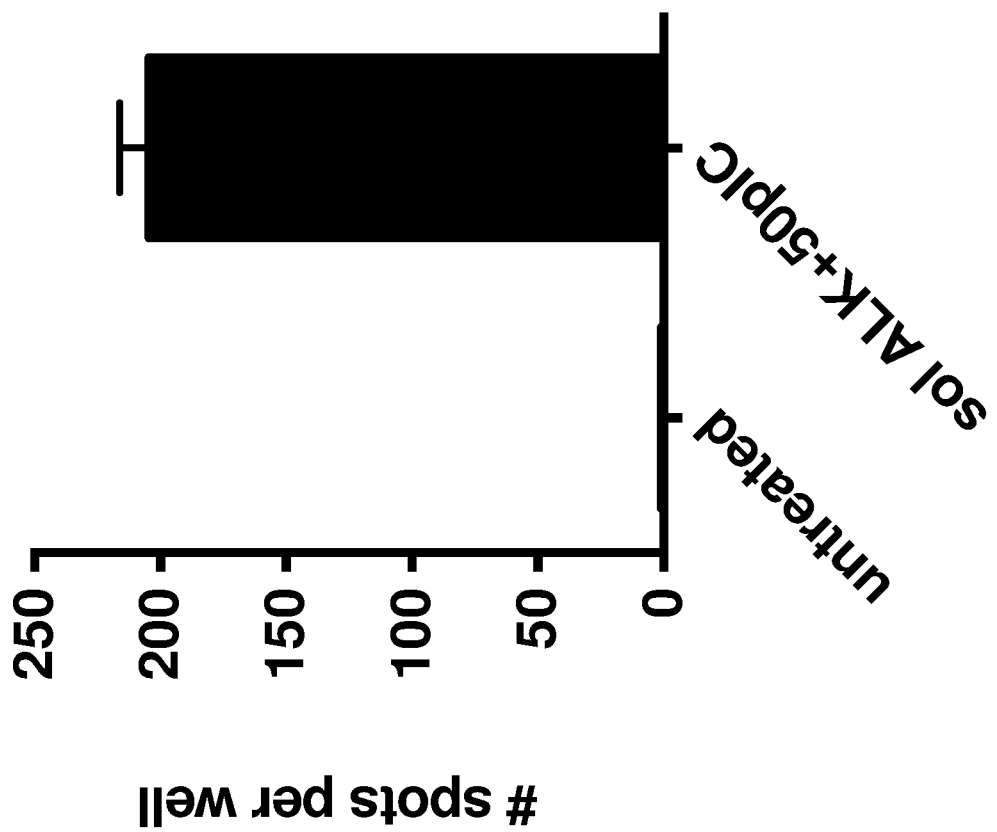
FIG. 3 shows the overall T-cell response stimulated by an ALK polypeptide pool containing 7 ALK polypeptides having the sequences of SEQ ID NOs: 60-66 listed in Table 1A.

An ALK polypeptide is a mutant or fragment of the cytoplasmic domain of ALK. FIGS. 4-1 to 4-3 show the sequence of wild-type, full-length ALK (SEQ ID NO: 67; UniProt ID NO: B6D4Y2), the sequence of full-length ALK having K1150R substitution (SEQ ID No: 68), the sequence of wild-type, cytoplasmic domain of ALK (SEQ ID NO: 69), and the sequence of cytoplasmic domain of ALK having K93R substitution (SEQ ID NO: 70). The amino acid substitution K1150R in SEQ ID NO: 68 and the amino acid substitution K93R in SEQ ID NO: 70 render the tyrosine kinase domain of ALK inactive and the resulting ALK non-oncogenic. ALK polypeptides that are specifically excluded from the claimed invention are: PSSLAMLDLLH-VARDIACGCQYLE (SEQ ID NO: 140), KFNHQNIVR-CIGVSLQSLPRFILL (SEQ ID NO: 141), PKNCPGPVYRIMTQCWQHQPEDRP (SEQ ID NO: 142), SLAMLDLLHV (SEQ ID NO: 143), AMLDLLHVA (SEQ ID NO: 144), and CIGVSLQSL (SEQ ID NO: 145).

In some embodiments, an ALK polypeptide includes at least 6 contiguous amino acids (e.g., 6, 7, 8, 9, 10, 11, 12, 13, 14, 15, 16, 17, 18, 19, 20, 21, 22, 23, 24, 25, 26, 27, 28, 29, 30, or 31 amino acids) from a sequence of any one of SEQ ID NOs: 1-66 (e.g., SEQ ID NOs: 10, 14, 17, 22, 33, 52, and 53 (e.g., SEQ ID NO: 33)) and 93-139 (see Tables 1A and 1B). In particular, an ALK polypeptide includes at least 6 contiguous amino acids (e.g., 6, 7, 8, 9, 10, 11, 12, 13, 14, 15, 16, 17, 18, 19, 20, 21, 22, 23, 24, 25, 26, 27, 28, 29, 30, or 31 amino acids) from a sequence of any one of SEQ ID NOs: 93, 96, 100, 106, 111-116, and 121-139 (see Table 10). An ALK polypeptide described herein does not include a sequence of any one of SEQ ID NOs: 67-70 and 140-145. In some embodiments, an ALK polypeptide is 8 to 230 amino acids in length (e.g., 8 to 200, 8 to 170, 8 to 140, 8 to 110, 8 to 70, 8 to 60, 8 to 30, or 8 to 15 amino acids in length, e.g., 8, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, or 230 amino acids in length), 8 to 60 amino acids in length, 8 to 30 amino acids in length, 8 to 15 amino acids in length, or 8 to 11 amino acids in length. In some embodiments, an ALK polypeptide is at least 9 amino acids in length, e.g., 9 to 40 amino acids in length (e.g., 15 to 40, 20 to 40, 25 to 40, or 30 to 40 amino acids in length, e.g., 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids in length).

In particular embodiments, an ALK polypeptide is 31 amino acids in length and consists of a sequence of any one of SEQ ID NOs: 93, 96, 100, 106, 111-116, and 121-139 (Table 10).

In some embodiments, an ALK polypeptide includes at least 9 contiguous amino acids (e.g., 9, 10, 11, 12, 13, 14, or 15 amino acids) from a sequence of any one of SEQ ID NOs: 1-66 (e.g., SEQ ID NOs: 10, 14, 17, 22, 33, 52, and 53 (e.g., SEQ ID NO: 33)) and 93-139. In some embodiments, an ALK polypeptide includes at least 11 contiguous amino acids (e.g., 11, 12, 13, 14, or 15 amino acids) from a sequence of any one of SEQ ID NOs: 1-59 (e.g., SEQ ID NOs: 10, 14, 17, 22, 33, 52, and 53 (e.g., SEQ ID NO: 33)) and 93-139. In some embodiments, an ALK polypeptide includes a sequence of any one of SEQ ID NOs: 1-66 (e.g., SEQ ID NOs: 10, 14, 17, 22, 33, 52, and 53 (e.g., SEQ ID NO: 33)) and 93-139.

In some embodiments, an ALK polypeptide includes at least 9 contiguous amino acids (e.g., 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids) from a sequence of any one of SEQ ID NOs: 93, 96, 100, 106, 111-116, and 121-139.

In some embodiments, an ALK polypeptide is 9 amino acids in length and includes 9 contiguous amino acids from a sequence of any one of SEQ ID NOs: 1-66 (e.g., SEQ ID NOs: 10, 14, 17, 22, 33, 52, and 53 (e.g., SEQ ID NO: 33)) and 93-139. In some embodiments, an ALK polypeptide is 11 amino acids in length and includes 11 contiguous amino acids from a sequence of any one of SEQ ID NOs: 1-59 (e.g., SEQ ID NOs: 10, 14, 17, 22, 33, 52, and 53 (e.g., SEQ ID NO: 33)) and 93-139. In some embodiments, an ALK polypeptide includes at least 6 contiguous amino acids (e.g., 6, 7, 8, or 9 amino acids) from a sequence of any one of SEQ ID NOs: 60-66.

In some embodiments, an ALK polypeptide is 9 amino acids in length and includes 9 contiguous amino acids from a sequence of any one of SEQ ID NOs: 93, 96, 100, 106, 111-116, and 121-139. In some embodiments, an ALK polypeptide is 11 amino acids in length and includes 11 contiguous amino acids from a sequence of any one of SEQ ID NOs: 93, 96, 100, 106, 111-116, and 121-139.

In some embodiments, an ALK polypeptide consists of a sequence selected from any one of SEQ ID NOs: 1-66 and 93-139. In some embodiments, an ALK polypeptide consists of a sequence selected from any one of SEQ ID NOs: 93, 96, 100, 106, 111-116, and 121-139. In some embodiments, an ALK polypeptide consists of a sequence selected from any one of SEQ ID NOs: 60-66. In some embodiments, an ALK polypeptide consists of a sequence selected from any one of SEQ ID NOs: 10, 14, 17, 22, 33, 52, and 53. In some embodiments, an ALK polypeptide consists of the sequence of SEQ ID NO: 10. In some embodiments, an ALK polypeptide consists of the sequence of SEQ ID NO: 14. In some embodiments, an ALK polypeptide consists of the sequence of SEQ ID NO: 17. In some embodiments, an ALK polypeptide consists of the sequence of SEQ ID NO: 22. In some embodiments, an ALK polypeptide consists of the sequence of SEQ ID NO: 33. In some embodiments, an ALK polypeptide consists of the sequence of SEQ ID NO: 52. In some embodiments, an ALK polypeptide consists of the sequence of SEQ ID NO: 53.

In some embodiments, one or more amino acid substitutions in an ALK polypeptide may improve its immunogenic property. In some embodiments, an amino acid in a wild-type ALK may be replaced by a different amino acid (e.g., a naturally occurring amino acid (e.g., Ala, Arg, Asn, Asp, Cys, Gln, Glu, Gly, His, Ile, Leu, Lys, Met, Phe, Pro, Ser, Thr, Trp, Tyr, or Val) or a non-naturally occurring amino acid). Examples of non-naturally occurring amino acids are described in detail further herein. In some embodiments, a Cys in an ALK polypeptide described herein (e.g., any one of the ALK polypeptides in Tables 1A and 1B) may be replaced by an Ala.

An ALK polypeptide described herein does not include a sequence of any one of SEQ ID NOs: 67-70 and 140-145.

In some embodiments, ALK polypeptides of the invention are shown in Tables 1A and 1B. Table 1A shows ALK polypeptides having 9-15 amino acids. Table 1B shows ALK polypeptides having 31 amino acids.

TABLE 1A

| SEQ ID NO | Sequence of an ALK Polypeptide | Length |
|---|---|---|
| 1 | CFAGKTSSISDLKEV | 15-mer |
| 2 | TSSISDLKEVPRKNI | 15-mer |
| 3 | DLKEVPRKNITLIRG | 15-mer |
| 4 | PRKNITLIRGLGHGA | 15-mer |
| 5 | TLIRGLGHGAFGEVY | 15-mer |
| 6 | LGHGAFGEVYEGQVS | 15-mer |
| 7 | FGEVYEGQVSGMPND | 15-mer |
| 8 | EGQVSGMPNDPSPLQ | 15-mer |
| 9 | GMPNDPSPLQVAVRT | 15-mer |
| 10 | PSPLQVAVRTLPEVC | 15-mer |
| 11 | VAVRTLPEVCSEQDE | 15-mer |
| 12 | LPEVCSEQDELDFLM | 15-mer |

TABLE 1A-continued

| SEQ ID NO | Sequence of an ALK Polypeptide | Length |
|---|---|---|
| 13 | SEQDELDFLMEALII | 15-mer |
| 14 | LDFLMEALIISKFNH | 15-mer |
| 15 | EALIISKFNHQNIVR | 15-mer |
| 16 | SKFNHQNIVRCIGVS | 15-mer |
| 17 | QNIVRCIGVSLQSLP | 15-mer |
| 18 | CIGVSLQSLPRFILL | 15-mer |
| 19 | LQSLPRFILLELMAG | 15-mer |
| 20 | RFILLELMAGGDLKS | 15-mer |
| 21 | ELMAGGDLKSFLRET | 15-mer |
| 22 | GDLKSFLRETRPRPS | 15-mer |
| 23 | FLRETRPRPSQPSSL | 15-mer |
| 24 | RPRPSQPSSLAMLDL | 15-mer |
| 25 | QPSSLAMLDLLHVAR | 15-mer |
| 26 | AMLDLLHVARDIACG | 15-mer |
| 27 | LHVARDIACGCQYLE | 15-mer |
| 28 | DIACGCQYLEENHFI | 15-mer |
| 29 | CQYLEENHFIHRDIA | 15-mer |
| 30 | ENHFIHRDIAARNCL | 15-mer |
| 31 | HRDIAARNCLLTCPG | 15-mer |
| 32 | ARNCLLTCPGPGRVA | 15-mer |
| 33 | LTCPGPGRVAKIGDF | 15-mer |
| 34 | PGRVAKIGDFGMARD | 15-mer |
| 35 | KIGDFGMARDIYRAS | 15-mer |
| 36 | GMARDIYRASYYRKG | 15-mer |
| 37 | IYRASYYRKGGCAML | 15-mer |
| 38 | YYRKGGCAMLPVKWM | 15-mer |
| 39 | GCAMLPVKWMPPEAF | 15-mer |
| 40 | PVKWMPPEAFMEGIF | 15-mer |
| 41 | PPEAFMEGIFTSKTD | 15-mer |
| 42 | MEGIFTSKTDTWSFG | 15-mer |
| 43 | TSKTDTWSFGVLLWE | 15-mer |
| 44 | TWSFGVLLWEIFSLG | 15-mer |
| 45 | VLLWEIFSLGYMPYP | 15-mer |
| 46 | IFSLGYMPYPSKSNQ | 15-mer |
| 47 | YMPYPSKSNQEVLEF | 15-mer |
| 48 | SKSNQEVLEFVTSGG | 15-mer |
| 49 | EVLEFVTSGGRMDPP | 15-mer |
| 50 | VTSGGRMDPPKNCPG | 15-mer |
| 51 | RMDPPKNCPGPVYRI | 15-mer |

TABLE 1A-continued

| SEQ ID NO | Sequence of an ALK Polypeptide | Length |
|---|---|---|
| 52 | KNCPGPVYRIMTQCW | 15-mer |
| 53 | PVYRIMTQCWQHPE | 15-mer |
| 54 | MTQCWQHPEDRPNF | 15-mer |
| 55 | QHQPEDRPNFAIILE | 15-mer |
| 56 | DRPNFAIILERIEYC | 15-mer |
| 57 | AIILERIEYCTQDPD | 15-mer |
| 58 | RIEYCTQDPDVINTA | 15-mer |
| 59 | TQDPDVINTALP | 12-mer |
| 60 | LTCPGPGRV | 9-mer |
| 61 | TCPGPGRVA | 9-mer |
| 62 | CPGPGRVAK | 9-mer |
| 63 | PGPGRVAKI | 9-mer |
| 64 | GPGRVAKIG | 9-mer |
| 65 | PGRVAKIGD | 9-mer |
| 66 | GRVAKIGDF | 9-mer |

TABLE 1B

| SEQ ID NO | Sequence of an ALK Polypeptide | Length |
|---|---|---|
| 93 | VYRRKHQELQAMQMELQSPEYKLSKLRTSTI | 31-mer |
| 94 | EYKLSKLRTSTIMTDYNPNYCFAGKTSSISD | 31-mer |
| 95 | YCFAGKTSSISDLKEVPRKNITLIRGLGHGA | 31-mer |
| 96 | NITLIRGLGHGAFGEVYEGQVSGMPNDPSPL | 31-mer |
| 97 | QVSGMPNDPSPLQVAVKTLPEVCSEQDELDF | 31-mer |
| 98 | PEVCSEQDELDFLMEALIISKFNHQNIVRCI | 31-mer |
| 99 | SKFNHQNIVRCIGVSLQSLPRFILLELMAGG | 31-mer |
| 100 | PRFILLELMAGGDLKSFLRETRPRPSQPSSL | 31-mer |
| 101 | ETRPRPSQPSSLAMLDLLHVARDIACGCQYL | 31-mer |
| 102 | VARDIACGCQYLEENHFIHRDIAARNCLLTC | 31-mer |
| 103 | RDIAARNCLLTCPGPGRVAKIGDFGMARDIY | 31-mer |
| 104 | KIGDFGMARDIYRASYYRKGGCAMLPVKWMP | 31-mer |
| 105 | GGCAMLPVKWMPPEAFMEGIFTSKTDTWSFG | 31-mer |

TABLE 1B-continued

| SEQ ID NO | Sequence of an ALK Polypeptide | Length |
|---|---|---|
| 106 | IFTSKTDTWSFGVLLWEIFSLGYMPYPSKSN | 31-mer |
| 107 | SLGYMPYPSKSNQEVLEFVTSGGRMDPPKNC | 31-mer |
| 108 | TSGGRMDPPKNCPGPVYRIMTQCWQHQPEDR | 31-mer |
| 109 | MTQCWQHQPEDRPNFAIILERIEYCTQDPDV | 31-mer |
| 110 | ERIEYCTQDPDVINTALPIEYGPLVEEEEKV | 31-mer |
| 111 | EYGPLVEEEEKVPVRPKDPEGVPPLLVSQQA | 31-mer |
| 112 | EGVPPLLVSQQAKREEERSPAAPPPLPTTSS | 31-mer |
| 113 | PAAPPPLPTTSSGKAAKKPTAAEISVRVPRG | 31-mer |
| 114 | TAAEISVRVPRGPAVEGGHVNMAFSQSNPPS | 31-mer |
| 115 | VNMAFSQSNPPSELHKVHGSRNKPTSLWNPT | 31-mer |
| 116 | SRNKPTSLWNPTYGSWFTEKPTKKNNPIAKK | 31-mer |
| 117 | KPTKKNNPIAKKEPHDRGNLGLEGSCTVPPN | 31-mer |
| 118 | LGLEGSCTVPPNVATGRLPGASLLLEPSSLT | 31-mer |
| 119 | GASLLLEPSSLTANMKEVPLFRLRHFPCGNV | 31-mer |
| 120 | LFRLRHFPCGNVNYGYQQQGLPLEAATAPGA | 31-mer |
| 121 | GLPLEAATAPGAGHYEDTILKSKNSMNQPGP | 31-mer |

In some embodiments, a Cys in an ALK polypeptide described herein (e.g., any one of the ALK polypeptides in Tables 1A and 1B) may be replaced by an Ala. In some embodiments, a Cys in an ALK polypeptide of any one of SEQ ID NOs: 94, 95, 97-99, 101-105, 107-110, and 117-120 may be replaced with an Ala, generating the ALK polypeptides of SEQ ID NOs:122-139 in Table 10.

TABLE 1C

| SEQ ID NO | Sequence of an ALK Polypeptide | Length |
|---|---|---|
| 122 | EYKLSKLRTSTIMTDYNPNYAFAGKTSSISD | 31-mer |
| 123 | YAFAGKTSSISDLKEVPRKNITLIRGLGHGA | 31-mer |
| 124 | QVSGMPNDPSPLQVAVKTLPEVASEQDELDF | 31-mer |
| 125 | PEVASEQDELDFLMEALIISKFNHQNIVRAI | 31-mer |

TABLE 1C -continued

| SEQ ID NO | Sequence of an ALK Polypeptide | Length |
|---|---|---|
| 126 | SKFNHQNIVRAIGVSLQSLPRF ILLELMAGG | 31-mer |
| 127 | ETRPRPSQPSSLAMLDLLHVA RDIAAGAQYL | 31-mer |
| 128 | VARDIAAGAQYLEENHFIHRD IAARNALLTA | 31-mer |
| 129 | RDIAARNALLTAPGPGRVAKI GDFGMARDIY | 31-mer |
| 130 | KIGDFGMARDIYRASYYRKGG AAMLPVKWMP | 31-mer |
| 131 | GGAAMLPVKWMPPEAFMEGIF TSKTDTWSFG | 31-mer |
| 132 | SLGYMPYPSKSNQEVLEFVTS GGRMDPPKNA | 31-mer |
| 133 | TSGGRMDPPKNAPGPVYRIMT QAWQHQPEDR | 31-mer |
| 134 | MTQAWQHQPEDRPNFAIILER IEYATQDPDV | 31-mer |
| 135 | ERIEYATQDPDVINTALPIEY GPLVEEEEKV | 31-mer |
| 136 | KPTKKNNPIAKKEPHDRGNLG LEGSATVPPN | 31-mer |
| 137 | LGLEGSATVPPNVATGRLPGA SLLLEPSSLT | 31-mer |
| 138 | GASLLLEPSSLTANMKEVPLF RLRHFPAGNV | 31-mer |
| 139 | LFRLRHFPAGNVNYGYQQQGL PLEAATAPGA | 31-mer |

In some embodiments, an ALK polypeptide used in an aspect of the invention described herein may be selected from any of the polypeptides listed in Tables 1A, 1B, and 10.

In some embodiments, when two ALK polypeptides are used in an aspect of the invention described herein, one ALK polypeptide may be selected from the polypeptides listed in Table 1A and the other ALK polypeptide may be selected from the polypeptides listed in Tables 1B and 10 (e.g., ALK polypeptides having the sequences of SEQ ID NOs: 93, 96, 100, 106, 111-116, and 121-139).

In some embodiments, when an ALK polypeptide includes a first sequence and a second sequence in an aspect of the invention described herein, the first sequence may be selected from the polypeptides listed in Table 1 A and the second sequence may be selected from the polypeptides listed in Tables 1B and 10 (e.g., ALK polypeptides having the sequences of SEQ ID NOs: 93, 96, 100, 106, 111-116, and 121-139).

In some embodiments, when three ALK polypeptides are used in an aspect of the invention described herein, one or two ALK polypeptides may be selected from the polypeptides listed in Table 1A and the remaining ALK polypeptide(s) may be selected from the polypeptides listed in Tables 1B and 10 (e.g., ALK polypeptides having the sequences of SEQ ID NOs: 93, 96, 100, 106, 111-116, and 121-139).

In some embodiments, when an ALK polypeptide includes three sequences (e.g., a first sequence, a second sequence, and a third sequence) in an aspect of the invention described herein, one or two sequences may be selected from the polypeptides listed in Table 1A and the remaining sequence(s) may be selected from the polypeptides listed in Tables 1B and 10 (e.g., ALK polypeptides having the sequences of SEQ ID NOs: 93, 96, 100, 106, 111-116, and 121-139).

In particular embodiments, an ALK polypeptide includes a sequence selected from any one of SEQ ID NOs: 93, 96, 100, 106, 111-116, and 121-139. In particular embodiments, an ALK polypeptide consists of a sequence selected from any one of SEQ ID NOs: 93, 96, 100, 106, 111-116, and 121-139.

In some embodiments, an ALK polypeptide includes a first sequence selected from any one of SEQ ID NOs: 1-66 (e.g., SEQ ID NOs: 10, 14, 17, 22, 33, 52, and 53) and a second sequence selected from any one of SEQ ID NOs: 1-66 (e.g., SEQ ID NOs: 10, 14, 17, 22, 33, 52, and 53), in which the first and second sequences are different and include a pair of sequences of SEQ ID NOs recited in Table 2A, and in which the ALK polypeptide does not include a sequence of any one of SEQ ID NOs: 67-70 and 140-145. In some embodiments, the first and second sequences in the ALK polypeptide include one of the following pairs of sequences: SEQ ID NOs: 10 and 14, SEQ ID NOs: 10 and 17, SEQ ID NOs: 10 and 22, SEQ ID NOs: 10 and 33, SEQ ID NOs: 10 and 52, SEQ ID NOs: 10 and 53, SEQ ID NOs: 14 and 17, SEQ ID NOs: 14 and 22, SEQ ID NOs: 14 and 33, SEQ ID NOs: 14 and 52, SEQ ID NOs: 14 and 53, SEQ ID NOs: 17 and 22, SEQ ID NOs: 17 and 33, SEQ ID NOs: 17 and 52, SEQ ID NOs: 17 and 53, SEQ ID NOs: 22 and 33, SEQ ID NOs: 22 and 52, SEQ ID NOs: 22 and 53, SEQ ID NOs: 33 and 52, SEQ ID NOs: 33 and 53, and SEQ ID NOs: 52 and 53.

In some embodiments, an ALK polypeptide includes a first sequence selected from any one of SEQ ID NOs: 60-66 and a second sequence selected from any one of SEQ ID NOs: 60-66, in which the first and second sequences are different and include one of the following pairs of sequences: SEQ ID NOs: 60 and 61, SEQ ID NOs: 60 and 62, SEQ ID NOs: 60 and 63, SEQ ID NOs: 60 and 64, SEQ ID NOs: 60 and 65, SEQ ID NOs: 60 and 66, SEQ ID NOs: 61 and 62, SEQ ID NOs: 61 and 63, SEQ ID NOs: 61 and 64, SEQ ID NOs: 61 and 65, SEQ ID NOs: 61 and 66, SEQ ID NOs: 62 and 63, SEQ ID NOs: 62 and 64, SEQ ID NOs: 62 and 65, SEQ ID NOs: 62 and 66, SEQ ID NOs: 63 and 64, SEQ ID NOs: 63 and 65, SEQ ID NOs: 63 and 66, SEQ ID NOs: 64 and 65, SEQ ID NOs: 64 and 66, and SEQ ID NOs: 65 and 66, and in which the ALK polypeptide does not include a sequence of any one of SEQ ID NOs: 67-70 and 140-145.

In some embodiments, an ALK polypeptide includes a first sequence selected from any one of SEQ ID NOs: 93, 96, 100, 106, 111-116, and 121-139 and a second sequence selected from any one of SEQ ID NOs: 93, 96, 100, 106, 111-116, and 121-139, in which the first and second sequences are different and include a pair of sequences of SEQ ID NOs recited in Table 2B, and in which the ALK polypeptide does not include a sequence of any one of SEQ ID NOs: 67-70 and 140-145.

In the case that an ALK polypeptide includes a first sequence and a second sequence, each bracket listed in Tables 2A and 2B contains two SEQ ID NOs representing the first and second sequences in the ALK polypeptide. For example, {1,2} represents {a first sequence of SEQ ID NO: 1, a second sequence of SEQ ID NO: 2}.

An immunogenic composition may include at least one ALK polypeptide described herein. In some embodiments, an immunogenic composition includes an ALK polypeptide consisting of a sequence selected from any one of SEQ ID NOs: 1-66 and 93-139. In particular embodiments, an immunogenic composition includes an ALK polypeptide consisting of a sequence selected from any one of SEQ ID NOs: 93, 96, 100, 106, 111-116, and 121-139.

In some embodiments, an immunogenic composition includes two ALK polypeptides, a first ALK polypeptide including a first sequence of any one of SEQ ID NOs: 1-66 (e.g., SEQ ID NOs: 10, 14, 17, 22, 33, 52, and 53) and a second ALK polypeptide including a second sequence of any one of SEQ ID NOs: 1-66 (e.g., SEQ ID NOs: 10, 14, 17, 22, 33, 52, and 53), in which the first and second sequences are different and include a pair of sequences of SEQ ID NOs recited in Table 2A, and in which neither the first ALK polypeptide nor the second ALK polypeptide includes a sequence of any one of SEQ ID NOs: 67-70 and 140-145. In some embodiments, the first sequence in the first ALK polypeptide and second sequence in the second ALK polypeptide include one of the following pairs of sequences: SEQ ID NOs: 10 and 14, SEQ ID NOs: 10 and 17, SEQ ID NOs: 10 and 22, SEQ ID NOs: 10 and 33, SEQ ID NOs: 10 and 52, SEQ ID NOs: 10 and 53, SEQ ID NOs: 14 and 17, SEQ ID NOs: 14 and 22, SEQ ID NOs: 14 and 33, SEQ ID NOs: 14 and 52, SEQ ID NOs: 14 and 53, SEQ ID NOs: 17 and 22, SEQ ID NOs: 17 and 33, SEQ ID NOs: 17 and 52, SEQ ID NOs: 17 and 53, SEQ ID NOs: 22 and 33, SEQ ID NOs: 22 and 52, SEQ ID NOs: 22 and 53, SEQ ID NOs: 33 and 52, SEQ ID NOs: 33 and 53, and SEQ ID NOs: 52 and 53.

In some embodiments, an immunogenic composition includes two ALK polypeptides, a first ALK polypeptide including a first sequence of any one of SEQ ID NOs: 60-66 and a second ALK polypeptide including a second sequence of any one of SEQ ID NOs: 60-66, in which the first and second sequences are different and include one of the following pairs of sequences: SEQ ID NOs: 60 and 61, SEQ ID NOs: 60 and 62, SEQ ID NOs: 60 and 63, SEQ ID NOs: 60 and 64, SEQ ID NOs: 60 and 65, SEQ ID NOs: 60 and 66, SEQ ID NOs: 61 and 62, SEQ ID NOs: 61 and 63, SEQ ID NOs: 61 and 64, SEQ ID NOs: 61 and 65, SEQ ID NOs: 61 and 66, SEQ ID NOs: 62 and 63, SEQ ID NOs: 62 and 64, SEQ ID NOs: 62 and 65, SEQ ID NOs: 62 and 66, SEQ ID NOs: 63 and 64, SEQ ID NOs: 63 and 65, SEQ ID NOs: 63 and 66, SEQ ID NOs: 64 and 65, SEQ ID NOs: 64 and 66, and SEQ ID NOs: 65 and 66, and in which neither the first ALK polypeptide nor the second ALK polypeptide includes a sequence of any one of SEQ ID NOs: 67-70 and 140-145.

In some embodiments, an immunogenic composition includes two ALK polypeptides, a first ALK polypeptide including a first sequence of any one of SEQ ID NOs: 93, 96, 100, 106, 111-116, and 121-139 and a second ALK polypeptide including a second sequence of any one of SEQ ID NOs: 93, 96, 100, 106, 111-116, and 121-139, in which the first and second sequences are different and include a pair of sequences of SEQ ID NOs recited in Table 2B, and in which neither the first ALK polypeptide nor the second ALK polypeptide includes a sequence of any one of SEQ ID NOs: 67-70 and 140-145.

In the case for two ALK polypeptides in one immunogenic composition, a first ALK polypeptide including a first sequence and a second ALK polypeptide including a second sequence, each bracket listed in Tables 2A and 2B contains two SEQ ID NOs representing the first sequence in the first ALK polypeptide and the second sequence in the second ALK polypeptide. For example, {1,2} represents {the first sequence of SEQ ID NO: 1 in the first ALK polypeptide, the second sequence of SEQ ID NO: 2 in the second ALK polypeptide}.

TABLE 2A

{1, 2} {1, 3} {1, 4} {1, 5} {1, 6} {1, 7} {1, 8} {1, 9} {1, 10} {1, 11} {1, 12} {1, 13} {1, 14} {1, 15} {1, 16} {1, 17} {1, 18}
{1, 19} {1, 20} {1, 21} {1, 22} {1, 23} {1, 24} {1, 25} {1, 26} {1, 27} {1, 28} {1, 29} {1, 30} {1, 31} {1, 32} {1, 33} {1, 34}
{1, 35} {1, 36} {1, 37} {1, 38} {1, 39} {1, 40} {1, 41} {1, 42} {1, 43} {1, 44} {1, 45} {1, 46} {1, 47} {1, 48} {1, 49} {1, 50}
{1, 51} {1, 52} {1, 53} {1, 54} {1, 55} {1, 56} {1, 57} {1, 58} {1, 59} {1, 60} {1, 61} {1, 62} {1, 63} {1, 64} {1, 65} {1, 66}
{2, 3} {2, 4} {2, 5} {2, 6} {2, 7} {2, 8} {2, 9} {2, 10} {2, 11} {2, 12} {2, 13} {2, 14} {2, 15} {2, 16} {2, 17} {2, 18} {2, 19}
{2, 20} {2, 21} {2, 22} {2, 23} {2, 24} {2, 25} {2, 26} {2, 27} {2, 28} {2, 29} {2, 30} {2, 31} {2, 32} {2, 33} {2, 34} {2, 35}
{2, 36} {2, 37} {2, 38} {2, 39} {2, 40} {2, 41} {2, 42} {2, 43} {2, 44} {2, 45} {2, 46} {2, 47} {2, 48} {2, 49} {2, 50} {2, 51}
{2, 52} {2, 53} {2, 54} {2, 55} {2, 56} {2, 57} {2, 58} {2, 59} {2, 60} {2, 61} {2, 62} {2, 63} {2, 64} {2, 65} {2, 66} {3, 4}
{3, 5} {3, 6} {3, 7} {3, 8} {3, 9} {3, 10} {3, 11} {3, 12} {3, 13} {3, 14} {3, 15} {3, 16} {3, 17} {3, 18} {3, 19} {3, 20} {3, 21}
{3, 22} {3, 23} {3, 24} {3, 25} {3, 26} {3, 27} {3, 28} {3, 29} {3, 30} {3, 31} {3, 32} {3, 33} {3, 34} {3, 35} {3, 36} {3, 37}
{3, 38} {3, 39} {3, 40} {3, 41} {3, 42} {3, 43} {3, 44} {3, 45} {3, 46} {3, 47} {3, 48} {3, 49} {3, 50} {3, 51} {3, 52} {3, 53}
{3, 54} {3, 55} {3, 56} {3, 57} {3, 58} {3, 59} {3, 60} {3, 61} {3, 62} {3, 63} {3, 64} {3, 65} {3, 66} {4, 5} {4, 6} {4, 7} {4, 8}
{4, 9} {4, 10} {4, 11} {4, 12} {4, 13} {4, 14} {4, 15} {4, 16} {4, 17} {4, 18} {4, 19} {4, 20} {4, 21} {4, 22} {4, 23} {4, 24}
{4, 25} {4, 26} {4, 27} {4, 28} {4, 29} {4, 30} {4, 31} {4, 32} {4, 33} {4, 34} {4, 35} {4, 36} {4, 37} {4, 38} {4, 39} {4, 40}
{4, 41} {4, 42} {4, 43} {4, 44} {4, 45} {4, 46} {4, 47} {4, 48} {4, 49} {4, 50} {4, 51} {4, 52} {4, 53} {4, 54} {4, 55} {4, 56}
{4, 57} {4, 58} {4, 59} {4, 60} {4, 61} {4, 62} {4, 63} {4, 64} {4, 65} {4, 66} {5, 6} {5, 7} {5, 8} {5, 9} {5, 10} {5, 11} {5, 12}
{5, 13} {5, 14} {5, 15} {5, 16} {5, 17} {5, 18} {5, 19} {5, 20} {5, 21} {5, 22} {5, 23} {5, 24} {5, 25} {5, 26} {5, 27} {5, 28}
{5, 29} {5, 30} {5, 31} {5, 32} {5, 33} {5, 34} {5, 35} {5, 36} {5, 37} {5, 38} {5, 39} {5, 40} {5, 41} {5, 42} {5, 43} {5, 44}
{5, 45} {5, 46} {5, 47} {5, 48} {5, 49} {5, 50} {5, 51} {5, 52} {5, 53} {5, 54} {5, 55} {5, 56} {5, 57} {5, 58} {5, 59} {5, 60}
{5, 61} {5, 62} {5, 63} {5, 64} {5, 65} {5, 66} {6, 7} {6, 8} {6, 9} {6, 10} {6, 11} {6, 12} {6, 13} {6, 14} {6, 15} {6, 16}
{6, 17} {6, 18} {6, 19} {6, 20} {6, 21} {6, 22} {6, 23} {6, 24} {6, 25} {6, 26} {6, 27} {6, 28} {6, 29} {6, 30} {6, 31} {6, 32}
{6, 33} {6, 34} {6, 35} {6, 36} {6, 37} {6, 38} {6, 39} {6, 40} {6, 41} {6, 42} {6, 43} {6, 44} {6, 45} {6, 46} {6, 47} {6, 48}
{6, 49} {6, 50} {6, 51} {6, 52} {6, 53} {6, 54} {6, 55} {6, 56} {6, 57} {6, 58} {6, 59} {6, 60} {6, 61} {6, 62} {6, 63} {6, 64}
{6, 65} {6, 66} {7, 8} {7, 9} {7, 10} {7, 11} {7, 12} {7, 13} {7, 14} {7, 15} {7, 16} {7, 17} {7, 18} {7, 19} {7, 20} {7, 21}
{7, 22} {7, 23} {7, 24} {7, 25} {7, 26} {7, 27} {7, 28} {7, 29} {7, 30} {7, 31} {7, 32} {7, 33} {7, 34} {7, 35} {7, 36} {7, 37}
{7, 38} {7, 39} {7, 40} {7, 41} {7, 42} {7, 43} {7, 44} {7, 45} {7, 46} {7, 47} {7, 48} {7, 49} {7, 50} {7, 51} {7, 52} {7, 53}
{7, 54} {7, 55} {7, 56} {7, 57} {7, 58} {7, 59} {7, 60} {7, 61} {7, 62} {7, 63} {7, 64} {7, 65} {7, 66} {8, 9} {8, 10} {8, 11}
{8, 12} {8, 13} {8, 14} {8, 15} {8, 16} {8, 17} {8, 18} {8, 19} {8, 20} {8, 21} {8, 22} {8, 23} {8, 24} {8, 25} {8, 26} {8, 27}
{8, 28} {8, 29} {8, 30} {8, 31} {8, 32} {8, 33} {8, 34} {8, 35} {8, 36} {8, 37} {8, 38} {8, 39} {8, 40} {8, 41} {8, 42} {8, 43}
{8, 44} {8, 45} {8, 46} {8, 47} {8, 48} {8, 49} {8, 50} {8, 51} {8, 52} {8, 53} {8, 54} {8, 55} {8, 56} {8, 57} {8, 58} {8, 59}
{8, 60} {8, 61} {8, 62} {8, 63} {8, 64} {8, 65} {8, 66} {9, 10} {9, 11} {9, 12} {9, 13} {9, 14} {9, 15} {9, 16} {9, 17} {9, 18}
{9, 19} {9, 20} {9, 21} {9, 22} {9, 23} {9, 24} {9, 25} {9, 26} {9, 27} {9, 28} {9, 29} {9, 30} {9, 31} {9, 32} {9, 33} {9, 34}
{9, 35} {9, 36} {9, 37} {9, 38} {9, 39} {9, 40} {9, 41} {9, 42} {9, 43} {9, 44} {9, 45} {9, 46} {9, 47} {9, 48} {9, 49} {9, 50}
{9, 51} {9, 52} {9, 53} {9, 54} {9, 55} {9, 56} {9, 57} {9, 58} {9, 59} {9, 60} {9, 61} {9, 62} {9, 63} {9, 64} {9, 65} {9, 66}

TABLE 2A-continued

{10, 11} {10, 12} {10, 13} {10, 14} {10, 15} {10, 16} {10, 17} {10, 18} {10, 19} {10, 20} {10, 21} {10, 22} {10, 23}
{10, 24} {10, 25} {10, 26} {10, 27} {10, 28} {10, 29} {10, 30} {10, 31} {10, 32} {10, 33} {10, 34} {10, 35} {10, 36}
{10, 37} {10, 38} {10, 39} {10, 40} {10, 41} {10, 42} {10, 43} {10, 44} {10, 45} {10, 46} {10, 47} {10, 48} {10, 49}
{10, 50} {10, 51} {10, 52} {10, 53} {10, 54} {10, 55} {10, 56} {10, 57} {10, 58} {10, 59} {10, 60} {10, 61} {10, 62}
{10, 63} {10, 64} {10, 65} {10, 66} {11, 12} {11, 13} {11, 14} {11, 15} {11, 16} {11, 17} {11, 18} {11, 19} {11, 20}
{11, 21} {11, 22} {11, 23} {11, 24} {11, 25} {11, 26} {11, 27} {11, 28} {11, 29} {11, 30} {11, 31} {11, 32} {11, 33}
{11, 34} {11, 35} {11, 36} {11, 37} {11, 38} {11, 39} {11, 40} {11, 41} {11, 42} {11, 43} {11, 44} {11, 45} {11, 46}
{11, 47} {11, 48} {11, 49} {11, 50} {11, 51} {11, 52} {11, 53} {11, 54} {11, 55} {11, 56} {11, 57} {11, 58} {11, 59}
{11, 60} {11, 61} {11, 62} {11, 63} {11, 64} {11, 65} {11, 66} {12, 13} {12, 14} {12, 15} {12, 16} {12, 17} {12, 18}
{12, 19} {12, 20} {12, 21} {12, 22} {12, 23} {12, 24} {12, 25} {12, 26} {12, 27} {12, 28} {12, 29} {12, 30} {12, 31}
{12, 32} {12, 33} {12, 34} {12, 35} {12, 36} {12, 37} {12, 38} {12, 39} {12, 40} {12, 41} {12, 42} {12, 43} {12, 44}
{12, 45} {12, 46} {12, 47} {12, 48} {12, 49} {12, 50} {12, 51} {12, 52} {12, 53} {12, 54} {12, 55} {12, 56} {12, 57}
{12, 58} {12, 59} {12, 60} {12, 61} {12, 62} {12, 63} {12, 64} {12, 65} {12, 66} {13, 14} {13, 15} {13, 16} {13, 17}
{13, 18} {13, 19} {13, 20} {13, 21} {13, 22} {13, 23} {13, 24} {13, 25} {13, 26} {13, 27} {13, 28} {13, 29} {13, 30}
{13, 31} {13, 32} {13, 33} {13, 34} {13, 35} {13, 36} {13, 37} {13, 38} {13, 39} {13, 40} {13, 41} {13, 42} {13, 43}
{13, 44} {13, 45} {13, 46} {13, 47} {13, 48} {13, 49} {13, 50} {13, 51} {13, 52} {13, 53} {13, 54} {13, 55} {13, 56}
{13, 57} {13, 58} {13, 59} {13, 60} {13, 61} {13, 62} {13, 63} {13, 64} {13, 65} {13, 66} {14, 15} {14, 16} {14, 17}
{14, 18} {14, 19} {14, 20} {14, 21} {14, 22} {14, 23} {14, 24} {14, 25} {14, 26} {14, 27} {14, 28} {14, 29} {14, 30}
{14, 31} {14, 32} {14, 33} {14, 34} {14, 35} {14, 36} {14, 37} {14, 38} {14, 39} {14, 40} {14, 41} {14, 42} {14, 43}
{14, 44} {14, 45} {14, 46} {14, 47} {14, 48} {14, 49} {14, 50} {14, 51} {14, 52} {14, 53} {14, 54} {14, 55} {14, 56}
{14, 57} {14, 58} {14, 59} {14, 60} {14, 61} {14, 62} {14, 63} {14, 64} {14, 65} {14, 66} {15, 16} {15, 17} {15, 18}
{15, 19} {15, 20} {15, 21} {15, 22} {15, 23} {15, 24} {15, 25} {15, 26} {15, 27} {15, 28} {15, 29} {15, 30} {15, 31}
{15, 32} {15, 33} {15, 34} {15, 35} {15, 36} {15, 37} {15, 38} {15, 39} {15, 40} {15, 41} {15, 42} {15, 43} {15, 44}
{15, 45} {15, 46} {15, 47} {15, 48} {15, 49} {15, 50} {15, 51} {15, 52} {15, 53} {15, 54} {15, 55} {15, 56} {15, 57}
{15, 58} {15, 59} {15, 60} {15, 61} {15, 62} {15, 63} {15, 64} {15, 65} {15, 66} {16, 17} {16, 18} {16, 19} {16, 20}
{16, 21} {16, 22} {16, 23} {16, 24} {16, 25} {16, 26} {16, 27} {16, 28} {16, 29} {16, 30} {16, 31} {16, 32} {16, 33}
{16, 34} {16, 35} {16, 36} {16, 37} {16, 38} {16, 39} {16, 40} {16, 41} {16, 42} {16, 43} {16, 44} {16, 45} {16, 46}
{16, 47} {16, 48} {16, 49} {16, 50} {16, 51} {16, 52} {16, 53} {16, 54} {16, 55} {16, 56} {16, 57} {16, 58} {16, 59}
{16, 60} {16, 61} {16, 62} {16, 63} {16, 64} {16, 65} {16, 66} {17, 18} {17, 19} {17, 20} {17, 21} {17, 22} {17, 23}
{17, 24} {17, 25} {17, 26} {17, 27} {17, 28} {17, 29} {17, 30} {17, 31} {17, 32} {17, 33} {17, 34} {17, 35} {17, 36}
{17, 37} {17, 38} {17, 39} {17, 40} {17, 41} {17, 42} {17, 43} {17, 44} {17, 45} {17, 46} {17, 47} {17, 48} {17, 49}
{17, 50} {17, 51} {17, 52} {17, 53} {17, 54} {17, 55} {17, 56} {17, 57} {17, 58} {17, 59} {17, 60} {17, 61} {17, 62}
{17, 63} {17, 64} {17, 65} {17, 66} {18, 19} {18, 20} {18, 21} {18, 22} {18, 23} {18, 24} {18, 25} {18, 26} {18, 27}
{18, 28} {18, 29} {18, 30} {18, 31} {18, 32} {18, 33} {18, 34} {18, 35} {18, 36} {18, 37} {18, 38} {18, 39} {18, 40}
{18, 41} {18, 42} {18, 43} {18, 44} {18, 45} {18, 46} {18, 47} {18, 48} {18, 49} {18, 50} {18, 51} {18, 52} {18, 53}
{18, 54} {18, 55} {18, 56} {18, 57} {18, 58} {18, 59} {18, 60} {18, 61} {18, 62} {18, 63} {18, 64} {18, 65} {18, 66}
{19, 20} {19, 21} {19, 22} {19, 23} {19, 24} {19, 25} {19, 26} {19, 27} {19, 28} {19, 29} {19, 30} {19, 31} {19, 32}
{19, 33} {19, 34} {19, 35} {19, 36} {19, 37} {19, 38} {19, 39} {19, 40} {19, 41} {19, 42} {19, 43} {19, 44} {19, 45}
{19, 46} {19, 47} {19, 48} {19, 49} {19, 50} {19, 51} {19, 52} {19, 53} {19, 54} {19, 55} {19, 56} {19, 57} {19, 58}
{19, 59} {19, 60} {19, 61} {19, 62} {19, 63} {19, 64} {19, 65} {19, 66} {20, 21} {20, 22} {20, 23} {20, 24} {20, 25}
{20, 26} {20, 27} {20, 28} {20, 29} {20, 30} {20, 31} {20, 32} {20, 33} {20, 34} {20, 35} {20, 36} {20, 37} {20, 38}
{20, 39} {20, 40} {20, 41} {20, 42} {20, 43} {20, 44} {20, 45} {20, 46} {20, 47} {20, 48} {20, 49} {20, 50} {20, 51}
{20, 52} {20, 53} {20, 54} {20, 55} {20, 56} {20, 57} {20, 58} {20, 59} {20, 60} {20, 61} {20, 62} {20, 63} {20, 64}
{20, 65} {20, 66} {21, 22} {21, 23} {21, 24} {21, 25} {21, 26} {21, 27} {21, 28} {21, 29} {21, 30} {21, 31} {21, 32}
{21, 33} {21, 34} {21, 35} {21, 36} {21, 37} {21, 38} {21, 39} {21, 40} {21, 41} {21, 42} {21, 43} {21, 44} {21, 45}
{21, 46} {21, 47} {21, 48} {21, 49} {21, 50} {21, 51} {21, 52} {21, 53} {21, 54} {21, 55} {21, 56} {21, 57} {21, 58}
{21, 59} {21, 60} {21, 61} {21, 62} {21, 63} {21, 64} {21, 65} {21, 66} {22, 23} {22, 24} {22, 25} {22, 26} {22, 27}
{22, 28} {22, 29} {22, 30} {22, 31} {22, 32} {22, 33} {22, 34} {22, 35} {22, 36} {22, 37} {22, 38} {22, 39} {22, 40}
{22, 41} {22, 42} {22, 43} {22, 44} {22, 45} {22, 46} {22, 47} {22, 48} {22, 49} {22, 50} {22, 51} {22, 52} {22, 53}
{22, 54} {22, 55} {22, 56} {22, 57} {22, 58} {22, 59} {22, 60} {22, 61} {22, 62} {22, 63} {22, 64} {22, 65} {22, 66}
{23, 24} {23, 25} {23, 26} {23, 27} {23, 28} {23, 29} {23, 30} {23, 31} {23, 32} {23, 33} {23, 34} {23, 35} {23, 36}
{23, 37} {23, 38} {23, 39} {23, 40} {23, 41} {23, 42} {23, 43} {23, 44} {23, 45} {23, 46} {23, 47} {23, 48} {23, 49}
{23, 50} {23, 51} {23, 52} {23, 53} {23, 54} {23, 55} {23, 56} {23, 57} {23, 58} {23, 59} {23, 60} {23, 61} {23, 62}
{23, 63} {23, 64} {23, 65} {23, 66} {24, 25} {24, 26} {24, 27} {24, 28} {24, 29} {24, 30} {24, 31} {24, 32} {24, 33}
{24, 34} {24, 35} {24, 36} {24, 37} {24, 38} {24, 39} {24, 40} {24, 41} {24, 42} {24, 43} {24, 44} {24, 45} {24, 46}
{24, 47} {24, 48} {24, 49} {24, 50} {24, 51} {24, 52} {24, 53} {24, 54} {24, 55} {24, 56} {24, 57} {24, 58} {24, 59}
{24, 60} {24, 61} {24, 62} {24, 63} {24, 64} {24, 65} {24, 66} {25, 26} {25, 27} {25, 28} {25, 29} {25, 30} {25, 31}
{25, 32} {25, 33} {25, 34} {25, 35} {25, 36} {25, 37} {25, 38} {25, 39} {25, 40} {25, 41} {25, 42} {25, 43} {25, 44}
{25, 45} {25, 46} {25, 47} {25, 48} {25, 49} {25, 50} {25, 51} {25, 52} {25, 53} {25, 54} {25, 55} {25, 56} {25, 57}
{25, 58} {25, 59} {25, 60} {25, 61} {25, 62} {25, 63} {25, 64} {25, 65} {25, 66} {26, 27} {26, 28} {26, 29} {26, 30}
{26, 31} {26, 32} {26, 33} {26, 34} {26, 35} {26, 36} {26, 37} {26, 38} {26, 39} {26, 40} {26, 41} {26, 42} {26, 43}
{26, 44} {26, 45} {26, 46} {26, 47} {26, 48} {26, 49} {26, 50} {26, 51} {26, 52} {26, 53} {26, 54} {26, 55} {26, 56}
{26, 57} {26, 58} {26, 59} {26, 60} {26, 61} {26, 62} {26, 63} {26, 64} {26, 65} {26, 66} {27, 28} {27, 29} {27, 30}
{27, 31} {27, 32} {27, 33} {27, 34} {27, 35} {27, 36} {27, 37} {27, 38} {27, 39} {27, 40} {27, 41} {27, 42} {27, 43}
{27, 44} {27, 45} {27, 46} {27, 47} {27, 48} {27, 49} {27, 50} {27, 51} {27, 52} {27, 53} {27, 54} {27, 55} {27, 56}
{27, 57} {27, 58} {27, 59} {27, 60} {27, 61} {27, 62} {27, 63} {27, 64} {27, 65} {27, 66} {28, 29} {28, 30} {28, 31}
{28, 32} {28, 33} {28, 34} {28, 35} {28, 36} {28, 37} {28, 38} {28, 39} {28, 40} {28, 41} {28, 42} {28, 43} {28, 44}
{28, 45} {28, 46} {28, 47} {28, 48} {28, 49} {28, 50} {28, 51} {28, 52} {28, 53} {28, 54} {28, 55} {28, 56} {28, 57}
{28, 58} {28, 59} {28, 60} {28, 61} {28, 62} {28, 63} {28, 64} {28, 65} {28, 66} {29, 30} {29, 31} {29, 32} {29, 33}
{29, 34} {29, 35} {29, 36} {29, 37} {29, 38} {29, 39} {29, 40} {29, 41} {29, 42} {29, 43} {29, 44} {29, 45} {29, 46}
{29, 47} {29, 48} {29, 49} {29, 50} {29, 51} {29, 52} {29, 53} {29, 54} {29, 55} {29, 56} {29, 57} {29, 58} {29, 59}
{29, 60} {29, 61} {29, 62} {29, 63} {29, 64} {29, 65} {29, 66} {30, 31} {30, 32} {30, 33} {30, 34} {30, 35} {30, 36}
{30, 37} {30, 38} {30, 39} {30, 40} {30, 41} {30, 42} {30, 43} {30, 44} {30, 45} {30, 46} {30, 47} {30, 48} {30, 49}
{30, 50} {30, 51} {30, 52} {30, 53} {30, 54} {30, 55} {30, 56} {30, 57} {30, 58} {30, 59} {30, 60} {30, 61} {30, 62}
{30, 63} {30, 64} {30, 65} {30, 66} {31, 32} {31, 33} {31, 34} {31, 35} {31, 36} {31, 37} {31, 38} {31, 39} {31, 40}
{31, 41} {31, 42} {31, 43} {31, 44} {31, 45} {31, 46} {31, 47} {31, 48} {31, 49} {31, 50} {31, 51} {31, 52} {31, 53}
{31, 54} {31, 55} {31, 56} {31, 57} {31, 58} {31, 59} {31, 60} {31, 61} {31, 62} {31, 63} {31, 64} {31, 65} {31, 66}
{32, 33} {32, 34} {32, 35} {32, 36} {32, 37} {32, 38} {32, 39} {32, 40} {32, 41} {32, 42} {32, 43} {32, 44} {32, 45}
{32, 46} {32, 47} {32, 48} {32, 49} {32, 50} {32, 51} {32, 52} {32, 53} {32, 54} {32, 55} {32, 56} {32, 57} {32, 58}
{32, 59} {32, 60} {32, 61} {32, 62} {32, 63} {32, 64} {32, 65} {32, 66} {33, 34} {33, 35} {33, 36} {33, 37} {33, 38}

TABLE 2A-continued

{33, 39} {33, 40} {33, 41} {33, 42} {33, 43} {33, 44} {33, 45} {33, 46} {33, 47} {33, 48} {33, 49} {33, 50} {33, 51}
{33, 52} {33, 53} {33, 54} {33, 55} {33, 56} {33, 57} {33, 58} {33, 59} {33, 60} {33, 61} {33, 62} {33, 63} {33, 64}
{33, 65} {33, 66} {34, 35} {34, 36} {34, 37} {34, 38} {34, 39} {34, 40} {34, 41} {34, 42} {34, 43} {34, 44} {34, 45}
{34, 46} {34, 47} {34, 48} {34, 49} {34, 50} {34, 51} {34, 52} {34, 53} {34, 54} {34, 55} {34, 56} {34, 57} {34, 58}
{34, 59} {34, 60} {34, 61} {34, 62} {34, 63} {34, 64} {34, 65} {34, 66} {35, 36} {35, 37} {35, 38} {35, 39} {35, 40}
{35, 41} {35, 42} {35, 43} {35, 44} {35, 45} {35, 46} {35, 47} {35, 48} {35, 49} {35, 50} {35, 51} {35, 52} {35, 53}
{35, 54} {35, 55} {35, 56} {35, 57} {35, 58} {35, 59} {35, 60} {35, 61} {35, 62} {35, 63} {35, 64} {35, 65} {35, 66}
{36, 37} {36, 38} {36, 39} {36, 40} {36, 41} {36, 42} {36, 43} {36, 44} {36, 45} {36, 46} {36, 47} {36, 48} {36, 49}
{36, 50} {36, 51} {36, 52} {36, 53} {36, 54} {36, 55} {36, 56} {36, 57} {36, 58} {36, 59} {36, 60} {36, 61} {36, 62}
{36, 63} {36, 64} {36, 65} {36, 66} {37, 38} {37, 39} {37, 40} {37, 41} {37, 42} {37, 43} {37, 44} {37, 45} {37, 46}
{37, 47} {37, 48} {37, 49} {37, 50} {37, 51} {37, 52} {37, 53} {37, 54} {37, 55} {37, 56} {37, 57} {37, 58} {37, 59}
{37, 60} {37, 61} {37, 62} {37, 63} {37, 64} {37, 65} {37, 66} {38, 39} {38, 40} {38, 41} {38, 42} {38, 43} {38, 44}
{38, 45} {38, 46} {38, 47} {38, 48} {38, 49} {38, 50} {38, 51} {38, 52} {38, 53} {38, 54} {38, 55} {38, 56} {38, 57}
{38, 58} {38, 59} {38, 60} {38, 61} {38, 62} {38, 63} {38, 64} {38, 65} {38, 66} {39, 40} {39, 41} {39, 42} {39, 43}
{39, 44} {39, 45} {39, 46} {39, 47} {39, 48} {39, 49} {39, 50} {39, 51} {39, 52} {39, 53} {39, 54} {39, 55} {39, 56}
{39, 57} {39, 58} {39, 59} {39, 60} {39, 61} {39, 62} {39, 63} {39, 64} {39, 65} {39, 66} {40, 41} {40, 42} {40, 43}
{40, 44} {40, 45} {40, 46} {40, 47} {40, 48} {40, 49} {40, 50} {40, 51} {40, 52} {40, 53} {40, 54} {40, 55} {40, 56}
{40, 57} {40, 58} {40, 59} {40, 60} {40, 61} {40, 62} {40, 63} {40, 64} {40, 65} {40, 66} {41, 42} {41, 43} {41, 44}
{41, 45} {41, 46} {41, 47} {41, 48} {41, 49} {41, 50} {41, 51} {41, 52} {41, 53} {41, 54} {41, 55} {41, 56} {41, 57}
{41, 58} {41, 59} {41, 60} {41, 61} {41, 62} {41, 63} {41, 64} {41, 65} {41, 66} {42, 43} {42, 44} {42, 45} {42, 46}
{42, 47} {42, 48} {42, 49} {42, 50} {42, 51} {42, 52} {42, 53} {42, 54} {42, 55} {42, 56} {42, 57} {42, 58} {42, 59}
{42, 60} {42, 61} {42, 62} {42, 63} {42, 64} {42, 65} {42, 66} {43, 44} {43, 45} {43, 46} {43, 47} {43, 48} {43, 49}
{43, 50} {43, 51} {43, 52} {43, 53} {43, 54} {43, 55} {43, 56} {43, 57} {43, 58} {43, 59} {43, 60} {43, 61} {43, 62}
{43, 63} {43, 64} {43, 65} {43, 66} {44, 45} {44, 46} {44, 47} {44, 48} {44, 49} {44, 50} {44, 51} {44, 52} {44, 53}
{44, 54} {44, 55} {44, 56} {44, 57} {44, 58} {44, 59} {44, 60} {44, 61} {44, 62} {44, 63} {44, 64} {44, 65} {44, 66}
{45, 46} {45, 47} {45, 48} {45, 49} {45, 50} {45, 51} {45, 52} {45, 53} {45, 54} {45, 55} {45, 56} {45, 57} {45, 58}
{45, 59} {45, 60} {45, 61} {45, 62} {45, 63} {45, 64} {45, 65} {45, 66} {46, 47} {46, 48} {46, 49} {46, 50} {46, 51}
{46, 52} {46, 53} {46, 54} {46, 55} {46, 56} {46, 57} {46, 58} {46, 59} {46, 60} {46, 61} {46, 62} {46, 63} {46, 64}
{46, 65} {46, 66} {47, 48} {47, 49} {47, 50} {47, 51} {47, 52} {47, 53} {47, 54} {47, 55} {47, 56} {47, 57} {47, 58}
{47, 59} {47, 60} {47, 61} {47, 62} {47, 63} {47, 64} {47, 65} {47, 66} {48, 49} {48, 50} {48, 51} {48, 52} {48, 53}
{48, 54} {48, 55} {48, 56} {48, 57} {48, 58} {48, 59} {48, 60} {48, 61} {48, 62} {48, 63} {48, 64} {48, 65} {48, 66}
{49, 50} {49, 51} {49, 52} {49, 53} {49, 54} {49, 55} {49, 56} {49, 57} {49, 58} {49, 59} {49, 60} {49, 61} {49, 62}
{49, 63} {49, 64} {49, 65} {49, 66} {50, 51} {50, 52} {50, 53} {50, 54} {50, 55} {50, 56} {50, 57} {50, 58} {50, 59}
{50, 60} {50, 61} {50, 62} {50, 63} {50, 64} {50, 65} {50, 66} {51, 52} {51, 53} {51, 54} {51, 55} {51, 56} {51, 57}
{51, 58} {51, 59} {51, 60} {51, 61} {51, 62} {51, 63} {51, 64} {51, 65} {51, 66} {52, 53} {52, 54} {52, 55} {52, 56}
{52, 57} {52, 58} {52, 59} {52, 60} {52, 61} {52, 62} {52, 63} {52, 64} {52, 65} {52, 66} {53, 54} {53, 55} {53, 56}
{53, 57} {53, 58} {53, 59} {53, 60} {53, 61} {53, 62} {53, 63} {53, 64} {53, 65} {53, 66} {54, 55} {54, 56} {54, 57}
{54, 58} {54, 59} {54, 60} {54, 61} {54, 62} {54, 63} {54, 64} {54, 65} {54, 66} {55, 56} {55, 57} {55, 58} {55, 59}
{55, 60} {55, 61} {55, 62} {55, 63} {55, 64} {55, 65} {55, 66} {56, 57} {56, 58} {56, 59} {56, 60} {56, 61} {56, 62}
{56, 63} {56, 64} {56, 65} {56, 66} {57, 58} {57, 59} {57, 60} {57, 61} {57, 62} {57, 63} {57, 64} {57, 65} {57, 66}
{58, 59} {58, 60} {58, 61} {58, 62} {58, 63} {58, 64} {58, 65} {58, 66} {59, 60} {59, 61} {59, 62} {59, 63} {59, 64}
{59, 65} {59, 66} {60, 61} {60, 62} {60, 63} {60, 64} {60, 65} {60, 66} {61, 62} {61, 63} {61, 64} {61, 65} {61, 66}
{62, 63} {62, 64} {62, 65} {62, 66} {63, 64} {63, 65} {63, 66} {64, 65} {64, 66} {65, 66}

TABLE 2B

{93, 96} {93, 100} {93, 106} {93, 111} {93, 112} {93, 113} {93, 114} {93, 115} {93, 116} {93, 121} {93, 122} {93, 123}
{93, 124} {93, 125} {93, 126} {93, 127} {93, 128} {93, 129} {93, 130} {93, 131} {93, 132} {93, 133} {93, 134} {93, 135}
{93, 136} {93, 137} {93, 138} {93, 139} {96, 100} {96, 106} {96, 111} {96, 112} {96, 113} {96, 114} {96, 115} {96, 116}
{96, 121} {96, 122} {96, 123} {96, 124} {96, 125} {96, 126} {96, 127} {96, 128} {96, 129} {96, 130} {96, 131} {96, 132}
{96, 133} {96, 134} {96, 135} {96, 136} {96, 137} {96, 138} {96, 139} {100, 106} {100, 111} {100, 112} {100, 113}
{100, 114} {100, 115} {100, 116} {100, 121} {100, 122} {100, 123} {100, 124} {100, 125} {100, 126} {100, 127}
{100, 128} {100, 129} {100, 130} {100, 131} {100, 132} {100, 133} {100, 134} {100, 135} {100, 136} {100, 137}
{100, 138} {100, 139} {106, 111} {106, 112} {106, 113} {106, 114} {106, 115} {106, 116} {106, 121} {106, 122}
{106, 123} {106, 124} {106, 125} {106, 126} {106, 127} {106, 128} {106, 129} {106, 130} {106, 131} {106, 132}
{106, 133} {106, 134} {106, 135} {106, 136} {106, 137} {106, 138} {111, 112} {111, 113} {111, 114}
{111, 115} {111, 116} {111, 121} {111, 122} {111, 123} {111, 124} {111, 125} {111, 126} {111, 127} {111, 128}
{111, 129} {111, 130} {111, 131} {111, 132} {111, 133} {111, 134} {111, 135} {111, 136} {111, 137} {111, 138}
{111, 139} {112, 113} {112, 114} {112, 115} {112, 116} {112, 121} {112, 122} {112, 123} {112, 124} {112, 125}
{112, 126} {112, 127} {112, 128} {112, 129} {112, 130} {112, 131} {112, 132} {112, 133} {112, 134} {112, 135}
{112, 136} {112, 137} {112, 138} {112, 139} {113, 114} {113, 115} {113, 116} {113, 121} {113, 122} {113, 123}
{113, 124} {113, 125} {113, 126} {113, 127} {113, 128} {113, 129} {113, 130} {113, 131} {113, 132} {113, 133}
{113, 134} {113, 135} {113, 136} {113, 137} {113, 138} {113, 139} {114, 115} {114, 116} {114, 121} {114, 122}
{114, 123} {114, 124} {114, 125} {114, 126} {114, 127} {114, 128} {114, 129} {114, 130} {114, 131} {114, 132}
{114, 133} {114, 134} {114, 135} {114, 136} {114, 137} {114, 138} {115, 116} {115, 121} {115, 122}
{115, 123} {115, 124} {115, 125} {115, 126} {115, 127} {115, 128} {115, 129} {115, 130} {115, 131} {115, 132}
{115, 133} {115, 134} {115, 135} {115, 136} {115, 137} {115, 138} {115, 139} {116, 121} {116, 122} {116, 123}
{116, 124} {116, 125} {116, 126} {116, 127} {116, 128} {116, 129} {116, 130} {116, 131} {116, 132} {116, 133}
{116, 134} {116, 135} {116, 136} {116, 137} {116, 138} {116, 139} {121, 122} {121, 123} {121, 124} {121, 125}
{121, 126} {121, 127} {121, 128} {121, 129} {121, 130} {121, 131} {121, 132} {121, 133} {121, 134} {121, 135}
{121, 136} {121, 137} {121, 138} {121, 139} {122, 123} {122, 124} {122, 125} {122, 126} {122, 127} {122, 128}
{122, 129} {122, 130} {122, 131} {122, 132} {122, 133} {122, 134} {122, 135} {122, 136} {122, 137} {122, 138}
{122, 139} {123, 124} {123, 125} {123, 126} {123, 127} {123, 128} {123, 129} {123, 130} {123, 131} {123, 132}
{123, 133} {123, 134} {123, 135} {123, 136} {123, 137} {123, 138} {123, 139} {124, 125} {124, 126} {124, 127}
{124, 128} {124, 129} {124, 130} {124, 131} {124, 132} {124, 133} {124, 134} {124, 135} {124, 136} {124, 137}
{124, 138} {124, 139} {125, 126} {125, 127} {125, 128} {125, 129} {125, 130} {125, 131} {125, 132} {125, 133}
{125, 134} {125, 135} {125, 136} {125, 137} {125, 138} {125, 139} {126, 127} {126, 128} {126, 129} {126, 130}

TABLE 2B-continued

{126, 131} {126, 132} {126, 133} {126, 134} {126, 135} {126, 136} {126, 137} {126, 138} {126, 139} {127, 128}
{127, 129} {127, 130} {127, 131} {127, 132} {127, 133} {127, 134} {127, 135} {127, 136} {127, 137} {127, 138}
{127, 139} {128, 129} {128, 130} {128, 131} {128, 132} {128, 133} {128, 134} {128, 135} {128, 136} {128, 137}
{128, 138} {128, 139} {129, 130} {129, 131} {129, 132} {129, 133} {129, 134} {129, 135} {129, 136} {129, 137}
{129, 138} {129, 139} {130, 131} {130, 132} {130, 133} {130, 134} {130, 135} {130, 136} {130, 137} {130, 138}
{130, 139} {131, 132} {131, 133} {131, 134} {131, 135} {131, 136} {131, 137} {131, 138} {131, 139} {132, 133}
{132, 134} {132, 135} {132, 136} {132, 137} {132, 138} {132, 139} {133, 134} {133, 135} {133, 136} {133, 137}
{133, 138} {133, 139} {134, 135} {134, 136} {134, 137} {134, 138} {134, 139} {135, 136} {135, 137} {135, 138}
{135, 139} {136, 137} {136, 138} {136, 139} {137, 138} {137, 139} {138, 139}

In some embodiments, an ALK polypeptide includes a first sequence selected from any one of SEQ ID NOs: 1-66 (e.g., SEQ ID NOs: 10, 14, 17, 22, 33, 52, and 53), a second sequence selected from any one of SEQ ID NOs: 1-66 (e.g., SEQ ID NOs: 10, 14, 17, 22, 33, 52, and 53), and a third sequence selected from any one of SEQ ID NOs: 1-66 (e.g., SEQ ID NOs: 10, 14, 17, 22, 33, 52, and 53), in which the first, second, and third sequences are different and include a set of sequences of SEQ ID NOs recited in Table 3A, and in which the ALK polypeptide does not include a sequence of any one of SEQ ID NOs: 67-70 and 140-145. In some embodiments, the first, second, and third sequences in the ALK polypeptide include one of the following sets of sequences: SEQ ID NOs: 10, 14, and 17, SEQ ID NOs; 10, 14, and 22, SEQ ID NOs: 10, 14, and 33, SEQ ID NOs:10, 14, and 52, SEQ ID NOs:10, 14, and 53, SEQ ID NOs:10, 17, and 22, SEQ ID NOs:10, 17, and 33, SEQ ID NOs:10, 17, and 52, SEQ ID NOs:10, 17, and 53, SEQ ID NOs:10, 22, and 33, SEQ ID NOs:10, 22, and 52, SEQ ID NOs:10, 22, and 53, SEQ ID NOs:10, 33, and 52, SEQ ID NOs:10, 33, and 53, SEQ ID NOs:10, 52, and 53, SEQ ID NOs:14, 17, and 22, SEQ ID NOs:14, 17, and 33, SEQ ID NOs:14, 17, and 52, SEQ ID NOs:14, 17, and 53, SEQ ID NOs:14, 22, and 33, SEQ ID NOs:14, 22, and 52, SEQ ID NOs:14, 22, and 53, SEQ ID NOs:14, 33, and 52, SEQ ID NOs:14, 33, and 53, SEQ ID NOs:14, 52, and 53, SEQ ID NOs:17, 22, and 33, SEQ ID NOs:17, 22, and 52, SEQ ID NOs:17, 22, and 53, SEQ ID NOs:17, 33, and 52, SEQ ID NOs:17, 33, and 53, SEQ ID NOs:17, 52, and 53, SEQ ID NOs:22, 33, and 52, SEQ ID NOs:22, 33, and 53, SEQ ID NOs:22, 52, and 53, and SEQ ID NOs: 33, 52, and 53.

In some embodiments, an ALK polypeptide includes a first sequence selected from any one of SEQ ID NOs: 60-66, a second sequence selected from any one of SEQ ID NOs: 60-66, and a third sequence selected from any one of SEQ ID NOs: 60-66, in which the first and second sequences are different and include one of the following pairs of sequences: SEQ ID NOs: 60, 61, and 62; SEQ ID NOs: 60, 61, and 63; SEQ ID NOs: 60, 61, and 64; SEQ ID NOs: 60, 61, and 65; SEQ ID NOs: 60, 61, and 66; SEQ ID NOs: 60, 62, and 63; SEQ ID NOs: 60, 62, and 64; SEQ ID NOs: 60, 62, and 65; SEQ ID NOs: 60, 62, and 66; SEQ ID NOs: 60, 63, and 64; SEQ ID NOs: 60, 63, and 65; SEQ ID NOs: 60, 63, and 66; SEQ ID NOs: 60, 64, and 65; SEQ ID NOs: 60, 64, and 66; SEQ ID NOs: 60, 65, and 66; SEQ ID NOs: 61, 62, and 63; SEQ ID NOs: 61, 62, and 64; SEQ ID NOs: 61, 62, and 65; SEQ ID NOs: 61, 62, and 66; SEQ ID NOs: 61, 63, and 64; SEQ ID NOs: 61, 63, and 65; SEQ ID NOs: 61, 63, and 66; SEQ ID NOs: 61, 64, and 65; SEQ ID NOs: 61, 64, and 66; SEQ ID NOs: 61, 65, and 66; SEQ ID NOs: 62, 63, and 64; SEQ ID NOs: 62, 63, and 65; SEQ ID NOs: 62, 63, and 66; SEQ ID NOs: 62, 64, and 65; SEQ ID NOs: 62, 64, and 66; SEQ ID NOs: 62, 65, and 66; SEQ ID NOs: 63, 64, and 65; SEQ ID NOs: 63, 64, and 66; SEQ ID NOs: 63, 65, and 66; SEQ ID NOs: 64, 65, and 66, and in which the ALK polypeptide does not include a sequence of any one of SEQ ID NOs: 67-70 and 140-145.

In some embodiments, an ALK polypeptide includes a first sequence selected from any one of SEQ ID NOs: 93, 96, 100, 106, 111-116, and 121-139, a second sequence selected from any one of SEQ ID NOs: 93, 96, 100, 106, 111-116, and 121-139, and a third sequence selected from any one of SEQ ID NOs: 93, 96, 100, 106, 111-116, and 121-139, in which the first, second, and third sequences are different and include a set of sequences of SEQ ID NOs recited in Table 3B, and in which the ALK polypeptide does not include a sequence of any one of SEQ ID NOs: 67-70 and 140-145.

In the case that an ALK polypeptide includes a first sequence, a second sequence, and a third sequence, each bracket listed in Tables 3A and 3B contains three SEQ ID NOs representing the first, second, and third sequences in the ALK polypeptide. For example, {1,2,3} represents {a first sequence of SEQ ID NO: 1, a second sequence of SEQ ID NO: 2, a third sequence of SEQ ID NO: 3}.

In some embodiments, an immunogenic composition includes three ALK polypeptides, a first ALK polypeptide including a first sequence of any one of SEQ ID NOs: 1-66 (e.g., SEQ ID NOs: 10, 14, 17, 22, 33, 52, and 53), a second ALK polypeptide including a second sequence of any one of SEQ ID NOs: 1-66 (e.g., SEQ ID NOs: 10, 14, 17, 22, 33, 52, and 53), and a third ALK polypeptide including a third sequence of any one of SEQ ID NOs: 1-66 (e.g., SEQ ID NOs: 10, 14, 17, 22, 33, 52, and 53), in which the first, second, and third sequences are different and include a set of sequences of SEQ ID NOs recited in Table 3A, and in which none of the first, second, and third ALK polypeptides includes a sequence of any one of SEQ ID NOs: 67-70 and 140-145. In some embodiments, the first sequence in the first ALK polypeptide, the second sequence in the second ALK polypeptide, and the third sequence in the third ALK polypeptide include one of the following sets of sequences: SEQ ID NOs: 10, 14, and 17, SEQ ID NOs; 10, 14, and 22, SEQ ID NOs: 10, 14, and 33, SEQ ID NOs:10, 14, and 52, SEQ ID NOs:10, 14, and 53, SEQ ID NOs:10, 17, and 22, SEQ ID NOs:10, 17, and 33, SEQ ID NOs:10, 17, and 52, SEQ ID NOs:10, 17, and 53, SEQ ID NOs:10, 22, and 33, SEQ ID NOs:10, 22, and 52, SEQ ID NOs:10, 22, and 53, SEQ ID NOs:10, 33, and 52, SEQ ID NOs:10, 33, and 53, SEQ ID NOs:10, 52, and 53, SEQ ID NOs:14, 17, and 22, SEQ ID NOs:14, 17, and 33, SEQ ID NOs:14, 17, and 52, SEQ ID NOs:14, 17, and 53, SEQ ID NOs:14, 22, and 33, SEQ ID NOs:14, 22, and 52, SEQ ID NOs:14, 22, and 53, SEQ ID NOs:14, 33, and 52, SEQ ID NOs:14, 33, and 53, SEQ ID NOs:14, 52, and 53, SEQ ID NOs:17, 22, and 33, SEQ ID NOs:17, 22, and 52, SEQ ID NOs:17, 22, and 53, SEQ ID NOs:17, 33, and 52, SEQ ID NOs:17, 33, and 53, SEQ ID NOs:17, 52, and 53, SEQ ID NOs:22, 33, and 52, SEQ ID NOs:22, 33, and 53, SEQ ID NOs:22, 52, and 53, and SEQ ID NOs: 33, 52, and 53.

In some embodiments, an immunogenic composition includes three ALK polypeptides, a first ALK polypeptide including a first sequence selected from any one of SEQ ID NOs: 60-66, a second ALK polypeptide including a second sequence selected from any one of SEQ ID NOs: 60-66, and a third ALK polypeptide including a third sequence selected from any one of SEQ ID NOs: 60-66, in which the first, second, and third sequences are different and include one of the following sets of sequences: SEQ ID NOs: 60, 61, and 62; SEQ ID NOs: 60, 61, and 63; SEQ ID NOs: 60, 61, and 64; SEQ ID NOs: 60, 61, and 65; SEQ ID NOs: 60, 61, and 66; SEQ ID NOs: 60, 62, and 63; SEQ ID NOs: 60, 62, and 64; SEQ ID NOs: 60, 62, and 65; SEQ ID NOs: 60, 62, and 66; SEQ ID NOs: 60, 63, and 64; SEQ ID NOs: 60, 63, and 65; SEQ ID NOs: 60, 63, and 66; SEQ ID NOs: 60, 64, and 65; SEQ ID NOs: 60, 64, and 66; SEQ ID NOs: 60, 65, and 66; SEQ ID NOs: 61, 62, and 63; SEQ ID NOs: 61, 62, and 64; SEQ ID NOs: 61, 62, and 65; SEQ ID NOs: 61, 62, and 66; SEQ ID NOs: 61, 63, and 64; SEQ ID NOs: 61, 63, and 65; SEQ ID NOs: 61, 63, and 66; SEQ ID NOs: 61, 64, and 65; SEQ ID NOs: 61, 64, and 66; SEQ ID NOs: 61, 65, and 66; SEQ ID NOs: 62, 63, and 64; SEQ ID NOs: 62, 63, and 65; SEQ ID NOs: 62, 63, and 66; SEQ ID NOs: 62, 64, and 65; SEQ ID NOs: 62, 64, and 66; SEQ ID NOs: 62, 65, and 66; SEQ ID NOs: 63, 64, and 65; SEQ ID NOs: 63, 64, and 66; SEQ ID NOs: 63, 65, and 66; SEQ ID NOs: 64, 65, and 66, and which none of the first, second, and third ALK polypeptides includes a sequence of any one of SEQ ID NOs: 67-70 and 140-145.

In some embodiments, an immunogenic composition includes three ALK polypeptides, a first ALK polypeptide including a first sequence of any one of SEQ ID NOs: 93, 96, 100, 106, 111-116, and 121-139, a second ALK polypeptide including a second sequence of any one of SEQ ID NOs: 93, 96, 100, 106, 111-116, and 121-139, and a third ALK polypeptide including a third sequence of any one of SEQ ID NOs: 93, 96, 100, 106, 111-116, and 121-139, in which the first, second, and third sequences are different and include a set of sequences of SEQ ID NOs recited in Table 3B, and in which none of the first, second, and third ALK polypeptides includes a sequence of any one of SEQ ID NOs: 67-70 and 140-145

In the case for three ALK polypeptides in one immunogenic composition, a first ALK polypeptide including a first sequence, a second ALK polypeptide including a second sequence, and a third ALK polypeptide including a third sequence, each bracket listed in Tables 3A and 3B contains three SEQ ID NOs representing the first sequence in the first ALK polypeptide, the second sequence in the second ALK polypeptide, and the third sequence in the third ALK polypeptide. For example, {1,2,3} represents {the first sequence of SEQ ID NO: 1 in the first ALK polypeptide, the second sequence of SEQ ID NO: 2 in the second ALK polypeptide, the third sequence of SEQ ID NO: 3 in the third ALK polypeptide}.

TABLE 3A

{1, 2, 3} {1, 2, 4} {1, 2, 5} {1, 2, 6} {1, 2, 7} {1, 2, 8} {1, 2, 9} {1, 2, 10} {1, 2, 11} {1, 2, 12} {1, 2, 13} {1, 2, 14} {1, 2, 15}
{1, 2, 16} {1, 2, 17} {1, 2, 18} {1, 2, 19} {1, 2, 20} {1, 2, 21} {1, 2, 22} {1, 2, 23} {1, 2, 24} {1, 2, 25} {1, 2, 26} {1, 2, 27}
{1, 2, 28} {1, 2, 29} {1, 2, 30} {1, 2, 31} {1, 2, 32} {1, 2, 33} {1, 2, 34} {1, 2, 35} {1, 2, 36} {1, 2, 37} {1, 2, 38} {1, 2, 39}
{1, 2, 40} {1, 2, 41} {1, 2, 42} {1, 2, 43} {1, 2, 44} {1, 2, 45} {1, 2, 46} {1, 2, 47} {1, 2, 48} {1, 2, 49} {1, 2, 50} {1, 2, 51}
{1, 2, 52} {1, 2, 53} {1, 2, 54} {1, 2, 55} {1, 2, 56} {1, 2, 57} {1, 2, 58} {1, 2, 59} {1, 2, 60} {1, 2, 61} {1, 2, 62} {1, 2, 63}
{1, 2, 64} {1, 2, 65} {1, 2, 66} {1, 3, 4} {1, 3, 5} {1, 3, 6} {1, 3, 7} {1, 3, 8} {1, 3, 9} {1, 3, 10} {1, 3, 11} {1, 3, 12} {1, 3, 13}
{1, 3, 14} {1, 3, 15} {1, 3, 16} {1, 3, 17} {1, 3, 18} {1, 3, 19} {1, 3, 20} {1, 3, 21} {1, 3, 22} {1, 3, 23} {1, 3, 24} {1, 3, 25}
{1, 3, 26} {1, 3, 27} {1, 3, 28} {1, 3, 29} {1, 3, 30} {1, 3, 31} {1, 3, 32} {1, 3, 33} {1, 3, 34} {1, 3, 35} {1, 3, 36} {1, 3, 37}
{1, 3, 38} {1, 3, 39} {1, 3, 40} {1, 3, 41} {1, 3, 42} {1, 3, 43} {1, 3, 44} {1, 3, 45} {1, 3, 46} {1, 3, 47} {1, 3, 48} {1, 3, 49}
{1, 3, 50} {1, 3, 51} {1, 3, 52} {1, 3, 53} {1, 3, 54} {1, 3, 55} {1, 3, 56} {1, 3, 57} {1, 3, 58} {1, 3, 59} {1, 3, 60} {1, 3, 61}
{1, 3, 62} {1, 3, 63} {1, 3, 64} {1, 3, 65} {1, 3, 66} {1, 4, 5} {1, 4, 6} {1, 4, 7} {1, 4, 8} {1, 4, 9} {1, 4, 10} {1, 4, 11} {1, 4, 12}
{1, 4, 13} {1, 4, 14} {1, 4, 15} {1, 4, 16} {1, 4, 17} {1, 4, 18} {1, 4, 19} {1, 4, 20} {1, 4, 21} {1, 4, 22} {1, 4, 23} {1, 4, 24}
{1, 4, 25} {1, 4, 26} {1, 4, 27} {1, 4, 28} {1, 4, 29} {1, 4, 30} {1, 4, 31} {1, 4, 32} {1, 4, 33} {1, 4, 34} {1, 4, 35} {1, 4, 36}
{1, 4, 37} {1, 4, 38} {1, 4, 39} {1, 4, 40} {1, 4, 41} {1, 4, 42} {1, 4, 43} {1, 4, 44} {1, 4, 45} {1, 4, 46} {1, 4, 47} {1, 4, 48}
{1, 4, 49} {1, 4, 50} {1, 4, 51} {1, 4, 52} {1, 4, 53} {1, 4, 54} {1, 4, 55} {1, 4, 56} {1, 4, 57} {1, 4, 58} {1, 4, 59} {1, 4, 60}
{1, 4, 61} {1, 4, 62} {1, 4, 63} {1, 4, 64} {1, 4, 65} {1, 4, 66} {1, 5, 6} {1, 5, 7} {1, 5, 8} {1, 5, 9} {1, 5, 10} {1, 5, 11} {1, 5, 12}
{1, 5, 13} {1, 5, 14} {1, 5, 15} {1, 5, 16} {1, 5, 17} {1, 5, 18} {1, 5, 19} {1, 5, 20} {1, 5, 21} {1, 5, 22} {1, 5, 23} {1, 5, 24}
{1, 5, 25} {1, 5, 26} {1, 5, 27} {1, 5, 28} {1, 5, 29} {1, 5, 30} {1, 5, 31} {1, 5, 32} {1, 5, 33} {1, 5, 34} {1, 5, 35} {1, 5, 36}
{1, 5, 37} {1, 5, 38} {1, 5, 39} {1, 5, 40} {1, 5, 41} {1, 5, 42} {1, 5, 43} {1, 5, 44} {1, 5, 45} {1, 5, 46} {1, 5, 47} {1, 5, 48}
{1, 5, 49} {1, 5, 50} {1, 5, 51} {1, 5, 52} {1, 5, 53} {1, 5, 54} {1, 5, 55} {1, 5, 56} {1, 5, 57} {1, 5, 58} {1, 5, 59} {1, 5, 60}
{1, 5, 61} {1, 5, 62} {1, 5, 63} {1, 5, 64} {1, 5, 65} {1, 5, 66} {1, 6, 7} {1, 6, 8} {1, 6, 9} {1, 6, 10} {1, 6, 11} {1, 6, 12} {1, 6, 13}
{1, 6, 14} {1, 6, 15} {1, 6, 16} {1, 6, 17} {1, 6, 18} {1, 6, 19} {1, 6, 20} {1, 6, 21} {1, 6, 22} {1, 6, 23} {1, 6, 24} {1, 6, 25}
{1, 6, 26} {1, 6, 27} {1, 6, 28} {1, 6, 29} {1, 6, 30} {1, 6, 31} {1, 6, 32} {1, 6, 33} {1, 6, 34} {1, 6, 35} {1, 6, 36} {1, 6, 37}
{1, 6, 38} {1, 6, 39} {1, 6, 40} {1, 6, 41} {1, 6, 42} {1, 6, 43} {1, 6, 44} {1, 6, 45} {1, 6, 46} {1, 6, 47} {1, 6, 48} {1, 6, 49}
{1, 6, 50} {1, 6, 51} {1, 6, 52} {1, 6, 53} {1, 6, 54} {1, 6, 55} {1, 6, 56} {1, 6, 57} {1, 6, 58} {1, 6, 59} {1, 6, 60} {1, 6, 61}
{1, 6, 62} {1, 6, 63} {1, 6, 64} {1, 6, 65} {1, 6, 66} {1, 7, 8} {1, 7, 9} {1, 7, 10} {1, 7, 11} {1, 7, 12} {1, 7, 13} {1, 7, 14}
{1, 7, 15} {1, 7, 16} {1, 7, 17} {1, 7, 18} {1, 7, 19} {1, 7, 20} {1, 7, 21} {1, 7, 22} {1, 7, 23} {1, 7, 24} {1, 7, 25} {1, 7, 26}
{1, 7, 27} {1, 7, 28} {1, 7, 29} {1, 7, 30} {1, 7, 31} {1, 7, 32} {1, 7, 33} {1, 7, 34} {1, 7, 35} {1, 7, 36} {1, 7, 37} {1, 7, 38}
{1, 7, 39} {1, 7, 40} {1, 7, 41} {1, 7, 42} {1, 7, 43} {1, 7, 44} {1, 7, 45} {1, 7, 46} {1, 7, 47} {1, 7, 48} {1, 7, 49} {1, 7, 50}
{1, 7, 51} {1, 7, 52} {1, 7, 53} {1, 7, 54} {1, 7, 55} {1, 7, 56} {1, 7, 57} {1, 7, 58} {1, 7, 59} {1, 7, 60} {1, 7, 61} {1, 7, 62}
{1, 7, 63} {1, 7, 64} {1, 7, 65} {1, 7, 66} {1, 8, 9} {1, 8, 10} {1, 8, 11} {1, 8, 12} {1, 8, 13} {1, 8, 14} {1, 8, 15} {1, 8, 16}
{1, 8, 17} {1, 8, 18} {1, 8, 19} {1, 8, 20} {1, 8, 21} {1, 8, 22} {1, 8, 23} {1, 8, 24} {1, 8, 25} {1, 8, 26} {1, 8, 27} {1, 8, 28}
{1, 8, 29} {1, 8, 30} {1, 8, 31} {1, 8, 32} {1, 8, 33} {1, 8, 34} {1, 8, 35} {1, 8, 36} {1, 8, 37} {1, 8, 38} {1, 8, 39} {1, 8, 40}
{1, 8, 41} {1, 8, 42} {1, 8, 43} {1, 8, 44} {1, 8, 45} {1, 8, 46} {1, 8, 47} {1, 8, 48} {1, 8, 49} {1, 8, 50} {1, 8, 51} {1, 8, 52}
{1, 8, 53} {1, 8, 54} {1, 8, 55} {1, 8, 56} {1, 8, 57} {1, 8, 58} {1, 8, 59} {1, 8, 60} {1, 8, 61} {1, 8, 62} {1, 8, 63} {1, 8, 64}
{1, 8, 65} {1, 8, 66} {1, 9, 10} {1, 9, 11} {1, 9, 12} {1, 9, 13} {1, 9, 14} {1, 9, 15} {1, 9, 16} {1, 9, 17} {1, 9, 18} {1, 9, 19}
{1, 9, 20} {1, 9, 21} {1, 9, 22} {1, 9, 23} {1, 9, 24} {1, 9, 25} {1, 9, 26} {1, 9, 27} {1, 9, 28} {1, 9, 29} {1, 9, 30} {1, 9, 31}
{1, 9, 32} {1, 9, 33} {1, 9, 34} {1, 9, 35} {1, 9, 36} {1, 9, 37} {1, 9, 38} {1, 9, 39} {1, 9, 40} {1, 9, 41} {1, 9, 42} {1, 9, 43}
{1, 9, 44} {1, 9, 45} {1, 9, 46} {1, 9, 47} {1, 9, 48} {1, 9, 49} {1, 9, 50} {1, 9, 51} {1, 9, 52} {1, 9, 53} {1, 9, 54} {1, 9, 55}
{1, 9, 56} {1, 9, 57} {1, 9, 58} {1, 9, 59} {1, 9, 60} {1, 9, 61} {1, 9, 62} {1, 9, 63} {1, 9, 64} {1, 9, 65} {1, 9, 66} {1, 10, 11}
{1, 10, 12} {1, 10, 13} {1, 10, 14} {1, 10, 15} {1, 10, 16} {1, 10, 17} {1, 10, 18} {1, 10, 19} {1, 10, 20} {1, 10, 21}
{1, 10, 22} {1, 10, 23} {1, 10, 24} {1, 10, 25} {1, 10, 26} {1, 10, 27} {1, 10, 28} {1, 10, 29} {1, 10, 30} {1, 10, 31}
{1, 10, 32} {1, 10, 33} {1, 10, 34} {1, 10, 35} {1, 10, 36} {1, 10, 37} {1, 10, 38} {1, 10, 39} {1, 10, 40} {1, 10, 41}
{1, 10, 42} {1, 10, 43} {1, 10, 44} {1, 10, 45} {1, 10, 46} {1, 10, 47} {1, 10, 48} {1, 10, 49} {1, 10, 50} {1, 10, 51}

TABLE 3A-continued

{1, 10, 52} {1, 10, 53} {1, 10, 54} {1, 10, 55} {1, 10, 56} {1, 10, 57} {1, 10, 58} {1, 10, 59} {1, 10, 60} {1, 10, 61}
{1, 10, 62} {1, 10, 63} {1, 10, 64} {1, 10, 65} {1, 10, 66} {1, 11, 12} {1, 11, 13} {1, 11, 14} {1, 11, 15} {1, 11, 16}
{1, 11, 17} {1, 11, 18} {1, 11, 19} {1, 11, 20} {1, 11, 21} {1, 11, 22} {1, 11, 23} {1, 11, 24} {1, 11, 25} {1, 11, 26}
{1, 11, 27} {1, 11, 28} {1, 11, 29} {1, 11, 30} {1, 11, 31} {1, 11, 32} {1, 11, 33} {1, 11, 34} {1, 11, 35} {1, 11, 36}
{1, 11, 37} {1, 11, 38} {1, 11, 39} {1, 11, 40} {1, 11, 41} {1, 11, 42} {1, 11, 43} {1, 11, 44} {1, 11, 45} {1, 11, 46}
{1, 11, 47} {1, 11, 48} {1, 11, 49} {1, 11, 50} {1, 11, 51} {1, 11, 52} {1, 11, 53} {1, 11, 54} {1, 11, 55} {1, 11, 56}
{1, 11, 57} {1, 11, 58} {1, 11, 59} {1, 11, 60} {1, 11, 61} {1, 11, 62} {1, 11, 63} {1, 11, 64} {1, 11, 65} {1, 11, 66}
{1, 12, 13} {1, 12, 14} {1, 12, 15} {1, 12, 16} {1, 12, 17} {1, 12, 18} {1, 12, 19} {1, 12, 20} {1, 12, 21} {1, 12, 22}
{1, 12, 23} {1, 12, 24} {1, 12, 25} {1, 12, 26} {1, 12, 27} {1, 12, 28} {1, 12, 29} {1, 12, 30} {1, 12, 31} {1, 12, 32}
{1, 12, 33} {1, 12, 34} {1, 12, 35} {1, 12, 36} {1, 12, 37} {1, 12, 38} {1, 12, 39} {1, 12, 40} {1, 12, 41} {1, 12, 42}
{1, 12, 43} {1, 12, 44} {1, 12, 45} {1, 12, 46} {1, 12, 47} {1, 12, 48} {1, 12, 49} {1, 12, 50} {1, 12, 51} {1, 12, 52}
{1, 12, 53} {1, 12, 54} {1, 12, 55} {1, 12, 56} {1, 12, 57} {1, 12, 58} {1, 12, 59} {1, 12, 60} {1, 12, 61} {1, 12, 62}
{1, 12, 63} {1, 12, 64} {1, 12, 65} {1, 12, 66} {1, 13, 14} {1, 13, 15} {1, 13, 16} {1, 13, 17} {1, 13, 18} {1, 13, 19}
{1, 13, 20} {1, 13, 21} {1, 13, 22} {1, 13, 23} {1, 13, 24} {1, 13, 25} {1, 13, 26} {1, 13, 27} {1, 13, 28} {1, 13, 29}
{1, 13, 30} {1, 13, 31} {1, 13, 32} {1, 13, 33} {1, 13, 34} {1, 13, 35} {1, 13, 36} {1, 13, 37} {1, 13, 38} {1, 13, 39}
{1, 13, 40} {1, 13, 41} {1, 13, 42} {1, 13, 43} {1, 13, 44} {1, 13, 45} {1, 13, 46} {1, 13, 47} {1, 13, 48} {1, 13, 49}
{1, 13, 50} {1, 13, 51} {1, 13, 52} {1, 13, 53} {1, 13, 54} {1, 13, 55} {1, 13, 56} {1, 13, 57} {1, 13, 58} {1, 13, 59}
{1, 13, 60} {1, 13, 61} {1, 13, 62} {1, 13, 63} {1, 13, 64} {1, 13, 65} {1, 13, 66} {1, 14, 15} {1, 14, 16} {1, 14, 17}
{1, 14, 18} {1, 14, 19} {1, 14, 20} {1, 14, 21} {1, 14, 22} {1, 14, 23} {1, 14, 24} {1, 14, 25} {1, 14, 26} {1, 14, 27}
{1, 14, 28} {1, 14, 29} {1, 14, 30} {1, 14, 31} {1, 14, 32} {1, 14, 33} {1, 14, 34} {1, 14, 35} {1, 14, 36} {1, 14, 37}
{1, 14, 38} {1, 14, 39} {1, 14, 40} {1, 14, 41} {1, 14, 42} {1, 14, 43} {1, 14, 44} {1, 14, 45} {1, 14, 46} {1, 14, 47}
{1, 14, 48} {1, 14, 49} {1, 14, 50} {1, 14, 51} {1, 14, 52} {1, 14, 53} {1, 14, 54} {1, 14, 55} {1, 14, 56} {1, 14, 57}
{1, 14, 58} {1, 14, 59} {1, 14, 60} {1, 14, 61} {1, 14, 62} {1, 14, 63} {1, 14, 64} {1, 14, 65} {1, 14, 66} {1, 15, 16}
{1, 15, 17} {1, 15, 18} {1, 15, 19} {1, 15, 20} {1, 15, 21} {1, 15, 22} {1, 15, 23} {1, 15, 24} {1, 15, 25} {1, 15, 26}
{1, 15, 27} {1, 15, 28} {1, 15, 29} {1, 15, 30} {1, 15, 31} {1, 15, 32} {1, 15, 33} {1, 15, 34} {1, 15, 35} {1, 15, 36}
{1, 15, 37} {1, 15, 38} {1, 15, 39} {1, 15, 40} {1, 15, 41} {1, 15, 42} {1, 15, 43} {1, 15, 44} {1, 15, 45} {1, 15, 46}
{1, 15, 47} {1, 15, 48} {1, 15, 49} {1, 15, 50} {1, 15, 51} {1, 15, 52} {1, 15, 53} {1, 15, 54} {1, 15, 55} {1, 15, 56}
{1, 15, 57} {1, 15, 58} {1, 15, 59} {1, 15, 60} {1, 15, 61} {1, 15, 62} {1, 15, 63} {1, 15, 64} {1, 15, 65} {1, 15, 66}
{1, 16, 17} {1, 16, 18} {1, 16, 19} {1, 16, 20} {1, 16, 21} {1, 16, 22} {1, 16, 23} {1, 16, 24} {1, 16, 25} {1, 16, 26}
{1, 16, 27} {1, 16, 28} {1, 16, 29} {1, 16, 30} {1, 16, 31} {1, 16, 32} {1, 16, 33} {1, 16, 34} {1, 16, 35} {1, 16, 36}
{1, 16, 37} {1, 16, 38} {1, 16, 39} {1, 16, 40} {1, 16, 41} {1, 16, 42} {1, 16, 43} {1, 16, 44} {1, 16, 45} {1, 16, 46}
{1, 16, 47} {1, 16, 48} {1, 16, 49} {1, 16, 50} {1, 16, 51} {1, 16, 52} {1, 16, 53} {1, 16, 54} {1, 16, 55} {1, 16, 56}
{1, 16, 57} {1, 16, 58} {1, 16, 59} {1, 16, 60} {1, 16, 61} {1, 16, 62} {1, 16, 63} {1, 16, 64} {1, 16, 65} {1, 16, 66}
{1, 17, 18} {1, 17, 19} {1, 17, 20} {1, 17, 21} {1, 17, 22} {1, 17, 23} {1, 17, 24} {1, 17, 25} {1, 17, 26} {1, 17, 27}
{1, 17, 28} {1, 17, 29} {1, 17, 30} {1, 17, 31} {1, 17, 32} {1, 17, 33} {1, 17, 34} {1, 17, 35} {1, 17, 36} {1, 17, 37}
{1, 17, 38} {1, 17, 39} {1, 17, 40} {1, 17, 41} {1, 17, 42} {1, 17, 43} {1, 17, 44} {1, 17, 45} {1, 17, 46} {1, 17, 47}
{1, 17, 48} {1, 17, 49} {1, 17, 50} {1, 17, 51} {1, 17, 52} {1, 17, 53} {1, 17, 54} {1, 17, 55} {1, 17, 56} {1, 17, 57}
{1, 17, 58} {1, 17, 59} {1, 17, 60} {1, 17, 61} {1, 17, 62} {1, 17, 63} {1, 17, 64} {1, 17, 65} {1, 17, 66} {1, 18, 19}
{1, 18, 20} {1, 18, 21} {1, 18, 22} {1, 18, 23} {1, 18, 24} {1, 18, 25} {1, 18, 26} {1, 18, 27} {1, 18, 28} {1, 18, 29}
{1, 18, 30} {1, 18, 31} {1, 18, 32} {1, 18, 33} {1, 18, 34} {1, 18, 35} {1, 18, 36} {1, 18, 37} {1, 18, 38} {1, 18, 39}
{1, 18, 40} {1, 18, 41} {1, 18, 42} {1, 18, 43} {1, 18, 44} {1, 18, 45} {1, 18, 46} {1, 18, 47} {1, 18, 48} {1, 18, 49}
{1, 18, 50} {1, 18, 51} {1, 18, 52} {1, 18, 53} {1, 18, 54} {1, 18, 55} {1, 18, 56} {1, 18, 57} {1, 18, 58} {1, 18, 59}
{1, 18, 60} {1, 18, 61} {1, 18, 62} {1, 18, 63} {1, 18, 64} {1, 18, 65} {1, 18, 66} {1, 19, 20} {1, 19, 21} {1, 19, 22}
{1, 19, 23} {1, 19, 24} {1, 19, 25} {1, 19, 26} {1, 19, 27} {1, 19, 28} {1, 19, 29} {1, 19, 30} {1, 19, 31} {1, 19, 32}
{1, 19, 33} {1, 19, 34} {1, 19, 35} {1, 19, 36} {1, 19, 37} {1, 19, 38} {1, 19, 39} {1, 19, 40} {1, 19, 41} {1, 19, 42}
{1, 19, 43} {1, 19, 44} {1, 19, 45} {1, 19, 46} {1, 19, 47} {1, 19, 48} {1, 19, 49} {1, 19, 50} {1, 19, 51} {1, 19, 52}
{1, 19, 53} {1, 19, 54} {1, 19, 55} {1, 19, 56} {1, 19, 57} {1, 19, 58} {1, 19, 59} {1, 19, 60} {1, 19, 61} {1, 19, 62}
{1, 19, 63} {1, 19, 64} {1, 19, 65} {1, 19, 66} {1, 20, 21} {1, 20, 22} {1, 20, 23} {1, 20, 24} {1, 20, 25} {1, 20, 26}
{1, 20, 27} {1, 20, 28} {1, 20, 29} {1, 20, 30} {1, 20, 31} {1, 20, 32} {1, 20, 33} {1, 20, 34} {1, 20, 35} {1, 20, 36}
{1, 20, 37} {1, 20, 38} {1, 20, 39} {1, 20, 40} {1, 20, 41} {1, 20, 42} {1, 20, 43} {1, 20, 44} {1, 20, 45} {1, 20, 46}
{1, 20, 47} {1, 20, 48} {1, 20, 49} {1, 20, 50} {1, 20, 51} {1, 20, 52} {1, 20, 53} {1, 20, 54} {1, 20, 55} {1, 20, 56}
{1, 20, 57} {1, 20, 58} {1, 20, 59} {1, 20, 60} {1, 20, 61} {1, 20, 62} {1, 20, 63} {1, 20, 64} {1, 20, 65} {1, 20, 66}
{1, 21, 22} {1, 21, 23} {1, 21, 24} {1, 21, 25} {1, 21, 26} {1, 21, 27} {1, 21, 28} {1, 21, 29} {1, 21, 30} {1, 21, 31}
{1, 21, 32} {1, 21, 33} {1, 21, 34} {1, 21, 35} {1, 21, 36} {1, 21, 37} {1, 21, 38} {1, 21, 39} {1, 21, 40} {1, 21, 41}
{1, 21, 42} {1, 21, 43} {1, 21, 44} {1, 21, 45} {1, 21, 46} {1, 21, 47} {1, 21, 48} {1, 21, 49} {1, 21, 50} {1, 21, 51}
{1, 21, 52} {1, 21, 53} {1, 21, 54} {1, 21, 55} {1, 21, 56} {1, 21, 57} {1, 21, 58} {1, 21, 59} {1, 21, 60} {1, 21, 61}
{1, 21, 62} {1, 21, 63} {1, 21, 64} {1, 21, 65} {1, 21, 66} {1, 22, 23} {1, 22, 24} {1, 22, 25} {1, 22, 26} {1, 22, 27}
{1, 22, 28} {1, 22, 29} {1, 22, 30} {1, 22, 31} {1, 22, 32} {1, 22, 33} {1, 22, 34} {1, 22, 35} {1, 22, 36} {1, 22, 37}
{1, 22, 38} {1, 22, 39} {1, 22, 40} {1, 22, 41} {1, 22, 42} {1, 22, 43} {1, 22, 44} {1, 22, 45} {1, 22, 46} {1, 22, 47}
{1, 22, 48} {1, 22, 49} {1, 22, 50} {1, 22, 51} {1, 22, 52} {1, 22, 53} {1, 22, 54} {1, 22, 55} {1, 22, 56} {1, 22, 57}
{1, 22, 58} {1, 22, 59} {1, 22, 60} {1, 22, 61} {1, 22, 62} {1, 22, 63} {1, 22, 64} {1, 22, 65} {1, 22, 66} {1, 23, 24}
{1, 23, 25} {1, 23, 26} {1, 23, 27} {1, 23, 28} {1, 23, 29} {1, 23, 30} {1, 23, 31} {1, 23, 32} {1, 23, 33} {1, 23, 34}
{1, 23, 35} {1, 23, 36} {1, 23, 37} {1, 23, 38} {1, 23, 39} {1, 23, 40} {1, 23, 41} {1, 23, 42} {1, 23, 43} {1, 23, 44}
{1, 23, 45} {1, 23, 46} {1, 23, 47} {1, 23, 48} {1, 23, 49} {1, 23, 50} {1, 23, 51} {1, 23, 52} {1, 23, 53} {1, 23, 54}
{1, 23, 55} {1, 23, 56} {1, 23, 57} {1, 23, 58} {1, 23, 59} {1, 23, 60} {1, 23, 61} {1, 23, 62} {1, 23, 63} {1, 23, 64}
{1, 23, 65} {1, 23, 66} {1, 24, 25} {1, 24, 26} {1, 24, 27} {1, 24, 28} {1, 24, 29} {1, 24, 30} {1, 24, 31} {1, 24, 32}
{1, 24, 33} {1, 24, 34} {1, 24, 35} {1, 24, 36} {1, 24, 37} {1, 24, 38} {1, 24, 39} {1, 24, 40} {1, 24, 41} {1, 24, 42}
{1, 24, 43} {1, 24, 44} {1, 24, 45} {1, 24, 46} {1, 24, 47} {1, 24, 48} {1, 24, 49} {1, 24, 50} {1, 24, 51} {1, 24, 52}
{1, 24, 53} {1, 24, 54} {1, 24, 55} {1, 24, 56} {1, 24, 57} {1, 24, 58} {1, 24, 59} {1, 24, 60} {1, 24, 61} {1, 24, 62}
{1, 24, 63} {1, 24, 64} {1, 24, 65} {1, 24, 66} {1, 25, 26} {1, 25, 27} {1, 25, 28} {1, 25, 29} {1, 25, 30} {1, 25, 31}
{1, 25, 32} {1, 25, 33} {1, 25, 34} {1, 25, 35} {1, 25, 36} {1, 25, 37} {1, 25, 38} {1, 25, 39} {1, 25, 40} {1, 25, 41}
{1, 25, 42} {1, 25, 43} {1, 25, 44} {1, 25, 45} {1, 25, 46} {1, 25, 47} {1, 25, 48} {1, 25, 49} {1, 25, 50} {1, 25, 51}
{1, 25, 52} {1, 25, 53} {1, 25, 54} {1, 25, 55} {1, 25, 56} {1, 25, 57} {1, 25, 58} {1, 25, 59} {1, 25, 60} {1, 25, 61}
{1, 25, 62} {1, 25, 63} {1, 25, 64} {1, 25, 65} {1, 25, 66} {1, 26, 27} {1, 26, 28} {1, 26, 29} {1, 26, 30} {1, 26, 31}
{1, 26, 32} {1, 26, 33} {1, 26, 34} {1, 26, 35} {1, 26, 36} {1, 26, 37} {1, 26, 38} {1, 26, 39} {1, 26, 40} {1, 26, 41}
{1, 26, 42} {1, 26, 43} {1, 26, 44} {1, 26, 45} {1, 26, 46} {1, 26, 47} {1, 26, 48} {1, 26, 49} {1, 26, 50} {1, 26, 51}
{1, 26, 52} {1, 26, 53} {1, 26, 54} {1, 26, 55} {1, 26, 56} {1, 26, 57} {1, 26, 58} {1, 26, 59} {1, 26, 60} {1, 26, 61}
{1, 26, 62} {1, 26, 63} {1, 26, 64} {1, 26, 65} {1, 26, 66} {1, 27, 28} {1, 27, 29} {1, 27, 30} {1, 27, 31} {1, 27, 32}
{1, 27, 33} {1, 27, 34} {1, 27, 35} {1, 27, 36} {1, 27, 37} {1, 27, 38} {1, 27, 39} {1, 27, 40} {1, 27, 41} {1, 27, 42}
{1, 27, 43} {1, 27, 44} {1, 27, 45} {1, 27, 46} {1, 27, 47} {1, 27, 48} {1, 27, 49} {1, 27, 50} {1, 27, 51} {1, 27, 52}

TABLE 3A-continued

{1, 27, 53} {1, 27, 54} {1, 27, 55} {1, 27, 56} {1, 27, 57} {1, 27, 58} {1, 27, 59} {1, 27, 60} {1, 27, 61} {1, 27, 62}
{1, 27, 63} {1, 27, 64} {1, 27, 65} {1, 27, 66} {1, 28, 29} {1, 28, 30} {1, 28, 31} {1, 28, 32} {1, 28, 33} {1, 28, 34}
{1, 28, 35} {1, 28, 36} {1, 28, 37} {1, 28, 38} {1, 28, 39} {1, 28, 40} {1, 28, 41} {1, 28, 42} {1, 28, 43} {1, 28, 44}
{1, 28, 45} {1, 28, 46} {1, 28, 47} {1, 28, 48} {1, 28, 49} {1, 28, 50} {1, 28, 51} {1, 28, 52} {1, 28, 53} {1, 28, 54}
{1, 28, 55} {1, 28, 56} {1, 28, 57} {1, 28, 58} {1, 28, 59} {1, 28, 60} {1, 28, 61} {1, 28, 62} {1, 28, 63} {1, 28, 64}
{1, 28, 65} {1, 28, 66} {1, 29, 30} {1, 29, 31} {1, 29, 32} {1, 29, 33} {1, 29, 34} {1, 29, 35} {1, 29, 36} {1, 29, 37}
{1, 29, 38} {1, 29, 39} {1, 29, 40} {1, 29, 41} {1, 29, 42} {1, 29, 43} {1, 29, 44} {1, 29, 45} {1, 29, 46} {1, 29, 47}
{1, 29, 48} {1, 29, 49} {1, 29, 50} {1, 29, 51} {1, 29, 52} {1, 29, 53} {1, 29, 54} {1, 29, 55} {1, 29, 56} {1, 29, 57}
{1, 29, 58} {1, 29, 59} {1, 29, 60} {1, 29, 61} {1, 29, 62} {1, 29, 63} {1, 29, 64} {1, 29, 65} {1, 29, 66} {1, 30, 31}
{1, 30, 32} {1, 30, 33} {1, 30, 34} {1, 30, 35} {1, 30, 36} {1, 30, 37} {1, 30, 38} {1, 30, 39} {1, 30, 40} {1, 30, 41}
{1, 30, 42} {1, 30, 43} {1, 30, 44} {1, 30, 45} {1, 30, 46} {1, 30, 47} {1, 30, 48} {1, 30, 49} {1, 30, 50} {1, 30, 51}
{1, 30, 52} {1, 30, 53} {1, 30, 54} {1, 30, 55} {1, 30, 56} {1, 30, 57} {1, 30, 58} {1, 30, 59} {1, 30, 60} {1, 30, 61}
{1, 30, 62} {1, 30, 63} {1, 30, 64} {1, 30, 65} {1, 30, 66} {1, 31, 32} {1, 31, 33} {1, 31, 34} {1, 31, 35} {1, 31, 36}
{1, 31, 37} {1, 31, 38} {1, 31, 39} {1, 31, 40} {1, 31, 41} {1, 31, 42} {1, 31, 43} {1, 31, 44} {1, 31, 45} {1, 31, 46}
{1, 31, 47} {1, 31, 48} {1, 31, 49} {1, 31, 50} {1, 31, 51} {1, 31, 52} {1, 31, 53} {1, 31, 54} {1, 31, 55} {1, 31, 56}
{1, 31, 57} {1, 31, 58} {1, 31, 59} {1, 31, 60} {1, 31, 61} {1, 31, 62} {1, 31, 63} {1, 31, 64} {1, 31, 65} {1, 31, 66}
{1, 32, 33} {1, 32, 34} {1, 32, 35} {1, 32, 36} {1, 32, 37} {1, 32, 38} {1, 32, 39} {1, 32, 40} {1, 32, 41} {1, 32, 42}
{1, 32, 43} {1, 32, 44} {1, 32, 45} {1, 32, 46} {1, 32, 47} {1, 32, 48} {1, 32, 49} {1, 32, 50} {1, 32, 51} {1, 32, 52}
{1, 32, 53} {1, 32, 54} {1, 32, 55} {1, 32, 56} {1, 32, 57} {1, 32, 58} {1, 32, 59} {1, 32, 60} {1, 32, 61} {1, 32, 62}
{1, 32, 63} {1, 32, 64} {1, 32, 65} {1, 32, 66} {1, 33, 34} {1, 33, 35} {1, 33, 36} {1, 33, 37} {1, 33, 38} {1, 33, 39}
{1, 33, 40} {1, 33, 41} {1, 33, 42} {1, 33, 43} {1, 33, 44} {1, 33, 45} {1, 33, 46} {1, 33, 47} {1, 33, 48} {1, 33, 49}
{1, 33, 50} {1, 33, 51} {1, 33, 52} {1, 33, 53} {1, 33, 54} {1, 33, 55} {1, 33, 56} {1, 33, 57} {1, 33, 58} {1, 33, 59}
{1, 33, 60} {1, 33, 61} {1, 33, 62} {1, 33, 63} {1, 33, 64} {1, 33, 65} {1, 33, 66} {1, 34, 35} {1, 34, 36} {1, 34, 37}
{1, 34, 38} {1, 34, 39} {1, 34, 40} {1, 34, 41} {1, 34, 42} {1, 34, 43} {1, 34, 44} {1, 34, 45} {1, 34, 46} {1, 34, 47}
{1, 34, 48} {1, 34, 49} {1, 34, 50} {1, 34, 51} {1, 34, 52} {1, 34, 53} {1, 34, 54} {1, 34, 55} {1, 34, 56} {1, 34, 57}
{1, 34, 58} {1, 34, 59} {1, 34, 60} {1, 34, 61} {1, 34, 62} {1, 34, 63} {1, 34, 64} {1, 34, 65} {1, 34, 66} {1, 35, 36}
{1, 35, 37} {1, 35, 38} {1, 35, 39} {1, 35, 40} {1, 35, 41} {1, 35, 42} {1, 35, 43} {1, 35, 44} {1, 35, 45} {1, 35, 46}
{1, 35, 47} {1, 35, 48} {1, 35, 49} {1, 35, 50} {1, 35, 51} {1, 35, 52} {1, 35, 53} {1, 35, 54} {1, 35, 55} {1, 35, 56}
{1, 35, 57} {1, 35, 58} {1, 35, 59} {1, 35, 60} {1, 35, 61} {1, 35, 62} {1, 35, 63} {1, 35, 64} {1, 35, 65} {1, 35, 66}
{1, 36, 37} {1, 36, 38} {1, 36, 39} {1, 36, 40} {1, 36, 41} {1, 36, 42} {1, 36, 43} {1, 36, 44} {1, 36, 45} {1, 36, 46}
{1, 36, 47} {1, 36, 48} {1, 36, 49} {1, 36, 50} {1, 36, 51} {1, 36, 52} {1, 36, 53} {1, 36, 54} {1, 36, 55} {1, 36, 56}
{1, 36, 57} {1, 36, 58} {1, 36, 59} {1, 36, 60} {1, 36, 61} {1, 36, 62} {1, 36, 63} {1, 36, 64} {1, 36, 65} {1, 36, 66}
{1, 37, 38} {1, 37, 39} {1, 37, 40} {1, 37, 41} {1, 37, 42} {1, 37, 43} {1, 37, 44} {1, 37, 45} {1, 37, 46} {1, 37, 47}
{1, 37, 48} {1, 37, 49} {1, 37, 50} {1, 37, 51} {1, 37, 52} {1, 37, 53} {1, 37, 54} {1, 37, 55} {1, 37, 56} {1, 37, 57}
{1, 37, 58} {1, 37, 59} {1, 37, 60} {1, 37, 61} {1, 37, 62} {1, 37, 63} {1, 37, 64} {1, 37, 65} {1, 37, 66} {1, 38, 39}
{1, 38, 40} {1, 38, 41} {1, 38, 42} {1, 38, 43} {1, 38, 44} {1, 38, 45} {1, 38, 46} {1, 38, 47} {1, 38, 48} {1, 38, 49}
{1, 38, 50} {1, 38, 51} {1, 38, 52} {1, 38, 53} {1, 38, 54} {1, 38, 55} {1, 38, 56} {1, 38, 57} {1, 38, 58} {1, 38, 59}
{1, 38, 60} {1, 38, 61} {1, 38, 62} {1, 38, 63} {1, 38, 64} {1, 38, 65} {1, 38, 66} {1, 39, 40} {1, 39, 41} {1, 39, 42}
{1, 39, 43} {1, 39, 44} {1, 39, 45} {1, 39, 46} {1, 39, 47} {1, 39, 48} {1, 39, 49} {1, 39, 50} {1, 39, 51} {1, 39, 52}
{1, 39, 53} {1, 39, 54} {1, 39, 55} {1, 39, 56} {1, 39, 57} {1, 39, 58} {1, 39, 59} {1, 39, 60} {1, 39, 61} {1, 39, 62}
{1, 39, 63} {1, 39, 64} {1, 39, 65} {1, 39, 66} {1, 40, 41} {1, 40, 42} {1, 40, 43} {1, 40, 44} {1, 40, 45} {1, 40, 46}
{1, 40, 47} {1, 40, 48} {1, 40, 49} {1, 40, 50} {1, 40, 51} {1, 40, 52} {1, 40, 53} {1, 40, 54} {1, 40, 55} {1, 40, 56}
{1, 40, 57} {1, 40, 58} {1, 40, 59} {1, 40, 60} {1, 40, 61} {1, 40, 62} {1, 40, 63} {1, 40, 64} {1, 40, 65} {1, 40, 66}
{1, 41, 42} {1, 41, 43} {1, 41, 44} {1, 41, 45} {1, 41, 46} {1, 41, 47} {1, 41, 48} {1, 41, 49} {1, 41, 50} {1, 41, 51}
{1, 41, 52} {1, 41, 53} {1, 41, 54} {1, 41, 55} {1, 41, 56} {1, 41, 57} {1, 41, 58} {1, 41, 59} {1, 41, 60} {1, 41, 61}
{1, 41, 62} {1, 41, 63} {1, 41, 64} {1, 41, 65} {1, 41, 66} {1, 42, 43} {1, 42, 44} {1, 42, 45} {1, 42, 46} {1, 42, 47}
{1, 42, 48} {1, 42, 49} {1, 42, 50} {1, 42, 51} {1, 42, 52} {1, 42, 53} {1, 42, 54} {1, 42, 55} {1, 42, 56} {1, 42, 57}
{1, 42, 58} {1, 42, 59} {1, 42, 60} {1, 42, 61} {1, 42, 62} {1, 42, 63} {1, 42, 64} {1, 42, 65} {1, 42, 66} {1, 43, 44}
{1, 43, 45} {1, 43, 46} {1, 43, 47} {1, 43, 48} {1, 43, 49} {1, 43, 50} {1, 43, 51} {1, 43, 52} {1, 43, 53} {1, 43, 54}
{1, 43, 55} {1, 43, 56} {1, 43, 57} {1, 43, 58} {1, 43, 59} {1, 43, 60} {1, 43, 61} {1, 43, 62} {1, 43, 63} {1, 43, 64}
{1, 43, 65} {1, 43, 66} {1, 44, 45} {1, 44, 46} {1, 44, 47} {1, 44, 48} {1, 44, 49} {1, 44, 50} {1, 44, 51} {1, 44, 52}
{1, 44, 53} {1, 44, 54} {1, 44, 55} {1, 44, 56} {1, 44, 57} {1, 44, 58} {1, 44, 59} {1, 44, 60} {1, 44, 61} {1, 44, 62}
{1, 44, 63} {1, 44, 64} {1, 44, 65} {1, 44, 66} {1, 45, 46} {1, 45, 47} {1, 45, 48} {1, 45, 49} {1, 45, 50} {1, 45, 51}
{1, 45, 52} {1, 45, 53} {1, 45, 54} {1, 45, 55} {1, 45, 56} {1, 45, 57} {1, 45, 58} {1, 45, 59} {1, 45, 60} {1, 45, 61}
{1, 45, 62} {1, 45, 63} {1, 45, 64} {1, 45, 65} {1, 45, 66} {1, 46, 47} {1, 46, 48} {1, 46, 49} {1, 46, 50} {1, 46, 51}
{1, 46, 52} {1, 46, 53} {1, 46, 54} {1, 46, 55} {1, 46, 56} {1, 46, 57} {1, 46, 58} {1, 46, 59} {1, 46, 60} {1, 46, 61}
{1, 46, 62} {1, 46, 63} {1, 46, 64} {1, 46, 65} {1, 46, 66} {1, 47, 48} {1, 47, 49} {1, 47, 50} {1, 47, 51} {1, 47, 52}
{1, 47, 53} {1, 47, 54} {1, 47, 55} {1, 47, 56} {1, 47, 57} {1, 47, 58} {1, 47, 59} {1, 47, 60} {1, 47, 61} {1, 47, 62}
{1, 47, 63} {1, 47, 64} {1, 47, 65} {1, 47, 66} {1, 48, 49} {1, 48, 50} {1, 48, 51} {1, 48, 52} {1, 48, 53} {1, 48, 54}
{1, 48, 55} {1, 48, 56} {1, 48, 57} {1, 48, 58} {1, 48, 59} {1, 48, 60} {1, 48, 61} {1, 48, 62} {1, 48, 63} {1, 48, 64}
{1, 48, 65} {1, 48, 66} {1, 49, 50} {1, 49, 51} {1, 49, 52} {1, 49, 53} {1, 49, 54} {1, 49, 55} {1, 49, 56} {1, 49, 57}
{1, 49, 58} {1, 49, 59} {1, 49, 60} {1, 49, 61} {1, 49, 62} {1, 49, 63} {1, 49, 64} {1, 49, 65} {1, 49, 66} {1, 50, 51}
{1, 50, 52} {1, 50, 53} {1, 50, 54} {1, 50, 55} {1, 50, 56} {1, 50, 57} {1, 50, 58} {1, 50, 59} {1, 50, 60} {1, 50, 61}
{1, 50, 62} {1, 50, 63} {1, 50, 64} {1, 50, 65} {1, 50, 66} {1, 51, 52} {1, 51, 53} {1, 51, 54} {1, 51, 55} {1, 51, 56}
{1, 51, 57} {1, 51, 58} {1, 51, 59} {1, 51, 60} {1, 51, 61} {1, 51, 62} {1, 51, 63} {1, 51, 64} {1, 51, 65} {1, 51, 66}
{1, 52, 53} {1, 52, 54} {1, 52, 55} {1, 52, 56} {1, 52, 57} {1, 52, 58} {1, 52, 59} {1, 52, 60} {1, 52, 61} {1, 52, 62}
{1, 52, 63} {1, 52, 64} {1, 52, 65} {1, 52, 66} {1, 53, 54} {1, 53, 55} {1, 53, 56} {1, 53, 57} {1, 53, 58} {1, 53, 59}
{1, 53, 60} {1, 53, 61} {1, 53, 62} {1, 53, 63} {1, 53, 64} {1, 53, 65} {1, 53, 66} {1, 54, 55} {1, 54, 56} {1, 54, 57}
{1, 54, 58} {1, 54, 59} {1, 54, 60} {1, 54, 61} {1, 54, 62} {1, 54, 63} {1, 54, 64} {1, 54, 65} {1, 54, 66} {1, 55, 56}
{1, 55, 57} {1, 55, 58} {1, 55, 59} {1, 55, 60} {1, 55, 61} {1, 55, 62} {1, 55, 63} {1, 55, 64} {1, 55, 65} {1, 55, 66}
{1, 56, 57} {1, 56, 58} {1, 56, 59} {1, 56, 60} {1, 56, 61} {1, 56, 62} {1, 56, 63} {1, 56, 64} {1, 56, 65} {1, 56, 66}
{1, 57, 58} {1, 57, 59} {1, 57, 60} {1, 57, 61} {1, 57, 62} {1, 57, 63} {1, 57, 64} {1, 57, 65} {1, 57, 66} {1, 58, 59}
{1, 58, 60} {1, 58, 61} {1, 58, 62} {1, 58, 63} {1, 58, 64} {1, 58, 65} {1, 58, 66} {1, 59, 60} {1, 59, 61} {1, 59, 62}
{1, 59, 63} {1, 59, 64} {1, 59, 65} {1, 59, 66} {1, 60, 61} {1, 60, 62} {1, 60, 63} {1, 60, 64} {1, 60, 65} {1, 60, 66}
{1, 61, 62} {1, 61, 63} {1, 61, 64} {1, 61, 65} {1, 61, 66} {1, 62, 63} {1, 62, 64} {1, 62, 65} {1, 62, 66} {1, 63, 64}
{1, 63, 65} {1, 63, 66} {1, 64, 65} {1, 64, 66} {1, 65, 66} {2, 3, 4} {2, 3, 5} {2, 3, 6} {2, 3, 7} {2, 3, 8} {2, 3, 9} {2, 3, 10}
{2, 3, 11} {2, 3, 12} {2, 3, 13} {2, 3, 14} {2, 3, 15} {2, 3, 16} {2, 3, 17} {2, 3, 18} {2, 3, 19} {2, 3, 20} {2, 3, 21} {2, 3, 22}
{2, 3, 23} {2, 3, 24} {2, 3, 25} {2, 3, 26} {2, 3, 27} {2, 3, 28} {2, 3, 29} {2, 3, 30} {2, 3, 31} {2, 3, 32} {2, 3, 33} {2, 3, 34}
{2, 3, 35} {2, 3, 36} {2, 3, 37} {2, 3, 38} {2, 3, 39} {2, 3, 40} {2, 3, 41} {2, 3, 42} {2, 3, 43} {2, 3, 44} {2, 3, 45} {2, 3, 46}
{2, 3, 47} {2, 3, 48} {2, 3, 49} {2, 3, 50} {2, 3, 51} {2, 3, 52} {2, 3, 53} {2, 3, 54} {2, 3, 55} {2, 3, 56} {2, 3, 57} {2, 3, 58}

TABLE 3A-continued

{2, 3, 59} {2, 3, 60} {2, 3, 61} {2, 3, 62} {2, 3, 63} {2, 3, 64} {2, 3, 65} {2, 3, 66} {2, 4, 5} {2, 4, 6} {2, 4, 7} {2, 4, 8} {2, 4, 9}
{2, 4, 10} {2, 4, 11} {2, 4, 12} {2, 4, 13} {2, 4, 14} {2, 4, 15} {2, 4, 16} {2, 4, 17} {2, 4, 18} {2, 4, 19} {2, 4, 20} {2, 4, 21}
{2, 4, 22} {2, 4, 23} {2, 4, 24} {2, 4, 25} {2, 4, 26} {2, 4, 27} {2, 4, 28} {2, 4, 29} {2, 4, 30} {2, 4, 31} {2, 4, 32} {2, 4, 33}
{2, 4, 34} {2, 4, 35} {2, 4, 36} {2, 4, 37} {2, 4, 38} {2, 4, 39} {2, 4, 40} {2, 4, 41} {2, 4, 42} {2, 4, 43} {2, 4, 44} {2, 4, 45}
{2, 4, 46} {2, 4, 47} {2, 4, 48} {2, 4, 49} {2, 4, 50} {2, 4, 51} {2, 4, 52} {2, 4, 53} {2, 4, 54} {2, 4, 55} {2, 4, 56} {2, 4, 57}
{2, 4, 58} {2, 4, 59} {2, 4, 60} {2, 4, 61} {2, 4, 62} {2, 4, 63} {2, 4, 64} {2, 4, 65} {2, 4, 66} {2, 5, 6} {2, 5, 7} {2, 5, 8} {2, 5, 9}
{2, 5, 10} {2, 5, 11} {2, 5, 12} {2, 5, 13} {2, 5, 14} {2, 5, 15} {2, 5, 16} {2, 5, 17} {2, 5, 18} {2, 5, 19} {2, 5, 20} {2, 5, 21}
{2, 5, 22} {2, 5, 23} {2, 5, 24} {2, 5, 25} {2, 5, 26} {2, 5, 27} {2, 5, 28} {2, 5, 29} {2, 5, 30} {2, 5, 31} {2, 5, 32} {2, 5, 33}
{2, 5, 34} {2, 5, 35} {2, 5, 36} {2, 5, 37} {2, 5, 38} {2, 5, 39} {2, 5, 40} {2, 5, 41} {2, 5, 42} {2, 5, 43} {2, 5, 44} {2, 5, 45}
{2, 5, 46} {2, 5, 47} {2, 5, 48} {2, 5, 49} {2, 5, 50} {2, 5, 51} {2, 5, 52} {2, 5, 53} {2, 5, 54} {2, 5, 55} {2, 5, 56} {2, 5, 57}
{2, 5, 58} {2, 5, 59} {2, 5, 60} {2, 5, 61} {2, 5, 62} {2, 5, 63} {2, 5, 64} {2, 5, 65} {2, 5, 66} {2, 6, 7} {2, 6, 8} {2, 6, 9} {2, 6, 10}
{2, 6, 11} {2, 6, 12} {2, 6, 13} {2, 6, 14} {2, 6, 15} {2, 6, 16} {2, 6, 17} {2, 6, 18} {2, 6, 19} {2, 6, 20} {2, 6, 21} {2, 6, 22}
{2, 6, 23} {2, 6, 24} {2, 6, 25} {2, 6, 26} {2, 6, 27} {2, 6, 28} {2, 6, 29} {2, 6, 30} {2, 6, 31} {2, 6, 32} {2, 6, 33} {2, 6, 34}
{2, 6, 35} {2, 6, 36} {2, 6, 37} {2, 6, 38} {2, 6, 39} {2, 6, 40} {2, 6, 41} {2, 6, 42} {2, 6, 43} {2, 6, 44} {2, 6, 45} {2, 6, 46}
{2, 6, 47} {2, 6, 48} {2, 6, 49} {2, 6, 50} {2, 6, 51} {2, 6, 52} {2, 6, 53} {2, 6, 54} {2, 6, 55} {2, 6, 56} {2, 6, 57} {2, 6, 58}
{2, 6, 59} {2, 6, 60} {2, 6, 61} {2, 6, 62} {2, 6, 63} {2, 6, 64} {2, 6, 65} {2, 6, 66} {2, 7, 8} {2, 7, 9} {2, 7, 10} {2, 7, 11}
{2, 7, 12} {2, 7, 13} {2, 7, 14} {2, 7, 15} {2, 7, 16} {2, 7, 17} {2, 7, 18} {2, 7, 19} {2, 7, 20} {2, 7, 21} {2, 7, 22} {2, 7, 23}
{2, 7, 24} {2, 7, 25} {2, 7, 26} {2, 7, 27} {2, 7, 28} {2, 7, 29} {2, 7, 30} {2, 7, 31} {2, 7, 32} {2, 7, 33} {2, 7, 34} {2, 7, 35}
{2, 7, 36} {2, 7, 37} {2, 7, 38} {2, 7, 39} {2, 7, 40} {2, 7, 41} {2, 7, 42} {2, 7, 43} {2, 7, 44} {2, 7, 45} {2, 7, 46} {2, 7, 47}
{2, 7, 48} {2, 7, 49} {2, 7, 50} {2, 7, 51} {2, 7, 52} {2, 7, 53} {2, 7, 54} {2, 7, 55} {2, 7, 56} {2, 7, 57} {2, 7, 58} {2, 7, 59}
{2, 7, 60} {2, 7, 61} {2, 7, 62} {2, 7, 63} {2, 7, 64} {2, 7, 65} {2, 7, 66} {2, 8, 9} {2, 8, 10} {2, 8, 11} {2, 8, 12} {2, 8, 13}
{2, 8, 14} {2, 8, 15} {2, 8, 16} {2, 8, 17} {2, 8, 18} {2, 8, 19} {2, 8, 20} {2, 8, 21} {2, 8, 22} {2, 8, 23} {2, 8, 24} {2, 8, 25}
{2, 8, 26} {2, 8, 27} {2, 8, 28} {2, 8, 29} {2, 8, 30} {2, 8, 31} {2, 8, 32} {2, 8, 33} {2, 8, 34} {2, 8, 35} {2, 8, 36} {2, 8, 37}
{2, 8, 38} {2, 8, 39} {2, 8, 40} {2, 8, 41} {2, 8, 42} {2, 8, 43} {2, 8, 44} {2, 8, 45} {2, 8, 46} {2, 8, 47} {2, 8, 48} {2, 8, 49}
{2, 8, 50} {2, 8, 51} {2, 8, 52} {2, 8, 53} {2, 8, 54} {2, 8, 55} {2, 8, 56} {2, 8, 57} {2, 8, 58} {2, 8, 59} {2, 8, 60} {2, 8, 61}
{2, 8, 62} {2, 8, 63} {2, 8, 64} {2, 8, 65} {2, 8, 66} {2, 9, 10} {2, 9, 11} {2, 9, 12} {2, 9, 13} {2, 9, 14} {2, 9, 15} {2, 9, 16}
{2, 9, 17} {2, 9, 18} {2, 9, 19} {2, 9, 20} {2, 9, 21} {2, 9, 22} {2, 9, 23} {2, 9, 24} {2, 9, 25} {2, 9, 26} {2, 9, 27} {2, 9, 28}
{2, 9, 29} {2, 9, 30} {2, 9, 31} {2, 9, 32} {2, 9, 33} {2, 9, 34} {2, 9, 35} {2, 9, 36} {2, 9, 37} {2, 9, 38} {2, 9, 39} {2, 9, 40}
{2, 9, 41} {2, 9, 42} {2, 9, 43} {2, 9, 44} {2, 9, 45} {2, 9, 46} {2, 9, 47} {2, 9, 48} {2, 9, 49} {2, 9, 50} {2, 9, 51} {2, 9, 52}
{2, 9, 53} {2, 9, 54} {2, 9, 55} {2, 9, 56} {2, 9, 57} {2, 9, 58} {2, 9, 59} {2, 9, 60} {2, 9, 61} {2, 9, 62} {2, 9, 63} {2, 9, 64}
{2, 9, 65} {2, 9, 66} {2, 10, 11} {2, 10, 12} {2, 10, 13} {2, 10, 14} {2, 10, 15} {2, 10, 16} {2, 10, 17} {2, 10, 18} {2, 10, 19}
{2, 10, 20} {2, 10, 21} {2, 10, 22} {2, 10, 23} {2, 10, 24} {2, 10, 25} {2, 10, 26} {2, 10, 27} {2, 10, 28} {2, 10, 29}
{2, 10, 30} {2, 10, 31} {2, 10, 32} {2, 10, 33} {2, 10, 34} {2, 10, 35} {2, 10, 36} {2, 10, 37} {2, 10, 38} {2, 10, 39}
{2, 10, 40} {2, 10, 41} {2, 10, 42} {2, 10, 43} {2, 10, 44} {2, 10, 45} {2, 10, 46} {2, 10, 47} {2, 10, 48} {2, 10, 49}
{2, 10, 50} {2, 10, 51} {2, 10, 52} {2, 10, 53} {2, 10, 54} {2, 10, 55} {2, 10, 56} {2, 10, 57} {2, 10, 58} {2, 10, 59}
{2, 10, 60} {2, 10, 61} {2, 10, 62} {2, 10, 63} {2, 10, 64} {2, 10, 65} {2, 10, 66} {2, 11, 12} {2, 11, 13} {2, 11, 14}
{2, 11, 15} {2, 11, 16} {2, 11, 17} {2, 11, 18} {2, 11, 19} {2, 11, 20} {2, 11, 21} {2, 11, 22} {2, 11, 23} {2, 11, 24}
{2, 11, 25} {2, 11, 26} {2, 11, 27} {2, 11, 28} {2, 11, 29} {2, 11, 30} {2, 11, 31} {2, 11, 32} {2, 11, 33} {2, 11, 34}
{2, 11, 35} {2, 11, 36} {2, 11, 37} {2, 11, 38} {2, 11, 39} {2, 11, 40} {2, 11, 41} {2, 11, 42} {2, 11, 43} {2, 11, 44}
{2, 11, 45} {2, 11, 46} {2, 11, 47} {2, 11, 48} {2, 11, 49} {2, 11, 50} {2, 11, 51} {2, 11, 52} {2, 11, 53} {2, 11, 54}
{2, 11, 55} {2, 11, 56} {2, 11, 57} {2, 11, 58} {2, 11, 59} {2, 11, 60} {2, 11, 61} {2, 11, 62} {2, 11, 63} {2, 11, 64}
{2, 11, 65} {2, 11, 66} {2, 12, 13} {2, 12, 14} {2, 12, 15} {2, 12, 16} {2, 12, 17} {2, 12, 18} {2, 12, 19} {2, 12, 20}
{2, 12, 21} {2, 12, 22} {2, 12, 23} {2, 12, 24} {2, 12, 25} {2, 12, 26} {2, 12, 27} {2, 12, 28} {2, 12, 29} {2, 12, 30}
{2, 12, 31} {2, 12, 32} {2, 12, 33} {2, 12, 34} {2, 12, 35} {2, 12, 36} {2, 12, 37} {2, 12, 38} {2, 12, 39} {2, 12, 40}
{2, 12, 41} {2, 12, 42} {2, 12, 43} {2, 12, 44} {2, 12, 45} {2, 12, 46} {2, 12, 47} {2, 12, 48} {2, 12, 49} {2, 12, 50}
{2, 12, 51} {2, 12, 52} {2, 12, 53} {2, 12, 54} {2, 12, 55} {2, 12, 56} {2, 12, 57} {2, 12, 58} {2, 12, 59} {2, 12, 60}
{2, 12, 61} {2, 12, 62} {2, 12, 63} {2, 12, 64} {2, 12, 65} {2, 12, 66} {2, 13, 14} {2, 13, 15} {2, 13, 16} {2, 13, 17}
{2, 13, 18} {2, 13, 19} {2, 13, 20} {2, 13, 21} {2, 13, 22} {2, 13, 23} {2, 13, 24} {2, 13, 25} {2, 13, 26} {2, 13, 27}
{2, 13, 28} {2, 13, 29} {2, 13, 30} {2, 13, 31} {2, 13, 32} {2, 13, 33} {2, 13, 34} {2, 13, 35} {2, 13, 36} {2, 13, 37}
{2, 13, 38} {2, 13, 39} {2, 13, 40} {2, 13, 41} {2, 13, 42} {2, 13, 43} {2, 13, 44} {2, 13, 45} {2, 13, 46} {2, 13, 47}
{2, 13, 48} {2, 13, 49} {2, 13, 50} {2, 13, 51} {2, 13, 52} {2, 13, 53} {2, 13, 54} {2, 13, 55} {2, 13, 56} {2, 13, 57}
{2, 13, 58} {2, 13, 59} {2, 13, 60} {2, 13, 61} {2, 13, 62} {2, 13, 63} {2, 13, 64} {2, 13, 65} {2, 13, 66} {2, 14, 15}
{2, 14, 16} {2, 14, 17} {2, 14, 18} {2, 14, 19} {2, 14, 20} {2, 14, 21} {2, 14, 22} {2, 14, 23} {2, 14, 24} {2, 14, 25}
{2, 14, 26} {2, 14, 27} {2, 14, 28} {2, 14, 29} {2, 14, 30} {2, 14, 31} {2, 14, 32} {2, 14, 33} {2, 14, 34} {2, 14, 35}
{2, 14, 36} {2, 14, 37} {2, 14, 38} {2, 14, 39} {2, 14, 40} {2, 14, 41} {2, 14, 42} {2, 14, 43} {2, 14, 44} {2, 14, 45}
{2, 14, 46} {2, 14, 47} {2, 14, 48} {2, 14, 49} {2, 14, 50} {2, 14, 51} {2, 14, 52} {2, 14, 53} {2, 14, 54} {2, 14, 55}
{2, 14, 56} {2, 14, 57} {2, 14, 58} {2, 14, 59} {2, 14, 60} {2, 14, 61} {2, 14, 62} {2, 14, 63} {2, 14, 64} {2, 14, 65}
{2, 14, 66} {2, 15, 16} {2, 15, 17} {2, 15, 18} {2, 15, 19} {2, 15, 20} {2, 15, 21} {2, 15, 22} {2, 15, 23} {2, 15, 24}
{2, 15, 25} {2, 15, 26} {2, 15, 27} {2, 15, 28} {2, 15, 29} {2, 15, 30} {2, 15, 31} {2, 15, 32} {2, 15, 33} {2, 15, 34}
{2, 15, 35} {2, 15, 36} {2, 15, 37} {2, 15, 38} {2, 15, 39} {2, 15, 40} {2, 15, 41} {2, 15, 42} {2, 15, 43} {2, 15, 44}
{2, 15, 45} {2, 15, 46} {2, 15, 47} {2, 15, 48} {2, 15, 49} {2, 15, 50} {2, 15, 51} {2, 15, 52} {2, 15, 53} {2, 15, 54}
{2, 15, 55} {2, 15, 56} {2, 15, 57} {2, 15, 58} {2, 15, 59} {2, 15, 60} {2, 15, 61} {2, 15, 62} {2, 15, 63} {2, 15, 64}
{2, 15, 65} {2, 15, 66} {2, 16, 17} {2, 16, 18} {2, 16, 19} {2, 16, 20} {2, 16, 21} {2, 16, 22} {2, 16, 23} {2, 16, 24}
{2, 16, 25} {2, 16, 26} {2, 16, 27} {2, 16, 28} {2, 16, 29} {2, 16, 30} {2, 16, 31} {2, 16, 32} {2, 16, 33} {2, 16, 34}
{2, 16, 35} {2, 16, 36} {2, 16, 37} {2, 16, 38} {2, 16, 39} {2, 16, 40} {2, 16, 41} {2, 16, 42} {2, 16, 43} {2, 16, 44}
{2, 16, 45} {2, 16, 46} {2, 16, 47} {2, 16, 48} {2, 16, 49} {2, 16, 50} {2, 16, 51} {2, 16, 52} {2, 16, 53} {2, 16, 54}
{2, 16, 55} {2, 16, 56} {2, 16, 57} {2, 16, 58} {2, 16, 59} {2, 16, 60} {2, 16, 61} {2, 16, 62} {2, 16, 63} {2, 16, 64}
{2, 16, 65} {2, 16, 66} {2, 17, 18} {2, 17, 19} {2, 17, 20} {2, 17, 21} {2, 17, 22} {2, 17, 23} {2, 17, 24} {2, 17, 25}
{2, 17, 26} {2, 17, 27} {2, 17, 28} {2, 17, 29} {2, 17, 30} {2, 17, 31} {2, 17, 32} {2, 17, 33} {2, 17, 34} {2, 17, 35}
{2, 17, 36} {2, 17, 37} {2, 17, 38} {2, 17, 39} {2, 17, 40} {2, 17, 41} {2, 17, 42} {2, 17, 43} {2, 17, 44} {2, 17, 45}
{2, 17, 46} {2, 17, 47} {2, 17, 48} {2, 17, 49} {2, 17, 50} {2, 17, 51} {2, 17, 52} {2, 17, 53} {2, 17, 54} {2, 17, 55}
{2, 17, 56} {2, 17, 57} {2, 17, 58} {2, 17, 59} {2, 17, 60} {2, 17, 61} {2, 17, 62} {2, 17, 63} {2, 17, 64} {2, 17, 65}
{2, 17, 66} {2, 18, 19} {2, 18, 20} {2, 18, 21} {2, 18, 22} {2, 18, 23} {2, 18, 24} {2, 18, 25} {2, 18, 26} {2, 18, 27}
{2, 18, 28} {2, 18, 29} {2, 18, 30} {2, 18, 31} {2, 18, 32} {2, 18, 33} {2, 18, 34} {2, 18, 35} {2, 18, 36} {2, 18, 37}
{2, 18, 38} {2, 18, 39} {2, 18, 40} {2, 18, 41} {2, 18, 42} {2, 18, 43} {2, 18, 44} {2, 18, 45} {2, 18, 46} {2, 18, 47}
{2, 18, 48} {2, 18, 49} {2, 18, 50} {2, 18, 51} {2, 18, 52} {2, 18, 53} {2, 18, 54} {2, 18, 55} {2, 18, 56} {2, 18, 57}
{2, 18, 58} {2, 18, 59} {2, 18, 60} {2, 18, 61} {2, 18, 62} {2, 18, 63} {2, 18, 64} {2, 18, 65} {2, 18, 66} {2, 19, 20}
{2, 19, 21} {2, 19, 22} {2, 19, 23} {2, 19, 24} {2, 19, 25} {2, 19, 26} {2, 19, 27} {2, 19, 28} {2, 19, 29} {2, 19, 30}
{2, 19, 31} {2, 19, 32} {2, 19, 33} {2, 19, 34} {2, 19, 35} {2, 19, 36} {2, 19, 37} {2, 19, 38} {2, 19, 39} {2, 19, 40}
{2, 19, 41} {2, 19, 42} {2, 19, 43} {2, 19, 44} {2, 19, 45} {2, 19, 46} {2, 19, 47} {2, 19, 48} {2, 19, 49} {2, 19, 50}

TABLE 3A-continued

{2, 19, 51} {2, 19, 52} {2, 19, 53} {2, 19, 54} {2, 19, 55} {2, 19, 56} {2, 19, 57} {2, 19, 58} {2, 19, 59} {2, 19, 60}
{2, 19, 61} {2, 19, 62} {2, 19, 63} {2, 19, 64} {2, 19, 65} {2, 19, 66} {2, 20, 21} {2, 20, 22} {2, 20, 23} {2, 20, 24}
{2, 20, 25} {2, 20, 26} {2, 20, 27} {2, 20, 28} {2, 20, 29} {2, 20, 30} {2, 20, 31} {2, 20, 32} {2, 20, 33} {2, 20, 34}
{2, 20, 35} {2, 20, 36} {2, 20, 37} {2, 20, 38} {2, 20, 39} {2, 20, 40} {2, 20, 41} {2, 20, 42} {2, 20, 43} {2, 20, 44}
{2, 20, 45} {2, 20, 46} {2, 20, 47} {2, 20, 48} {2, 20, 49} {2, 20, 50} {2, 20, 51} {2, 20, 52} {2, 20, 53} {2, 20, 54}
{2, 20, 55} {2, 20, 56} {2, 20, 57} {2, 20, 58} {2, 20, 59} {2, 20, 60} {2, 20, 61} {2, 20, 62} {2, 20, 63} {2, 20, 64}
{2, 20, 65} {2, 20, 66} {2, 21, 22} {2, 21, 23} {2, 21, 24} {2, 21, 25} {2, 21, 26} {2, 21, 27} {2, 21, 28} {2, 21, 29}
{2, 21, 30} {2, 21, 31} {2, 21, 32} {2, 21, 33} {2, 21, 34} {2, 21, 35} {2, 21, 36} {2, 21, 37} {2, 21, 38} {2, 21, 39}
{2, 21, 40} {2, 21, 41} {2, 21, 42} {2, 21, 43} {2, 21, 44} {2, 21, 45} {2, 21, 46} {2, 21, 47} {2, 21, 48} {2, 21, 49}
{2, 21, 50} {2, 21, 51} {2, 21, 52} {2, 21, 53} {2, 21, 54} {2, 21, 55} {2, 21, 56} {2, 21, 57} {2, 21, 58} {2, 21, 59}
{2, 21, 60} {2, 21, 61} {2, 21, 62} {2, 21, 63} {2, 21, 64} {2, 21, 65} {2, 21, 66} {2, 22, 23} {2, 22, 24} {2, 22, 25}
{2, 22, 26} {2, 22, 27} {2, 22, 28} {2, 22, 29} {2, 22, 30} {2, 22, 31} {2, 22, 32} {2, 22, 33} {2, 22, 34} {2, 22, 35}
{2, 22, 36} {2, 22, 37} {2, 22, 38} {2, 22, 39} {2, 22, 40} {2, 22, 41} {2, 22, 42} {2, 22, 43} {2, 22, 44} {2, 22, 45}
{2, 22, 46} {2, 22, 47} {2, 22, 48} {2, 22, 49} {2, 22, 50} {2, 22, 51} {2, 22, 52} {2, 22, 53} {2, 22, 54} {2, 22, 55}
{2, 22, 56} {2, 22, 57} {2, 22, 58} {2, 22, 59} {2, 22, 60} {2, 22, 61} {2, 22, 62} {2, 22, 63} {2, 22, 64} {2, 22, 65}
{2, 22, 66} {2, 23, 24} {2, 23, 25} {2, 23, 26} {2, 23, 27} {2, 23, 28} {2, 23, 29} {2, 23, 30} {2, 23, 31} {2, 23, 32}
{2, 23, 33} {2, 23, 34} {2, 23, 35} {2, 23, 36} {2, 23, 37} {2, 23, 38} {2, 23, 39} {2, 23, 40} {2, 23, 41} {2, 23, 42}
{2, 23, 43} {2, 23, 44} {2, 23, 45} {2, 23, 46} {2, 23, 47} {2, 23, 48} {2, 23, 49} {2, 23, 50} {2, 23, 51} {2, 23, 52}
{2, 23, 53} {2, 23, 54} {2, 23, 55} {2, 23, 56} {2, 23, 57} {2, 23, 58} {2, 23, 59} {2, 23, 60} {2, 23, 61} {2, 23, 62}
{2, 23, 63} {2, 23, 64} {2, 23, 65} {2, 23, 66} {2, 24, 25} {2, 24, 26} {2, 24, 27} {2, 24, 28} {2, 24, 29} {2, 24, 30}
{2, 24, 31} {2, 24, 32} {2, 24, 33} {2, 24, 34} {2, 24, 35} {2, 24, 36} {2, 24, 37} {2, 24, 38} {2, 24, 39} {2, 24, 40}
{2, 24, 41} {2, 24, 42} {2, 24, 43} {2, 24, 44} {2, 24, 45} {2, 24, 46} {2, 24, 47} {2, 24, 48} {2, 24, 49} {2, 24, 50}
{2, 24, 51} {2, 24, 52} {2, 24, 53} {2, 24, 54} {2, 24, 55} {2, 24, 56} {2, 24, 57} {2, 24, 58} {2, 24, 59} {2, 24, 60}
{2, 24, 61} {2, 24, 62} {2, 24, 63} {2, 24, 64} {2, 24, 65} {2, 24, 66} {2, 25, 26} {2, 25, 27} {2, 25, 28} {2, 25, 29}
{2, 25, 30} {2, 25, 31} {2, 25, 32} {2, 25, 33} {2, 25, 34} {2, 25, 35} {2, 25, 36} {2, 25, 37} {2, 25, 38} {2, 25, 39}
{2, 25, 40} {2, 25, 41} {2, 25, 42} {2, 25, 43} {2, 25, 44} {2, 25, 45} {2, 25, 46} {2, 25, 47} {2, 25, 48} {2, 25, 49}
{2, 25, 50} {2, 25, 51} {2, 25, 52} {2, 25, 53} {2, 25, 54} {2, 25, 55} {2, 25, 56} {2, 25, 57} {2, 25, 58} {2, 25, 59}
{2, 25, 60} {2, 25, 61} {2, 25, 62} {2, 25, 63} {2, 25, 64} {2, 25, 65} {2, 25, 66} {2, 26, 27} {2, 26, 28} {2, 26, 29}
{2, 26, 30} {2, 26, 31} {2, 26, 32} {2, 26, 33} {2, 26, 34} {2, 26, 35} {2, 26, 36} {2, 26, 37} {2, 26, 38} {2, 26, 39}
{2, 26, 40} {2, 26, 41} {2, 26, 42} {2, 26, 43} {2, 26, 44} {2, 26, 45} {2, 26, 46} {2, 26, 47} {2, 26, 48} {2, 26, 49}
{2, 26, 50} {2, 26, 51} {2, 26, 52} {2, 26, 53} {2, 26, 54} {2, 26, 55} {2, 26, 56} {2, 26, 57} {2, 26, 58} {2, 26, 59}
{2, 26, 60} {2, 26, 61} {2, 26, 62} {2, 26, 63} {2, 26, 64} {2, 26, 65} {2, 26, 66} {2, 27, 28} {2, 27, 29} {2, 27, 30}
{2, 27, 31} {2, 27, 32} {2, 27, 33} {2, 27, 34} {2, 27, 35} {2, 27, 36} {2, 27, 37} {2, 27, 38} {2, 27, 39} {2, 27, 40}
{2, 27, 41} {2, 27, 42} {2, 27, 43} {2, 27, 44} {2, 27, 45} {2, 27, 46} {2, 27, 47} {2, 27, 48} {2, 27, 49} {2, 27, 50}
{2, 27, 51} {2, 27, 52} {2, 27, 53} {2, 27, 54} {2, 27, 55} {2, 27, 56} {2, 27, 57} {2, 27, 58} {2, 27, 59} {2, 27, 60}
{2, 27, 61} {2, 27, 62} {2, 27, 63} {2, 27, 64} {2, 27, 65} {2, 27, 66} {2, 28, 29} {2, 28, 30} {2, 28, 31} {2, 28, 32}
{2, 28, 33} {2, 28, 34} {2, 28, 35} {2, 28, 36} {2, 28, 37} {2, 28, 38} {2, 28, 39} {2, 28, 40} {2, 28, 41} {2, 28, 42}
{2, 28, 43} {2, 28, 44} {2, 28, 45} {2, 28, 46} {2, 28, 47} {2, 28, 48} {2, 28, 49} {2, 28, 50} {2, 28, 51} {2, 28, 52}
{2, 28, 53} {2, 28, 54} {2, 28, 55} {2, 28, 56} {2, 28, 57} {2, 28, 58} {2, 28, 59} {2, 28, 60} {2, 28, 61} {2, 28, 62}
{2, 28, 63} {2, 28, 64} {2, 28, 65} {2, 28, 66} {2, 29, 30} {2, 29, 31} {2, 29, 32} {2, 29, 33} {2, 29, 34} {2, 29, 35}
{2, 29, 36} {2, 29, 37} {2, 29, 38} {2, 29, 39} {2, 29, 40} {2, 29, 41} {2, 29, 42} {2, 29, 43} {2, 29, 44} {2, 29, 45}
{2, 29, 46} {2, 29, 47} {2, 29, 48} {2, 29, 49} {2, 29, 50} {2, 29, 51} {2, 29, 52} {2, 29, 53} {2, 29, 54} {2, 29, 55}
{2, 29, 56} {2, 29, 57} {2, 29, 58} {2, 29, 59} {2, 29, 60} {2, 29, 61} {2, 29, 62} {2, 29, 63} {2, 29, 64} {2, 29, 65}
{2, 29, 66} {2, 30, 31} {2, 30, 32} {2, 30, 33} {2, 30, 34} {2, 30, 35} {2, 30, 36} {2, 30, 37} {2, 30, 38} {2, 30, 39}
{2, 30, 40} {2, 30, 41} {2, 30, 42} {2, 30, 43} {2, 30, 44} {2, 30, 45} {2, 30, 46} {2, 30, 47} {2, 30, 48} {2, 30, 49}
{2, 30, 50} {2, 30, 51} {2, 30, 52} {2, 30, 53} {2, 30, 54} {2, 30, 55} {2, 30, 56} {2, 30, 57} {2, 30, 58} {2, 30, 59}
{2, 30, 60} {2, 30, 61} {2, 30, 62} {2, 30, 63} {2, 30, 64} {2, 30, 65} {2, 30, 66} {2, 31, 32} {2, 31, 33} {2, 31, 34}
{2, 31, 35} {2, 31, 36} {2, 31, 37} {2, 31, 38} {2, 31, 39} {2, 31, 40} {2, 31, 41} {2, 31, 42} {2, 31, 43} {2, 31, 44}
{2, 31, 45} {2, 31, 46} {2, 31, 47} {2, 31, 48} {2, 31, 49} {2, 31, 50} {2, 31, 51} {2, 31, 52} {2, 31, 53} {2, 31, 54}
{2, 31, 55} {2, 31, 56} {2, 31, 57} {2, 31, 58} {2, 31, 59} {2, 31, 60} {2, 31, 61} {2, 31, 62} {2, 31, 63} {2, 31, 64}
{2, 31, 65} {2, 31, 66} {2, 32, 33} {2, 32, 34} {2, 32, 35} {2, 32, 36} {2, 32, 37} {2, 32, 38} {2, 32, 39} {2, 32, 40}
{2, 32, 41} {2, 32, 42} {2, 32, 43} {2, 32, 44} {2, 32, 45} {2, 32, 46} {2, 32, 47} {2, 32, 48} {2, 32, 49} {2, 32, 50}
{2, 32, 51} {2, 32, 52} {2, 32, 53} {2, 32, 54} {2, 32, 55} {2, 32, 56} {2, 32, 57} {2, 32, 58} {2, 32, 59} {2, 32, 60}
{2, 32, 61} {2, 32, 62} {2, 32, 63} {2, 32, 64} {2, 32, 65} {2, 32, 66} {2, 33, 34} {2, 33, 35} {2, 33, 36} {2, 33, 37}
{2, 33, 38} {2, 33, 39} {2, 33, 40} {2, 33, 41} {2, 33, 42} {2, 33, 43} {2, 33, 44} {2, 33, 45} {2, 33, 46} {2, 33, 47}
{2, 33, 48} {2, 33, 49} {2, 33, 50} {2, 33, 51} {2, 33, 52} {2, 33, 53} {2, 33, 54} {2, 33, 55} {2, 33, 56} {2, 33, 57}
{2, 33, 58} {2, 33, 59} {2, 33, 60} {2, 33, 61} {2, 33, 62} {2, 33, 63} {2, 33, 64} {2, 33, 65} {2, 33, 66} {2, 34, 35}
{2, 34, 36} {2, 34, 37} {2, 34, 38} {2, 34, 39} {2, 34, 40} {2, 34, 41} {2, 34, 42} {2, 34, 43} {2, 34, 44} {2, 34, 45}
{2, 34, 46} {2, 34, 47} {2, 34, 48} {2, 34, 49} {2, 34, 50} {2, 34, 51} {2, 34, 52} {2, 34, 53} {2, 34, 54} {2, 34, 55}
{2, 34, 56} {2, 34, 57} {2, 34, 58} {2, 34, 59} {2, 34, 60} {2, 34, 61} {2, 34, 62} {2, 34, 63} {2, 34, 64} {2, 34, 65}
{2, 34, 66} {2, 35, 36} {2, 35, 37} {2, 35, 38} {2, 35, 39} {2, 35, 40} {2, 35, 41} {2, 35, 42} {2, 35, 43} {2, 35, 44}
{2, 35, 45} {2, 35, 46} {2, 35, 47} {2, 35, 48} {2, 35, 49} {2, 35, 50} {2, 35, 51} {2, 35, 52} {2, 35, 53} {2, 35, 54}
{2, 35, 55} {2, 35, 56} {2, 35, 57} {2, 35, 58} {2, 35, 59} {2, 35, 60} {2, 35, 61} {2, 35, 62} {2, 35, 63} {2, 35, 64}
{2, 35, 65} {2, 35, 66} {2, 36, 37} {2, 36, 38} {2, 36, 39} {2, 36, 40} {2, 36, 41} {2, 36, 42} {2, 36, 43} {2, 36, 44}
{2, 36, 45} {2, 36, 46} {2, 36, 47} {2, 36, 48} {2, 36, 49} {2, 36, 50} {2, 36, 51} {2, 36, 52} {2, 36, 53} {2, 36, 54}
{2, 36, 55} {2, 36, 56} {2, 36, 57} {2, 36, 58} {2, 36, 59} {2, 36, 60} {2, 36, 61} {2, 36, 62} {2, 36, 63} {2, 36, 64}
{2, 36, 65} {2, 36, 66} {2, 37, 38} {2, 37, 39} {2, 37, 40} {2, 37, 41} {2, 37, 42} {2, 37, 43} {2, 37, 44} {2, 37, 45}
{2, 37, 46} {2, 37, 47} {2, 37, 48} {2, 37, 49} {2, 37, 50} {2, 37, 51} {2, 37, 52} {2, 37, 53} {2, 37, 54} {2, 37, 55}
{2, 37, 56} {2, 37, 57} {2, 37, 58} {2, 37, 59} {2, 37, 60} {2, 37, 61} {2, 37, 62} {2, 37, 63} {2, 37, 64} {2, 37, 65}
{2, 37, 66} {2, 38, 39} {2, 38, 40} {2, 38, 41} {2, 38, 42} {2, 38, 43} {2, 38, 44} {2, 38, 45} {2, 38, 46} {2, 38, 47}
{2, 38, 48} {2, 38, 49} {2, 38, 50} {2, 38, 51} {2, 38, 52} {2, 38, 53} {2, 38, 54} {2, 38, 55} {2, 38, 56} {2, 38, 57}
{2, 38, 58} {2, 38, 59} {2, 38, 60} {2, 38, 61} {2, 38, 62} {2, 38, 63} {2, 38, 64} {2, 38, 65} {2, 38, 66} {2, 39, 40}
{2, 39, 41} {2, 39, 42} {2, 39, 43} {2, 39, 44} {2, 39, 45} {2, 39, 46} {2, 39, 47} {2, 39, 48} {2, 39, 49} {2, 39, 50}
{2, 39, 51} {2, 39, 52} {2, 39, 53} {2, 39, 54} {2, 39, 55} {2, 39, 56} {2, 39, 57} {2, 39, 58} {2, 39, 59} {2, 39, 60}
{2, 39, 61} {2, 39, 62} {2, 39, 63} {2, 39, 64} {2, 39, 65} {2, 39, 66} {2, 40, 41} {2, 40, 42} {2, 40, 43} {2, 40, 44}
{2, 40, 45} {2, 40, 46} {2, 40, 47} {2, 40, 48} {2, 40, 49} {2, 40, 50} {2, 40, 51} {2, 40, 52} {2, 40, 53} {2, 40, 54}
{2, 40, 55} {2, 40, 56} {2, 40, 57} {2, 40, 58} {2, 40, 59} {2, 40, 60} {2, 40, 61} {2, 40, 62} {2, 40, 63} {2, 40, 64}
{2, 40, 65} {2, 40, 66} {2, 41, 42} {2, 41, 43} {2, 41, 44} {2, 41, 45} {2, 41, 46} {2, 41, 47} {2, 41, 48} {2, 41, 49}
{2, 41, 50} {2, 41, 51} {2, 41, 52} {2, 41, 53} {2, 41, 54} {2, 41, 55} {2, 41, 56} {2, 41, 57} {2, 41, 58} {2, 41, 59}
{2, 41, 60} {2, 41, 61} {2, 41, 62} {2, 41, 63} {2, 41, 64} {2, 41, 65} {2, 41, 66} {2, 42, 43} {2, 42, 44} {2, 42, 45}

TABLE 3A-continued

{2, 42, 46} {2, 42, 47} {2, 42, 48} {2, 42, 49} {2, 42, 50} {2, 42, 51} {2, 42, 52} {2, 42, 53} {2, 42, 54} {2, 42, 55}
{2, 42, 56} {2, 42, 57} {2, 42, 58} {2, 42, 59} {2, 42, 60} {2, 42, 61} {2, 42, 62} {2, 42, 63} {2, 42, 64} {2, 42, 65}
{2, 42, 66} {2, 43, 44} {2, 43, 45} {2, 43, 46} {2, 43, 47} {2, 43, 48} {2, 43, 49} {2, 43, 50} {2, 43, 51} {2, 43, 52}
{2, 43, 53} {2, 43, 54} {2, 43, 55} {2, 43, 56} {2, 43, 57} {2, 43, 58} {2, 43, 59} {2, 43, 60} {2, 43, 61} {2, 43, 62}
{2, 43, 63} {2, 43, 64} {2, 43, 65} {2, 43, 66} {2, 44, 45} {2, 44, 46} {2, 44, 47} {2, 44, 48} {2, 44, 49} {2, 44, 50}
{2, 44, 51} {2, 44, 52} {2, 44, 53} {2, 44, 54} {2, 44, 55} {2, 44, 56} {2, 44, 57} {2, 44, 58} {2, 44, 59} {2, 44, 60}
{2, 44, 61} {2, 44, 62} {2, 44, 63} {2, 44, 64} {2, 44, 65} {2, 44, 66} {2, 45, 46} {2, 45, 47} {2, 45, 48} {2, 45, 49}
{2, 45, 50} {2, 45, 51} {2, 45, 52} {2, 45, 53} {2, 45, 54} {2, 45, 55} {2, 45, 56} {2, 45, 57} {2, 45, 58} {2, 45, 59}
{2, 45, 60} {2, 45, 61} {2, 45, 62} {2, 45, 63} {2, 45, 64} {2, 45, 65} {2, 45, 66} {2, 46, 47} {2, 46, 48} {2, 46, 49}
{2, 46, 50} {2, 46, 51} {2, 46, 52} {2, 46, 53} {2, 46, 54} {2, 46, 55} {2, 46, 56} {2, 46, 57} {2, 46, 58} {2, 46, 59}
{2, 46, 60} {2, 46, 61} {2, 46, 62} {2, 46, 63} {2, 46, 64} {2, 46, 65} {2, 46, 66} {2, 47, 48} {2, 47, 49} {2, 47, 50}
{2, 47, 51} {2, 47, 52} {2, 47, 53} {2, 47, 54} {2, 47, 55} {2, 47, 56} {2, 47, 57} {2, 47, 58} {2, 47, 59} {2, 47, 60}
{2, 47, 61} {2, 47, 62} {2, 47, 63} {2, 47, 64} {2, 47, 65} {2, 47, 66} {2, 48, 49} {2, 48, 50} {2, 48, 51} {2, 48, 52}
{2, 48, 53} {2, 48, 54} {2, 48, 55} {2, 48, 56} {2, 48, 57} {2, 48, 58} {2, 48, 59} {2, 48, 60} {2, 48, 61} {2, 48, 62}
{2, 48, 63} {2, 48, 64} {2, 48, 65} {2, 48, 66} {2, 49, 50} {2, 49, 51} {2, 49, 52} {2, 49, 53} {2, 49, 54} {2, 49, 55}
{2, 49, 56} {2, 49, 57} {2, 49, 58} {2, 49, 59} {2, 49, 60} {2, 49, 61} {2, 49, 62} {2, 49, 63} {2, 49, 64} {2, 49, 65}
{2, 49, 66} {2, 50, 51} {2, 50, 52} {2, 50, 53} {2, 50, 54} {2, 50, 55} {2, 50, 56} {2, 50, 57} {2, 50, 58} {2, 50, 59}
{2, 50, 60} {2, 50, 61} {2, 50, 62} {2, 50, 63} {2, 50, 64} {2, 50, 65} {2, 50, 66} {2, 51, 52} {2, 51, 53} {2, 51, 54}
{2, 51, 55} {2, 51, 56} {2, 51, 57} {2, 51, 58} {2, 51, 59} {2, 51, 60} {2, 51, 61} {2, 51, 62} {2, 51, 63} {2, 51, 64}
{2, 51, 65} {2, 51, 66} {2, 52, 53} {2, 52, 54} {2, 52, 55} {2, 52, 56} {2, 52, 57} {2, 52, 58} {2, 52, 59} {2, 52, 60}
{2, 52, 61} {2, 52, 62} {2, 52, 63} {2, 52, 64} {2, 52, 65} {2, 52, 66} {2, 53, 54} {2, 53, 55} {2, 53, 56} {2, 53, 57}
{2, 53, 58} {2, 53, 59} {2, 53, 60} {2, 53, 61} {2, 53, 62} {2, 53, 63} {2, 53, 64} {2, 53, 65} {2, 53, 66} {2, 54, 55}
{2, 54, 56} {2, 54, 57} {2, 54, 58} {2, 54, 59} {2, 54, 60} {2, 54, 61} {2, 54, 62} {2, 54, 63} {2, 54, 64} {2, 54, 65}
{2, 54, 66} {2, 55, 56} {2, 55, 57} {2, 55, 58} {2, 55, 59} {2, 55, 60} {2, 55, 61} {2, 55, 62} {2, 55, 63} {2, 55, 64}
{2, 55, 65} {2, 55, 66} {2, 56, 57} {2, 56, 58} {2, 56, 59} {2, 56, 60} {2, 56, 61} {2, 56, 62} {2, 56, 63} {2, 56, 64}
{2, 56, 65} {2, 56, 66} {2, 57, 58} {2, 57, 59} {2, 57, 60} {2, 57, 61} {2, 57, 62} {2, 57, 63} {2, 57, 64} {2, 57, 65}
{2, 57, 66} {2, 58, 59} {2, 58, 60} {2, 58, 61} {2, 58, 62} {2, 58, 63} {2, 58, 64} {2, 58, 65} {2, 58, 66} {2, 59, 60}
{2, 59, 61} {2, 59, 62} {2, 59, 63} {2, 59, 64} {2, 59, 65} {2, 59, 66} {2, 60, 61} {2, 60, 62} {2, 60, 63} {2, 60, 64}
{2, 60, 65} {2, 60, 66} {2, 61, 62} {2, 61, 63} {2, 61, 64} {2, 61, 65} {2, 61, 66} {2, 62, 63} {2, 62, 64} {2, 62, 65}
{2, 62, 66} {2, 63, 64} {2, 63, 65} {2, 63, 66} {2, 64, 65} {2, 64, 66} {2, 65, 66} {3, 4, 5} {3, 4, 6} {3, 4, 7} {3, 4, 8} {3, 4, 9}
{3, 4, 10} {3, 4, 11} {3, 4, 12} {3, 4, 13} {3, 4, 14} {3, 4, 15} {3, 4, 16} {3, 4, 17} {3, 4, 18} {3, 4, 19} {3, 4, 20} {3, 4, 21}
{3, 4, 22} {3, 4, 23} {3, 4, 24} {3, 4, 25} {3, 4, 26} {3, 4, 27} {3, 4, 28} {3, 4, 29} {3, 4, 30} {3, 4, 31} {3, 4, 32} {3, 4, 33}
{3, 4, 34} {3, 4, 35} {3, 4, 36} {3, 4, 37} {3, 4, 38} {3, 4, 39} {3, 4, 40} {3, 4, 41} {3, 4, 42} {3, 4, 43} {3, 4, 44} {3, 4, 45}
{3, 4, 46} {3, 4, 47} {3, 4, 48} {3, 4, 49} {3, 4, 50} {3, 4, 51} {3, 4, 52} {3, 4, 53} {3, 4, 54} {3, 4, 55} {3, 4, 56} {3, 4, 57}
{3, 4, 58} {3, 4, 59} {3, 4, 60} {3, 4, 61} {3, 4, 62} {3, 4, 63} {3, 4, 64} {3, 4, 65} {3, 4, 66} {3, 5, 6} {3, 5, 7} {3, 5, 8} {3, 5, 9}
{3, 5, 10} {3, 5, 11} {3, 5, 12} {3, 5, 13} {3, 5, 14} {3, 5, 15} {3, 5, 16} {3, 5, 17} {3, 5, 18} {3, 5, 19} {3, 5, 20} {3, 5, 21}
{3, 5, 22} {3, 5, 23} {3, 5, 24} {3, 5, 25} {3, 5, 26} {3, 5, 27} {3, 5, 28} {3, 5, 29} {3, 5, 30} {3, 5, 31} {3, 5, 32} {3, 5, 33}
{3, 5, 34} {3, 5, 35} {3, 5, 36} {3, 5, 37} {3, 5, 38} {3, 5, 39} {3, 5, 40} {3, 5, 41} {3, 5, 42} {3, 5, 43} {3, 5, 44} {3, 5, 45}
{3, 5, 46} {3, 5, 47} {3, 5, 48} {3, 5, 49} {3, 5, 50} {3, 5, 51} {3, 5, 52} {3, 5, 53} {3, 5, 54} {3, 5, 55} {3, 5, 56} {3, 5, 57}
{3, 5, 58} {3, 5, 59} {3, 5, 60} {3, 5, 61} {3, 5, 62} {3, 5, 63} {3, 5, 64} {3, 5, 65} {3, 5, 66} {3, 6, 7} {3, 6, 8} {3, 6, 9} {3, 6, 10}
{3, 6, 11} {3, 6, 12} {3, 6, 13} {3, 6, 14} {3, 6, 15} {3, 6, 16} {3, 6, 17} {3, 6, 18} {3, 6, 19} {3, 6, 20} {3, 6, 21} {3, 6, 22}
{3, 6, 23} {3, 6, 24} {3, 6, 25} {3, 6, 26} {3, 6, 27} {3, 6, 28} {3, 6, 29} {3, 6, 30} {3, 6, 31} {3, 6, 32} {3, 6, 33} {3, 6, 34}
{3, 6, 35} {3, 6, 36} {3, 6, 37} {3, 6, 38} {3, 6, 39} {3, 6, 40} {3, 6, 41} {3, 6, 42} {3, 6, 43} {3, 6, 44} {3, 6, 45} {3, 6, 46}
{3, 6, 47} {3, 6, 48} {3, 6, 49} {3, 6, 50} {3, 6, 51} {3, 6, 52} {3, 6, 53} {3, 6, 54} {3, 6, 55} {3, 6, 56} {3, 6, 57} {3, 6, 58}
{3, 6, 59} {3, 6, 60} {3, 6, 61} {3, 6, 62} {3, 6, 63} {3, 6, 64} {3, 6, 65} {3, 6, 66} {3, 7, 8} {3, 7, 9} {3, 7, 10} {3, 7, 11}
{3, 7, 12} {3, 7, 13} {3, 7, 14} {3, 7, 15} {3, 7, 16} {3, 7, 17} {3, 7, 18} {3, 7, 19} {3, 7, 20} {3, 7, 21} {3, 7, 22} {3, 7, 23}
{3, 7, 24} {3, 7, 25} {3, 7, 26} {3, 7, 27} {3, 7, 28} {3, 7, 29} {3, 7, 30} {3, 7, 31} {3, 7, 32} {3, 7, 33} {3, 7, 34} {3, 7, 35}
{3, 7, 36} {3, 7, 37} {3, 7, 38} {3, 7, 39} {3, 7, 40} {3, 7, 41} {3, 7, 42} {3, 7, 43} {3, 7, 44} {3, 7, 45} {3, 7, 46} {3, 7, 47}
{3, 7, 48} {3, 7, 49} {3, 7, 50} {3, 7, 51} {3, 7, 52} {3, 7, 53} {3, 7, 54} {3, 7, 55} {3, 7, 56} {3, 7, 57} {3, 7, 58} {3, 7, 59}
{3, 7, 60} {3, 7, 61} {3, 7, 62} {3, 7, 63} {3, 7, 64} {3, 7, 65} {3, 7, 66} {3, 8, 9} {3, 8, 10} {3, 8, 11} {3, 8, 12} {3, 8, 13}
{3, 8, 14} {3, 8, 15} {3, 8, 16} {3, 8, 17} {3, 8, 18} {3, 8, 19} {3, 8, 20} {3, 8, 21} {3, 8, 22} {3, 8, 23} {3, 8, 24} {3, 8, 25}
{3, 8, 26} {3, 8, 27} {3, 8, 28} {3, 8, 29} {3, 8, 30} {3, 8, 31} {3, 8, 32} {3, 8, 33} {3, 8, 34} {3, 8, 35} {3, 8, 36} {3, 8, 37}
{3, 8, 38} {3, 8, 39} {3, 8, 40} {3, 8, 41} {3, 8, 42} {3, 8, 43} {3, 8, 44} {3, 8, 45} {3, 8, 46} {3, 8, 47} {3, 8, 48} {3, 8, 49}
{3, 8, 50} {3, 8, 51} {3, 8, 52} {3, 8, 53} {3, 8, 54} {3, 8, 55} {3, 8, 56} {3, 8, 57} {3, 8, 58} {3, 8, 59} {3, 8, 60} {3, 8, 61}
{3, 8, 62} {3, 8, 63} {3, 8, 64} {3, 8, 65} {3, 8, 66} {3, 9, 10} {3, 9, 11} {3, 9, 12} {3, 9, 13} {3, 9, 14} {3, 9, 15} {3, 9, 16}
{3, 9, 17} {3, 9, 18} {3, 9, 19} {3, 9, 20} {3, 9, 21} {3, 9, 22} {3, 9, 23} {3, 9, 24} {3, 9, 25} {3, 9, 26} {3, 9, 27} {3, 9, 28}
{3, 9, 29} {3, 9, 30} {3, 9, 31} {3, 9, 32} {3, 9, 33} {3, 9, 34} {3, 9, 35} {3, 9, 36} {3, 9, 37} {3, 9, 38} {3, 9, 39} {3, 9, 40}
{3, 9, 41} {3, 9, 42} {3, 9, 43} {3, 9, 44} {3, 9, 45} {3, 9, 46} {3, 9, 47} {3, 9, 48} {3, 9, 49} {3, 9, 50} {3, 9, 51} {3, 9, 52}
{3, 9, 53} {3, 9, 54} {3, 9, 55} {3, 9, 56} {3, 9, 57} {3, 9, 58} {3, 9, 59} {3, 9, 60} {3, 9, 61} {3, 9, 62} {3, 9, 63} {3, 9, 64}
{3, 9, 65} {3, 9, 66} {3, 10, 11} {3, 10, 12} {3, 10, 13} {3, 10, 14} {3, 10, 15} {3, 10, 16} {3, 10, 17} {3, 10, 18} {3, 10, 19}
{3, 10, 20} {3, 10, 21} {3, 10, 22} {3, 10, 23} {3, 10, 24} {3, 10, 25} {3, 10, 26} {3, 10, 27} {3, 10, 28} {3, 10, 29}
{3, 10, 30} {3, 10, 31} {3, 10, 32} {3, 10, 33} {3, 10, 34} {3, 10, 35} {3, 10, 36} {3, 10, 37} {3, 10, 38} {3, 10, 39}
{3, 10, 40} {3, 10, 41} {3, 10, 42} {3, 10, 43} {3, 10, 44} {3, 10, 45} {3, 10, 46} {3, 10, 47} {3, 10, 48} {3, 10, 49}
{3, 10, 50} {3, 10, 51} {3, 10, 52} {3, 10, 53} {3, 10, 54} {3, 10, 55} {3, 10, 56} {3, 10, 57} {3, 10, 58} {3, 10, 59}
{3, 10, 60} {3, 10, 61} {3, 10, 62} {3, 10, 63} {3, 10, 64} {3, 10, 65} {3, 10, 66} {3, 11, 12} {3, 11, 13} {3, 11, 14}
{3, 11, 15} {3, 11, 16} {3, 11, 17} {3, 11, 18} {3, 11, 19} {3, 11, 20} {3, 11, 21} {3, 11, 22} {3, 11, 23} {3, 11, 24}
{3, 11, 25} {3, 11, 26} {3, 11, 27} {3, 11, 28} {3, 11, 29} {3, 11, 30} {3, 11, 31} {3, 11, 32} {3, 11, 33} {3, 11, 34}
{3, 11, 35} {3, 11, 36} {3, 11, 37} {3, 11, 38} {3, 11, 39} {3, 11, 40} {3, 11, 41} {3, 11, 42} {3, 11, 43} {3, 11, 44}
{3, 11, 45} {3, 11, 46} {3, 11, 47} {3, 11, 48} {3, 11, 49} {3, 11, 50} {3, 11, 51} {3, 11, 52} {3, 11, 53} {3, 11, 54}
{3, 11, 55} {3, 11, 56} {3, 11, 57} {3, 11, 58} {3, 11, 59} {3, 11, 60} {3, 11, 61} {3, 11, 62} {3, 11, 63} {3, 11, 64}
{3, 11, 65} {3, 11, 66} {3, 12, 13} {3, 12, 14} {3, 12, 15} {3, 12, 16} {3, 12, 17} {3, 12, 18} {3, 12, 19} {3, 12, 20}
{3, 12, 21} {3, 12, 22} {3, 12, 23} {3, 12, 24} {3, 12, 25} {3, 12, 26} {3, 12, 27} {3, 12, 28} {3, 12, 29} {3, 12, 30}
{3, 12, 31} {3, 12, 32} {3, 12, 33} {3, 12, 34} {3, 12, 35} {3, 12, 36} {3, 12, 37} {3, 12, 38} {3, 12, 39} {3, 12, 40}
{3, 12, 41} {3, 12, 42} {3, 12, 43} {3, 12, 44} {3, 12, 45} {3, 12, 46} {3, 12, 47} {3, 12, 48} {3, 12, 49} {3, 12, 50}
{3, 12, 51} {3, 12, 52} {3, 12, 53} {3, 12, 54} {3, 12, 55} {3, 12, 56} {3, 12, 57} {3, 12, 58} {3, 12, 59} {3, 12, 60}
{3, 12, 61} {3, 12, 62} {3, 12, 63} {3, 12, 64} {3, 12, 65} {3, 12, 66} {3, 13, 14} {3, 13, 15} {3, 13, 16} {3, 13, 17}
{3, 13, 18} {3, 13, 19} {3, 13, 20} {3, 13, 21} {3, 13, 22} {3, 13, 23} {3, 13, 24} {3, 13, 25} {3, 13, 26} {3, 13, 27}
{3, 13, 28} {3, 13, 29} {3, 13, 30} {3, 13, 31} {3, 13, 32} {3, 13, 33} {3, 13, 34} {3, 13, 35} {3, 13, 36} {3, 13, 37}
{3, 13, 38} {3, 13, 39} {3, 13, 40} {3, 13, 41} {3, 13, 42} {3, 13, 43} {3, 13, 44} {3, 13, 45} {3, 13, 46} {3, 13, 47}
{3, 13, 48} {3, 13, 49} {3, 13, 50} {3, 13, 51} {3, 13, 52} {3, 13, 53} {3, 13, 54} {3, 13, 55} {3, 13, 56} {3, 13, 57}

TABLE 3A-continued

| | | | | | | | | |
|---|---|---|---|---|---|---|---|---|
| {3, 13, 58} | {3, 13, 59} | {3, 13, 60} | {3, 13, 61} | {3, 13, 62} | {3, 13, 63} | {3, 13, 64} | {3, 13, 65} | {3, 13, 66} | {3, 14, 15} |
| {3, 14, 16} | {3, 14, 17} | {3, 14, 18} | {3, 14, 19} | {3, 14, 20} | {3, 14, 21} | {3, 14, 22} | {3, 14, 23} | {3, 14, 24} | {3, 14, 25} |
| {3, 14, 26} | {3, 14, 27} | {3, 14, 28} | {3, 14, 29} | {3, 14, 30} | {3, 14, 31} | {3, 14, 32} | {3, 14, 33} | {3, 14, 34} | {3, 14, 35} |
| {3, 14, 36} | {3, 14, 37} | {3, 14, 38} | {3, 14, 39} | {3, 14, 40} | {3, 14, 41} | {3, 14, 42} | {3, 14, 43} | {3, 14, 44} | {3, 14, 45} |
| {3, 14, 46} | {3, 14, 47} | {3, 14, 48} | {3, 14, 49} | {3, 14, 50} | {3, 14, 51} | {3, 14, 52} | {3, 14, 53} | {3, 14, 54} | {3, 14, 55} |
| {3, 14, 56} | {3, 14, 57} | {3, 14, 58} | {3, 14, 59} | {3, 14, 60} | {3, 14, 61} | {3, 14, 62} | {3, 14, 63} | {3, 14, 64} | {3, 14, 65} |
| {3, 14, 66} | {3, 15, 16} | {3, 15, 17} | {3, 15, 18} | {3, 15, 19} | {3, 15, 20} | {3, 15, 21} | {3, 15, 22} | {3, 15, 23} | {3, 15, 24} |
| {3, 15, 25} | {3, 15, 26} | {3, 15, 27} | {3, 15, 28} | {3, 15, 29} | {3, 15, 30} | {3, 15, 31} | {3, 15, 32} | {3, 15, 33} | {3, 15, 34} |
| {3, 15, 35} | {3, 15, 36} | {3, 15, 37} | {3, 15, 38} | {3, 15, 39} | {3, 15, 40} | {3, 15, 41} | {3, 15, 42} | {3, 15, 43} | {3, 15, 44} |
| {3, 15, 45} | {3, 15, 46} | {3, 15, 47} | {3, 15, 48} | {3, 15, 49} | {3, 15, 50} | {3, 15, 51} | {3, 15, 52} | {3, 15, 53} | {3, 15, 54} |
| {3, 15, 55} | {3, 15, 56} | {3, 15, 57} | {3, 15, 58} | {3, 15, 59} | {3, 15, 60} | {3, 15, 61} | {3, 15, 62} | {3, 15, 63} | {3, 15, 64} |
| {3, 15, 65} | {3, 15, 66} | {3, 16, 17} | {3, 16, 18} | {3, 16, 19} | {3, 16, 20} | {3, 16, 21} | {3, 16, 22} | {3, 16, 23} | {3, 16, 24} |
| {3, 16, 25} | {3, 16, 26} | {3, 16, 27} | {3, 16, 28} | {3, 16, 29} | {3, 16, 30} | {3, 16, 31} | {3, 16, 32} | {3, 16, 33} | {3, 16, 34} |
| {3, 16, 35} | {3, 16, 36} | {3, 16, 37} | {3, 16, 38} | {3, 16, 39} | {3, 16, 40} | {3, 16, 41} | {3, 16, 42} | {3, 16, 43} | {3, 16, 44} |
| {3, 16, 45} | {3, 16, 46} | {3, 16, 47} | {3, 16, 48} | {3, 16, 49} | {3, 16, 50} | {3, 16, 51} | {3, 16, 52} | {3, 16, 53} | {3, 16, 54} |
| {3, 16, 55} | {3, 16, 56} | {3, 16, 57} | {3, 16, 58} | {3, 16, 59} | {3, 16, 60} | {3, 16, 61} | {3, 16, 62} | {3, 16, 63} | {3, 16, 64} |
| {3, 16, 65} | {3, 16, 66} | {3, 17, 18} | {3, 17, 19} | {3, 17, 20} | {3, 17, 21} | {3, 17, 22} | {3, 17, 23} | {3, 17, 24} | {3, 17, 25} |
| {3, 17, 26} | {3, 17, 27} | {3, 17, 28} | {3, 17, 29} | {3, 17, 30} | {3, 17, 31} | {3, 17, 32} | {3, 17, 33} | {3, 17, 34} | {3, 17, 35} |
| {3, 17, 36} | {3, 17, 37} | {3, 17, 38} | {3, 17, 39} | {3, 17, 40} | {3, 17, 41} | {3, 17, 42} | {3, 17, 43} | {3, 17, 44} | {3, 17, 45} |
| {3, 17, 46} | {3, 17, 47} | {3, 17, 48} | {3, 17, 49} | {3, 17, 50} | {3, 17, 51} | {3, 17, 52} | {3, 17, 53} | {3, 17, 54} | {3, 17, 55} |
| {3, 17, 56} | {3, 17, 57} | {3, 17, 58} | {3, 17, 59} | {3, 17, 60} | {3, 17, 61} | {3, 17, 62} | {3, 17, 63} | {3, 17, 64} | {3, 17, 65} |
| {3, 17, 66} | {3, 18, 19} | {3, 18, 20} | {3, 18, 21} | {3, 18, 22} | {3, 18, 23} | {3, 18, 24} | {3, 18, 25} | {3, 18, 26} | {3, 18, 27} |
| {3, 18, 28} | {3, 18, 29} | {3, 18, 30} | {3, 18, 31} | {3, 18, 32} | {3, 18, 33} | {3, 18, 34} | {3, 18, 35} | {3, 18, 36} | {3, 18, 37} |
| {3, 18, 38} | {3, 18, 39} | {3, 18, 40} | {3, 18, 41} | {3, 18, 42} | {3, 18, 43} | {3, 18, 44} | {3, 18, 45} | {3, 18, 46} | {3, 18, 47} |
| {3, 18, 48} | {3, 18, 49} | {3, 18, 50} | {3, 18, 51} | {3, 18, 52} | {3, 18, 53} | {3, 18, 54} | {3, 18, 55} | {3, 18, 56} | {3, 18, 57} |
| {3, 18, 58} | {3, 18, 59} | {3, 18, 60} | {3, 18, 61} | {3, 18, 62} | {3, 18, 63} | {3, 18, 64} | {3, 18, 65} | {3, 18, 66} | {3, 19, 20} |
| {3, 19, 21} | {3, 19, 22} | {3, 19, 23} | {3, 19, 24} | {3, 19, 25} | {3, 19, 26} | {3, 19, 27} | {3, 19, 28} | {3, 19, 29} | {3, 19, 30} |
| {3, 19, 31} | {3, 19, 32} | {3, 19, 33} | {3, 19, 34} | {3, 19, 35} | {3, 19, 36} | {3, 19, 37} | {3, 19, 38} | {3, 19, 39} | {3, 19, 40} |
| {3, 19, 41} | {3, 19, 42} | {3, 19, 43} | {3, 19, 44} | {3, 19, 45} | {3, 19, 46} | {3, 19, 47} | {3, 19, 48} | {3, 19, 49} | {3, 19, 50} |
| {3, 19, 51} | {3, 19, 52} | {3, 19, 53} | {3, 19, 54} | {3, 19, 55} | {3, 19, 56} | {3, 19, 57} | {3, 19, 58} | {3, 19, 59} | {3, 19, 60} |
| {3, 19, 61} | {3, 19, 62} | {3, 19, 63} | {3, 19, 64} | {3, 19, 65} | {3, 19, 66} | {3, 20, 21} | {3, 20, 22} | {3, 20, 23} | {3, 20, 24} |
| {3, 20, 25} | {3, 20, 26} | {3, 20, 27} | {3, 20, 28} | {3, 20, 29} | {3, 20, 30} | {3, 20, 31} | {3, 20, 32} | {3, 20, 33} | {3, 20, 34} |
| {3, 20, 35} | {3, 20, 36} | {3, 20, 37} | {3, 20, 38} | {3, 20, 39} | {3, 20, 40} | {3, 20, 41} | {3, 20, 42} | {3, 20, 43} | {3, 20, 44} |
| {3, 20, 45} | {3, 20, 46} | {3, 20, 47} | {3, 20, 48} | {3, 20, 49} | {3, 20, 50} | {3, 20, 51} | {3, 20, 52} | {3, 20, 53} | {3, 20, 54} |
| {3, 20, 55} | {3, 20, 56} | {3, 20, 57} | {3, 20, 58} | {3, 20, 59} | {3, 20, 60} | {3, 20, 61} | {3, 20, 62} | {3, 20, 63} | {3, 20, 64} |
| {3, 20, 65} | {3, 20, 66} | {3, 21, 22} | {3, 21, 23} | {3, 21, 24} | {3, 21, 25} | {3, 21, 26} | {3, 21, 27} | {3, 21, 28} | {3, 21, 29} |
| {3, 21, 30} | {3, 21, 31} | {3, 21, 32} | {3, 21, 33} | {3, 21, 34} | {3, 21, 35} | {3, 21, 36} | {3, 21, 37} | {3, 21, 38} | {3, 21, 39} |
| {3, 21, 40} | {3, 21, 41} | {3, 21, 42} | {3, 21, 43} | {3, 21, 44} | {3, 21, 45} | {3, 21, 46} | {3, 21, 47} | {3, 21, 48} | {3, 21, 49} |
| {3, 21, 50} | {3, 21, 51} | {3, 21, 52} | {3, 21, 53} | {3, 21, 54} | {3, 21, 55} | {3, 21, 56} | {3, 21, 57} | {3, 21, 58} | {3, 21, 59} |
| {3, 21, 60} | {3, 21, 61} | {3, 21, 62} | {3, 21, 63} | {3, 21, 64} | {3, 21, 65} | {3, 21, 66} | {3, 22, 23} | {3, 22, 24} | {3, 22, 25} |
| {3, 22, 26} | {3, 22, 27} | {3, 22, 28} | {3, 22, 29} | {3, 22, 30} | {3, 22, 31} | {3, 22, 32} | {3, 22, 33} | {3, 22, 34} | {3, 22, 35} |
| {3, 22, 36} | {3, 22, 37} | {3, 22, 38} | {3, 22, 39} | {3, 22, 40} | {3, 22, 41} | {3, 22, 42} | {3, 22, 43} | {3, 22, 44} | {3, 22, 45} |
| {3, 22, 46} | {3, 22, 47} | {3, 22, 48} | {3, 22, 49} | {3, 22, 50} | {3, 22, 51} | {3, 22, 52} | {3, 22, 53} | {3, 22, 54} | {3, 22, 55} |
| {3, 22, 56} | {3, 22, 57} | {3, 22, 58} | {3, 22, 59} | {3, 22, 60} | {3, 22, 61} | {3, 22, 62} | {3, 22, 63} | {3, 22, 64} | {3, 22, 65} |
| {3, 22, 66} | {3, 23, 24} | {3, 23, 25} | {3, 23, 26} | {3, 23, 27} | {3, 23, 28} | {3, 23, 29} | {3, 23, 30} | {3, 23, 31} | {3, 23, 32} |
| {3, 23, 33} | {3, 23, 34} | {3, 23, 35} | {3, 23, 36} | {3, 23, 37} | {3, 23, 38} | {3, 23, 39} | {3, 23, 40} | {3, 23, 41} | {3, 23, 42} |
| {3, 23, 43} | {3, 23, 44} | {3, 23, 45} | {3, 23, 46} | {3, 23, 47} | {3, 23, 48} | {3, 23, 49} | {3, 23, 50} | {3, 23, 51} | {3, 23, 52} |
| {3, 23, 53} | {3, 23, 54} | {3, 23, 55} | {3, 23, 56} | {3, 23, 57} | {3, 23, 58} | {3, 23, 59} | {3, 23, 60} | {3, 23, 61} | {3, 23, 62} |
| {3, 23, 63} | {3, 23, 64} | {3, 23, 65} | {3, 23, 66} | {3, 24, 25} | {3, 24, 26} | {3, 24, 27} | {3, 24, 28} | {3, 24, 29} | {3, 24, 30} |
| {3, 24, 31} | {3, 24, 32} | {3, 24, 33} | {3, 24, 34} | {3, 24, 35} | {3, 24, 36} | {3, 24, 37} | {3, 24, 38} | {3, 24, 39} | {3, 24, 40} |
| {3, 24, 41} | {3, 24, 42} | {3, 24, 43} | {3, 24, 44} | {3, 24, 45} | {3, 24, 46} | {3, 24, 47} | {3, 24, 48} | {3, 24, 49} | {3, 24, 50} |
| {3, 24, 51} | {3, 24, 52} | {3, 24, 53} | {3, 24, 54} | {3, 24, 55} | {3, 24, 56} | {3, 24, 57} | {3, 24, 58} | {3, 24, 59} | {3, 24, 60} |
| {3, 24, 61} | {3, 24, 62} | {3, 24, 63} | {3, 24, 64} | {3, 24, 65} | {3, 24, 66} | {3, 25, 26} | {3, 25, 27} | {3, 25, 28} | {3, 25, 29} |
| {3, 25, 30} | {3, 25, 31} | {3, 25, 32} | {3, 25, 33} | {3, 25, 34} | {3, 25, 35} | {3, 25, 36} | {3, 25, 37} | {3, 25, 38} | {3, 25, 39} |
| {3, 25, 40} | {3, 25, 41} | {3, 25, 42} | {3, 25, 43} | {3, 25, 44} | {3, 25, 45} | {3, 25, 46} | {3, 25, 47} | {3, 25, 48} | {3, 25, 49} |
| {3, 25, 50} | {3, 25, 51} | {3, 25, 52} | {3, 25, 53} | {3, 25, 54} | {3, 25, 55} | {3, 25, 56} | {3, 25, 57} | {3, 25, 58} | {3, 25, 59} |
| {3, 25, 60} | {3, 25, 61} | {3, 25, 62} | {3, 25, 63} | {3, 25, 64} | {3, 25, 65} | {3, 25, 66} | {3, 26, 27} | {3, 26, 28} | {3, 26, 29} |
| {3, 26, 30} | {3, 26, 31} | {3, 26, 32} | {3, 26, 33} | {3, 26, 34} | {3, 26, 35} | {3, 26, 36} | {3, 26, 37} | {3, 26, 38} | {3, 26, 39} |
| {3, 26, 40} | {3, 26, 41} | {3, 26, 42} | {3, 26, 43} | {3, 26, 44} | {3, 26, 45} | {3, 26, 46} | {3, 26, 47} | {3, 26, 48} | {3, 26, 49} |
| {3, 26, 50} | {3, 26, 51} | {3, 26, 52} | {3, 26, 53} | {3, 26, 54} | {3, 26, 55} | {3, 26, 56} | {3, 26, 57} | {3, 26, 58} | {3, 26, 59} |
| {3, 26, 60} | {3, 26, 61} | {3, 26, 62} | {3, 26, 63} | {3, 26, 64} | {3, 26, 65} | {3, 26, 66} | {3, 27, 28} | {3, 27, 29} | {3, 27, 30} |
| {3, 27, 31} | {3, 27, 32} | {3, 27, 33} | {3, 27, 34} | {3, 27, 35} | {3, 27, 36} | {3, 27, 37} | {3, 27, 38} | {3, 27, 39} | {3, 27, 40} |
| {3, 27, 41} | {3, 27, 42} | {3, 27, 43} | {3, 27, 44} | {3, 27, 45} | {3, 27, 46} | {3, 27, 47} | {3, 27, 48} | {3, 27, 49} | {3, 27, 50} |
| {3, 27, 51} | {3, 27, 52} | {3, 27, 53} | {3, 27, 54} | {3, 27, 55} | {3, 27, 56} | {3, 27, 57} | {3, 27, 58} | {3, 27, 59} | {3, 27, 60} |
| {3, 27, 61} | {3, 27, 62} | {3, 27, 63} | {3, 27, 64} | {3, 27, 65} | {3, 27, 66} | {3, 28, 29} | {3, 28, 30} | {3, 28, 31} | {3, 28, 32} |
| {3, 28, 33} | {3, 28, 34} | {3, 28, 35} | {3, 28, 36} | {3, 28, 37} | {3, 28, 38} | {3, 28, 39} | {3, 28, 40} | {3, 28, 41} | {3, 28, 42} |
| {3, 28, 43} | {3, 28, 44} | {3, 28, 45} | {3, 28, 46} | {3, 28, 47} | {3, 28, 48} | {3, 28, 49} | {3, 28, 50} | {3, 28, 51} | {3, 28, 52} |
| {3, 28, 53} | {3, 28, 54} | {3, 28, 55} | {3, 28, 56} | {3, 28, 57} | {3, 28, 58} | {3, 28, 59} | {3, 28, 60} | {3, 28, 61} | {3, 28, 62} |
| {3, 28, 63} | {3, 28, 64} | {3, 28, 65} | {3, 28, 66} | {3, 29, 30} | {3, 29, 31} | {3, 29, 32} | {3, 29, 33} | {3, 29, 34} | {3, 29, 35} |
| {3, 29, 36} | {3, 29, 37} | {3, 29, 38} | {3, 29, 39} | {3, 29, 40} | {3, 29, 41} | {3, 29, 42} | {3, 29, 43} | {3, 29, 44} | {3, 29, 45} |
| {3, 29, 46} | {3, 29, 47} | {3, 29, 48} | {3, 29, 49} | {3, 29, 50} | {3, 29, 51} | {3, 29, 52} | {3, 29, 53} | {3, 29, 54} | {3, 29, 55} |
| {3, 29, 56} | {3, 29, 57} | {3, 29, 58} | {3, 29, 59} | {3, 29, 60} | {3, 29, 61} | {3, 29, 62} | {3, 29, 63} | {3, 29, 64} | {3, 29, 65} |
| {3, 29, 66} | {3, 30, 31} | {3, 30, 32} | {3, 30, 33} | {3, 30, 34} | {3, 30, 35} | {3, 30, 36} | {3, 30, 37} | {3, 30, 38} | {3, 30, 39} |
| {3, 30, 40} | {3, 30, 41} | {3, 30, 42} | {3, 30, 43} | {3, 30, 44} | {3, 30, 45} | {3, 30, 46} | {3, 30, 47} | {3, 30, 48} | {3, 30, 49} |
| {3, 30, 50} | {3, 30, 51} | {3, 30, 52} | {3, 30, 53} | {3, 30, 54} | {3, 30, 55} | {3, 30, 56} | {3, 30, 57} | {3, 30, 58} | {3, 30, 59} |
| {3, 30, 60} | {3, 30, 61} | {3, 30, 62} | {3, 30, 63} | {3, 30, 64} | {3, 30, 65} | {3, 30, 66} | {3, 31, 32} | {3, 31, 33} | {3, 31, 34} |
| {3, 31, 35} | {3, 31, 36} | {3, 31, 37} | {3, 31, 38} | {3, 31, 39} | {3, 31, 40} | {3, 31, 41} | {3, 31, 42} | {3, 31, 43} | {3, 31, 44} |
| {3, 31, 45} | {3, 31, 46} | {3, 31, 47} | {3, 31, 48} | {3, 31, 49} | {3, 31, 50} | {3, 31, 51} | {3, 31, 52} | {3, 31, 53} | {3, 31, 54} |
| {3, 31, 55} | {3, 31, 56} | {3, 31, 57} | {3, 31, 58} | {3, 31, 59} | {3, 31, 60} | {3, 31, 61} | {3, 31, 62} | {3, 31, 63} | {3, 31, 64} |
| {3, 31, 65} | {3, 31, 66} | {3, 32, 33} | {3, 32, 34} | {3, 32, 35} | {3, 32, 36} | {3, 32, 37} | {3, 32, 38} | {3, 32, 39} | {3, 32, 40} |

TABLE 3A-continued

{3, 32, 41} {3, 32, 42} {3, 32, 43} {3, 32, 44} {3, 32, 45} {3, 32, 46} {3, 32, 47} {3, 32, 48} {3, 32, 49} {3, 32, 50}
{3, 32, 51} {3, 32, 52} {3, 32, 53} {3, 32, 54} {3, 32, 55} {3, 32, 56} {3, 32, 57} {3, 32, 58} {3, 32, 59} {3, 32, 60}
{3, 32, 61} {3, 32, 62} {3, 32, 63} {3, 32, 64} {3, 32, 65} {3, 32, 66} {3, 33, 34} {3, 33, 35} {3, 33, 36} {3, 33, 37}
{3, 33, 38} {3, 33, 39} {3, 33, 40} {3, 33, 41} {3, 33, 42} {3, 33, 43} {3, 33, 44} {3, 33, 45} {3, 33, 46} {3, 33, 47}
{3, 33, 48} {3, 33, 49} {3, 33, 50} {3, 33, 51} {3, 33, 52} {3, 33, 53} {3, 33, 54} {3, 33, 55} {3, 33, 56} {3, 33, 57}
{3, 33, 58} {3, 33, 59} {3, 33, 60} {3, 33, 61} {3, 33, 62} {3, 33, 63} {3, 33, 64} {3, 33, 65} {3, 33, 66} {3, 34, 35}
{3, 34, 36} {3, 34, 37} {3, 34, 38} {3, 34, 39} {3, 34, 40} {3, 34, 41} {3, 34, 42} {3, 34, 43} {3, 34, 44} {3, 34, 45}
{3, 34, 46} {3, 34, 47} {3, 34, 48} {3, 34, 49} {3, 34, 50} {3, 34, 51} {3, 34, 52} {3, 34, 53} {3, 34, 54} {3, 34, 55}
{3, 34, 56} {3, 34, 57} {3, 34, 58} {3, 34, 59} {3, 34, 60} {3, 34, 61} {3, 34, 62} {3, 34, 63} {3, 34, 64} {3, 34, 65}
{3, 34, 66} {3, 35, 36} {3, 35, 37} {3, 35, 38} {3, 35, 39} {3, 35, 40} {3, 35, 41} {3, 35, 42} {3, 35, 43} {3, 35, 44}
{3, 35, 45} {3, 35, 46} {3, 35, 47} {3, 35, 48} {3, 35, 49} {3, 35, 50} {3, 35, 51} {3, 35, 52} {3, 35, 53} {3, 35, 54}
{3, 35, 55} {3, 35, 56} {3, 35, 57} {3, 35, 58} {3, 35, 59} {3, 35, 60} {3, 35, 61} {3, 35, 62} {3, 35, 63} {3, 35, 64}
{3, 35, 65} {3, 35, 66} {3, 36, 37} {3, 36, 38} {3, 36, 39} {3, 36, 40} {3, 36, 41} {3, 36, 42} {3, 36, 43} {3, 36, 44}
{3, 36, 45} {3, 36, 46} {3, 36, 47} {3, 36, 48} {3, 36, 49} {3, 36, 50} {3, 36, 51} {3, 36, 52} {3, 36, 53} {3, 36, 54}
{3, 36, 55} {3, 36, 56} {3, 36, 57} {3, 36, 58} {3, 36, 59} {3, 36, 60} {3, 36, 61} {3, 36, 62} {3, 36, 63} {3, 36, 64}
{3, 36, 65} {3, 36, 66} {3, 37, 38} {3, 37, 39} {3, 37, 40} {3, 37, 41} {3, 37, 42} {3, 37, 43} {3, 37, 44} {3, 37, 45}
{3, 37, 46} {3, 37, 47} {3, 37, 48} {3, 37, 49} {3, 37, 50} {3, 37, 51} {3, 37, 52} {3, 37, 53} {3, 37, 54} {3, 37, 55}
{3, 37, 56} {3, 37, 57} {3, 37, 58} {3, 37, 59} {3, 37, 60} {3, 37, 61} {3, 37, 62} {3, 37, 63} {3, 37, 64} {3, 37, 65}
{3, 37, 66} {3, 38, 39} {3, 38, 40} {3, 38, 41} {3, 38, 42} {3, 38, 43} {3, 38, 44} {3, 38, 45} {3, 38, 46} {3, 38, 47}
{3, 38, 48} {3, 38, 49} {3, 38, 50} {3, 38, 51} {3, 38, 52} {3, 38, 53} {3, 38, 54} {3, 38, 55} {3, 38, 56} {3, 38, 57}
{3, 38, 58} {3, 38, 59} {3, 38, 60} {3, 38, 61} {3, 38, 62} {3, 38, 63} {3, 38, 64} {3, 38, 65} {3, 38, 66} {3, 39, 40}
{3, 39, 41} {3, 39, 42} {3, 39, 43} {3, 39, 44} {3, 39, 45} {3, 39, 46} {3, 39, 47} {3, 39, 48} {3, 39, 49} {3, 39, 50}
{3, 39, 51} {3, 39, 52} {3, 39, 53} {3, 39, 54} {3, 39, 55} {3, 39, 56} {3, 39, 57} {3, 39, 58} {3, 39, 59} {3, 39, 60}
{3, 39, 61} {3, 39, 62} {3, 39, 63} {3, 39, 64} {3, 39, 65} {3, 39, 66} {3, 40, 41} {3, 40, 42} {3, 40, 43} {3, 40, 44}
{3, 40, 45} {3, 40, 46} {3, 40, 47} {3, 40, 48} {3, 40, 49} {3, 40, 50} {3, 40, 51} {3, 40, 52} {3, 40, 53} {3, 40, 54}
{3, 40, 55} {3, 40, 56} {3, 40, 57} {3, 40, 58} {3, 40, 59} {3, 40, 60} {3, 40, 61} {3, 40, 62} {3, 40, 63} {3, 40, 64}
{3, 40, 65} {3, 40, 66} {3, 41, 42} {3, 41, 43} {3, 41, 44} {3, 41, 45} {3, 41, 46} {3, 41, 47} {3, 41, 48} {3, 41, 49}
{3, 41, 50} {3, 41, 51} {3, 41, 52} {3, 41, 53} {3, 41, 54} {3, 41, 55} {3, 41, 56} {3, 41, 57} {3, 41, 58} {3, 41, 59}
{3, 41, 60} {3, 41, 61} {3, 41, 62} {3, 41, 63} {3, 41, 64} {3, 41, 65} {3, 41, 66} {3, 42, 43} {3, 42, 44} {3, 42, 45}
{3, 42, 46} {3, 42, 47} {3, 42, 48} {3, 42, 49} {3, 42, 50} {3, 42, 51} {3, 42, 52} {3, 42, 53} {3, 42, 54} {3, 42, 55}
{3, 42, 56} {3, 42, 57} {3, 42, 58} {3, 42, 59} {3, 42, 60} {3, 42, 61} {3, 42, 62} {3, 42, 63} {3, 42, 64} {3, 42, 65}
{3, 42, 66} {3, 43, 44} {3, 43, 45} {3, 43, 46} {3, 43, 47} {3, 43, 48} {3, 43, 49} {3, 43, 50} {3, 43, 51} {3, 43, 52}
{3, 43, 53} {3, 43, 54} {3, 43, 55} {3, 43, 56} {3, 43, 57} {3, 43, 58} {3, 43, 59} {3, 43, 60} {3, 43, 61} {3, 43, 62}
{3, 43, 63} {3, 43, 64} {3, 43, 65} {3, 43, 66} {3, 44, 45} {3, 44, 46} {3, 44, 47} {3, 44, 48} {3, 44, 49} {3, 44, 50}
{3, 44, 51} {3, 44, 52} {3, 44, 53} {3, 44, 54} {3, 44, 55} {3, 44, 56} {3, 44, 57} {3, 44, 58} {3, 44, 59} {3, 44, 60}
{3, 44, 61} {3, 44, 62} {3, 44, 63} {3, 44, 64} {3, 44, 65} {3, 44, 66} {3, 45, 46} {3, 45, 47} {3, 45, 48} {3, 45, 49}
{3, 45, 50} {3, 45, 51} {3, 45, 52} {3, 45, 53} {3, 45, 54} {3, 45, 55} {3, 45, 56} {3, 45, 57} {3, 45, 58} {3, 45, 59}
{3, 45, 60} {3, 45, 61} {3, 45, 62} {3, 45, 63} {3, 45, 64} {3, 45, 65} {3, 45, 66} {3, 46, 47} {3, 46, 48} {3, 46, 49}
{3, 46, 50} {3, 46, 51} {3, 46, 52} {3, 46, 53} {3, 46, 54} {3, 46, 55} {3, 46, 56} {3, 46, 57} {3, 46, 58} {3, 46, 59}
{3, 46, 60} {3, 46, 61} {3, 46, 62} {3, 46, 63} {3, 46, 64} {3, 46, 65} {3, 46, 66} {3, 47, 48} {3, 47, 49} {3, 47, 50}
{3, 47, 51} {3, 47, 52} {3, 47, 53} {3, 47, 54} {3, 47, 55} {3, 47, 56} {3, 47, 57} {3, 47, 58} {3, 47, 59} {3, 47, 60}
{3, 47, 61} {3, 47, 62} {3, 47, 63} {3, 47, 64} {3, 47, 65} {3, 47, 66} {3, 48, 49} {3, 48, 50} {3, 48, 51} {3, 48, 52}
{3, 48, 53} {3, 48, 54} {3, 48, 55} {3, 48, 56} {3, 48, 57} {3, 48, 58} {3, 48, 59} {3, 48, 60} {3, 48, 61} {3, 48, 62}
{3, 48, 63} {3, 48, 64} {3, 48, 65} {3, 48, 66} {3, 49, 50} {3, 49, 51} {3, 49, 52} {3, 49, 53} {3, 49, 54} {3, 49, 55}
{3, 49, 56} {3, 49, 57} {3, 49, 58} {3, 49, 59} {3, 49, 60} {3, 49, 61} {3, 49, 62} {3, 49, 63} {3, 49, 64} {3, 49, 65}
{3, 49, 66} {3, 50, 51} {3, 50, 52} {3, 50, 53} {3, 50, 54} {3, 50, 55} {3, 50, 56} {3, 50, 57} {3, 50, 58} {3, 50, 59}
{3, 50, 60} {3, 50, 61} {3, 50, 62} {3, 50, 63} {3, 50, 64} {3, 50, 65} {3, 50, 66} {3, 51, 52} {3, 51, 53} {3, 51, 54}
{3, 51, 55} {3, 51, 56} {3, 51, 57} {3, 51, 58} {3, 51, 59} {3, 51, 60} {3, 51, 61} {3, 51, 62} {3, 51, 63} {3, 51, 64}
{3, 51, 65} {3, 51, 66} {3, 52, 53} {3, 52, 54} {3, 52, 55} {3, 52, 56} {3, 52, 57} {3, 52, 58} {3, 52, 59} {3, 52, 60}
{3, 52, 61} {3, 52, 62} {3, 52, 63} {3, 52, 64} {3, 52, 65} {3, 52, 66} {3, 53, 54} {3, 53, 55} {3, 53, 56} {3, 53, 57}
{3, 53, 58} {3, 53, 59} {3, 53, 60} {3, 53, 61} {3, 53, 62} {3, 53, 63} {3, 53, 64} {3, 53, 65} {3, 53, 66} {3, 54, 55}
{3, 54, 56} {3, 54, 57} {3, 54, 58} {3, 54, 59} {3, 54, 60} {3, 54, 61} {3, 54, 62} {3, 54, 63} {3, 54, 64} {3, 54, 65}
{3, 54, 66} {3, 55, 56} {3, 55, 57} {3, 55, 58} {3, 55, 59} {3, 55, 60} {3, 55, 61} {3, 55, 62} {3, 55, 63} {3, 55, 64}
{3, 55, 65} {3, 55, 66} {3, 56, 57} {3, 56, 58} {3, 56, 59} {3, 56, 60} {3, 56, 61} {3, 56, 62} {3, 56, 63} {3, 56, 64}
{3, 56, 65} {3, 56, 66} {3, 57, 58} {3, 57, 59} {3, 57, 60} {3, 57, 61} {3, 57, 62} {3, 57, 63} {3, 57, 64} {3, 57, 65}
{3, 57, 66} {3, 58, 59} {3, 58, 60} {3, 58, 61} {3, 58, 62} {3, 58, 63} {3, 58, 64} {3, 58, 65} {3, 58, 66} {3, 59, 60}
{3, 59, 61} {3, 59, 62} {3, 59, 63} {3, 59, 64} {3, 59, 65} {3, 59, 66} {3, 60, 61} {3, 60, 62} {3, 60, 63} {3, 60, 64}
{3, 60, 65} {3, 60, 66} {3, 61, 62} {3, 61, 63} {3, 61, 64} {3, 61, 65} {3, 61, 66} {3, 62, 63} {3, 62, 64} {3, 62, 65}
{3, 62, 66} {3, 63, 64} {3, 63, 65} {3, 63, 66} {3, 64, 65} {3, 64, 66} {3, 65, 66} {4, 5, 6} {4, 5, 7} {4, 5, 8} {4, 5, 9} {4, 5, 10}
{4, 5, 11} {4, 5, 12} {4, 5, 13} {4, 5, 14} {4, 5, 15} {4, 5, 16} {4, 5, 17} {4, 5, 18} {4, 5, 19} {4, 5, 20} {4, 5, 21} {4, 5, 22}
{4, 5, 23} {4, 5, 24} {4, 5, 25} {4, 5, 26} {4, 5, 27} {4, 5, 28} {4, 5, 29} {4, 5, 30} {4, 5, 31} {4, 5, 32} {4, 5, 33} {4, 5, 34}
{4, 5, 35} {4, 5, 36} {4, 5, 37} {4, 5, 38} {4, 5, 39} {4, 5, 40} {4, 5, 41} {4, 5, 42} {4, 5, 43} {4, 5, 44} {4, 5, 45} {4, 5, 46}
{4, 5, 47} {4, 5, 48} {4, 5, 49} {4, 5, 50} {4, 5, 51} {4, 5, 52} {4, 5, 53} {4, 5, 54} {4, 5, 55} {4, 5, 56} {4, 5, 57} {4, 5, 58}
{4, 5, 59} {4, 5, 60} {4, 5, 61} {4, 5, 62} {4, 5, 63} {4, 5, 64} {4, 5, 65} {4, 5, 66} {4, 6, 7} {4, 6, 8} {4, 6, 9} {4, 6, 10} {4, 6, 11}
{4, 6, 12} {4, 6, 13} {4, 6, 14} {4, 6, 15} {4, 6, 16} {4, 6, 17} {4, 6, 18} {4, 6, 19} {4, 6, 20} {4, 6, 21} {4, 6, 22} {4, 6, 23}
{4, 6, 24} {4, 6, 25} {4, 6, 26} {4, 6, 27} {4, 6, 28} {4, 6, 29} {4, 6, 30} {4, 6, 31} {4, 6, 32} {4, 6, 33} {4, 6, 34} {4, 6, 35}
{4, 6, 36} {4, 6, 37} {4, 6, 38} {4, 6, 39} {4, 6, 40} {4, 6, 41} {4, 6, 42} {4, 6, 43} {4, 6, 44} {4, 6, 45} {4, 6, 46} {4, 6, 47}
{4, 6, 48} {4, 6, 49} {4, 6, 50} {4, 6, 51} {4, 6, 52} {4, 6, 53} {4, 6, 54} {4, 6, 55} {4, 6, 56} {4, 6, 57} {4, 6, 58} {4, 6, 59}
{4, 6, 60} {4, 6, 61} {4, 6, 62} {4, 6, 63} {4, 6, 64} {4, 6, 65} {4, 6, 66} {4, 7, 8} {4, 7, 9} {4, 7, 10} {4, 7, 11} {4, 7, 12}
{4, 7, 13} {4, 7, 14} {4, 7, 15} {4, 7, 16} {4, 7, 17} {4, 7, 18} {4, 7, 19} {4, 7, 20} {4, 7, 21} {4, 7, 22} {4, 7, 23} {4, 7, 24}
{4, 7, 25} {4, 7, 26} {4, 7, 27} {4, 7, 28} {4, 7, 29} {4, 7, 30} {4, 7, 31} {4, 7, 32} {4, 7, 33} {4, 7, 34} {4, 7, 35} {4, 7, 36}
{4, 7, 37} {4, 7, 38} {4, 7, 39} {4, 7, 40} {4, 7, 41} {4, 7, 42} {4, 7, 43} {4, 7, 44} {4, 7, 45} {4, 7, 46} {4, 7, 47} {4, 7, 48}
{4, 7, 49} {4, 7, 50} {4, 7, 51} {4, 7, 52} {4, 7, 53} {4, 7, 54} {4, 7, 55} {4, 7, 56} {4, 7, 57} {4, 7, 58} {4, 7, 59} {4, 7, 60}
{4, 7, 61} {4, 7, 62} {4, 7, 63} {4, 7, 64} {4, 7, 65} {4, 7, 66} {4, 8, 9} {4, 8, 10} {4, 8, 11} {4, 8, 12} {4, 8, 13} {4, 8, 14}
{4, 8, 15} {4, 8, 16} {4, 8, 17} {4, 8, 18} {4, 8, 19} {4, 8, 20} {4, 8, 21} {4, 8, 22} {4, 8, 23} {4, 8, 24} {4, 8, 25} {4, 8, 26}
{4, 8, 27} {4, 8, 28} {4, 8, 29} {4, 8, 30} {4, 8, 31} {4, 8, 32} {4, 8, 33} {4, 8, 34} {4, 8, 35} {4, 8, 36} {4, 8, 37} {4, 8, 38}
{4, 8, 39} {4, 8, 40} {4, 8, 41} {4, 8, 42} {4, 8, 43} {4, 8, 44} {4, 8, 45} {4, 8, 46} {4, 8, 47} {4, 8, 48} {4, 8, 49} {4, 8, 50}
{4, 8, 51} {4, 8, 52} {4, 8, 53} {4, 8, 54} {4, 8, 55} {4, 8, 56} {4, 8, 57} {4, 8, 58} {4, 8, 59} {4, 8, 60} {4, 8, 61} {4, 8, 62}
{4, 8, 63} {4, 8, 64} {4, 8, 65} {4, 8, 66} {4, 9, 10} {4, 9, 11} {4, 9, 12} {4, 9, 13} {4, 9, 14} {4, 9, 15} {4, 9, 16} {4, 9, 17}
{4, 9, 18} {4, 9, 19} {4, 9, 20} {4, 9, 21} {4, 9, 22} {4, 9, 23} {4, 9, 24} {4, 9, 25} {4, 9, 26} {4, 9, 27} {4, 9, 28} {4, 9, 29}

TABLE 3A-continued

{4, 9, 30} {4, 9, 31} {4, 9, 32} {4, 9, 33} {4, 9, 34} {4, 9, 35} {4, 9, 36} {4, 9, 37} {4, 9, 38} {4, 9, 39} {4, 9, 40} {4, 9, 41}
{4, 9, 42} {4, 9, 43} {4, 9, 44} {4, 9, 45} {4, 9, 46} {4, 9, 47} {4, 9, 48} {4, 9, 49} {4, 9, 50} {4, 9, 51} {4, 9, 52} {4, 9, 53}
{4, 9, 54} {4, 9, 55} {4, 9, 56} {4, 9, 57} {4, 9, 58} {4, 9, 59} {4, 9, 60} {4, 9, 61} {4, 9, 62} {4, 9, 63} {4, 9, 64} {4, 9, 65}
{4, 9, 66} {4, 10, 11} {4, 10, 12} {4, 10, 13} {4, 10, 14} {4, 10, 15} {4, 10, 16} {4, 10, 17} {4, 10, 18} {4, 10, 19} {4, 10, 20}
{4, 10, 21} {4, 10, 22} {4, 10, 23} {4, 10, 24} {4, 10, 25} {4, 10, 26} {4, 10, 27} {4, 10, 28} {4, 10, 29} {4, 10, 30}
{4, 10, 31} {4, 10, 32} {4, 10, 33} {4, 10, 34} {4, 10, 35} {4, 10, 36} {4, 10, 37} {4, 10, 38} {4, 10, 39} {4, 10, 40}
{4, 10, 41} {4, 10, 42} {4, 10, 43} {4, 10, 44} {4, 10, 45} {4, 10, 46} {4, 10, 47} {4, 10, 48} {4, 10, 49} {4, 10, 50}
{4, 10, 51} {4, 10, 52} {4, 10, 53} {4, 10, 54} {4, 10, 55} {4, 10, 56} {4, 10, 57} {4, 10, 58} {4, 10, 59} {4, 10, 60}
{4, 10, 61} {4, 10, 62} {4, 10, 63} {4, 10, 64} {4, 10, 65} {4, 10, 66} {4, 11, 12} {4, 11, 13} {4, 11, 14} {4, 11, 15}
{4, 11, 16} {4, 11, 17} {4, 11, 18} {4, 11, 19} {4, 11, 20} {4, 11, 21} {4, 11, 22} {4, 11, 23} {4, 11, 24} {4, 11, 25}
{4, 11, 26} {4, 11, 27} {4, 11, 28} {4, 11, 29} {4, 11, 30} {4, 11, 31} {4, 11, 32} {4, 11, 33} {4, 11, 34} {4, 11, 35}
{4, 11, 36} {4, 11, 37} {4, 11, 38} {4, 11, 39} {4, 11, 40} {4, 11, 41} {4, 11, 42} {4, 11, 43} {4, 11, 44} {4, 11, 45}
{4, 11, 46} {4, 11, 47} {4, 11, 48} {4, 11, 49} {4, 11, 50} {4, 11, 51} {4, 11, 52} {4, 11, 53} {4, 11, 54} {4, 11, 55}
{4, 11, 56} {4, 11, 57} {4, 11, 58} {4, 11, 59} {4, 11, 60} {4, 11, 61} {4, 11, 62} {4, 11, 63} {4, 11, 64} {4, 11, 65}
{4, 11, 66} {4, 12, 13} {4, 12, 14} {4, 12, 15} {4, 12, 16} {4, 12, 17} {4, 12, 18} {4, 12, 19} {4, 12, 20} {4, 12, 21}
{4, 12, 22} {4, 12, 23} {4, 12, 24} {4, 12, 25} {4, 12, 26} {4, 12, 27} {4, 12, 28} {4, 12, 29} {4, 12, 30} {4, 12, 31}
{4, 12, 32} {4, 12, 33} {4, 12, 34} {4, 12, 35} {4, 12, 36} {4, 12, 37} {4, 12, 38} {4, 12, 39} {4, 12, 40} {4, 12, 41}
{4, 12, 42} {4, 12, 43} {4, 12, 44} {4, 12, 45} {4, 12, 46} {4, 12, 47} {4, 12, 48} {4, 12, 49} {4, 12, 50} {4, 12, 51}
{4, 12, 52} {4, 12, 53} {4, 12, 54} {4, 12, 55} {4, 12, 56} {4, 12, 57} {4, 12, 58} {4, 12, 59} {4, 12, 60} {4, 12, 61}
{4, 12, 62} {4, 12, 63} {4, 12, 64} {4, 12, 65} {4, 12, 66} {4, 13, 14} {4, 13, 15} {4, 13, 16} {4, 13, 17} {4, 13, 18}
{4, 13, 19} {4, 13, 20} {4, 13, 21} {4, 13, 22} {4, 13, 23} {4, 13, 24} {4, 13, 25} {4, 13, 26} {4, 13, 27} {4, 13, 28}
{4, 13, 29} {4, 13, 30} {4, 13, 31} {4, 13, 32} {4, 13, 33} {4, 13, 34} {4, 13, 35} {4, 13, 36} {4, 13, 37} {4, 13, 38}
{4, 13, 39} {4, 13, 40} {4, 13, 41} {4, 13, 42} {4, 13, 43} {4, 13, 44} {4, 13, 45} {4, 13, 46} {4, 13, 47} {4, 13, 48}
{4, 13, 49} {4, 13, 50} {4, 13, 51} {4, 13, 52} {4, 13, 53} {4, 13, 54} {4, 13, 55} {4, 13, 56} {4, 13, 57} {4, 13, 58}
{4, 13, 59} {4, 13, 60} {4, 13, 61} {4, 13, 62} {4, 13, 63} {4, 13, 64} {4, 13, 65} {4, 13, 66} {4, 14, 15} {4, 14, 16}
{4, 14, 17} {4, 14, 18} {4, 14, 19} {4, 14, 20} {4, 14, 21} {4, 14, 22} {4, 14, 23} {4, 14, 24} {4, 14, 25} {4, 14, 26}
{4, 14, 27} {4, 14, 28} {4, 14, 29} {4, 14, 30} {4, 14, 31} {4, 14, 32} {4, 14, 33} {4, 14, 34} {4, 14, 35} {4, 14, 36}
{4, 14, 37} {4, 14, 38} {4, 14, 39} {4, 14, 40} {4, 14, 41} {4, 14, 42} {4, 14, 43} {4, 14, 44} {4, 14, 45} {4, 14, 46}
{4, 14, 47} {4, 14, 48} {4, 14, 49} {4, 14, 50} {4, 14, 51} {4, 14, 52} {4, 14, 53} {4, 14, 54} {4, 14, 55} {4, 14, 56}
{4, 14, 57} {4, 14, 58} {4, 14, 59} {4, 14, 60} {4, 14, 61} {4, 14, 62} {4, 14, 63} {4, 14, 64} {4, 14, 65} {4, 14, 66}
{4, 15, 16} {4, 15, 17} {4, 15, 18} {4, 15, 19} {4, 15, 20} {4, 15, 21} {4, 15, 22} {4, 15, 23} {4, 15, 24} {4, 15, 25}
{4, 15, 26} {4, 15, 27} {4, 15, 28} {4, 15, 29} {4, 15, 30} {4, 15, 31} {4, 15, 32} {4, 15, 33} {4, 15, 34} {4, 15, 35}
{4, 15, 36} {4, 15, 37} {4, 15, 38} {4, 15, 39} {4, 15, 40} {4, 15, 41} {4, 15, 42} {4, 15, 43} {4, 15, 44} {4, 15, 45}
{4, 15, 46} {4, 15, 47} {4, 15, 48} {4, 15, 49} {4, 15, 50} {4, 15, 51} {4, 15, 52} {4, 15, 53} {4, 15, 54} {4, 15, 55}
{4, 15, 56} {4, 15, 57} {4, 15, 58} {4, 15, 59} {4, 15, 60} {4, 15, 61} {4, 15, 62} {4, 15, 63} {4, 15, 64} {4, 15, 65}
{4, 15, 66} {4, 16, 17} {4, 16, 18} {4, 16, 19} {4, 16, 20} {4, 16, 21} {4, 16, 22} {4, 16, 23} {4, 16, 24} {4, 16, 25}
{4, 16, 26} {4, 16, 27} {4, 16, 28} {4, 16, 29} {4, 16, 30} {4, 16, 31} {4, 16, 32} {4, 16, 33} {4, 16, 34} {4, 16, 35}
{4, 16, 36} {4, 16, 37} {4, 16, 38} {4, 16, 39} {4, 16, 40} {4, 16, 41} {4, 16, 42} {4, 16, 43} {4, 16, 44} {4, 16, 45}
{4, 16, 46} {4, 16, 47} {4, 16, 48} {4, 16, 49} {4, 16, 50} {4, 16, 51} {4, 16, 52} {4, 16, 53} {4, 16, 54} {4, 16, 55}
{4, 16, 56} {4, 16, 57} {4, 16, 58} {4, 16, 59} {4, 16, 60} {4, 16, 61} {4, 16, 62} {4, 16, 63} {4, 16, 64} {4, 16, 65}
{4, 16, 66} {4, 17, 18} {4, 17, 19} {4, 17, 20} {4, 17, 21} {4, 17, 22} {4, 17, 23} {4, 17, 24} {4, 17, 25} {4, 17, 26}
{4, 17, 27} {4, 17, 28} {4, 17, 29} {4, 17, 30} {4, 17, 31} {4, 17, 32} {4, 17, 33} {4, 17, 34} {4, 17, 35} {4, 17, 36}
{4, 17, 37} {4, 17, 38} {4, 17, 39} {4, 17, 40} {4, 17, 41} {4, 17, 42} {4, 17, 43} {4, 17, 44} {4, 17, 45} {4, 17, 46}
{4, 17, 47} {4, 17, 48} {4, 17, 49} {4, 17, 50} {4, 17, 51} {4, 17, 52} {4, 17, 53} {4, 17, 54} {4, 17, 55} {4, 17, 56}
{4, 17, 57} {4, 17, 58} {4, 17, 59} {4, 17, 60} {4, 17, 61} {4, 17, 62} {4, 17, 63} {4, 17, 64} {4, 17, 65} {4, 17, 66}
{4, 18, 19} {4, 18, 20} {4, 18, 21} {4, 18, 22} {4, 18, 23} {4, 18, 24} {4, 18, 25} {4, 18, 26} {4, 18, 27} {4, 18, 28}
{4, 18, 29} {4, 18, 30} {4, 18, 31} {4, 18, 32} {4, 18, 33} {4, 18, 34} {4, 18, 35} {4, 18, 36} {4, 18, 37} {4, 18, 38}
{4, 18, 39} {4, 18, 40} {4, 18, 41} {4, 18, 42} {4, 18, 43} {4, 18, 44} {4, 18, 45} {4, 18, 46} {4, 18, 47} {4, 18, 48}
{4, 18, 49} {4, 18, 50} {4, 18, 51} {4, 18, 52} {4, 18, 53} {4, 18, 54} {4, 18, 55} {4, 18, 56} {4, 18, 57} {4, 18, 58}
{4, 18, 59} {4, 18, 60} {4, 18, 61} {4, 18, 62} {4, 18, 63} {4, 18, 64} {4, 18, 65} {4, 18, 66} {4, 19, 20} {4, 19, 21}
{4, 19, 22} {4, 19, 23} {4, 19, 24} {4, 19, 25} {4, 19, 26} {4, 19, 27} {4, 19, 28} {4, 19, 29} {4, 19, 30} {4, 19, 31}
{4, 19, 32} {4, 19, 33} {4, 19, 34} {4, 19, 35} {4, 19, 36} {4, 19, 37} {4, 19, 38} {4, 19, 39} {4, 19, 40} {4, 19, 41}
{4, 19, 42} {4, 19, 43} {4, 19, 44} {4, 19, 45} {4, 19, 46} {4, 19, 47} {4, 19, 48} {4, 19, 49} {4, 19, 50} {4, 19, 51}
{4, 19, 52} {4, 19, 53} {4, 19, 54} {4, 19, 55} {4, 19, 56} {4, 19, 57} {4, 19, 58} {4, 19, 59} {4, 19, 60} {4, 19, 61}
{4, 19, 62} {4, 19, 63} {4, 19, 64} {4, 19, 65} {4, 19, 66} {4, 20, 21} {4, 20, 22} {4, 20, 23} {4, 20, 24} {4, 20, 25}
{4, 20, 26} {4, 20, 27} {4, 20, 28} {4, 20, 29} {4, 20, 30} {4, 20, 31} {4, 20, 32} {4, 20, 33} {4, 20, 34} {4, 20, 35}
{4, 20, 36} {4, 20, 37} {4, 20, 38} {4, 20, 39} {4, 20, 40} {4, 20, 41} {4, 20, 42} {4, 20, 43} {4, 20, 44} {4, 20, 45}
{4, 20, 46} {4, 20, 47} {4, 20, 48} {4, 20, 49} {4, 20, 50} {4, 20, 51} {4, 20, 52} {4, 20, 53} {4, 20, 54} {4, 20, 55}
{4, 20, 56} {4, 20, 57} {4, 20, 58} {4, 20, 59} {4, 20, 60} {4, 20, 61} {4, 20, 62} {4, 20, 63} {4, 20, 64} {4, 20, 65}
{4, 20, 66} {4, 21, 22} {4, 21, 23} {4, 21, 24} {4, 21, 25} {4, 21, 26} {4, 21, 27} {4, 21, 28} {4, 21, 29} {4, 21, 30}
{4, 21, 31} {4, 21, 32} {4, 21, 33} {4, 21, 34} {4, 21, 35} {4, 21, 36} {4, 21, 37} {4, 21, 38} {4, 21, 39} {4, 21, 40}
{4, 21, 41} {4, 21, 42} {4, 21, 43} {4, 21, 44} {4, 21, 45} {4, 21, 46} {4, 21, 47} {4, 21, 48} {4, 21, 49} {4, 21, 50}
{4, 21, 51} {4, 21, 52} {4, 21, 53} {4, 21, 54} {4, 21, 55} {4, 21, 56} {4, 21, 57} {4, 21, 58} {4, 21, 59} {4, 21, 60}
{4, 21, 61} {4, 21, 62} {4, 21, 63} {4, 21, 64} {4, 21, 65} {4, 21, 66} {4, 22, 23} {4, 22, 24} {4, 22, 25} {4, 22, 26}
{4, 22, 27} {4, 22, 28} {4, 22, 29} {4, 22, 30} {4, 22, 31} {4, 22, 32} {4, 22, 33} {4, 22, 34} {4, 22, 35} {4, 22, 36}
{4, 22, 37} {4, 22, 38} {4, 22, 39} {4, 22, 40} {4, 22, 41} {4, 22, 42} {4, 22, 43} {4, 22, 44} {4, 22, 45} {4, 22, 46}
{4, 22, 47} {4, 22, 48} {4, 22, 49} {4, 22, 50} {4, 22, 51} {4, 22, 52} {4, 22, 53} {4, 22, 54} {4, 22, 55} {4, 22, 56}
{4, 22, 57} {4, 22, 58} {4, 22, 59} {4, 22, 60} {4, 22, 61} {4, 22, 62} {4, 22, 63} {4, 22, 64} {4, 22, 65} {4, 22, 66}
{4, 23, 24} {4, 23, 25} {4, 23, 26} {4, 23, 27} {4, 23, 28} {4, 23, 29} {4, 23, 30} {4, 23, 31} {4, 23, 32} {4, 23, 33}
{4, 23, 34} {4, 23, 35} {4, 23, 36} {4, 23, 37} {4, 23, 38} {4, 23, 39} {4, 23, 40} {4, 23, 41} {4, 23, 42} {4, 23, 43}
{4, 23, 44} {4, 23, 45} {4, 23, 46} {4, 23, 47} {4, 23, 48} {4, 23, 49} {4, 23, 50} {4, 23, 51} {4, 23, 52} {4, 23, 53}
{4, 23, 54} {4, 23, 55} {4, 23, 56} {4, 23, 57} {4, 23, 58} {4, 23, 59} {4, 23, 60} {4, 23, 61} {4, 23, 62} {4, 23, 63}
{4, 23, 64} {4, 23, 65} {4, 23, 66} {4, 24, 25} {4, 24, 26} {4, 24, 27} {4, 24, 28} {4, 24, 29} {4, 24, 30} {4, 24, 31}
{4, 24, 32} {4, 24, 33} {4, 24, 34} {4, 24, 35} {4, 24, 36} {4, 24, 37} {4, 24, 38} {4, 24, 39} {4, 24, 40} {4, 24, 41}
{4, 24, 42} {4, 24, 43} {4, 24, 44} {4, 24, 45} {4, 24, 46} {4, 24, 47} {4, 24, 48} {4, 24, 49} {4, 24, 50} {4, 24, 51}
{4, 24, 52} {4, 24, 53} {4, 24, 54} {4, 24, 55} {4, 24, 56} {4, 24, 57} {4, 24, 58} {4, 24, 59} {4, 24, 60} {4, 24, 61}
{4, 24, 62} {4, 24, 63} {4, 24, 64} {4, 24, 65} {4, 24, 66} {4, 25, 26} {4, 25, 27} {4, 25, 28} {4, 25, 29} {4, 25, 30}
{4, 25, 31} {4, 25, 32} {4, 25, 33} {4, 25, 34} {4, 25, 35} {4, 25, 36} {4, 25, 37} {4, 25, 38} {4, 25, 39} {4, 25, 40}
{4, 25, 41} {4, 25, 42} {4, 25, 43} {4, 25, 44} {4, 25, 45} {4, 25, 46} {4, 25, 47} {4, 25, 48} {4, 25, 49} {4, 25, 50}
{4, 25, 51} {4, 25, 52} {4, 25, 53} {4, 25, 54} {4, 25, 55} {4, 25, 56} {4, 25, 57} {4, 25, 58} {4, 25, 59} {4, 25, 60}

TABLE 3A-continued

{4, 25, 61} {4, 25, 62} {4, 25, 63} {4, 25, 64} {4, 25, 65} {4, 25, 66} {4, 26, 27} {4, 26, 28} {4, 26, 29} {4, 26, 30}
{4, 26, 31} {4, 26, 32} {4, 26, 33} {4, 26, 34} {4, 26, 35} {4, 26, 36} {4, 26, 37} {4, 26, 38} {4, 26, 39} {4, 26, 40}
{4, 26, 41} {4, 26, 42} {4, 26, 43} {4, 26, 44} {4, 26, 45} {4, 26, 46} {4, 26, 47} {4, 26, 48} {4, 26, 49} {4, 26, 50}
{4, 26, 51} {4, 26, 52} {4, 26, 53} {4, 26, 54} {4, 26, 55} {4, 26, 56} {4, 26, 57} {4, 26, 58} {4, 26, 59} {4, 26, 60}
{4, 26, 61} {4, 26, 62} {4, 26, 63} {4, 26, 64} {4, 26, 65} {4, 26, 66} {4, 27, 28} {4, 27, 29} {4, 27, 30} {4, 27, 31}
{4, 27, 32} {4, 27, 33} {4, 27, 34} {4, 27, 35} {4, 27, 36} {4, 27, 37} {4, 27, 38} {4, 27, 39} {4, 27, 40} {4, 27, 41}
{4, 27, 42} {4, 27, 43} {4, 27, 44} {4, 27, 45} {4, 27, 46} {4, 27, 47} {4, 27, 48} {4, 27, 49} {4, 27, 50} {4, 27, 51}
{4, 27, 52} {4, 27, 53} {4, 27, 54} {4, 27, 55} {4, 27, 56} {4, 27, 57} {4, 27, 58} {4, 27, 59} {4, 27, 60} {4, 27, 61}
{4, 27, 62} {4, 27, 63} {4, 27, 64} {4, 27, 65} {4, 27, 66} {4, 28, 29} {4, 28, 30} {4, 28, 31} {4, 28, 32} {4, 28, 33}
{4, 28, 34} {4, 28, 35} {4, 28, 36} {4, 28, 37} {4, 28, 38} {4, 28, 39} {4, 28, 40} {4, 28, 41} {4, 28, 42} {4, 28, 43}
{4, 28, 44} {4, 28, 45} {4, 28, 46} {4, 28, 47} {4, 28, 48} {4, 28, 49} {4, 28, 50} {4, 28, 51} {4, 28, 52} {4, 28, 53}
{4, 28, 54} {4, 28, 55} {4, 28, 56} {4, 28, 57} {4, 28, 58} {4, 28, 59} {4, 28, 60} {4, 28, 61} {4, 28, 62} {4, 28, 63}
{4, 28, 64} {4, 28, 65} {4, 28, 66} {4, 29, 30} {4, 29, 31} {4, 29, 32} {4, 29, 33} {4, 29, 34} {4, 29, 35} {4, 29, 36}
{4, 29, 37} {4, 29, 38} {4, 29, 39} {4, 29, 40} {4, 29, 41} {4, 29, 42} {4, 29, 43} {4, 29, 44} {4, 29, 45} {4, 29, 46}
{4, 29, 47} {4, 29, 48} {4, 29, 49} {4, 29, 50} {4, 29, 51} {4, 29, 52} {4, 29, 53} {4, 29, 54} {4, 29, 55} {4, 29, 56}
{4, 29, 57} {4, 29, 58} {4, 29, 59} {4, 29, 60} {4, 29, 61} {4, 29, 62} {4, 29, 63} {4, 29, 64} {4, 29, 65} {4, 29, 66}
{4, 30, 31} {4, 30, 32} {4, 30, 33} {4, 30, 34} {4, 30, 35} {4, 30, 36} {4, 30, 37} {4, 30, 38} {4, 30, 39} {4, 30, 40}
{4, 30, 41} {4, 30, 42} {4, 30, 43} {4, 30, 44} {4, 30, 45} {4, 30, 46} {4, 30, 47} {4, 30, 48} {4, 30, 49} {4, 30, 50}
{4, 30, 51} {4, 30, 52} {4, 30, 53} {4, 30, 54} {4, 30, 55} {4, 30, 56} {4, 30, 57} {4, 30, 58} {4, 30, 59} {4, 30, 60}
{4, 30, 61} {4, 30, 62} {4, 30, 63} {4, 30, 64} {4, 30, 65} {4, 30, 66} {4, 31, 32} {4, 31, 33} {4, 31, 34} {4, 31, 35}
{4, 31, 36} {4, 31, 37} {4, 31, 38} {4, 31, 39} {4, 31, 40} {4, 31, 41} {4, 31, 42} {4, 31, 43} {4, 31, 44} {4, 31, 45}
{4, 31, 46} {4, 31, 47} {4, 31, 48} {4, 31, 49} {4, 31, 50} {4, 31, 51} {4, 31, 52} {4, 31, 53} {4, 31, 54} {4, 31, 55}
{4, 31, 56} {4, 31, 57} {4, 31, 58} {4, 31, 59} {4, 31, 60} {4, 31, 61} {4, 31, 62} {4, 31, 63} {4, 31, 64} {4, 31, 65}
{4, 31, 66} {4, 32, 33} {4, 32, 34} {4, 32, 35} {4, 32, 36} {4, 32, 37} {4, 32, 38} {4, 32, 39} {4, 32, 40} {4, 32, 41}
{4, 32, 42} {4, 32, 43} {4, 32, 44} {4, 32, 45} {4, 32, 46} {4, 32, 47} {4, 32, 48} {4, 32, 49} {4, 32, 50} {4, 32, 51}
{4, 32, 52} {4, 32, 53} {4, 32, 54} {4, 32, 55} {4, 32, 56} {4, 32, 57} {4, 32, 58} {4, 32, 59} {4, 32, 60} {4, 32, 61}
{4, 32, 62} {4, 32, 63} {4, 32, 64} {4, 32, 65} {4, 32, 66} {4, 33, 34} {4, 33, 35} {4, 33, 36} {4, 33, 37} {4, 33, 38}
{4, 33, 39} {4, 33, 40} {4, 33, 41} {4, 33, 42} {4, 33, 43} {4, 33, 44} {4, 33, 45} {4, 33, 46} {4, 33, 47} {4, 33, 48}
{4, 33, 49} {4, 33, 50} {4, 33, 51} {4, 33, 52} {4, 33, 53} {4, 33, 54} {4, 33, 55} {4, 33, 56} {4, 33, 57} {4, 33, 58}
{4, 33, 59} {4, 33, 60} {4, 33, 61} {4, 33, 62} {4, 33, 63} {4, 33, 64} {4, 33, 65} {4, 33, 66} {4, 34, 35} {4, 34, 36}
{4, 34, 37} {4, 34, 38} {4, 34, 39} {4, 34, 40} {4, 34, 41} {4, 34, 42} {4, 34, 43} {4, 34, 44} {4, 34, 45} {4, 34, 46}
{4, 34, 47} {4, 34, 48} {4, 34, 49} {4, 34, 50} {4, 34, 51} {4, 34, 52} {4, 34, 53} {4, 34, 54} {4, 34, 55} {4, 34, 56}
{4, 34, 57} {4, 34, 58} {4, 34, 59} {4, 34, 60} {4, 34, 61} {4, 34, 62} {4, 34, 63} {4, 34, 64} {4, 34, 65} {4, 34, 66}
{4, 35, 36} {4, 35, 37} {4, 35, 38} {4, 35, 39} {4, 35, 40} {4, 35, 41} {4, 35, 42} {4, 35, 43} {4, 35, 44} {4, 35, 45}
{4, 35, 46} {4, 35, 47} {4, 35, 48} {4, 35, 49} {4, 35, 50} {4, 35, 51} {4, 35, 52} {4, 35, 53} {4, 35, 54} {4, 35, 55}
{4, 35, 56} {4, 35, 57} {4, 35, 58} {4, 35, 59} {4, 35, 60} {4, 35, 61} {4, 35, 62} {4, 35, 63} {4, 35, 64} {4, 35, 65}
{4, 35, 66} {4, 36, 37} {4, 36, 38} {4, 36, 39} {4, 36, 40} {4, 36, 41} {4, 36, 42} {4, 36, 43} {4, 36, 44} {4, 36, 45}
{4, 36, 46} {4, 36, 47} {4, 36, 48} {4, 36, 49} {4, 36, 50} {4, 36, 51} {4, 36, 52} {4, 36, 53} {4, 36, 54} {4, 36, 55}
{4, 36, 56} {4, 36, 57} {4, 36, 58} {4, 36, 59} {4, 36, 60} {4, 36, 61} {4, 36, 62} {4, 36, 63} {4, 36, 64} {4, 36, 65}
{4, 36, 66} {4, 37, 38} {4, 37, 39} {4, 37, 40} {4, 37, 41} {4, 37, 42} {4, 37, 43} {4, 37, 44} {4, 37, 45} {4, 37, 46}
{4, 37, 47} {4, 37, 48} {4, 37, 49} {4, 37, 50} {4, 37, 51} {4, 37, 52} {4, 37, 53} {4, 37, 54} {4, 37, 55} {4, 37, 56}
{4, 37, 57} {4, 37, 58} {4, 37, 59} {4, 37, 60} {4, 37, 61} {4, 37, 62} {4, 37, 63} {4, 37, 64} {4, 37, 65} {4, 37, 66}
{4, 38, 39} {4, 38, 40} {4, 38, 41} {4, 38, 42} {4, 38, 43} {4, 38, 44} {4, 38, 45} {4, 38, 46} {4, 38, 47} {4, 38, 48}
{4, 38, 49} {4, 38, 50} {4, 38, 51} {4, 38, 52} {4, 38, 53} {4, 38, 54} {4, 38, 55} {4, 38, 56} {4, 38, 57} {4, 38, 58}
{4, 38, 59} {4, 38, 60} {4, 38, 61} {4, 38, 62} {4, 38, 63} {4, 38, 64} {4, 38, 65} {4, 38, 66} {4, 39, 40} {4, 39, 41}
{4, 39, 42} {4, 39, 43} {4, 39, 44} {4, 39, 45} {4, 39, 46} {4, 39, 47} {4, 39, 48} {4, 39, 49} {4, 39, 50} {4, 39, 51}
{4, 39, 52} {4, 39, 53} {4, 39, 54} {4, 39, 55} {4, 39, 56} {4, 39, 57} {4, 39, 58} {4, 39, 59} {4, 39, 60} {4, 39, 61}
{4, 39, 62} {4, 39, 63} {4, 39, 64} {4, 39, 65} {4, 39, 66} {4, 40, 41} {4, 40, 42} {4, 40, 43} {4, 40, 44} {4, 40, 45}
{4, 40, 46} {4, 40, 47} {4, 40, 48} {4, 40, 49} {4, 40, 50} {4, 40, 51} {4, 40, 52} {4, 40, 53} {4, 40, 54} {4, 40, 55}
{4, 40, 56} {4, 40, 57} {4, 40, 58} {4, 40, 59} {4, 40, 60} {4, 40, 61} {4, 40, 62} {4, 40, 63} {4, 40, 64} {4, 40, 65}
{4, 40, 66} {4, 41, 42} {4, 41, 43} {4, 41, 44} {4, 41, 45} {4, 41, 46} {4, 41, 47} {4, 41, 48} {4, 41, 49} {4, 41, 50}
{4, 41, 51} {4, 41, 52} {4, 41, 53} {4, 41, 54} {4, 41, 55} {4, 41, 56} {4, 41, 57} {4, 41, 58} {4, 41, 59} {4, 41, 60}
{4, 41, 61} {4, 41, 62} {4, 41, 63} {4, 41, 64} {4, 41, 65} {4, 41, 66} {4, 42, 43} {4, 42, 44} {4, 42, 45} {4, 42, 46}
{4, 42, 47} {4, 42, 48} {4, 42, 49} {4, 42, 50} {4, 42, 51} {4, 42, 52} {4, 42, 53} {4, 42, 54} {4, 42, 55} {4, 42, 56}
{4, 42, 57} {4, 42, 58} {4, 42, 59} {4, 42, 60} {4, 42, 61} {4, 42, 62} {4, 42, 63} {4, 42, 64} {4, 42, 65} {4, 42, 66}
{4, 43, 44} {4, 43, 45} {4, 43, 46} {4, 43, 47} {4, 43, 48} {4, 43, 49} {4, 43, 50} {4, 43, 51} {4, 43, 52} {4, 43, 53}
{4, 43, 54} {4, 43, 55} {4, 43, 56} {4, 43, 57} {4, 43, 58} {4, 43, 59} {4, 43, 60} {4, 43, 61} {4, 43, 62} {4, 43, 63}
{4, 43, 64} {4, 43, 65} {4, 43, 66} {4, 44, 45} {4, 44, 46} {4, 44, 47} {4, 44, 48} {4, 44, 49} {4, 44, 50} {4, 44, 51}
{4, 44, 52} {4, 44, 53} {4, 44, 54} {4, 44, 55} {4, 44, 56} {4, 44, 57} {4, 44, 58} {4, 44, 59} {4, 44, 60} {4, 44, 61}
{4, 44, 62} {4, 44, 63} {4, 44, 64} {4, 44, 65} {4, 44, 66} {4, 45, 46} {4, 45, 47} {4, 45, 48} {4, 45, 49} {4, 45, 50}
{4, 45, 51} {4, 45, 52} {4, 45, 53} {4, 45, 54} {4, 45, 55} {4, 45, 56} {4, 45, 57} {4, 45, 58} {4, 45, 59} {4, 45, 60}
{4, 45, 61} {4, 45, 62} {4, 45, 63} {4, 45, 64} {4, 45, 65} {4, 45, 66} {4, 46, 47} {4, 46, 48} {4, 46, 49} {4, 46, 50}
{4, 46, 51} {4, 46, 52} {4, 46, 53} {4, 46, 54} {4, 46, 55} {4, 46, 56} {4, 46, 57} {4, 46, 58} {4, 46, 59} {4, 46, 60}
{4, 46, 61} {4, 46, 62} {4, 46, 63} {4, 46, 64} {4, 46, 65} {4, 46, 66} {4, 47, 48} {4, 47, 49} {4, 47, 50} {4, 47, 51}
{4, 47, 52} {4, 47, 53} {4, 47, 54} {4, 47, 55} {4, 47, 56} {4, 47, 57} {4, 47, 58} {4, 47, 59} {4, 47, 60} {4, 47, 61}
{4, 47, 62} {4, 47, 63} {4, 47, 64} {4, 47, 65} {4, 47, 66} {4, 48, 49} {4, 48, 50} {4, 48, 51} {4, 48, 52} {4, 48, 53}
{4, 48, 54} {4, 48, 55} {4, 48, 56} {4, 48, 57} {4, 48, 58} {4, 48, 59} {4, 48, 60} {4, 48, 61} {4, 48, 62} {4, 48, 63}
{4, 48, 64} {4, 48, 65} {4, 48, 66} {4, 49, 50} {4, 49, 51} {4, 49, 52} {4, 49, 53} {4, 49, 54} {4, 49, 55} {4, 49, 56}
{4, 49, 57} {4, 49, 58} {4, 49, 59} {4, 49, 60} {4, 49, 61} {4, 49, 62} {4, 49, 63} {4, 49, 64} {4, 49, 65} {4, 49, 66}
{4, 50, 51} {4, 50, 52} {4, 50, 53} {4, 50, 54} {4, 50, 55} {4, 50, 56} {4, 50, 57} {4, 50, 58} {4, 50, 59} {4, 50, 60}
{4, 50, 61} {4, 50, 62} {4, 50, 63} {4, 50, 64} {4, 50, 65} {4, 50, 66} {4, 51, 52} {4, 51, 53} {4, 51, 54} {4, 51, 55}
{4, 51, 56} {4, 51, 57} {4, 51, 58} {4, 51, 59} {4, 51, 60} {4, 51, 61} {4, 51, 62} {4, 51, 63} {4, 51, 64} {4, 51, 65}
{4, 51, 66} {4, 52, 53} {4, 52, 54} {4, 52, 55} {4, 52, 56} {4, 52, 57} {4, 52, 58} {4, 52, 59} {4, 52, 60} {4, 52, 61}
{4, 52, 62} {4, 52, 63} {4, 52, 64} {4, 52, 65} {4, 52, 66} {4, 53, 54} {4, 53, 55} {4, 53, 56} {4, 53, 57} {4, 53, 58}
{4, 53, 59} {4, 53, 60} {4, 53, 61} {4, 53, 62} {4, 53, 63} {4, 53, 64} {4, 53, 65} {4, 53, 66} {4, 54, 55} {4, 54, 56}
{4, 54, 57} {4, 54, 58} {4, 54, 59} {4, 54, 60} {4, 54, 61} {4, 54, 62} {4, 54, 63} {4, 54, 64} {4, 54, 65} {4, 54, 66}
{4, 55, 56} {4, 55, 57} {4, 55, 58} {4, 55, 59} {4, 55, 60} {4, 55, 61} {4, 55, 62} {4, 55, 63} {4, 55, 64} {4, 55, 65}
{4, 55, 66} {4, 56, 57} {4, 56, 58} {4, 56, 59} {4, 56, 60} {4, 56, 61} {4, 56, 62} {4, 56, 63} {4, 56, 64} {4, 56, 65}
{4, 56, 66} {4, 57, 58} {4, 57, 59} {4, 57, 60} {4, 57, 61} {4, 57, 62} {4, 57, 63} {4, 57, 64} {4, 57, 65} {4, 57, 66}
{4, 58, 59} {4, 58, 60} {4, 58, 61} {4, 58, 62} {4, 58, 63} {4, 58, 64} {4, 58, 65} {4, 58, 66} {4, 59, 60} {4, 59, 61}

TABLE 3A-continued

{4, 59, 62} {4, 59, 63} {4, 59, 64} {4, 59, 65} {4, 59, 66} {4, 60, 61} {4, 60, 62} {4, 60, 63} {4, 60, 64} {4, 60, 65}
{4, 60, 66} {4, 61, 62} {4, 61, 63} {4, 61, 64} {4, 61, 65} {4, 61, 66} {4, 62, 63} {4, 62, 64} {4, 62, 65} {4, 62, 66}
{4, 63, 64} {4, 63, 65} {4, 63, 66} {4, 64, 65} {4, 64, 66} {4, 65, 66} {5, 6, 7} {5, 6, 8} {5, 6, 9} {5, 6, 10} {5, 6, 11} {5, 6, 12}
{5, 6, 13} {5, 6, 14} {5, 6, 15} {5, 6, 16} {5, 6, 17} {5, 6, 18} {5, 6, 19} {5, 6, 20} {5, 6, 21} {5, 6, 22} {5, 6, 23} {5, 6, 24}
{5, 6, 25} {5, 6, 26} {5, 6, 27} {5, 6, 28} {5, 6, 29} {5, 6, 30} {5, 6, 31} {5, 6, 32} {5, 6, 33} {5, 6, 34} {5, 6, 35} {5, 6, 36}
{5, 6, 37} {5, 6, 38} {5, 6, 39} {5, 6, 40} {5, 6, 41} {5, 6, 42} {5, 6, 43} {5, 6, 44} {5, 6, 45} {5, 6, 46} {5, 6, 47} {5, 6, 48}
{5, 6, 49} {5, 6, 50} {5, 6, 51} {5, 6, 52} {5, 6, 53} {5, 6, 54} {5, 6, 55} {5, 6, 56} {5, 6, 57} {5, 6, 58} {5, 6, 59} {5, 6, 60}
{5, 6, 61} {5, 6, 62} {5, 6, 63} {5, 6, 64} {5, 6, 65} {5, 6, 66} {5, 7, 8} {5, 7, 9} {5, 7, 10} {5, 7, 11} {5, 7, 12} {5, 7, 13}
{5, 7, 14} {5, 7, 15} {5, 7, 16} {5, 7, 17} {5, 7, 18} {5, 7, 19} {5, 7, 20} {5, 7, 21} {5, 7, 22} {5, 7, 23} {5, 7, 24} {5, 7, 25}
{5, 7, 26} {5, 7, 27} {5, 7, 28} {5, 7, 29} {5, 7, 30} {5, 7, 31} {5, 7, 32} {5, 7, 33} {5, 7, 34} {5, 7, 35} {5, 7, 36} {5, 7, 37}
{5, 7, 38} {5, 7, 39} {5, 7, 40} {5, 7, 41} {5, 7, 42} {5, 7, 43} {5, 7, 44} {5, 7, 45} {5, 7, 46} {5, 7, 47} {5, 7, 48} {5, 7, 49}
{5, 7, 50} {5, 7, 51} {5, 7, 52} {5, 7, 53} {5, 7, 54} {5, 7, 55} {5, 7, 56} {5, 7, 57} {5, 7, 58} {5, 7, 59} {5, 7, 60} {5, 7, 61}
{5, 7, 62} {5, 7, 63} {5, 7, 64} {5, 7, 65} {5, 7, 66} {5, 8, 9} {5, 8, 10} {5, 8, 11} {5, 8, 12} {5, 8, 13} {5, 8, 14} {5, 8, 15}
{5, 8, 16} {5, 8, 17} {5, 8, 18} {5, 8, 19} {5, 8, 20} {5, 8, 21} {5, 8, 22} {5, 8, 23} {5, 8, 24} {5, 8, 25} {5, 8, 26} {5, 8, 27}
{5, 8, 28} {5, 8, 29} {5, 8, 30} {5, 8, 31} {5, 8, 32} {5, 8, 33} {5, 8, 34} {5, 8, 35} {5, 8, 36} {5, 8, 37} {5, 8, 38} {5, 8, 39}
{5, 8, 40} {5, 8, 41} {5, 8, 42} {5, 8, 43} {5, 8, 44} {5, 8, 45} {5, 8, 46} {5, 8, 47} {5, 8, 48} {5, 8, 49} {5, 8, 50} {5, 8, 51}
{5, 8, 52} {5, 8, 53} {5, 8, 54} {5, 8, 55} {5, 8, 56} {5, 8, 57} {5, 8, 58} {5, 8, 59} {5, 8, 60} {5, 8, 61} {5, 8, 62} {5, 8, 63}
{5, 8, 64} {5, 8, 65} {5, 8, 66} {5, 9, 10} {5, 9, 11} {5, 9, 12} {5, 9, 13} {5, 9, 14} {5, 9, 15} {5, 9, 16} {5, 9, 17} {5, 9, 18}
{5, 9, 19} {5, 9, 20} {5, 9, 21} {5, 9, 22} {5, 9, 23} {5, 9, 24} {5, 9, 25} {5, 9, 26} {5, 9, 27} {5, 9, 28} {5, 9, 29} {5, 9, 30}
{5, 9, 31} {5, 9, 32} {5, 9, 33} {5, 9, 34} {5, 9, 35} {5, 9, 36} {5, 9, 37} {5, 9, 38} {5, 9, 39} {5, 9, 40} {5, 9, 41} {5, 9, 42}
{5, 9, 43} {5, 9, 44} {5, 9, 45} {5, 9, 46} {5, 9, 47} {5, 9, 48} {5, 9, 49} {5, 9, 50} {5, 9, 51} {5, 9, 52} {5, 9, 53} {5, 9, 54}
{5, 9, 55} {5, 9, 56} {5, 9, 57} {5, 9, 58} {5, 9, 59} {5, 9, 60} {5, 9, 61} {5, 9, 62} {5, 9, 63} {5, 9, 64} {5, 9, 65} {5, 9, 66}
{5, 10, 11} {5, 10, 12} {5, 10, 13} {5, 10, 14} {5, 10, 15} {5, 10, 16} {5, 10, 17} {5, 10, 18} {5, 10, 19} {5, 10, 20}
{5, 10, 21} {5, 10, 22} {5, 10, 23} {5, 10, 24} {5, 10, 25} {5, 10, 26} {5, 10, 27} {5, 10, 28} {5, 10, 29} {5, 10, 30}
{5, 10, 31} {5, 10, 32} {5, 10, 33} {5, 10, 34} {5, 10, 35} {5, 10, 36} {5, 10, 37} {5, 10, 38} {5, 10, 39} {5, 10, 40}
{5, 10, 41} {5, 10, 42} {5, 10, 43} {5, 10, 44} {5, 10, 45} {5, 10, 46} {5, 10, 47} {5, 10, 48} {5, 10, 49} {5, 10, 50}
{5, 10, 51} {5, 10, 52} {5, 10, 53} {5, 10, 54} {5, 10, 55} {5, 10, 56} {5, 10, 57} {5, 10, 58} {5, 10, 59} {5, 10, 60}
{5, 10, 61} {5, 10, 62} {5, 10, 63} {5, 10, 64} {5, 10, 65} {5, 10, 66} {5, 11, 12} {5, 11, 13} {5, 11, 14} {5, 11, 15}
{5, 11, 16} {5, 11, 17} {5, 11, 18} {5, 11, 19} {5, 11, 20} {5, 11, 21} {5, 11, 22} {5, 11, 23} {5, 11, 24} {5, 11, 25}
{5, 11, 26} {5, 11, 27} {5, 11, 28} {5, 11, 29} {5, 11, 30} {5, 11, 31} {5, 11, 32} {5, 11, 33} {5, 11, 34} {5, 11, 35}
{5, 11, 36} {5, 11, 37} {5, 11, 38} {5, 11, 39} {5, 11, 40} {5, 11, 41} {5, 11, 42} {5, 11, 43} {5, 11, 44} {5, 11, 45}
{5, 11, 46} {5, 11, 47} {5, 11, 48} {5, 11, 49} {5, 11, 50} {5, 11, 51} {5, 11, 52} {5, 11, 53} {5, 11, 54} {5, 11, 55}
{5, 11, 56} {5, 11, 57} {5, 11, 58} {5, 11, 59} {5, 11, 60} {5, 11, 61} {5, 11, 62} {5, 11, 63} {5, 11, 64} {5, 11, 65}
{5, 11, 66} {5, 12, 13} {5, 12, 14} {5, 12, 15} {5, 12, 16} {5, 12, 17} {5, 12, 18} {5, 12, 19} {5, 12, 20} {5, 12, 21}
{5, 12, 22} {5, 12, 23} {5, 12, 24} {5, 12, 25} {5, 12, 26} {5, 12, 27} {5, 12, 28} {5, 12, 29} {5, 12, 30} {5, 12, 31}
{5, 12, 32} {5, 12, 33} {5, 12, 34} {5, 12, 35} {5, 12, 36} {5, 12, 37} {5, 12, 38} {5, 12, 39} {5, 12, 40} {5, 12, 41}
{5, 12, 42} {5, 12, 43} {5, 12, 44} {5, 12, 45} {5, 12, 46} {5, 12, 47} {5, 12, 48} {5, 12, 49} {5, 12, 50} {5, 12, 51}
{5, 12, 52} {5, 12, 53} {5, 12, 54} {5, 12, 55} {5, 12, 56} {5, 12, 57} {5, 12, 58} {5, 12, 59} {5, 12, 60} {5, 12, 61}
{5, 12, 62} {5, 12, 63} {5, 12, 64} {5, 12, 65} {5, 12, 66} {5, 13, 14} {5, 13, 15} {5, 13, 16} {5, 13, 17} {5, 13, 18}
{5, 13, 19} {5, 13, 20} {5, 13, 21} {5, 13, 22} {5, 13, 23} {5, 13, 24} {5, 13, 25} {5, 13, 26} {5, 13, 27} {5, 13, 28}
{5, 13, 29} {5, 13, 30} {5, 13, 31} {5, 13, 32} {5, 13, 33} {5, 13, 34} {5, 13, 35} {5, 13, 36} {5, 13, 37} {5, 13, 38}
{5, 13, 39} {5, 13, 40} {5, 13, 41} {5, 13, 42} {5, 13, 43} {5, 13, 44} {5, 13, 45} {5, 13, 46} {5, 13, 47} {5, 13, 48}
{5, 13, 49} {5, 13, 50} {5, 13, 51} {5, 13, 52} {5, 13, 53} {5, 13, 54} {5, 13, 55} {5, 13, 56} {5, 13, 57} {5, 13, 58}
{5, 13, 59} {5, 13, 60} {5, 13, 61} {5, 13, 62} {5, 13, 63} {5, 13, 64} {5, 13, 65} {5, 13, 66} {5, 14, 15} {5, 14, 16}
{5, 14, 17} {5, 14, 18} {5, 14, 19} {5, 14, 20} {5, 14, 21} {5, 14, 22} {5, 14, 23} {5, 14, 24} {5, 14, 25} {5, 14, 26}
{5, 14, 27} {5, 14, 28} {5, 14, 29} {5, 14, 30} {5, 14, 31} {5, 14, 32} {5, 14, 33} {5, 14, 34} {5, 14, 35} {5, 14, 36}
{5, 14, 37} {5, 14, 38} {5, 14, 39} {5, 14, 40} {5, 14, 41} {5, 14, 42} {5, 14, 43} {5, 14, 44} {5, 14, 45} {5, 14, 46}
{5, 14, 47} {5, 14, 48} {5, 14, 49} {5, 14, 50} {5, 14, 51} {5, 14, 52} {5, 14, 53} {5, 14, 54} {5, 14, 55} {5, 14, 56}
{5, 14, 57} {5, 14, 58} {5, 14, 59} {5, 14, 60} {5, 14, 61} {5, 14, 62} {5, 14, 63} {5, 14, 64} {5, 14, 65} {5, 14, 66}
{5, 15, 16} {5, 15, 17} {5, 15, 18} {5, 15, 19} {5, 15, 20} {5, 15, 21} {5, 15, 22} {5, 15, 23} {5, 15, 24} {5, 15, 25}
{5, 15, 26} {5, 15, 27} {5, 15, 28} {5, 15, 29} {5, 15, 30} {5, 15, 31} {5, 15, 32} {5, 15, 33} {5, 15, 34} {5, 15, 35}
{5, 15, 36} {5, 15, 37} {5, 15, 38} {5, 15, 39} {5, 15, 40} {5, 15, 41} {5, 15, 42} {5, 15, 43} {5, 15, 44} {5, 15, 45}
{5, 15, 46} {5, 15, 47} {5, 15, 48} {5, 15, 49} {5, 15, 50} {5, 15, 51} {5, 15, 52} {5, 15, 53} {5, 15, 54} {5, 15, 55}
{5, 15, 56} {5, 15, 57} {5, 15, 58} {5, 15, 59} {5, 15, 60} {5, 15, 61} {5, 15, 62} {5, 15, 63} {5, 15, 64} {5, 15, 65}
{5, 15, 66} {5, 16, 17} {5, 16, 18} {5, 16, 19} {5, 16, 20} {5, 16, 21} {5, 16, 22} {5, 16, 23} {5, 16, 24} {5, 16, 25}
{5, 16, 26} {5, 16, 27} {5, 16, 28} {5, 16, 29} {5, 16, 30} {5, 16, 31} {5, 16, 32} {5, 16, 33} {5, 16, 34} {5, 16, 35}
{5, 16, 36} {5, 16, 37} {5, 16, 38} {5, 16, 39} {5, 16, 40} {5, 16, 41} {5, 16, 42} {5, 16, 43} {5, 16, 44} {5, 16, 45}
{5, 16, 46} {5, 16, 47} {5, 16, 48} {5, 16, 49} {5, 16, 50} {5, 16, 51} {5, 16, 52} {5, 16, 53} {5, 16, 54} {5, 16, 55}
{5, 16, 56} {5, 16, 57} {5, 16, 58} {5, 16, 59} {5, 16, 60} {5, 16, 61} {5, 16, 62} {5, 16, 63} {5, 16, 64} {5, 16, 65}
{5, 16, 66} {5, 17, 18} {5, 17, 19} {5, 17, 20} {5, 17, 21} {5, 17, 22} {5, 17, 23} {5, 17, 24} {5, 17, 25} {5, 17, 26}
{5, 17, 27} {5, 17, 28} {5, 17, 29} {5, 17, 30} {5, 17, 31} {5, 17, 32} {5, 17, 33} {5, 17, 34} {5, 17, 35} {5, 17, 36}
{5, 17, 37} {5, 17, 38} {5, 17, 39} {5, 17, 40} {5, 17, 41} {5, 17, 42} {5, 17, 43} {5, 17, 44} {5, 17, 45} {5, 17, 46}
{5, 17, 47} {5, 17, 48} {5, 17, 49} {5, 17, 50} {5, 17, 51} {5, 17, 52} {5, 17, 53} {5, 17, 54} {5, 17, 55} {5, 17, 56}
{5, 17, 57} {5, 17, 58} {5, 17, 59} {5, 17, 60} {5, 17, 61} {5, 17, 62} {5, 17, 63} {5, 17, 64} {5, 17, 65} {5, 17, 66}
{5, 18, 19} {5, 18, 20} {5, 18, 21} {5, 18, 22} {5, 18, 23} {5, 18, 24} {5, 18, 25} {5, 18, 26} {5, 18, 27} {5, 18, 28}
{5, 18, 29} {5, 18, 30} {5, 18, 31} {5, 18, 32} {5, 18, 33} {5, 18, 34} {5, 18, 35} {5, 18, 36} {5, 18, 37} {5, 18, 38}
{5, 18, 39} {5, 18, 40} {5, 18, 41} {5, 18, 42} {5, 18, 43} {5, 18, 44} {5, 18, 45} {5, 18, 46} {5, 18, 47} {5, 18, 48}
{5, 18, 49} {5, 18, 50} {5, 18, 51} {5, 18, 52} {5, 18, 53} {5, 18, 54} {5, 18, 55} {5, 18, 56} {5, 18, 57} {5, 18, 58}
{5, 18, 59} {5, 18, 60} {5, 18, 61} {5, 18, 62} {5, 18, 63} {5, 18, 64} {5, 18, 65} {5, 18, 66} {5, 19, 20} {5, 19, 21}
{5, 19, 22} {5, 19, 23} {5, 19, 24} {5, 19, 25} {5, 19, 26} {5, 19, 27} {5, 19, 28} {5, 19, 29} {5, 19, 30} {5, 19, 31}
{5, 19, 32} {5, 19, 33} {5, 19, 34} {5, 19, 35} {5, 19, 36} {5, 19, 37} {5, 19, 38} {5, 19, 39} {5, 19, 40} {5, 19, 41}
{5, 19, 42} {5, 19, 43} {5, 19, 44} {5, 19, 45} {5, 19, 46} {5, 19, 47} {5, 19, 48} {5, 19, 49} {5, 19, 50} {5, 19, 51}
{5, 19, 52} {5, 19, 53} {5, 19, 54} {5, 19, 55} {5, 19, 56} {5, 19, 57} {5, 19, 58} {5, 19, 59} {5, 19, 60} {5, 19, 61}
{5, 19, 62} {5, 19, 63} {5, 19, 64} {5, 19, 65} {5, 19, 66} {5, 20, 21} {5, 20, 22} {5, 20, 23} {5, 20, 24} {5, 20, 25}
{5, 20, 26} {5, 20, 27} {5, 20, 28} {5, 20, 29} {5, 20, 30} {5, 20, 31} {5, 20, 32} {5, 20, 33} {5, 20, 34} {5, 20, 35}
{5, 20, 36} {5, 20, 37} {5, 20, 38} {5, 20, 39} {5, 20, 40} {5, 20, 41} {5, 20, 42} {5, 20, 43} {5, 20, 44} {5, 20, 45}
{5, 20, 46} {5, 20, 47} {5, 20, 48} {5, 20, 49} {5, 20, 50} {5, 20, 51} {5, 20, 52} {5, 20, 53} {5, 20, 54} {5, 20, 55}
{5, 20, 56} {5, 20, 57} {5, 20, 58} {5, 20, 59} {5, 20, 60} {5, 20, 61} {5, 20, 62} {5, 20, 63} {5, 20, 64} {5, 20, 65}
{5, 20, 66} {5, 21, 22} {5, 21, 23} {5, 21, 24} {5, 21, 25} {5, 21, 26} {5, 21, 27} {5, 21, 28} {5, 21, 29} {5, 21, 30}
{5, 21, 31} {5, 21, 32} {5, 21, 33} {5, 21, 34} {5, 21, 35} {5, 21, 36} {5, 21, 37} {5, 21, 38} {5, 21, 39} {5, 21, 40}

TABLE 3A-continued

{5, 21, 41} {5, 21, 42} {5, 21, 43} {5, 21, 44} {5, 21, 45} {5, 21, 46} {5, 21, 47} {5, 21, 48} {5, 21, 49} {5, 21, 50}
{5, 21, 51} {5, 21, 52} {5, 21, 53} {5, 21, 54} {5, 21, 55} {5, 21, 56} {5, 21, 57} {5, 21, 58} {5, 21, 59} {5, 21, 60}
{5, 21, 61} {5, 21, 62} {5, 21, 63} {5, 21, 64} {5, 21, 65} {5, 21, 66} {5, 22, 23} {5, 22, 24} {5, 22, 25} {5, 22, 26}
{5, 22, 27} {5, 22, 28} {5, 22, 29} {5, 22, 30} {5, 22, 31} {5, 22, 32} {5, 22, 33} {5, 22, 34} {5, 22, 35} {5, 22, 36}
{5, 22, 37} {5, 22, 38} {5, 22, 39} {5, 22, 40} {5, 22, 41} {5, 22, 42} {5, 22, 43} {5, 22, 44} {5, 22, 45} {5, 22, 46}
{5, 22, 47} {5, 22, 48} {5, 22, 49} {5, 22, 50} {5, 22, 51} {5, 22, 52} {5, 22, 53} {5, 22, 54} {5, 22, 55} {5, 22, 56}
{5, 22, 57} {5, 22, 58} {5, 22, 59} {5, 22, 60} {5, 22, 61} {5, 22, 62} {5, 22, 63} {5, 22, 64} {5, 22, 65} {5, 22, 66}
{5, 23, 24} {5, 23, 25} {5, 23, 26} {5, 23, 27} {5, 23, 28} {5, 23, 29} {5, 23, 30} {5, 23, 31} {5, 23, 32} {5, 23, 33}
{5, 23, 34} {5, 23, 35} {5, 23, 36} {5, 23, 37} {5, 23, 38} {5, 23, 39} {5, 23, 40} {5, 23, 41} {5, 23, 42} {5, 23, 43}
{5, 23, 44} {5, 23, 45} {5, 23, 46} {5, 23, 47} {5, 23, 48} {5, 23, 49} {5, 23, 50} {5, 23, 51} {5, 23, 52} {5, 23, 53}
{5, 23, 54} {5, 23, 55} {5, 23, 56} {5, 23, 57} {5, 23, 58} {5, 23, 59} {5, 23, 60} {5, 23, 61} {5, 23, 62} {5, 23, 63}
{5, 23, 64} {5, 23, 65} {5, 23, 66} {5, 24, 25} {5, 24, 26} {5, 24, 27} {5, 24, 28} {5, 24, 29} {5, 24, 30} {5, 24, 31}
{5, 24, 32} {5, 24, 33} {5, 24, 34} {5, 24, 35} {5, 24, 36} {5, 24, 37} {5, 24, 38} {5, 24, 39} {5, 24, 40} {5, 24, 41}
{5, 24, 42} {5, 24, 43} {5, 24, 44} {5, 24, 45} {5, 24, 46} {5, 24, 47} {5, 24, 48} {5, 24, 49} {5, 24, 50} {5, 24, 51}
{5, 24, 52} {5, 24, 53} {5, 24, 54} {5, 24, 55} {5, 24, 56} {5, 24, 57} {5, 24, 58} {5, 24, 59} {5, 24, 60} {5, 24, 61}
{5, 24, 62} {5, 24, 63} {5, 24, 64} {5, 24, 65} {5, 24, 66} {5, 25, 26} {5, 25, 27} {5, 25, 28} {5, 25, 29} {5, 25, 30}
{5, 25, 31} {5, 25, 32} {5, 25, 33} {5, 25, 34} {5, 25, 35} {5, 25, 36} {5, 25, 37} {5, 25, 38} {5, 25, 39} {5, 25, 40}
{5, 25, 41} {5, 25, 42} {5, 25, 43} {5, 25, 44} {5, 25, 45} {5, 25, 46} {5, 25, 47} {5, 25, 48} {5, 25, 49} {5, 25, 50}
{5, 25, 51} {5, 25, 52} {5, 25, 53} {5, 25, 54} {5, 25, 55} {5, 25, 56} {5, 25, 57} {5, 25, 58} {5, 25, 59} {5, 25, 60}
{5, 25, 61} {5, 25, 62} {5, 25, 63} {5, 25, 64} {5, 25, 65} {5, 25, 66} {5, 26, 27} {5, 26, 28} {5, 26, 29} {5, 26, 30}
{5, 26, 31} {5, 26, 32} {5, 26, 33} {5, 26, 34} {5, 26, 35} {5, 26, 36} {5, 26, 37} {5, 26, 38} {5, 26, 39} {5, 26, 40}
{5, 26, 41} {5, 26, 42} {5, 26, 43} {5, 26, 44} {5, 26, 45} {5, 26, 46} {5, 26, 47} {5, 26, 48} {5, 26, 49} {5, 26, 50}
{5, 26, 51} {5, 26, 52} {5, 26, 53} {5, 26, 54} {5, 26, 55} {5, 26, 56} {5, 26, 57} {5, 26, 58} {5, 26, 59} {5, 26, 60}
{5, 26, 61} {5, 26, 62} {5, 26, 63} {5, 26, 64} {5, 26, 65} {5, 26, 66} {5, 27, 28} {5, 27, 29} {5, 27, 30} {5, 27, 31}
{5, 27, 32} {5, 27, 33} {5, 27, 34} {5, 27, 35} {5, 27, 36} {5, 27, 37} {5, 27, 38} {5, 27, 39} {5, 27, 40} {5, 27, 41}
{5, 27, 42} {5, 27, 43} {5, 27, 44} {5, 27, 45} {5, 27, 46} {5, 27, 47} {5, 27, 48} {5, 27, 49} {5, 27, 50} {5, 27, 51}
{5, 27, 52} {5, 27, 53} {5, 27, 54} {5, 27, 55} {5, 27, 56} {5, 27, 57} {5, 27, 58} {5, 27, 59} {5, 27, 60} {5, 27, 61}
{5, 27, 62} {5, 27, 63} {5, 27, 64} {5, 27, 65} {5, 27, 66} {5, 28, 29} {5, 28, 30} {5, 28, 31} {5, 28, 32} {5, 28, 33}
{5, 28, 34} {5, 28, 35} {5, 28, 36} {5, 28, 37} {5, 28, 38} {5, 28, 39} {5, 28, 40} {5, 28, 41} {5, 28, 42} {5, 28, 43}
{5, 28, 44} {5, 28, 45} {5, 28, 46} {5, 28, 47} {5, 28, 48} {5, 28, 49} {5, 28, 50} {5, 28, 51} {5, 28, 52} {5, 28, 53}
{5, 28, 54} {5, 28, 55} {5, 28, 56} {5, 28, 57} {5, 28, 58} {5, 28, 59} {5, 28, 60} {5, 28, 61} {5, 28, 62} {5, 28, 63}
{5, 28, 64} {5, 28, 65} {5, 28, 66} {5, 29, 30} {5, 29, 31} {5, 29, 32} {5, 29, 33} {5, 29, 34} {5, 29, 35} {5, 29, 36}
{5, 29, 37} {5, 29, 38} {5, 29, 39} {5, 29, 40} {5, 29, 41} {5, 29, 42} {5, 29, 43} {5, 29, 44} {5, 29, 45} {5, 29, 46}
{5, 29, 47} {5, 29, 48} {5, 29, 49} {5, 29, 50} {5, 29, 51} {5, 29, 52} {5, 29, 53} {5, 29, 54} {5, 29, 55} {5, 29, 56}
{5, 29, 57} {5, 29, 58} {5, 29, 59} {5, 29, 60} {5, 29, 61} {5, 29, 62} {5, 29, 63} {5, 29, 64} {5, 29, 65} {5, 29, 66}
{5, 30, 31} {5, 30, 32} {5, 30, 33} {5, 30, 34} {5, 30, 35} {5, 30, 36} {5, 30, 37} {5, 30, 38} {5, 30, 39} {5, 30, 40}
{5, 30, 41} {5, 30, 42} {5, 30, 43} {5, 30, 44} {5, 30, 45} {5, 30, 46} {5, 30, 47} {5, 30, 48} {5, 30, 49} {5, 30, 50}
{5, 30, 51} {5, 30, 52} {5, 30, 53} {5, 30, 54} {5, 30, 55} {5, 30, 56} {5, 30, 57} {5, 30, 58} {5, 30, 59} {5, 30, 60}
{5, 30, 61} {5, 30, 62} {5, 30, 63} {5, 30, 64} {5, 30, 65} {5, 30, 66} {5, 31, 32} {5, 31, 33} {5, 31, 34} {5, 31, 35}
{5, 31, 36} {5, 31, 37} {5, 31, 38} {5, 31, 39} {5, 31, 40} {5, 31, 41} {5, 31, 42} {5, 31, 43} {5, 31, 44} {5, 31, 45}
{5, 31, 46} {5, 31, 47} {5, 31, 48} {5, 31, 49} {5, 31, 50} {5, 31, 51} {5, 31, 52} {5, 31, 53} {5, 31, 54} {5, 31, 55}
{5, 31, 56} {5, 31, 57} {5, 31, 58} {5, 31, 59} {5, 31, 60} {5, 31, 61} {5, 31, 62} {5, 31, 63} {5, 31, 64} {5, 31, 65}
{5, 31, 66} {5, 32, 33} {5, 32, 34} {5, 32, 35} {5, 32, 36} {5, 32, 37} {5, 32, 38} {5, 32, 39} {5, 32, 40} {5, 32, 41}
{5, 32, 42} {5, 32, 43} {5, 32, 44} {5, 32, 45} {5, 32, 46} {5, 32, 47} {5, 32, 48} {5, 32, 49} {5, 32, 50} {5, 32, 51}
{5, 32, 52} {5, 32, 53} {5, 32, 54} {5, 32, 55} {5, 32, 56} {5, 32, 57} {5, 32, 58} {5, 32, 59} {5, 32, 60} {5, 32, 61}
{5, 32, 62} {5, 32, 63} {5, 32, 64} {5, 32, 65} {5, 32, 66} {5, 33, 34} {5, 33, 35} {5, 33, 36} {5, 33, 37} {5, 33, 38}
{5, 33, 39} {5, 33, 40} {5, 33, 41} {5, 33, 42} {5, 33, 43} {5, 33, 44} {5, 33, 45} {5, 33, 46} {5, 33, 47} {5, 33, 48}
{5, 33, 49} {5, 33, 50} {5, 33, 51} {5, 33, 52} {5, 33, 53} {5, 33, 54} {5, 33, 55} {5, 33, 56} {5, 33, 57} {5, 33, 58}
{5, 33, 59} {5, 33, 60} {5, 33, 61} {5, 33, 62} {5, 33, 63} {5, 33, 64} {5, 33, 65} {5, 33, 66} {5, 34, 35} {5, 34, 36}
{5, 34, 37} {5, 34, 38} {5, 34, 39} {5, 34, 40} {5, 34, 41} {5, 34, 42} {5, 34, 43} {5, 34, 44} {5, 34, 45} {5, 34, 46}
{5, 34, 47} {5, 34, 48} {5, 34, 49} {5, 34, 50} {5, 34, 51} {5, 34, 52} {5, 34, 53} {5, 34, 54} {5, 34, 55} {5, 34, 56}
{5, 34, 57} {5, 34, 58} {5, 34, 59} {5, 34, 60} {5, 34, 61} {5, 34, 62} {5, 34, 63} {5, 34, 64} {5, 34, 65} {5, 34, 66}
{5, 35, 36} {5, 35, 37} {5, 35, 38} {5, 35, 39} {5, 35, 40} {5, 35, 41} {5, 35, 42} {5, 35, 43} {5, 35, 44} {5, 35, 45}
{5, 35, 46} {5, 35, 47} {5, 35, 48} {5, 35, 49} {5, 35, 50} {5, 35, 51} {5, 35, 52} {5, 35, 53} {5, 35, 54} {5, 35, 55}
{5, 35, 56} {5, 35, 57} {5, 35, 58} {5, 35, 59} {5, 35, 60} {5, 35, 61} {5, 35, 62} {5, 35, 63} {5, 35, 64} {5, 35, 65}
{5, 35, 66} {5, 36, 37} {5, 36, 38} {5, 36, 39} {5, 36, 40} {5, 36, 41} {5, 36, 42} {5, 36, 43} {5, 36, 44} {5, 36, 45}
{5, 36, 46} {5, 36, 47} {5, 36, 48} {5, 36, 49} {5, 36, 50} {5, 36, 51} {5, 36, 52} {5, 36, 53} {5, 36, 54} {5, 36, 55}
{5, 36, 56} {5, 36, 57} {5, 36, 58} {5, 36, 59} {5, 36, 60} {5, 36, 61} {5, 36, 62} {5, 36, 63} {5, 36, 64} {5, 36, 65}
{5, 36, 66} {5, 37, 38} {5, 37, 39} {5, 37, 40} {5, 37, 41} {5, 37, 42} {5, 37, 43} {5, 37, 44} {5, 37, 45} {5, 37, 46}
{5, 37, 47} {5, 37, 48} {5, 37, 49} {5, 37, 50} {5, 37, 51} {5, 37, 52} {5, 37, 53} {5, 37, 54} {5, 37, 55} {5, 37, 56}
{5, 37, 57} {5, 37, 58} {5, 37, 59} {5, 37, 60} {5, 37, 61} {5, 37, 62} {5, 37, 63} {5, 37, 64} {5, 37, 65} {5, 37, 66}
{5, 38, 39} {5, 38, 40} {5, 38, 41} {5, 38, 42} {5, 38, 43} {5, 38, 44} {5, 38, 45} {5, 38, 46} {5, 38, 47} {5, 38, 48}
{5, 38, 49} {5, 38, 50} {5, 38, 51} {5, 38, 52} {5, 38, 53} {5, 38, 54} {5, 38, 55} {5, 38, 56} {5, 38, 57} {5, 38, 58}
{5, 38, 59} {5, 38, 60} {5, 38, 61} {5, 38, 62} {5, 38, 63} {5, 38, 64} {5, 38, 65} {5, 38, 66} {5, 39, 40} {5, 39, 41}
{5, 39, 42} {5, 39, 43} {5, 39, 44} {5, 39, 45} {5, 39, 46} {5, 39, 47} {5, 39, 48} {5, 39, 49} {5, 39, 50} {5, 39, 51}
{5, 39, 52} {5, 39, 53} {5, 39, 54} {5, 39, 55} {5, 39, 56} {5, 39, 57} {5, 39, 58} {5, 39, 59} {5, 39, 60} {5, 39, 61}
{5, 39, 62} {5, 39, 63} {5, 39, 64} {5, 39, 65} {5, 39, 66} {5, 40, 41} {5, 40, 42} {5, 40, 43} {5, 40, 44} {5, 40, 45}
{5, 40, 46} {5, 40, 47} {5, 40, 48} {5, 40, 49} {5, 40, 50} {5, 40, 51} {5, 40, 52} {5, 40, 53} {5, 40, 54} {5, 40, 55}
{5, 40, 56} {5, 40, 57} {5, 40, 58} {5, 40, 59} {5, 40, 60} {5, 40, 61} {5, 40, 62} {5, 40, 63} {5, 40, 64} {5, 40, 65}
{5, 40, 66} {5, 41, 42} {5, 41, 43} {5, 41, 44} {5, 41, 45} {5, 41, 46} {5, 41, 47} {5, 41, 48} {5, 41, 49} {5, 41, 50}
{5, 41, 51} {5, 41, 52} {5, 41, 53} {5, 41, 54} {5, 41, 55} {5, 41, 56} {5, 41, 57} {5, 41, 58} {5, 41, 59} {5, 41, 60}
{5, 41, 61} {5, 41, 62} {5, 41, 63} {5, 41, 64} {5, 41, 65} {5, 41, 66} {5, 42, 43} {5, 42, 44} {5, 42, 45} {5, 42, 46}
{5, 42, 47} {5, 42, 48} {5, 42, 49} {5, 42, 50} {5, 42, 51} {5, 42, 52} {5, 42, 53} {5, 42, 54} {5, 42, 55} {5, 42, 56}
{5, 42, 57} {5, 42, 58} {5, 42, 59} {5, 42, 60} {5, 42, 61} {5, 42, 62} {5, 42, 63} {5, 42, 64} {5, 42, 65} {5, 42, 66}
{5, 43, 44} {5, 43, 45} {5, 43, 46} {5, 43, 47} {5, 43, 48} {5, 43, 49} {5, 43, 50} {5, 43, 51} {5, 43, 52} {5, 43, 53}
{5, 43, 54} {5, 43, 55} {5, 43, 56} {5, 43, 57} {5, 43, 58} {5, 43, 59} {5, 43, 60} {5, 43, 61} {5, 43, 62} {5, 43, 63}
{5, 43, 64} {5, 43, 65} {5, 43, 66} {5, 44, 45} {5, 44, 46} {5, 44, 47} {5, 44, 48} {5, 44, 49} {5, 44, 50} {5, 44, 51}
{5, 44, 52} {5, 44, 53} {5, 44, 54} {5, 44, 55} {5, 44, 56} {5, 44, 57} {5, 44, 58} {5, 44, 59} {5, 44, 60} {5, 44, 61}
{5, 44, 62} {5, 44, 63} {5, 44, 64} {5, 44, 65} {5, 44, 66} {5, 45, 46} {5, 45, 47} {5, 45, 48} {5, 45, 49} {5, 45, 50}
{5, 45, 51} {5, 45, 52} {5, 45, 53} {5, 45, 54} {5, 45, 55} {5, 45, 56} {5, 45, 57} {5, 45, 58} {5, 45, 59} {5, 45, 60}

TABLE 3A-continued

{5, 45, 61} {5, 45, 62} {5, 45, 63} {5, 45, 64} {5, 45, 65} {5, 45, 66} {5, 46, 47} {5, 46, 48} {5, 46, 49} {5, 46, 50}
{5, 46, 51} {5, 46, 52} {5, 46, 53} {5, 46, 54} {5, 46, 55} {5, 46, 56} {5, 46, 57} {5, 46, 58} {5, 46, 59} {5, 46, 60}
{5, 46, 61} {5, 46, 62} {5, 46, 63} {5, 46, 64} {5, 46, 65} {5, 46, 66} {5, 47, 48} {5, 47, 49} {5, 47, 50} {5, 47, 51}
{5, 47, 52} {5, 47, 53} {5, 47, 54} {5, 47, 55} {5, 47, 56} {5, 47, 57} {5, 47, 58} {5, 47, 59} {5, 47, 60} {5, 47, 61}
{5, 47, 62} {5, 47, 63} {5, 47, 64} {5, 47, 65} {5, 47, 66} {5, 48, 49} {5, 48, 50} {5, 48, 51} {5, 48, 52} {5, 48, 53}
{5, 48, 54} {5, 48, 55} {5, 48, 56} {5, 48, 57} {5, 48, 58} {5, 48, 59} {5, 48, 60} {5, 48, 61} {5, 48, 62} {5, 48, 63}
{5, 48, 64} {5, 48, 65} {5, 48, 66} {5, 49, 50} {5, 49, 51} {5, 49, 52} {5, 49, 53} {5, 49, 54} {5, 49, 55} {5, 49, 56}
{5, 49, 57} {5, 49, 58} {5, 49, 59} {5, 49, 60} {5, 49, 61} {5, 49, 62} {5, 49, 63} {5, 49, 64} {5, 49, 65} {5, 49, 66}
{5, 50, 51} {5, 50, 52} {5, 50, 53} {5, 50, 54} {5, 50, 55} {5, 50, 56} {5, 50, 57} {5, 50, 58} {5, 50, 59} {5, 50, 60}
{5, 50, 61} {5, 50, 62} {5, 50, 63} {5, 50, 64} {5, 50, 65} {5, 50, 66} {5, 51, 52} {5, 51, 53} {5, 51, 54} {5, 51, 55}
{5, 51, 56} {5, 51, 57} {5, 51, 58} {5, 51, 59} {5, 51, 60} {5, 51, 61} {5, 51, 62} {5, 51, 63} {5, 51, 64} {5, 51, 65}
{5, 51, 66} {5, 52, 53} {5, 52, 54} {5, 52, 55} {5, 52, 56} {5, 52, 57} {5, 52, 58} {5, 52, 59} {5, 52, 60} {5, 52, 61}
{5, 52, 62} {5, 52, 63} {5, 52, 64} {5, 52, 65} {5, 52, 66} {5, 53, 54} {5, 53, 55} {5, 53, 56} {5, 53, 57} {5, 53, 58}
{5, 53, 59} {5, 53, 60} {5, 53, 61} {5, 53, 62} {5, 53, 63} {5, 53, 64} {5, 53, 65} {5, 53, 66} {5, 54, 55} {5, 54, 56}
{5, 54, 57} {5, 54, 58} {5, 54, 59} {5, 54, 60} {5, 54, 61} {5, 54, 62} {5, 54, 63} {5, 54, 64} {5, 54, 65} {5, 54, 66}
{5, 55, 56} {5, 55, 57} {5, 55, 58} {5, 55, 59} {5, 55, 60} {5, 55, 61} {5, 55, 62} {5, 55, 63} {5, 55, 64} {5, 55, 65}
{5, 55, 66} {5, 56, 57} {5, 56, 58} {5, 56, 59} {5, 56, 60} {5, 56, 61} {5, 56, 62} {5, 56, 63} {5, 56, 64} {5, 56, 65}
{5, 56, 66} {5, 57, 58} {5, 57, 59} {5, 57, 60} {5, 57, 61} {5, 57, 62} {5, 57, 63} {5, 57, 64} {5, 57, 65} {5, 57, 66}
{5, 58, 59} {5, 58, 60} {5, 58, 61} {5, 58, 62} {5, 58, 63} {5, 58, 64} {5, 58, 65} {5, 58, 66} {5, 59, 60} {5, 59, 61}
{5, 59, 62} {5, 59, 63} {5, 59, 64} {5, 59, 65} {5, 59, 66} {5, 60, 61} {5, 60, 62} {5, 60, 63} {5, 60, 64} {5, 60, 65}
{5, 60, 66} {5, 61, 62} {5, 61, 63} {5, 61, 64} {5, 61, 65} {5, 61, 66} {5, 62, 63} {5, 62, 64} {5, 62, 65} {5, 62, 66}
{5, 63, 64} {5, 63, 65} {5, 63, 66} {5, 64, 65} {5, 64, 66} {5, 65, 66} {6, 7, 8} {6, 7, 9} {6, 7, 10} {6, 7, 11} {6, 7, 12} {6, 7, 13}
{6, 7, 14} {6, 7, 15} {6, 7, 16} {6, 7, 17} {6, 7, 18} {6, 7, 19} {6, 7, 20} {6, 7, 21} {6, 7, 22} {6, 7, 23} {6, 7, 24} {6, 7, 25}
{6, 7, 26} {6, 7, 27} {6, 7, 28} {6, 7, 29} {6, 7, 30} {6, 7, 31} {6, 7, 32} {6, 7, 33} {6, 7, 34} {6, 7, 35} {6, 7, 36} {6, 7, 37}
{6, 7, 38} {6, 7, 39} {6, 7, 40} {6, 7, 41} {6, 7, 42} {6, 7, 43} {6, 7, 44} {6, 7, 45} {6, 7, 46} {6, 7, 47} {6, 7, 48} {6, 7, 49}
{6, 7, 50} {6, 7, 51} {6, 7, 52} {6, 7, 53} {6, 7, 54} {6, 7, 55} {6, 7, 56} {6, 7, 57} {6, 7, 58} {6, 7, 59} {6, 7, 60} {6, 7, 61}
{6, 7, 62} {6, 7, 63} {6, 7, 64} {6, 7, 65} {6, 7, 66} {6, 8, 9} {6, 8, 10} {6, 8, 11} {6, 8, 12} {6, 8, 13} {6, 8, 14} {6, 8, 15}
{6, 8, 16} {6, 8, 17} {6, 8, 18} {6, 8, 19} {6, 8, 20} {6, 8, 21} {6, 8, 22} {6, 8, 23} {6, 8, 24} {6, 8, 25} {6, 8, 26} {6, 8, 27}
{6, 8, 28} {6, 8, 29} {6, 8, 30} {6, 8, 31} {6, 8, 32} {6, 8, 33} {6, 8, 34} {6, 8, 35} {6, 8, 36} {6, 8, 37} {6, 8, 38} {6, 8, 39}
{6, 8, 40} {6, 8, 41} {6, 8, 42} {6, 8, 43} {6, 8, 44} {6, 8, 45} {6, 8, 46} {6, 8, 47} {6, 8, 48} {6, 8, 49} {6, 8, 50} {6, 8, 51}
{6, 8, 52} {6, 8, 53} {6, 8, 54} {6, 8, 55} {6, 8, 56} {6, 8, 57} {6, 8, 58} {6, 8, 59} {6, 8, 60} {6, 8, 61} {6, 8, 62} {6, 8, 63}
{6, 8, 64} {6, 8, 65} {6, 8, 66} {6, 9, 10} {6, 9, 11} {6, 9, 12} {6, 9, 13} {6, 9, 14} {6, 9, 15} {6, 9, 16} {6, 9, 17} {6, 9, 18}
{6, 9, 19} {6, 9, 20} {6, 9, 21} {6, 9, 22} {6, 9, 23} {6, 9, 24} {6, 9, 25} {6, 9, 26} {6, 9, 27} {6, 9, 28} {6, 9, 29} {6, 9, 30}
{6, 9, 31} {6, 9, 32} {6, 9, 33} {6, 9, 34} {6, 9, 35} {6, 9, 36} {6, 9, 37} {6, 9, 38} {6, 9, 39} {6, 9, 40} {6, 9, 41} {6, 9, 42}
{6, 9, 43} {6, 9, 44} {6, 9, 45} {6, 9, 46} {6, 9, 47} {6, 9, 48} {6, 9, 49} {6, 9, 50} {6, 9, 51} {6, 9, 52} {6, 9, 53} {6, 9, 54}
{6, 9, 55} {6, 9, 56} {6, 9, 57} {6, 9, 58} {6, 9, 59} {6, 9, 60} {6, 9, 61} {6, 9, 62} {6, 9, 63} {6, 9, 64} {6, 9, 65} {6, 9, 66}
{6, 10, 11} {6, 10, 12} {6, 10, 13} {6, 10, 14} {6, 10, 15} {6, 10, 16} {6, 10, 17} {6, 10, 18} {6, 10, 19} {6, 10, 20}
{6, 10, 21} {6, 10, 22} {6, 10, 23} {6, 10, 24} {6, 10, 25} {6, 10, 26} {6, 10, 27} {6, 10, 28} {6, 10, 29} {6, 10, 30}
{6, 10, 31} {6, 10, 32} {6, 10, 33} {6, 10, 34} {6, 10, 35} {6, 10, 36} {6, 10, 37} {6, 10, 38} {6, 10, 39} {6, 10, 40}
{6, 10, 41} {6, 10, 42} {6, 10, 43} {6, 10, 44} {6, 10, 45} {6, 10, 46} {6, 10, 47} {6, 10, 48} {6, 10, 49} {6, 10, 50}
{6, 10, 51} {6, 10, 52} {6, 10, 53} {6, 10, 54} {6, 10, 55} {6, 10, 56} {6, 10, 57} {6, 10, 58} {6, 10, 59} {6, 10, 60}
{6, 10, 61} {6, 10, 62} {6, 10, 63} {6, 10, 64} {6, 10, 65} {6, 10, 66} {6, 11, 12} {6, 11, 13} {6, 11, 14} {6, 11, 15}
{6, 11, 16} {6, 11, 17} {6, 11, 18} {6, 11, 19} {6, 11, 20} {6, 11, 21} {6, 11, 22} {6, 11, 23} {6, 11, 24} {6, 11, 25}
{6, 11, 26} {6, 11, 27} {6, 11, 28} {6, 11, 29} {6, 11, 30} {6, 11, 31} {6, 11, 32} {6, 11, 33} {6, 11, 34} {6, 11, 35}
{6, 11, 36} {6, 11, 37} {6, 11, 38} {6, 11, 39} {6, 11, 40} {6, 11, 41} {6, 11, 42} {6, 11, 43} {6, 11, 44} {6, 11, 45}
{6, 11, 46} {6, 11, 47} {6, 11, 48} {6, 11, 49} {6, 11, 50} {6, 11, 51} {6, 11, 52} {6, 11, 53} {6, 11, 54} {6, 11, 55}
{6, 11, 56} {6, 11, 57} {6, 11, 58} {6, 11, 59} {6, 11, 60} {6, 11, 61} {6, 11, 62} {6, 11, 63} {6, 11, 64} {6, 11, 65}
{6, 11, 66} {6, 12, 13} {6, 12, 14} {6, 12, 15} {6, 12, 16} {6, 12, 17} {6, 12, 18} {6, 12, 19} {6, 12, 20} {6, 12, 21}
{6, 12, 22} {6, 12, 23} {6, 12, 24} {6, 12, 25} {6, 12, 26} {6, 12, 27} {6, 12, 28} {6, 12, 29} {6, 12, 30} {6, 12, 31}
{6, 12, 32} {6, 12, 33} {6, 12, 34} {6, 12, 35} {6, 12, 36} {6, 12, 37} {6, 12, 38} {6, 12, 39} {6, 12, 40} {6, 12, 41}
{6, 12, 42} {6, 12, 43} {6, 12, 44} {6, 12, 45} {6, 12, 46} {6, 12, 47} {6, 12, 48} {6, 12, 49} {6, 12, 50} {6, 12, 51}
{6, 12, 52} {6, 12, 53} {6, 12, 54} {6, 12, 55} {6, 12, 56} {6, 12, 57} {6, 12, 58} {6, 12, 59} {6, 12, 60} {6, 12, 61}
{6, 12, 62} {6, 12, 63} {6, 12, 64} {6, 12, 65} {6, 12, 66} {6, 13, 14} {6, 13, 15} {6, 13, 16} {6, 13, 17} {6, 13, 18}
{6, 13, 19} {6, 13, 20} {6, 13, 21} {6, 13, 22} {6, 13, 23} {6, 13, 24} {6, 13, 25} {6, 13, 26} {6, 13, 27} {6, 13, 28}
{6, 13, 29} {6, 13, 30} {6, 13, 31} {6, 13, 32} {6, 13, 33} {6, 13, 34} {6, 13, 35} {6, 13, 36} {6, 13, 37} {6, 13, 38}
{6, 13, 39} {6, 13, 40} {6, 13, 41} {6, 13, 42} {6, 13, 43} {6, 13, 44} {6, 13, 45} {6, 13, 46} {6, 13, 47} {6, 13, 48}
{6, 13, 49} {6, 13, 50} {6, 13, 51} {6, 13, 52} {6, 13, 53} {6, 13, 54} {6, 13, 55} {6, 13, 56} {6, 13, 57} {6, 13, 58}
{6, 13, 59} {6, 13, 60} {6, 13, 61} {6, 13, 62} {6, 13, 63} {6, 13, 64} {6, 13, 65} {6, 13, 66} {6, 14, 15} {6, 14, 16}
{6, 14, 17} {6, 14, 18} {6, 14, 19} {6, 14, 20} {6, 14, 21} {6, 14, 22} {6, 14, 23} {6, 14, 24} {6, 14, 25} {6, 14, 26}
{6, 14, 27} {6, 14, 28} {6, 14, 29} {6, 14, 30} {6, 14, 31} {6, 14, 32} {6, 14, 33} {6, 14, 34} {6, 14, 35} {6, 14, 36}
{6, 14, 37} {6, 14, 38} {6, 14, 39} {6, 14, 40} {6, 14, 41} {6, 14, 42} {6, 14, 43} {6, 14, 44} {6, 14, 45} {6, 14, 46}
{6, 14, 47} {6, 14, 48} {6, 14, 49} {6, 14, 50} {6, 14, 51} {6, 14, 52} {6, 14, 53} {6, 14, 54} {6, 14, 55} {6, 14, 56}
{6, 14, 57} {6, 14, 58} {6, 14, 59} {6, 14, 60} {6, 14, 61} {6, 14, 62} {6, 14, 63} {6, 14, 64} {6, 14, 65} {6, 14, 66}
{6, 15, 16} {6, 15, 17} {6, 15, 18} {6, 15, 19} {6, 15, 20} {6, 15, 21} {6, 15, 22} {6, 15, 23} {6, 15, 24} {6, 15, 25}
{6, 15, 26} {6, 15, 27} {6, 15, 28} {6, 15, 29} {6, 15, 30} {6, 15, 31} {6, 15, 32} {6, 15, 33} {6, 15, 34} {6, 15, 35}
{6, 15, 36} {6, 15, 37} {6, 15, 38} {6, 15, 39} {6, 15, 40} {6, 15, 41} {6, 15, 42} {6, 15, 43} {6, 15, 44} {6, 15, 45}
{6, 15, 46} {6, 15, 47} {6, 15, 48} {6, 15, 49} {6, 15, 50} {6, 15, 51} {6, 15, 52} {6, 15, 53} {6, 15, 54} {6, 15, 55}
{6, 15, 56} {6, 15, 57} {6, 15, 58} {6, 15, 59} {6, 15, 60} {6, 15, 61} {6, 15, 62} {6, 15, 63} {6, 15, 64} {6, 15, 65}
{6, 15, 66} {6, 16, 17} {6, 16, 18} {6, 16, 19} {6, 16, 20} {6, 16, 21} {6, 16, 22} {6, 16, 23} {6, 16, 24} {6, 16, 25}
{6, 16, 26} {6, 16, 27} {6, 16, 28} {6, 16, 29} {6, 16, 30} {6, 16, 31} {6, 16, 32} {6, 16, 33} {6, 16, 34} {6, 16, 35}
{6, 16, 36} {6, 16, 37} {6, 16, 38} {6, 16, 39} {6, 16, 40} {6, 16, 41} {6, 16, 42} {6, 16, 43} {6, 16, 44} {6, 16, 45}
{6, 16, 46} {6, 16, 47} {6, 16, 48} {6, 16, 49} {6, 16, 50} {6, 16, 51} {6, 16, 52} {6, 16, 53} {6, 16, 54} {6, 16, 55}
{6, 16, 56} {6, 16, 57} {6, 16, 58} {6, 16, 59} {6, 16, 60} {6, 16, 61} {6, 16, 62} {6, 16, 63} {6, 16, 64} {6, 16, 65}
{6, 16, 66} {6, 17, 18} {6, 17, 19} {6, 17, 20} {6, 17, 21} {6, 17, 22} {6, 17, 23} {6, 17, 24} {6, 17, 25} {6, 17, 26}
{6, 17, 27} {6, 17, 28} {6, 17, 29} {6, 17, 30} {6, 17, 31} {6, 17, 32} {6, 17, 33} {6, 17, 34} {6, 17, 35} {6, 17, 36}
{6, 17, 37} {6, 17, 38} {6, 17, 39} {6, 17, 40} {6, 17, 41} {6, 17, 42} {6, 17, 43} {6, 17, 44} {6, 17, 45} {6, 17, 46}
{6, 17, 47} {6, 17, 48} {6, 17, 49} {6, 17, 50} {6, 17, 51} {6, 17, 52} {6, 17, 53} {6, 17, 54} {6, 17, 55} {6, 17, 56}
{6, 17, 57} {6, 17, 58} {6, 17, 59} {6, 17, 60} {6, 17, 61} {6, 17, 62} {6, 17, 63} {6, 17, 64} {6, 17, 65} {6, 17, 66}
{6, 18, 19} {6, 18, 20} {6, 18, 21} {6, 18, 22} {6, 18, 23} {6, 18, 24} {6, 18, 25} {6, 18, 26} {6, 18, 27} {6, 18, 28}
{6, 18, 29} {6, 18, 30} {6, 18, 31} {6, 18, 32} {6, 18, 33} {6, 18, 34} {6, 18, 35} {6, 18, 36} {6, 18, 37} {6, 18, 38}

TABLE 3A-continued

| | | | | | | | | |
|---|---|---|---|---|---|---|---|---|
| {6, 18, 39} | {6, 18, 40} | {6, 18, 41} | {6, 18, 42} | {6, 18, 43} | {6, 18, 44} | {6, 18, 45} | {6, 18, 46} | {6, 18, 47} | {6, 18, 48} |
| {6, 18, 49} | {6, 18, 50} | {6, 18, 51} | {6, 18, 52} | {6, 18, 53} | {6, 18, 54} | {6, 18, 55} | {6, 18, 56} | {6, 18, 57} | {6, 18, 58} |
| {6, 18, 59} | {6, 18, 60} | {6, 18, 61} | {6, 18, 62} | {6, 18, 63} | {6, 18, 64} | {6, 18, 65} | {6, 18, 66} | {6, 19, 20} | {6, 19, 21} |
| {6, 19, 22} | {6, 19, 23} | {6, 19, 24} | {6, 19, 25} | {6, 19, 26} | {6, 19, 27} | {6, 19, 28} | {6, 19, 29} | {6, 19, 30} | {6, 19, 31} |
| {6, 19, 32} | {6, 19, 33} | {6, 19, 34} | {6, 19, 35} | {6, 19, 36} | {6, 19, 37} | {6, 19, 38} | {6, 19, 39} | {6, 19, 40} | {6, 19, 41} |
| {6, 19, 42} | {6, 19, 43} | {6, 19, 44} | {6, 19, 45} | {6, 19, 46} | {6, 19, 47} | {6, 19, 48} | {6, 19, 49} | {6, 19, 50} | {6, 19, 51} |
| {6, 19, 52} | {6, 19, 53} | {6, 19, 54} | {6, 19, 55} | {6, 19, 56} | {6, 19, 57} | {6, 19, 58} | {6, 19, 59} | {6, 19, 60} | {6, 19, 61} |
| {6, 19, 62} | {6, 19, 63} | {6, 19, 64} | {6, 19, 65} | {6, 19, 66} | {6, 20, 21} | {6, 20, 22} | {6, 20, 23} | {6, 20, 24} | {6, 20, 25} |
| {6, 20, 26} | {6, 20, 27} | {6, 20, 28} | {6, 20, 29} | {6, 20, 30} | {6, 20, 31} | {6, 20, 32} | {6, 20, 33} | {6, 20, 34} | {6, 20, 35} |
| {6, 20, 36} | {6, 20, 37} | {6, 20, 38} | {6, 20, 39} | {6, 20, 40} | {6, 20, 41} | {6, 20, 42} | {6, 20, 43} | {6, 20, 44} | {6, 20, 45} |
| {6, 20, 46} | {6, 20, 47} | {6, 20, 48} | {6, 20, 49} | {6, 20, 50} | {6, 20, 51} | {6, 20, 52} | {6, 20, 53} | {6, 20, 54} | {6, 20, 55} |
| {6, 20, 56} | {6, 20, 57} | {6, 20, 58} | {6, 20, 59} | {6, 20, 60} | {6, 20, 61} | {6, 20, 62} | {6, 20, 63} | {6, 20, 64} | {6, 20, 65} |
| {6, 20, 66} | {6, 21, 22} | {6, 21, 23} | {6, 21, 24} | {6, 21, 25} | {6, 21, 26} | {6, 21, 27} | {6, 21, 28} | {6, 21, 29} | {6, 21, 30} |
| {6, 21, 31} | {6, 21, 32} | {6, 21, 33} | {6, 21, 34} | {6, 21, 35} | {6, 21, 36} | {6, 21, 37} | {6, 21, 38} | {6, 21, 39} | {6, 21, 40} |
| {6, 21, 41} | {6, 21, 42} | {6, 21, 43} | {6, 21, 44} | {6, 21, 45} | {6, 21, 46} | {6, 21, 47} | {6, 21, 48} | {6, 21, 49} | {6, 21, 50} |
| {6, 21, 51} | {6, 21, 52} | {6, 21, 53} | {6, 21, 54} | {6, 21, 55} | {6, 21, 56} | {6, 21, 57} | {6, 21, 58} | {6, 21, 59} | {6, 21, 60} |
| {6, 21, 61} | {6, 21, 62} | {6, 21, 63} | {6, 21, 64} | {6, 21, 65} | {6, 21, 66} | {6, 22, 23} | {6, 22, 24} | {6, 22, 25} | {6, 22, 26} |
| {6, 22, 27} | {6, 22, 28} | {6, 22, 29} | {6, 22, 30} | {6, 22, 31} | {6, 22, 32} | {6, 22, 33} | {6, 22, 34} | {6, 22, 35} | {6, 22, 36} |
| {6, 22, 37} | {6, 22, 38} | {6, 22, 39} | {6, 22, 40} | {6, 22, 41} | {6, 22, 42} | {6, 22, 43} | {6, 22, 44} | {6, 22, 45} | {6, 22, 46} |
| {6, 22, 47} | {6, 22, 48} | {6, 22, 49} | {6, 22, 50} | {6, 22, 51} | {6, 22, 52} | {6, 22, 53} | {6, 22, 54} | {6, 22, 55} | {6, 22, 56} |
| {6, 22, 57} | {6, 22, 58} | {6, 22, 59} | {6, 22, 60} | {6, 22, 61} | {6, 22, 62} | {6, 22, 63} | {6, 22, 64} | {6, 22, 65} | {6, 22, 66} |
| {6, 23, 24} | {6, 23, 25} | {6, 23, 26} | {6, 23, 27} | {6, 23, 28} | {6, 23, 29} | {6, 23, 30} | {6, 23, 31} | {6, 23, 32} | {6, 23, 33} |
| {6, 23, 34} | {6, 23, 35} | {6, 23, 36} | {6, 23, 37} | {6, 23, 38} | {6, 23, 39} | {6, 23, 40} | {6, 23, 41} | {6, 23, 42} | {6, 23, 43} |
| {6, 23, 44} | {6, 23, 45} | {6, 23, 46} | {6, 23, 47} | {6, 23, 48} | {6, 23, 49} | {6, 23, 50} | {6, 23, 51} | {6, 23, 52} | {6, 23, 53} |
| {6, 23, 54} | {6, 23, 55} | {6, 23, 56} | {6, 23, 57} | {6, 23, 58} | {6, 23, 59} | {6, 23, 60} | {6, 23, 61} | {6, 23, 62} | {6, 23, 63} |
| {6, 23, 64} | {6, 23, 65} | {6, 23, 66} | {6, 24, 25} | {6, 24, 26} | {6, 24, 27} | {6, 24, 28} | {6, 24, 29} | {6, 24, 30} | {6, 24, 31} |
| {6, 24, 32} | {6, 24, 33} | {6, 24, 34} | {6, 24, 35} | {6, 24, 36} | {6, 24, 37} | {6, 24, 38} | {6, 24, 39} | {6, 24, 40} | {6, 24, 41} |
| {6, 24, 42} | {6, 24, 43} | {6, 24, 44} | {6, 24, 45} | {6, 24, 46} | {6, 24, 47} | {6, 24, 48} | {6, 24, 49} | {6, 24, 50} | {6, 24, 51} |
| {6, 24, 52} | {6, 24, 53} | {6, 24, 54} | {6, 24, 55} | {6, 24, 56} | {6, 24, 57} | {6, 24, 58} | {6, 24, 59} | {6, 24, 60} | {6, 24, 61} |
| {6, 24, 62} | {6, 24, 63} | {6, 24, 64} | {6, 24, 65} | {6, 24, 66} | {6, 25, 26} | {6, 25, 27} | {6, 25, 28} | {6, 25, 29} | {6, 25, 30} |
| {6, 25, 31} | {6, 25, 32} | {6, 25, 33} | {6, 25, 34} | {6, 25, 35} | {6, 25, 36} | {6, 25, 37} | {6, 25, 38} | {6, 25, 39} | {6, 25, 40} |
| {6, 25, 41} | {6, 25, 42} | {6, 25, 43} | {6, 25, 44} | {6, 25, 45} | {6, 25, 46} | {6, 25, 47} | {6, 25, 48} | {6, 25, 49} | {6, 25, 50} |
| {6, 25, 51} | {6, 25, 52} | {6, 25, 53} | {6, 25, 54} | {6, 25, 55} | {6, 25, 56} | {6, 25, 57} | {6, 25, 58} | {6, 25, 59} | {6, 25, 60} |
| {6, 25, 61} | {6, 25, 62} | {6, 25, 63} | {6, 25, 64} | {6, 25, 65} | {6, 25, 66} | {6, 26, 27} | {6, 26, 28} | {6, 26, 29} | {6, 26, 30} |
| {6, 26, 31} | {6, 26, 32} | {6, 26, 33} | {6, 26, 34} | {6, 26, 35} | {6, 26, 36} | {6, 26, 37} | {6, 26, 38} | {6, 26, 39} | {6, 26, 40} |
| {6, 26, 41} | {6, 26, 42} | {6, 26, 43} | {6, 26, 44} | {6, 26, 45} | {6, 26, 46} | {6, 26, 47} | {6, 26, 48} | {6, 26, 49} | {6, 26, 50} |
| {6, 26, 51} | {6, 26, 52} | {6, 26, 53} | {6, 26, 54} | {6, 26, 55} | {6, 26, 56} | {6, 26, 57} | {6, 26, 58} | {6, 26, 59} | {6, 26, 60} |
| {6, 26, 61} | {6, 26, 62} | {6, 26, 63} | {6, 26, 64} | {6, 26, 65} | {6, 26, 66} | {6, 27, 28} | {6, 27, 29} | {6, 27, 30} | {6, 27, 31} |
| {6, 27, 32} | {6, 27, 33} | {6, 27, 34} | {6, 27, 35} | {6, 27, 36} | {6, 27, 37} | {6, 27, 38} | {6, 27, 39} | {6, 27, 40} | {6, 27, 41} |
| {6, 27, 42} | {6, 27, 43} | {6, 27, 44} | {6, 27, 45} | {6, 27, 46} | {6, 27, 47} | {6, 27, 48} | {6, 27, 49} | {6, 27, 50} | {6, 27, 51} |
| {6, 27, 52} | {6, 27, 53} | {6, 27, 54} | {6, 27, 55} | {6, 27, 56} | {6, 27, 57} | {6, 27, 58} | {6, 27, 59} | {6, 27, 60} | {6, 27, 61} |
| {6, 27, 62} | {6, 27, 63} | {6, 27, 64} | {6, 27, 65} | {6, 27, 66} | {6, 28, 29} | {6, 28, 30} | {6, 28, 31} | {6, 28, 32} | {6, 28, 33} |
| {6, 28, 34} | {6, 28, 35} | {6, 28, 36} | {6, 28, 37} | {6, 28, 38} | {6, 28, 39} | {6, 28, 40} | {6, 28, 41} | {6, 28, 42} | {6, 28, 43} |
| {6, 28, 44} | {6, 28, 45} | {6, 28, 46} | {6, 28, 47} | {6, 28, 48} | {6, 28, 49} | {6, 28, 50} | {6, 28, 51} | {6, 28, 52} | {6, 28, 53} |
| {6, 28, 54} | {6, 28, 55} | {6, 28, 56} | {6, 28, 57} | {6, 28, 58} | {6, 28, 59} | {6, 28, 60} | {6, 28, 61} | {6, 28, 62} | {6, 28, 63} |
| {6, 28, 64} | {6, 28, 65} | {6, 28, 66} | {6, 29, 30} | {6, 29, 31} | {6, 29, 32} | {6, 29, 33} | {6, 29, 34} | {6, 29, 35} | {6, 29, 36} |
| {6, 29, 37} | {6, 29, 38} | {6, 29, 39} | {6, 29, 40} | {6, 29, 41} | {6, 29, 42} | {6, 29, 43} | {6, 29, 44} | {6, 29, 45} | {6, 29, 46} |
| {6, 29, 47} | {6, 29, 48} | {6, 29, 49} | {6, 29, 50} | {6, 29, 51} | {6, 29, 52} | {6, 29, 53} | {6, 29, 54} | {6, 29, 55} | {6, 29, 56} |
| {6, 29, 57} | {6, 29, 58} | {6, 29, 59} | {6, 29, 60} | {6, 29, 61} | {6, 29, 62} | {6, 29, 63} | {6, 29, 64} | {6, 29, 65} | {6, 29, 66} |
| {6, 30, 31} | {6, 30, 32} | {6, 30, 33} | {6, 30, 34} | {6, 30, 35} | {6, 30, 36} | {6, 30, 37} | {6, 30, 38} | {6, 30, 39} | {6, 30, 40} |
| {6, 30, 41} | {6, 30, 42} | {6, 30, 43} | {6, 30, 44} | {6, 30, 45} | {6, 30, 46} | {6, 30, 47} | {6, 30, 48} | {6, 30, 49} | {6, 30, 50} |
| {6, 30, 51} | {6, 30, 52} | {6, 30, 53} | {6, 30, 54} | {6, 30, 55} | {6, 30, 56} | {6, 30, 57} | {6, 30, 58} | {6, 30, 59} | {6, 30, 60} |
| {6, 30, 61} | {6, 30, 62} | {6, 30, 63} | {6, 30, 64} | {6, 30, 65} | {6, 30, 66} | {6, 31, 32} | {6, 31, 33} | {6, 31, 34} | {6, 31, 35} |
| {6, 31, 36} | {6, 31, 37} | {6, 31, 38} | {6, 31, 39} | {6, 31, 40} | {6, 31, 41} | {6, 31, 42} | {6, 31, 43} | {6, 31, 44} | {6, 31, 45} |
| {6, 31, 46} | {6, 31, 47} | {6, 31, 48} | {6, 31, 49} | {6, 31, 50} | {6, 31, 51} | {6, 31, 52} | {6, 31, 53} | {6, 31, 54} | {6, 31, 55} |
| {6, 31, 56} | {6, 31, 57} | {6, 31, 58} | {6, 31, 59} | {6, 31, 60} | {6, 31, 61} | {6, 31, 62} | {6, 31, 63} | {6, 31, 64} | {6, 31, 65} |
| {6, 31, 66} | {6, 32, 33} | {6, 32, 34} | {6, 32, 35} | {6, 32, 36} | {6, 32, 37} | {6, 32, 38} | {6, 32, 39} | {6, 32, 40} | {6, 32, 41} |
| {6, 32, 42} | {6, 32, 43} | {6, 32, 44} | {6, 32, 45} | {6, 32, 46} | {6, 32, 47} | {6, 32, 48} | {6, 32, 49} | {6, 32, 50} | {6, 32, 51} |
| {6, 32, 52} | {6, 32, 53} | {6, 32, 54} | {6, 32, 55} | {6, 32, 56} | {6, 32, 57} | {6, 32, 58} | {6, 32, 59} | {6, 32, 60} | {6, 32, 61} |
| {6, 32, 62} | {6, 32, 63} | {6, 32, 64} | {6, 32, 65} | {6, 32, 66} | {6, 33, 34} | {6, 33, 35} | {6, 33, 36} | {6, 33, 37} | {6, 33, 38} |
| {6, 33, 39} | {6, 33, 40} | {6, 33, 41} | {6, 33, 42} | {6, 33, 43} | {6, 33, 44} | {6, 33, 45} | {6, 33, 46} | {6, 33, 47} | {6, 33, 48} |
| {6, 33, 49} | {6, 33, 50} | {6, 33, 51} | {6, 33, 52} | {6, 33, 53} | {6, 33, 54} | {6, 33, 55} | {6, 33, 56} | {6, 33, 57} | {6, 33, 58} |
| {6, 33, 59} | {6, 33, 60} | {6, 33, 61} | {6, 33, 62} | {6, 33, 63} | {6, 33, 64} | {6, 33, 65} | {6, 33, 66} | {6, 34, 35} | {6, 34, 36} |
| {6, 34, 37} | {6, 34, 38} | {6, 34, 39} | {6, 34, 40} | {6, 34, 41} | {6, 34, 42} | {6, 34, 43} | {6, 34, 44} | {6, 34, 45} | {6, 34, 46} |
| {6, 34, 47} | {6, 34, 48} | {6, 34, 49} | {6, 34, 50} | {6, 34, 51} | {6, 34, 52} | {6, 34, 53} | {6, 34, 54} | {6, 34, 55} | {6, 34, 56} |
| {6, 34, 57} | {6, 34, 58} | {6, 34, 59} | {6, 34, 60} | {6, 34, 61} | {6, 34, 62} | {6, 34, 63} | {6, 34, 64} | {6, 34, 65} | {6, 34, 66} |
| {6, 35, 36} | {6, 35, 37} | {6, 35, 38} | {6, 35, 39} | {6, 35, 40} | {6, 35, 41} | {6, 35, 42} | {6, 35, 43} | {6, 35, 44} | {6, 35, 45} |
| {6, 35, 46} | {6, 35, 47} | {6, 35, 48} | {6, 35, 49} | {6, 35, 50} | {6, 35, 51} | {6, 35, 52} | {6, 35, 53} | {6, 35, 54} | {6, 35, 55} |
| {6, 35, 56} | {6, 35, 57} | {6, 35, 58} | {6, 35, 59} | {6, 35, 60} | {6, 35, 61} | {6, 35, 62} | {6, 35, 63} | {6, 35, 64} | {6, 35, 65} |
| {6, 35, 66} | {6, 36, 37} | {6, 36, 38} | {6, 36, 39} | {6, 36, 40} | {6, 36, 41} | {6, 36, 42} | {6, 36, 43} | {6, 36, 44} | {6, 36, 45} |
| {6, 36, 46} | {6, 36, 47} | {6, 36, 48} | {6, 36, 49} | {6, 36, 50} | {6, 36, 51} | {6, 36, 52} | {6, 36, 53} | {6, 36, 54} | {6, 36, 55} |
| {6, 36, 56} | {6, 36, 57} | {6, 36, 58} | {6, 36, 59} | {6, 36, 60} | {6, 36, 61} | {6, 36, 62} | {6, 36, 63} | {6, 36, 64} | {6, 36, 65} |
| {6, 36, 66} | {6, 37, 38} | {6, 37, 39} | {6, 37, 40} | {6, 37, 41} | {6, 37, 42} | {6, 37, 43} | {6, 37, 44} | {6, 37, 45} | {6, 37, 46} |
| {6, 37, 47} | {6, 37, 48} | {6, 37, 49} | {6, 37, 50} | {6, 37, 51} | {6, 37, 52} | {6, 37, 53} | {6, 37, 54} | {6, 37, 55} | {6, 37, 56} |
| {6, 37, 57} | {6, 37, 58} | {6, 37, 59} | {6, 37, 60} | {6, 37, 61} | {6, 37, 62} | {6, 37, 63} | {6, 37, 64} | {6, 37, 65} | {6, 37, 66} |
| {6, 38, 39} | {6, 38, 40} | {6, 38, 41} | {6, 38, 42} | {6, 38, 43} | {6, 38, 44} | {6, 38, 45} | {6, 38, 46} | {6, 38, 47} | {6, 38, 48} |
| {6, 38, 49} | {6, 38, 50} | {6, 38, 51} | {6, 38, 52} | {6, 38, 53} | {6, 38, 54} | {6, 38, 55} | {6, 38, 56} | {6, 38, 57} | {6, 38, 58} |
| {6, 38, 59} | {6, 38, 60} | {6, 38, 61} | {6, 38, 62} | {6, 38, 63} | {6, 38, 64} | {6, 38, 65} | {6, 38, 66} | {6, 39, 40} | {6, 39, 41} |
| {6, 39, 42} | {6, 39, 43} | {6, 39, 44} | {6, 39, 45} | {6, 39, 46} | {6, 39, 47} | {6, 39, 48} | {6, 39, 49} | {6, 39, 50} | {6, 39, 51} |
| {6, 39, 52} | {6, 39, 53} | {6, 39, 54} | {6, 39, 55} | {6, 39, 56} | {6, 39, 57} | {6, 39, 58} | {6, 39, 59} | {6, 39, 60} | {6, 39, 61} |

TABLE 3A-continued

{6, 39, 62} {6, 39, 63} {6, 39, 64} {6, 39, 65} {6, 39, 66} {6, 40, 41} {6, 40, 42} {6, 40, 43} {6, 40, 44} {6, 40, 45}
{6, 40, 46} {6, 40, 47} {6, 40, 48} {6, 40, 49} {6, 40, 50} {6, 40, 51} {6, 40, 52} {6, 40, 53} {6, 40, 54} {6, 40, 55}
{6, 40, 56} {6, 40, 57} {6, 40, 58} {6, 40, 59} {6, 40, 60} {6, 40, 61} {6, 40, 62} {6, 40, 63} {6, 40, 64} {6, 40, 65}
{6, 40, 66} {6, 41, 42} {6, 41, 43} {6, 41, 44} {6, 41, 45} {6, 41, 46} {6, 41, 47} {6, 41, 48} {6, 41, 49} {6, 41, 50}
{6, 41, 51} {6, 41, 52} {6, 41, 53} {6, 41, 54} {6, 41, 55} {6, 41, 56} {6, 41, 57} {6, 41, 58} {6, 41, 59} {6, 41, 60}
{6, 41, 61} {6, 41, 62} {6, 41, 63} {6, 41, 64} {6, 41, 65} {6, 41, 66} {6, 42, 43} {6, 42, 44} {6, 42, 45} {6, 42, 46}
{6, 42, 47} {6, 42, 48} {6, 42, 49} {6, 42, 50} {6, 42, 51} {6, 42, 52} {6, 42, 53} {6, 42, 54} {6, 42, 55} {6, 42, 56}
{6, 42, 57} {6, 42, 58} {6, 42, 59} {6, 42, 60} {6, 42, 61} {6, 42, 62} {6, 42, 63} {6, 42, 64} {6, 42, 65} {6, 42, 66}
{6, 43, 44} {6, 43, 45} {6, 43, 46} {6, 43, 47} {6, 43, 48} {6, 43, 49} {6, 43, 50} {6, 43, 51} {6, 43, 52} {6, 43, 53}
{6, 43, 54} {6, 43, 55} {6, 43, 56} {6, 43, 57} {6, 43, 58} {6, 43, 59} {6, 43, 60} {6, 43, 61} {6, 43, 62} {6, 43, 63}
{6, 43, 64} {6, 43, 65} {6, 43, 66} {6, 44, 45} {6, 44, 46} {6, 44, 47} {6, 44, 48} {6, 44, 49} {6, 44, 50} {6, 44, 51}
{6, 44, 52} {6, 44, 53} {6, 44, 54} {6, 44, 55} {6, 44, 56} {6, 44, 57} {6, 44, 58} {6, 44, 59} {6, 44, 60} {6, 44, 61}
{6, 44, 62} {6, 44, 63} {6, 44, 64} {6, 44, 65} {6, 44, 66} {6, 45, 46} {6, 45, 47} {6, 45, 48} {6, 45, 49} {6, 45, 50}
{6, 45, 51} {6, 45, 52} {6, 45, 53} {6, 45, 54} {6, 45, 55} {6, 45, 56} {6, 45, 57} {6, 45, 58} {6, 45, 59} {6, 45, 60}
{6, 45, 61} {6, 45, 62} {6, 45, 63} {6, 45, 64} {6, 45, 65} {6, 45, 66} {6, 46, 47} {6, 46, 48} {6, 46, 49} {6, 46, 50}
{6, 46, 51} {6, 46, 52} {6, 46, 53} {6, 46, 54} {6, 46, 55} {6, 46, 56} {6, 46, 57} {6, 46, 58} {6, 46, 59} {6, 46, 60}
{6, 46, 61} {6, 46, 62} {6, 46, 63} {6, 46, 64} {6, 46, 65} {6, 46, 66} {6, 47, 48} {6, 47, 49} {6, 47, 50} {6, 47, 51}
{6, 47, 52} {6, 47, 53} {6, 47, 54} {6, 47, 55} {6, 47, 56} {6, 47, 57} {6, 47, 58} {6, 47, 59} {6, 47, 60} {6, 47, 61}
{6, 47, 62} {6, 47, 63} {6, 47, 64} {6, 47, 65} {6, 47, 66} {6, 48, 49} {6, 48, 50} {6, 48, 51} {6, 48, 52} {6, 48, 53}
{6, 48, 54} {6, 48, 55} {6, 48, 56} {6, 48, 57} {6, 48, 58} {6, 48, 59} {6, 48, 60} {6, 48, 61} {6, 48, 62} {6, 48, 63}
{6, 48, 64} {6, 48, 65} {6, 48, 66} {6, 49, 50} {6, 49, 51} {6, 49, 52} {6, 49, 53} {6, 49, 54} {6, 49, 55} {6, 49, 56}
{6, 49, 57} {6, 49, 58} {6, 49, 59} {6, 49, 60} {6, 49, 61} {6, 49, 62} {6, 49, 63} {6, 49, 64} {6, 49, 65} {6, 49, 66}
{6, 50, 51} {6, 50, 52} {6, 50, 53} {6, 50, 54} {6, 50, 55} {6, 50, 56} {6, 50, 57} {6, 50, 58} {6, 50, 59} {6, 50, 60}
{6, 50, 61} {6, 50, 62} {6, 50, 63} {6, 50, 64} {6, 50, 65} {6, 50, 66} {6, 51, 52} {6, 51, 53} {6, 51, 54} {6, 51, 55}
{6, 51, 56} {6, 51, 57} {6, 51, 58} {6, 51, 59} {6, 51, 60} {6, 51, 61} {6, 51, 62} {6, 51, 63} {6, 51, 64} {6, 51, 65}
{6, 51, 66} {6, 52, 53} {6, 52, 54} {6, 52, 55} {6, 52, 56} {6, 52, 57} {6, 52, 58} {6, 52, 59} {6, 52, 60} {6, 52, 61}
{6, 52, 62} {6, 52, 63} {6, 52, 64} {6, 52, 65} {6, 52, 66} {6, 53, 54} {6, 53, 55} {6, 53, 56} {6, 53, 57} {6, 53, 58}
{6, 53, 59} {6, 53, 60} {6, 53, 61} {6, 53, 62} {6, 53, 63} {6, 53, 64} {6, 53, 65} {6, 53, 66} {6, 54, 55} {6, 54, 56}
{6, 54, 57} {6, 54, 58} {6, 54, 59} {6, 54, 60} {6, 54, 61} {6, 54, 62} {6, 54, 63} {6, 54, 64} {6, 54, 65} {6, 54, 66}
{6, 55, 56} {6, 55, 57} {6, 55, 58} {6, 55, 59} {6, 55, 60} {6, 55, 61} {6, 55, 62} {6, 55, 63} {6, 55, 64} {6, 55, 65}
{6, 55, 66} {6, 56, 57} {6, 56, 58} {6, 56, 59} {6, 56, 60} {6, 56, 61} {6, 56, 62} {6, 56, 63} {6, 56, 64} {6, 56, 65}
{6, 56, 66} {6, 57, 58} {6, 57, 59} {6, 57, 60} {6, 57, 61} {6, 57, 62} {6, 57, 63} {6, 57, 64} {6, 57, 65} {6, 57, 66}
{6, 58, 59} {6, 58, 60} {6, 58, 61} {6, 58, 62} {6, 58, 63} {6, 58, 64} {6, 58, 65} {6, 58, 66} {6, 59, 60} {6, 59, 61}
{6, 59, 62} {6, 59, 63} {6, 59, 64} {6, 59, 65} {6, 59, 66} {6, 60, 61} {6, 60, 62} {6, 60, 63} {6, 60, 64} {6, 60, 65}
{6, 60, 66} {6, 61, 62} {6, 61, 63} {6, 61, 64} {6, 61, 65} {6, 61, 66} {6, 62, 63} {6, 62, 64} {6, 62, 65} {6, 62, 66}
{6, 63, 64} {6, 63, 65} {6, 63, 66} {6, 64, 65} {6, 64, 66} {6, 65, 66} {7, 8, 9} {7, 8, 10} {7, 8, 11} {7, 8, 12} {7, 8, 13}
{7, 8, 14} {7, 8, 15} {7, 8, 16} {7, 8, 17} {7, 8, 18} {7, 8, 19} {7, 8, 20} {7, 8, 21} {7, 8, 22} {7, 8, 23} {7, 8, 24} {7, 8, 25}
{7, 8, 26} {7, 8, 27} {7, 8, 28} {7, 8, 29} {7, 8, 30} {7, 8, 31} {7, 8, 32} {7, 8, 33} {7, 8, 34} {7, 8, 35} {7, 8, 36} {7, 8, 37}
{7, 8, 38} {7, 8, 39} {7, 8, 40} {7, 8, 41} {7, 8, 42} {7, 8, 43} {7, 8, 44} {7, 8, 45} {7, 8, 46} {7, 8, 47} {7, 8, 48} {7, 8, 49}
{7, 8, 50} {7, 8, 51} {7, 8, 52} {7, 8, 53} {7, 8, 54} {7, 8, 55} {7, 8, 56} {7, 8, 57} {7, 8, 58} {7, 8, 59} {7, 8, 60} {7, 8, 61}
{7, 8, 62} {7, 8, 63} {7, 8, 64} {7, 8, 65} {7, 8, 66} {7, 9, 10} {7, 9, 11} {7, 9, 12} {7, 9, 13} {7, 9, 14} {7, 9, 15} {7, 9, 16}
{7, 9, 17} {7, 9, 18} {7, 9, 19} {7, 9, 20} {7, 9, 21} {7, 9, 22} {7, 9, 23} {7, 9, 24} {7, 9, 25} {7, 9, 26} {7, 9, 27} {7, 9, 28}
{7, 9, 29} {7, 9, 30} {7, 9, 31} {7, 9, 32} {7, 9, 33} {7, 9, 34} {7, 9, 35} {7, 9, 36} {7, 9, 37} {7, 9, 38} {7, 9, 39} {7, 9, 40}
{7, 9, 41} {7, 9, 42} {7, 9, 43} {7, 9, 44} {7, 9, 45} {7, 9, 46} {7, 9, 47} {7, 9, 48} {7, 9, 49} {7, 9, 50} {7, 9, 51} {7, 9, 52}
{7, 9, 53} {7, 9, 54} {7, 9, 55} {7, 9, 56} {7, 9, 57} {7, 9, 58} {7, 9, 59} {7, 9, 60} {7, 9, 61} {7, 9, 62} {7, 9, 63} {7, 9, 64}
{7, 9, 65} {7, 9, 66} {7, 10, 11} {7, 10, 12} {7, 10, 13} {7, 10, 14} {7, 10, 15} {7, 10, 16} {7, 10, 17} {7, 10, 18} {7, 10, 19}
{7, 10, 20} {7, 10, 21} {7, 10, 22} {7, 10, 23} {7, 10, 24} {7, 10, 25} {7, 10, 26} {7, 10, 27} {7, 10, 28} {7, 10, 29}
{7, 10, 30} {7, 10, 31} {7, 10, 32} {7, 10, 33} {7, 10, 34} {7, 10, 35} {7, 10, 36} {7, 10, 37} {7, 10, 38} {7, 10, 39}
{7, 10, 40} {7, 10, 41} {7, 10, 42} {7, 10, 43} {7, 10, 44} {7, 10, 45} {7, 10, 46} {7, 10, 47} {7, 10, 48} {7, 10, 49}
{7, 10, 50} {7, 10, 51} {7, 10, 52} {7, 10, 53} {7, 10, 54} {7, 10, 55} {7, 10, 56} {7, 10, 57} {7, 10, 58} {7, 10, 59}
{7, 10, 60} {7, 10, 61} {7, 10, 62} {7, 10, 63} {7, 10, 64} {7, 10, 65} {7, 10, 66} {7, 11, 12} {7, 11, 13} {7, 11, 14}
{7, 11, 15} {7, 11, 16} {7, 11, 17} {7, 11, 18} {7, 11, 19} {7, 11, 20} {7, 11, 21} {7, 11, 22} {7, 11, 23} {7, 11, 24}
{7, 11, 25} {7, 11, 26} {7, 11, 27} {7, 11, 28} {7, 11, 29} {7, 11, 30} {7, 11, 31} {7, 11, 32} {7, 11, 33} {7, 11, 34}
{7, 11, 35} {7, 11, 36} {7, 11, 37} {7, 11, 38} {7, 11, 39} {7, 11, 40} {7, 11, 41} {7, 11, 42} {7, 11, 43} {7, 11, 44}
{7, 11, 45} {7, 11, 46} {7, 11, 47} {7, 11, 48} {7, 11, 49} {7, 11, 50} {7, 11, 51} {7, 11, 52} {7, 11, 53} {7, 11, 54}
{7, 11, 55} {7, 11, 56} {7, 11, 57} {7, 11, 58} {7, 11, 59} {7, 11, 60} {7, 11, 61} {7, 11, 62} {7, 11, 63} {7, 11, 64}
{7, 11, 65} {7, 11, 66} {7, 12, 13} {7, 12, 14} {7, 12, 15} {7, 12, 16} {7, 12, 17} {7, 12, 18} {7, 12, 19} {7, 12, 20}
{7, 12, 21} {7, 12, 22} {7, 12, 23} {7, 12, 24} {7, 12, 25} {7, 12, 26} {7, 12, 27} {7, 12, 28} {7, 12, 29} {7, 12, 30}
{7, 12, 31} {7, 12, 32} {7, 12, 33} {7, 12, 34} {7, 12, 35} {7, 12, 36} {7, 12, 37} {7, 12, 38} {7, 12, 39} {7, 12, 40}
{7, 12, 41} {7, 12, 42} {7, 12, 43} {7, 12, 44} {7, 12, 45} {7, 12, 46} {7, 12, 47} {7, 12, 48} {7, 12, 49} {7, 12, 50}
{7, 12, 51} {7, 12, 52} {7, 12, 53} {7, 12, 54} {7, 12, 55} {7, 12, 56} {7, 12, 57} {7, 12, 58} {7, 12, 59} {7, 12, 60}
{7, 12, 61} {7, 12, 62} {7, 12, 63} {7, 12, 64} {7, 12, 65} {7, 12, 66} {7, 13, 14} {7, 13, 15} {7, 13, 16} {7, 13, 17}
{7, 13, 18} {7, 13, 19} {7, 13, 20} {7, 13, 21} {7, 13, 22} {7, 13, 23} {7, 13, 24} {7, 13, 25} {7, 13, 26} {7, 13, 27}
{7, 13, 28} {7, 13, 29} {7, 13, 30} {7, 13, 31} {7, 13, 32} {7, 13, 33} {7, 13, 34} {7, 13, 35} {7, 13, 36} {7, 13, 37}
{7, 13, 38} {7, 13, 39} {7, 13, 40} {7, 13, 41} {7, 13, 42} {7, 13, 43} {7, 13, 44} {7, 13, 45} {7, 13, 46} {7, 13, 47}
{7, 13, 48} {7, 13, 49} {7, 13, 50} {7, 13, 51} {7, 13, 52} {7, 13, 53} {7, 13, 54} {7, 13, 55} {7, 13, 56} {7, 13, 57}
{7, 13, 58} {7, 13, 59} {7, 13, 60} {7, 13, 61} {7, 13, 62} {7, 13, 63} {7, 13, 64} {7, 13, 65} {7, 13, 66} {7, 14, 15}
{7, 14, 16} {7, 14, 17} {7, 14, 18} {7, 14, 19} {7, 14, 20} {7, 14, 21} {7, 14, 22} {7, 14, 23} {7, 14, 24} {7, 14, 25}
{7, 14, 26} {7, 14, 27} {7, 14, 28} {7, 14, 29} {7, 14, 30} {7, 14, 31} {7, 14, 32} {7, 14, 33} {7, 14, 34} {7, 14, 35}
{7, 14, 36} {7, 14, 37} {7, 14, 38} {7, 14, 39} {7, 14, 40} {7, 14, 41} {7, 14, 42} {7, 14, 43} {7, 14, 44} {7, 14, 45}
{7, 14, 46} {7, 14, 47} {7, 14, 48} {7, 14, 49} {7, 14, 50} {7, 14, 51} {7, 14, 52} {7, 14, 53} {7, 14, 54} {7, 14, 55}
{7, 14, 56} {7, 14, 57} {7, 14, 58} {7, 14, 59} {7, 14, 60} {7, 14, 61} {7, 14, 62} {7, 14, 63} {7, 14, 64} {7, 14, 65}
{7, 14, 66} {7, 15, 16} {7, 15, 17} {7, 15, 18} {7, 15, 19} {7, 15, 20} {7, 15, 21} {7, 15, 22} {7, 15, 23} {7, 15, 24}
{7, 15, 25} {7, 15, 26} {7, 15, 27} {7, 15, 28} {7, 15, 29} {7, 15, 30} {7, 15, 31} {7, 15, 32} {7, 15, 33} {7, 15, 34}
{7, 15, 35} {7, 15, 36} {7, 15, 37} {7, 15, 38} {7, 15, 39} {7, 15, 40} {7, 15, 41} {7, 15, 42} {7, 15, 43} {7, 15, 44}
{7, 15, 45} {7, 15, 46} {7, 15, 47} {7, 15, 48} {7, 15, 49} {7, 15, 50} {7, 15, 51} {7, 15, 52} {7, 15, 53} {7, 15, 54}
{7, 15, 55} {7, 15, 56} {7, 15, 57} {7, 15, 58} {7, 15, 59} {7, 15, 60} {7, 15, 61} {7, 15, 62} {7, 15, 63} {7, 15, 64}
{7, 15, 65} {7, 15, 66} {7, 16, 17} {7, 16, 18} {7, 16, 19} {7, 16, 20} {7, 16, 21} {7, 16, 22} {7, 16, 23} {7, 16, 24}
{7, 16, 25} {7, 16, 26} {7, 16, 27} {7, 16, 28} {7, 16, 29} {7, 16, 30} {7, 16, 31} {7, 16, 32} {7, 16, 33} {7, 16, 34}
{7, 16, 35} {7, 16, 36} {7, 16, 37} {7, 16, 38} {7, 16, 39} {7, 16, 40} {7, 16, 41} {7, 16, 42} {7, 16, 43} {7, 16, 44}

TABLE 3A-continued

{7, 16, 45} {7, 16, 46} {7, 16, 47} {7, 16, 48} {7, 16, 49} {7, 16, 50} {7, 16, 51} {7, 16, 52} {7, 16, 53} {7, 16, 54}
{7, 16, 55} {7, 16, 56} {7, 16, 57} {7, 16, 58} {7, 16, 59} {7, 16, 60} {7, 16, 61} {7, 16, 62} {7, 16, 63} {7, 16, 64}
{7, 16, 65} {7, 16, 66} {7, 17, 18} {7, 17, 19} {7, 17, 20} {7, 17, 21} {7, 17, 22} {7, 17, 23} {7, 17, 24} {7, 17, 25}
{7, 17, 26} {7, 17, 27} {7, 17, 28} {7, 17, 29} {7, 17, 30} {7, 17, 31} {7, 17, 32} {7, 17, 33} {7, 17, 34} {7, 17, 35}
{7, 17, 36} {7, 17, 37} {7, 17, 38} {7, 17, 39} {7, 17, 40} {7, 17, 41} {7, 17, 42} {7, 17, 43} {7, 17, 44} {7, 17, 45}
{7, 17, 46} {7, 17, 47} {7, 17, 48} {7, 17, 49} {7, 17, 50} {7, 17, 51} {7, 17, 52} {7, 17, 53} {7, 17, 54} {7, 17, 55}
{7, 17, 56} {7, 17, 57} {7, 17, 58} {7, 17, 59} {7, 17, 60} {7, 17, 61} {7, 17, 62} {7, 17, 63} {7, 17, 64} {7, 17, 65}
{7, 17, 66} {7, 18, 19} {7, 18, 20} {7, 18, 21} {7, 18, 22} {7, 18, 23} {7, 18, 24} {7, 18, 25} {7, 18, 26} {7, 18, 27}
{7, 18, 28} {7, 18, 29} {7, 18, 30} {7, 18, 31} {7, 18, 32} {7, 18, 33} {7, 18, 34} {7, 18, 35} {7, 18, 36} {7, 18, 37}
{7, 18, 38} {7, 18, 39} {7, 18, 40} {7, 18, 41} {7, 18, 42} {7, 18, 43} {7, 18, 44} {7, 18, 45} {7, 18, 46} {7, 18, 47}
{7, 18, 48} {7, 18, 49} {7, 18, 50} {7, 18, 51} {7, 18, 52} {7, 18, 53} {7, 18, 54} {7, 18, 55} {7, 18, 56} {7, 18, 57}
{7, 18, 58} {7, 18, 59} {7, 18, 60} {7, 18, 61} {7, 18, 62} {7, 18, 63} {7, 18, 64} {7, 18, 65} {7, 18, 66} {7, 19, 20}
{7, 19, 21} {7, 19, 22} {7, 19, 23} {7, 19, 24} {7, 19, 25} {7, 19, 26} {7, 19, 27} {7, 19, 28} {7, 19, 29} {7, 19, 30}
{7, 19, 31} {7, 19, 32} {7, 19, 33} {7, 19, 34} {7, 19, 35} {7, 19, 36} {7, 19, 37} {7, 19, 38} {7, 19, 39} {7, 19, 40}
{7, 19, 41} {7, 19, 42} {7, 19, 43} {7, 19, 44} {7, 19, 45} {7, 19, 46} {7, 19, 47} {7, 19, 48} {7, 19, 49} {7, 19, 50}
{7, 19, 51} {7, 19, 52} {7, 19, 53} {7, 19, 54} {7, 19, 55} {7, 19, 56} {7, 19, 57} {7, 19, 58} {7, 19, 59} {7, 19, 60}
{7, 19, 61} {7, 19, 62} {7, 19, 63} {7, 19, 64} {7, 19, 65} {7, 19, 66} {7, 20, 21} {7, 20, 22} {7, 20, 23} {7, 20, 24}
{7, 20, 25} {7, 20, 26} {7, 20, 27} {7, 20, 28} {7, 20, 29} {7, 20, 30} {7, 20, 31} {7, 20, 32} {7, 20, 33} {7, 20, 34}
{7, 20, 35} {7, 20, 36} {7, 20, 37} {7, 20, 38} {7, 20, 39} {7, 20, 40} {7, 20, 41} {7, 20, 42} {7, 20, 43} {7, 20, 44}
{7, 20, 45} {7, 20, 46} {7, 20, 47} {7, 20, 48} {7, 20, 49} {7, 20, 50} {7, 20, 51} {7, 20, 52} {7, 20, 53} {7, 20, 54}
{7, 20, 55} {7, 20, 56} {7, 20, 57} {7, 20, 58} {7, 20, 59} {7, 20, 60} {7, 20, 61} {7, 20, 62} {7, 20, 63} {7, 20, 64}
{7, 20, 65} {7, 20, 66} {7, 21, 22} {7, 21, 23} {7, 21, 24} {7, 21, 25} {7, 21, 26} {7, 21, 27} {7, 21, 28} {7, 21, 29}
{7, 21, 30} {7, 21, 31} {7, 21, 32} {7, 21, 33} {7, 21, 34} {7, 21, 35} {7, 21, 36} {7, 21, 37} {7, 21, 38} {7, 21, 39}
{7, 21, 40} {7, 21, 41} {7, 21, 42} {7, 21, 43} {7, 21, 44} {7, 21, 45} {7, 21, 46} {7, 21, 47} {7, 21, 48} {7, 21, 49}
{7, 21, 50} {7, 21, 51} {7, 21, 52} {7, 21, 53} {7, 21, 54} {7, 21, 55} {7, 21, 56} {7, 21, 57} {7, 21, 58} {7, 21, 59}
{7, 21, 60} {7, 21, 61} {7, 21, 62} {7, 21, 63} {7, 21, 64} {7, 21, 65} {7, 21, 66} {7, 22, 23} {7, 22, 24} {7, 22, 25}
{7, 22, 26} {7, 22, 27} {7, 22, 28} {7, 22, 29} {7, 22, 30} {7, 22, 31} {7, 22, 32} {7, 22, 33} {7, 22, 34} {7, 22, 35}
{7, 22, 36} {7, 22, 37} {7, 22, 38} {7, 22, 39} {7, 22, 40} {7, 22, 41} {7, 22, 42} {7, 22, 43} {7, 22, 44} {7, 22, 45}
{7, 22, 46} {7, 22, 47} {7, 22, 48} {7, 22, 49} {7, 22, 50} {7, 22, 51} {7, 22, 52} {7, 22, 53} {7, 22, 54} {7, 22, 55}
{7, 22, 56} {7, 22, 57} {7, 22, 58} {7, 22, 59} {7, 22, 60} {7, 22, 61} {7, 22, 62} {7, 22, 63} {7, 22, 64} {7, 22, 65}
{7, 22, 66} {7, 23, 24} {7, 23, 25} {7, 23, 26} {7, 23, 27} {7, 23, 28} {7, 23, 29} {7, 23, 30} {7, 23, 31} {7, 23, 32}
{7, 23, 33} {7, 23, 34} {7, 23, 35} {7, 23, 36} {7, 23, 37} {7, 23, 38} {7, 23, 39} {7, 23, 40} {7, 23, 41} {7, 23, 42}
{7, 23, 43} {7, 23, 44} {7, 23, 45} {7, 23, 46} {7, 23, 47} {7, 23, 48} {7, 23, 49} {7, 23, 50} {7, 23, 51} {7, 23, 52}
{7, 23, 53} {7, 23, 54} {7, 23, 55} {7, 23, 56} {7, 23, 57} {7, 23, 58} {7, 23, 59} {7, 23, 60} {7, 23, 61} {7, 23, 62}
{7, 23, 63} {7, 23, 64} {7, 23, 65} {7, 23, 66} {7, 24, 25} {7, 24, 26} {7, 24, 27} {7, 24, 28} {7, 24, 29} {7, 24, 30}
{7, 24, 31} {7, 24, 32} {7, 24, 33} {7, 24, 34} {7, 24, 35} {7, 24, 36} {7, 24, 37} {7, 24, 38} {7, 24, 39} {7, 24, 40}
{7, 24, 41} {7, 24, 42} {7, 24, 43} {7, 24, 44} {7, 24, 45} {7, 24, 46} {7, 24, 47} {7, 24, 48} {7, 24, 49} {7, 24, 50}
{7, 24, 51} {7, 24, 52} {7, 24, 53} {7, 24, 54} {7, 24, 55} {7, 24, 56} {7, 24, 57} {7, 24, 58} {7, 24, 59} {7, 24, 60}
{7, 24, 61} {7, 24, 62} {7, 24, 63} {7, 24, 64} {7, 24, 65} {7, 24, 66} {7, 25, 26} {7, 25, 27} {7, 25, 28} {7, 25, 29}
{7, 25, 30} {7, 25, 31} {7, 25, 32} {7, 25, 33} {7, 25, 34} {7, 25, 35} {7, 25, 36} {7, 25, 37} {7, 25, 38} {7, 25, 39}
{7, 25, 40} {7, 25, 41} {7, 25, 42} {7, 25, 43} {7, 25, 44} {7, 25, 45} {7, 25, 46} {7, 25, 47} {7, 25, 48} {7, 25, 49}
{7, 25, 50} {7, 25, 51} {7, 25, 52} {7, 25, 53} {7, 25, 54} {7, 25, 55} {7, 25, 56} {7, 25, 57} {7, 25, 58} {7, 25, 59}
{7, 25, 60} {7, 25, 61} {7, 25, 62} {7, 25, 63} {7, 25, 64} {7, 25, 65} {7, 25, 66} {7, 26, 27} {7, 26, 28} {7, 26, 29}
{7, 26, 30} {7, 26, 31} {7, 26, 32} {7, 26, 33} {7, 26, 34} {7, 26, 35} {7, 26, 36} {7, 26, 37} {7, 26, 38} {7, 26, 39}
{7, 26, 40} {7, 26, 41} {7, 26, 42} {7, 26, 43} {7, 26, 44} {7, 26, 45} {7, 26, 46} {7, 26, 47} {7, 26, 48} {7, 26, 49}
{7, 26, 50} {7, 26, 51} {7, 26, 52} {7, 26, 53} {7, 26, 54} {7, 26, 55} {7, 26, 56} {7, 26, 57} {7, 26, 58} {7, 26, 59}
{7, 26, 60} {7, 26, 61} {7, 26, 62} {7, 26, 63} {7, 26, 64} {7, 26, 65} {7, 26, 66} {7, 27, 28} {7, 27, 29} {7, 27, 30}
{7, 27, 31} {7, 27, 32} {7, 27, 33} {7, 27, 34} {7, 27, 35} {7, 27, 36} {7, 27, 37} {7, 27, 38} {7, 27, 39} {7, 27, 40}
{7, 27, 41} {7, 27, 42} {7, 27, 43} {7, 27, 44} {7, 27, 45} {7, 27, 46} {7, 27, 47} {7, 27, 48} {7, 27, 49} {7, 27, 50}
{7, 27, 51} {7, 27, 52} {7, 27, 53} {7, 27, 54} {7, 27, 55} {7, 27, 56} {7, 27, 57} {7, 27, 58} {7, 27, 59} {7, 27, 60}
{7, 27, 61} {7, 27, 62} {7, 27, 63} {7, 27, 64} {7, 27, 65} {7, 27, 66} {7, 28, 29} {7, 28, 30} {7, 28, 31} {7, 28, 32}
{7, 28, 33} {7, 28, 34} {7, 28, 35} {7, 28, 36} {7, 28, 37} {7, 28, 38} {7, 28, 39} {7, 28, 40} {7, 28, 41} {7, 28, 42}
{7, 28, 43} {7, 28, 44} {7, 28, 45} {7, 28, 46} {7, 28, 47} {7, 28, 48} {7, 28, 49} {7, 28, 50} {7, 28, 51} {7, 28, 52}
{7, 28, 53} {7, 28, 54} {7, 28, 55} {7, 28, 56} {7, 28, 57} {7, 28, 58} {7, 28, 59} {7, 28, 60} {7, 28, 61} {7, 28, 62}
{7, 28, 63} {7, 28, 64} {7, 28, 65} {7, 28, 66} {7, 29, 30} {7, 29, 31} {7, 29, 32} {7, 29, 33} {7, 29, 34} {7, 29, 35}
{7, 29, 36} {7, 29, 37} {7, 29, 38} {7, 29, 39} {7, 29, 40} {7, 29, 41} {7, 29, 42} {7, 29, 43} {7, 29, 44} {7, 29, 45}
{7, 29, 46} {7, 29, 47} {7, 29, 48} {7, 29, 49} {7, 29, 50} {7, 29, 51} {7, 29, 52} {7, 29, 53} {7, 29, 54} {7, 29, 55}
{7, 29, 56} {7, 29, 57} {7, 29, 58} {7, 29, 59} {7, 29, 60} {7, 29, 61} {7, 29, 62} {7, 29, 63} {7, 29, 64} {7, 29, 65}
{7, 29, 66} {7, 30, 31} {7, 30, 32} {7, 30, 33} {7, 30, 34} {7, 30, 35} {7, 30, 36} {7, 30, 37} {7, 30, 38} {7, 30, 39}
{7, 30, 40} {7, 30, 41} {7, 30, 42} {7, 30, 43} {7, 30, 44} {7, 30, 45} {7, 30, 46} {7, 30, 47} {7, 30, 48} {7, 30, 49}
{7, 30, 50} {7, 30, 51} {7, 30, 52} {7, 30, 53} {7, 30, 54} {7, 30, 55} {7, 30, 56} {7, 30, 57} {7, 30, 58} {7, 30, 59}
{7, 30, 60} {7, 30, 61} {7, 30, 62} {7, 30, 63} {7, 30, 64} {7, 30, 65} {7, 30, 66} {7, 31, 32} {7, 31, 33} {7, 31, 34}
{7, 31, 35} {7, 31, 36} {7, 31, 37} {7, 31, 38} {7, 31, 39} {7, 31, 40} {7, 31, 41} {7, 31, 42} {7, 31, 43} {7, 31, 44}
{7, 31, 45} {7, 31, 46} {7, 31, 47} {7, 31, 48} {7, 31, 49} {7, 31, 50} {7, 31, 51} {7, 31, 52} {7, 31, 53} {7, 31, 54}
{7, 31, 55} {7, 31, 56} {7, 31, 57} {7, 31, 58} {7, 31, 59} {7, 31, 60} {7, 31, 61} {7, 31, 62} {7, 31, 63} {7, 31, 64}
{7, 31, 65} {7, 31, 66} {7, 32, 33} {7, 32, 34} {7, 32, 35} {7, 32, 36} {7, 32, 37} {7, 32, 38} {7, 32, 39} {7, 32, 40}
{7, 32, 41} {7, 32, 42} {7, 32, 43} {7, 32, 44} {7, 32, 45} {7, 32, 46} {7, 32, 47} {7, 32, 48} {7, 32, 49} {7, 32, 50}
{7, 32, 51} {7, 32, 52} {7, 32, 53} {7, 32, 54} {7, 32, 55} {7, 32, 56} {7, 32, 57} {7, 32, 58} {7, 32, 59} {7, 32, 60}
{7, 32, 61} {7, 32, 62} {7, 32, 63} {7, 32, 64} {7, 32, 65} {7, 32, 66} {7, 33, 34} {7, 33, 35} {7, 33, 36} {7, 33, 37}
{7, 33, 38} {7, 33, 39} {7, 33, 40} {7, 33, 41} {7, 33, 42} {7, 33, 43} {7, 33, 44} {7, 33, 45} {7, 33, 46} {7, 33, 47}
{7, 33, 48} {7, 33, 49} {7, 33, 50} {7, 33, 51} {7, 33, 52} {7, 33, 53} {7, 33, 54} {7, 33, 55} {7, 33, 56} {7, 33, 57}
{7, 33, 58} {7, 33, 59} {7, 33, 60} {7, 33, 61} {7, 33, 62} {7, 33, 63} {7, 33, 64} {7, 33, 65} {7, 33, 66} {7, 34, 35}
{7, 34, 36} {7, 34, 37} {7, 34, 38} {7, 34, 39} {7, 34, 40} {7, 34, 41} {7, 34, 42} {7, 34, 43} {7, 34, 44} {7, 34, 45}
{7, 34, 46} {7, 34, 47} {7, 34, 48} {7, 34, 49} {7, 34, 50} {7, 34, 51} {7, 34, 52} {7, 34, 53} {7, 34, 54} {7, 34, 55}
{7, 34, 56} {7, 34, 57} {7, 34, 58} {7, 34, 59} {7, 34, 60} {7, 34, 61} {7, 34, 62} {7, 34, 63} {7, 34, 64} {7, 34, 65}
{7, 34, 66} {7, 35, 36} {7, 35, 37} {7, 35, 38} {7, 35, 39} {7, 35, 40} {7, 35, 41} {7, 35, 42} {7, 35, 43} {7, 35, 44}
{7, 35, 45} {7, 35, 46} {7, 35, 47} {7, 35, 48} {7, 35, 49} {7, 35, 50} {7, 35, 51} {7, 35, 52} {7, 35, 53} {7, 35, 54}
{7, 35, 55} {7, 35, 56} {7, 35, 57} {7, 35, 58} {7, 35, 59} {7, 35, 60} {7, 35, 61} {7, 35, 62} {7, 35, 63} {7, 35, 64}
{7, 35, 65} {7, 35, 66} {7, 36, 37} {7, 36, 38} {7, 36, 39} {7, 36, 40} {7, 36, 41} {7, 36, 42} {7, 36, 43} {7, 36, 44}
{7, 36, 45} {7, 36, 46} {7, 36, 47} {7, 36, 48} {7, 36, 49} {7, 36, 50} {7, 36, 51} {7, 36, 52} {7, 36, 53} {7, 36, 54}

TABLE 3A-continued

{7, 36, 55} {7, 36, 56} {7, 36, 57} {7, 36, 58} {7, 36, 59} {7, 36, 60} {7, 36, 61} {7, 36, 62} {7, 36, 63} {7, 36, 64}
{7, 36, 65} {7, 36, 66} {7, 37, 38} {7, 37, 39} {7, 37, 40} {7, 37, 41} {7, 37, 42} {7, 37, 43} {7, 37, 44} {7, 37, 45}
{7, 37, 46} {7, 37, 47} {7, 37, 48} {7, 37, 49} {7, 37, 50} {7, 37, 51} {7, 37, 52} {7, 37, 53} {7, 37, 54} {7, 37, 55}
{7, 37, 56} {7, 37, 57} {7, 37, 58} {7, 37, 59} {7, 37, 60} {7, 37, 61} {7, 37, 62} {7, 37, 63} {7, 37, 64} {7, 37, 65}
{7, 37, 66} {7, 38, 39} {7, 38, 40} {7, 38, 41} {7, 38, 42} {7, 38, 43} {7, 38, 44} {7, 38, 45} {7, 38, 46} {7, 38, 47}
{7, 38, 48} {7, 38, 49} {7, 38, 50} {7, 38, 51} {7, 38, 52} {7, 38, 53} {7, 38, 54} {7, 38, 55} {7, 38, 56} {7, 38, 57}
{7, 38, 58} {7, 38, 59} {7, 38, 60} {7, 38, 61} {7, 38, 62} {7, 38, 63} {7, 38, 64} {7, 38, 65} {7, 38, 66} {7, 39, 40}
{7, 39, 41} {7, 39, 42} {7, 39, 43} {7, 39, 44} {7, 39, 45} {7, 39, 46} {7, 39, 47} {7, 39, 48} {7, 39, 49} {7, 39, 50}
{7, 39, 51} {7, 39, 52} {7, 39, 53} {7, 39, 54} {7, 39, 55} {7, 39, 56} {7, 39, 57} {7, 39, 58} {7, 39, 59} {7, 39, 60}
{7, 39, 61} {7, 39, 62} {7, 39, 63} {7, 39, 64} {7, 39, 65} {7, 39, 66} {7, 40, 41} {7, 40, 42} {7, 40, 43} {7, 40, 44}
{7, 40, 45} {7, 40, 46} {7, 40, 47} {7, 40, 48} {7, 40, 49} {7, 40, 50} {7, 40, 51} {7, 40, 52} {7, 40, 53} {7, 40, 54}
{7, 40, 55} {7, 40, 56} {7, 40, 57} {7, 40, 58} {7, 40, 59} {7, 40, 60} {7, 40, 61} {7, 40, 62} {7, 40, 63} {7, 40, 64}
{7, 40, 65} {7, 40, 66} {7, 41, 42} {7, 41, 43} {7, 41, 44} {7, 41, 45} {7, 41, 46} {7, 41, 47} {7, 41, 48} {7, 41, 49}
{7, 41, 50} {7, 41, 51} {7, 41, 52} {7, 41, 53} {7, 41, 54} {7, 41, 55} {7, 41, 56} {7, 41, 57} {7, 41, 58} {7, 41, 59}
{7, 41, 60} {7, 41, 61} {7, 41, 62} {7, 41, 63} {7, 41, 64} {7, 41, 65} {7, 41, 66} {7, 42, 43} {7, 42, 44} {7, 42, 45}
{7, 42, 46} {7, 42, 47} {7, 42, 48} {7, 42, 49} {7, 42, 50} {7, 42, 51} {7, 42, 52} {7, 42, 53} {7, 42, 54} {7, 42, 55}
{7, 42, 56} {7, 42, 57} {7, 42, 58} {7, 42, 59} {7, 42, 60} {7, 42, 61} {7, 42, 62} {7, 42, 63} {7, 42, 64} {7, 42, 65}
{7, 42, 66} {7, 43, 44} {7, 43, 45} {7, 43, 46} {7, 43, 47} {7, 43, 48} {7, 43, 49} {7, 43, 50} {7, 43, 51} {7, 43, 52}
{7, 43, 53} {7, 43, 54} {7, 43, 55} {7, 43, 56} {7, 43, 57} {7, 43, 58} {7, 43, 59} {7, 43, 60} {7, 43, 61} {7, 43, 62}
{7, 43, 63} {7, 43, 64} {7, 43, 65} {7, 43, 66} {7, 44, 45} {7, 44, 46} {7, 44, 47} {7, 44, 48} {7, 44, 49} {7, 44, 50}
{7, 44, 51} {7, 44, 52} {7, 44, 53} {7, 44, 54} {7, 44, 55} {7, 44, 56} {7, 44, 57} {7, 44, 58} {7, 44, 59} {7, 44, 60}
{7, 44, 61} {7, 44, 62} {7, 44, 63} {7, 44, 64} {7, 44, 65} {7, 44, 66} {7, 45, 46} {7, 45, 47} {7, 45, 48} {7, 45, 49}
{7, 45, 50} {7, 45, 51} {7, 45, 52} {7, 45, 53} {7, 45, 54} {7, 45, 55} {7, 45, 56} {7, 45, 57} {7, 45, 58} {7, 45, 59}
{7, 45, 60} {7, 45, 61} {7, 45, 62} {7, 45, 63} {7, 45, 64} {7, 45, 65} {7, 45, 66} {7, 46, 47} {7, 46, 48} {7, 46, 49}
{7, 46, 50} {7, 46, 51} {7, 46, 52} {7, 46, 53} {7, 46, 54} {7, 46, 55} {7, 46, 56} {7, 46, 57} {7, 46, 58} {7, 46, 59}
{7, 46, 60} {7, 46, 61} {7, 46, 62} {7, 46, 63} {7, 46, 64} {7, 46, 65} {7, 46, 66} {7, 47, 48} {7, 47, 49} {7, 47, 50}
{7, 47, 51} {7, 47, 52} {7, 47, 53} {7, 47, 54} {7, 47, 55} {7, 47, 56} {7, 47, 57} {7, 47, 58} {7, 47, 59} {7, 47, 60}
{7, 47, 61} {7, 47, 62} {7, 47, 63} {7, 47, 64} {7, 47, 65} {7, 47, 66} {7, 48, 49} {7, 48, 50} {7, 48, 51} {7, 48, 52}
{7, 48, 53} {7, 48, 54} {7, 48, 55} {7, 48, 56} {7, 48, 57} {7, 48, 58} {7, 48, 59} {7, 48, 60} {7, 48, 61} {7, 48, 62}
{7, 48, 63} {7, 48, 64} {7, 48, 65} {7, 48, 66} {7, 49, 50} {7, 49, 51} {7, 49, 52} {7, 49, 53} {7, 49, 54} {7, 49, 55}
{7, 49, 56} {7, 49, 57} {7, 49, 58} {7, 49, 59} {7, 49, 60} {7, 49, 61} {7, 49, 62} {7, 49, 63} {7, 49, 64} {7, 49, 65}
{7, 49, 66} {7, 50, 51} {7, 50, 52} {7, 50, 53} {7, 50, 54} {7, 50, 55} {7, 50, 56} {7, 50, 57} {7, 50, 58} {7, 50, 59}
{7, 50, 60} {7, 50, 61} {7, 50, 62} {7, 50, 63} {7, 50, 64} {7, 50, 65} {7, 50, 66} {7, 51, 52} {7, 51, 53} {7, 51, 54}
{7, 51, 55} {7, 51, 56} {7, 51, 57} {7, 51, 58} {7, 51, 59} {7, 51, 60} {7, 51, 61} {7, 51, 62} {7, 51, 63} {7, 51, 64}
{7, 51, 65} {7, 51, 66} {7, 52, 53} {7, 52, 54} {7, 52, 55} {7, 52, 56} {7, 52, 57} {7, 52, 58} {7, 52, 59} {7, 52, 60}
{7, 52, 61} {7, 52, 62} {7, 52, 63} {7, 52, 64} {7, 52, 65} {7, 52, 66} {7, 53, 54} {7, 53, 55} {7, 53, 56} {7, 53, 57}
{7, 53, 58} {7, 53, 59} {7, 53, 60} {7, 53, 61} {7, 53, 62} {7, 53, 63} {7, 53, 64} {7, 53, 65} {7, 53, 66} {7, 54, 55}
{7, 54, 56} {7, 54, 57} {7, 54, 58} {7, 54, 59} {7, 54, 60} {7, 54, 61} {7, 54, 62} {7, 54, 63} {7, 54, 64} {7, 54, 65}
{7, 54, 66} {7, 55, 56} {7, 55, 57} {7, 55, 58} {7, 55, 59} {7, 55, 60} {7, 55, 61} {7, 55, 62} {7, 55, 63} {7, 55, 64}
{7, 55, 65} {7, 55, 66} {7, 56, 57} {7, 56, 58} {7, 56, 59} {7, 56, 60} {7, 56, 61} {7, 56, 62} {7, 56, 63} {7, 56, 64}
{7, 56, 65} {7, 56, 66} {7, 57, 58} {7, 57, 59} {7, 57, 60} {7, 57, 61} {7, 57, 62} {7, 57, 63} {7, 57, 64} {7, 57, 65}
{7, 57, 66} {7, 58, 59} {7, 58, 60} {7, 58, 61} {7, 58, 62} {7, 58, 63} {7, 58, 64} {7, 58, 65} {7, 58, 66} {7, 59, 60}
{7, 59, 61} {7, 59, 62} {7, 59, 63} {7, 59, 64} {7, 59, 65} {7, 59, 66} {7, 60, 61} {7, 60, 62} {7, 60, 63} {7, 60, 64}
{7, 60, 65} {7, 60, 66} {7, 61, 62} {7, 61, 63} {7, 61, 64} {7, 61, 65} {7, 61, 66} {7, 62, 63} {7, 62, 64} {7, 62, 65}
{7, 62, 66} {7, 63, 64} {7, 63, 65} {7, 63, 66} {7, 64, 65} {7, 64, 66} {7, 65, 66} {8, 9, 10} {8, 9, 11} {8, 9, 12} {8, 9, 13}
{8, 9, 14} {8, 9, 15} {8, 9, 16} {8, 9, 17} {8, 9, 18} {8, 9, 19} {8, 9, 20} {8, 9, 21} {8, 9, 22} {8, 9, 23} {8, 9, 24} {8, 9, 25}
{8, 9, 26} {8, 9, 27} {8, 9, 28} {8, 9, 29} {8, 9, 30} {8, 9, 31} {8, 9, 32} {8, 9, 33} {8, 9, 34} {8, 9, 35} {8, 9, 36} {8, 9, 37}
{8, 9, 38} {8, 9, 39} {8, 9, 40} {8, 9, 41} {8, 9, 42} {8, 9, 43} {8, 9, 44} {8, 9, 45} {8, 9, 46} {8, 9, 47} {8, 9, 48} {8, 9, 49}
{8, 9, 50} {8, 9, 51} {8, 9, 52} {8, 9, 53} {8, 9, 54} {8, 9, 55} {8, 9, 56} {8, 9, 57} {8, 9, 58} {8, 9, 59} {8, 9, 60} {8, 9, 61}
{8, 9, 62} {8, 9, 63} {8, 9, 64} {8, 9, 65} {8, 9, 66} {8, 10, 11} {8, 10, 12} {8, 10, 13} {8, 10, 14} {8, 10, 15} {8, 10, 16}
{8, 10, 17} {8, 10, 18} {8, 10, 19} {8, 10, 20} {8, 10, 21} {8, 10, 22} {8, 10, 23} {8, 10, 24} {8, 10, 25} {8, 10, 26}
{8, 10, 27} {8, 10, 28} {8, 10, 29} {8, 10, 30} {8, 10, 31} {8, 10, 32} {8, 10, 33} {8, 10, 34} {8, 10, 35} {8, 10, 36}
{8, 10, 37} {8, 10, 38} {8, 10, 39} {8, 10, 40} {8, 10, 41} {8, 10, 42} {8, 10, 43} {8, 10, 44} {8, 10, 45} {8, 10, 46}
{8, 10, 47} {8, 10, 48} {8, 10, 49} {8, 10, 50} {8, 10, 51} {8, 10, 52} {8, 10, 53} {8, 10, 54} {8, 10, 55} {8, 10, 56}
{8, 10, 57} {8, 10, 58} {8, 10, 59} {8, 10, 60} {8, 10, 61} {8, 10, 62} {8, 10, 63} {8, 10, 64} {8, 10, 65} {8, 10, 66}
{8, 11, 12} {8, 11, 13} {8, 11, 14} {8, 11, 15} {8, 11, 16} {8, 11, 17} {8, 11, 18} {8, 11, 19} {8, 11, 20} {8, 11, 21}
{8, 11, 22} {8, 11, 23} {8, 11, 24} {8, 11, 25} {8, 11, 26} {8, 11, 27} {8, 11, 28} {8, 11, 29} {8, 11, 30} {8, 11, 31}
{8, 11, 32} {8, 11, 33} {8, 11, 34} {8, 11, 35} {8, 11, 36} {8, 11, 37} {8, 11, 38} {8, 11, 39} {8, 11, 40} {8, 11, 41}
{8, 11, 42} {8, 11, 43} {8, 11, 44} {8, 11, 45} {8, 11, 46} {8, 11, 47} {8, 11, 48} {8, 11, 49} {8, 11, 50} {8, 11, 51}
{8, 11, 52} {8, 11, 53} {8, 11, 54} {8, 11, 55} {8, 11, 56} {8, 11, 57} {8, 11, 58} {8, 11, 59} {8, 11, 60} {8, 11, 61}
{8, 11, 62} {8, 11, 63} {8, 11, 64} {8, 11, 65} {8, 11, 66} {8, 12, 13} {8, 12, 14} {8, 12, 15} {8, 12, 16} {8, 12, 17}
{8, 12, 18} {8, 12, 19} {8, 12, 20} {8, 12, 21} {8, 12, 22} {8, 12, 23} {8, 12, 24} {8, 12, 25} {8, 12, 26} {8, 12, 27}
{8, 12, 28} {8, 12, 29} {8, 12, 30} {8, 12, 31} {8, 12, 32} {8, 12, 33} {8, 12, 34} {8, 12, 35} {8, 12, 36} {8, 12, 37}
{8, 12, 38} {8, 12, 39} {8, 12, 40} {8, 12, 41} {8, 12, 42} {8, 12, 43} {8, 12, 44} {8, 12, 45} {8, 12, 46} {8, 12, 47}
{8, 12, 48} {8, 12, 49} {8, 12, 50} {8, 12, 51} {8, 12, 52} {8, 12, 53} {8, 12, 54} {8, 12, 55} {8, 12, 56} {8, 12, 57}
{8, 12, 58} {8, 12, 59} {8, 12, 60} {8, 12, 61} {8, 12, 62} {8, 12, 63} {8, 12, 64} {8, 12, 65} {8, 12, 66} {8, 13, 14}
{8, 13, 15} {8, 13, 16} {8, 13, 17} {8, 13, 18} {8, 13, 19} {8, 13, 20} {8, 13, 21} {8, 13, 22} {8, 13, 23} {8, 13, 24}
{8, 13, 25} {8, 13, 26} {8, 13, 27} {8, 13, 28} {8, 13, 29} {8, 13, 30} {8, 13, 31} {8, 13, 32} {8, 13, 33} {8, 13, 34}
{8, 13, 35} {8, 13, 36} {8, 13, 37} {8, 13, 38} {8, 13, 39} {8, 13, 40} {8, 13, 41} {8, 13, 42} {8, 13, 43} {8, 13, 44}
{8, 13, 45} {8, 13, 46} {8, 13, 47} {8, 13, 48} {8, 13, 49} {8, 13, 50} {8, 13, 51} {8, 13, 52} {8, 13, 53} {8, 13, 54}
{8, 13, 55} {8, 13, 56} {8, 13, 57} {8, 13, 58} {8, 13, 59} {8, 13, 60} {8, 13, 61} {8, 13, 62} {8, 13, 63} {8, 13, 64}
{8, 13, 65} {8, 13, 66} {8, 14, 15} {8, 14, 16} {8, 14, 17} {8, 14, 18} {8, 14, 19} {8, 14, 20} {8, 14, 21} {8, 14, 22}
{8, 14, 23} {8, 14, 24} {8, 14, 25} {8, 14, 26} {8, 14, 27} {8, 14, 28} {8, 14, 29} {8, 14, 30} {8, 14, 31} {8, 14, 32}
{8, 14, 33} {8, 14, 34} {8, 14, 35} {8, 14, 36} {8, 14, 37} {8, 14, 38} {8, 14, 39} {8, 14, 40} {8, 14, 41} {8, 14, 42}
{8, 14, 43} {8, 14, 44} {8, 14, 45} {8, 14, 46} {8, 14, 47} {8, 14, 48} {8, 14, 49} {8, 14, 50} {8, 14, 51} {8, 14, 52}
{8, 14, 53} {8, 14, 54} {8, 14, 55} {8, 14, 56} {8, 14, 57} {8, 14, 58} {8, 14, 59} {8, 14, 60} {8, 14, 61} {8, 14, 62}
{8, 14, 63} {8, 14, 64} {8, 14, 65} {8, 14, 66} {8, 15, 16} {8, 15, 17} {8, 15, 18} {8, 15, 19} {8, 15, 20} {8, 15, 21}
{8, 15, 22} {8, 15, 23} {8, 15, 24} {8, 15, 25} {8, 15, 26} {8, 15, 27} {8, 15, 28} {8, 15, 29} {8, 15, 30} {8, 15, 31}
{8, 15, 32} {8, 15, 33} {8, 15, 34} {8, 15, 35} {8, 15, 36} {8, 15, 37} {8, 15, 38} {8, 15, 39} {8, 15, 40} {8, 15, 41}
{8, 15, 42} {8, 15, 43} {8, 15, 44} {8, 15, 45} {8, 15, 46} {8, 15, 47} {8, 15, 48} {8, 15, 49} {8, 15, 50} {8, 15, 51}

TABLE 3A-continued

| | | | | | | | | |
|---|---|---|---|---|---|---|---|---|
| {8, 15, 52} | {8, 15, 53} | {8, 15, 54} | {8, 15, 55} | {8, 15, 56} | {8, 15, 57} | {8, 15, 58} | {8, 15, 59} | {8, 15, 60} | {8, 15, 61} |
| {8, 15, 62} | {8, 15, 63} | {8, 15, 64} | {8, 15, 65} | {8, 15, 66} | {8, 16, 17} | {8, 16, 18} | {8, 16, 19} | {8, 16, 20} | {8, 16, 21} |
| {8, 16, 22} | {8, 16, 23} | {8, 16, 24} | {8, 16, 25} | {8, 16, 26} | {8, 16, 27} | {8, 16, 28} | {8, 16, 29} | {8, 16, 30} | {8, 16, 31} |
| {8, 16, 32} | {8, 16, 33} | {8, 16, 34} | {8, 16, 35} | {8, 16, 36} | {8, 16, 37} | {8, 16, 38} | {8, 16, 39} | {8, 16, 40} | {8, 16, 41} |
| {8, 16, 42} | {8, 16, 43} | {8, 16, 44} | {8, 16, 45} | {8, 16, 46} | {8, 16, 47} | {8, 16, 48} | {8, 16, 49} | {8, 16, 50} | {8, 16, 51} |
| {8, 16, 52} | {8, 16, 53} | {8, 16, 54} | {8, 16, 55} | {8, 16, 56} | {8, 16, 57} | {8, 16, 58} | {8, 16, 59} | {8, 16, 60} | {8, 16, 61} |
| {8, 16, 62} | {8, 16, 63} | {8, 16, 64} | {8, 16, 65} | {8, 16, 66} | {8, 17, 18} | {8, 17, 19} | {8, 17, 20} | {8, 17, 21} | {8, 17, 22} |
| {8, 17, 23} | {8, 17, 24} | {8, 17, 25} | {8, 17, 26} | {8, 17, 27} | {8, 17, 28} | {8, 17, 29} | {8, 17, 30} | {8, 17, 31} | {8, 17, 32} |
| {8, 17, 33} | {8, 17, 34} | {8, 17, 35} | {8, 17, 36} | {8, 17, 37} | {8, 17, 38} | {8, 17, 39} | {8, 17, 40} | {8, 17, 41} | {8, 17, 42} |
| {8, 17, 43} | {8, 17, 44} | {8, 17, 45} | {8, 17, 46} | {8, 17, 47} | {8, 17, 48} | {8, 17, 49} | {8, 17, 50} | {8, 17, 51} | {8, 17, 52} |
| {8, 17, 53} | {8, 17, 54} | {8, 17, 55} | {8, 17, 56} | {8, 17, 57} | {8, 17, 58} | {8, 17, 59} | {8, 17, 60} | {8, 17, 61} | {8, 17, 62} |
| {8, 17, 63} | {8, 17, 64} | {8, 17, 65} | {8, 17, 66} | {8, 18, 19} | {8, 18, 20} | {8, 18, 21} | {8, 18, 22} | {8, 18, 23} | {8, 18, 24} |
| {8, 18, 25} | {8, 18, 26} | {8, 18, 27} | {8, 18, 28} | {8, 18, 29} | {8, 18, 30} | {8, 18, 31} | {8, 18, 32} | {8, 18, 33} | {8, 18, 34} |
| {8, 18, 35} | {8, 18, 36} | {8, 18, 37} | {8, 18, 38} | {8, 18, 39} | {8, 18, 40} | {8, 18, 41} | {8, 18, 42} | {8, 18, 43} | {8, 18, 44} |
| {8, 18, 45} | {8, 18, 46} | {8, 18, 47} | {8, 18, 48} | {8, 18, 49} | {8, 18, 50} | {8, 18, 51} | {8, 18, 52} | {8, 18, 53} | {8, 18, 54} |
| {8, 18, 55} | {8, 18, 56} | {8, 18, 57} | {8, 18, 58} | {8, 18, 59} | {8, 18, 60} | {8, 18, 61} | {8, 18, 62} | {8, 18, 63} | {8, 18, 64} |
| {8, 18, 65} | {8, 18, 66} | {8, 19, 20} | {8, 19, 21} | {8, 19, 22} | {8, 19, 23} | {8, 19, 24} | {8, 19, 25} | {8, 19, 26} | {8, 19, 27} |
| {8, 19, 28} | {8, 19, 29} | {8, 19, 30} | {8, 19, 31} | {8, 19, 32} | {8, 19, 33} | {8, 19, 34} | {8, 19, 35} | {8, 19, 36} | {8, 19, 37} |
| {8, 19, 38} | {8, 19, 39} | {8, 19, 40} | {8, 19, 41} | {8, 19, 42} | {8, 19, 43} | {8, 19, 44} | {8, 19, 45} | {8, 19, 46} | {8, 19, 47} |
| {8, 19, 48} | {8, 19, 49} | {8, 19, 50} | {8, 19, 51} | {8, 19, 52} | {8, 19, 53} | {8, 19, 54} | {8, 19, 55} | {8, 19, 56} | {8, 19, 57} |
| {8, 19, 58} | {8, 19, 59} | {8, 19, 60} | {8, 19, 61} | {8, 19, 62} | {8, 19, 63} | {8, 19, 64} | {8, 19, 65} | {8, 19, 66} | {8, 20, 21} |
| {8, 20, 22} | {8, 20, 23} | {8, 20, 24} | {8, 20, 25} | {8, 20, 26} | {8, 20, 27} | {8, 20, 28} | {8, 20, 29} | {8, 20, 30} | {8, 20, 31} |
| {8, 20, 32} | {8, 20, 33} | {8, 20, 34} | {8, 20, 35} | {8, 20, 36} | {8, 20, 37} | {8, 20, 38} | {8, 20, 39} | {8, 20, 40} | {8, 20, 41} |
| {8, 20, 42} | {8, 20, 43} | {8, 20, 44} | {8, 20, 45} | {8, 20, 46} | {8, 20, 47} | {8, 20, 48} | {8, 20, 49} | {8, 20, 50} | {8, 20, 51} |
| {8, 20, 52} | {8, 20, 53} | {8, 20, 54} | {8, 20, 55} | {8, 20, 56} | {8, 20, 57} | {8, 20, 58} | {8, 20, 59} | {8, 20, 60} | {8, 20, 61} |
| {8, 20, 62} | {8, 20, 63} | {8, 20, 64} | {8, 20, 65} | {8, 20, 66} | {8, 21, 22} | {8, 21, 23} | {8, 21, 24} | {8, 21, 25} | {8, 21, 26} |
| {8, 21, 27} | {8, 21, 28} | {8, 21, 29} | {8, 21, 30} | {8, 21, 31} | {8, 21, 32} | {8, 21, 33} | {8, 21, 34} | {8, 21, 35} | {8, 21, 36} |
| {8, 21, 37} | {8, 21, 38} | {8, 21, 39} | {8, 21, 40} | {8, 21, 41} | {8, 21, 42} | {8, 21, 43} | {8, 21, 44} | {8, 21, 45} | {8, 21, 46} |
| {8, 21, 47} | {8, 21, 48} | {8, 21, 49} | {8, 21, 50} | {8, 21, 51} | {8, 21, 52} | {8, 21, 53} | {8, 21, 54} | {8, 21, 55} | {8, 21, 56} |
| {8, 21, 57} | {8, 21, 58} | {8, 21, 59} | {8, 21, 60} | {8, 21, 61} | {8, 21, 62} | {8, 21, 63} | {8, 21, 64} | {8, 21, 65} | {8, 21, 66} |
| {8, 22, 23} | {8, 22, 24} | {8, 22, 25} | {8, 22, 26} | {8, 22, 27} | {8, 22, 28} | {8, 22, 29} | {8, 22, 30} | {8, 22, 31} | {8, 22, 32} |
| {8, 22, 33} | {8, 22, 34} | {8, 22, 35} | {8, 22, 36} | {8, 22, 37} | {8, 22, 38} | {8, 22, 39} | {8, 22, 40} | {8, 22, 41} | {8, 22, 42} |
| {8, 22, 43} | {8, 22, 44} | {8, 22, 45} | {8, 22, 46} | {8, 22, 47} | {8, 22, 48} | {8, 22, 49} | {8, 22, 50} | {8, 22, 51} | {8, 22, 52} |
| {8, 22, 53} | {8, 22, 54} | {8, 22, 55} | {8, 22, 56} | {8, 22, 57} | {8, 22, 58} | {8, 22, 59} | {8, 22, 60} | {8, 22, 61} | {8, 22, 62} |
| {8, 22, 63} | {8, 22, 64} | {8, 22, 65} | {8, 22, 66} | {8, 23, 24} | {8, 23, 25} | {8, 23, 26} | {8, 23, 27} | {8, 23, 28} | {8, 23, 29} |
| {8, 23, 30} | {8, 23, 31} | {8, 23, 32} | {8, 23, 33} | {8, 23, 34} | {8, 23, 35} | {8, 23, 36} | {8, 23, 37} | {8, 23, 38} | {8, 23, 39} |
| {8, 23, 40} | {8, 23, 41} | {8, 23, 42} | {8, 23, 43} | {8, 23, 44} | {8, 23, 45} | {8, 23, 46} | {8, 23, 47} | {8, 23, 48} | {8, 23, 49} |
| {8, 23, 50} | {8, 23, 51} | {8, 23, 52} | {8, 23, 53} | {8, 23, 54} | {8, 23, 55} | {8, 23, 56} | {8, 23, 57} | {8, 23, 58} | {8, 23, 59} |
| {8, 23, 60} | {8, 23, 61} | {8, 23, 62} | {8, 23, 63} | {8, 23, 64} | {8, 23, 65} | {8, 23, 66} | {8, 24, 25} | {8, 24, 26} | {8, 24, 27} |
| {8, 24, 28} | {8, 24, 29} | {8, 24, 30} | {8, 24, 31} | {8, 24, 32} | {8, 24, 33} | {8, 24, 34} | {8, 24, 35} | {8, 24, 36} | {8, 24, 37} |
| {8, 24, 38} | {8, 24, 39} | {8, 24, 40} | {8, 24, 41} | {8, 24, 42} | {8, 24, 43} | {8, 24, 44} | {8, 24, 45} | {8, 24, 46} | {8, 24, 47} |
| {8, 24, 48} | {8, 24, 49} | {8, 24, 50} | {8, 24, 51} | {8, 24, 52} | {8, 24, 53} | {8, 24, 54} | {8, 24, 55} | {8, 24, 56} | {8, 24, 57} |
| {8, 24, 58} | {8, 24, 59} | {8, 24, 60} | {8, 24, 61} | {8, 24, 62} | {8, 24, 63} | {8, 24, 64} | {8, 24, 65} | {8, 24, 66} | {8, 25, 26} |
| {8, 25, 27} | {8, 25, 28} | {8, 25, 29} | {8, 25, 30} | {8, 25, 31} | {8, 25, 32} | {8, 25, 33} | {8, 25, 34} | {8, 25, 35} | {8, 25, 36} |
| {8, 25, 37} | {8, 25, 38} | {8, 25, 39} | {8, 25, 40} | {8, 25, 41} | {8, 25, 42} | {8, 25, 43} | {8, 25, 44} | {8, 25, 45} | {8, 25, 46} |
| {8, 25, 47} | {8, 25, 48} | {8, 25, 49} | {8, 25, 50} | {8, 25, 51} | {8, 25, 52} | {8, 25, 53} | {8, 25, 54} | {8, 25, 55} | {8, 25, 56} |
| {8, 25, 57} | {8, 25, 58} | {8, 25, 59} | {8, 25, 60} | {8, 25, 61} | {8, 25, 62} | {8, 25, 63} | {8, 25, 64} | {8, 25, 65} | {8, 25, 66} |
| {8, 26, 27} | {8, 26, 28} | {8, 26, 29} | {8, 26, 30} | {8, 26, 31} | {8, 26, 32} | {8, 26, 33} | {8, 26, 34} | {8, 26, 35} | {8, 26, 36} |
| {8, 26, 37} | {8, 26, 38} | {8, 26, 39} | {8, 26, 40} | {8, 26, 41} | {8, 26, 42} | {8, 26, 43} | {8, 26, 44} | {8, 26, 45} | {8, 26, 46} |
| {8, 26, 47} | {8, 26, 48} | {8, 26, 49} | {8, 26, 50} | {8, 26, 51} | {8, 26, 52} | {8, 26, 53} | {8, 26, 54} | {8, 26, 55} | {8, 26, 56} |
| {8, 26, 57} | {8, 26, 58} | {8, 26, 59} | {8, 26, 60} | {8, 26, 61} | {8, 26, 62} | {8, 26, 63} | {8, 26, 64} | {8, 26, 65} | {8, 26, 66} |
| {8, 27, 28} | {8, 27, 29} | {8, 27, 30} | {8, 27, 31} | {8, 27, 32} | {8, 27, 33} | {8, 27, 34} | {8, 27, 35} | {8, 27, 36} | {8, 27, 37} |
| {8, 27, 38} | {8, 27, 39} | {8, 27, 40} | {8, 27, 41} | {8, 27, 42} | {8, 27, 43} | {8, 27, 44} | {8, 27, 45} | {8, 27, 46} | {8, 27, 47} |
| {8, 27, 48} | {8, 27, 49} | {8, 27, 50} | {8, 27, 51} | {8, 27, 52} | {8, 27, 53} | {8, 27, 54} | {8, 27, 55} | {8, 27, 56} | {8, 27, 57} |
| {8, 27, 58} | {8, 27, 59} | {8, 27, 60} | {8, 27, 61} | {8, 27, 62} | {8, 27, 63} | {8, 27, 64} | {8, 27, 65} | {8, 27, 66} | {8, 28, 29} |
| {8, 28, 30} | {8, 28, 31} | {8, 28, 32} | {8, 28, 33} | {8, 28, 34} | {8, 28, 35} | {8, 28, 36} | {8, 28, 37} | {8, 28, 38} | {8, 28, 39} |
| {8, 28, 40} | {8, 28, 41} | {8, 28, 42} | {8, 28, 43} | {8, 28, 44} | {8, 28, 45} | {8, 28, 46} | {8, 28, 47} | {8, 28, 48} | {8, 28, 49} |
| {8, 28, 50} | {8, 28, 51} | {8, 28, 52} | {8, 28, 53} | {8, 28, 54} | {8, 28, 55} | {8, 28, 56} | {8, 28, 57} | {8, 28, 58} | {8, 28, 59} |
| {8, 28, 60} | {8, 28, 61} | {8, 28, 62} | {8, 28, 63} | {8, 28, 64} | {8, 28, 65} | {8, 28, 66} | {8, 29, 30} | {8, 29, 31} | {8, 29, 32} |
| {8, 29, 33} | {8, 29, 34} | {8, 29, 35} | {8, 29, 36} | {8, 29, 37} | {8, 29, 38} | {8, 29, 39} | {8, 29, 40} | {8, 29, 41} | {8, 29, 42} |
| {8, 29, 43} | {8, 29, 44} | {8, 29, 45} | {8, 29, 46} | {8, 29, 47} | {8, 29, 48} | {8, 29, 49} | {8, 29, 50} | {8, 29, 51} | {8, 29, 52} |
| {8, 29, 53} | {8, 29, 54} | {8, 29, 55} | {8, 29, 56} | {8, 29, 57} | {8, 29, 58} | {8, 29, 59} | {8, 29, 60} | {8, 29, 61} | {8, 29, 62} |
| {8, 29, 63} | {8, 29, 64} | {8, 29, 65} | {8, 29, 66} | {8, 30, 31} | {8, 30, 32} | {8, 30, 33} | {8, 30, 34} | {8, 30, 35} | {8, 30, 36} |
| {8, 30, 37} | {8, 30, 38} | {8, 30, 39} | {8, 30, 40} | {8, 30, 41} | {8, 30, 42} | {8, 30, 43} | {8, 30, 44} | {8, 30, 45} | {8, 30, 46} |
| {8, 30, 47} | {8, 30, 48} | {8, 30, 49} | {8, 30, 50} | {8, 30, 51} | {8, 30, 52} | {8, 30, 53} | {8, 30, 54} | {8, 30, 55} | {8, 30, 56} |
| {8, 30, 57} | {8, 30, 58} | {8, 30, 59} | {8, 30, 60} | {8, 30, 61} | {8, 30, 62} | {8, 30, 63} | {8, 30, 64} | {8, 30, 65} | {8, 30, 66} |
| {8, 31, 32} | {8, 31, 33} | {8, 31, 34} | {8, 31, 35} | {8, 31, 36} | {8, 31, 37} | {8, 31, 38} | {8, 31, 39} | {8, 31, 40} | {8, 31, 41} |
| {8, 31, 42} | {8, 31, 43} | {8, 31, 44} | {8, 31, 45} | {8, 31, 46} | {8, 31, 47} | {8, 31, 48} | {8, 31, 49} | {8, 31, 50} | {8, 31, 51} |
| {8, 31, 52} | {8, 31, 53} | {8, 31, 54} | {8, 31, 55} | {8, 31, 56} | {8, 31, 57} | {8, 31, 58} | {8, 31, 59} | {8, 31, 60} | {8, 31, 61} |
| {8, 31, 62} | {8, 31, 63} | {8, 31, 64} | {8, 31, 65} | {8, 31, 66} | {8, 32, 33} | {8, 32, 34} | {8, 32, 35} | {8, 32, 36} | {8, 32, 37} |
| {8, 32, 38} | {8, 32, 39} | {8, 32, 40} | {8, 32, 41} | {8, 32, 42} | {8, 32, 43} | {8, 32, 44} | {8, 32, 45} | {8, 32, 46} | {8, 32, 47} |
| {8, 32, 48} | {8, 32, 49} | {8, 32, 50} | {8, 32, 51} | {8, 32, 52} | {8, 32, 53} | {8, 32, 54} | {8, 32, 55} | {8, 32, 56} | {8, 32, 57} |
| {8, 32, 58} | {8, 32, 59} | {8, 32, 60} | {8, 32, 61} | {8, 32, 62} | {8, 32, 63} | {8, 32, 64} | {8, 32, 65} | {8, 32, 66} | {8, 33, 34} |
| {8, 33, 35} | {8, 33, 36} | {8, 33, 37} | {8, 33, 38} | {8, 33, 39} | {8, 33, 40} | {8, 33, 41} | {8, 33, 42} | {8, 33, 43} | {8, 33, 44} |
| {8, 33, 45} | {8, 33, 46} | {8, 33, 47} | {8, 33, 48} | {8, 33, 49} | {8, 33, 50} | {8, 33, 51} | {8, 33, 52} | {8, 33, 53} | {8, 33, 54} |
| {8, 33, 55} | {8, 33, 56} | {8, 33, 57} | {8, 33, 58} | {8, 33, 59} | {8, 33, 60} | {8, 33, 61} | {8, 33, 62} | {8, 33, 63} | {8, 33, 64} |
| {8, 33, 65} | {8, 33, 66} | {8, 34, 35} | {8, 34, 36} | {8, 34, 37} | {8, 34, 38} | {8, 34, 39} | {8, 34, 40} | {8, 34, 41} | {8, 34, 42} |
| {8, 34, 43} | {8, 34, 44} | {8, 34, 45} | {8, 34, 46} | {8, 34, 47} | {8, 34, 48} | {8, 34, 49} | {8, 34, 50} | {8, 34, 51} | {8, 34, 52} |
| {8, 34, 53} | {8, 34, 54} | {8, 34, 55} | {8, 34, 56} | {8, 34, 57} | {8, 34, 58} | {8, 34, 59} | {8, 34, 60} | {8, 34, 61} | {8, 34, 62} |
| {8, 34, 63} | {8, 34, 64} | {8, 34, 65} | {8, 34, 66} | {8, 35, 36} | {8, 35, 37} | {8, 35, 38} | {8, 35, 39} | {8, 35, 40} | {8, 35, 41} |

TABLE 3A-continued

{8, 35, 42} {8, 35, 43} {8, 35, 44} {8, 35, 45} {8, 35, 46} {8, 35, 47} {8, 35, 48} {8, 35, 49} {8, 35, 50} {8, 35, 51}
{8, 35, 52} {8, 35, 53} {8, 35, 54} {8, 35, 55} {8, 35, 56} {8, 35, 57} {8, 35, 58} {8, 35, 59} {8, 35, 60} {8, 35, 61}
{8, 35, 62} {8, 35, 63} {8, 35, 64} {8, 35, 65} {8, 35, 66} {8, 36, 37} {8, 36, 38} {8, 36, 39} {8, 36, 40} {8, 36, 41}
{8, 36, 42} {8, 36, 43} {8, 36, 44} {8, 36, 45} {8, 36, 46} {8, 36, 47} {8, 36, 48} {8, 36, 49} {8, 36, 50} {8, 36, 51}
{8, 36, 52} {8, 36, 53} {8, 36, 54} {8, 36, 55} {8, 36, 56} {8, 36, 57} {8, 36, 58} {8, 36, 59} {8, 36, 60} {8, 36, 61}
{8, 36, 62} {8, 36, 63} {8, 36, 64} {8, 36, 65} {8, 36, 66} {8, 37, 38} {8, 37, 39} {8, 37, 40} {8, 37, 41} {8, 37, 42}
{8, 37, 43} {8, 37, 44} {8, 37, 45} {8, 37, 46} {8, 37, 47} {8, 37, 48} {8, 37, 49} {8, 37, 50} {8, 37, 51} {8, 37, 52}
{8, 37, 53} {8, 37, 54} {8, 37, 55} {8, 37, 56} {8, 37, 57} {8, 37, 58} {8, 37, 59} {8, 37, 60} {8, 37, 61} {8, 37, 62}
{8, 37, 63} {8, 37, 64} {8, 37, 65} {8, 37, 66} {8, 38, 39} {8, 38, 40} {8, 38, 41} {8, 38, 42} {8, 38, 43} {8, 38, 44}
{8, 38, 45} {8, 38, 46} {8, 38, 47} {8, 38, 48} {8, 38, 49} {8, 38, 50} {8, 38, 51} {8, 38, 52} {8, 38, 53} {8, 38, 54}
{8, 38, 55} {8, 38, 56} {8, 38, 57} {8, 38, 58} {8, 38, 59} {8, 38, 60} {8, 38, 61} {8, 38, 62} {8, 38, 63} {8, 38, 64}
{8, 38, 65} {8, 38, 66} {8, 39, 40} {8, 39, 41} {8, 39, 42} {8, 39, 43} {8, 39, 44} {8, 39, 45} {8, 39, 46} {8, 39, 47}
{8, 39, 48} {8, 39, 49} {8, 39, 50} {8, 39, 51} {8, 39, 52} {8, 39, 53} {8, 39, 54} {8, 39, 55} {8, 39, 56} {8, 39, 57}
{8, 39, 58} {8, 39, 59} {8, 39, 60} {8, 39, 61} {8, 39, 62} {8, 39, 63} {8, 39, 64} {8, 39, 65} {8, 39, 66} {8, 40, 41}
{8, 40, 42} {8, 40, 43} {8, 40, 44} {8, 40, 45} {8, 40, 46} {8, 40, 47} {8, 40, 48} {8, 40, 49} {8, 40, 50} {8, 40, 51}
{8, 40, 52} {8, 40, 53} {8, 40, 54} {8, 40, 55} {8, 40, 56} {8, 40, 57} {8, 40, 58} {8, 40, 59} {8, 40, 60} {8, 40, 61}
{8, 40, 62} {8, 40, 63} {8, 40, 64} {8, 40, 65} {8, 40, 66} {8, 41, 42} {8, 41, 43} {8, 41, 44} {8, 41, 45} {8, 41, 46}
{8, 41, 47} {8, 41, 48} {8, 41, 49} {8, 41, 50} {8, 41, 51} {8, 41, 52} {8, 41, 53} {8, 41, 54} {8, 41, 55} {8, 41, 56}
{8, 41, 57} {8, 41, 58} {8, 41, 59} {8, 41, 60} {8, 41, 61} {8, 41, 62} {8, 41, 63} {8, 41, 64} {8, 41, 65} {8, 41, 66}
{8, 42, 43} {8, 42, 44} {8, 42, 45} {8, 42, 46} {8, 42, 47} {8, 42, 48} {8, 42, 49} {8, 42, 50} {8, 42, 51} {8, 42, 52}
{8, 42, 53} {8, 42, 54} {8, 42, 55} {8, 42, 56} {8, 42, 57} {8, 42, 58} {8, 42, 59} {8, 42, 60} {8, 42, 61} {8, 42, 62}
{8, 42, 63} {8, 42, 64} {8, 42, 65} {8, 42, 66} {8, 43, 44} {8, 43, 45} {8, 43, 46} {8, 43, 47} {8, 43, 48} {8, 43, 49}
{8, 43, 50} {8, 43, 51} {8, 43, 52} {8, 43, 53} {8, 43, 54} {8, 43, 55} {8, 43, 56} {8, 43, 57} {8, 43, 58} {8, 43, 59}
{8, 43, 60} {8, 43, 61} {8, 43, 62} {8, 43, 63} {8, 43, 64} {8, 43, 65} {8, 43, 66} {8, 44, 45} {8, 44, 46} {8, 44, 47}
{8, 44, 48} {8, 44, 49} {8, 44, 50} {8, 44, 51} {8, 44, 52} {8, 44, 53} {8, 44, 54} {8, 44, 55} {8, 44, 56} {8, 44, 57}
{8, 44, 58} {8, 44, 59} {8, 44, 60} {8, 44, 61} {8, 44, 62} {8, 44, 63} {8, 44, 64} {8, 44, 65} {8, 44, 66} {8, 45, 46}
{8, 45, 47} {8, 45, 48} {8, 45, 49} {8, 45, 50} {8, 45, 51} {8, 45, 52} {8, 45, 53} {8, 45, 54} {8, 45, 55} {8, 45, 56}
{8, 45, 57} {8, 45, 58} {8, 45, 59} {8, 45, 60} {8, 45, 61} {8, 45, 62} {8, 45, 63} {8, 45, 64} {8, 45, 65} {8, 45, 66}
{8, 46, 47} {8, 46, 48} {8, 46, 49} {8, 46, 50} {8, 46, 51} {8, 46, 52} {8, 46, 53} {8, 46, 54} {8, 46, 55} {8, 46, 56}
{8, 46, 57} {8, 46, 58} {8, 46, 59} {8, 46, 60} {8, 46, 61} {8, 46, 62} {8, 46, 63} {8, 46, 64} {8, 46, 65} {8, 46, 66}
{8, 47, 48} {8, 47, 49} {8, 47, 50} {8, 47, 51} {8, 47, 52} {8, 47, 53} {8, 47, 54} {8, 47, 55} {8, 47, 56} {8, 47, 57}
{8, 47, 58} {8, 47, 59} {8, 47, 60} {8, 47, 61} {8, 47, 62} {8, 47, 63} {8, 47, 64} {8, 47, 65} {8, 47, 66} {8, 48, 49}
{8, 48, 50} {8, 48, 51} {8, 48, 52} {8, 48, 53} {8, 48, 54} {8, 48, 55} {8, 48, 56} {8, 48, 57} {8, 48, 58} {8, 48, 59}
{8, 48, 60} {8, 48, 61} {8, 48, 62} {8, 48, 63} {8, 48, 64} {8, 48, 65} {8, 48, 66} {8, 49, 50} {8, 49, 51} {8, 49, 52}
{8, 49, 53} {8, 49, 54} {8, 49, 55} {8, 49, 56} {8, 49, 57} {8, 49, 58} {8, 49, 59} {8, 49, 60} {8, 49, 61} {8, 49, 62}
{8, 49, 63} {8, 49, 64} {8, 49, 65} {8, 49, 66} {8, 50, 51} {8, 50, 52} {8, 50, 53} {8, 50, 54} {8, 50, 55} {8, 50, 56}
{8, 50, 57} {8, 50, 58} {8, 50, 59} {8, 50, 60} {8, 50, 61} {8, 50, 62} {8, 50, 63} {8, 50, 64} {8, 50, 65} {8, 50, 66}
{8, 51, 52} {8, 51, 53} {8, 51, 54} {8, 51, 55} {8, 51, 56} {8, 51, 57} {8, 51, 58} {8, 51, 59} {8, 51, 60} {8, 51, 61}
{8, 51, 62} {8, 51, 63} {8, 51, 64} {8, 51, 65} {8, 51, 66} {8, 52, 53} {8, 52, 54} {8, 52, 55} {8, 52, 56} {8, 52, 57}
{8, 52, 58} {8, 52, 59} {8, 52, 60} {8, 52, 61} {8, 52, 62} {8, 52, 63} {8, 52, 64} {8, 52, 65} {8, 52, 66} {8, 53, 54}
{8, 53, 55} {8, 53, 56} {8, 53, 57} {8, 53, 58} {8, 53, 59} {8, 53, 60} {8, 53, 61} {8, 53, 62} {8, 53, 63} {8, 53, 64}
{8, 53, 65} {8, 53, 66} {8, 54, 55} {8, 54, 56} {8, 54, 57} {8, 54, 58} {8, 54, 59} {8, 54, 60} {8, 54, 61} {8, 54, 62}
{8, 54, 63} {8, 54, 64} {8, 54, 65} {8, 54, 66} {8, 55, 56} {8, 55, 57} {8, 55, 58} {8, 55, 59} {8, 55, 60} {8, 55, 61}
{8, 55, 62} {8, 55, 63} {8, 55, 64} {8, 55, 65} {8, 55, 66} {8, 56, 57} {8, 56, 58} {8, 56, 59} {8, 56, 60} {8, 56, 61}
{8, 56, 62} {8, 56, 63} {8, 56, 64} {8, 56, 65} {8, 56, 66} {8, 57, 58} {8, 57, 59} {8, 57, 60} {8, 57, 61} {8, 57, 62}
{8, 57, 63} {8, 57, 64} {8, 57, 65} {8, 57, 66} {8, 58, 59} {8, 58, 60} {8, 58, 61} {8, 58, 62} {8, 58, 63} {8, 58, 64}
{8, 58, 65} {8, 58, 66} {8, 59, 60} {8, 59, 61} {8, 59, 62} {8, 59, 63} {8, 59, 64} {8, 59, 65} {8, 59, 66} {8, 60, 61}
{8, 60, 62} {8, 60, 63} {8, 60, 64} {8, 60, 65} {8, 60, 66} {8, 61, 62} {8, 61, 63} {8, 61, 64} {8, 61, 65} {8, 61, 66}
{8, 62, 63} {8, 62, 64} {8, 62, 65} {8, 62, 66} {8, 63, 64} {8, 63, 65} {8, 63, 66} {8, 64, 65} {8, 64, 66} {8, 65, 66}
{9, 10, 11} {9, 10, 12} {9, 10, 13} {9, 10, 14} {9, 10, 15} {9, 10, 16} {9, 10, 17} {9, 10, 18} {9, 10, 19} {9, 10, 20}
{9, 10, 21} {9, 10, 22} {9, 10, 23} {9, 10, 24} {9, 10, 25} {9, 10, 26} {9, 10, 27} {9, 10, 28} {9, 10, 29} {9, 10, 30}
{9, 10, 31} {9, 10, 32} {9, 10, 33} {9, 10, 34} {9, 10, 35} {9, 10, 36} {9, 10, 37} {9, 10, 38} {9, 10, 39} {9, 10, 40}
{9, 10, 41} {9, 10, 42} {9, 10, 43} {9, 10, 44} {9, 10, 45} {9, 10, 46} {9, 10, 47} {9, 10, 48} {9, 10, 49} {9, 10, 50}
{9, 10, 51} {9, 10, 52} {9, 10, 53} {9, 10, 54} {9, 10, 55} {9, 10, 56} {9, 10, 57} {9, 10, 58} {9, 10, 59} {9, 10, 60}
{9, 10, 61} {9, 10, 62} {9, 10, 63} {9, 10, 64} {9, 10, 65} {9, 10, 66} {9, 11, 12} {9, 11, 13} {9, 11, 14} {9, 11, 15}
{9, 11, 16} {9, 11, 17} {9, 11, 18} {9, 11, 19} {9, 11, 20} {9, 11, 21} {9, 11, 22} {9, 11, 23} {9, 11, 24} {9, 11, 25}
{9, 11, 26} {9, 11, 27} {9, 11, 28} {9, 11, 29} {9, 11, 30} {9, 11, 31} {9, 11, 32} {9, 11, 33} {9, 11, 34} {9, 11, 35}
{9, 11, 36} {9, 11, 37} {9, 11, 38} {9, 11, 39} {9, 11, 40} {9, 11, 41} {9, 11, 42} {9, 11, 43} {9, 11, 44} {9, 11, 45}
{9, 11, 46} {9, 11, 47} {9, 11, 48} {9, 11, 49} {9, 11, 50} {9, 11, 51} {9, 11, 52} {9, 11, 53} {9, 11, 54} {9, 11, 55}
{9, 11, 56} {9, 11, 57} {9, 11, 58} {9, 11, 59} {9, 11, 60} {9, 11, 61} {9, 11, 62} {9, 11, 63} {9, 11, 64} {9, 11, 65}
{9, 11, 66} {9, 12, 13} {9, 12, 14} {9, 12, 15} {9, 12, 16} {9, 12, 17} {9, 12, 18} {9, 12, 19} {9, 12, 20} {9, 12, 21}
{9, 12, 22} {9, 12, 23} {9, 12, 24} {9, 12, 25} {9, 12, 26} {9, 12, 27} {9, 12, 28} {9, 12, 29} {9, 12, 30} {9, 12, 31}
{9, 12, 32} {9, 12, 33} {9, 12, 34} {9, 12, 35} {9, 12, 36} {9, 12, 37} {9, 12, 38} {9, 12, 39} {9, 12, 40} {9, 12, 41}
{9, 12, 42} {9, 12, 43} {9, 12, 44} {9, 12, 45} {9, 12, 46} {9, 12, 47} {9, 12, 48} {9, 12, 49} {9, 12, 50} {9, 12, 51}
{9, 12, 52} {9, 12, 53} {9, 12, 54} {9, 12, 55} {9, 12, 56} {9, 12, 57} {9, 12, 58} {9, 12, 59} {9, 12, 60} {9, 12, 61}
{9, 12, 62} {9, 12, 63} {9, 12, 64} {9, 12, 65} {9, 12, 66} {9, 13, 14} {9, 13, 15} {9, 13, 16} {9, 13, 17} {9, 13, 18}
{9, 13, 19} {9, 13, 20} {9, 13, 21} {9, 13, 22} {9, 13, 23} {9, 13, 24} {9, 13, 25} {9, 13, 26} {9, 13, 27} {9, 13, 28}
{9, 13, 29} {9, 13, 30} {9, 13, 31} {9, 13, 32} {9, 13, 33} {9, 13, 34} {9, 13, 35} {9, 13, 36} {9, 13, 37} {9, 13, 38}
{9, 13, 39} {9, 13, 40} {9, 13, 41} {9, 13, 42} {9, 13, 43} {9, 13, 44} {9, 13, 45} {9, 13, 46} {9, 13, 47} {9, 13, 48}
{9, 13, 49} {9, 13, 50} {9, 13, 51} {9, 13, 52} {9, 13, 53} {9, 13, 54} {9, 13, 55} {9, 13, 56} {9, 13, 57} {9, 13, 58}
{9, 13, 59} {9, 13, 60} {9, 13, 61} {9, 13, 62} {9, 13, 63} {9, 13, 64} {9, 13, 65} {9, 13, 66} {9, 14, 15} {9, 14, 16}
{9, 14, 17} {9, 14, 18} {9, 14, 19} {9, 14, 20} {9, 14, 21} {9, 14, 22} {9, 14, 23} {9, 14, 24} {9, 14, 25} {9, 14, 26}
{9, 14, 27} {9, 14, 28} {9, 14, 29} {9, 14, 30} {9, 14, 31} {9, 14, 32} {9, 14, 33} {9, 14, 34} {9, 14, 35} {9, 14, 36}
{9, 14, 37} {9, 14, 38} {9, 14, 39} {9, 14, 40} {9, 14, 41} {9, 14, 42} {9, 14, 43} {9, 14, 44} {9, 14, 45} {9, 14, 46}
{9, 14, 47} {9, 14, 48} {9, 14, 49} {9, 14, 50} {9, 14, 51} {9, 14, 52} {9, 14, 53} {9, 14, 54} {9, 14, 55} {9, 14, 56}
{9, 14, 57} {9, 14, 58} {9, 14, 59} {9, 14, 60} {9, 14, 61} {9, 14, 62} {9, 14, 63} {9, 14, 64} {9, 14, 65} {9, 14, 66}
{9, 15, 16} {9, 15, 17} {9, 15, 18} {9, 15, 19} {9, 15, 20} {9, 15, 21} {9, 15, 22} {9, 15, 23} {9, 15, 24} {9, 15, 25}
{9, 15, 26} {9, 15, 27} {9, 15, 28} {9, 15, 29} {9, 15, 30} {9, 15, 31} {9, 15, 32} {9, 15, 33} {9, 15, 34} {9, 15, 35}
{9, 15, 36} {9, 15, 37} {9, 15, 38} {9, 15, 39} {9, 15, 40} {9, 15, 41} {9, 15, 42} {9, 15, 43} {9, 15, 44} {9, 15, 45}
{9, 15, 46} {9, 15, 47} {9, 15, 48} {9, 15, 49} {9, 15, 50} {9, 15, 51} {9, 15, 52} {9, 15, 53} {9, 15, 54} {9, 15, 55}

TABLE 3A-continued

| | | | | | | | | |
|---|---|---|---|---|---|---|---|---|
| {9, 15, 56} | {9, 15, 57} | {9, 15, 58} | {9, 15, 59} | {9, 15, 60} | {9, 15, 61} | {9, 15, 62} | {9, 15, 63} | {9, 15, 64} | {9, 15, 65} |
| {9, 15, 66} | {9, 16, 17} | {9, 16, 18} | {9, 16, 19} | {9, 16, 20} | {9, 16, 21} | {9, 16, 22} | {9, 16, 23} | {9, 16, 24} | {9, 16, 25} |
| {9, 16, 26} | {9, 16, 27} | {9, 16, 28} | {9, 16, 29} | {9, 16, 30} | {9, 16, 31} | {9, 16, 32} | {9, 16, 33} | {9, 16, 34} | {9, 16, 35} |
| {9, 16, 36} | {9, 16, 37} | {9, 16, 38} | {9, 16, 39} | {9, 16, 40} | {9, 16, 41} | {9, 16, 42} | {9, 16, 43} | {9, 16, 44} | {9, 16, 45} |
| {9, 16, 46} | {9, 16, 47} | {9, 16, 48} | {9, 16, 49} | {9, 16, 50} | {9, 16, 51} | {9, 16, 52} | {9, 16, 53} | {9, 16, 54} | {9, 16, 55} |
| {9, 16, 56} | {9, 16, 57} | {9, 16, 58} | {9, 16, 59} | {9, 16, 60} | {9, 16, 61} | {9, 16, 62} | {9, 16, 63} | {9, 16, 64} | {9, 16, 65} |
| {9, 16, 66} | {9, 17, 18} | {9, 17, 19} | {9, 17, 20} | {9, 17, 21} | {9, 17, 22} | {9, 17, 23} | {9, 17, 24} | {9, 17, 25} | {9, 17, 26} |
| {9, 17, 27} | {9, 17, 28} | {9, 17, 29} | {9, 17, 30} | {9, 17, 31} | {9, 17, 32} | {9, 17, 33} | {9, 17, 34} | {9, 17, 35} | {9, 17, 36} |
| {9, 17, 37} | {9, 17, 38} | {9, 17, 39} | {9, 17, 40} | {9, 17, 41} | {9, 17, 42} | {9, 17, 43} | {9, 17, 44} | {9, 17, 45} | {9, 17, 46} |
| {9, 17, 47} | {9, 17, 48} | {9, 17, 49} | {9, 17, 50} | {9, 17, 51} | {9, 17, 52} | {9, 17, 53} | {9, 17, 54} | {9, 17, 55} | {9, 17, 56} |
| {9, 17, 57} | {9, 17, 58} | {9, 17, 59} | {9, 17, 60} | {9, 17, 61} | {9, 17, 62} | {9, 17, 63} | {9, 17, 64} | {9, 17, 65} | {9, 17, 66} |
| {9, 18, 19} | {9, 18, 20} | {9, 18, 21} | {9, 18, 22} | {9, 18, 23} | {9, 18, 24} | {9, 18, 25} | {9, 18, 26} | {9, 18, 27} | {9, 18, 28} |
| {9, 18, 29} | {9, 18, 30} | {9, 18, 31} | {9, 18, 32} | {9, 18, 33} | {9, 18, 34} | {9, 18, 35} | {9, 18, 36} | {9, 18, 37} | {9, 18, 38} |
| {9, 18, 39} | {9, 18, 40} | {9, 18, 41} | {9, 18, 42} | {9, 18, 43} | {9, 18, 44} | {9, 18, 45} | {9, 18, 46} | {9, 18, 47} | {9, 18, 48} |
| {9, 18, 49} | {9, 18, 50} | {9, 18, 51} | {9, 18, 52} | {9, 18, 53} | {9, 18, 54} | {9, 18, 55} | {9, 18, 56} | {9, 18, 57} | {9, 18, 58} |
| {9, 18, 59} | {9, 18, 60} | {9, 18, 61} | {9, 18, 62} | {9, 18, 63} | {9, 18, 64} | {9, 18, 65} | {9, 18, 66} | {9, 19, 20} | {9, 19, 21} |
| {9, 19, 22} | {9, 19, 23} | {9, 19, 24} | {9, 19, 25} | {9, 19, 26} | {9, 19, 27} | {9, 19, 28} | {9, 19, 29} | {9, 19, 30} | {9, 19, 31} |
| {9, 19, 32} | {9, 19, 33} | {9, 19, 34} | {9, 19, 35} | {9, 19, 36} | {9, 19, 37} | {9, 19, 38} | {9, 19, 39} | {9, 19, 40} | {9, 19, 41} |
| {9, 19, 42} | {9, 19, 43} | {9, 19, 44} | {9, 19, 45} | {9, 19, 46} | {9, 19, 47} | {9, 19, 48} | {9, 19, 49} | {9, 19, 50} | {9, 19, 51} |
| {9, 19, 52} | {9, 19, 53} | {9, 19, 54} | {9, 19, 55} | {9, 19, 56} | {9, 19, 57} | {9, 19, 58} | {9, 19, 59} | {9, 19, 60} | {9, 19, 61} |
| {9, 19, 62} | {9, 19, 63} | {9, 19, 64} | {9, 19, 65} | {9, 19, 66} | {9, 20, 21} | {9, 20, 22} | {9, 20, 23} | {9, 20, 24} | {9, 20, 25} |
| {9, 20, 26} | {9, 20, 27} | {9, 20, 28} | {9, 20, 29} | {9, 20, 30} | {9, 20, 31} | {9, 20, 32} | {9, 20, 33} | {9, 20, 34} | {9, 20, 35} |
| {9, 20, 36} | {9, 20, 37} | {9, 20, 38} | {9, 20, 39} | {9, 20, 40} | {9, 20, 41} | {9, 20, 42} | {9, 20, 43} | {9, 20, 44} | {9, 20, 45} |
| {9, 20, 46} | {9, 20, 47} | {9, 20, 48} | {9, 20, 49} | {9, 20, 50} | {9, 20, 51} | {9, 20, 52} | {9, 20, 53} | {9, 20, 54} | {9, 20, 55} |
| {9, 20, 56} | {9, 20, 57} | {9, 20, 58} | {9, 20, 59} | {9, 20, 60} | {9, 20, 61} | {9, 20, 62} | {9, 20, 63} | {9, 20, 64} | {9, 20, 65} |
| {9, 20, 66} | {9, 21, 22} | {9, 21, 23} | {9, 21, 24} | {9, 21, 25} | {9, 21, 26} | {9, 21, 27} | {9, 21, 28} | {9, 21, 29} | {9, 21, 30} |
| {9, 21, 31} | {9, 21, 32} | {9, 21, 33} | {9, 21, 34} | {9, 21, 35} | {9, 21, 36} | {9, 21, 37} | {9, 21, 38} | {9, 21, 39} | {9, 21, 40} |
| {9, 21, 41} | {9, 21, 42} | {9, 21, 43} | {9, 21, 44} | {9, 21, 45} | {9, 21, 46} | {9, 21, 47} | {9, 21, 48} | {9, 21, 49} | {9, 21, 50} |
| {9, 21, 51} | {9, 21, 52} | {9, 21, 53} | {9, 21, 54} | {9, 21, 55} | {9, 21, 56} | {9, 21, 57} | {9, 21, 58} | {9, 21, 59} | {9, 21, 60} |
| {9, 21, 61} | {9, 21, 62} | {9, 21, 63} | {9, 21, 64} | {9, 21, 65} | {9, 21, 66} | {9, 22, 23} | {9, 22, 24} | {9, 22, 25} | {9, 22, 26} |
| {9, 22, 27} | {9, 22, 28} | {9, 22, 29} | {9, 22, 30} | {9, 22, 31} | {9, 22, 32} | {9, 22, 33} | {9, 22, 34} | {9, 22, 35} | {9, 22, 36} |
| {9, 22, 37} | {9, 22, 38} | {9, 22, 39} | {9, 22, 40} | {9, 22, 41} | {9, 22, 42} | {9, 22, 43} | {9, 22, 44} | {9, 22, 45} | {9, 22, 46} |
| {9, 22, 47} | {9, 22, 48} | {9, 22, 49} | {9, 22, 50} | {9, 22, 51} | {9, 22, 52} | {9, 22, 53} | {9, 22, 54} | {9, 22, 55} | {9, 22, 56} |
| {9, 22, 57} | {9, 22, 58} | {9, 22, 59} | {9, 22, 60} | {9, 22, 61} | {9, 22, 62} | {9, 22, 63} | {9, 22, 64} | {9, 22, 65} | {9, 22, 66} |
| {9, 23, 24} | {9, 23, 25} | {9, 23, 26} | {9, 23, 27} | {9, 23, 28} | {9, 23, 29} | {9, 23, 30} | {9, 23, 31} | {9, 23, 32} | {9, 23, 33} |
| {9, 23, 34} | {9, 23, 35} | {9, 23, 36} | {9, 23, 37} | {9, 23, 38} | {9, 23, 39} | {9, 23, 40} | {9, 23, 41} | {9, 23, 42} | {9, 23, 43} |
| {9, 23, 44} | {9, 23, 45} | {9, 23, 46} | {9, 23, 47} | {9, 23, 48} | {9, 23, 49} | {9, 23, 50} | {9, 23, 51} | {9, 23, 52} | {9, 23, 53} |
| {9, 23, 54} | {9, 23, 55} | {9, 23, 56} | {9, 23, 57} | {9, 23, 58} | {9, 23, 59} | {9, 23, 60} | {9, 23, 61} | {9, 23, 62} | {9, 23, 63} |
| {9, 23, 64} | {9, 23, 65} | {9, 23, 66} | {9, 24, 25} | {9, 24, 26} | {9, 24, 27} | {9, 24, 28} | {9, 24, 29} | {9, 24, 30} | {9, 24, 31} |
| {9, 24, 32} | {9, 24, 33} | {9, 24, 34} | {9, 24, 35} | {9, 24, 36} | {9, 24, 37} | {9, 24, 38} | {9, 24, 39} | {9, 24, 40} | {9, 24, 41} |
| {9, 24, 42} | {9, 24, 43} | {9, 24, 44} | {9, 24, 45} | {9, 24, 46} | {9, 24, 47} | {9, 24, 48} | {9, 24, 49} | {9, 24, 50} | {9, 24, 51} |
| {9, 24, 52} | {9, 24, 53} | {9, 24, 54} | {9, 24, 55} | {9, 24, 56} | {9, 24, 57} | {9, 24, 58} | {9, 24, 59} | {9, 24, 60} | {9, 24, 61} |
| {9, 24, 62} | {9, 24, 63} | {9, 24, 64} | {9, 24, 65} | {9, 24, 66} | {9, 25, 26} | {9, 25, 27} | {9, 25, 28} | {9, 25, 29} | {9, 25, 30} |
| {9, 25, 31} | {9, 25, 32} | {9, 25, 33} | {9, 25, 34} | {9, 25, 35} | {9, 25, 36} | {9, 25, 37} | {9, 25, 38} | {9, 25, 39} | {9, 25, 40} |
| {9, 25, 41} | {9, 25, 42} | {9, 25, 43} | {9, 25, 44} | {9, 25, 45} | {9, 25, 46} | {9, 25, 47} | {9, 25, 48} | {9, 25, 49} | {9, 25, 50} |
| {9, 25, 51} | {9, 25, 52} | {9, 25, 53} | {9, 25, 54} | {9, 25, 55} | {9, 25, 56} | {9, 25, 57} | {9, 25, 58} | {9, 25, 59} | {9, 25, 60} |
| {9, 25, 61} | {9, 25, 62} | {9, 25, 63} | {9, 25, 64} | {9, 25, 65} | {9, 25, 66} | {9, 26, 27} | {9, 26, 28} | {9, 26, 29} | {9, 26, 30} |
| {9, 26, 31} | {9, 26, 32} | {9, 26, 33} | {9, 26, 34} | {9, 26, 35} | {9, 26, 36} | {9, 26, 37} | {9, 26, 38} | {9, 26, 39} | {9, 26, 40} |
| {9, 26, 41} | {9, 26, 42} | {9, 26, 43} | {9, 26, 44} | {9, 26, 45} | {9, 26, 46} | {9, 26, 47} | {9, 26, 48} | {9, 26, 49} | {9, 26, 50} |
| {9, 26, 51} | {9, 26, 52} | {9, 26, 53} | {9, 26, 54} | {9, 26, 55} | {9, 26, 56} | {9, 26, 57} | {9, 26, 58} | {9, 26, 59} | {9, 26, 60} |
| {9, 26, 61} | {9, 26, 62} | {9, 26, 63} | {9, 26, 64} | {9, 26, 65} | {9, 26, 66} | {9, 27, 28} | {9, 27, 29} | {9, 27, 30} | {9, 27, 31} |
| {9, 27, 32} | {9, 27, 33} | {9, 27, 34} | {9, 27, 35} | {9, 27, 36} | {9, 27, 37} | {9, 27, 38} | {9, 27, 39} | {9, 27, 40} | {9, 27, 41} |
| {9, 27, 42} | {9, 27, 43} | {9, 27, 44} | {9, 27, 45} | {9, 27, 46} | {9, 27, 47} | {9, 27, 48} | {9, 27, 49} | {9, 27, 50} | {9, 27, 51} |
| {9, 27, 52} | {9, 27, 53} | {9, 27, 54} | {9, 27, 55} | {9, 27, 56} | {9, 27, 57} | {9, 27, 58} | {9, 27, 59} | {9, 27, 60} | {9, 27, 61} |
| {9, 27, 62} | {9, 27, 63} | {9, 27, 64} | {9, 27, 65} | {9, 27, 66} | {9, 28, 29} | {9, 28, 30} | {9, 28, 31} | {9, 28, 32} | {9, 28, 33} |
| {9, 28, 34} | {9, 28, 35} | {9, 28, 36} | {9, 28, 37} | {9, 28, 38} | {9, 28, 39} | {9, 28, 40} | {9, 28, 41} | {9, 28, 42} | {9, 28, 43} |
| {9, 28, 44} | {9, 28, 45} | {9, 28, 46} | {9, 28, 47} | {9, 28, 48} | {9, 28, 49} | {9, 28, 50} | {9, 28, 51} | {9, 28, 52} | {9, 28, 53} |
| {9, 28, 54} | {9, 28, 55} | {9, 28, 56} | {9, 28, 57} | {9, 28, 58} | {9, 28, 59} | {9, 28, 60} | {9, 28, 61} | {9, 28, 62} | {9, 28, 63} |
| {9, 28, 64} | {9, 28, 65} | {9, 28, 66} | {9, 29, 30} | {9, 29, 31} | {9, 29, 32} | {9, 29, 33} | {9, 29, 34} | {9, 29, 35} | {9, 29, 36} |
| {9, 29, 37} | {9, 29, 38} | {9, 29, 39} | {9, 29, 40} | {9, 29, 41} | {9, 29, 42} | {9, 29, 43} | {9, 29, 44} | {9, 29, 45} | {9, 29, 46} |
| {9, 29, 47} | {9, 29, 48} | {9, 29, 49} | {9, 29, 50} | {9, 29, 51} | {9, 29, 52} | {9, 29, 53} | {9, 29, 54} | {9, 29, 55} | {9, 29, 56} |
| {9, 29, 57} | {9, 29, 58} | {9, 29, 59} | {9, 29, 60} | {9, 29, 61} | {9, 29, 62} | {9, 29, 63} | {9, 29, 64} | {9, 29, 65} | {9, 29, 66} |
| {9, 30, 31} | {9, 30, 32} | {9, 30, 33} | {9, 30, 34} | {9, 30, 35} | {9, 30, 36} | {9, 30, 37} | {9, 30, 38} | {9, 30, 39} | {9, 30, 40} |
| {9, 30, 41} | {9, 30, 42} | {9, 30, 43} | {9, 30, 44} | {9, 30, 45} | {9, 30, 46} | {9, 30, 47} | {9, 30, 48} | {9, 30, 49} | {9, 30, 50} |
| {9, 30, 51} | {9, 30, 52} | {9, 30, 53} | {9, 30, 54} | {9, 30, 55} | {9, 30, 56} | {9, 30, 57} | {9, 30, 58} | {9, 30, 59} | {9, 30, 60} |
| {9, 30, 61} | {9, 30, 62} | {9, 30, 63} | {9, 30, 64} | {9, 30, 65} | {9, 30, 66} | {9, 31, 32} | {9, 31, 33} | {9, 31, 34} | {9, 31, 35} |
| {9, 31, 36} | {9, 31, 37} | {9, 31, 38} | {9, 31, 39} | {9, 31, 40} | {9, 31, 41} | {9, 31, 42} | {9, 31, 43} | {9, 31, 44} | {9, 31, 45} |
| {9, 31, 46} | {9, 31, 47} | {9, 31, 48} | {9, 31, 49} | {9, 31, 50} | {9, 31, 51} | {9, 31, 52} | {9, 31, 53} | {9, 31, 54} | {9, 31, 55} |
| {9, 31, 56} | {9, 31, 57} | {9, 31, 58} | {9, 31, 59} | {9, 31, 60} | {9, 31, 61} | {9, 31, 62} | {9, 31, 63} | {9, 31, 64} | {9, 31, 65} |
| {9, 31, 66} | {9, 32, 33} | {9, 32, 34} | {9, 32, 35} | {9, 32, 36} | {9, 32, 37} | {9, 32, 38} | {9, 32, 39} | {9, 32, 40} | {9, 32, 41} |
| {9, 32, 42} | {9, 32, 43} | {9, 32, 44} | {9, 32, 45} | {9, 32, 46} | {9, 32, 47} | {9, 32, 48} | {9, 32, 49} | {9, 32, 50} | {9, 32, 51} |
| {9, 32, 52} | {9, 32, 53} | {9, 32, 54} | {9, 32, 55} | {9, 32, 56} | {9, 32, 57} | {9, 32, 58} | {9, 32, 59} | {9, 32, 60} | {9, 32, 61} |
| {9, 32, 62} | {9, 32, 63} | {9, 32, 64} | {9, 32, 65} | {9, 32, 66} | {9, 33, 34} | {9, 33, 35} | {9, 33, 36} | {9, 33, 37} | {9, 33, 38} |
| {9, 33, 39} | {9, 33, 40} | {9, 33, 41} | {9, 33, 42} | {9, 33, 43} | {9, 33, 44} | {9, 33, 45} | {9, 33, 46} | {9, 33, 47} | {9, 33, 48} |
| {9, 33, 49} | {9, 33, 50} | {9, 33, 51} | {9, 33, 52} | {9, 33, 53} | {9, 33, 54} | {9, 33, 55} | {9, 33, 56} | {9, 33, 57} | {9, 33, 58} |
| {9, 33, 59} | {9, 33, 60} | {9, 33, 61} | {9, 33, 62} | {9, 33, 63} | {9, 33, 64} | {9, 33, 65} | {9, 33, 66} | {9, 34, 35} | {9, 34, 36} |
| {9, 34, 37} | {9, 34, 38} | {9, 34, 39} | {9, 34, 40} | {9, 34, 41} | {9, 34, 42} | {9, 34, 43} | {9, 34, 44} | {9, 34, 45} | {9, 34, 46} |
| {9, 34, 47} | {9, 34, 48} | {9, 34, 49} | {9, 34, 50} | {9, 34, 51} | {9, 34, 52} | {9, 34, 53} | {9, 34, 54} | {9, 34, 55} | {9, 34, 56} |
| {9, 34, 57} | {9, 34, 58} | {9, 34, 59} | {9, 34, 60} | {9, 34, 61} | {9, 34, 62} | {9, 34, 63} | {9, 34, 64} | {9, 34, 65} | {9, 34, 66} |
| {9, 35, 36} | {9, 35, 37} | {9, 35, 38} | {9, 35, 39} | {9, 35, 40} | {9, 35, 41} | {9, 35, 42} | {9, 35, 43} | {9, 35, 44} | {9, 35, 45} |

TABLE 3A-continued

{9, 35, 46} {9, 35, 47} {9, 35, 48} {9, 35, 49} {9, 35, 50} {9, 35, 51} {9, 35, 52} {9, 35, 53} {9, 35, 54} {9, 35, 55}
{9, 35, 56} {9, 35, 57} {9, 35, 58} {9, 35, 59} {9, 35, 60} {9, 35, 61} {9, 35, 62} {9, 35, 63} {9, 35, 64} {9, 35, 65}
{9, 35, 66} {9, 36, 37} {9, 36, 38} {9, 36, 39} {9, 36, 40} {9, 36, 41} {9, 36, 42} {9, 36, 43} {9, 36, 44} {9, 36, 45}
{9, 36, 46} {9, 36, 47} {9, 36, 48} {9, 36, 49} {9, 36, 50} {9, 36, 51} {9, 36, 52} {9, 36, 53} {9, 36, 54} {9, 36, 55}
{9, 36, 56} {9, 36, 57} {9, 36, 58} {9, 36, 59} {9, 36, 60} {9, 36, 61} {9, 36, 62} {9, 36, 63} {9, 36, 64} {9, 36, 65}
{9, 36, 66} {9, 37, 38} {9, 37, 39} {9, 37, 40} {9, 37, 41} {9, 37, 42} {9, 37, 43} {9, 37, 44} {9, 37, 45} {9, 37, 46}
{9, 37, 47} {9, 37, 48} {9, 37, 49} {9, 37, 50} {9, 37, 51} {9, 37, 52} {9, 37, 53} {9, 37, 54} {9, 37, 55} {9, 37, 56}
{9, 37, 57} {9, 37, 58} {9, 37, 59} {9, 37, 60} {9, 37, 61} {9, 37, 62} {9, 37, 63} {9, 37, 64} {9, 37, 65} {9, 37, 66}
{9, 38, 39} {9, 38, 40} {9, 38, 41} {9, 38, 42} {9, 38, 43} {9, 38, 44} {9, 38, 45} {9, 38, 46} {9, 38, 47} {9, 38, 48}
{9, 38, 49} {9, 38, 50} {9, 38, 51} {9, 38, 52} {9, 38, 53} {9, 38, 54} {9, 38, 55} {9, 38, 56} {9, 38, 57} {9, 38, 58}
{9, 38, 59} {9, 38, 60} {9, 38, 61} {9, 38, 62} {9, 38, 63} {9, 38, 64} {9, 38, 65} {9, 38, 66} {9, 39, 40} {9, 39, 41}
{9, 39, 42} {9, 39, 43} {9, 39, 44} {9, 39, 45} {9, 39, 46} {9, 39, 47} {9, 39, 48} {9, 39, 49} {9, 39, 50} {9, 39, 51}
{9, 39, 52} {9, 39, 53} {9, 39, 54} {9, 39, 55} {9, 39, 56} {9, 39, 57} {9, 39, 58} {9, 39, 59} {9, 39, 60} {9, 39, 61}
{9, 39, 62} {9, 39, 63} {9, 39, 64} {9, 39, 65} {9, 39, 66} {9, 40, 41} {9, 40, 42} {9, 40, 43} {9, 40, 44} {9, 40, 45}
{9, 40, 46} {9, 40, 47} {9, 40, 48} {9, 40, 49} {9, 40, 50} {9, 40, 51} {9, 40, 52} {9, 40, 53} {9, 40, 54} {9, 40, 55}
{9, 40, 56} {9, 40, 57} {9, 40, 58} {9, 40, 59} {9, 40, 60} {9, 40, 61} {9, 40, 62} {9, 40, 63} {9, 40, 64} {9, 40, 65}
{9, 40, 66} {9, 41, 42} {9, 41, 43} {9, 41, 44} {9, 41, 45} {9, 41, 46} {9, 41, 47} {9, 41, 48} {9, 41, 49} {9, 41, 50}
{9, 41, 51} {9, 41, 52} {9, 41, 53} {9, 41, 54} {9, 41, 55} {9, 41, 56} {9, 41, 57} {9, 41, 58} {9, 41, 59} {9, 41, 60}
{9, 41, 61} {9, 41, 62} {9, 41, 63} {9, 41, 64} {9, 41, 65} {9, 41, 66} {9, 42, 43} {9, 42, 44} {9, 42, 45} {9, 42, 46}
{9, 42, 47} {9, 42, 48} {9, 42, 49} {9, 42, 50} {9, 42, 51} {9, 42, 52} {9, 42, 53} {9, 42, 54} {9, 42, 55} {9, 42, 56}
{9, 42, 57} {9, 42, 58} {9, 42, 59} {9, 42, 60} {9, 42, 61} {9, 42, 62} {9, 42, 63} {9, 42, 64} {9, 42, 65} {9, 42, 66}
{9, 43, 44} {9, 43, 45} {9, 43, 46} {9, 43, 47} {9, 43, 48} {9, 43, 49} {9, 43, 50} {9, 43, 51} {9, 43, 52} {9, 43, 53}
{9, 43, 54} {9, 43, 55} {9, 43, 56} {9, 43, 57} {9, 43, 58} {9, 43, 59} {9, 43, 60} {9, 43, 61} {9, 43, 62} {9, 43, 63}
{9, 43, 64} {9, 43, 65} {9, 43, 66} {9, 44, 45} {9, 44, 46} {9, 44, 47} {9, 44, 48} {9, 44, 49} {9, 44, 50} {9, 44, 51}
{9, 44, 52} {9, 44, 53} {9, 44, 54} {9, 44, 55} {9, 44, 56} {9, 44, 57} {9, 44, 58} {9, 44, 59} {9, 44, 60} {9, 44, 61}
{9, 44, 62} {9, 44, 63} {9, 44, 64} {9, 44, 65} {9, 44, 66} {9, 45, 46} {9, 45, 47} {9, 45, 48} {9, 45, 49} {9, 45, 50}
{9, 45, 51} {9, 45, 52} {9, 45, 53} {9, 45, 54} {9, 45, 55} {9, 45, 56} {9, 45, 57} {9, 45, 58} {9, 45, 59} {9, 45, 60}
{9, 45, 61} {9, 45, 62} {9, 45, 63} {9, 45, 64} {9, 45, 65} {9, 45, 66} {9, 46, 47} {9, 46, 48} {9, 46, 49} {9, 46, 50}
{9, 46, 51} {9, 46, 52} {9, 46, 53} {9, 46, 54} {9, 46, 55} {9, 46, 56} {9, 46, 57} {9, 46, 58} {9, 46, 59} {9, 46, 60}
{9, 46, 61} {9, 46, 62} {9, 46, 63} {9, 46, 64} {9, 46, 65} {9, 46, 66} {9, 47, 48} {9, 47, 49} {9, 47, 50} {9, 47, 51}
{9, 47, 52} {9, 47, 53} {9, 47, 54} {9, 47, 55} {9, 47, 56} {9, 47, 57} {9, 47, 58} {9, 47, 59} {9, 47, 60} {9, 47, 61}
{9, 47, 62} {9, 47, 63} {9, 47, 64} {9, 47, 65} {9, 47, 66} {9, 48, 49} {9, 48, 50} {9, 48, 51} {9, 48, 52} {9, 48, 53}
{9, 48, 54} {9, 48, 55} {9, 48, 56} {9, 48, 57} {9, 48, 58} {9, 48, 59} {9, 48, 60} {9, 48, 61} {9, 48, 62} {9, 48, 63}
{9, 48, 64} {9, 48, 65} {9, 48, 66} {9, 49, 50} {9, 49, 51} {9, 49, 52} {9, 49, 53} {9, 49, 54} {9, 49, 55} {9, 49, 56}
{9, 49, 57} {9, 49, 58} {9, 49, 59} {9, 49, 60} {9, 49, 61} {9, 49, 62} {9, 49, 63} {9, 49, 64} {9, 49, 65} {9, 49, 66}
{9, 50, 51} {9, 50, 52} {9, 50, 53} {9, 50, 54} {9, 50, 55} {9, 50, 56} {9, 50, 57} {9, 50, 58} {9, 50, 59} {9, 50, 60}
{9, 50, 61} {9, 50, 62} {9, 50, 63} {9, 50, 64} {9, 50, 65} {9, 50, 66} {9, 51, 52} {9, 51, 53} {9, 51, 54} {9, 51, 55}
{9, 51, 56} {9, 51, 57} {9, 51, 58} {9, 51, 59} {9, 51, 60} {9, 51, 61} {9, 51, 62} {9, 51, 63} {9, 51, 64} {9, 51, 65}
{9, 51, 66} {9, 52, 53} {9, 52, 54} {9, 52, 55} {9, 52, 56} {9, 52, 57} {9, 52, 58} {9, 52, 59} {9, 52, 60} {9, 52, 61}
{9, 52, 62} {9, 52, 63} {9, 52, 64} {9, 52, 65} {9, 52, 66} {9, 53, 54} {9, 53, 55} {9, 53, 56} {9, 53, 57} {9, 53, 58}
{9, 53, 59} {9, 53, 60} {9, 53, 61} {9, 53, 62} {9, 53, 63} {9, 53, 64} {9, 53, 65} {9, 53, 66} {9, 54, 55} {9, 54, 56}
{9, 54, 57} {9, 54, 58} {9, 54, 59} {9, 54, 60} {9, 54, 61} {9, 54, 62} {9, 54, 63} {9, 54, 64} {9, 54, 65} {9, 54, 66}
{9, 55, 56} {9, 55, 57} {9, 55, 58} {9, 55, 59} {9, 55, 60} {9, 55, 61} {9, 55, 62} {9, 55, 63} {9, 55, 64} {9, 55, 65}
{9, 55, 66} {9, 56, 57} {9, 56, 58} {9, 56, 59} {9, 56, 60} {9, 56, 61} {9, 56, 62} {9, 56, 63} {9, 56, 64} {9, 56, 65}
{9, 56, 66} {9, 57, 58} {9, 57, 59} {9, 57, 60} {9, 57, 61} {9, 57, 62} {9, 57, 63} {9, 57, 64} {9, 57, 65} {9, 57, 66}
{9, 58, 59} {9, 58, 60} {9, 58, 61} {9, 58, 62} {9, 58, 63} {9, 58, 64} {9, 58, 65} {9, 58, 66} {9, 59, 60} {9, 59, 61}
{9, 59, 62} {9, 59, 63} {9, 59, 64} {9, 59, 65} {9, 59, 66} {9, 60, 61} {9, 60, 62} {9, 60, 63} {9, 60, 64} {9, 60, 65}
{9, 60, 66} {9, 61, 62} {9, 61, 63} {9, 61, 64} {9, 61, 65} {9, 61, 66} {9, 62, 63} {9, 62, 64} {9, 62, 65} {9, 62, 66}
{9, 63, 64} {9, 63, 65} {9, 63, 66} {9, 64, 65} {9, 64, 66} {9, 65, 66} {10, 11, 12} {10, 11, 13} {10, 11, 14} {10, 11, 15}
{10, 11, 16} {10, 11, 17} {10, 11, 18} {10, 11, 19} {10, 11, 20} {10, 11, 21} {10, 11, 22} {10, 11, 23} {10, 11, 24}
{10, 11, 25} {10, 11, 26} {10, 11, 27} {10, 11, 28} {10, 11, 29} {10, 11, 30} {10, 11, 31} {10, 11, 32} {10, 11, 33}
{10, 11, 34} {10, 11, 35} {10, 11, 36} {10, 11, 37} {10, 11, 38} {10, 11, 39} {10, 11, 40} {10, 11, 41} {10, 11, 42}
{10, 11, 43} {10, 11, 44} {10, 11, 45} {10, 11, 46} {10, 11, 47} {10, 11, 48} {10, 11, 49} {10, 11, 50} {10, 11, 51}
{10, 11, 52} {10, 11, 53} {10, 11, 54} {10, 11, 55} {10, 11, 56} {10, 11, 57} {10, 11, 58} {10, 11, 59} {10, 11, 60}
{10, 11, 61} {10, 11, 62} {10, 11, 63} {10, 11, 64} {10, 11, 65} {10, 11, 66} {10, 12, 13} {10, 12, 14} {10, 12, 15}
{10, 12, 16} {10, 12, 17} {10, 12, 18} {10, 12, 19} {10, 12, 20} {10, 12, 21} {10, 12, 22} {10, 12, 23} {10, 12, 24}
{10, 12, 25} {10, 12, 26} {10, 12, 27} {10, 12, 28} {10, 12, 29} {10, 12, 30} {10, 12, 31} {10, 12, 32} {10, 12, 33}
{10, 12, 34} {10, 12, 35} {10, 12, 36} {10, 12, 37} {10, 12, 38} {10, 12, 39} {10, 12, 40} {10, 12, 41} {10, 12, 42}
{10, 12, 43} {10, 12, 44} {10, 12, 45} {10, 12, 46} {10, 12, 47} {10, 12, 48} {10, 12, 49} {10, 12, 50} {10, 12, 51}
{10, 12, 52} {10, 12, 53} {10, 12, 54} {10, 12, 55} {10, 12, 56} {10, 12, 57} {10, 12, 58} {10, 12, 59} {10, 12, 60}
{10, 12, 61} {10, 12, 62} {10, 12, 63} {10, 12, 64} {10, 12, 65} {10, 12, 66} {10, 13, 14} {10, 13, 15} {10, 13, 16}
{10, 13, 17} {10, 13, 18} {10, 13, 19} {10, 13, 20} {10, 13, 21} {10, 13, 22} {10, 13, 23} {10, 13, 24} {10, 13, 25}
{10, 13, 26} {10, 13, 27} {10, 13, 28} {10, 13, 29} {10, 13, 30} {10, 13, 31} {10, 13, 32} {10, 13, 33} {10, 13, 34}
{10, 13, 35} {10, 13, 36} {10, 13, 37} {10, 13, 38} {10, 13, 39} {10, 13, 40} {10, 13, 41} {10, 13, 42} {10, 13, 43}
{10, 13, 44} {10, 13, 45} {10, 13, 46} {10, 13, 47} {10, 13, 48} {10, 13, 49} {10, 13, 50} {10, 13, 51} {10, 13, 52}
{10, 13, 53} {10, 13, 54} {10, 13, 55} {10, 13, 56} {10, 13, 57} {10, 13, 58} {10, 13, 59} {10, 13, 60} {10, 13, 61}
{10, 13, 62} {10, 13, 63} {10, 13, 64} {10, 13, 65} {10, 13, 66} {10, 14, 15} {10, 14, 16} {10, 14, 17} {10, 14, 18}
{10, 14, 19} {10, 14, 20} {10, 14, 21} {10, 14, 22} {10, 14, 23} {10, 14, 24} {10, 14, 25} {10, 14, 26} {10, 14, 27}
{10, 14, 28} {10, 14, 29} {10, 14, 30} {10, 14, 31} {10, 14, 32} {10, 14, 33} {10, 14, 34} {10, 14, 35} {10, 14, 36}
{10, 14, 37} {10, 14, 38} {10, 14, 39} {10, 14, 40} {10, 14, 41} {10, 14, 42} {10, 14, 43} {10, 14, 44} {10, 14, 45}
{10, 14, 46} {10, 14, 47} {10, 14, 48} {10, 14, 49} {10, 14, 50} {10, 14, 51} {10, 14, 52} {10, 14, 53} {10, 14, 54}
{10, 14, 55} {10, 14, 56} {10, 14, 57} {10, 14, 58} {10, 14, 59} {10, 14, 60} {10, 14, 61} {10, 14, 62} {10, 14, 63}
{10, 14, 64} {10, 14, 65} {10, 14, 66} {10, 15, 16} {10, 15, 17} {10, 15, 18} {10, 15, 19} {10, 15, 20} {10, 15, 21}
{10, 15, 22} {10, 15, 23} {10, 15, 24} {10, 15, 25} {10, 15, 26} {10, 15, 27} {10, 15, 28} {10, 15, 29} {10, 15, 30}
{10, 15, 31} {10, 15, 32} {10, 15, 33} {10, 15, 34} {10, 15, 35} {10, 15, 36} {10, 15, 37} {10, 15, 38} {10, 15, 39}
{10, 15, 40} {10, 15, 41} {10, 15, 42} {10, 15, 43} {10, 15, 44} {10, 15, 45} {10, 15, 46} {10, 15, 47} {10, 15, 48}
{10, 15, 49} {10, 15, 50} {10, 15, 51} {10, 15, 52} {10, 15, 53} {10, 15, 54} {10, 15, 55} {10, 15, 56} {10, 15, 57}
{10, 15, 58} {10, 15, 59} {10, 15, 60} {10, 15, 61} {10, 15, 62} {10, 15, 63} {10, 15, 64} {10, 15, 65} {10, 15, 66}
{10, 16, 17} {10, 16, 18} {10, 16, 19} {10, 16, 20} {10, 16, 21} {10, 16, 22} {10, 16, 23} {10, 16, 24} {10, 16, 25}
{10, 16, 26} {10, 16, 27} {10, 16, 28} {10, 16, 29} {10, 16, 30} {10, 16, 31} {10, 16, 32} {10, 16, 33} {10, 16, 34}

TABLE 3A-continued

| | | | | | | | |
|---|---|---|---|---|---|---|---|
| {10, 16, 35} | {10, 16, 36} | {10, 16, 37} | {10, 16, 38} | {10, 16, 39} | {10, 16, 40} | {10, 16, 41} | {10, 16, 42} | {10, 16, 43} |
| {10, 16, 44} | {10, 16, 45} | {10, 16, 46} | {10, 16, 47} | {10, 16, 48} | {10, 16, 49} | {10, 16, 50} | {10, 16, 51} | {10, 16, 52} |
| {10, 16, 53} | {10, 16, 54} | {10, 16, 55} | {10, 16, 56} | {10, 16, 57} | {10, 16, 58} | {10, 16, 59} | {10, 16, 60} | {10, 16, 61} |
| {10, 16, 62} | {10, 16, 63} | {10, 16, 64} | {10, 16, 65} | {10, 16, 66} | {10, 17, 18} | {10, 17, 19} | {10, 17, 20} | {10, 17, 21} |
| {10, 17, 22} | {10, 17, 23} | {10, 17, 24} | {10, 17, 25} | {10, 17, 26} | {10, 17, 27} | {10, 17, 28} | {10, 17, 29} | {10, 17, 30} |
| {10, 17, 31} | {10, 17, 32} | {10, 17, 33} | {10, 17, 34} | {10, 17, 35} | {10, 17, 36} | {10, 17, 37} | {10, 17, 38} | {10, 17, 39} |
| {10, 17, 40} | {10, 17, 41} | {10, 17, 42} | {10, 17, 43} | {10, 17, 44} | {10, 17, 45} | {10, 17, 46} | {10, 17, 47} | {10, 17, 48} |
| {10, 17, 49} | {10, 17, 50} | {10, 17, 51} | {10, 17, 52} | {10, 17, 53} | {10, 17, 54} | {10, 17, 55} | {10, 17, 56} | {10, 17, 57} |
| {10, 17, 58} | {10, 17, 59} | {10, 17, 60} | {10, 17, 61} | {10, 17, 62} | {10, 17, 63} | {10, 17, 64} | {10, 17, 65} | {10, 17, 66} |
| {10, 18, 19} | {10, 18, 20} | {10, 18, 21} | {10, 18, 22} | {10, 18, 23} | {10, 18, 24} | {10, 18, 25} | {10, 18, 26} | {10, 18, 27} |
| {10, 18, 28} | {10, 18, 29} | {10, 18, 30} | {10, 18, 31} | {10, 18, 32} | {10, 18, 33} | {10, 18, 34} | {10, 18, 35} | {10, 18, 36} |
| {10, 18, 37} | {10, 18, 38} | {10, 18, 39} | {10, 18, 40} | {10, 18, 41} | {10, 18, 42} | {10, 18, 43} | {10, 18, 44} | {10, 18, 45} |
| {10, 18, 46} | {10, 18, 47} | {10, 18, 48} | {10, 18, 49} | {10, 18, 50} | {10, 18, 51} | {10, 18, 52} | {10, 18, 53} | {10, 18, 54} |
| {10, 18, 55} | {10, 18, 56} | {10, 18, 57} | {10, 18, 58} | {10, 18, 59} | {10, 18, 60} | {10, 18, 61} | {10, 18, 62} | {10, 18, 63} |
| {10, 18, 64} | {10, 18, 65} | {10, 18, 66} | {10, 19, 20} | {10, 19, 21} | {10, 19, 22} | {10, 19, 23} | {10, 19, 24} | {10, 19, 25} |
| {10, 19, 26} | {10, 19, 27} | {10, 19, 28} | {10, 19, 29} | {10, 19, 30} | {10, 19, 31} | {10, 19, 32} | {10, 19, 33} | {10, 19, 34} |
| {10, 19, 35} | {10, 19, 36} | {10, 19, 37} | {10, 19, 38} | {10, 19, 39} | {10, 19, 40} | {10, 19, 41} | {10, 19, 42} | {10, 19, 43} |
| {10, 19, 44} | {10, 19, 45} | {10, 19, 46} | {10, 19, 47} | {10, 19, 48} | {10, 19, 49} | {10, 19, 50} | {10, 19, 51} | {10, 19, 52} |
| {10, 19, 53} | {10, 19, 54} | {10, 19, 55} | {10, 19, 56} | {10, 19, 57} | {10, 19, 58} | {10, 19, 59} | {10, 19, 60} | {10, 19, 61} |
| {10, 19, 62} | {10, 19, 63} | {10, 19, 64} | {10, 19, 65} | {10, 19, 66} | {10, 20, 21} | {10, 20, 22} | {10, 20, 23} | {10, 20, 24} |
| {10, 20, 25} | {10, 20, 26} | {10, 20, 27} | {10, 20, 28} | {10, 20, 29} | {10, 20, 30} | {10, 20, 31} | {10, 20, 32} | {10, 20, 33} |
| {10, 20, 34} | {10, 20, 35} | {10, 20, 36} | {10, 20, 37} | {10, 20, 38} | {10, 20, 39} | {10, 20, 40} | {10, 20, 41} | {10, 20, 42} |
| {10, 20, 43} | {10, 20, 44} | {10, 20, 45} | {10, 20, 46} | {10, 20, 47} | {10, 20, 48} | {10, 20, 49} | {10, 20, 50} | {10, 20, 51} |
| {10, 20, 52} | {10, 20, 53} | {10, 20, 54} | {10, 20, 55} | {10, 20, 56} | {10, 20, 57} | {10, 20, 58} | {10, 20, 59} | {10, 20, 60} |
| {10, 20, 61} | {10, 20, 62} | {10, 20, 63} | {10, 20, 64} | {10, 20, 65} | {10, 20, 66} | {10, 21, 22} | {10, 21, 23} | {10, 21, 24} |
| {10, 21, 25} | {10, 21, 26} | {10, 21, 27} | {10, 21, 28} | {10, 21, 29} | {10, 21, 30} | {10, 21, 31} | {10, 21, 32} | {10, 21, 33} |
| {10, 21, 34} | {10, 21, 35} | {10, 21, 36} | {10, 21, 37} | {10, 21, 38} | {10, 21, 39} | {10, 21, 40} | {10, 21, 41} | {10, 21, 42} |
| {10, 21, 43} | {10, 21, 44} | {10, 21, 45} | {10, 21, 46} | {10, 21, 47} | {10, 21, 48} | {10, 21, 49} | {10, 21, 50} | {10, 21, 51} |
| {10, 21, 52} | {10, 21, 53} | {10, 21, 54} | {10, 21, 55} | {10, 21, 56} | {10, 21, 57} | {10, 21, 58} | {10, 21, 59} | {10, 21, 60} |
| {10, 21, 61} | {10, 21, 62} | {10, 21, 63} | {10, 21, 64} | {10, 21, 65} | {10, 21, 66} | {10, 22, 23} | {10, 22, 24} | {10, 22, 25} |
| {10, 22, 26} | {10, 22, 27} | {10, 22, 28} | {10, 22, 29} | {10, 22, 30} | {10, 22, 31} | {10, 22, 32} | {10, 22, 33} | {10, 22, 34} |
| {10, 22, 35} | {10, 22, 36} | {10, 22, 37} | {10, 22, 38} | {10, 22, 39} | {10, 22, 40} | {10, 22, 41} | {10, 22, 42} | {10, 22, 43} |
| {10, 22, 44} | {10, 22, 45} | {10, 22, 46} | {10, 22, 47} | {10, 22, 48} | {10, 22, 49} | {10, 22, 50} | {10, 22, 51} | {10, 22, 52} |
| {10, 22, 53} | {10, 22, 54} | {10, 22, 55} | {10, 22, 56} | {10, 22, 57} | {10, 22, 58} | {10, 22, 59} | {10, 22, 60} | {10, 22, 61} |
| {10, 22, 62} | {10, 22, 63} | {10, 22, 64} | {10, 22, 65} | {10, 22, 66} | {10, 23, 24} | {10, 23, 25} | {10, 23, 26} | {10, 23, 27} |
| {10, 23, 28} | {10, 23, 29} | {10, 23, 30} | {10, 23, 31} | {10, 23, 32} | {10, 23, 33} | {10, 23, 34} | {10, 23, 35} | {10, 23, 36} |
| {10, 23, 37} | {10, 23, 38} | {10, 23, 39} | {10, 23, 40} | {10, 23, 41} | {10, 23, 42} | {10, 23, 43} | {10, 23, 44} | {10, 23, 45} |
| {10, 23, 46} | {10, 23, 47} | {10, 23, 48} | {10, 23, 49} | {10, 23, 50} | {10, 23, 51} | {10, 23, 52} | {10, 23, 53} | {10, 23, 54} |
| {10, 23, 55} | {10, 23, 56} | {10, 23, 57} | {10, 23, 58} | {10, 23, 59} | {10, 23, 60} | {10, 23, 61} | {10, 23, 62} | {10, 23, 63} |
| {10, 23, 64} | {10, 23, 65} | {10, 23, 66} | {10, 24, 25} | {10, 24, 26} | {10, 24, 27} | {10, 24, 28} | {10, 24, 29} | {10, 24, 30} |
| {10, 24, 31} | {10, 24, 32} | {10, 24, 33} | {10, 24, 34} | {10, 24, 35} | {10, 24, 36} | {10, 24, 37} | {10, 24, 38} | {10, 24, 39} |
| {10, 24, 40} | {10, 24, 41} | {10, 24, 42} | {10, 24, 43} | {10, 24, 44} | {10, 24, 45} | {10, 24, 46} | {10, 24, 47} | {10, 24, 48} |
| {10, 24, 49} | {10, 24, 50} | {10, 24, 51} | {10, 24, 52} | {10, 24, 53} | {10, 24, 54} | {10, 24, 55} | {10, 24, 56} | {10, 24, 57} |
| {10, 24, 58} | {10, 24, 59} | {10, 24, 60} | {10, 24, 61} | {10, 24, 62} | {10, 24, 63} | {10, 24, 64} | {10, 24, 65} | {10, 24, 66} |
| {10, 25, 26} | {10, 25, 27} | {10, 25, 28} | {10, 25, 29} | {10, 25, 30} | {10, 25, 31} | {10, 25, 32} | {10, 25, 33} | {10, 25, 34} |
| {10, 25, 35} | {10, 25, 36} | {10, 25, 37} | {10, 25, 38} | {10, 25, 39} | {10, 25, 40} | {10, 25, 41} | {10, 25, 42} | {10, 25, 43} |
| {10, 25, 44} | {10, 25, 45} | {10, 25, 46} | {10, 25, 47} | {10, 25, 48} | {10, 25, 49} | {10, 25, 50} | {10, 25, 51} | {10, 25, 52} |
| {10, 25, 53} | {10, 25, 54} | {10, 25, 55} | {10, 25, 56} | {10, 25, 57} | {10, 25, 58} | {10, 25, 59} | {10, 25, 60} | {10, 25, 61} |
| {10, 25, 62} | {10, 25, 63} | {10, 25, 64} | {10, 25, 65} | {10, 25, 66} | {10, 26, 27} | {10, 26, 28} | {10, 26, 29} | {10, 26, 30} |
| {10, 26, 31} | {10, 26, 32} | {10, 26, 33} | {10, 26, 34} | {10, 26, 35} | {10, 26, 36} | {10, 26, 37} | {10, 26, 38} | {10, 26, 39} |
| {10, 26, 40} | {10, 26, 41} | {10, 26, 42} | {10, 26, 43} | {10, 26, 44} | {10, 26, 45} | {10, 26, 46} | {10, 26, 47} | {10, 26, 48} |
| {10, 26, 49} | {10, 26, 50} | {10, 26, 51} | {10, 26, 52} | {10, 26, 53} | {10, 26, 54} | {10, 26, 55} | {10, 26, 56} | {10, 26, 57} |
| {10, 26, 58} | {10, 26, 59} | {10, 26, 60} | {10, 26, 61} | {10, 26, 62} | {10, 26, 63} | {10, 26, 64} | {10, 26, 65} | {10, 26, 66} |
| {10, 27, 28} | {10, 27, 29} | {10, 27, 30} | {10, 27, 31} | {10, 27, 32} | {10, 27, 33} | {10, 27, 34} | {10, 27, 35} | {10, 27, 36} |
| {10, 27, 37} | {10, 27, 38} | {10, 27, 39} | {10, 27, 40} | {10, 27, 41} | {10, 27, 42} | {10, 27, 43} | {10, 27, 44} | {10, 27, 45} |
| {10, 27, 46} | {10, 27, 47} | {10, 27, 48} | {10, 27, 49} | {10, 27, 50} | {10, 27, 51} | {10, 27, 52} | {10, 27, 53} | {10, 27, 54} |
| {10, 27, 55} | {10, 27, 56} | {10, 27, 57} | {10, 27, 58} | {10, 27, 59} | {10, 27, 60} | {10, 27, 61} | {10, 27, 62} | {10, 27, 63} |
| {10, 27, 64} | {10, 27, 65} | {10, 27, 66} | {10, 28, 29} | {10, 28, 30} | {10, 28, 31} | {10, 28, 32} | {10, 28, 33} | {10, 28, 34} |
| {10, 28, 35} | {10, 28, 36} | {10, 28, 37} | {10, 28, 38} | {10, 28, 39} | {10, 28, 40} | {10, 28, 41} | {10, 28, 42} | {10, 28, 43} |
| {10, 28, 44} | {10, 28, 45} | {10, 28, 46} | {10, 28, 47} | {10, 28, 48} | {10, 28, 49} | {10, 28, 50} | {10, 28, 51} | {10, 28, 52} |
| {10, 28, 53} | {10, 28, 54} | {10, 28, 55} | {10, 28, 56} | {10, 28, 57} | {10, 28, 58} | {10, 28, 59} | {10, 28, 60} | {10, 28, 61} |
| {10, 28, 62} | {10, 28, 63} | {10, 28, 64} | {10, 28, 65} | {10, 28, 66} | {10, 29, 30} | {10, 29, 31} | {10, 29, 32} | {10, 29, 33} |
| {10, 29, 34} | {10, 29, 35} | {10, 29, 36} | {10, 29, 37} | {10, 29, 38} | {10, 29, 39} | {10, 29, 40} | {10, 29, 41} | {10, 29, 42} |
| {10, 29, 43} | {10, 29, 44} | {10, 29, 45} | {10, 29, 46} | {10, 29, 47} | {10, 29, 48} | {10, 29, 49} | {10, 29, 50} | {10, 29, 51} |
| {10, 29, 52} | {10, 29, 53} | {10, 29, 54} | {10, 29, 55} | {10, 29, 56} | {10, 29, 57} | {10, 29, 58} | {10, 29, 59} | {10, 29, 60} |
| {10, 29, 61} | {10, 29, 62} | {10, 29, 63} | {10, 29, 64} | {10, 29, 65} | {10, 29, 66} | {10, 30, 31} | {10, 30, 32} | {10, 30, 33} |
| {10, 30, 34} | {10, 30, 35} | {10, 30, 36} | {10, 30, 37} | {10, 30, 38} | {10, 30, 39} | {10, 30, 40} | {10, 30, 41} | {10, 30, 42} |
| {10, 30, 43} | {10, 30, 44} | {10, 30, 45} | {10, 30, 46} | {10, 30, 47} | {10, 30, 48} | {10, 30, 49} | {10, 30, 50} | {10, 30, 51} |
| {10, 30, 52} | {10, 30, 53} | {10, 30, 54} | {10, 30, 55} | {10, 30, 56} | {10, 30, 57} | {10, 30, 58} | {10, 30, 59} | {10, 30, 60} |
| {10, 30, 61} | {10, 30, 62} | {10, 30, 63} | {10, 30, 64} | {10, 30, 65} | {10, 30, 66} | {10, 31, 32} | {10, 31, 33} | {10, 31, 34} |
| {10, 31, 35} | {10, 31, 36} | {10, 31, 37} | {10, 31, 38} | {10, 31, 39} | {10, 31, 40} | {10, 31, 41} | {10, 31, 42} | {10, 31, 43} |
| {10, 31, 44} | {10, 31, 45} | {10, 31, 46} | {10, 31, 47} | {10, 31, 48} | {10, 31, 49} | {10, 31, 50} | {10, 31, 51} | {10, 31, 52} |
| {10, 31, 53} | {10, 31, 54} | {10, 31, 55} | {10, 31, 56} | {10, 31, 57} | {10, 31, 58} | {10, 31, 59} | {10, 31, 60} | {10, 31, 61} |
| {10, 31, 62} | {10, 31, 63} | {10, 31, 64} | {10, 31, 65} | {10, 31, 66} | {10, 32, 33} | {10, 32, 34} | {10, 32, 35} | {10, 32, 36} |
| {10, 32, 37} | {10, 32, 38} | {10, 32, 39} | {10, 32, 40} | {10, 32, 41} | {10, 32, 42} | {10, 32, 43} | {10, 32, 44} | {10, 32, 45} |
| {10, 32, 46} | {10, 32, 47} | {10, 32, 48} | {10, 32, 49} | {10, 32, 50} | {10, 32, 51} | {10, 32, 52} | {10, 32, 53} | {10, 32, 54} |
| {10, 32, 55} | {10, 32, 56} | {10, 32, 57} | {10, 32, 58} | {10, 32, 59} | {10, 32, 60} | {10, 32, 61} | {10, 32, 62} | {10, 32, 63} |
| {10, 32, 64} | {10, 32, 65} | {10, 32, 66} | {10, 33, 34} | {10, 33, 35} | {10, 33, 36} | {10, 33, 37} | {10, 33, 38} | {10, 33, 39} |
| {10, 33, 40} | {10, 33, 41} | {10, 33, 42} | {10, 33, 43} | {10, 33, 44} | {10, 33, 45} | {10, 33, 46} | {10, 33, 47} | {10, 33, 48} |
| {10, 33, 49} | {10, 33, 50} | {10, 33, 51} | {10, 33, 52} | {10, 33, 53} | {10, 33, 54} | {10, 33, 55} | {10, 33, 56} | {10, 33, 57} |

TABLE 3A-continued

{10, 33, 58} {10, 33, 59} {10, 33, 60} {10, 33, 61} {10, 33, 62} {10, 33, 63} {10, 33, 64} {10, 33, 65} {10, 33, 66}
{10, 34, 35} {10, 34, 36} {10, 34, 37} {10, 34, 38} {10, 34, 39} {10, 34, 40} {10, 34, 41} {10, 34, 42} {10, 34, 43}
{10, 34, 44} {10, 34, 45} {10, 34, 46} {10, 34, 47} {10, 34, 48} {10, 34, 49} {10, 34, 50} {10, 34, 51} {10, 34, 52}
{10, 34, 53} {10, 34, 54} {10, 34, 55} {10, 34, 56} {10, 34, 57} {10, 34, 58} {10, 34, 59} {10, 34, 60} {10, 34, 61}
{10, 34, 62} {10, 34, 63} {10, 34, 64} {10, 34, 65} {10, 34, 66} {10, 35, 36} {10, 35, 37} {10, 35, 38} {10, 35, 39}
{10, 35, 40} {10, 35, 41} {10, 35, 42} {10, 35, 43} {10, 35, 44} {10, 35, 45} {10, 35, 46} {10, 35, 47} {10, 35, 48}
{10, 35, 49} {10, 35, 50} {10, 35, 51} {10, 35, 52} {10, 35, 53} {10, 35, 54} {10, 35, 55} {10, 35, 56} {10, 35, 57}
{10, 35, 58} {10, 35, 59} {10, 35, 60} {10, 35, 61} {10, 35, 62} {10, 35, 63} {10, 35, 64} {10, 35, 65} {10, 35, 66}
{10, 36, 37} {10, 36, 38} {10, 36, 39} {10, 36, 40} {10, 36, 41} {10, 36, 42} {10, 36, 43} {10, 36, 44} {10, 36, 45}
{10, 36, 46} {10, 36, 47} {10, 36, 48} {10, 36, 49} {10, 36, 50} {10, 36, 51} {10, 36, 52} {10, 36, 53} {10, 36, 54}
{10, 36, 55} {10, 36, 56} {10, 36, 57} {10, 36, 58} {10, 36, 59} {10, 36, 60} {10, 36, 61} {10, 36, 62} {10, 36, 63}
{10, 36, 64} {10, 36, 65} {10, 36, 66} {10, 37, 38} {10, 37, 39} {10, 37, 40} {10, 37, 41} {10, 37, 42} {10, 37, 43}
{10, 37, 44} {10, 37, 45} {10, 37, 46} {10, 37, 47} {10, 37, 48} {10, 37, 49} {10, 37, 50} {10, 37, 51} {10, 37, 52}
{10, 37, 53} {10, 37, 54} {10, 37, 55} {10, 37, 56} {10, 37, 57} {10, 37, 58} {10, 37, 59} {10, 37, 60} {10, 37, 61}
{10, 37, 62} {10, 37, 63} {10, 37, 64} {10, 37, 65} {10, 37, 66} {10, 38, 39} {10, 38, 40} {10, 38, 41} {10, 38, 42}
{10, 38, 43} {10, 38, 44} {10, 38, 45} {10, 38, 46} {10, 38, 47} {10, 38, 48} {10, 38, 49} {10, 38, 50} {10, 38, 51}
{10, 38, 52} {10, 38, 53} {10, 38, 54} {10, 38, 55} {10, 38, 56} {10, 38, 57} {10, 38, 58} {10, 38, 59} {10, 38, 60}
{10, 38, 61} {10, 38, 62} {10, 38, 63} {10, 38, 64} {10, 38, 65} {10, 38, 66} {10, 39, 40} {10, 39, 41} {10, 39, 42}
{10, 39, 43} {10, 39, 44} {10, 39, 45} {10, 39, 46} {10, 39, 47} {10, 39, 48} {10, 39, 49} {10, 39, 50} {10, 39, 51}
{10, 39, 52} {10, 39, 53} {10, 39, 54} {10, 39, 55} {10, 39, 56} {10, 39, 57} {10, 39, 58} {10, 39, 59} {10, 39, 60}
{10, 39, 61} {10, 39, 62} {10, 39, 63} {10, 39, 64} {10, 39, 65} {10, 39, 66} {10, 40, 41} {10, 40, 42} {10, 40, 43}
{10, 40, 44} {10, 40, 45} {10, 40, 46} {10, 40, 47} {10, 40, 48} {10, 40, 49} {10, 40, 50} {10, 40, 51} {10, 40, 52}
{10, 40, 53} {10, 40, 54} {10, 40, 55} {10, 40, 56} {10, 40, 57} {10, 40, 58} {10, 40, 59} {10, 40, 60} {10, 40, 61}
{10, 40, 62} {10, 40, 63} {10, 40, 64} {10, 40, 65} {10, 40, 66} {10, 41, 42} {10, 41, 43} {10, 41, 44} {10, 41, 45}
{10, 41, 46} {10, 41, 47} {10, 41, 48} {10, 41, 49} {10, 41, 50} {10, 41, 51} {10, 41, 52} {10, 41, 53} {10, 41, 54}
{10, 41, 55} {10, 41, 56} {10, 41, 57} {10, 41, 58} {10, 41, 59} {10, 41, 60} {10, 41, 61} {10, 41, 62} {10, 41, 63}
{10, 41, 64} {10, 41, 65} {10, 41, 66} {10, 42, 43} {10, 42, 44} {10, 42, 45} {10, 42, 46} {10, 42, 47} {10, 42, 48}
{10, 42, 49} {10, 42, 50} {10, 42, 51} {10, 42, 52} {10, 42, 53} {10, 42, 54} {10, 42, 55} {10, 42, 56} {10, 42, 57}
{10, 42, 58} {10, 42, 59} {10, 42, 60} {10, 42, 61} {10, 42, 62} {10, 42, 63} {10, 42, 64} {10, 42, 65} {10, 42, 66}
{10, 43, 44} {10, 43, 45} {10, 43, 46} {10, 43, 47} {10, 43, 48} {10, 43, 49} {10, 43, 50} {10, 43, 51} {10, 43, 52}
{10, 43, 53} {10, 43, 54} {10, 43, 55} {10, 43, 56} {10, 43, 57} {10, 43, 58} {10, 43, 59} {10, 43, 60} {10, 43, 61}
{10, 43, 62} {10, 43, 63} {10, 43, 64} {10, 43, 65} {10, 43, 66} {10, 44, 45} {10, 44, 46} {10, 44, 47} {10, 44, 48}
{10, 44, 49} {10, 44, 50} {10, 44, 51} {10, 44, 52} {10, 44, 53} {10, 44, 54} {10, 44, 55} {10, 44, 56} {10, 44, 57}
{10, 44, 58} {10, 44, 59} {10, 44, 60} {10, 44, 61} {10, 44, 62} {10, 44, 63} {10, 44, 64} {10, 44, 65} {10, 44, 66}
{10, 45, 46} {10, 45, 47} {10, 45, 48} {10, 45, 49} {10, 45, 50} {10, 45, 51} {10, 45, 52} {10, 45, 53} {10, 45, 54}
{10, 45, 55} {10, 45, 56} {10, 45, 57} {10, 45, 58} {10, 45, 59} {10, 45, 60} {10, 45, 61} {10, 45, 62} {10, 45, 63}
{10, 45, 64} {10, 45, 65} {10, 45, 66} {10, 46, 47} {10, 46, 48} {10, 46, 49} {10, 46, 50} {10, 46, 51} {10, 46, 52}
{10, 46, 53} {10, 46, 54} {10, 46, 55} {10, 46, 56} {10, 46, 57} {10, 46, 58} {10, 46, 59} {10, 46, 60} {10, 46, 61}
{10, 46, 62} {10, 46, 63} {10, 46, 64} {10, 46, 65} {10, 46, 66} {10, 47, 48} {10, 47, 49} {10, 47, 50} {10, 47, 51}
{10, 47, 52} {10, 47, 53} {10, 47, 54} {10, 47, 55} {10, 47, 56} {10, 47, 57} {10, 47, 58} {10, 47, 59} {10, 47, 60}
{10, 47, 61} {10, 47, 62} {10, 47, 63} {10, 47, 64} {10, 47, 65} {10, 47, 66} {10, 48, 49} {10, 48, 50} {10, 48, 51}
{10, 48, 52} {10, 48, 53} {10, 48, 54} {10, 48, 55} {10, 48, 56} {10, 48, 57} {10, 48, 58} {10, 48, 59} {10, 48, 60}
{10, 48, 61} {10, 48, 62} {10, 48, 63} {10, 48, 64} {10, 48, 65} {10, 48, 66} {10, 49, 50} {10, 49, 51} {10, 49, 52}
{10, 49, 53} {10, 49, 54} {10, 49, 55} {10, 49, 56} {10, 49, 57} {10, 49, 58} {10, 49, 59} {10, 49, 60} {10, 49, 61}
{10, 49, 62} {10, 49, 63} {10, 49, 64} {10, 49, 65} {10, 49, 66} {10, 50, 51} {10, 50, 52} {10, 50, 53} {10, 50, 54}
{10, 50, 55} {10, 50, 56} {10, 50, 57} {10, 50, 58} {10, 50, 59} {10, 50, 60} {10, 50, 61} {10, 50, 62} {10, 50, 63}
{10, 50, 64} {10, 50, 65} {10, 50, 66} {10, 51, 52} {10, 51, 53} {10, 51, 54} {10, 51, 55} {10, 51, 56} {10, 51, 57}
{10, 51, 58} {10, 51, 59} {10, 51, 60} {10, 51, 61} {10, 51, 62} {10, 51, 63} {10, 51, 64} {10, 51, 65} {10, 51, 66}
{10, 52, 53} {10, 52, 54} {10, 52, 55} {10, 52, 56} {10, 52, 57} {10, 52, 58} {10, 52, 59} {10, 52, 60} {10, 52, 61}
{10, 52, 62} {10, 52, 63} {10, 52, 64} {10, 52, 65} {10, 52, 66} {10, 53, 54} {10, 53, 55} {10, 53, 56} {10, 53, 57}
{10, 53, 58} {10, 53, 59} {10, 53, 60} {10, 53, 61} {10, 53, 62} {10, 53, 63} {10, 53, 64} {10, 53, 65} {10, 53, 66}
{10, 54, 55} {10, 54, 56} {10, 54, 57} {10, 54, 58} {10, 54, 59} {10, 54, 60} {10, 54, 61} {10, 54, 62} {10, 54, 63}
{10, 54, 64} {10, 54, 65} {10, 54, 66} {10, 55, 56} {10, 55, 57} {10, 55, 58} {10, 55, 59} {10, 55, 60} {10, 55, 61}
{10, 55, 62} {10, 55, 63} {10, 55, 64} {10, 55, 65} {10, 55, 66} {10, 56, 57} {10, 56, 58} {10, 56, 59} {10, 56, 60}
{10, 56, 61} {10, 56, 62} {10, 56, 63} {10, 56, 64} {10, 56, 65} {10, 56, 66} {10, 57, 58} {10, 57, 59} {10, 57, 60}
{10, 57, 61} {10, 57, 62} {10, 57, 63} {10, 57, 64} {10, 57, 65} {10, 57, 66} {10, 58, 59} {10, 58, 60} {10, 58, 61}
{10, 58, 62} {10, 58, 63} {10, 58, 64} {10, 58, 65} {10, 58, 66} {10, 59, 60} {10, 59, 61} {10, 59, 62} {10, 59, 63}
{10, 59, 64} {10, 59, 65} {10, 59, 66} {10, 60, 61} {10, 60, 62} {10, 60, 63} {10, 60, 64} {10, 60, 65} {10, 60, 66}
{10, 61, 62} {10, 61, 63} {10, 61, 64} {10, 61, 65} {10, 61, 66} {10, 62, 63} {10, 62, 64} {10, 62, 65} {10, 62, 66}
{10, 63, 64} {10, 63, 65} {10, 63, 66} {10, 64, 65} {10, 64, 66} {10, 65, 66} {11, 12, 13} {11, 12, 14} {11, 12, 15}
{11, 12, 16} {11, 12, 17} {11, 12, 18} {11, 12, 19} {11, 12, 20} {11, 12, 21} {11, 12, 22} {11, 12, 23} {11, 12, 24}
{11, 12, 25} {11, 12, 26} {11, 12, 27} {11, 12, 28} {11, 12, 29} {11, 12, 30} {11, 12, 31} {11, 12, 32} {11, 12, 33}
{11, 12, 34} {11, 12, 35} {11, 12, 36} {11, 12, 37} {11, 12, 38} {11, 12, 39} {11, 12, 40} {11, 12, 41} {11, 12, 42}
{11, 12, 43} {11, 12, 44} {11, 12, 45} {11, 12, 46} {11, 12, 47} {11, 12, 48} {11, 12, 49} {11, 12, 50} {11, 12, 51}
{11, 12, 52} {11, 12, 53} {11, 12, 54} {11, 12, 55} {11, 12, 56} {11, 12, 57} {11, 12, 58} {11, 12, 59} {11, 12, 60}
{11, 12, 61} {11, 12, 62} {11, 12, 63} {11, 12, 64} {11, 12, 65} {11, 12, 66} {11, 13, 14} {11, 13, 15} {11, 13, 16}
{11, 13, 17} {11, 13, 18} {11, 13, 19} {11, 13, 20} {11, 13, 21} {11, 13, 22} {11, 13, 23} {11, 13, 24} {11, 13, 25}
{11, 13, 26} {11, 13, 27} {11, 13, 28} {11, 13, 29} {11, 13, 30} {11, 13, 31} {11, 13, 32} {11, 13, 33} {11, 13, 34}
{11, 13, 35} {11, 13, 36} {11, 13, 37} {11, 13, 38} {11, 13, 39} {11, 13, 40} {11, 13, 41} {11, 13, 42} {11, 13, 43}
{11, 13, 44} {11, 13, 45} {11, 13, 46} {11, 13, 47} {11, 13, 48} {11, 13, 49} {11, 13, 50} {11, 13, 51} {11, 13, 52}
{11, 13, 53} {11, 13, 54} {11, 13, 55} {11, 13, 56} {11, 13, 57} {11, 13, 58} {11, 13, 59} {11, 13, 60} {11, 13, 61}
{11, 13, 62} {11, 13, 63} {11, 13, 64} {11, 13, 65} {11, 13, 66} {11, 14, 15} {11, 14, 16} {11, 14, 17} {11, 14, 18}
{11, 14, 19} {11, 14, 20} {11, 14, 21} {11, 14, 22} {11, 14, 23} {11, 14, 24} {11, 14, 25} {11, 14, 26} {11, 14, 27}
{11, 14, 28} {11, 14, 29} {11, 14, 30} {11, 14, 31} {11, 14, 32} {11, 14, 33} {11, 14, 34} {11, 14, 35} {11, 14, 36}
{11, 14, 37} {11, 14, 38} {11, 14, 39} {11, 14, 40} {11, 14, 41} {11, 14, 42} {11, 14, 43} {11, 14, 44} {11, 14, 45}
{11, 14, 46} {11, 14, 47} {11, 14, 48} {11, 14, 49} {11, 14, 50} {11, 14, 51} {11, 14, 52} {11, 14, 53} {11, 14, 54}
{11, 14, 55} {11, 14, 56} {11, 14, 57} {11, 14, 58} {11, 14, 59} {11, 14, 60} {11, 14, 61} {11, 14, 62} {11, 14, 63}
{11, 14, 64} {11, 14, 65} {11, 14, 66} {11, 15, 16} {11, 15, 17} {11, 15, 18} {11, 15, 19} {11, 15, 20} {11, 15, 21}
{11, 15, 22} {11, 15, 23} {11, 15, 24} {11, 15, 25} {11, 15, 26} {11, 15, 27} {11, 15, 28} {11, 15, 29} {11, 15, 30}
{11, 15, 31} {11, 15, 32} {11, 15, 33} {11, 15, 34} {11, 15, 35} {11, 15, 36} {11, 15, 37} {11, 15, 38} {11, 15, 39}

TABLE 3A-continued

{11, 15, 40} {11, 15, 41} {11, 15, 42} {11, 15, 43} {11, 15, 44} {11, 15, 45} {11, 15, 46} {11, 15, 47} {11, 15, 48}
{11, 15, 49} {11, 15, 50} {11, 15, 51} {11, 15, 52} {11, 15, 53} {11, 15, 54} {11, 15, 55} {11, 15, 56} {11, 15, 57}
{11, 15, 58} {11, 15, 59} {11, 15, 60} {11, 15, 61} {11, 15, 62} {11, 15, 63} {11, 15, 64} {11, 15, 65} {11, 15, 66}
{11, 16, 17} {11, 16, 18} {11, 16, 19} {11, 16, 20} {11, 16, 21} {11, 16, 22} {11, 16, 23} {11, 16, 24} {11, 16, 25}
{11, 16, 26} {11, 16, 27} {11, 16, 28} {11, 16, 29} {11, 16, 30} {11, 16, 31} {11, 16, 32} {11, 16, 33} {11, 16, 34}
{11, 16, 35} {11, 16, 36} {11, 16, 37} {11, 16, 38} {11, 16, 39} {11, 16, 40} {11, 16, 41} {11, 16, 42} {11, 16, 43}
{11, 16, 44} {11, 16, 45} {11, 16, 46} {11, 16, 47} {11, 16, 48} {11, 16, 49} {11, 16, 50} {11, 16, 51} {11, 16, 52}
{11, 16, 53} {11, 16, 54} {11, 16, 55} {11, 16, 56} {11, 16, 57} {11, 16, 58} {11, 16, 59} {11, 16, 60} {11, 16, 61}
{11, 16, 62} {11, 16, 63} {11, 16, 64} {11, 16, 65} {11, 16, 66} {11, 17, 18} {11, 17, 19} {11, 17, 20} {11, 17, 21}
{11, 17, 22} {11, 17, 23} {11, 17, 24} {11, 17, 25} {11, 17, 26} {11, 17, 27} {11, 17, 28} {11, 17, 29} {11, 17, 30}
{11, 17, 31} {11, 17, 32} {11, 17, 33} {11, 17, 34} {11, 17, 35} {11, 17, 36} {11, 17, 37} {11, 17, 38} {11, 17, 39}
{11, 17, 40} {11, 17, 41} {11, 17, 42} {11, 17, 43} {11, 17, 44} {11, 17, 45} {11, 17, 46} {11, 17, 47} {11, 17, 48}
{11, 17, 49} {11, 17, 50} {11, 17, 51} {11, 17, 52} {11, 17, 53} {11, 17, 54} {11, 17, 55} {11, 17, 56} {11, 17, 57}
{11, 17, 58} {11, 17, 59} {11, 17, 60} {11, 17, 61} {11, 17, 62} {11, 17, 63} {11, 17, 64} {11, 17, 65} {11, 17, 66}
{11, 18, 19} {11, 18, 20} {11, 18, 21} {11, 18, 22} {11, 18, 23} {11, 18, 24} {11, 18, 25} {11, 18, 26} {11, 18, 27}
{11, 18, 28} {11, 18, 29} {11, 18, 30} {11, 18, 31} {11, 18, 32} {11, 18, 33} {11, 18, 34} {11, 18, 35} {11, 18, 36}
{11, 18, 37} {11, 18, 38} {11, 18, 39} {11, 18, 40} {11, 18, 41} {11, 18, 42} {11, 18, 43} {11, 18, 44} {11, 18, 45}
{11, 18, 46} {11, 18, 47} {11, 18, 48} {11, 18, 49} {11, 18, 50} {11, 18, 51} {11, 18, 52} {11, 18, 53} {11, 18, 54}
{11, 18, 55} {11, 18, 56} {11, 18, 57} {11, 18, 58} {11, 18, 59} {11, 18, 60} {11, 18, 61} {11, 18, 62} {11, 18, 63}
{11, 18, 64} {11, 18, 65} {11, 18, 66} {11, 19, 20} {11, 19, 21} {11, 19, 22} {11, 19, 23} {11, 19, 24} {11, 19, 25}
{11, 19, 26} {11, 19, 27} {11, 19, 28} {11, 19, 29} {11, 19, 30} {11, 19, 31} {11, 19, 32} {11, 19, 33} {11, 19, 34}
{11, 19, 35} {11, 19, 36} {11, 19, 37} {11, 19, 38} {11, 19, 39} {11, 19, 40} {11, 19, 41} {11, 19, 42} {11, 19, 43}
{11, 19, 44} {11, 19, 45} {11, 19, 46} {11, 19, 47} {11, 19, 48} {11, 19, 49} {11, 19, 50} {11, 19, 51} {11, 19, 52}
{11, 19, 53} {11, 19, 54} {11, 19, 55} {11, 19, 56} {11, 19, 57} {11, 19, 58} {11, 19, 59} {11, 19, 60} {11, 19, 61}
{11, 19, 62} {11, 19, 63} {11, 19, 64} {11, 19, 65} {11, 19, 66} {11, 20, 21} {11, 20, 22} {11, 20, 23} {11, 20, 24}
{11, 20, 25} {11, 20, 26} {11, 20, 27} {11, 20, 28} {11, 20, 29} {11, 20, 30} {11, 20, 31} {11, 20, 32} {11, 20, 33}
{11, 20, 34} {11, 20, 35} {11, 20, 36} {11, 20, 37} {11, 20, 38} {11, 20, 39} {11, 20, 40} {11, 20, 41} {11, 20, 42}
{11, 20, 43} {11, 20, 44} {11, 20, 45} {11, 20, 46} {11, 20, 47} {11, 20, 48} {11, 20, 49} {11, 20, 50} {11, 20, 51}
{11, 20, 52} {11, 20, 53} {11, 20, 54} {11, 20, 55} {11, 20, 56} {11, 20, 57} {11, 20, 58} {11, 20, 59} {11, 20, 60}
{11, 20, 61} {11, 20, 62} {11, 20, 63} {11, 20, 64} {11, 20, 65} {11, 20, 66} {11, 21, 22} {11, 21, 23} {11, 21, 24}
{11, 21, 25} {11, 21, 26} {11, 21, 27} {11, 21, 28} {11, 21, 29} {11, 21, 30} {11, 21, 31} {11, 21, 32} {11, 21, 33}
{11, 21, 34} {11, 21, 35} {11, 21, 36} {11, 21, 37} {11, 21, 38} {11, 21, 39} {11, 21, 40} {11, 21, 41} {11, 21, 42}
{11, 21, 43} {11, 21, 44} {11, 21, 45} {11, 21, 46} {11, 21, 47} {11, 21, 48} {11, 21, 49} {11, 21, 50} {11, 21, 51}
{11, 21, 52} {11, 21, 53} {11, 21, 54} {11, 21, 55} {11, 21, 56} {11, 21, 57} {11, 21, 58} {11, 21, 59} {11, 21, 60}
{11, 21, 61} {11, 21, 62} {11, 21, 63} {11, 21, 64} {11, 21, 65} {11, 21, 66} {11, 22, 23} {11, 22, 24} {11, 22, 25}
{11, 22, 26} {11, 22, 27} {11, 22, 28} {11, 22, 29} {11, 22, 30} {11, 22, 31} {11, 22, 32} {11, 22, 33} {11, 22, 34}
{11, 22, 35} {11, 22, 36} {11, 22, 37} {11, 22, 38} {11, 22, 39} {11, 22, 40} {11, 22, 41} {11, 22, 42} {11, 22, 43}
{11, 22, 44} {11, 22, 45} {11, 22, 46} {11, 22, 47} {11, 22, 48} {11, 22, 49} {11, 22, 50} {11, 22, 51} {11, 22, 52}
{11, 22, 53} {11, 22, 54} {11, 22, 55} {11, 22, 56} {11, 22, 57} {11, 22, 58} {11, 22, 59} {11, 22, 60} {11, 22, 61}
{11, 22, 62} {11, 22, 63} {11, 22, 64} {11, 22, 65} {11, 22, 66} {11, 23, 24} {11, 23, 25} {11, 23, 26} {11, 23, 27}
{11, 23, 28} {11, 23, 29} {11, 23, 30} {11, 23, 31} {11, 23, 32} {11, 23, 33} {11, 23, 34} {11, 23, 35} {11, 23, 36}
{11, 23, 37} {11, 23, 38} {11, 23, 39} {11, 23, 40} {11, 23, 41} {11, 23, 42} {11, 23, 43} {11, 23, 44} {11, 23, 45}
{11, 23, 46} {11, 23, 47} {11, 23, 48} {11, 23, 49} {11, 23, 50} {11, 23, 51} {11, 23, 52} {11, 23, 53} {11, 23, 54}
{11, 23, 55} {11, 23, 56} {11, 23, 57} {11, 23, 58} {11, 23, 59} {11, 23, 60} {11, 23, 61} {11, 23, 62} {11, 23, 63}
{11, 23, 64} {11, 23, 65} {11, 23, 66} {11, 24, 25} {11, 24, 26} {11, 24, 27} {11, 24, 28} {11, 24, 29} {11, 24, 30}
{11, 24, 31} {11, 24, 32} {11, 24, 33} {11, 24, 34} {11, 24, 35} {11, 24, 36} {11, 24, 37} {11, 24, 38} {11, 24, 39}
{11, 24, 40} {11, 24, 41} {11, 24, 42} {11, 24, 43} {11, 24, 44} {11, 24, 45} {11, 24, 46} {11, 24, 47} {11, 24, 48}
{11, 24, 49} {11, 24, 50} {11, 24, 51} {11, 24, 52} {11, 24, 53} {11, 24, 54} {11, 24, 55} {11, 24, 56} {11, 24, 57}
{11, 24, 58} {11, 24, 59} {11, 24, 60} {11, 24, 61} {11, 24, 62} {11, 24, 63} {11, 24, 64} {11, 24, 65} {11, 24, 66}
{11, 25, 26} {11, 25, 27} {11, 25, 28} {11, 25, 29} {11, 25, 30} {11, 25, 31} {11, 25, 32} {11, 25, 33} {11, 25, 34}
{11, 25, 35} {11, 25, 36} {11, 25, 37} {11, 25, 38} {11, 25, 39} {11, 25, 40} {11, 25, 41} {11, 25, 42} {11, 25, 43}
{11, 25, 44} {11, 25, 45} {11, 25, 46} {11, 25, 47} {11, 25, 48} {11, 25, 49} {11, 25, 50} {11, 25, 51} {11, 25, 52}
{11, 25, 53} {11, 25, 54} {11, 25, 55} {11, 25, 56} {11, 25, 57} {11, 25, 58} {11, 25, 59} {11, 25, 60} {11, 25, 61}
{11, 25, 62} {11, 25, 63} {11, 25, 64} {11, 25, 65} {11, 25, 66} {11, 26, 27} {11, 26, 28} {11, 26, 29} {11, 26, 30}
{11, 26, 31} {11, 26, 32} {11, 26, 33} {11, 26, 34} {11, 26, 35} {11, 26, 36} {11, 26, 37} {11, 26, 38} {11, 26, 39}
{11, 26, 40} {11, 26, 41} {11, 26, 42} {11, 26, 43} {11, 26, 44} {11, 26, 45} {11, 26, 46} {11, 26, 47} {11, 26, 48}
{11, 26, 49} {11, 26, 50} {11, 26, 51} {11, 26, 52} {11, 26, 53} {11, 26, 54} {11, 26, 55} {11, 26, 56} {11, 26, 57}
{11, 26, 58} {11, 26, 59} {11, 26, 60} {11, 26, 61} {11, 26, 62} {11, 26, 63} {11, 26, 64} {11, 26, 65} {11, 26, 66}
{11, 27, 28} {11, 27, 29} {11, 27, 30} {11, 27, 31} {11, 27, 32} {11, 27, 33} {11, 27, 34} {11, 27, 35} {11, 27, 36}
{11, 27, 37} {11, 27, 38} {11, 27, 39} {11, 27, 40} {11, 27, 41} {11, 27, 42} {11, 27, 43} {11, 27, 44} {11, 27, 45}
{11, 27, 46} {11, 27, 47} {11, 27, 48} {11, 27, 49} {11, 27, 50} {11, 27, 51} {11, 27, 52} {11, 27, 53} {11, 27, 54}
{11, 27, 55} {11, 27, 56} {11, 27, 57} {11, 27, 58} {11, 27, 59} {11, 27, 60} {11, 27, 61} {11, 27, 62} {11, 27, 63}
{11, 27, 64} {11, 27, 65} {11, 27, 66} {11, 28, 29} {11, 28, 30} {11, 28, 31} {11, 28, 32} {11, 28, 33} {11, 28, 34}
{11, 28, 35} {11, 28, 36} {11, 28, 37} {11, 28, 38} {11, 28, 39} {11, 28, 40} {11, 28, 41} {11, 28, 42} {11, 28, 43}
{11, 28, 44} {11, 28, 45} {11, 28, 46} {11, 28, 47} {11, 28, 48} {11, 28, 49} {11, 28, 50} {11, 28, 51} {11, 28, 52}
{11, 28, 53} {11, 28, 54} {11, 28, 55} {11, 28, 56} {11, 28, 57} {11, 28, 58} {11, 28, 59} {11, 28, 60} {11, 28, 61}
{11, 28, 62} {11, 28, 63} {11, 28, 64} {11, 28, 65} {11, 28, 66} {11, 29, 30} {11, 29, 31} {11, 29, 32} {11, 29, 33}
{11, 29, 34} {11, 29, 35} {11, 29, 36} {11, 29, 37} {11, 29, 38} {11, 29, 39} {11, 29, 40} {11, 29, 41} {11, 29, 42}
{11, 29, 43} {11, 29, 44} {11, 29, 45} {11, 29, 46} {11, 29, 47} {11, 29, 48} {11, 29, 49} {11, 29, 50} {11, 29, 51}
{11, 29, 52} {11, 29, 53} {11, 29, 54} {11, 29, 55} {11, 29, 56} {11, 29, 57} {11, 29, 58} {11, 29, 59} {11, 29, 60}
{11, 29, 61} {11, 29, 62} {11, 29, 63} {11, 29, 64} {11, 29, 65} {11, 29, 66} {11, 30, 31} {11, 30, 32} {11, 30, 33}
{11, 30, 34} {11, 30, 35} {11, 30, 36} {11, 30, 37} {11, 30, 38} {11, 30, 39} {11, 30, 40} {11, 30, 41} {11, 30, 42}
{11, 30, 43} {11, 30, 44} {11, 30, 45} {11, 30, 46} {11, 30, 47} {11, 30, 48} {11, 30, 49} {11, 30, 50} {11, 30, 51}
{11, 30, 52} {11, 30, 53} {11, 30, 54} {11, 30, 55} {11, 30, 56} {11, 30, 57} {11, 30, 58} {11, 30, 59} {11, 30, 60}
{11, 30, 61} {11, 30, 62} {11, 30, 63} {11, 30, 64} {11, 30, 65} {11, 30, 66} {11, 31, 32} {11, 31, 33} {11, 31, 34}
{11, 31, 35} {11, 31, 36} {11, 31, 37} {11, 31, 38} {11, 31, 39} {11, 31, 40} {11, 31, 41} {11, 31, 42} {11, 31, 43}
{11, 31, 44} {11, 31, 45} {11, 31, 46} {11, 31, 47} {11, 31, 48} {11, 31, 49} {11, 31, 50} {11, 31, 51} {11, 31, 52}
{11, 31, 53} {11, 31, 54} {11, 31, 55} {11, 31, 56} {11, 31, 57} {11, 31, 58} {11, 31, 59} {11, 31, 60} {11, 31, 61}
{11, 31, 62} {11, 31, 63} {11, 31, 64} {11, 31, 65} {11, 31, 66} {11, 32, 33} {11, 32, 34} {11, 32, 35} {11, 32, 36}
{11, 32, 37} {11, 32, 38} {11, 32, 39} {11, 32, 40} {11, 32, 41} {11, 32, 42} {11, 32, 43} {11, 32, 44} {11, 32, 45}

TABLE 3A-continued

{11, 32, 46} {11, 32, 47} {11, 32, 48} {11, 32, 49} {11, 32, 50} {11, 32, 51} {11, 32, 52} {11, 32, 53} {11, 32, 54}
{11, 32, 55} {11, 32, 56} {11, 32, 57} {11, 32, 58} {11, 32, 59} {11, 32, 60} {11, 32, 61} {11, 32, 62} {11, 32, 63}
{11, 32, 64} {11, 32, 65} {11, 32, 66} {11, 33, 34} {11, 33, 35} {11, 33, 36} {11, 33, 37} {11, 33, 38} {11, 33, 39}
{11, 33, 40} {11, 33, 41} {11, 33, 42} {11, 33, 43} {11, 33, 44} {11, 33, 45} {11, 33, 46} {11, 33, 47} {11, 33, 48}
{11, 33, 49} {11, 33, 50} {11, 33, 51} {11, 33, 52} {11, 33, 53} {11, 33, 54} {11, 33, 55} {11, 33, 56} {11, 33, 57}
{11, 33, 58} {11, 33, 59} {11, 33, 60} {11, 33, 61} {11, 33, 62} {11, 33, 63} {11, 33, 64} {11, 33, 65} {11, 33, 66}
{11, 34, 35} {11, 34, 36} {11, 34, 37} {11, 34, 38} {11, 34, 39} {11, 34, 40} {11, 34, 41} {11, 34, 42} {11, 34, 43}
{11, 34, 44} {11, 34, 45} {11, 34, 46} {11, 34, 47} {11, 34, 48} {11, 34, 49} {11, 34, 50} {11, 34, 51} {11, 34, 52}
{11, 34, 53} {11, 34, 54} {11, 34, 55} {11, 34, 56} {11, 34, 57} {11, 34, 58} {11, 34, 59} {11, 34, 60} {11, 34, 61}
{11, 34, 62} {11, 34, 63} {11, 34, 64} {11, 34, 65} {11, 34, 66} {11, 35, 36} {11, 35, 37} {11, 35, 38} {11, 35, 39}
{11, 35, 40} {11, 35, 41} {11, 35, 42} {11, 35, 43} {11, 35, 44} {11, 35, 45} {11, 35, 46} {11, 35, 47} {11, 35, 48}
{11, 35, 49} {11, 35, 50} {11, 35, 51} {11, 35, 52} {11, 35, 53} {11, 35, 54} {11, 35, 55} {11, 35, 56} {11, 35, 57}
{11, 35, 58} {11, 35, 59} {11, 35, 60} {11, 35, 61} {11, 35, 62} {11, 35, 63} {11, 35, 64} {11, 35, 65} {11, 35, 66}
{11, 36, 37} {11, 36, 38} {11, 36, 39} {11, 36, 40} {11, 36, 41} {11, 36, 42} {11, 36, 43} {11, 36, 44} {11, 36, 45}
{11, 36, 46} {11, 36, 47} {11, 36, 48} {11, 36, 49} {11, 36, 50} {11, 36, 51} {11, 36, 52} {11, 36, 53} {11, 36, 54}
{11, 36, 55} {11, 36, 56} {11, 36, 57} {11, 36, 58} {11, 36, 59} {11, 36, 60} {11, 36, 61} {11, 36, 62} {11, 36, 63}
{11, 36, 64} {11, 36, 65} {11, 36, 66} {11, 37, 38} {11, 37, 39} {11, 37, 40} {11, 37, 41} {11, 37, 42} {11, 37, 43}
{11, 37, 44} {11, 37, 45} {11, 37, 46} {11, 37, 47} {11, 37, 48} {11, 37, 49} {11, 37, 50} {11, 37, 51} {11, 37, 52}
{11, 37, 53} {11, 37, 54} {11, 37, 55} {11, 37, 56} {11, 37, 57} {11, 37, 58} {11, 37, 59} {11, 37, 60} {11, 37, 61}
{11, 37, 62} {11, 37, 63} {11, 37, 64} {11, 37, 65} {11, 37, 66} {11, 38, 39} {11, 38, 40} {11, 38, 41} {11, 38, 42}
{11, 38, 43} {11, 38, 44} {11, 38, 45} {11, 38, 46} {11, 38, 47} {11, 38, 48} {11, 38, 49} {11, 38, 50} {11, 38, 51}
{11, 38, 52} {11, 38, 53} {11, 38, 54} {11, 38, 55} {11, 38, 56} {11, 38, 57} {11, 38, 58} {11, 38, 59} {11, 38, 60}
{11, 38, 61} {11, 38, 62} {11, 38, 63} {11, 38, 64} {11, 38, 65} {11, 38, 66} {11, 39, 40} {11, 39, 41} {11, 39, 42}
{11, 39, 43} {11, 39, 44} {11, 39, 45} {11, 39, 46} {11, 39, 47} {11, 39, 48} {11, 39, 49} {11, 39, 50} {11, 39, 51}
{11, 39, 52} {11, 39, 53} {11, 39, 54} {11, 39, 55} {11, 39, 56} {11, 39, 57} {11, 39, 58} {11, 39, 59} {11, 39, 60}
{11, 39, 61} {11, 39, 62} {11, 39, 63} {11, 39, 64} {11, 39, 65} {11, 39, 66} {11, 40, 41} {11, 40, 42} {11, 40, 43}
{11, 40, 44} {11, 40, 45} {11, 40, 46} {11, 40, 47} {11, 40, 48} {11, 40, 49} {11, 40, 50} {11, 40, 51} {11, 40, 52}
{11, 40, 53} {11, 40, 54} {11, 40, 55} {11, 40, 56} {11, 40, 57} {11, 40, 58} {11, 40, 59} {11, 40, 60} {11, 40, 61}
{11, 40, 62} {11, 40, 63} {11, 40, 64} {11, 40, 65} {11, 40, 66} {11, 41, 42} {11, 41, 43} {11, 41, 44} {11, 41, 45}
{11, 41, 46} {11, 41, 47} {11, 41, 48} {11, 41, 49} {11, 41, 50} {11, 41, 51} {11, 41, 52} {11, 41, 53} {11, 41, 54}
{11, 41, 55} {11, 41, 56} {11, 41, 57} {11, 41, 58} {11, 41, 59} {11, 41, 60} {11, 41, 61} {11, 41, 62} {11, 41, 63}
{11, 41, 64} {11, 41, 65} {11, 41, 66} {11, 42, 43} {11, 42, 44} {11, 42, 45} {11, 42, 46} {11, 42, 47} {11, 42, 48}
{11, 42, 49} {11, 42, 50} {11, 42, 51} {11, 42, 52} {11, 42, 53} {11, 42, 54} {11, 42, 55} {11, 42, 56} {11, 42, 57}
{11, 42, 58} {11, 42, 59} {11, 42, 60} {11, 42, 61} {11, 42, 62} {11, 42, 63} {11, 42, 64} {11, 42, 65} {11, 42, 66}
{11, 43, 44} {11, 43, 45} {11, 43, 46} {11, 43, 47} {11, 43, 48} {11, 43, 49} {11, 43, 50} {11, 43, 51} {11, 43, 52}
{11, 43, 53} {11, 43, 54} {11, 43, 55} {11, 43, 56} {11, 43, 57} {11, 43, 58} {11, 43, 59} {11, 43, 60} {11, 43, 61}
{11, 43, 62} {11, 43, 63} {11, 43, 64} {11, 43, 65} {11, 43, 66} {11, 44, 45} {11, 44, 46} {11, 44, 47} {11, 44, 48}
{11, 44, 49} {11, 44, 50} {11, 44, 51} {11, 44, 52} {11, 44, 53} {11, 44, 54} {11, 44, 55} {11, 44, 56} {11, 44, 57}
{11, 44, 58} {11, 44, 59} {11, 44, 60} {11, 44, 61} {11, 44, 62} {11, 44, 63} {11, 44, 64} {11, 44, 65} {11, 44, 66}
{11, 45, 46} {11, 45, 47} {11, 45, 48} {11, 45, 49} {11, 45, 50} {11, 45, 51} {11, 45, 52} {11, 45, 53} {11, 45, 54}
{11, 45, 55} {11, 45, 56} {11, 45, 57} {11, 45, 58} {11, 45, 59} {11, 45, 60} {11, 45, 61} {11, 45, 62} {11, 45, 63}
{11, 45, 64} {11, 45, 65} {11, 45, 66} {11, 46, 47} {11, 46, 48} {11, 46, 49} {11, 46, 50} {11, 46, 51} {11, 46, 52}
{11, 46, 53} {11, 46, 54} {11, 46, 55} {11, 46, 56} {11, 46, 57} {11, 46, 58} {11, 46, 59} {11, 46, 60} {11, 46, 61}
{11, 46, 62} {11, 46, 63} {11, 46, 64} {11, 46, 65} {11, 46, 66} {11, 47, 48} {11, 47, 49} {11, 47, 50} {11, 47, 51}
{11, 47, 52} {11, 47, 53} {11, 47, 54} {11, 47, 55} {11, 47, 56} {11, 47, 57} {11, 47, 58} {11, 47, 59} {11, 47, 60}
{11, 47, 61} {11, 47, 62} {11, 47, 63} {11, 47, 64} {11, 47, 65} {11, 47, 66} {11, 48, 49} {11, 48, 50} {11, 48, 51}
{11, 48, 52} {11, 48, 53} {11, 48, 54} {11, 48, 55} {11, 48, 56} {11, 48, 57} {11, 48, 58} {11, 48, 59} {11, 48, 60}
{11, 48, 61} {11, 48, 62} {11, 48, 63} {11, 48, 64} {11, 48, 65} {11, 48, 66} {11, 49, 50} {11, 49, 51} {11, 49, 52}
{11, 49, 53} {11, 49, 54} {11, 49, 55} {11, 49, 56} {11, 49, 57} {11, 49, 58} {11, 49, 59} {11, 49, 60} {11, 49, 61}
{11, 49, 62} {11, 49, 63} {11, 49, 64} {11, 49, 65} {11, 49, 66} {11, 50, 51} {11, 50, 52} {11, 50, 53} {11, 50, 54}
{11, 50, 55} {11, 50, 56} {11, 50, 57} {11, 50, 58} {11, 50, 59} {11, 50, 60} {11, 50, 61} {11, 50, 62} {11, 50, 63}
{11, 50, 64} {11, 50, 65} {11, 50, 66} {11, 51, 52} {11, 51, 53} {11, 51, 54} {11, 51, 55} {11, 51, 56} {11, 51, 57}
{11, 51, 58} {11, 51, 59} {11, 51, 60} {11, 51, 61} {11, 51, 62} {11, 51, 63} {11, 51, 64} {11, 51, 65} {11, 51, 66}
{11, 52, 53} {11, 52, 54} {11, 52, 55} {11, 52, 56} {11, 52, 57} {11, 52, 58} {11, 52, 59} {11, 52, 60} {11, 52, 61}
{11, 52, 62} {11, 52, 63} {11, 52, 64} {11, 52, 65} {11, 52, 66} {11, 53, 54} {11, 53, 55} {11, 53, 56} {11, 53, 57}
{11, 53, 58} {11, 53, 59} {11, 53, 60} {11, 53, 61} {11, 53, 62} {11, 53, 63} {11, 53, 64} {11, 53, 65} {11, 53, 66}
{11, 54, 55} {11, 54, 56} {11, 54, 57} {11, 54, 58} {11, 54, 59} {11, 54, 60} {11, 54, 61} {11, 54, 62} {11, 54, 63}
{11, 54, 64} {11, 54, 65} {11, 54, 66} {11, 55, 56} {11, 55, 57} {11, 55, 58} {11, 55, 59} {11, 55, 60} {11, 55, 61}
{11, 55, 62} {11, 55, 63} {11, 55, 64} {11, 55, 65} {11, 55, 66} {11, 56, 57} {11, 56, 58} {11, 56, 59} {11, 56, 60}
{11, 56, 61} {11, 56, 62} {11, 56, 63} {11, 56, 64} {11, 56, 65} {11, 56, 66} {11, 57, 58} {11, 57, 59} {11, 57, 60}
{11, 57, 61} {11, 57, 62} {11, 57, 63} {11, 57, 64} {11, 57, 65} {11, 57, 66} {11, 58, 59} {11, 58, 60} {11, 58, 61}
{11, 58, 62} {11, 58, 63} {11, 58, 64} {11, 58, 65} {11, 58, 66} {11, 59, 60} {11, 59, 61} {11, 59, 62} {11, 59, 63}
{11, 59, 64} {11, 59, 65} {11, 59, 66} {11, 60, 61} {11, 60, 62} {11, 60, 63} {11, 60, 64} {11, 60, 65} {11, 60, 66}
{11, 61, 62} {11, 61, 63} {11, 61, 64} {11, 61, 65} {11, 61, 66} {11, 62, 63} {11, 62, 64} {11, 62, 65} {11, 62, 66}
{11, 63, 64} {11, 63, 65} {11, 63, 66} {11, 64, 65} {11, 64, 66} {11, 65, 66} {12, 13, 14} {12, 13, 15} {12, 13, 16}
{12, 13, 17} {12, 13, 18} {12, 13, 19} {12, 13, 20} {12, 13, 21} {12, 13, 22} {12, 13, 23} {12, 13, 24} {12, 13, 25}
{12, 13, 26} {12, 13, 27} {12, 13, 28} {12, 13, 29} {12, 13, 30} {12, 13, 31} {12, 13, 32} {12, 13, 33} {12, 13, 34}
{12, 13, 35} {12, 13, 36} {12, 13, 37} {12, 13, 38} {12, 13, 39} {12, 13, 40} {12, 13, 41} {12, 13, 42} {12, 13, 43}
{12, 13, 44} {12, 13, 45} {12, 13, 46} {12, 13, 47} {12, 13, 48} {12, 13, 49} {12, 13, 50} {12, 13, 51} {12, 13, 52}
{12, 13, 53} {12, 13, 54} {12, 13, 55} {12, 13, 56} {12, 13, 57} {12, 13, 58} {12, 13, 59} {12, 13, 60} {12, 13, 61}
{12, 13, 62} {12, 13, 63} {12, 13, 64} {12, 13, 65} {12, 13, 66} {12, 14, 15} {12, 14, 16} {12, 14, 17} {12, 14, 18}
{12, 14, 19} {12, 14, 20} {12, 14, 21} {12, 14, 22} {12, 14, 23} {12, 14, 24} {12, 14, 25} {12, 14, 26} {12, 14, 27}
{12, 14, 28} {12, 14, 29} {12, 14, 30} {12, 14, 31} {12, 14, 32} {12, 14, 33} {12, 14, 34} {12, 14, 35} {12, 14, 36}
{12, 14, 37} {12, 14, 38} {12, 14, 39} {12, 14, 40} {12, 14, 41} {12, 14, 42} {12, 14, 43} {12, 14, 44} {12, 14, 45}
{12, 14, 46} {12, 14, 47} {12, 14, 48} {12, 14, 49} {12, 14, 50} {12, 14, 51} {12, 14, 52} {12, 14, 53} {12, 14, 54}
{12, 14, 55} {12, 14, 56} {12, 14, 57} {12, 14, 58} {12, 14, 59} {12, 14, 60} {12, 14, 61} {12, 14, 62} {12, 14, 63}
{12, 14, 64} {12, 14, 65} {12, 14, 66} {12, 15, 16} {12, 15, 17} {12, 15, 18} {12, 15, 19} {12, 15, 20} {12, 15, 21}
{12, 15, 22} {12, 15, 23} {12, 15, 24} {12, 15, 25} {12, 15, 26} {12, 15, 27} {12, 15, 28} {12, 15, 29} {12, 15, 30}
{12, 15, 31} {12, 15, 32} {12, 15, 33} {12, 15, 34} {12, 15, 35} {12, 15, 36} {12, 15, 37} {12, 15, 38} {12, 15, 39}
{12, 15, 40} {12, 15, 41} {12, 15, 42} {12, 15, 43} {12, 15, 44} {12, 15, 45} {12, 15, 46} {12, 15, 47} {12, 15, 48}

TABLE 3A-continued

| | | | | | | | |
|---|---|---|---|---|---|---|---|
| {12, 15, 49} | {12, 15, 50} | {12, 15, 51} | {12, 15, 52} | {12, 15, 53} | {12, 15, 54} | {12, 15, 55} | {12, 15, 56} | {12, 15, 57} |
| {12, 15, 58} | {12, 15, 59} | {12, 15, 60} | {12, 15, 61} | {12, 15, 62} | {12, 15, 63} | {12, 15, 64} | {12, 15, 65} | {12, 15, 66} |
| {12, 16, 17} | {12, 16, 18} | {12, 16, 19} | {12, 16, 20} | {12, 16, 21} | {12, 16, 22} | {12, 16, 23} | {12, 16, 24} | {12, 16, 25} |
| {12, 16, 26} | {12, 16, 27} | {12, 16, 28} | {12, 16, 29} | {12, 16, 30} | {12, 16, 31} | {12, 16, 32} | {12, 16, 33} | {12, 16, 34} |
| {12, 16, 35} | {12, 16, 36} | {12, 16, 37} | {12, 16, 38} | {12, 16, 39} | {12, 16, 40} | {12, 16, 41} | {12, 16, 42} | {12, 16, 43} |
| {12, 16, 44} | {12, 16, 45} | {12, 16, 46} | {12, 16, 47} | {12, 16, 48} | {12, 16, 49} | {12, 16, 50} | {12, 16, 51} | {12, 16, 52} |
| {12, 16, 53} | {12, 16, 54} | {12, 16, 55} | {12, 16, 56} | {12, 16, 57} | {12, 16, 58} | {12, 16, 59} | {12, 16, 60} | {12, 16, 61} |
| {12, 16, 62} | {12, 16, 63} | {12, 16, 64} | {12, 16, 65} | {12, 16, 66} | {12, 17, 18} | {12, 17, 19} | {12, 17, 20} | {12, 17, 21} |
| {12, 17, 22} | {12, 17, 23} | {12, 17, 24} | {12, 17, 25} | {12, 17, 26} | {12, 17, 27} | {12, 17, 28} | {12, 17, 29} | {12, 17, 30} |
| {12, 17, 31} | {12, 17, 32} | {12, 17, 33} | {12, 17, 34} | {12, 17, 35} | {12, 17, 36} | {12, 17, 37} | {12, 17, 38} | {12, 17, 39} |
| {12, 17, 40} | {12, 17, 41} | {12, 17, 42} | {12, 17, 43} | {12, 17, 44} | {12, 17, 45} | {12, 17, 46} | {12, 17, 47} | {12, 17, 48} |
| {12, 17, 49} | {12, 17, 50} | {12, 17, 51} | {12, 17, 52} | {12, 17, 53} | {12, 17, 54} | {12, 17, 55} | {12, 17, 56} | {12, 17, 57} |
| {12, 17, 58} | {12, 17, 59} | {12, 17, 60} | {12, 17, 61} | {12, 17, 62} | {12, 17, 63} | {12, 17, 64} | {12, 17, 65} | {12, 17, 66} |
| {12, 18, 19} | {12, 18, 20} | {12, 18, 21} | {12, 18, 22} | {12, 18, 23} | {12, 18, 24} | {12, 18, 25} | {12, 18, 26} | {12, 18, 27} |
| {12, 18, 28} | {12, 18, 29} | {12, 18, 30} | {12, 18, 31} | {12, 18, 32} | {12, 18, 33} | {12, 18, 34} | {12, 18, 35} | {12, 18, 36} |
| {12, 18, 37} | {12, 18, 38} | {12, 18, 39} | {12, 18, 40} | {12, 18, 41} | {12, 18, 42} | {12, 18, 43} | {12, 18, 44} | {12, 18, 45} |
| {12, 18, 46} | {12, 18, 47} | {12, 18, 48} | {12, 18, 49} | {12, 18, 50} | {12, 18, 51} | {12, 18, 52} | {12, 18, 53} | {12, 18, 54} |
| {12, 18, 55} | {12, 18, 56} | {12, 18, 57} | {12, 18, 58} | {12, 18, 59} | {12, 18, 60} | {12, 18, 61} | {12, 18, 62} | {12, 18, 63} |
| {12, 18, 64} | {12, 18, 65} | {12, 18, 66} | {12, 19, 20} | {12, 19, 21} | {12, 19, 22} | {12, 19, 23} | {12, 19, 24} | {12, 19, 25} |
| {12, 19, 26} | {12, 19, 27} | {12, 19, 28} | {12, 19, 29} | {12, 19, 30} | {12, 19, 31} | {12, 19, 32} | {12, 19, 33} | {12, 19, 34} |
| {12, 19, 35} | {12, 19, 36} | {12, 19, 37} | {12, 19, 38} | {12, 19, 39} | {12, 19, 40} | {12, 19, 41} | {12, 19, 42} | {12, 19, 43} |
| {12, 19, 44} | {12, 19, 45} | {12, 19, 46} | {12, 19, 47} | {12, 19, 48} | {12, 19, 49} | {12, 19, 50} | {12, 19, 51} | {12, 19, 52} |
| {12, 19, 53} | {12, 19, 54} | {12, 19, 55} | {12, 19, 56} | {12, 19, 57} | {12, 19, 58} | {12, 19, 59} | {12, 19, 60} | {12, 19, 61} |
| {12, 19, 62} | {12, 19, 63} | {12, 19, 64} | {12, 19, 65} | {12, 19, 66} | {12, 20, 21} | {12, 20, 22} | {12, 20, 23} | {12, 20, 24} |
| {12, 20, 25} | {12, 20, 26} | {12, 20, 27} | {12, 20, 28} | {12, 20, 29} | {12, 20, 30} | {12, 20, 31} | {12, 20, 32} | {12, 20, 33} |
| {12, 20, 34} | {12, 20, 35} | {12, 20, 36} | {12, 20, 37} | {12, 20, 38} | {12, 20, 39} | {12, 20, 40} | {12, 20, 41} | {12, 20, 42} |
| {12, 20, 43} | {12, 20, 44} | {12, 20, 45} | {12, 20, 46} | {12, 20, 47} | {12, 20, 48} | {12, 20, 49} | {12, 20, 50} | {12, 20, 51} |
| {12, 20, 52} | {12, 20, 53} | {12, 20, 54} | {12, 20, 55} | {12, 20, 56} | {12, 20, 57} | {12, 20, 58} | {12, 20, 59} | {12, 20, 60} |
| {12, 20, 61} | {12, 20, 62} | {12, 20, 63} | {12, 20, 64} | {12, 20, 65} | {12, 20, 66} | {12, 21, 22} | {12, 21, 23} | {12, 21, 24} |
| {12, 21, 25} | {12, 21, 26} | {12, 21, 27} | {12, 21, 28} | {12, 21, 29} | {12, 21, 30} | {12, 21, 31} | {12, 21, 32} | {12, 21, 33} |
| {12, 21, 34} | {12, 21, 35} | {12, 21, 36} | {12, 21, 37} | {12, 21, 38} | {12, 21, 39} | {12, 21, 40} | {12, 21, 41} | {12, 21, 42} |
| {12, 21, 43} | {12, 21, 44} | {12, 21, 45} | {12, 21, 46} | {12, 21, 47} | {12, 21, 48} | {12, 21, 49} | {12, 21, 50} | {12, 21, 51} |
| {12, 21, 52} | {12, 21, 53} | {12, 21, 54} | {12, 21, 55} | {12, 21, 56} | {12, 21, 57} | {12, 21, 58} | {12, 21, 59} | {12, 21, 60} |
| {12, 21, 61} | {12, 21, 62} | {12, 21, 63} | {12, 21, 64} | {12, 21, 65} | {12, 21, 66} | {12, 22, 23} | {12, 22, 24} | {12, 22, 25} |
| {12, 22, 26} | {12, 22, 27} | {12, 22, 28} | {12, 22, 29} | {12, 22, 30} | {12, 22, 31} | {12, 22, 32} | {12, 22, 33} | {12, 22, 34} |
| {12, 22, 35} | {12, 22, 36} | {12, 22, 37} | {12, 22, 38} | {12, 22, 39} | {12, 22, 40} | {12, 22, 41} | {12, 22, 42} | {12, 22, 43} |
| {12, 22, 44} | {12, 22, 45} | {12, 22, 46} | {12, 22, 47} | {12, 22, 48} | {12, 22, 49} | {12, 22, 50} | {12, 22, 51} | {12, 22, 52} |
| {12, 22, 53} | {12, 22, 54} | {12, 22, 55} | {12, 22, 56} | {12, 22, 57} | {12, 22, 58} | {12, 22, 59} | {12, 22, 60} | {12, 22, 61} |
| {12, 22, 62} | {12, 22, 63} | {12, 22, 64} | {12, 22, 65} | {12, 22, 66} | {12, 23, 24} | {12, 23, 25} | {12, 23, 26} | {12, 23, 27} |
| {12, 23, 28} | {12, 23, 29} | {12, 23, 30} | {12, 23, 31} | {12, 23, 32} | {12, 23, 33} | {12, 23, 34} | {12, 23, 35} | {12, 23, 36} |
| {12, 23, 37} | {12, 23, 38} | {12, 23, 39} | {12, 23, 40} | {12, 23, 41} | {12, 23, 42} | {12, 23, 43} | {12, 23, 44} | {12, 23, 45} |
| {12, 23, 46} | {12, 23, 47} | {12, 23, 48} | {12, 23, 49} | {12, 23, 50} | {12, 23, 51} | {12, 23, 52} | {12, 23, 53} | {12, 23, 54} |
| {12, 23, 55} | {12, 23, 56} | {12, 23, 57} | {12, 23, 58} | {12, 23, 59} | {12, 23, 60} | {12, 23, 61} | {12, 23, 62} | {12, 23, 63} |
| {12, 23, 64} | {12, 23, 65} | {12, 23, 66} | {12, 24, 25} | {12, 24, 26} | {12, 24, 27} | {12, 24, 28} | {12, 24, 29} | {12, 24, 30} |
| {12, 24, 31} | {12, 24, 32} | {12, 24, 33} | {12, 24, 34} | {12, 24, 35} | {12, 24, 36} | {12, 24, 37} | {12, 24, 38} | {12, 24, 39} |
| {12, 24, 40} | {12, 24, 41} | {12, 24, 42} | {12, 24, 43} | {12, 24, 44} | {12, 24, 45} | {12, 24, 46} | {12, 24, 47} | {12, 24, 48} |
| {12, 24, 49} | {12, 24, 50} | {12, 24, 51} | {12, 24, 52} | {12, 24, 53} | {12, 24, 54} | {12, 24, 55} | {12, 24, 56} | {12, 24, 57} |
| {12, 24, 58} | {12, 24, 59} | {12, 24, 60} | {12, 24, 61} | {12, 24, 62} | {12, 24, 63} | {12, 24, 64} | {12, 24, 65} | {12, 24, 66} |
| {12, 25, 26} | {12, 25, 27} | {12, 25, 28} | {12, 25, 29} | {12, 25, 30} | {12, 25, 31} | {12, 25, 32} | {12, 25, 33} | {12, 25, 34} |
| {12, 25, 35} | {12, 25, 36} | {12, 25, 37} | {12, 25, 38} | {12, 25, 39} | {12, 25, 40} | {12, 25, 41} | {12, 25, 42} | {12, 25, 43} |
| {12, 25, 44} | {12, 25, 45} | {12, 25, 46} | {12, 25, 47} | {12, 25, 48} | {12, 25, 49} | {12, 25, 50} | {12, 25, 51} | {12, 25, 52} |
| {12, 25, 53} | {12, 25, 54} | {12, 25, 55} | {12, 25, 56} | {12, 25, 57} | {12, 25, 58} | {12, 25, 59} | {12, 25, 60} | {12, 25, 61} |
| {12, 25, 62} | {12, 25, 63} | {12, 25, 64} | {12, 25, 65} | {12, 25, 66} | {12, 26, 27} | {12, 26, 28} | {12, 26, 29} | {12, 26, 30} |
| {12, 26, 31} | {12, 26, 32} | {12, 26, 33} | {12, 26, 34} | {12, 26, 35} | {12, 26, 36} | {12, 26, 37} | {12, 26, 38} | {12, 26, 39} |
| {12, 26, 40} | {12, 26, 41} | {12, 26, 42} | {12, 26, 43} | {12, 26, 44} | {12, 26, 45} | {12, 26, 46} | {12, 26, 47} | {12, 26, 48} |
| {12, 26, 49} | {12, 26, 50} | {12, 26, 51} | {12, 26, 52} | {12, 26, 53} | {12, 26, 54} | {12, 26, 55} | {12, 26, 56} | {12, 26, 57} |
| {12, 26, 58} | {12, 26, 59} | {12, 26, 60} | {12, 26, 61} | {12, 26, 62} | {12, 26, 63} | {12, 26, 64} | {12, 26, 65} | {12, 26, 66} |
| {12, 27, 28} | {12, 27, 29} | {12, 27, 30} | {12, 27, 31} | {12, 27, 32} | {12, 27, 33} | {12, 27, 34} | {12, 27, 35} | {12, 27, 36} |
| {12, 27, 37} | {12, 27, 38} | {12, 27, 39} | {12, 27, 40} | {12, 27, 41} | {12, 27, 42} | {12, 27, 43} | {12, 27, 44} | {12, 27, 45} |
| {12, 27, 46} | {12, 27, 47} | {12, 27, 48} | {12, 27, 49} | {12, 27, 50} | {12, 27, 51} | {12, 27, 52} | {12, 27, 53} | {12, 27, 54} |
| {12, 27, 55} | {12, 27, 56} | {12, 27, 57} | {12, 27, 58} | {12, 27, 59} | {12, 27, 60} | {12, 27, 61} | {12, 27, 62} | {12, 27, 63} |
| {12, 27, 64} | {12, 27, 65} | {12, 27, 66} | {12, 28, 29} | {12, 28, 30} | {12, 28, 31} | {12, 28, 32} | {12, 28, 33} | {12, 28, 34} |
| {12, 28, 35} | {12, 28, 36} | {12, 28, 37} | {12, 28, 38} | {12, 28, 39} | {12, 28, 40} | {12, 28, 41} | {12, 28, 42} | {12, 28, 43} |
| {12, 28, 44} | {12, 28, 45} | {12, 28, 46} | {12, 28, 47} | {12, 28, 48} | {12, 28, 49} | {12, 28, 50} | {12, 28, 51} | {12, 28, 52} |
| {12, 28, 53} | {12, 28, 54} | {12, 28, 55} | {12, 28, 56} | {12, 28, 57} | {12, 28, 58} | {12, 28, 59} | {12, 28, 60} | {12, 28, 61} |
| {12, 28, 62} | {12, 28, 63} | {12, 28, 64} | {12, 28, 65} | {12, 28, 66} | {12, 29, 30} | {12, 29, 31} | {12, 29, 32} | {12, 29, 33} |
| {12, 29, 34} | {12, 29, 35} | {12, 29, 36} | {12, 29, 37} | {12, 29, 38} | {12, 29, 39} | {12, 29, 40} | {12, 29, 41} | {12, 29, 42} |
| {12, 29, 43} | {12, 29, 44} | {12, 29, 45} | {12, 29, 46} | {12, 29, 47} | {12, 29, 48} | {12, 29, 49} | {12, 29, 50} | {12, 29, 51} |
| {12, 29, 52} | {12, 29, 53} | {12, 29, 54} | {12, 29, 55} | {12, 29, 56} | {12, 29, 57} | {12, 29, 58} | {12, 29, 59} | {12, 29, 60} |
| {12, 29, 61} | {12, 29, 62} | {12, 29, 63} | {12, 29, 64} | {12, 29, 65} | {12, 29, 66} | {12, 30, 31} | {12, 30, 32} | {12, 30, 33} |
| {12, 30, 34} | {12, 30, 35} | {12, 30, 36} | {12, 30, 37} | {12, 30, 38} | {12, 30, 39} | {12, 30, 40} | {12, 30, 41} | {12, 30, 42} |
| {12, 30, 43} | {12, 30, 44} | {12, 30, 45} | {12, 30, 46} | {12, 30, 47} | {12, 30, 48} | {12, 30, 49} | {12, 30, 50} | {12, 30, 51} |
| {12, 30, 52} | {12, 30, 53} | {12, 30, 54} | {12, 30, 55} | {12, 30, 56} | {12, 30, 57} | {12, 30, 58} | {12, 30, 59} | {12, 30, 60} |
| {12, 30, 61} | {12, 30, 62} | {12, 30, 63} | {12, 30, 64} | {12, 30, 65} | {12, 30, 66} | {12, 31, 32} | {12, 31, 33} | {12, 31, 34} |
| {12, 31, 35} | {12, 31, 36} | {12, 31, 37} | {12, 31, 38} | {12, 31, 39} | {12, 31, 40} | {12, 31, 41} | {12, 31, 42} | {12, 31, 43} |
| {12, 31, 44} | {12, 31, 45} | {12, 31, 46} | {12, 31, 47} | {12, 31, 48} | {12, 31, 49} | {12, 31, 50} | {12, 31, 51} | {12, 31, 52} |
| {12, 31, 53} | {12, 31, 54} | {12, 31, 55} | {12, 31, 56} | {12, 31, 57} | {12, 31, 58} | {12, 31, 59} | {12, 31, 60} | {12, 31, 61} |
| {12, 31, 62} | {12, 31, 63} | {12, 31, 64} | {12, 31, 65} | {12, 31, 66} | {12, 32, 33} | {12, 32, 34} | {12, 32, 35} | {12, 32, 36} |
| {12, 32, 37} | {12, 32, 38} | {12, 32, 39} | {12, 32, 40} | {12, 32, 41} | {12, 32, 42} | {12, 32, 43} | {12, 32, 44} | {12, 32, 45} |
| {12, 32, 46} | {12, 32, 47} | {12, 32, 48} | {12, 32, 49} | {12, 32, 50} | {12, 32, 51} | {12, 32, 52} | {12, 32, 53} | {12, 32, 54} |

TABLE 3A-continued

{12, 32, 55} {12, 32, 56} {12, 32, 57} {12, 32, 58} {12, 32, 59} {12, 32, 60} {12, 32, 61} {12, 32, 62} {12, 32, 63}
{12, 32, 64} {12, 32, 65} {12, 32, 66} {12, 33, 34} {12, 33, 35} {12, 33, 36} {12, 33, 37} {12, 33, 38} {12, 33, 39}
{12, 33, 40} {12, 33, 41} {12, 33, 42} {12, 33, 43} {12, 33, 44} {12, 33, 45} {12, 33, 46} {12, 33, 47} {12, 33, 48}
{12, 33, 49} {12, 33, 50} {12, 33, 51} {12, 33, 52} {12, 33, 53} {12, 33, 54} {12, 33, 55} {12, 33, 56} {12, 33, 57}
{12, 33, 58} {12, 33, 59} {12, 33, 60} {12, 33, 61} {12, 33, 62} {12, 33, 63} {12, 33, 64} {12, 33, 65} {12, 33, 66}
{12, 34, 35} {12, 34, 36} {12, 34, 37} {12, 34, 38} {12, 34, 39} {12, 34, 40} {12, 34, 41} {12, 34, 42} {12, 34, 43}
{12, 34, 44} {12, 34, 45} {12, 34, 46} {12, 34, 47} {12, 34, 48} {12, 34, 49} {12, 34, 50} {12, 34, 51} {12, 34, 52}
{12, 34, 53} {12, 34, 54} {12, 34, 55} {12, 34, 56} {12, 34, 57} {12, 34, 58} {12, 34, 59} {12, 34, 60} {12, 34, 61}
{12, 34, 62} {12, 34, 63} {12, 34, 64} {12, 34, 65} {12, 34, 66} {12, 35, 36} {12, 35, 37} {12, 35, 38} {12, 35, 39}
{12, 35, 40} {12, 35, 41} {12, 35, 42} {12, 35, 43} {12, 35, 44} {12, 35, 45} {12, 35, 46} {12, 35, 47} {12, 35, 48}
{12, 35, 49} {12, 35, 50} {12, 35, 51} {12, 35, 52} {12, 35, 53} {12, 35, 54} {12, 35, 55} {12, 35, 56} {12, 35, 57}
{12, 35, 58} {12, 35, 59} {12, 35, 60} {12, 35, 61} {12, 35, 62} {12, 35, 63} {12, 35, 64} {12, 35, 65} {12, 35, 66}
{12, 36, 37} {12, 36, 38} {12, 36, 39} {12, 36, 40} {12, 36, 41} {12, 36, 42} {12, 36, 43} {12, 36, 44} {12, 36, 45}
{12, 36, 46} {12, 36, 47} {12, 36, 48} {12, 36, 49} {12, 36, 50} {12, 36, 51} {12, 36, 52} {12, 36, 53} {12, 36, 54}
{12, 36, 55} {12, 36, 56} {12, 36, 57} {12, 36, 58} {12, 36, 59} {12, 36, 60} {12, 36, 61} {12, 36, 62} {12, 36, 63}
{12, 36, 64} {12, 36, 65} {12, 36, 66} {12, 37, 38} {12, 37, 39} {12, 37, 40} {12, 37, 41} {12, 37, 42} {12, 37, 43}
{12, 37, 44} {12, 37, 45} {12, 37, 46} {12, 37, 47} {12, 37, 48} {12, 37, 49} {12, 37, 50} {12, 37, 51} {12, 37, 52}
{12, 37, 53} {12, 37, 54} {12, 37, 55} {12, 37, 56} {12, 37, 57} {12, 37, 58} {12, 37, 59} {12, 37, 60} {12, 37, 61}
{12, 37, 62} {12, 37, 63} {12, 37, 64} {12, 37, 65} {12, 37, 66} {12, 38, 39} {12, 38, 40} {12, 38, 41} {12, 38, 42}
{12, 38, 43} {12, 38, 44} {12, 38, 45} {12, 38, 46} {12, 38, 47} {12, 38, 48} {12, 38, 49} {12, 38, 50} {12, 38, 51}
{12, 38, 52} {12, 38, 53} {12, 38, 54} {12, 38, 55} {12, 38, 56} {12, 38, 57} {12, 38, 58} {12, 38, 59} {12, 38, 60}
{12, 38, 61} {12, 38, 62} {12, 38, 63} {12, 38, 64} {12, 38, 65} {12, 38, 66} {12, 39, 40} {12, 39, 41} {12, 39, 42}
{12, 39, 43} {12, 39, 44} {12, 39, 45} {12, 39, 46} {12, 39, 47} {12, 39, 48} {12, 39, 49} {12, 39, 50} {12, 39, 51}
{12, 39, 52} {12, 39, 53} {12, 39, 54} {12, 39, 55} {12, 39, 56} {12, 39, 57} {12, 39, 58} {12, 39, 59} {12, 39, 60}
{12, 39, 61} {12, 39, 62} {12, 39, 63} {12, 39, 64} {12, 39, 65} {12, 39, 66} {12, 40, 41} {12, 40, 42} {12, 40, 43}
{12, 40, 44} {12, 40, 45} {12, 40, 46} {12, 40, 47} {12, 40, 48} {12, 40, 49} {12, 40, 50} {12, 40, 51} {12, 40, 52}
{12, 40, 53} {12, 40, 54} {12, 40, 55} {12, 40, 56} {12, 40, 57} {12, 40, 58} {12, 40, 59} {12, 40, 60} {12, 40, 61}
{12, 40, 62} {12, 40, 63} {12, 40, 64} {12, 40, 65} {12, 40, 66} {12, 41, 42} {12, 41, 43} {12, 41, 44} {12, 41, 45}
{12, 41, 46} {12, 41, 47} {12, 41, 48} {12, 41, 49} {12, 41, 50} {12, 41, 51} {12, 41, 52} {12, 41, 53} {12, 41, 54}
{12, 41, 55} {12, 41, 56} {12, 41, 57} {12, 41, 58} {12, 41, 59} {12, 41, 60} {12, 41, 61} {12, 41, 62} {12, 41, 63}
{12, 41, 64} {12, 41, 65} {12, 41, 66} {12, 42, 43} {12, 42, 44} {12, 42, 45} {12, 42, 46} {12, 42, 47} {12, 42, 48}
{12, 42, 49} {12, 42, 50} {12, 42, 51} {12, 42, 52} {12, 42, 53} {12, 42, 54} {12, 42, 55} {12, 42, 56} {12, 42, 57}
{12, 42, 58} {12, 42, 59} {12, 42, 60} {12, 42, 61} {12, 42, 62} {12, 42, 63} {12, 42, 64} {12, 42, 65} {12, 42, 66}
{12, 43, 44} {12, 43, 45} {12, 43, 46} {12, 43, 47} {12, 43, 48} {12, 43, 49} {12, 43, 50} {12, 43, 51} {12, 43, 52}
{12, 43, 53} {12, 43, 54} {12, 43, 55} {12, 43, 56} {12, 43, 57} {12, 43, 58} {12, 43, 59} {12, 43, 60} {12, 43, 61}
{12, 43, 62} {12, 43, 63} {12, 43, 64} {12, 43, 65} {12, 43, 66} {12, 44, 45} {12, 44, 46} {12, 44, 47} {12, 44, 48}
{12, 44, 49} {12, 44, 50} {12, 44, 51} {12, 44, 52} {12, 44, 53} {12, 44, 54} {12, 44, 55} {12, 44, 56} {12, 44, 57}
{12, 44, 58} {12, 44, 59} {12, 44, 60} {12, 44, 61} {12, 44, 62} {12, 44, 63} {12, 44, 64} {12, 44, 65} {12, 44, 66}
{12, 45, 46} {12, 45, 47} {12, 45, 48} {12, 45, 49} {12, 45, 50} {12, 45, 51} {12, 45, 52} {12, 45, 53} {12, 45, 54}
{12, 45, 55} {12, 45, 56} {12, 45, 57} {12, 45, 58} {12, 45, 59} {12, 45, 60} {12, 45, 61} {12, 45, 62} {12, 45, 63}
{12, 45, 64} {12, 45, 65} {12, 45, 66} {12, 46, 47} {12, 46, 48} {12, 46, 49} {12, 46, 50} {12, 46, 51} {12, 46, 52}
{12, 46, 53} {12, 46, 54} {12, 46, 55} {12, 46, 56} {12, 46, 57} {12, 46, 58} {12, 46, 59} {12, 46, 60} {12, 46, 61}
{12, 46, 62} {12, 46, 63} {12, 46, 64} {12, 46, 65} {12, 47, 48} {12, 47, 49} {12, 47, 50} {12, 47, 51}
{12, 47, 52} {12, 47, 53} {12, 47, 54} {12, 47, 55} {12, 47, 56} {12, 47, 57} {12, 47, 58} {12, 47, 59} {12, 47, 60}
{12, 47, 61} {12, 47, 62} {12, 47, 63} {12, 47, 64} {12, 47, 65} {12, 47, 66} {12, 48, 49} {12, 48, 50} {12, 48, 51}
{12, 48, 52} {12, 48, 53} {12, 48, 54} {12, 48, 55} {12, 48, 56} {12, 48, 57} {12, 48, 58} {12, 48, 59} {12, 48, 60}
{12, 48, 61} {12, 48, 62} {12, 48, 63} {12, 48, 64} {12, 48, 65} {12, 48, 66} {12, 49, 50} {12, 49, 51} {12, 49, 52}
{12, 49, 53} {12, 49, 54} {12, 49, 55} {12, 49, 56} {12, 49, 57} {12, 49, 58} {12, 49, 59} {12, 49, 60} {12, 49, 61}
{12, 49, 62} {12, 49, 63} {12, 49, 64} {12, 49, 65} {12, 49, 66} {12, 50, 51} {12, 50, 52} {12, 50, 53} {12, 50, 54}
{12, 50, 55} {12, 50, 56} {12, 50, 57} {12, 50, 58} {12, 50, 59} {12, 50, 60} {12, 50, 61} {12, 50, 62} {12, 50, 63}
{12, 50, 64} {12, 50, 65} {12, 50, 66} {12, 51, 52} {12, 51, 53} {12, 51, 54} {12, 51, 55} {12, 51, 56} {12, 51, 57}
{12, 51, 58} {12, 51, 59} {12, 51, 60} {12, 51, 61} {12, 51, 62} {12, 51, 63} {12, 51, 64} {12, 51, 65} {12, 51, 66}
{12, 52, 53} {12, 52, 54} {12, 52, 55} {12, 52, 56} {12, 52, 57} {12, 52, 58} {12, 52, 59} {12, 52, 60} {12, 52, 61}
{12, 52, 62} {12, 52, 63} {12, 52, 64} {12, 52, 65} {12, 53, 54} {12, 53, 55} {12, 53, 56} {12, 53, 57}
{12, 53, 58} {12, 53, 59} {12, 53, 60} {12, 53, 61} {12, 53, 62} {12, 53, 63} {12, 53, 64} {12, 53, 65} {12, 53, 66}
{12, 54, 55} {12, 54, 56} {12, 54, 57} {12, 54, 58} {12, 54, 59} {12, 54, 60} {12, 54, 61} {12, 54, 62} {12, 54, 63}
{12, 54, 64} {12, 54, 65} {12, 54, 66} {12, 55, 56} {12, 55, 57} {12, 55, 58} {12, 55, 59} {12, 55, 60} {12, 55, 61}
{12, 55, 62} {12, 55, 63} {12, 55, 64} {12, 55, 65} {12, 56, 57} {12, 56, 58} {12, 56, 59} {12, 56, 60}
{12, 56, 61} {12, 56, 62} {12, 56, 63} {12, 56, 64} {12, 56, 65} {12, 56, 66} {12, 57, 58} {12, 57, 59} {12, 57, 60}
{12, 57, 61} {12, 57, 62} {12, 57, 63} {12, 57, 64} {12, 57, 65} {12, 57, 66} {12, 58, 59} {12, 58, 60} {12, 58, 61}
{12, 58, 62} {12, 58, 63} {12, 58, 64} {12, 58, 65} {12, 58, 66} {12, 59, 60} {12, 59, 61} {12, 59, 62} {12, 59, 63}
{12, 59, 64} {12, 59, 65} {12, 59, 66} {12, 60, 61} {12, 60, 62} {12, 60, 63} {12, 60, 64} {12, 60, 65} {12, 60, 66}
{12, 61, 62} {12, 61, 63} {12, 61, 64} {12, 61, 65} {12, 61, 66} {12, 62, 63} {12, 62, 64} {12, 62, 65} {12, 62, 66}
{12, 63, 64} {12, 63, 65} {12, 63, 66} {12, 64, 65} {12, 64, 66} {12, 65, 66} {13, 14, 15} {13, 14, 16} {13, 14, 17}
{13, 14, 18} {13, 14, 19} {13, 14, 20} {13, 14, 21} {13, 14, 22} {13, 14, 23} {13, 14, 24} {13, 14, 25} {13, 14, 26}
{13, 14, 27} {13, 14, 28} {13, 14, 29} {13, 14, 30} {13, 14, 31} {13, 14, 32} {13, 14, 33} {13, 14, 34} {13, 14, 35}
{13, 14, 36} {13, 14, 37} {13, 14, 38} {13, 14, 39} {13, 14, 40} {13, 14, 41} {13, 14, 42} {13, 14, 43} {13, 14, 44}
{13, 14, 45} {13, 14, 46} {13, 14, 47} {13, 14, 48} {13, 14, 49} {13, 14, 50} {13, 14, 51} {13, 14, 52} {13, 14, 53}
{13, 14, 54} {13, 14, 55} {13, 14, 56} {13, 14, 57} {13, 14, 58} {13, 14, 59} {13, 14, 60} {13, 14, 61} {13, 14, 62}
{13, 14, 63} {13, 14, 64} {13, 14, 65} {13, 14, 66} {13, 15, 16} {13, 15, 17} {13, 15, 18} {13, 15, 19} {13, 15, 20}
{13, 15, 21} {13, 15, 22} {13, 15, 23} {13, 15, 24} {13, 15, 25} {13, 15, 26} {13, 15, 27} {13, 15, 28} {13, 15, 29}
{13, 15, 30} {13, 15, 31} {13, 15, 32} {13, 15, 33} {13, 15, 34} {13, 15, 35} {13, 15, 36} {13, 15, 37} {13, 15, 38}
{13, 15, 39} {13, 15, 40} {13, 15, 41} {13, 15, 42} {13, 15, 43} {13, 15, 44} {13, 15, 45} {13, 15, 46} {13, 15, 47}
{13, 15, 48} {13, 15, 49} {13, 15, 50} {13, 15, 51} {13, 15, 52} {13, 15, 53} {13, 15, 54} {13, 15, 55} {13, 15, 56}
{13, 15, 57} {13, 15, 58} {13, 15, 59} {13, 15, 60} {13, 15, 61} {13, 15, 62} {13, 15, 63} {13, 15, 64} {13, 15, 65}
{13, 15, 66} {13, 16, 17} {13, 16, 18} {13, 16, 19} {13, 16, 20} {13, 16, 21} {13, 16, 22} {13, 16, 23} {13, 16, 24}
{13, 16, 25} {13, 16, 26} {13, 16, 27} {13, 16, 28} {13, 16, 29} {13, 16, 30} {13, 16, 31} {13, 16, 32} {13, 16, 33}
{13, 16, 34} {13, 16, 35} {13, 16, 36} {13, 16, 37} {13, 16, 38} {13, 16, 39} {13, 16, 40} {13, 16, 41} {13, 16, 42}
{13, 16, 43} {13, 16, 44} {13, 16, 45} {13, 16, 46} {13, 16, 47} {13, 16, 48} {13, 16, 49} {13, 16, 50} {13, 16, 51}
{13, 16, 52} {13, 16, 53} {13, 16, 54} {13, 16, 55} {13, 16, 56} {13, 16, 57} {13, 16, 58} {13, 16, 59} {13, 16, 60}

TABLE 3A-continued

{13, 16, 61} {13, 16, 62} {13, 16, 63} {13, 16, 64} {13, 16, 65} {13, 16, 66} {13, 17, 18} {13, 17, 19} {13, 17, 20}
{13, 17, 21} {13, 17, 22} {13, 17, 23} {13, 17, 24} {13, 17, 25} {13, 17, 26} {13, 17, 27} {13, 17, 28} {13, 17, 29}
{13, 17, 30} {13, 17, 31} {13, 17, 32} {13, 17, 33} {13, 17, 34} {13, 17, 35} {13, 17, 36} {13, 17, 37} {13, 17, 38}
{13, 17, 39} {13, 17, 40} {13, 17, 41} {13, 17, 42} {13, 17, 43} {13, 17, 44} {13, 17, 45} {13, 17, 46} {13, 17, 47}
{13, 17, 48} {13, 17, 49} {13, 17, 50} {13, 17, 51} {13, 17, 52} {13, 17, 53} {13, 17, 54} {13, 17, 55} {13, 17, 56}
{13, 17, 57} {13, 17, 58} {13, 17, 59} {13, 17, 60} {13, 17, 61} {13, 17, 62} {13, 17, 63} {13, 17, 64} {13, 17, 65}
{13, 17, 66} {13, 18, 19} {13, 18, 20} {13, 18, 21} {13, 18, 22} {13, 18, 23} {13, 18, 24} {13, 18, 25} {13, 18, 26}
{13, 18, 27} {13, 18, 28} {13, 18, 29} {13, 18, 30} {13, 18, 31} {13, 18, 32} {13, 18, 33} {13, 18, 34} {13, 18, 35}
{13, 18, 36} {13, 18, 37} {13, 18, 38} {13, 18, 39} {13, 18, 40} {13, 18, 41} {13, 18, 42} {13, 18, 43} {13, 18, 44}
{13, 18, 45} {13, 18, 46} {13, 18, 47} {13, 18, 48} {13, 18, 49} {13, 18, 50} {13, 18, 51} {13, 18, 52} {13, 18, 53}
{13, 18, 54} {13, 18, 55} {13, 18, 56} {13, 18, 57} {13, 18, 58} {13, 18, 59} {13, 18, 60} {13, 18, 61} {13, 18, 62}
{13, 18, 63} {13, 18, 64} {13, 18, 65} {13, 18, 66} {13, 19, 20} {13, 19, 21} {13, 19, 22} {13, 19, 23} {13, 19, 24}
{13, 19, 25} {13, 19, 26} {13, 19, 27} {13, 19, 28} {13, 19, 29} {13, 19, 30} {13, 19, 31} {13, 19, 32} {13, 19, 33}
{13, 19, 34} {13, 19, 35} {13, 19, 36} {13, 19, 37} {13, 19, 38} {13, 19, 39} {13, 19, 40} {13, 19, 41} {13, 19, 42}
{13, 19, 43} {13, 19, 44} {13, 19, 45} {13, 19, 46} {13, 19, 47} {13, 19, 48} {13, 19, 49} {13, 19, 50} {13, 19, 51}
{13, 19, 52} {13, 19, 53} {13, 19, 54} {13, 19, 55} {13, 19, 56} {13, 19, 57} {13, 19, 58} {13, 19, 59} {13, 19, 60}
{13, 19, 61} {13, 19, 62} {13, 19, 63} {13, 19, 64} {13, 19, 65} {13, 19, 66} {13, 20, 21} {13, 20, 22} {13, 20, 23}
{13, 20, 24} {13, 20, 25} {13, 20, 26} {13, 20, 27} {13, 20, 28} {13, 20, 29} {13, 20, 30} {13, 20, 31} {13, 20, 32}
{13, 20, 33} {13, 20, 34} {13, 20, 35} {13, 20, 36} {13, 20, 37} {13, 20, 38} {13, 20, 39} {13, 20, 40} {13, 20, 41}
{13, 20, 42} {13, 20, 43} {13, 20, 44} {13, 20, 45} {13, 20, 46} {13, 20, 47} {13, 20, 48} {13, 20, 49} {13, 20, 50}
{13, 20, 51} {13, 20, 52} {13, 20, 53} {13, 20, 54} {13, 20, 55} {13, 20, 56} {13, 20, 57} {13, 20, 58} {13, 20, 59}
{13, 20, 60} {13, 20, 61} {13, 20, 62} {13, 20, 63} {13, 20, 64} {13, 20, 65} {13, 20, 66} {13, 21, 22} {13, 21, 23}
{13, 21, 24} {13, 21, 25} {13, 21, 26} {13, 21, 27} {13, 21, 28} {13, 21, 29} {13, 21, 30} {13, 21, 31} {13, 21, 32}
{13, 21, 33} {13, 21, 34} {13, 21, 35} {13, 21, 36} {13, 21, 37} {13, 21, 38} {13, 21, 39} {13, 21, 40} {13, 21, 41}
{13, 21, 42} {13, 21, 43} {13, 21, 44} {13, 21, 45} {13, 21, 46} {13, 21, 47} {13, 21, 48} {13, 21, 49} {13, 21, 50}
{13, 21, 51} {13, 21, 52} {13, 21, 53} {13, 21, 54} {13, 21, 55} {13, 21, 56} {13, 21, 57} {13, 21, 58} {13, 21, 59}
{13, 21, 60} {13, 21, 61} {13, 21, 62} {13, 21, 63} {13, 21, 64} {13, 21, 65} {13, 21, 66} {13, 22, 23} {13, 22, 24}
{13, 22, 25} {13, 22, 26} {13, 22, 27} {13, 22, 28} {13, 22, 29} {13, 22, 30} {13, 22, 31} {13, 22, 32} {13, 22, 33}
{13, 22, 34} {13, 22, 35} {13, 22, 36} {13, 22, 37} {13, 22, 38} {13, 22, 39} {13, 22, 40} {13, 22, 41} {13, 22, 42}
{13, 22, 43} {13, 22, 44} {13, 22, 45} {13, 22, 46} {13, 22, 47} {13, 22, 48} {13, 22, 49} {13, 22, 50} {13, 22, 51}
{13, 22, 52} {13, 22, 53} {13, 22, 54} {13, 22, 55} {13, 22, 56} {13, 22, 57} {13, 22, 58} {13, 22, 59} {13, 22, 60}
{13, 22, 61} {13, 22, 62} {13, 22, 63} {13, 22, 64} {13, 22, 65} {13, 22, 66} {13, 23, 24} {13, 23, 25} {13, 23, 26}
{13, 23, 27} {13, 23, 28} {13, 23, 29} {13, 23, 30} {13, 23, 31} {13, 23, 32} {13, 23, 33} {13, 23, 34} {13, 23, 35}
{13, 23, 36} {13, 23, 37} {13, 23, 38} {13, 23, 39} {13, 23, 40} {13, 23, 41} {13, 23, 42} {13, 23, 43} {13, 23, 44}
{13, 23, 45} {13, 23, 46} {13, 23, 47} {13, 23, 48} {13, 23, 49} {13, 23, 50} {13, 23, 51} {13, 23, 52} {13, 23, 53}
{13, 23, 54} {13, 23, 55} {13, 23, 56} {13, 23, 57} {13, 23, 58} {13, 23, 59} {13, 23, 60} {13, 23, 61} {13, 23, 62}
{13, 23, 63} {13, 23, 64} {13, 23, 65} {13, 23, 66} {13, 24, 25} {13, 24, 26} {13, 24, 27} {13, 24, 28} {13, 24, 29}
{13, 24, 30} {13, 24, 31} {13, 24, 32} {13, 24, 33} {13, 24, 34} {13, 24, 35} {13, 24, 36} {13, 24, 37} {13, 24, 38}
{13, 24, 39} {13, 24, 40} {13, 24, 41} {13, 24, 42} {13, 24, 43} {13, 24, 44} {13, 24, 45} {13, 24, 46} {13, 24, 47}
{13, 24, 48} {13, 24, 49} {13, 24, 50} {13, 24, 51} {13, 24, 52} {13, 24, 53} {13, 24, 54} {13, 24, 55} {13, 24, 56}
{13, 24, 57} {13, 24, 58} {13, 24, 59} {13, 24, 60} {13, 24, 61} {13, 24, 62} {13, 24, 63} {13, 24, 64} {13, 24, 65}
{13, 24, 66} {13, 25, 26} {13, 25, 27} {13, 25, 28} {13, 25, 29} {13, 25, 30} {13, 25, 31} {13, 25, 32} {13, 25, 33}
{13, 25, 34} {13, 25, 35} {13, 25, 36} {13, 25, 37} {13, 25, 38} {13, 25, 39} {13, 25, 40} {13, 25, 41} {13, 25, 42}
{13, 25, 43} {13, 25, 44} {13, 25, 45} {13, 25, 46} {13, 25, 47} {13, 25, 48} {13, 25, 49} {13, 25, 50} {13, 25, 51}
{13, 25, 52} {13, 25, 53} {13, 25, 54} {13, 25, 55} {13, 25, 56} {13, 25, 57} {13, 25, 58} {13, 25, 59} {13, 25, 60}
{13, 25, 61} {13, 25, 62} {13, 25, 63} {13, 25, 64} {13, 25, 65} {13, 25, 66} {13, 26, 27} {13, 26, 28} {13, 26, 29}
{13, 26, 30} {13, 26, 31} {13, 26, 32} {13, 26, 33} {13, 26, 34} {13, 26, 35} {13, 26, 36} {13, 26, 37} {13, 26, 38}
{13, 26, 39} {13, 26, 40} {13, 26, 41} {13, 26, 42} {13, 26, 43} {13, 26, 44} {13, 26, 45} {13, 26, 46} {13, 26, 47}
{13, 26, 48} {13, 26, 49} {13, 26, 50} {13, 26, 51} {13, 26, 52} {13, 26, 53} {13, 26, 54} {13, 26, 55} {13, 26, 56}
{13, 26, 57} {13, 26, 58} {13, 26, 59} {13, 26, 60} {13, 26, 61} {13, 26, 62} {13, 26, 63} {13, 26, 64} {13, 26, 65}
{13, 26, 66} {13, 27, 28} {13, 27, 29} {13, 27, 30} {13, 27, 31} {13, 27, 32} {13, 27, 33} {13, 27, 34} {13, 27, 35}
{13, 27, 36} {13, 27, 37} {13, 27, 38} {13, 27, 39} {13, 27, 40} {13, 27, 41} {13, 27, 42} {13, 27, 43} {13, 27, 44}
{13, 27, 45} {13, 27, 46} {13, 27, 47} {13, 27, 48} {13, 27, 49} {13, 27, 50} {13, 27, 51} {13, 27, 52} {13, 27, 53}
{13, 27, 54} {13, 27, 55} {13, 27, 56} {13, 27, 57} {13, 27, 58} {13, 27, 59} {13, 27, 60} {13, 27, 61} {13, 27, 62}
{13, 27, 63} {13, 27, 64} {13, 27, 65} {13, 27, 66} {13, 28, 29} {13, 28, 30} {13, 28, 31} {13, 28, 32} {13, 28, 33}
{13, 28, 34} {13, 28, 35} {13, 28, 36} {13, 28, 37} {13, 28, 38} {13, 28, 39} {13, 28, 40} {13, 28, 41} {13, 28, 42}
{13, 28, 43} {13, 28, 44} {13, 28, 45} {13, 28, 46} {13, 28, 47} {13, 28, 48} {13, 28, 49} {13, 28, 50} {13, 28, 51}
{13, 28, 52} {13, 28, 53} {13, 28, 54} {13, 28, 55} {13, 28, 56} {13, 28, 57} {13, 28, 58} {13, 28, 59} {13, 28, 60}
{13, 28, 61} {13, 28, 62} {13, 28, 63} {13, 28, 64} {13, 28, 65} {13, 28, 66} {13, 29, 30} {13, 29, 31} {13, 29, 32}
{13, 29, 33} {13, 29, 34} {13, 29, 35} {13, 29, 36} {13, 29, 37} {13, 29, 38} {13, 29, 39} {13, 29, 40} {13, 29, 41}
{13, 29, 42} {13, 29, 43} {13, 29, 44} {13, 29, 45} {13, 29, 46} {13, 29, 47} {13, 29, 48} {13, 29, 49} {13, 29, 50}
{13, 29, 51} {13, 29, 52} {13, 29, 53} {13, 29, 54} {13, 29, 55} {13, 29, 56} {13, 29, 57} {13, 29, 58} {13, 29, 59}
{13, 29, 60} {13, 29, 61} {13, 29, 62} {13, 29, 63} {13, 29, 64} {13, 29, 65} {13, 29, 66} {13, 30, 31} {13, 30, 32}
{13, 30, 33} {13, 30, 34} {13, 30, 35} {13, 30, 36} {13, 30, 37} {13, 30, 38} {13, 30, 39} {13, 30, 40} {13, 30, 41}
{13, 30, 42} {13, 30, 43} {13, 30, 44} {13, 30, 45} {13, 30, 46} {13, 30, 47} {13, 30, 48} {13, 30, 49} {13, 30, 50}
{13, 30, 51} {13, 30, 52} {13, 30, 53} {13, 30, 54} {13, 30, 55} {13, 30, 56} {13, 30, 57} {13, 30, 58} {13, 30, 59}
{13, 30, 60} {13, 30, 61} {13, 30, 62} {13, 30, 63} {13, 30, 64} {13, 30, 65} {13, 30, 66} {13, 31, 32} {13, 31, 33}
{13, 31, 34} {13, 31, 35} {13, 31, 36} {13, 31, 37} {13, 31, 38} {13, 31, 39} {13, 31, 40} {13, 31, 41} {13, 31, 42}
{13, 31, 43} {13, 31, 44} {13, 31, 45} {13, 31, 46} {13, 31, 47} {13, 31, 48} {13, 31, 49} {13, 31, 50} {13, 31, 51}
{13, 31, 52} {13, 31, 53} {13, 31, 54} {13, 31, 55} {13, 31, 56} {13, 31, 57} {13, 31, 58} {13, 31, 59} {13, 31, 60}
{13, 31, 61} {13, 31, 62} {13, 31, 63} {13, 31, 64} {13, 31, 65} {13, 31, 66} {13, 32, 33} {13, 32, 34} {13, 32, 35}
{13, 32, 36} {13, 32, 37} {13, 32, 38} {13, 32, 39} {13, 32, 40} {13, 32, 41} {13, 32, 42} {13, 32, 43} {13, 32, 44}
{13, 32, 45} {13, 32, 46} {13, 32, 47} {13, 32, 48} {13, 32, 49} {13, 32, 50} {13, 32, 51} {13, 32, 52} {13, 32, 53}
{13, 32, 54} {13, 32, 55} {13, 32, 56} {13, 32, 57} {13, 32, 58} {13, 32, 59} {13, 32, 60} {13, 32, 61} {13, 32, 62}
{13, 32, 63} {13, 32, 64} {13, 32, 65} {13, 32, 66} {13, 33, 34} {13, 33, 35} {13, 33, 36} {13, 33, 37} {13, 33, 38}
{13, 33, 39} {13, 33, 40} {13, 33, 41} {13, 33, 42} {13, 33, 43} {13, 33, 44} {13, 33, 45} {13, 33, 46} {13, 33, 47}
{13, 33, 48} {13, 33, 49} {13, 33, 50} {13, 33, 51} {13, 33, 52} {13, 33, 53} {13, 33, 54} {13, 33, 55} {13, 33, 56}
{13, 33, 57} {13, 33, 58} {13, 33, 59} {13, 33, 60} {13, 33, 61} {13, 33, 62} {13, 33, 63} {13, 33, 64} {13, 33, 65}
{13, 33, 66} {13, 34, 35} {13, 34, 36} {13, 34, 37} {13, 34, 38} {13, 34, 39} {13, 34, 40} {13, 34, 41} {13, 34, 42}
{13, 34, 43} {13, 34, 44} {13, 34, 45} {13, 34, 46} {13, 34, 47} {13, 34, 48} {13, 34, 49} {13, 34, 50} {13, 34, 51}

TABLE 3A-continued

{13, 34, 52} {13, 34, 53} {13, 34, 54} {13, 34, 55} {13, 34, 56} {13, 34, 57} {13, 34, 58} {13, 34, 59} {13, 34, 60}
{13, 34, 61} {13, 34, 62} {13, 34, 63} {13, 34, 64} {13, 34, 65} {13, 34, 66} {13, 35, 36} {13, 35, 37} {13, 35, 38}
{13, 35, 39} {13, 35, 40} {13, 35, 41} {13, 35, 42} {13, 35, 43} {13, 35, 44} {13, 35, 45} {13, 35, 46} {13, 35, 47}
{13, 35, 48} {13, 35, 49} {13, 35, 50} {13, 35, 51} {13, 35, 52} {13, 35, 53} {13, 35, 54} {13, 35, 55} {13, 35, 56}
{13, 35, 57} {13, 35, 58} {13, 35, 59} {13, 35, 60} {13, 35, 61} {13, 35, 62} {13, 35, 63} {13, 35, 64} {13, 35, 65}
{13, 35, 66} {13, 36, 37} {13, 36, 38} {13, 36, 39} {13, 36, 40} {13, 36, 41} {13, 36, 42} {13, 36, 43} {13, 36, 44}
{13, 36, 45} {13, 36, 46} {13, 36, 47} {13, 36, 48} {13, 36, 49} {13, 36, 50} {13, 36, 51} {13, 36, 52} {13, 36, 53}
{13, 36, 54} {13, 36, 55} {13, 36, 56} {13, 36, 57} {13, 36, 58} {13, 36, 59} {13, 36, 60} {13, 36, 61} {13, 36, 62}
{13, 36, 63} {13, 36, 64} {13, 36, 65} {13, 36, 66} {13, 37, 38} {13, 37, 39} {13, 37, 40} {13, 37, 41} {13, 37, 42}
{13, 37, 43} {13, 37, 44} {13, 37, 45} {13, 37, 46} {13, 37, 47} {13, 37, 48} {13, 37, 49} {13, 37, 50} {13, 37, 51}
{13, 37, 52} {13, 37, 53} {13, 37, 54} {13, 37, 55} {13, 37, 56} {13, 37, 57} {13, 37, 58} {13, 37, 59} {13, 37, 60}
{13, 37, 61} {13, 37, 62} {13, 37, 63} {13, 37, 64} {13, 37, 65} {13, 37, 66} {13, 38, 39} {13, 38, 40} {13, 38, 41}
{13, 38, 42} {13, 38, 43} {13, 38, 44} {13, 38, 45} {13, 38, 46} {13, 38, 47} {13, 38, 48} {13, 38, 49} {13, 38, 50}
{13, 38, 51} {13, 38, 52} {13, 38, 53} {13, 38, 54} {13, 38, 55} {13, 38, 56} {13, 38, 57} {13, 38, 58} {13, 38, 59}
{13, 38, 60} {13, 38, 61} {13, 38, 62} {13, 38, 63} {13, 38, 64} {13, 38, 65} {13, 38, 66} {13, 39, 40} {13, 39, 41}
{13, 39, 42} {13, 39, 43} {13, 39, 44} {13, 39, 45} {13, 39, 46} {13, 39, 47} {13, 39, 48} {13, 39, 49} {13, 39, 50}
{13, 39, 51} {13, 39, 52} {13, 39, 53} {13, 39, 54} {13, 39, 55} {13, 39, 56} {13, 39, 57} {13, 39, 58} {13, 39, 59}
{13, 39, 60} {13, 39, 61} {13, 39, 62} {13, 39, 63} {13, 39, 64} {13, 39, 65} {13, 39, 66} {13, 40, 41} {13, 40, 42}
{13, 40, 43} {13, 40, 44} {13, 40, 45} {13, 40, 46} {13, 40, 47} {13, 40, 48} {13, 40, 49} {13, 40, 50} {13, 40, 51}
{13, 40, 52} {13, 40, 53} {13, 40, 54} {13, 40, 55} {13, 40, 56} {13, 40, 57} {13, 40, 58} {13, 40, 59} {13, 40, 60}
{13, 40, 61} {13, 40, 62} {13, 40, 63} {13, 40, 64} {13, 40, 65} {13, 40, 66} {13, 41, 42} {13, 41, 43} {13, 41, 44}
{13, 41, 45} {13, 41, 46} {13, 41, 47} {13, 41, 48} {13, 41, 49} {13, 41, 50} {13, 41, 51} {13, 41, 52} {13, 41, 53}
{13, 41, 54} {13, 41, 55} {13, 41, 56} {13, 41, 57} {13, 41, 58} {13, 41, 59} {13, 41, 60} {13, 41, 61} {13, 41, 62}
{13, 41, 63} {13, 41, 64} {13, 41, 65} {13, 41, 66} {13, 42, 43} {13, 42, 44} {13, 42, 45} {13, 42, 46} {13, 42, 47}
{13, 42, 48} {13, 42, 49} {13, 42, 50} {13, 42, 51} {13, 42, 52} {13, 42, 53} {13, 42, 54} {13, 42, 55} {13, 42, 56}
{13, 42, 57} {13, 42, 58} {13, 42, 59} {13, 42, 60} {13, 42, 61} {13, 42, 62} {13, 42, 63} {13, 42, 64} {13, 42, 65}
{13, 42, 66} {13, 43, 44} {13, 43, 45} {13, 43, 46} {13, 43, 47} {13, 43, 48} {13, 43, 49} {13, 43, 50} {13, 43, 51}
{13, 43, 52} {13, 43, 53} {13, 43, 54} {13, 43, 55} {13, 43, 56} {13, 43, 57} {13, 43, 58} {13, 43, 59} {13, 43, 60}
{13, 43, 61} {13, 43, 62} {13, 43, 63} {13, 43, 64} {13, 43, 65} {13, 43, 66} {13, 44, 45} {13, 44, 46} {13, 44, 47}
{13, 44, 48} {13, 44, 49} {13, 44, 50} {13, 44, 51} {13, 44, 52} {13, 44, 53} {13, 44, 54} {13, 44, 55} {13, 44, 56}
{13, 44, 57} {13, 44, 58} {13, 44, 59} {13, 44, 60} {13, 44, 61} {13, 44, 62} {13, 44, 63} {13, 44, 64} {13, 44, 65}
{13, 44, 66} {13, 45, 46} {13, 45, 47} {13, 45, 48} {13, 45, 49} {13, 45, 50} {13, 45, 51} {13, 45, 52} {13, 45, 53}
{13, 45, 54} {13, 45, 55} {13, 45, 56} {13, 45, 57} {13, 45, 58} {13, 45, 59} {13, 45, 60} {13, 45, 61} {13, 45, 62}
{13, 45, 63} {13, 45, 64} {13, 45, 65} {13, 45, 66} {13, 46, 47} {13, 46, 48} {13, 46, 49} {13, 46, 50} {13, 46, 51}
{13, 46, 52} {13, 46, 53} {13, 46, 54} {13, 46, 55} {13, 46, 56} {13, 46, 57} {13, 46, 58} {13, 46, 59} {13, 46, 60}
{13, 46, 61} {13, 46, 62} {13, 46, 63} {13, 46, 64} {13, 46, 65} {13, 46, 66} {13, 47, 48} {13, 47, 49} {13, 47, 50}
{13, 47, 51} {13, 47, 52} {13, 47, 53} {13, 47, 54} {13, 47, 55} {13, 47, 56} {13, 47, 57} {13, 47, 58} {13, 47, 59}
{13, 47, 60} {13, 47, 61} {13, 47, 62} {13, 47, 63} {13, 47, 64} {13, 47, 65} {13, 47, 66} {13, 48, 49} {13, 48, 50}
{13, 48, 51} {13, 48, 52} {13, 48, 53} {13, 48, 54} {13, 48, 55} {13, 48, 56} {13, 48, 57} {13, 48, 58} {13, 48, 59}
{13, 48, 60} {13, 48, 61} {13, 48, 62} {13, 48, 63} {13, 48, 64} {13, 48, 65} {13, 48, 66} {13, 49, 50} {13, 49, 51}
{13, 49, 52} {13, 49, 53} {13, 49, 54} {13, 49, 55} {13, 49, 56} {13, 49, 57} {13, 49, 58} {13, 49, 59} {13, 49, 60}
{13, 49, 61} {13, 49, 62} {13, 49, 63} {13, 49, 64} {13, 49, 65} {13, 49, 66} {13, 50, 51} {13, 50, 52} {13, 50, 53}
{13, 50, 54} {13, 50, 55} {13, 50, 56} {13, 50, 57} {13, 50, 58} {13, 50, 59} {13, 50, 60} {13, 50, 61} {13, 50, 62}
{13, 50, 63} {13, 50, 64} {13, 50, 65} {13, 50, 66} {13, 51, 52} {13, 51, 53} {13, 51, 54} {13, 51, 55} {13, 51, 56}
{13, 51, 57} {13, 51, 58} {13, 51, 59} {13, 51, 60} {13, 51, 61} {13, 51, 62} {13, 51, 63} {13, 51, 64} {13, 51, 65}
{13, 51, 66} {13, 52, 53} {13, 52, 54} {13, 52, 55} {13, 52, 56} {13, 52, 57} {13, 52, 58} {13, 52, 59} {13, 52, 60}
{13, 52, 61} {13, 52, 62} {13, 52, 63} {13, 52, 64} {13, 52, 65} {13, 52, 66} {13, 53, 54} {13, 53, 55} {13, 53, 56}
{13, 53, 57} {13, 53, 58} {13, 53, 59} {13, 53, 60} {13, 53, 61} {13, 53, 62} {13, 53, 63} {13, 53, 64} {13, 53, 65}
{13, 53, 66} {13, 54, 55} {13, 54, 56} {13, 54, 57} {13, 54, 58} {13, 54, 59} {13, 54, 60} {13, 54, 61} {13, 54, 62}
{13, 54, 63} {13, 54, 64} {13, 54, 65} {13, 54, 66} {13, 55, 56} {13, 55, 57} {13, 55, 58} {13, 55, 59} {13, 55, 60}
{13, 55, 61} {13, 55, 62} {13, 55, 63} {13, 55, 64} {13, 55, 65} {13, 55, 66} {13, 56, 57} {13, 56, 58} {13, 56, 59}
{13, 56, 60} {13, 56, 61} {13, 56, 62} {13, 56, 63} {13, 56, 64} {13, 56, 65} {13, 56, 66} {13, 57, 58} {13, 57, 59}
{13, 57, 60} {13, 57, 61} {13, 57, 62} {13, 57, 63} {13, 57, 64} {13, 57, 65} {13, 57, 66} {13, 58, 59} {13, 58, 60}
{13, 58, 61} {13, 58, 62} {13, 58, 63} {13, 58, 64} {13, 58, 65} {13, 58, 66} {13, 59, 60} {13, 59, 61} {13, 59, 62}
{13, 59, 63} {13, 59, 64} {13, 59, 65} {13, 59, 66} {13, 60, 61} {13, 60, 62} {13, 60, 63} {13, 60, 64} {13, 60, 65}
{13, 60, 66} {13, 61, 62} {13, 61, 63} {13, 61, 64} {13, 61, 65} {13, 61, 66} {13, 62, 63} {13, 62, 64} {13, 62, 65}
{13, 62, 66} {13, 63, 64} {13, 63, 65} {13, 63, 66} {13, 64, 65} {13, 64, 66} {13, 65, 66} {14, 15, 16} {14, 15, 17}
{14, 15, 18} {14, 15, 19} {14, 15, 20} {14, 15, 21} {14, 15, 22} {14, 15, 23} {14, 15, 24} {14, 15, 25} {14, 15, 26}
{14, 15, 27} {14, 15, 28} {14, 15, 29} {14, 15, 30} {14, 15, 31} {14, 15, 32} {14, 15, 33} {14, 15, 34} {14, 15, 35}
{14, 15, 36} {14, 15, 37} {14, 15, 38} {14, 15, 39} {14, 15, 40} {14, 15, 41} {14, 15, 42} {14, 15, 43} {14, 15, 44}
{14, 15, 45} {14, 15, 46} {14, 15, 47} {14, 15, 48} {14, 15, 49} {14, 15, 50} {14, 15, 51} {14, 15, 52} {14, 15, 53}
{14, 15, 54} {14, 15, 55} {14, 15, 56} {14, 15, 57} {14, 15, 58} {14, 15, 59} {14, 15, 60} {14, 15, 61} {14, 15, 62}
{14, 15, 63} {14, 15, 64} {14, 15, 65} {14, 15, 66} {14, 16, 17} {14, 16, 18} {14, 16, 19} {14, 16, 20} {14, 16, 21}
{14, 16, 22} {14, 16, 23} {14, 16, 24} {14, 16, 25} {14, 16, 26} {14, 16, 27} {14, 16, 28} {14, 16, 29} {14, 16, 30}
{14, 16, 31} {14, 16, 32} {14, 16, 33} {14, 16, 34} {14, 16, 35} {14, 16, 36} {14, 16, 37} {14, 16, 38} {14, 16, 39}
{14, 16, 40} {14, 16, 41} {14, 16, 42} {14, 16, 43} {14, 16, 44} {14, 16, 45} {14, 16, 46} {14, 16, 47} {14, 16, 48}
{14, 16, 49} {14, 16, 50} {14, 16, 51} {14, 16, 52} {14, 16, 53} {14, 16, 54} {14, 16, 55} {14, 16, 56} {14, 16, 57}
{14, 16, 58} {14, 16, 59} {14, 16, 60} {14, 16, 61} {14, 16, 62} {14, 16, 63} {14, 16, 64} {14, 16, 65} {14, 16, 66}
{14, 17, 18} {14, 17, 19} {14, 17, 20} {14, 17, 21} {14, 17, 22} {14, 17, 23} {14, 17, 24} {14, 17, 25} {14, 17, 26}
{14, 17, 27} {14, 17, 28} {14, 17, 29} {14, 17, 30} {14, 17, 31} {14, 17, 32} {14, 17, 33} {14, 17, 34} {14, 17, 35}
{14, 17, 36} {14, 17, 37} {14, 17, 38} {14, 17, 39} {14, 17, 40} {14, 17, 41} {14, 17, 42} {14, 17, 43} {14, 17, 44}
{14, 17, 45} {14, 17, 46} {14, 17, 47} {14, 17, 48} {14, 17, 49} {14, 17, 50} {14, 17, 51} {14, 17, 52} {14, 17, 53}
{14, 17, 54} {14, 17, 55} {14, 17, 56} {14, 17, 57} {14, 17, 58} {14, 17, 59} {14, 17, 60} {14, 17, 61} {14, 17, 62}
{14, 17, 63} {14, 17, 64} {14, 17, 65} {14, 17, 66} {14, 18, 19} {14, 18, 20} {14, 18, 21} {14, 18, 22} {14, 18, 23}
{14, 18, 24} {14, 18, 25} {14, 18, 26} {14, 18, 27} {14, 18, 28} {14, 18, 29} {14, 18, 30} {14, 18, 31} {14, 18, 32}
{14, 18, 33} {14, 18, 34} {14, 18, 35} {14, 18, 36} {14, 18, 37} {14, 18, 38} {14, 18, 39} {14, 18, 40} {14, 18, 41}
{14, 18, 42} {14, 18, 43} {14, 18, 44} {14, 18, 45} {14, 18, 46} {14, 18, 47} {14, 18, 48} {14, 18, 49} {14, 18, 50}
{14, 18, 51} {14, 18, 52} {14, 18, 53} {14, 18, 54} {14, 18, 55} {14, 18, 56} {14, 18, 57} {14, 18, 58} {14, 18, 59}
{14, 18, 60} {14, 18, 61} {14, 18, 62} {14, 18, 63} {14, 18, 64} {14, 18, 65} {14, 18, 66} {14, 19, 20} {14, 19, 21}
{14, 19, 22} {14, 19, 23} {14, 19, 24} {14, 19, 25} {14, 19, 26} {14, 19, 27} {14, 19, 28} {14, 19, 29} {14, 19, 30}

TABLE 3A-continued

{14, 19, 31} {14, 19, 32} {14, 19, 33} {14, 19, 34} {14, 19, 35} {14, 19, 36} {14, 19, 37} {14, 19, 38} {14, 19, 39}
{14, 19, 40} {14, 19, 41} {14, 19, 42} {14, 19, 43} {14, 19, 44} {14, 19, 45} {14, 19, 46} {14, 19, 47} {14, 19, 48}
{14, 19, 49} {14, 19, 50} {14, 19, 51} {14, 19, 52} {14, 19, 53} {14, 19, 54} {14, 19, 55} {14, 19, 56} {14, 19, 57}
{14, 19, 58} {14, 19, 59} {14, 19, 60} {14, 19, 61} {14, 19, 62} {14, 19, 63} {14, 19, 64} {14, 19, 65} {14, 19, 66}
{14, 20, 21} {14, 20, 22} {14, 20, 23} {14, 20, 24} {14, 20, 25} {14, 20, 26} {14, 20, 27} {14, 20, 28} {14, 20, 29}
{14, 20, 30} {14, 20, 31} {14, 20, 32} {14, 20, 33} {14, 20, 34} {14, 20, 35} {14, 20, 36} {14, 20, 37} {14, 20, 38}
{14, 20, 39} {14, 20, 40} {14, 20, 41} {14, 20, 42} {14, 20, 43} {14, 20, 44} {14, 20, 45} {14, 20, 46} {14, 20, 47}
{14, 20, 48} {14, 20, 49} {14, 20, 50} {14, 20, 51} {14, 20, 52} {14, 20, 53} {14, 20, 54} {14, 20, 55} {14, 20, 56}
{14, 20, 57} {14, 20, 58} {14, 20, 59} {14, 20, 60} {14, 20, 61} {14, 20, 62} {14, 20, 63} {14, 20, 64} {14, 20, 65}
{14, 20, 66} {14, 21, 22} {14, 21, 23} {14, 21, 24} {14, 21, 25} {14, 21, 26} {14, 21, 27} {14, 21, 28} {14, 21, 29}
{14, 21, 30} {14, 21, 31} {14, 21, 32} {14, 21, 33} {14, 21, 34} {14, 21, 35} {14, 21, 36} {14, 21, 37} {14, 21, 38}
{14, 21, 39} {14, 21, 40} {14, 21, 41} {14, 21, 42} {14, 21, 43} {14, 21, 44} {14, 21, 45} {14, 21, 46} {14, 21, 47}
{14, 21, 48} {14, 21, 49} {14, 21, 50} {14, 21, 51} {14, 21, 52} {14, 21, 53} {14, 21, 54} {14, 21, 55} {14, 21, 56}
{14, 21, 57} {14, 21, 58} {14, 21, 59} {14, 21, 60} {14, 21, 61} {14, 21, 62} {14, 21, 63} {14, 21, 64} {14, 21, 65}
{14, 21, 66} {14, 22, 23} {14, 22, 24} {14, 22, 25} {14, 22, 26} {14, 22, 27} {14, 22, 28} {14, 22, 29} {14, 22, 30}
{14, 22, 31} {14, 22, 32} {14, 22, 33} {14, 22, 34} {14, 22, 35} {14, 22, 36} {14, 22, 37} {14, 22, 38} {14, 22, 39}
{14, 22, 40} {14, 22, 41} {14, 22, 42} {14, 22, 43} {14, 22, 44} {14, 22, 45} {14, 22, 46} {14, 22, 47} {14, 22, 48}
{14, 22, 49} {14, 22, 50} {14, 22, 51} {14, 22, 52} {14, 22, 53} {14, 22, 54} {14, 22, 55} {14, 22, 56} {14, 22, 57}
{14, 22, 58} {14, 22, 59} {14, 22, 60} {14, 22, 61} {14, 22, 62} {14, 22, 63} {14, 22, 64} {14, 22, 65} {14, 22, 66}
{14, 23, 24} {14, 23, 25} {14, 23, 26} {14, 23, 27} {14, 23, 28} {14, 23, 29} {14, 23, 30} {14, 23, 31} {14, 23, 32}
{14, 23, 33} {14, 23, 34} {14, 23, 35} {14, 23, 36} {14, 23, 37} {14, 23, 38} {14, 23, 39} {14, 23, 40} {14, 23, 41}
{14, 23, 42} {14, 23, 43} {14, 23, 44} {14, 23, 45} {14, 23, 46} {14, 23, 47} {14, 23, 48} {14, 23, 49} {14, 23, 50}
{14, 23, 51} {14, 23, 52} {14, 23, 53} {14, 23, 54} {14, 23, 55} {14, 23, 56} {14, 23, 57} {14, 23, 58} {14, 23, 59}
{14, 23, 60} {14, 23, 61} {14, 23, 62} {14, 23, 63} {14, 23, 64} {14, 23, 65} {14, 23, 66} {14, 24, 25} {14, 24, 26}
{14, 24, 27} {14, 24, 28} {14, 24, 29} {14, 24, 30} {14, 24, 31} {14, 24, 32} {14, 24, 33} {14, 24, 34} {14, 24, 35}
{14, 24, 36} {14, 24, 37} {14, 24, 38} {14, 24, 39} {14, 24, 40} {14, 24, 41} {14, 24, 42} {14, 24, 43} {14, 24, 44}
{14, 24, 45} {14, 24, 46} {14, 24, 47} {14, 24, 48} {14, 24, 49} {14, 24, 50} {14, 24, 51} {14, 24, 52} {14, 24, 53}
{14, 24, 54} {14, 24, 55} {14, 24, 56} {14, 24, 57} {14, 24, 58} {14, 24, 59} {14, 24, 60} {14, 24, 61} {14, 24, 62}
{14, 24, 63} {14, 24, 64} {14, 24, 65} {14, 24, 66} {14, 25, 26} {14, 25, 27} {14, 25, 28} {14, 25, 29} {14, 25, 30}
{14, 25, 31} {14, 25, 32} {14, 25, 33} {14, 25, 34} {14, 25, 35} {14, 25, 36} {14, 25, 37} {14, 25, 38} {14, 25, 39}
{14, 25, 40} {14, 25, 41} {14, 25, 42} {14, 25, 43} {14, 25, 44} {14, 25, 45} {14, 25, 46} {14, 25, 47} {14, 25, 48}
{14, 25, 49} {14, 25, 50} {14, 25, 51} {14, 25, 52} {14, 25, 53} {14, 25, 54} {14, 25, 55} {14, 25, 56} {14, 25, 57}
{14, 25, 58} {14, 25, 59} {14, 25, 60} {14, 25, 61} {14, 25, 62} {14, 25, 63} {14, 25, 64} {14, 25, 65} {14, 25, 66}
{14, 26, 27} {14, 26, 28} {14, 26, 29} {14, 26, 30} {14, 26, 31} {14, 26, 32} {14, 26, 33} {14, 26, 34} {14, 26, 35}
{14, 26, 36} {14, 26, 37} {14, 26, 38} {14, 26, 39} {14, 26, 40} {14, 26, 41} {14, 26, 42} {14, 26, 43} {14, 26, 44}
{14, 26, 45} {14, 26, 46} {14, 26, 47} {14, 26, 48} {14, 26, 49} {14, 26, 50} {14, 26, 51} {14, 26, 52} {14, 26, 53}
{14, 26, 54} {14, 26, 55} {14, 26, 56} {14, 26, 57} {14, 26, 58} {14, 26, 59} {14, 26, 60} {14, 26, 61} {14, 26, 62}
{14, 26, 63} {14, 26, 64} {14, 26, 65} {14, 26, 66} {14, 27, 28} {14, 27, 29} {14, 27, 30} {14, 27, 31} {14, 27, 32}
{14, 27, 33} {14, 27, 34} {14, 27, 35} {14, 27, 36} {14, 27, 37} {14, 27, 38} {14, 27, 39} {14, 27, 40} {14, 27, 41}
{14, 27, 42} {14, 27, 43} {14, 27, 44} {14, 27, 45} {14, 27, 46} {14, 27, 47} {14, 27, 48} {14, 27, 49} {14, 27, 50}
{14, 27, 51} {14, 27, 52} {14, 27, 53} {14, 27, 54} {14, 27, 55} {14, 27, 56} {14, 27, 57} {14, 27, 58} {14, 27, 59}
{14, 27, 60} {14, 27, 61} {14, 27, 62} {14, 27, 63} {14, 27, 64} {14, 27, 65} {14, 27, 66} {14, 28, 29} {14, 28, 30}
{14, 28, 31} {14, 28, 32} {14, 28, 33} {14, 28, 34} {14, 28, 35} {14, 28, 36} {14, 28, 37} {14, 28, 38} {14, 28, 39}
{14, 28, 40} {14, 28, 41} {14, 28, 42} {14, 28, 43} {14, 28, 44} {14, 28, 45} {14, 28, 46} {14, 28, 47} {14, 28, 48}
{14, 28, 49} {14, 28, 50} {14, 28, 51} {14, 28, 52} {14, 28, 53} {14, 28, 54} {14, 28, 55} {14, 28, 56} {14, 28, 57}
{14, 28, 58} {14, 28, 59} {14, 28, 60} {14, 28, 61} {14, 28, 62} {14, 28, 63} {14, 28, 64} {14, 28, 65} {14, 28, 66}
{14, 29, 30} {14, 29, 31} {14, 29, 32} {14, 29, 33} {14, 29, 34} {14, 29, 35} {14, 29, 36} {14, 29, 37} {14, 29, 38}
{14, 29, 39} {14, 29, 40} {14, 29, 41} {14, 29, 42} {14, 29, 43} {14, 29, 44} {14, 29, 45} {14, 29, 46} {14, 29, 47}
{14, 29, 48} {14, 29, 49} {14, 29, 50} {14, 29, 51} {14, 29, 52} {14, 29, 53} {14, 29, 54} {14, 29, 55} {14, 29, 56}
{14, 29, 57} {14, 29, 58} {14, 29, 59} {14, 29, 60} {14, 29, 61} {14, 29, 62} {14, 29, 63} {14, 29, 64} {14, 29, 65}
{14, 29, 66} {14, 30, 31} {14, 30, 32} {14, 30, 33} {14, 30, 34} {14, 30, 35} {14, 30, 36} {14, 30, 37} {14, 30, 38}
{14, 30, 39} {14, 30, 40} {14, 30, 41} {14, 30, 42} {14, 30, 43} {14, 30, 44} {14, 30, 45} {14, 30, 46} {14, 30, 47}
{14, 30, 48} {14, 30, 49} {14, 30, 50} {14, 30, 51} {14, 30, 52} {14, 30, 53} {14, 30, 54} {14, 30, 55} {14, 30, 56}
{14, 30, 57} {14, 30, 58} {14, 30, 59} {14, 30, 60} {14, 30, 61} {14, 30, 62} {14, 30, 63} {14, 30, 64} {14, 30, 65}
{14, 30, 66} {14, 31, 32} {14, 31, 33} {14, 31, 34} {14, 31, 35} {14, 31, 36} {14, 31, 37} {14, 31, 38} {14, 31, 39}
{14, 31, 40} {14, 31, 41} {14, 31, 42} {14, 31, 43} {14, 31, 44} {14, 31, 45} {14, 31, 46} {14, 31, 47} {14, 31, 48}
{14, 31, 49} {14, 31, 50} {14, 31, 51} {14, 31, 52} {14, 31, 53} {14, 31, 54} {14, 31, 55} {14, 31, 56} {14, 31, 57}
{14, 31, 58} {14, 31, 59} {14, 31, 60} {14, 31, 61} {14, 31, 62} {14, 31, 63} {14, 31, 64} {14, 31, 65} {14, 31, 66}
{14, 32, 33} {14, 32, 34} {14, 32, 35} {14, 32, 36} {14, 32, 37} {14, 32, 38} {14, 32, 39} {14, 32, 40} {14, 32, 41}
{14, 32, 42} {14, 32, 43} {14, 32, 44} {14, 32, 45} {14, 32, 46} {14, 32, 47} {14, 32, 48} {14, 32, 49} {14, 32, 50}
{14, 32, 51} {14, 32, 52} {14, 32, 53} {14, 32, 54} {14, 32, 55} {14, 32, 56} {14, 32, 57} {14, 32, 58} {14, 32, 59}
{14, 32, 60} {14, 32, 61} {14, 32, 62} {14, 32, 63} {14, 32, 64} {14, 32, 65} {14, 32, 66} {14, 33, 34} {14, 33, 35}
{14, 33, 36} {14, 33, 37} {14, 33, 38} {14, 33, 39} {14, 33, 40} {14, 33, 41} {14, 33, 42} {14, 33, 43} {14, 33, 44}
{14, 33, 45} {14, 33, 46} {14, 33, 47} {14, 33, 48} {14, 33, 49} {14, 33, 50} {14, 33, 51} {14, 33, 52} {14, 33, 53}
{14, 33, 54} {14, 33, 55} {14, 33, 56} {14, 33, 57} {14, 33, 58} {14, 33, 59} {14, 33, 60} {14, 33, 61} {14, 33, 62}
{14, 33, 63} {14, 33, 64} {14, 33, 65} {14, 33, 66} {14, 34, 35} {14, 34, 36} {14, 34, 37} {14, 34, 38} {14, 34, 39}
{14, 34, 40} {14, 34, 41} {14, 34, 42} {14, 34, 43} {14, 34, 44} {14, 34, 45} {14, 34, 46} {14, 34, 47} {14, 34, 48}
{14, 34, 49} {14, 34, 50} {14, 34, 51} {14, 34, 52} {14, 34, 53} {14, 34, 54} {14, 34, 55} {14, 34, 56} {14, 34, 57}
{14, 34, 58} {14, 34, 59} {14, 34, 60} {14, 34, 61} {14, 34, 62} {14, 34, 63} {14, 34, 64} {14, 34, 65} {14, 34, 66}
{14, 35, 36} {14, 35, 37} {14, 35, 38} {14, 35, 39} {14, 35, 40} {14, 35, 41} {14, 35, 42} {14, 35, 43} {14, 35, 44}
{14, 35, 45} {14, 35, 46} {14, 35, 47} {14, 35, 48} {14, 35, 49} {14, 35, 50} {14, 35, 51} {14, 35, 52} {14, 35, 53}
{14, 35, 54} {14, 35, 55} {14, 35, 56} {14, 35, 57} {14, 35, 58} {14, 35, 59} {14, 35, 60} {14, 35, 61} {14, 35, 62}
{14, 35, 63} {14, 35, 64} {14, 35, 65} {14, 35, 66} {14, 36, 37} {14, 36, 38} {14, 36, 39} {14, 36, 40} {14, 36, 41}
{14, 36, 42} {14, 36, 43} {14, 36, 44} {14, 36, 45} {14, 36, 46} {14, 36, 47} {14, 36, 48} {14, 36, 49} {14, 36, 50}
{14, 36, 51} {14, 36, 52} {14, 36, 53} {14, 36, 54} {14, 36, 55} {14, 36, 56} {14, 36, 57} {14, 36, 58} {14, 36, 59}
{14, 36, 60} {14, 36, 61} {14, 36, 62} {14, 36, 63} {14, 36, 64} {14, 36, 65} {14, 36, 66} {14, 37, 38} {14, 37, 39}
{14, 37, 40} {14, 37, 41} {14, 37, 42} {14, 37, 43} {14, 37, 44} {14, 37, 45} {14, 37, 46} {14, 37, 47} {14, 37, 48}
{14, 37, 49} {14, 37, 50} {14, 37, 51} {14, 37, 52} {14, 37, 53} {14, 37, 54} {14, 37, 55} {14, 37, 56} {14, 37, 57}
{14, 37, 58} {14, 37, 59} {14, 37, 60} {14, 37, 61} {14, 37, 62} {14, 37, 63} {14, 37, 64} {14, 37, 65} {14, 37, 66}
{14, 38, 39} {14, 38, 40} {14, 38, 41} {14, 38, 42} {14, 38, 43} {14, 38, 44} {14, 38, 45} {14, 38, 46} {14, 38, 47}

TABLE 3A-continued

{14, 38, 48} {14, 38, 49} {14, 38, 50} {14, 38, 51} {14, 38, 52} {14, 38, 53} {14, 38, 54} {14, 38, 55} {14, 38, 56}
{14, 38, 57} {14, 38, 58} {14, 38, 59} {14, 38, 60} {14, 38, 61} {14, 38, 62} {14, 38, 63} {14, 38, 64} {14, 38, 65}
{14, 38, 66} {14, 39, 40} {14, 39, 41} {14, 39, 42} {14, 39, 43} {14, 39, 44} {14, 39, 45} {14, 39, 46} {14, 39, 47}
{14, 39, 48} {14, 39, 49} {14, 39, 50} {14, 39, 51} {14, 39, 52} {14, 39, 53} {14, 39, 54} {14, 39, 55} {14, 39, 56}
{14, 39, 57} {14, 39, 58} {14, 39, 59} {14, 39, 60} {14, 39, 61} {14, 39, 62} {14, 39, 63} {14, 39, 64} {14, 39, 65}
{14, 39, 66} {14, 40, 41} {14, 40, 42} {14, 40, 43} {14, 40, 44} {14, 40, 45} {14, 40, 46} {14, 40, 47} {14, 40, 48}
{14, 40, 49} {14, 40, 50} {14, 40, 51} {14, 40, 52} {14, 40, 53} {14, 40, 54} {14, 40, 55} {14, 40, 56} {14, 40, 57}
{14, 40, 58} {14, 40, 59} {14, 40, 60} {14, 40, 61} {14, 40, 62} {14, 40, 63} {14, 40, 64} {14, 40, 65} {14, 40, 66}
{14, 41, 42} {14, 41, 43} {14, 41, 44} {14, 41, 45} {14, 41, 46} {14, 41, 47} {14, 41, 48} {14, 41, 49} {14, 41, 50}
{14, 41, 51} {14, 41, 52} {14, 41, 53} {14, 41, 54} {14, 41, 55} {14, 41, 56} {14, 41, 57} {14, 41, 58} {14, 41, 59}
{14, 41, 60} {14, 41, 61} {14, 41, 62} {14, 41, 63} {14, 41, 64} {14, 41, 65} {14, 41, 66} {14, 42, 43} {14, 42, 44}
{14, 42, 45} {14, 42, 46} {14, 42, 47} {14, 42, 48} {14, 42, 49} {14, 42, 50} {14, 42, 51} {14, 42, 52} {14, 42, 53}
{14, 42, 54} {14, 42, 55} {14, 42, 56} {14, 42, 57} {14, 42, 58} {14, 42, 59} {14, 42, 60} {14, 42, 61} {14, 42, 62}
{14, 42, 63} {14, 42, 64} {14, 42, 65} {14, 42, 66} {14, 43, 44} {14, 43, 45} {14, 43, 46} {14, 43, 47} {14, 43, 48}
{14, 43, 49} {14, 43, 50} {14, 43, 51} {14, 43, 52} {14, 43, 53} {14, 43, 54} {14, 43, 55} {14, 43, 56} {14, 43, 57}
{14, 43, 58} {14, 43, 59} {14, 43, 60} {14, 43, 61} {14, 43, 62} {14, 43, 63} {14, 43, 64} {14, 43, 65} {14, 43, 66}
{14, 44, 45} {14, 44, 46} {14, 44, 47} {14, 44, 48} {14, 44, 49} {14, 44, 50} {14, 44, 51} {14, 44, 52} {14, 44, 53}
{14, 44, 54} {14, 44, 55} {14, 44, 56} {14, 44, 57} {14, 44, 58} {14, 44, 59} {14, 44, 60} {14, 44, 61} {14, 44, 62}
{14, 44, 63} {14, 44, 64} {14, 44, 65} {14, 44, 66} {14, 45, 46} {14, 45, 47} {14, 45, 48} {14, 45, 49} {14, 45, 50}
{14, 45, 51} {14, 45, 52} {14, 45, 53} {14, 45, 54} {14, 45, 55} {14, 45, 56} {14, 45, 57} {14, 45, 58} {14, 45, 59}
{14, 45, 60} {14, 45, 61} {14, 45, 62} {14, 45, 63} {14, 45, 64} {14, 45, 65} {14, 45, 66} {14, 46, 47} {14, 46, 48}
{14, 46, 49} {14, 46, 50} {14, 46, 51} {14, 46, 52} {14, 46, 53} {14, 46, 54} {14, 46, 55} {14, 46, 56} {14, 46, 57}
{14, 46, 58} {14, 46, 59} {14, 46, 60} {14, 46, 61} {14, 46, 62} {14, 46, 63} {14, 46, 64} {14, 46, 65} {14, 46, 66}
{14, 47, 48} {14, 47, 49} {14, 47, 50} {14, 47, 51} {14, 47, 52} {14, 47, 53} {14, 47, 54} {14, 47, 55} {14, 47, 56}
{14, 47, 57} {14, 47, 58} {14, 47, 59} {14, 47, 60} {14, 47, 61} {14, 47, 62} {14, 47, 63} {14, 47, 64} {14, 47, 65}
{14, 47, 66} {14, 48, 49} {14, 48, 50} {14, 48, 51} {14, 48, 52} {14, 48, 53} {14, 48, 54} {14, 48, 55} {14, 48, 56}
{14, 48, 57} {14, 48, 58} {14, 48, 59} {14, 48, 60} {14, 48, 61} {14, 48, 62} {14, 48, 63} {14, 48, 64} {14, 48, 65}
{14, 48, 66} {14, 49, 50} {14, 49, 51} {14, 49, 52} {14, 49, 53} {14, 49, 54} {14, 49, 55} {14, 49, 56} {14, 49, 57}
{14, 49, 58} {14, 49, 59} {14, 49, 60} {14, 49, 61} {14, 49, 62} {14, 49, 63} {14, 49, 64} {14, 49, 65} {14, 49, 66}
{14, 50, 51} {14, 50, 52} {14, 50, 53} {14, 50, 54} {14, 50, 55} {14, 50, 56} {14, 50, 57} {14, 50, 58} {14, 50, 59}
{14, 50, 60} {14, 50, 61} {14, 50, 62} {14, 50, 63} {14, 50, 64} {14, 50, 65} {14, 50, 66} {14, 51, 52} {14, 51, 53}
{14, 51, 54} {14, 51, 55} {14, 51, 56} {14, 51, 57} {14, 51, 58} {14, 51, 59} {14, 51, 60} {14, 51, 61} {14, 51, 62}
{14, 51, 63} {14, 51, 64} {14, 51, 65} {14, 51, 66} {14, 52, 53} {14, 52, 54} {14, 52, 55} {14, 52, 56} {14, 52, 57}
{14, 52, 58} {14, 52, 59} {14, 52, 60} {14, 52, 61} {14, 52, 62} {14, 52, 63} {14, 52, 64} {14, 52, 65} {14, 52, 66}
{14, 53, 54} {14, 53, 55} {14, 53, 56} {14, 53, 57} {14, 53, 58} {14, 53, 59} {14, 53, 60} {14, 53, 61} {14, 53, 62}
{14, 53, 63} {14, 53, 64} {14, 53, 65} {14, 53, 66} {14, 54, 55} {14, 54, 56} {14, 54, 57} {14, 54, 58} {14, 54, 59}
{14, 54, 60} {14, 54, 61} {14, 54, 62} {14, 54, 63} {14, 54, 64} {14, 54, 65} {14, 54, 66} {14, 55, 56} {14, 55, 57}
{14, 55, 58} {14, 55, 59} {14, 55, 60} {14, 55, 61} {14, 55, 62} {14, 55, 63} {14, 55, 64} {14, 55, 65} {14, 55, 66}
{14, 56, 57} {14, 56, 58} {14, 56, 59} {14, 56, 60} {14, 56, 61} {14, 56, 62} {14, 56, 63} {14, 56, 64} {14, 56, 65}
{14, 56, 66} {14, 57, 58} {14, 57, 59} {14, 57, 60} {14, 57, 61} {14, 57, 62} {14, 57, 63} {14, 57, 64} {14, 57, 65}
{14, 57, 66} {14, 58, 59} {14, 58, 60} {14, 58, 61} {14, 58, 62} {14, 58, 63} {14, 58, 64} {14, 58, 65} {14, 58, 66}
{14, 59, 60} {14, 59, 61} {14, 59, 62} {14, 59, 63} {14, 59, 64} {14, 59, 65} {14, 59, 66} {14, 60, 61} {14, 60, 62}
{14, 60, 63} {14, 60, 64} {14, 60, 65} {14, 60, 66} {14, 61, 62} {14, 61, 63} {14, 61, 64} {14, 61, 65} {14, 61, 66}
{14, 62, 63} {14, 62, 64} {14, 62, 65} {14, 62, 66} {14, 63, 64} {14, 63, 65} {14, 63, 66} {14, 64, 65} {14, 64, 66}
{14, 65, 66} {15, 16, 17} {15, 16, 18} {15, 16, 19} {15, 16, 20} {15, 16, 21} {15, 16, 22} {15, 16, 23} {15, 16, 24}
{15, 16, 25} {15, 16, 26} {15, 16, 27} {15, 16, 28} {15, 16, 29} {15, 16, 30} {15, 16, 31} {15, 16, 32} {15, 16, 33}
{15, 16, 34} {15, 16, 35} {15, 16, 36} {15, 16, 37} {15, 16, 38} {15, 16, 39} {15, 16, 40} {15, 16, 41} {15, 16, 42}
{15, 16, 43} {15, 16, 44} {15, 16, 45} {15, 16, 46} {15, 16, 47} {15, 16, 48} {15, 16, 49} {15, 16, 50} {15, 16, 51}
{15, 16, 52} {15, 16, 53} {15, 16, 54} {15, 16, 55} {15, 16, 56} {15, 16, 57} {15, 16, 58} {15, 16, 59} {15, 16, 60}
{15, 16, 61} {15, 16, 62} {15, 16, 63} {15, 16, 64} {15, 16, 65} {15, 16, 66} {15, 17, 18} {15, 17, 19} {15, 17, 20}
{15, 17, 21} {15, 17, 22} {15, 17, 23} {15, 17, 24} {15, 17, 25} {15, 17, 26} {15, 17, 27} {15, 17, 28} {15, 17, 29}
{15, 17, 30} {15, 17, 31} {15, 17, 32} {15, 17, 33} {15, 17, 34} {15, 17, 35} {15, 17, 36} {15, 17, 37} {15, 17, 38}
{15, 17, 39} {15, 17, 40} {15, 17, 41} {15, 17, 42} {15, 17, 43} {15, 17, 44} {15, 17, 45} {15, 17, 46} {15, 17, 47}
{15, 17, 48} {15, 17, 49} {15, 17, 50} {15, 17, 51} {15, 17, 52} {15, 17, 53} {15, 17, 54} {15, 17, 55} {15, 17, 56}
{15, 17, 57} {15, 17, 58} {15, 17, 59} {15, 17, 60} {15, 17, 61} {15, 17, 62} {15, 17, 63} {15, 17, 64} {15, 17, 65}
{15, 17, 66} {15, 18, 19} {15, 18, 20} {15, 18, 21} {15, 18, 22} {15, 18, 23} {15, 18, 24} {15, 18, 25} {15, 18, 26}
{15, 18, 27} {15, 18, 28} {15, 18, 29} {15, 18, 30} {15, 18, 31} {15, 18, 32} {15, 18, 33} {15, 18, 34} {15, 18, 35}
{15, 18, 36} {15, 18, 37} {15, 18, 38} {15, 18, 39} {15, 18, 40} {15, 18, 41} {15, 18, 42} {15, 18, 43} {15, 18, 44}
{15, 18, 45} {15, 18, 46} {15, 18, 47} {15, 18, 48} {15, 18, 49} {15, 18, 50} {15, 18, 51} {15, 18, 52} {15, 18, 53}
{15, 18, 54} {15, 18, 55} {15, 18, 56} {15, 18, 57} {15, 18, 58} {15, 18, 59} {15, 18, 60} {15, 18, 61} {15, 18, 62}
{15, 18, 63} {15, 18, 64} {15, 18, 65} {15, 18, 66} {15, 19, 20} {15, 19, 21} {15, 19, 22} {15, 19, 23} {15, 19, 24}
{15, 19, 25} {15, 19, 26} {15, 19, 27} {15, 19, 28} {15, 19, 29} {15, 19, 30} {15, 19, 31} {15, 19, 32} {15, 19, 33}
{15, 19, 34} {15, 19, 35} {15, 19, 36} {15, 19, 37} {15, 19, 38} {15, 19, 39} {15, 19, 40} {15, 19, 41} {15, 19, 42}
{15, 19, 43} {15, 19, 44} {15, 19, 45} {15, 19, 46} {15, 19, 47} {15, 19, 48} {15, 19, 49} {15, 19, 50} {15, 19, 51}
{15, 19, 52} {15, 19, 53} {15, 19, 54} {15, 19, 55} {15, 19, 56} {15, 19, 57} {15, 19, 58} {15, 19, 59} {15, 19, 60}
{15, 19, 61} {15, 19, 62} {15, 19, 63} {15, 19, 64} {15, 19, 65} {15, 19, 66} {15, 20, 21} {15, 20, 22} {15, 20, 23}
{15, 20, 24} {15, 20, 25} {15, 20, 26} {15, 20, 27} {15, 20, 28} {15, 20, 29} {15, 20, 30} {15, 20, 31} {15, 20, 32}
{15, 20, 33} {15, 20, 34} {15, 20, 35} {15, 20, 36} {15, 20, 37} {15, 20, 38} {15, 20, 39} {15, 20, 40} {15, 20, 41}
{15, 20, 42} {15, 20, 43} {15, 20, 44} {15, 20, 45} {15, 20, 46} {15, 20, 47} {15, 20, 48} {15, 20, 49} {15, 20, 50}
{15, 20, 51} {15, 20, 52} {15, 20, 53} {15, 20, 54} {15, 20, 55} {15, 20, 56} {15, 20, 57} {15, 20, 58} {15, 20, 59}
{15, 20, 60} {15, 20, 61} {15, 20, 62} {15, 20, 63} {15, 20, 64} {15, 20, 65} {15, 20, 66} {15, 21, 22} {15, 21, 23}
{15, 21, 24} {15, 21, 25} {15, 21, 26} {15, 21, 27} {15, 21, 28} {15, 21, 29} {15, 21, 30} {15, 21, 31} {15, 21, 32}
{15, 21, 33} {15, 21, 34} {15, 21, 35} {15, 21, 36} {15, 21, 37} {15, 21, 38} {15, 21, 39} {15, 21, 40} {15, 21, 41}
{15, 21, 42} {15, 21, 43} {15, 21, 44} {15, 21, 45} {15, 21, 46} {15, 21, 47} {15, 21, 48} {15, 21, 49} {15, 21, 50}
{15, 21, 51} {15, 21, 52} {15, 21, 53} {15, 21, 54} {15, 21, 55} {15, 21, 56} {15, 21, 57} {15, 21, 58} {15, 21, 59}
{15, 21, 60} {15, 21, 61} {15, 21, 62} {15, 21, 63} {15, 21, 64} {15, 21, 65} {15, 21, 66} {15, 22, 23} {15, 22, 24}
{15, 22, 25} {15, 22, 26} {15, 22, 27} {15, 22, 28} {15, 22, 29} {15, 22, 30} {15, 22, 31} {15, 22, 32} {15, 22, 33}
{15, 22, 34} {15, 22, 35} {15, 22, 36} {15, 22, 37} {15, 22, 38} {15, 22, 39} {15, 22, 40} {15, 22, 41} {15, 22, 42}
{15, 22, 43} {15, 22, 44} {15, 22, 45} {15, 22, 46} {15, 22, 47} {15, 22, 48} {15, 22, 49} {15, 22, 50} {15, 22, 51}
{15, 22, 52} {15, 22, 53} {15, 22, 54} {15, 22, 55} {15, 22, 56} {15, 22, 57} {15, 22, 58} {15, 22, 59} {15, 22, 60}

TABLE 3A-continued

{15, 22, 61} {15, 22, 62} {15, 22, 63} {15, 22, 64} {15, 22, 65} {15, 22, 66} {15, 23, 24} {15, 23, 25} {15, 23, 26}
{15, 23, 27} {15, 23, 28} {15, 23, 29} {15, 23, 30} {15, 23, 31} {15, 23, 32} {15, 23, 33} {15, 23, 34} {15, 23, 35}
{15, 23, 36} {15, 23, 37} {15, 23, 38} {15, 23, 39} {15, 23, 40} {15, 23, 41} {15, 23, 42} {15, 23, 43} {15, 23, 44}
{15, 23, 45} {15, 23, 46} {15, 23, 47} {15, 23, 48} {15, 23, 49} {15, 23, 50} {15, 23, 51} {15, 23, 52} {15, 23, 53}
{15, 23, 54} {15, 23, 55} {15, 23, 56} {15, 23, 57} {15, 23, 58} {15, 23, 59} {15, 23, 60} {15, 23, 61} {15, 23, 62}
{15, 23, 63} {15, 23, 64} {15, 23, 65} {15, 23, 66} {15, 24, 25} {15, 24, 26} {15, 24, 27} {15, 24, 28} {15, 24, 29}
{15, 24, 30} {15, 24, 31} {15, 24, 32} {15, 24, 33} {15, 24, 34} {15, 24, 35} {15, 24, 36} {15, 24, 37} {15, 24, 38}
{15, 24, 39} {15, 24, 40} {15, 24, 41} {15, 24, 42} {15, 24, 43} {15, 24, 44} {15, 24, 45} {15, 24, 46} {15, 24, 47}
{15, 24, 48} {15, 24, 49} {15, 24, 50} {15, 24, 51} {15, 24, 52} {15, 24, 53} {15, 24, 54} {15, 24, 55} {15, 24, 56}
{15, 24, 57} {15, 24, 58} {15, 24, 59} {15, 24, 60} {15, 24, 61} {15, 24, 62} {15, 24, 63} {15, 24, 64} {15, 24, 65}
{15, 24, 66} {15, 25, 26} {15, 25, 27} {15, 25, 28} {15, 25, 29} {15, 25, 30} {15, 25, 31} {15, 25, 32} {15, 25, 33}
{15, 25, 34} {15, 25, 35} {15, 25, 36} {15, 25, 37} {15, 25, 38} {15, 25, 39} {15, 25, 40} {15, 25, 41} {15, 25, 42}
{15, 25, 43} {15, 25, 44} {15, 25, 45} {15, 25, 46} {15, 25, 47} {15, 25, 48} {15, 25, 49} {15, 25, 50} {15, 25, 51}
{15, 25, 52} {15, 25, 53} {15, 25, 54} {15, 25, 55} {15, 25, 56} {15, 25, 57} {15, 25, 58} {15, 25, 59} {15, 25, 60}
{15, 25, 61} {15, 25, 62} {15, 25, 63} {15, 25, 64} {15, 25, 65} {15, 25, 66} {15, 26, 27} {15, 26, 28} {15, 26, 29}
{15, 26, 30} {15, 26, 31} {15, 26, 32} {15, 26, 33} {15, 26, 34} {15, 26, 35} {15, 26, 36} {15, 26, 37} {15, 26, 38}
{15, 26, 39} {15, 26, 40} {15, 26, 41} {15, 26, 42} {15, 26, 43} {15, 26, 44} {15, 26, 45} {15, 26, 46} {15, 26, 47}
{15, 26, 48} {15, 26, 49} {15, 26, 50} {15, 26, 51} {15, 26, 52} {15, 26, 53} {15, 26, 54} {15, 26, 55} {15, 26, 56}
{15, 26, 57} {15, 26, 58} {15, 26, 59} {15, 26, 60} {15, 26, 61} {15, 26, 62} {15, 26, 63} {15, 26, 64} {15, 26, 65}
{15, 26, 66} {15, 27, 28} {15, 27, 29} {15, 27, 30} {15, 27, 31} {15, 27, 32} {15, 27, 33} {15, 27, 34} {15, 27, 35}
{15, 27, 36} {15, 27, 37} {15, 27, 38} {15, 27, 39} {15, 27, 40} {15, 27, 41} {15, 27, 42} {15, 27, 43} {15, 27, 44}
{15, 27, 45} {15, 27, 46} {15, 27, 47} {15, 27, 48} {15, 27, 49} {15, 27, 50} {15, 27, 51} {15, 27, 52} {15, 27, 53}
{15, 27, 54} {15, 27, 55} {15, 27, 56} {15, 27, 57} {15, 27, 58} {15, 27, 59} {15, 27, 60} {15, 27, 61} {15, 27, 62}
{15, 27, 63} {15, 27, 64} {15, 27, 65} {15, 27, 66} {15, 28, 29} {15, 28, 30} {15, 28, 31} {15, 28, 32} {15, 28, 33}
{15, 28, 34} {15, 28, 35} {15, 28, 36} {15, 28, 37} {15, 28, 38} {15, 28, 39} {15, 28, 40} {15, 28, 41} {15, 28, 42}
{15, 28, 43} {15, 28, 44} {15, 28, 45} {15, 28, 46} {15, 28, 47} {15, 28, 48} {15, 28, 49} {15, 28, 50} {15, 28, 51}
{15, 28, 52} {15, 28, 53} {15, 28, 54} {15, 28, 55} {15, 28, 56} {15, 28, 57} {15, 28, 58} {15, 28, 59} {15, 28, 60}
{15, 28, 61} {15, 28, 62} {15, 28, 63} {15, 28, 64} {15, 28, 65} {15, 28, 66} {15, 29, 30} {15, 29, 31} {15, 29, 32}
{15, 29, 33} {15, 29, 34} {15, 29, 35} {15, 29, 36} {15, 29, 37} {15, 29, 38} {15, 29, 39} {15, 29, 40} {15, 29, 41}
{15, 29, 42} {15, 29, 43} {15, 29, 44} {15, 29, 45} {15, 29, 46} {15, 29, 47} {15, 29, 48} {15, 29, 49} {15, 29, 50}
{15, 29, 51} {15, 29, 52} {15, 29, 53} {15, 29, 54} {15, 29, 55} {15, 29, 56} {15, 29, 57} {15, 29, 58} {15, 29, 59}
{15, 29, 60} {15, 29, 61} {15, 29, 62} {15, 29, 63} {15, 29, 64} {15, 29, 65} {15, 29, 66} {15, 30, 31} {15, 30, 32}
{15, 30, 33} {15, 30, 34} {15, 30, 35} {15, 30, 36} {15, 30, 37} {15, 30, 38} {15, 30, 39} {15, 30, 40} {15, 30, 41}
{15, 30, 42} {15, 30, 43} {15, 30, 44} {15, 30, 45} {15, 30, 46} {15, 30, 47} {15, 30, 48} {15, 30, 49} {15, 30, 50}
{15, 30, 51} {15, 30, 52} {15, 30, 53} {15, 30, 54} {15, 30, 55} {15, 30, 56} {15, 30, 57} {15, 30, 58} {15, 30, 59}
{15, 30, 60} {15, 30, 61} {15, 30, 62} {15, 30, 63} {15, 30, 64} {15, 30, 65} {15, 30, 66} {15, 31, 32} {15, 31, 33}
{15, 31, 34} {15, 31, 35} {15, 31, 36} {15, 31, 37} {15, 31, 38} {15, 31, 39} {15, 31, 40} {15, 31, 41} {15, 31, 42}
{15, 31, 43} {15, 31, 44} {15, 31, 45} {15, 31, 46} {15, 31, 47} {15, 31, 48} {15, 31, 49} {15, 31, 50} {15, 31, 51}
{15, 31, 52} {15, 31, 53} {15, 31, 54} {15, 31, 55} {15, 31, 56} {15, 31, 57} {15, 31, 58} {15, 31, 59} {15, 31, 60}
{15, 31, 61} {15, 31, 62} {15, 31, 63} {15, 31, 64} {15, 31, 65} {15, 31, 66} {15, 32, 33} {15, 32, 34} {15, 32, 35}
{15, 32, 36} {15, 32, 37} {15, 32, 38} {15, 32, 39} {15, 32, 40} {15, 32, 41} {15, 32, 42} {15, 32, 43} {15, 32, 44}
{15, 32, 45} {15, 32, 46} {15, 32, 47} {15, 32, 48} {15, 32, 49} {15, 32, 50} {15, 32, 51} {15, 32, 52} {15, 32, 53}
{15, 32, 54} {15, 32, 55} {15, 32, 56} {15, 32, 57} {15, 32, 58} {15, 32, 59} {15, 32, 60} {15, 32, 61} {15, 32, 62}
{15, 32, 63} {15, 32, 64} {15, 32, 65} {15, 32, 66} {15, 33, 34} {15, 33, 35} {15, 33, 36} {15, 33, 37} {15, 33, 38}
{15, 33, 39} {15, 33, 40} {15, 33, 41} {15, 33, 42} {15, 33, 43} {15, 33, 44} {15, 33, 45} {15, 33, 46} {15, 33, 47}
{15, 33, 48} {15, 33, 49} {15, 33, 50} {15, 33, 51} {15, 33, 52} {15, 33, 53} {15, 33, 54} {15, 33, 55} {15, 33, 56}
{15, 33, 57} {15, 33, 58} {15, 33, 59} {15, 33, 60} {15, 33, 61} {15, 33, 62} {15, 33, 63} {15, 33, 64} {15, 33, 65}
{15, 33, 66} {15, 34, 35} {15, 34, 36} {15, 34, 37} {15, 34, 38} {15, 34, 39} {15, 34, 40} {15, 34, 41} {15, 34, 42}
{15, 34, 43} {15, 34, 44} {15, 34, 45} {15, 34, 46} {15, 34, 47} {15, 34, 48} {15, 34, 49} {15, 34, 50} {15, 34, 51}
{15, 34, 52} {15, 34, 53} {15, 34, 54} {15, 34, 55} {15, 34, 56} {15, 34, 57} {15, 34, 58} {15, 34, 59} {15, 34, 60}
{15, 34, 61} {15, 34, 62} {15, 34, 63} {15, 34, 64} {15, 34, 65} {15, 34, 66} {15, 35, 36} {15, 35, 37} {15, 35, 38}
{15, 35, 39} {15, 35, 40} {15, 35, 41} {15, 35, 42} {15, 35, 43} {15, 35, 44} {15, 35, 45} {15, 35, 46} {15, 35, 47}
{15, 35, 48} {15, 35, 49} {15, 35, 50} {15, 35, 51} {15, 35, 52} {15, 35, 53} {15, 35, 54} {15, 35, 55} {15, 35, 56}
{15, 35, 57} {15, 35, 58} {15, 35, 59} {15, 35, 60} {15, 35, 61} {15, 35, 62} {15, 35, 63} {15, 35, 64} {15, 35, 65}
{15, 35, 66} {15, 36, 37} {15, 36, 38} {15, 36, 39} {15, 36, 40} {15, 36, 41} {15, 36, 42} {15, 36, 43} {15, 36, 44}
{15, 36, 45} {15, 36, 46} {15, 36, 47} {15, 36, 48} {15, 36, 49} {15, 36, 50} {15, 36, 51} {15, 36, 52} {15, 36, 53}
{15, 36, 54} {15, 36, 55} {15, 36, 56} {15, 36, 57} {15, 36, 58} {15, 36, 59} {15, 36, 60} {15, 36, 61} {15, 36, 62}
{15, 36, 63} {15, 36, 64} {15, 36, 65} {15, 36, 66} {15, 37, 38} {15, 37, 39} {15, 37, 40} {15, 37, 41} {15, 37, 42}
{15, 37, 43} {15, 37, 44} {15, 37, 45} {15, 37, 46} {15, 37, 47} {15, 37, 48} {15, 37, 49} {15, 37, 50} {15, 37, 51}
{15, 37, 52} {15, 37, 53} {15, 37, 54} {15, 37, 55} {15, 37, 56} {15, 37, 57} {15, 37, 58} {15, 37, 59} {15, 37, 60}
{15, 37, 61} {15, 37, 62} {15, 37, 63} {15, 37, 64} {15, 37, 65} {15, 37, 66} {15, 38, 39} {15, 38, 40} {15, 38, 41}
{15, 38, 42} {15, 38, 43} {15, 38, 44} {15, 38, 45} {15, 38, 46} {15, 38, 47} {15, 38, 48} {15, 38, 49} {15, 38, 50}
{15, 38, 51} {15, 38, 52} {15, 38, 53} {15, 38, 54} {15, 38, 55} {15, 38, 56} {15, 38, 57} {15, 38, 58} {15, 38, 59}
{15, 38, 60} {15, 38, 61} {15, 38, 62} {15, 38, 63} {15, 38, 64} {15, 38, 65} {15, 38, 66} {15, 39, 40} {15, 39, 41}
{15, 39, 42} {15, 39, 43} {15, 39, 44} {15, 39, 45} {15, 39, 46} {15, 39, 47} {15, 39, 48} {15, 39, 49} {15, 39, 50}
{15, 39, 51} {15, 39, 52} {15, 39, 53} {15, 39, 54} {15, 39, 55} {15, 39, 56} {15, 39, 57} {15, 39, 58} {15, 39, 59}
{15, 39, 60} {15, 39, 61} {15, 39, 62} {15, 39, 63} {15, 39, 64} {15, 39, 65} {15, 39, 66} {15, 40, 41} {15, 40, 42}
{15, 40, 43} {15, 40, 44} {15, 40, 45} {15, 40, 46} {15, 40, 47} {15, 40, 48} {15, 40, 49} {15, 40, 50} {15, 40, 51}
{15, 40, 52} {15, 40, 53} {15, 40, 54} {15, 40, 55} {15, 40, 56} {15, 40, 57} {15, 40, 58} {15, 40, 59} {15, 40, 60}
{15, 40, 61} {15, 40, 62} {15, 40, 63} {15, 40, 64} {15, 40, 65} {15, 40, 66} {15, 41, 42} {15, 41, 43} {15, 41, 44}
{15, 41, 45} {15, 41, 46} {15, 41, 47} {15, 41, 48} {15, 41, 49} {15, 41, 50} {15, 41, 51} {15, 41, 52} {15, 41, 53}
{15, 41, 54} {15, 41, 55} {15, 41, 56} {15, 41, 57} {15, 41, 58} {15, 41, 59} {15, 41, 60} {15, 41, 61} {15, 41, 62}
{15, 41, 63} {15, 41, 64} {15, 41, 65} {15, 41, 66} {15, 42, 43} {15, 42, 44} {15, 42, 45} {15, 42, 46} {15, 42, 47}
{15, 42, 48} {15, 42, 49} {15, 42, 50} {15, 42, 51} {15, 42, 52} {15, 42, 53} {15, 42, 54} {15, 42, 55} {15, 42, 56}
{15, 42, 57} {15, 42, 58} {15, 42, 59} {15, 42, 60} {15, 42, 61} {15, 42, 62} {15, 42, 63} {15, 42, 64} {15, 42, 65}
{15, 42, 66} {15, 43, 44} {15, 43, 45} {15, 43, 46} {15, 43, 47} {15, 43, 48} {15, 43, 49} {15, 43, 50} {15, 43, 51}
{15, 43, 52} {15, 43, 53} {15, 43, 54} {15, 43, 55} {15, 43, 56} {15, 43, 57} {15, 43, 58} {15, 43, 59} {15, 43, 60}
{15, 43, 61} {15, 43, 62} {15, 43, 63} {15, 43, 64} {15, 43, 65} {15, 43, 66} {15, 44, 45} {15, 44, 46} {15, 44, 47}
{15, 44, 48} {15, 44, 49} {15, 44, 50} {15, 44, 51} {15, 44, 52} {15, 44, 53} {15, 44, 54} {15, 44, 55} {15, 44, 56}
{15, 44, 57} {15, 44, 58} {15, 44, 59} {15, 44, 60} {15, 44, 61} {15, 44, 62} {15, 44, 63} {15, 44, 64} {15, 44, 65}

TABLE 3A-continued

{15, 44, 66} {15, 45, 46} {15, 45, 47} {15, 45, 48} {15, 45, 49} {15, 45, 50} {15, 45, 51} {15, 45, 52} {15, 45, 53}
{15, 45, 54} {15, 45, 55} {15, 45, 56} {15, 45, 57} {15, 45, 58} {15, 45, 59} {15, 45, 60} {15, 45, 61} {15, 45, 62}
{15, 45, 63} {15, 45, 64} {15, 45, 65} {15, 45, 66} {15, 46, 47} {15, 46, 48} {15, 46, 49} {15, 46, 50} {15, 46, 51}
{15, 46, 52} {15, 46, 53} {15, 46, 54} {15, 46, 55} {15, 46, 56} {15, 46, 57} {15, 46, 58} {15, 46, 59} {15, 46, 60}
{15, 46, 61} {15, 46, 62} {15, 46, 63} {15, 46, 64} {15, 46, 65} {15, 46, 66} {15, 47, 48} {15, 47, 49} {15, 47, 50}
{15, 47, 51} {15, 47, 52} {15, 47, 53} {15, 47, 54} {15, 47, 55} {15, 47, 56} {15, 47, 57} {15, 47, 58} {15, 47, 59}
{15, 47, 60} {15, 47, 61} {15, 47, 62} {15, 47, 63} {15, 47, 64} {15, 47, 65} {15, 47, 66} {15, 48, 49} {15, 48, 50}
{15, 48, 51} {15, 48, 52} {15, 48, 53} {15, 48, 54} {15, 48, 55} {15, 48, 56} {15, 48, 57} {15, 48, 58} {15, 48, 59}
{15, 48, 60} {15, 48, 61} {15, 48, 62} {15, 48, 63} {15, 48, 64} {15, 48, 65} {15, 48, 66} {15, 49, 50} {15, 49, 51}
{15, 49, 52} {15, 49, 53} {15, 49, 54} {15, 49, 55} {15, 49, 56} {15, 49, 57} {15, 49, 58} {15, 49, 59} {15, 49, 60}
{15, 49, 61} {15, 49, 62} {15, 49, 63} {15, 49, 64} {15, 49, 65} {15, 49, 66} {15, 50, 51} {15, 50, 52} {15, 50, 53}
{15, 50, 54} {15, 50, 55} {15, 50, 56} {15, 50, 57} {15, 50, 58} {15, 50, 59} {15, 50, 60} {15, 50, 61} {15, 50, 62}
{15, 50, 63} {15, 50, 64} {15, 50, 65} {15, 50, 66} {15, 51, 52} {15, 51, 53} {15, 51, 54} {15, 51, 55} {15, 51, 56}
{15, 51, 57} {15, 51, 58} {15, 51, 59} {15, 51, 60} {15, 51, 61} {15, 51, 62} {15, 51, 63} {15, 51, 64} {15, 51, 65}
{15, 51, 66} {15, 52, 53} {15, 52, 54} {15, 52, 55} {15, 52, 56} {15, 52, 57} {15, 52, 58} {15, 52, 59} {15, 52, 60}
{15, 52, 61} {15, 52, 62} {15, 52, 63} {15, 52, 64} {15, 52, 65} {15, 52, 66} {15, 53, 54} {15, 53, 55} {15, 53, 56}
{15, 53, 57} {15, 53, 58} {15, 53, 59} {15, 53, 60} {15, 53, 61} {15, 53, 62} {15, 53, 63} {15, 53, 64} {15, 53, 65}
{15, 53, 66} {15, 54, 55} {15, 54, 56} {15, 54, 57} {15, 54, 58} {15, 54, 59} {15, 54, 60} {15, 54, 61} {15, 54, 62}
{15, 54, 63} {15, 54, 64} {15, 54, 65} {15, 54, 66} {15, 55, 56} {15, 55, 57} {15, 55, 58} {15, 55, 59} {15, 55, 60}
{15, 55, 61} {15, 55, 62} {15, 55, 63} {15, 55, 64} {15, 55, 65} {15, 55, 66} {15, 56, 57} {15, 56, 58} {15, 56, 59}
{15, 56, 60} {15, 56, 61} {15, 56, 62} {15, 56, 63} {15, 56, 64} {15, 56, 65} {15, 56, 66} {15, 57, 58} {15, 57, 59}
{15, 57, 60} {15, 57, 61} {15, 57, 62} {15, 57, 63} {15, 57, 64} {15, 57, 65} {15, 57, 66} {15, 58, 59} {15, 58, 60}
{15, 58, 61} {15, 58, 62} {15, 58, 63} {15, 58, 64} {15, 58, 65} {15, 58, 66} {15, 59, 60} {15, 59, 61} {15, 59, 62}
{15, 59, 63} {15, 59, 64} {15, 59, 65} {15, 59, 66} {15, 60, 61} {15, 60, 62} {15, 60, 63} {15, 60, 64} {15, 60, 65}
{15, 60, 66} {15, 61, 62} {15, 61, 63} {15, 61, 64} {15, 61, 65} {15, 61, 66} {15, 62, 63} {15, 62, 64} {15, 62, 65}
{15, 62, 66} {15, 63, 64} {15, 63, 65} {15, 63, 66} {15, 64, 65} {15, 64, 66} {15, 65, 66} {16, 17, 18} {16, 17, 19}
{16, 17, 20} {16, 17, 21} {16, 17, 22} {16, 17, 23} {16, 17, 24} {16, 17, 25} {16, 17, 26} {16, 17, 27} {16, 17, 28}
{16, 17, 29} {16, 17, 30} {16, 17, 31} {16, 17, 32} {16, 17, 33} {16, 17, 34} {16, 17, 35} {16, 17, 36} {16, 17, 37}
{16, 17, 38} {16, 17, 39} {16, 17, 40} {16, 17, 41} {16, 17, 42} {16, 17, 43} {16, 17, 44} {16, 17, 45} {16, 17, 46}
{16, 17, 47} {16, 17, 48} {16, 17, 49} {16, 17, 50} {16, 17, 51} {16, 17, 52} {16, 17, 53} {16, 17, 54} {16, 17, 55}
{16, 17, 56} {16, 17, 57} {16, 17, 58} {16, 17, 59} {16, 17, 60} {16, 17, 61} {16, 17, 62} {16, 17, 63} {16, 17, 64}
{16, 17, 65} {16, 17, 66} {16, 18, 19} {16, 18, 20} {16, 18, 21} {16, 18, 22} {16, 18, 23} {16, 18, 24} {16, 18, 25}
{16, 18, 26} {16, 18, 27} {16, 18, 28} {16, 18, 29} {16, 18, 30} {16, 18, 31} {16, 18, 32} {16, 18, 33} {16, 18, 34}
{16, 18, 35} {16, 18, 36} {16, 18, 37} {16, 18, 38} {16, 18, 39} {16, 18, 40} {16, 18, 41} {16, 18, 42} {16, 18, 43}
{16, 18, 44} {16, 18, 45} {16, 18, 46} {16, 18, 47} {16, 18, 48} {16, 18, 49} {16, 18, 50} {16, 18, 51} {16, 18, 52}
{16, 18, 53} {16, 18, 54} {16, 18, 55} {16, 18, 56} {16, 18, 57} {16, 18, 58} {16, 18, 59} {16, 18, 60} {16, 18, 61}
{16, 18, 62} {16, 18, 63} {16, 18, 64} {16, 18, 65} {16, 18, 66} {16, 19, 20} {16, 19, 21} {16, 19, 22} {16, 19, 23}
{16, 19, 24} {16, 19, 25} {16, 19, 26} {16, 19, 27} {16, 19, 28} {16, 19, 29} {16, 19, 30} {16, 19, 31} {16, 19, 32}
{16, 19, 33} {16, 19, 34} {16, 19, 35} {16, 19, 36} {16, 19, 37} {16, 19, 38} {16, 19, 39} {16, 19, 40} {16, 19, 41}
{16, 19, 42} {16, 19, 43} {16, 19, 44} {16, 19, 45} {16, 19, 46} {16, 19, 47} {16, 19, 48} {16, 19, 49} {16, 19, 50}
{16, 19, 51} {16, 19, 52} {16, 19, 53} {16, 19, 54} {16, 19, 55} {16, 19, 56} {16, 19, 57} {16, 19, 58} {16, 19, 59}
{16, 19, 60} {16, 19, 61} {16, 19, 62} {16, 19, 63} {16, 19, 64} {16, 19, 65} {16, 19, 66} {16, 20, 21} {16, 20, 22}
{16, 20, 23} {16, 20, 24} {16, 20, 25} {16, 20, 26} {16, 20, 27} {16, 20, 28} {16, 20, 29} {16, 20, 30} {16, 20, 31}
{16, 20, 32} {16, 20, 33} {16, 20, 34} {16, 20, 35} {16, 20, 36} {16, 20, 37} {16, 20, 38} {16, 20, 39} {16, 20, 40}
{16, 20, 41} {16, 20, 42} {16, 20, 43} {16, 20, 44} {16, 20, 45} {16, 20, 46} {16, 20, 47} {16, 20, 48} {16, 20, 49}
{16, 20, 50} {16, 20, 51} {16, 20, 52} {16, 20, 53} {16, 20, 54} {16, 20, 55} {16, 20, 56} {16, 20, 57} {16, 20, 58}
{16, 20, 59} {16, 20, 60} {16, 20, 61} {16, 20, 62} {16, 20, 63} {16, 20, 64} {16, 20, 65} {16, 20, 66} {16, 21, 22}
{16, 21, 23} {16, 21, 24} {16, 21, 25} {16, 21, 26} {16, 21, 27} {16, 21, 28} {16, 21, 29} {16, 21, 30} {16, 21, 31}
{16, 21, 32} {16, 21, 33} {16, 21, 34} {16, 21, 35} {16, 21, 36} {16, 21, 37} {16, 21, 38} {16, 21, 39} {16, 21, 40}
{16, 21, 41} {16, 21, 42} {16, 21, 43} {16, 21, 44} {16, 21, 45} {16, 21, 46} {16, 21, 47} {16, 21, 48} {16, 21, 49}
{16, 21, 50} {16, 21, 51} {16, 21, 52} {16, 21, 53} {16, 21, 54} {16, 21, 55} {16, 21, 56} {16, 21, 57} {16, 21, 58}
{16, 21, 59} {16, 21, 60} {16, 21, 61} {16, 21, 62} {16, 21, 63} {16, 21, 64} {16, 21, 65} {16, 21, 66} {16, 22, 23}
{16, 22, 24} {16, 22, 25} {16, 22, 26} {16, 22, 27} {16, 22, 28} {16, 22, 29} {16, 22, 30} {16, 22, 31} {16, 22, 32}
{16, 22, 33} {16, 22, 34} {16, 22, 35} {16, 22, 36} {16, 22, 37} {16, 22, 38} {16, 22, 39} {16, 22, 40} {16, 22, 41}
{16, 22, 42} {16, 22, 43} {16, 22, 44} {16, 22, 45} {16, 22, 46} {16, 22, 47} {16, 22, 48} {16, 22, 49} {16, 22, 50}
{16, 22, 51} {16, 22, 52} {16, 22, 53} {16, 22, 54} {16, 22, 55} {16, 22, 56} {16, 22, 57} {16, 22, 58} {16, 22, 59}
{16, 22, 60} {16, 22, 61} {16, 22, 62} {16, 22, 63} {16, 22, 64} {16, 22, 65} {16, 22, 66} {16, 23, 24} {16, 23, 25}
{16, 23, 26} {16, 23, 27} {16, 23, 28} {16, 23, 29} {16, 23, 30} {16, 23, 31} {16, 23, 32} {16, 23, 33} {16, 23, 34}
{16, 23, 35} {16, 23, 36} {16, 23, 37} {16, 23, 38} {16, 23, 39} {16, 23, 40} {16, 23, 41} {16, 23, 42} {16, 23, 43}
{16, 23, 44} {16, 23, 45} {16, 23, 46} {16, 23, 47} {16, 23, 48} {16, 23, 49} {16, 23, 50} {16, 23, 51} {16, 23, 52}
{16, 23, 53} {16, 23, 54} {16, 23, 55} {16, 23, 56} {16, 23, 57} {16, 23, 58} {16, 23, 59} {16, 23, 60} {16, 23, 61}
{16, 23, 62} {16, 23, 63} {16, 23, 64} {16, 23, 65} {16, 23, 66} {16, 24, 25} {16, 24, 26} {16, 24, 27} {16, 24, 28}
{16, 24, 29} {16, 24, 30} {16, 24, 31} {16, 24, 32} {16, 24, 33} {16, 24, 34} {16, 24, 35} {16, 24, 36} {16, 24, 37}
{16, 24, 38} {16, 24, 39} {16, 24, 40} {16, 24, 41} {16, 24, 42} {16, 24, 43} {16, 24, 44} {16, 24, 45} {16, 24, 46}
{16, 24, 47} {16, 24, 48} {16, 24, 49} {16, 24, 50} {16, 24, 51} {16, 24, 52} {16, 24, 53} {16, 24, 54} {16, 24, 55}
{16, 24, 56} {16, 24, 57} {16, 24, 58} {16, 24, 59} {16, 24, 60} {16, 24, 61} {16, 24, 62} {16, 24, 63} {16, 24, 64}
{16, 24, 65} {16, 24, 66} {16, 25, 26} {16, 25, 27} {16, 25, 28} {16, 25, 29} {16, 25, 30} {16, 25, 31} {16, 25, 32}
{16, 25, 33} {16, 25, 34} {16, 25, 35} {16, 25, 36} {16, 25, 37} {16, 25, 38} {16, 25, 39} {16, 25, 40} {16, 25, 41}
{16, 25, 42} {16, 25, 43} {16, 25, 44} {16, 25, 45} {16, 25, 46} {16, 25, 47} {16, 25, 48} {16, 25, 49} {16, 25, 50}
{16, 25, 51} {16, 25, 52} {16, 25, 53} {16, 25, 54} {16, 25, 55} {16, 25, 56} {16, 25, 57} {16, 25, 58} {16, 25, 59}
{16, 25, 60} {16, 25, 61} {16, 25, 62} {16, 25, 63} {16, 25, 64} {16, 25, 65} {16, 25, 66} {16, 26, 27} {16, 26, 28}
{16, 26, 29} {16, 26, 30} {16, 26, 31} {16, 26, 32} {16, 26, 33} {16, 26, 34} {16, 26, 35} {16, 26, 36} {16, 26, 37}
{16, 26, 38} {16, 26, 39} {16, 26, 40} {16, 26, 41} {16, 26, 42} {16, 26, 43} {16, 26, 44} {16, 26, 45} {16, 26, 46}
{16, 26, 47} {16, 26, 48} {16, 26, 49} {16, 26, 50} {16, 26, 51} {16, 26, 52} {16, 26, 53} {16, 26, 54} {16, 26, 55}
{16, 26, 56} {16, 26, 57} {16, 26, 58} {16, 26, 59} {16, 26, 60} {16, 26, 61} {16, 26, 62} {16, 26, 63} {16, 26, 64}
{16, 26, 65} {16, 26, 66} {16, 27, 28} {16, 27, 29} {16, 27, 30} {16, 27, 31} {16, 27, 32} {16, 27, 33} {16, 27, 34}
{16, 27, 35} {16, 27, 36} {16, 27, 37} {16, 27, 38} {16, 27, 39} {16, 27, 40} {16, 27, 41} {16, 27, 42} {16, 27, 43}
{16, 27, 44} {16, 27, 45} {16, 27, 46} {16, 27, 47} {16, 27, 48} {16, 27, 49} {16, 27, 50} {16, 27, 51} {16, 27, 52}
{16, 27, 53} {16, 27, 54} {16, 27, 55} {16, 27, 56} {16, 27, 57} {16, 27, 58} {16, 27, 59} {16, 27, 60} {16, 27, 61}
{16, 27, 62} {16, 27, 63} {16, 27, 64} {16, 27, 65} {16, 27, 66} {16, 28, 29} {16, 28, 30} {16, 28, 31} {16, 28, 32}

TABLE 3A-continued

{16, 28, 33} {16, 28, 34} {16, 28, 35} {16, 28, 36} {16, 28, 37} {16, 28, 38} {16, 28, 39} {16, 28, 40} {16, 28, 41}
{16, 28, 42} {16, 28, 43} {16, 28, 44} {16, 28, 45} {16, 28, 46} {16, 28, 47} {16, 28, 48} {16, 28, 49} {16, 28, 50}
{16, 28, 51} {16, 28, 52} {16, 28, 53} {16, 28, 54} {16, 28, 55} {16, 28, 56} {16, 28, 57} {16, 28, 58} {16, 28, 59}
{16, 28, 60} {16, 28, 61} {16, 28, 62} {16, 28, 63} {16, 28, 64} {16, 28, 65} {16, 28, 66} {16, 29, 30} {16, 29, 31}
{16, 29, 32} {16, 29, 33} {16, 29, 34} {16, 29, 35} {16, 29, 36} {16, 29, 37} {16, 29, 38} {16, 29, 39} {16, 29, 40}
{16, 29, 41} {16, 29, 42} {16, 29, 43} {16, 29, 44} {16, 29, 45} {16, 29, 46} {16, 29, 47} {16, 29, 48} {16, 29, 49}
{16, 29, 50} {16, 29, 51} {16, 29, 52} {16, 29, 53} {16, 29, 54} {16, 29, 55} {16, 29, 56} {16, 29, 57} {16, 29, 58}
{16, 29, 59} {16, 29, 60} {16, 29, 61} {16, 29, 62} {16, 29, 63} {16, 29, 64} {16, 29, 65} {16, 29, 66} {16, 30, 31}
{16, 30, 32} {16, 30, 33} {16, 30, 34} {16, 30, 35} {16, 30, 36} {16, 30, 37} {16, 30, 38} {16, 30, 39} {16, 30, 40}
{16, 30, 41} {16, 30, 42} {16, 30, 43} {16, 30, 44} {16, 30, 45} {16, 30, 46} {16, 30, 47} {16, 30, 48} {16, 30, 49}
{16, 30, 50} {16, 30, 51} {16, 30, 52} {16, 30, 53} {16, 30, 54} {16, 30, 55} {16, 30, 56} {16, 30, 57} {16, 30, 58}
{16, 30, 59} {16, 30, 60} {16, 30, 61} {16, 30, 62} {16, 30, 63} {16, 30, 64} {16, 30, 65} {16, 30, 66} {16, 31, 32}
{16, 31, 33} {16, 31, 34} {16, 31, 35} {16, 31, 36} {16, 31, 37} {16, 31, 38} {16, 31, 39} {16, 31, 40} {16, 31, 41}
{16, 31, 42} {16, 31, 43} {16, 31, 44} {16, 31, 45} {16, 31, 46} {16, 31, 47} {16, 31, 48} {16, 31, 49} {16, 31, 50}
{16, 31, 51} {16, 31, 52} {16, 31, 53} {16, 31, 54} {16, 31, 55} {16, 31, 56} {16, 31, 57} {16, 31, 58} {16, 31, 59}
{16, 31, 60} {16, 31, 61} {16, 31, 62} {16, 31, 63} {16, 31, 64} {16, 31, 65} {16, 31, 66} {16, 32, 33} {16, 32, 34}
{16, 32, 35} {16, 32, 36} {16, 32, 37} {16, 32, 38} {16, 32, 39} {16, 32, 40} {16, 32, 41} {16, 32, 42} {16, 32, 43}
{16, 32, 44} {16, 32, 45} {16, 32, 46} {16, 32, 47} {16, 32, 48} {16, 32, 49} {16, 32, 50} {16, 32, 51} {16, 32, 52}
{16, 32, 53} {16, 32, 54} {16, 32, 55} {16, 32, 56} {16, 32, 57} {16, 32, 58} {16, 32, 59} {16, 32, 60} {16, 32, 61}
{16, 32, 62} {16, 32, 63} {16, 32, 64} {16, 32, 65} {16, 32, 66} {16, 33, 34} {16, 33, 35} {16, 33, 36} {16, 33, 37}
{16, 33, 38} {16, 33, 39} {16, 33, 40} {16, 33, 41} {16, 33, 42} {16, 33, 43} {16, 33, 44} {16, 33, 45} {16, 33, 46}
{16, 33, 47} {16, 33, 48} {16, 33, 49} {16, 33, 50} {16, 33, 51} {16, 33, 52} {16, 33, 53} {16, 33, 54} {16, 33, 55}
{16, 33, 56} {16, 33, 57} {16, 33, 58} {16, 33, 59} {16, 33, 60} {16, 33, 61} {16, 33, 62} {16, 33, 63} {16, 33, 64}
{16, 33, 65} {16, 33, 66} {16, 34, 35} {16, 34, 36} {16, 34, 37} {16, 34, 38} {16, 34, 39} {16, 34, 40} {16, 34, 41}
{16, 34, 42} {16, 34, 43} {16, 34, 44} {16, 34, 45} {16, 34, 46} {16, 34, 47} {16, 34, 48} {16, 34, 49} {16, 34, 50}
{16, 34, 51} {16, 34, 52} {16, 34, 53} {16, 34, 54} {16, 34, 55} {16, 34, 56} {16, 34, 57} {16, 34, 58} {16, 34, 59}
{16, 34, 60} {16, 34, 61} {16, 34, 62} {16, 34, 63} {16, 34, 64} {16, 34, 65} {16, 34, 66} {16, 35, 36} {16, 35, 37}
{16, 35, 38} {16, 35, 39} {16, 35, 40} {16, 35, 41} {16, 35, 42} {16, 35, 43} {16, 35, 44} {16, 35, 45} {16, 35, 46}
{16, 35, 47} {16, 35, 48} {16, 35, 49} {16, 35, 50} {16, 35, 51} {16, 35, 52} {16, 35, 53} {16, 35, 54} {16, 35, 55}
{16, 35, 56} {16, 35, 57} {16, 35, 58} {16, 35, 59} {16, 35, 60} {16, 35, 61} {16, 35, 62} {16, 35, 63} {16, 35, 64}
{16, 35, 65} {16, 35, 66} {16, 36, 37} {16, 36, 38} {16, 36, 39} {16, 36, 40} {16, 36, 41} {16, 36, 42} {16, 36, 43}
{16, 36, 44} {16, 36, 45} {16, 36, 46} {16, 36, 47} {16, 36, 48} {16, 36, 49} {16, 36, 50} {16, 36, 51} {16, 36, 52}
{16, 36, 53} {16, 36, 54} {16, 36, 55} {16, 36, 56} {16, 36, 57} {16, 36, 58} {16, 36, 59} {16, 36, 60} {16, 36, 61}
{16, 36, 62} {16, 36, 63} {16, 36, 64} {16, 36, 65} {16, 36, 66} {16, 37, 38} {16, 37, 39} {16, 37, 40} {16, 37, 41}
{16, 37, 42} {16, 37, 43} {16, 37, 44} {16, 37, 45} {16, 37, 46} {16, 37, 47} {16, 37, 48} {16, 37, 49} {16, 37, 50}
{16, 37, 51} {16, 37, 52} {16, 37, 53} {16, 37, 54} {16, 37, 55} {16, 37, 56} {16, 37, 57} {16, 37, 58} {16, 37, 59}
{16, 37, 60} {16, 37, 61} {16, 37, 62} {16, 37, 63} {16, 37, 64} {16, 37, 65} {16, 37, 66} {16, 38, 39} {16, 38, 40}
{16, 38, 41} {16, 38, 42} {16, 38, 43} {16, 38, 44} {16, 38, 45} {16, 38, 46} {16, 38, 47} {16, 38, 48} {16, 38, 49}
{16, 38, 50} {16, 38, 51} {16, 38, 52} {16, 38, 53} {16, 38, 54} {16, 38, 55} {16, 38, 56} {16, 38, 57} {16, 38, 58}
{16, 38, 59} {16, 38, 60} {16, 38, 61} {16, 38, 62} {16, 38, 63} {16, 38, 64} {16, 38, 65} {16, 38, 66} {16, 39, 40}
{16, 39, 41} {16, 39, 42} {16, 39, 43} {16, 39, 44} {16, 39, 45} {16, 39, 46} {16, 39, 47} {16, 39, 48} {16, 39, 49}
{16, 39, 50} {16, 39, 51} {16, 39, 52} {16, 39, 53} {16, 39, 54} {16, 39, 55} {16, 39, 56} {16, 39, 57} {16, 39, 58}
{16, 39, 59} {16, 39, 60} {16, 39, 61} {16, 39, 62} {16, 39, 63} {16, 39, 64} {16, 39, 65} {16, 39, 66} {16, 40, 41}
{16, 40, 42} {16, 40, 43} {16, 40, 44} {16, 40, 45} {16, 40, 46} {16, 40, 47} {16, 40, 48} {16, 40, 49} {16, 40, 50}
{16, 40, 51} {16, 40, 52} {16, 40, 53} {16, 40, 54} {16, 40, 55} {16, 40, 56} {16, 40, 57} {16, 40, 58} {16, 40, 59}
{16, 40, 60} {16, 40, 61} {16, 40, 62} {16, 40, 63} {16, 40, 64} {16, 40, 65} {16, 40, 66} {16, 41, 42} {16, 41, 43}
{16, 41, 44} {16, 41, 45} {16, 41, 46} {16, 41, 47} {16, 41, 48} {16, 41, 49} {16, 41, 50} {16, 41, 51} {16, 41, 52}
{16, 41, 53} {16, 41, 54} {16, 41, 55} {16, 41, 56} {16, 41, 57} {16, 41, 58} {16, 41, 59} {16, 41, 60} {16, 41, 61}
{16, 41, 62} {16, 41, 63} {16, 41, 64} {16, 41, 65} {16, 41, 66} {16, 42, 43} {16, 42, 44} {16, 42, 45} {16, 42, 46}
{16, 42, 47} {16, 42, 48} {16, 42, 49} {16, 42, 50} {16, 42, 51} {16, 42, 52} {16, 42, 53} {16, 42, 54} {16, 42, 55}
{16, 42, 56} {16, 42, 57} {16, 42, 58} {16, 42, 59} {16, 42, 60} {16, 42, 61} {16, 42, 62} {16, 42, 63} {16, 42, 64}
{16, 42, 65} {16, 42, 66} {16, 43, 44} {16, 43, 45} {16, 43, 46} {16, 43, 47} {16, 43, 48} {16, 43, 49} {16, 43, 50}
{16, 43, 51} {16, 43, 52} {16, 43, 53} {16, 43, 54} {16, 43, 55} {16, 43, 56} {16, 43, 57} {16, 43, 58} {16, 43, 59}
{16, 43, 60} {16, 43, 61} {16, 43, 62} {16, 43, 63} {16, 43, 64} {16, 43, 65} {16, 43, 66} {16, 44, 45} {16, 44, 46}
{16, 44, 47} {16, 44, 48} {16, 44, 49} {16, 44, 50} {16, 44, 51} {16, 44, 52} {16, 44, 53} {16, 44, 54} {16, 44, 55}
{16, 44, 56} {16, 44, 57} {16, 44, 58} {16, 44, 59} {16, 44, 60} {16, 44, 61} {16, 44, 62} {16, 44, 63} {16, 44, 64}
{16, 44, 65} {16, 44, 66} {16, 45, 46} {16, 45, 47} {16, 45, 48} {16, 45, 49} {16, 45, 50} {16, 45, 51} {16, 45, 52}
{16, 45, 53} {16, 45, 54} {16, 45, 55} {16, 45, 56} {16, 45, 57} {16, 45, 58} {16, 45, 59} {16, 45, 60} {16, 45, 61}
{16, 45, 62} {16, 45, 63} {16, 45, 64} {16, 45, 65} {16, 45, 66} {16, 46, 47} {16, 46, 48} {16, 46, 49} {16, 46, 50}
{16, 46, 51} {16, 46, 52} {16, 46, 53} {16, 46, 54} {16, 46, 55} {16, 46, 56} {16, 46, 57} {16, 46, 58} {16, 46, 59}
{16, 46, 60} {16, 46, 61} {16, 46, 62} {16, 46, 63} {16, 46, 64} {16, 46, 65} {16, 46, 66} {16, 47, 48} {16, 47, 49}
{16, 47, 50} {16, 47, 51} {16, 47, 52} {16, 47, 53} {16, 47, 54} {16, 47, 55} {16, 47, 56} {16, 47, 57} {16, 47, 58}
{16, 47, 59} {16, 47, 60} {16, 47, 61} {16, 47, 62} {16, 47, 63} {16, 47, 64} {16, 47, 65} {16, 47, 66} {16, 48, 49}
{16, 48, 50} {16, 48, 51} {16, 48, 52} {16, 48, 53} {16, 48, 54} {16, 48, 55} {16, 48, 56} {16, 48, 57} {16, 48, 58}
{16, 48, 59} {16, 48, 60} {16, 48, 61} {16, 48, 62} {16, 48, 63} {16, 48, 64} {16, 48, 65} {16, 48, 66} {16, 49, 50}
{16, 49, 51} {16, 49, 52} {16, 49, 53} {16, 49, 54} {16, 49, 55} {16, 49, 56} {16, 49, 57} {16, 49, 58} {16, 49, 59}
{16, 49, 60} {16, 49, 61} {16, 49, 62} {16, 49, 63} {16, 49, 64} {16, 49, 65} {16, 49, 66} {16, 50, 51} {16, 50, 52}
{16, 50, 53} {16, 50, 54} {16, 50, 55} {16, 50, 56} {16, 50, 57} {16, 50, 58} {16, 50, 59} {16, 50, 60} {16, 50, 61}
{16, 50, 62} {16, 50, 63} {16, 50, 64} {16, 50, 65} {16, 50, 66} {16, 51, 52} {16, 51, 53} {16, 51, 54} {16, 51, 55}
{16, 51, 56} {16, 51, 57} {16, 51, 58} {16, 51, 59} {16, 51, 60} {16, 51, 61} {16, 51, 62} {16, 51, 63} {16, 51, 64}
{16, 51, 65} {16, 51, 66} {16, 52, 53} {16, 52, 54} {16, 52, 55} {16, 52, 56} {16, 52, 57} {16, 52, 58} {16, 52, 59}
{16, 52, 60} {16, 52, 61} {16, 52, 62} {16, 52, 63} {16, 52, 64} {16, 52, 65} {16, 52, 66} {16, 53, 54} {16, 53, 55}
{16, 53, 56} {16, 53, 57} {16, 53, 58} {16, 53, 59} {16, 53, 60} {16, 53, 61} {16, 53, 62} {16, 53, 63} {16, 53, 64}
{16, 53, 65} {16, 53, 66} {16, 54, 55} {16, 54, 56} {16, 54, 57} {16, 54, 58} {16, 54, 59} {16, 54, 60} {16, 54, 61}
{16, 54, 62} {16, 54, 63} {16, 54, 64} {16, 54, 65} {16, 54, 66} {16, 55, 56} {16, 55, 57} {16, 55, 58} {16, 55, 59}
{16, 55, 60} {16, 55, 61} {16, 55, 62} {16, 55, 63} {16, 55, 64} {16, 55, 65} {16, 55, 66} {16, 56, 57} {16, 56, 58}
{16, 56, 59} {16, 56, 60} {16, 56, 61} {16, 56, 62} {16, 56, 63} {16, 56, 64} {16, 56, 65} {16, 56, 66} {16, 57, 58}
{16, 57, 59} {16, 57, 60} {16, 57, 61} {16, 57, 62} {16, 57, 63} {16, 57, 64} {16, 57, 65} {16, 57, 66} {16, 58, 59}
{16, 58, 60} {16, 58, 61} {16, 58, 62} {16, 58, 63} {16, 58, 64} {16, 58, 65} {16, 58, 66} {16, 59, 60} {16, 59, 61}
{16, 59, 62} {16, 59, 63} {16, 59, 64} {16, 59, 65} {16, 59, 66} {16, 60, 61} {16, 60, 62} {16, 60, 63} {16, 60, 64}

TABLE 3A-continued

{16, 60, 65} {16, 60, 66} {16, 61, 62} {16, 61, 63} {16, 61, 64} {16, 61, 65} {16, 61, 66} {16, 62, 63} {16, 62, 64}
{16, 62, 65} {16, 62, 66} {16, 63, 64} {16, 63, 65} {16, 63, 66} {16, 64, 65} {16, 64, 66} {16, 65, 66} {17, 18, 19}
{17, 18, 20} {17, 18, 21} {17, 18, 22} {17, 18, 23} {17, 18, 24} {17, 18, 25} {17, 18, 26} {17, 18, 27} {17, 18, 28}
{17, 18, 29} {17, 18, 30} {17, 18, 31} {17, 18, 32} {17, 18, 33} {17, 18, 34} {17, 18, 35} {17, 18, 36} {17, 18, 37}
{17, 18, 38} {17, 18, 39} {17, 18, 40} {17, 18, 41} {17, 18, 42} {17, 18, 43} {17, 18, 44} {17, 18, 45} {17, 18, 46}
{17, 18, 47} {17, 18, 48} {17, 18, 49} {17, 18, 50} {17, 18, 51} {17, 18, 52} {17, 18, 53} {17, 18, 54} {17, 18, 55}
{17, 18, 56} {17, 18, 57} {17, 18, 58} {17, 18, 59} {17, 18, 60} {17, 18, 61} {17, 18, 62} {17, 18, 63} {17, 18, 64}
{17, 18, 65} {17, 18, 66} {17, 19, 20} {17, 19, 21} {17, 19, 22} {17, 19, 23} {17, 19, 24} {17, 19, 25} {17, 19, 26}
{17, 19, 27} {17, 19, 28} {17, 19, 29} {17, 19, 30} {17, 19, 31} {17, 19, 32} {17, 19, 33} {17, 19, 34} {17, 19, 35}
{17, 19, 36} {17, 19, 37} {17, 19, 38} {17, 19, 39} {17, 19, 40} {17, 19, 41} {17, 19, 42} {17, 19, 43} {17, 19, 44}
{17, 19, 45} {17, 19, 46} {17, 19, 47} {17, 19, 48} {17, 19, 49} {17, 19, 50} {17, 19, 51} {17, 19, 52} {17, 19, 53}
{17, 19, 54} {17, 19, 55} {17, 19, 56} {17, 19, 57} {17, 19, 58} {17, 19, 59} {17, 19, 60} {17, 19, 61} {17, 19, 62}
{17, 19, 63} {17, 19, 64} {17, 19, 65} {17, 19, 66} {17, 20, 21} {17, 20, 22} {17, 20, 23} {17, 20, 24} {17, 20, 25}
{17, 20, 26} {17, 20, 27} {17, 20, 28} {17, 20, 29} {17, 20, 30} {17, 20, 31} {17, 20, 32} {17, 20, 33} {17, 20, 34}
{17, 20, 35} {17, 20, 36} {17, 20, 37} {17, 20, 38} {17, 20, 39} {17, 20, 40} {17, 20, 41} {17, 20, 42} {17, 20, 43}
{17, 20, 44} {17, 20, 45} {17, 20, 46} {17, 20, 47} {17, 20, 48} {17, 20, 49} {17, 20, 50} {17, 20, 51} {17, 20, 52}
{17, 20, 53} {17, 20, 54} {17, 20, 55} {17, 20, 56} {17, 20, 57} {17, 20, 58} {17, 20, 59} {17, 20, 60} {17, 20, 61}
{17, 20, 62} {17, 20, 63} {17, 20, 64} {17, 20, 65} {17, 20, 66} {17, 21, 22} {17, 21, 23} {17, 21, 24} {17, 21, 25}
{17, 21, 26} {17, 21, 27} {17, 21, 28} {17, 21, 29} {17, 21, 30} {17, 21, 31} {17, 21, 32} {17, 21, 33} {17, 21, 34}
{17, 21, 35} {17, 21, 36} {17, 21, 37} {17, 21, 38} {17, 21, 39} {17, 21, 40} {17, 21, 41} {17, 21, 42} {17, 21, 43}
{17, 21, 44} {17, 21, 45} {17, 21, 46} {17, 21, 47} {17, 21, 48} {17, 21, 49} {17, 21, 50} {17, 21, 51} {17, 21, 52}
{17, 21, 53} {17, 21, 54} {17, 21, 55} {17, 21, 56} {17, 21, 57} {17, 21, 58} {17, 21, 59} {17, 21, 60} {17, 21, 61}
{17, 21, 62} {17, 21, 63} {17, 21, 64} {17, 21, 65} {17, 21, 66} {17, 22, 23} {17, 22, 24} {17, 22, 25} {17, 22, 26}
{17, 22, 27} {17, 22, 28} {17, 22, 29} {17, 22, 30} {17, 22, 31} {17, 22, 32} {17, 22, 33} {17, 22, 34} {17, 22, 35}
{17, 22, 36} {17, 22, 37} {17, 22, 38} {17, 22, 39} {17, 22, 40} {17, 22, 41} {17, 22, 42} {17, 22, 43} {17, 22, 44}
{17, 22, 45} {17, 22, 46} {17, 22, 47} {17, 22, 48} {17, 22, 49} {17, 22, 50} {17, 22, 51} {17, 22, 52} {17, 22, 53}
{17, 22, 54} {17, 22, 55} {17, 22, 56} {17, 22, 57} {17, 22, 58} {17, 22, 59} {17, 22, 60} {17, 22, 61} {17, 22, 62}
{17, 22, 63} {17, 22, 64} {17, 22, 65} {17, 22, 66} {17, 23, 24} {17, 23, 25} {17, 23, 26} {17, 23, 27} {17, 23, 28}
{17, 23, 29} {17, 23, 30} {17, 23, 31} {17, 23, 32} {17, 23, 33} {17, 23, 34} {17, 23, 35} {17, 23, 36} {17, 23, 37}
{17, 23, 38} {17, 23, 39} {17, 23, 40} {17, 23, 41} {17, 23, 42} {17, 23, 43} {17, 23, 44} {17, 23, 45} {17, 23, 46}
{17, 23, 47} {17, 23, 48} {17, 23, 49} {17, 23, 50} {17, 23, 51} {17, 23, 52} {17, 23, 53} {17, 23, 54} {17, 23, 55}
{17, 23, 56} {17, 23, 57} {17, 23, 58} {17, 23, 59} {17, 23, 60} {17, 23, 61} {17, 23, 62} {17, 23, 63} {17, 23, 64}
{17, 23, 65} {17, 23, 66} {17, 24, 25} {17, 24, 26} {17, 24, 27} {17, 24, 28} {17, 24, 29} {17, 24, 30} {17, 24, 31}
{17, 24, 32} {17, 24, 33} {17, 24, 34} {17, 24, 35} {17, 24, 36} {17, 24, 37} {17, 24, 38} {17, 24, 39} {17, 24, 40}
{17, 24, 41} {17, 24, 42} {17, 24, 43} {17, 24, 44} {17, 24, 45} {17, 24, 46} {17, 24, 47} {17, 24, 48} {17, 24, 49}
{17, 24, 50} {17, 24, 51} {17, 24, 52} {17, 24, 53} {17, 24, 54} {17, 24, 55} {17, 24, 56} {17, 24, 57} {17, 24, 58}
{17, 24, 59} {17, 24, 60} {17, 24, 61} {17, 24, 62} {17, 24, 63} {17, 24, 64} {17, 24, 65} {17, 24, 66} {17, 25, 26}
{17, 25, 27} {17, 25, 28} {17, 25, 29} {17, 25, 30} {17, 25, 31} {17, 25, 32} {17, 25, 33} {17, 25, 34} {17, 25, 35}
{17, 25, 36} {17, 25, 37} {17, 25, 38} {17, 25, 39} {17, 25, 40} {17, 25, 41} {17, 25, 42} {17, 25, 43} {17, 25, 44}
{17, 25, 45} {17, 25, 46} {17, 25, 47} {17, 25, 48} {17, 25, 49} {17, 25, 50} {17, 25, 51} {17, 25, 52} {17, 25, 53}
{17, 25, 54} {17, 25, 55} {17, 25, 56} {17, 25, 57} {17, 25, 58} {17, 25, 59} {17, 25, 60} {17, 25, 61} {17, 25, 62}
{17, 25, 63} {17, 25, 64} {17, 25, 65} {17, 25, 66} {17, 26, 27} {17, 26, 28} {17, 26, 29} {17, 26, 30} {17, 26, 31}
{17, 26, 32} {17, 26, 33} {17, 26, 34} {17, 26, 35} {17, 26, 36} {17, 26, 37} {17, 26, 38} {17, 26, 39} {17, 26, 40}
{17, 26, 41} {17, 26, 42} {17, 26, 43} {17, 26, 44} {17, 26, 45} {17, 26, 46} {17, 26, 47} {17, 26, 48} {17, 26, 49}
{17, 26, 50} {17, 26, 51} {17, 26, 52} {17, 26, 53} {17, 26, 54} {17, 26, 55} {17, 26, 56} {17, 26, 57} {17, 26, 58}
{17, 26, 59} {17, 26, 60} {17, 26, 61} {17, 26, 62} {17, 26, 63} {17, 26, 64} {17, 26, 65} {17, 26, 66} {17, 27, 28}
{17, 27, 29} {17, 27, 30} {17, 27, 31} {17, 27, 32} {17, 27, 33} {17, 27, 34} {17, 27, 35} {17, 27, 36} {17, 27, 37}
{17, 27, 38} {17, 27, 39} {17, 27, 40} {17, 27, 41} {17, 27, 42} {17, 27, 43} {17, 27, 44} {17, 27, 45} {17, 27, 46}
{17, 27, 47} {17, 27, 48} {17, 27, 49} {17, 27, 50} {17, 27, 51} {17, 27, 52} {17, 27, 53} {17, 27, 54} {17, 27, 55}
{17, 27, 56} {17, 27, 57} {17, 27, 58} {17, 27, 59} {17, 27, 60} {17, 27, 61} {17, 27, 62} {17, 27, 63} {17, 27, 64}
{17, 27, 65} {17, 27, 66} {17, 28, 29} {17, 28, 30} {17, 28, 31} {17, 28, 32} {17, 28, 33} {17, 28, 34} {17, 28, 35}
{17, 28, 36} {17, 28, 37} {17, 28, 38} {17, 28, 39} {17, 28, 40} {17, 28, 41} {17, 28, 42} {17, 28, 43} {17, 28, 44}
{17, 28, 45} {17, 28, 46} {17, 28, 47} {17, 28, 48} {17, 28, 49} {17, 28, 50} {17, 28, 51} {17, 28, 52} {17, 28, 53}
{17, 28, 54} {17, 28, 55} {17, 28, 56} {17, 28, 57} {17, 28, 58} {17, 28, 59} {17, 28, 60} {17, 28, 61} {17, 28, 62}
{17, 28, 63} {17, 28, 64} {17, 28, 65} {17, 28, 66} {17, 29, 30} {17, 29, 31} {17, 29, 32} {17, 29, 33} {17, 29, 34}
{17, 29, 35} {17, 29, 36} {17, 29, 37} {17, 29, 38} {17, 29, 39} {17, 29, 40} {17, 29, 41} {17, 29, 42} {17, 29, 43}
{17, 29, 44} {17, 29, 45} {17, 29, 46} {17, 29, 47} {17, 29, 48} {17, 29, 49} {17, 29, 50} {17, 29, 51} {17, 29, 52}
{17, 29, 53} {17, 29, 54} {17, 29, 55} {17, 29, 56} {17, 29, 57} {17, 29, 58} {17, 29, 59} {17, 29, 60} {17, 29, 61}
{17, 29, 62} {17, 29, 63} {17, 29, 64} {17, 29, 65} {17, 29, 66} {17, 30, 31} {17, 30, 32} {17, 30, 33} {17, 30, 34}
{17, 30, 35} {17, 30, 36} {17, 30, 37} {17, 30, 38} {17, 30, 39} {17, 30, 40} {17, 30, 41} {17, 30, 42} {17, 30, 43}
{17, 30, 44} {17, 30, 45} {17, 30, 46} {17, 30, 47} {17, 30, 48} {17, 30, 49} {17, 30, 50} {17, 30, 51} {17, 30, 52}
{17, 30, 53} {17, 30, 54} {17, 30, 55} {17, 30, 56} {17, 30, 57} {17, 30, 58} {17, 30, 59} {17, 30, 60} {17, 30, 61}
{17, 30, 62} {17, 30, 63} {17, 30, 64} {17, 30, 65} {17, 30, 66} {17, 31, 32} {17, 31, 33} {17, 31, 34} {17, 31, 35}
{17, 31, 36} {17, 31, 37} {17, 31, 38} {17, 31, 39} {17, 31, 40} {17, 31, 41} {17, 31, 42} {17, 31, 43} {17, 31, 44}
{17, 31, 45} {17, 31, 46} {17, 31, 47} {17, 31, 48} {17, 31, 49} {17, 31, 50} {17, 31, 51} {17, 31, 52} {17, 31, 53}
{17, 31, 54} {17, 31, 55} {17, 31, 56} {17, 31, 57} {17, 31, 58} {17, 31, 59} {17, 31, 60} {17, 31, 61} {17, 31, 62}
{17, 31, 63} {17, 31, 64} {17, 31, 65} {17, 31, 66} {17, 32, 33} {17, 32, 34} {17, 32, 35} {17, 32, 36} {17, 32, 37}
{17, 32, 38} {17, 32, 39} {17, 32, 40} {17, 32, 41} {17, 32, 42} {17, 32, 43} {17, 32, 44} {17, 32, 45} {17, 32, 46}
{17, 32, 47} {17, 32, 48} {17, 32, 49} {17, 32, 50} {17, 32, 51} {17, 32, 52} {17, 32, 53} {17, 32, 54} {17, 32, 55}
{17, 32, 56} {17, 32, 57} {17, 32, 58} {17, 32, 59} {17, 32, 60} {17, 32, 61} {17, 32, 62} {17, 32, 63} {17, 32, 64}
{17, 32, 65} {17, 32, 66} {17, 33, 34} {17, 33, 35} {17, 33, 36} {17, 33, 37} {17, 33, 38} {17, 33, 39} {17, 33, 40}
{17, 33, 41} {17, 33, 42} {17, 33, 43} {17, 33, 44} {17, 33, 45} {17, 33, 46} {17, 33, 47} {17, 33, 48} {17, 33, 49}
{17, 33, 50} {17, 33, 51} {17, 33, 52} {17, 33, 53} {17, 33, 54} {17, 33, 55} {17, 33, 56} {17, 33, 57} {17, 33, 58}
{17, 33, 59} {17, 33, 60} {17, 33, 61} {17, 33, 62} {17, 33, 63} {17, 33, 64} {17, 33, 65} {17, 33, 66} {17, 34, 35}
{17, 34, 36} {17, 34, 37} {17, 34, 38} {17, 34, 39} {17, 34, 40} {17, 34, 41} {17, 34, 42} {17, 34, 43} {17, 34, 44}
{17, 34, 45} {17, 34, 46} {17, 34, 47} {17, 34, 48} {17, 34, 49} {17, 34, 50} {17, 34, 51} {17, 34, 52} {17, 34, 53}
{17, 34, 54} {17, 34, 55} {17, 34, 56} {17, 34, 57} {17, 34, 58} {17, 34, 59} {17, 34, 60} {17, 34, 61} {17, 34, 62}
{17, 34, 63} {17, 34, 64} {17, 34, 65} {17, 34, 66} {17, 35, 36} {17, 35, 37} {17, 35, 38} {17, 35, 39} {17, 35, 40}
{17, 35, 41} {17, 35, 42} {17, 35, 43} {17, 35, 44} {17, 35, 45} {17, 35, 46} {17, 35, 47} {17, 35, 48} {17, 35, 49}
{17, 35, 50} {17, 35, 51} {17, 35, 52} {17, 35, 53} {17, 35, 54} {17, 35, 55} {17, 35, 56} {17, 35, 57} {17, 35, 58}

TABLE 3A-continued

{17, 35, 59} {17, 35, 60} {17, 35, 61} {17, 35, 62} {17, 35, 63} {17, 35, 64} {17, 35, 65} {17, 35, 66} {17, 36, 37}
{17, 36, 38} {17, 36, 39} {17, 36, 40} {17, 36, 41} {17, 36, 42} {17, 36, 43} {17, 36, 44} {17, 36, 45} {17, 36, 46}
{17, 36, 47} {17, 36, 48} {17, 36, 49} {17, 36, 50} {17, 36, 51} {17, 36, 52} {17, 36, 53} {17, 36, 54} {17, 36, 55}
{17, 36, 56} {17, 36, 57} {17, 36, 58} {17, 36, 59} {17, 36, 60} {17, 36, 61} {17, 36, 62} {17, 36, 63} {17, 36, 64}
{17, 36, 65} {17, 36, 66} {17, 37, 38} {17, 37, 39} {17, 37, 40} {17, 37, 41} {17, 37, 42} {17, 37, 43} {17, 37, 44}
{17, 37, 45} {17, 37, 46} {17, 37, 47} {17, 37, 48} {17, 37, 49} {17, 37, 50} {17, 37, 51} {17, 37, 52} {17, 37, 53}
{17, 37, 54} {17, 37, 55} {17, 37, 56} {17, 37, 57} {17, 37, 58} {17, 37, 59} {17, 37, 60} {17, 37, 61} {17, 37, 62}
{17, 37, 63} {17, 37, 64} {17, 37, 65} {17, 37, 66} {17, 38, 39} {17, 38, 40} {17, 38, 41} {17, 38, 42} {17, 38, 43}
{17, 38, 44} {17, 38, 45} {17, 38, 46} {17, 38, 47} {17, 38, 48} {17, 38, 49} {17, 38, 50} {17, 38, 51} {17, 38, 52}
{17, 38, 53} {17, 38, 54} {17, 38, 55} {17, 38, 56} {17, 38, 57} {17, 38, 58} {17, 38, 59} {17, 38, 60} {17, 38, 61}
{17, 38, 62} {17, 38, 63} {17, 38, 64} {17, 38, 65} {17, 38, 66} {17, 39, 40} {17, 39, 41} {17, 39, 42} {17, 39, 43}
{17, 39, 44} {17, 39, 45} {17, 39, 46} {17, 39, 47} {17, 39, 48} {17, 39, 49} {17, 39, 50} {17, 39, 51} {17, 39, 52}
{17, 39, 53} {17, 39, 54} {17, 39, 55} {17, 39, 56} {17, 39, 57} {17, 39, 58} {17, 39, 59} {17, 39, 60} {17, 39, 61}
{17, 39, 62} {17, 39, 63} {17, 39, 64} {17, 39, 65} {17, 39, 66} {17, 40, 41} {17, 40, 42} {17, 40, 43} {17, 40, 44}
{17, 40, 45} {17, 40, 46} {17, 40, 47} {17, 40, 48} {17, 40, 49} {17, 40, 50} {17, 40, 51} {17, 40, 52} {17, 40, 53}
{17, 40, 54} {17, 40, 55} {17, 40, 56} {17, 40, 57} {17, 40, 58} {17, 40, 59} {17, 40, 60} {17, 40, 61} {17, 40, 62}
{17, 40, 63} {17, 40, 64} {17, 40, 65} {17, 40, 66} {17, 41, 42} {17, 41, 43} {17, 41, 44} {17, 41, 45} {17, 41, 46}
{17, 41, 47} {17, 41, 48} {17, 41, 49} {17, 41, 50} {17, 41, 51} {17, 41, 52} {17, 41, 53} {17, 41, 54} {17, 41, 55}
{17, 41, 56} {17, 41, 57} {17, 41, 58} {17, 41, 59} {17, 41, 60} {17, 41, 61} {17, 41, 62} {17, 41, 63} {17, 41, 64}
{17, 41, 65} {17, 41, 66} {17, 42, 43} {17, 42, 44} {17, 42, 45} {17, 42, 46} {17, 42, 47} {17, 42, 48} {17, 42, 49}
{17, 42, 50} {17, 42, 51} {17, 42, 52} {17, 42, 53} {17, 42, 54} {17, 42, 55} {17, 42, 56} {17, 42, 57} {17, 42, 58}
{17, 42, 59} {17, 42, 60} {17, 42, 61} {17, 42, 62} {17, 42, 63} {17, 42, 64} {17, 42, 65} {17, 42, 66} {17, 43, 44}
{17, 43, 45} {17, 43, 46} {17, 43, 47} {17, 43, 48} {17, 43, 49} {17, 43, 50} {17, 43, 51} {17, 43, 52} {17, 43, 53}
{17, 43, 54} {17, 43, 55} {17, 43, 56} {17, 43, 57} {17, 43, 58} {17, 43, 59} {17, 43, 60} {17, 43, 61} {17, 43, 62}
{17, 43, 63} {17, 43, 64} {17, 43, 65} {17, 43, 66} {17, 44, 45} {17, 44, 46} {17, 44, 47} {17, 44, 48} {17, 44, 49}
{17, 44, 50} {17, 44, 51} {17, 44, 52} {17, 44, 53} {17, 44, 54} {17, 44, 55} {17, 44, 56} {17, 44, 57} {17, 44, 58}
{17, 44, 59} {17, 44, 60} {17, 44, 61} {17, 44, 62} {17, 44, 63} {17, 44, 64} {17, 44, 65} {17, 44, 66} {17, 45, 46}
{17, 45, 47} {17, 45, 48} {17, 45, 49} {17, 45, 50} {17, 45, 51} {17, 45, 52} {17, 45, 53} {17, 45, 54} {17, 45, 55}
{17, 45, 56} {17, 45, 57} {17, 45, 58} {17, 45, 59} {17, 45, 60} {17, 45, 61} {17, 45, 62} {17, 45, 63} {17, 45, 64}
{17, 45, 65} {17, 45, 66} {17, 46, 47} {17, 46, 48} {17, 46, 49} {17, 46, 50} {17, 46, 51} {17, 46, 52} {17, 46, 53}
{17, 46, 54} {17, 46, 55} {17, 46, 56} {17, 46, 57} {17, 46, 58} {17, 46, 59} {17, 46, 60} {17, 46, 61} {17, 46, 62}
{17, 46, 63} {17, 46, 64} {17, 46, 65} {17, 46, 66} {17, 47, 48} {17, 47, 49} {17, 47, 50} {17, 47, 51} {17, 47, 52}
{17, 47, 53} {17, 47, 54} {17, 47, 55} {17, 47, 56} {17, 47, 57} {17, 47, 58} {17, 47, 59} {17, 47, 60} {17, 47, 61}
{17, 47, 62} {17, 47, 63} {17, 47, 64} {17, 47, 65} {17, 47, 66} {17, 48, 49} {17, 48, 50} {17, 48, 51} {17, 48, 52}
{17, 48, 53} {17, 48, 54} {17, 48, 55} {17, 48, 56} {17, 48, 57} {17, 48, 58} {17, 48, 59} {17, 48, 60} {17, 48, 61}
{17, 48, 62} {17, 48, 63} {17, 48, 64} {17, 48, 65} {17, 48, 66} {17, 49, 50} {17, 49, 51} {17, 49, 52} {17, 49, 53}
{17, 49, 54} {17, 49, 55} {17, 49, 56} {17, 49, 57} {17, 49, 58} {17, 49, 59} {17, 49, 60} {17, 49, 61} {17, 49, 62}
{17, 49, 63} {17, 49, 64} {17, 49, 65} {17, 49, 66} {17, 50, 51} {17, 50, 52} {17, 50, 53} {17, 50, 54} {17, 50, 55}
{17, 50, 56} {17, 50, 57} {17, 50, 58} {17, 50, 59} {17, 50, 60} {17, 50, 61} {17, 50, 62} {17, 50, 63} {17, 50, 64}
{17, 50, 65} {17, 50, 66} {17, 51, 52} {17, 51, 53} {17, 51, 54} {17, 51, 55} {17, 51, 56} {17, 51, 57} {17, 51, 58}
{17, 51, 59} {17, 51, 60} {17, 51, 61} {17, 51, 62} {17, 51, 63} {17, 51, 64} {17, 51, 65} {17, 51, 66} {17, 52, 53}
{17, 52, 54} {17, 52, 55} {17, 52, 56} {17, 52, 57} {17, 52, 58} {17, 52, 59} {17, 52, 60} {17, 52, 61} {17, 52, 62}
{17, 52, 63} {17, 52, 64} {17, 52, 65} {17, 52, 66} {17, 53, 54} {17, 53, 55} {17, 53, 56} {17, 53, 57} {17, 53, 58}
{17, 53, 59} {17, 53, 60} {17, 53, 61} {17, 53, 62} {17, 53, 63} {17, 53, 64} {17, 53, 65} {17, 53, 66} {17, 54, 55}
{17, 54, 56} {17, 54, 57} {17, 54, 58} {17, 54, 59} {17, 54, 60} {17, 54, 61} {17, 54, 62} {17, 54, 63} {17, 54, 64}
{17, 54, 65} {17, 54, 66} {17, 55, 56} {17, 55, 57} {17, 55, 58} {17, 55, 59} {17, 55, 60} {17, 55, 61} {17, 55, 62}
{17, 55, 63} {17, 55, 64} {17, 55, 65} {17, 55, 66} {17, 56, 57} {17, 56, 58} {17, 56, 59} {17, 56, 60} {17, 56, 61}
{17, 56, 62} {17, 56, 63} {17, 56, 64} {17, 56, 65} {17, 56, 66} {17, 57, 58} {17, 57, 59} {17, 57, 60} {17, 57, 61}
{17, 57, 62} {17, 57, 63} {17, 57, 64} {17, 57, 65} {17, 57, 66} {17, 58, 59} {17, 58, 60} {17, 58, 61} {17, 58, 62}
{17, 58, 63} {17, 58, 64} {17, 58, 65} {17, 58, 66} {17, 59, 60} {17, 59, 61} {17, 59, 62} {17, 59, 63} {17, 59, 64}
{17, 59, 65} {17, 59, 66} {17, 60, 61} {17, 60, 62} {17, 60, 63} {17, 60, 64} {17, 60, 65} {17, 60, 66} {17, 61, 62}
{17, 61, 63} {17, 61, 64} {17, 61, 65} {17, 61, 66} {17, 62, 63} {17, 62, 64} {17, 62, 65} {17, 62, 66} {17, 63, 64}
{17, 63, 65} {17, 63, 66} {17, 64, 65} {17, 64, 66} {17, 65, 66} {18, 19, 20} {18, 19, 21} {18, 19, 22} {18, 19, 23}
{18, 19, 24} {18, 19, 25} {18, 19, 26} {18, 19, 27} {18, 19, 28} {18, 19, 29} {18, 19, 30} {18, 19, 31} {18, 19, 32}
{18, 19, 33} {18, 19, 34} {18, 19, 35} {18, 19, 36} {18, 19, 37} {18, 19, 38} {18, 19, 39} {18, 19, 40} {18, 19, 41}
{18, 19, 42} {18, 19, 43} {18, 19, 44} {18, 19, 45} {18, 19, 46} {18, 19, 47} {18, 19, 48} {18, 19, 49} {18, 19, 50}
{18, 19, 51} {18, 19, 52} {18, 19, 53} {18, 19, 54} {18, 19, 55} {18, 19, 56} {18, 19, 57} {18, 19, 58} {18, 19, 59}
{18, 19, 60} {18, 19, 61} {18, 19, 62} {18, 19, 63} {18, 19, 64} {18, 19, 65} {18, 19, 66} {18, 20, 21} {18, 20, 22}
{18, 20, 23} {18, 20, 24} {18, 20, 25} {18, 20, 26} {18, 20, 27} {18, 20, 28} {18, 20, 29} {18, 20, 30} {18, 20, 31}
{18, 20, 32} {18, 20, 33} {18, 20, 34} {18, 20, 35} {18, 20, 36} {18, 20, 37} {18, 20, 38} {18, 20, 39} {18, 20, 40}
{18, 20, 41} {18, 20, 42} {18, 20, 43} {18, 20, 44} {18, 20, 45} {18, 20, 46} {18, 20, 47} {18, 20, 48} {18, 20, 49}
{18, 20, 50} {18, 20, 51} {18, 20, 52} {18, 20, 53} {18, 20, 54} {18, 20, 55} {18, 20, 56} {18, 20, 57} {18, 20, 58}
{18, 20, 59} {18, 20, 60} {18, 20, 61} {18, 20, 62} {18, 20, 63} {18, 20, 64} {18, 20, 65} {18, 20, 66} {18, 21, 22}
{18, 21, 23} {18, 21, 24} {18, 21, 25} {18, 21, 26} {18, 21, 27} {18, 21, 28} {18, 21, 29} {18, 21, 30} {18, 21, 31}
{18, 21, 32} {18, 21, 33} {18, 21, 34} {18, 21, 35} {18, 21, 36} {18, 21, 37} {18, 21, 38} {18, 21, 39} {18, 21, 40}
{18, 21, 41} {18, 21, 42} {18, 21, 43} {18, 21, 44} {18, 21, 45} {18, 21, 46} {18, 21, 47} {18, 21, 48} {18, 21, 49}
{18, 21, 50} {18, 21, 51} {18, 21, 52} {18, 21, 53} {18, 21, 54} {18, 21, 55} {18, 21, 56} {18, 21, 57} {18, 21, 58}
{18, 21, 59} {18, 21, 60} {18, 21, 61} {18, 21, 62} {18, 21, 63} {18, 21, 64} {18, 21, 65} {18, 21, 66} {18, 22, 23}
{18, 22, 24} {18, 22, 25} {18, 22, 26} {18, 22, 27} {18, 22, 28} {18, 22, 29} {18, 22, 30} {18, 22, 31} {18, 22, 32}
{18, 22, 33} {18, 22, 34} {18, 22, 35} {18, 22, 36} {18, 22, 37} {18, 22, 38} {18, 22, 39} {18, 22, 40} {18, 22, 41}
{18, 22, 42} {18, 22, 43} {18, 22, 44} {18, 22, 45} {18, 22, 46} {18, 22, 47} {18, 22, 48} {18, 22, 49} {18, 22, 50}
{18, 22, 51} {18, 22, 52} {18, 22, 53} {18, 22, 54} {18, 22, 55} {18, 22, 56} {18, 22, 57} {18, 22, 58} {18, 22, 59}
{18, 22, 60} {18, 22, 61} {18, 22, 62} {18, 22, 63} {18, 22, 64} {18, 22, 65} {18, 22, 66} {18, 23, 24} {18, 23, 25}
{18, 23, 26} {18, 23, 27} {18, 23, 28} {18, 23, 29} {18, 23, 30} {18, 23, 31} {18, 23, 32} {18, 23, 33} {18, 23, 34}
{18, 23, 35} {18, 23, 36} {18, 23, 37} {18, 23, 38} {18, 23, 39} {18, 23, 40} {18, 23, 41} {18, 23, 42} {18, 23, 43}
{18, 23, 44} {18, 23, 45} {18, 23, 46} {18, 23, 47} {18, 23, 48} {18, 23, 49} {18, 23, 50} {18, 23, 51} {18, 23, 52}
{18, 23, 53} {18, 23, 54} {18, 23, 55} {18, 23, 56} {18, 23, 57} {18, 23, 58} {18, 23, 59} {18, 23, 60} {18, 23, 61}
{18, 23, 62} {18, 23, 63} {18, 23, 64} {18, 23, 65} {18, 23, 66} {18, 24, 25} {18, 24, 26} {18, 24, 27} {18, 24, 28}
{18, 24, 29} {18, 24, 30} {18, 24, 31} {18, 24, 32} {18, 24, 33} {18, 24, 34} {18, 24, 35} {18, 24, 36} {18, 24, 37}
{18, 24, 38} {18, 24, 39} {18, 24, 40} {18, 24, 41} {18, 24, 42} {18, 24, 43} {18, 24, 44} {18, 24, 45} {18, 24, 46}

TABLE 3A-continued

{18, 24, 47} {18, 24, 48} {18, 24, 49} {18, 24, 50} {18, 24, 51} {18, 24, 52} {18, 24, 53} {18, 24, 54} {18, 24, 55}
{18, 24, 56} {18, 24, 57} {18, 24, 58} {18, 24, 59} {18, 24, 60} {18, 24, 61} {18, 24, 62} {18, 24, 63} {18, 24, 64}
{18, 24, 65} {18, 24, 66} {18, 25, 26} {18, 25, 27} {18, 25, 28} {18, 25, 29} {18, 25, 30} {18, 25, 31} {18, 25, 32}
{18, 25, 33} {18, 25, 34} {18, 25, 35} {18, 25, 36} {18, 25, 37} {18, 25, 38} {18, 25, 39} {18, 25, 40} {18, 25, 41}
{18, 25, 42} {18, 25, 43} {18, 25, 44} {18, 25, 45} {18, 25, 46} {18, 25, 47} {18, 25, 48} {18, 25, 49} {18, 25, 50}
{18, 25, 51} {18, 25, 52} {18, 25, 53} {18, 25, 54} {18, 25, 55} {18, 25, 56} {18, 25, 57} {18, 25, 58} {18, 25, 59}
{18, 25, 60} {18, 25, 61} {18, 25, 62} {18, 25, 63} {18, 25, 64} {18, 25, 65} {18, 25, 66} {18, 26, 27} {18, 26, 28}
{18, 26, 29} {18, 26, 30} {18, 26, 31} {18, 26, 32} {18, 26, 33} {18, 26, 34} {18, 26, 35} {18, 26, 36} {18, 26, 37}
{18, 26, 38} {18, 26, 39} {18, 26, 40} {18, 26, 41} {18, 26, 42} {18, 26, 43} {18, 26, 44} {18, 26, 45} {18, 26, 46}
{18, 26, 47} {18, 26, 48} {18, 26, 49} {18, 26, 50} {18, 26, 51} {18, 26, 52} {18, 26, 53} {18, 26, 54} {18, 26, 55}
{18, 26, 56} {18, 26, 57} {18, 26, 58} {18, 26, 59} {18, 26, 60} {18, 26, 61} {18, 26, 62} {18, 26, 63} {18, 26, 64}
{18, 26, 65} {18, 26, 66} {18, 27, 28} {18, 27, 29} {18, 27, 30} {18, 27, 31} {18, 27, 32} {18, 27, 33} {18, 27, 34}
{18, 27, 35} {18, 27, 36} {18, 27, 37} {18, 27, 38} {18, 27, 39} {18, 27, 40} {18, 27, 41} {18, 27, 42} {18, 27, 43}
{18, 27, 44} {18, 27, 45} {18, 27, 46} {18, 27, 47} {18, 27, 48} {18, 27, 49} {18, 27, 50} {18, 27, 51} {18, 27, 52}
{18, 27, 53} {18, 27, 54} {18, 27, 55} {18, 27, 56} {18, 27, 57} {18, 27, 58} {18, 27, 59} {18, 27, 60} {18, 27, 61}
{18, 27, 62} {18, 27, 63} {18, 27, 64} {18, 27, 65} {18, 27, 66} {18, 28, 29} {18, 28, 30} {18, 28, 31} {18, 28, 32}
{18, 28, 33} {18, 28, 34} {18, 28, 35} {18, 28, 36} {18, 28, 37} {18, 28, 38} {18, 28, 39} {18, 28, 40} {18, 28, 41}
{18, 28, 42} {18, 28, 43} {18, 28, 44} {18, 28, 45} {18, 28, 46} {18, 28, 47} {18, 28, 48} {18, 28, 49} {18, 28, 50}
{18, 28, 51} {18, 28, 52} {18, 28, 53} {18, 28, 54} {18, 28, 55} {18, 28, 56} {18, 28, 57} {18, 28, 58} {18, 28, 59}
{18, 28, 60} {18, 28, 61} {18, 28, 62} {18, 28, 63} {18, 28, 64} {18, 28, 65} {18, 28, 66} {18, 29, 30} {18, 29, 31}
{18, 29, 32} {18, 29, 33} {18, 29, 34} {18, 29, 35} {18, 29, 36} {18, 29, 37} {18, 29, 38} {18, 29, 39} {18, 29, 40}
{18, 29, 41} {18, 29, 42} {18, 29, 43} {18, 29, 44} {18, 29, 45} {18, 29, 46} {18, 29, 47} {18, 29, 48} {18, 29, 49}
{18, 29, 50} {18, 29, 51} {18, 29, 52} {18, 29, 53} {18, 29, 54} {18, 29, 55} {18, 29, 56} {18, 29, 57} {18, 29, 58}
{18, 29, 59} {18, 29, 60} {18, 29, 61} {18, 29, 62} {18, 29, 63} {18, 29, 64} {18, 29, 65} {18, 29, 66} {18, 30, 31}
{18, 30, 32} {18, 30, 33} {18, 30, 34} {18, 30, 35} {18, 30, 36} {18, 30, 37} {18, 30, 38} {18, 30, 39} {18, 30, 40}
{18, 30, 41} {18, 30, 42} {18, 30, 43} {18, 30, 44} {18, 30, 45} {18, 30, 46} {18, 30, 47} {18, 30, 48} {18, 30, 49}
{18, 30, 50} {18, 30, 51} {18, 30, 52} {18, 30, 53} {18, 30, 54} {18, 30, 55} {18, 30, 56} {18, 30, 57} {18, 30, 58}
{18, 30, 59} {18, 30, 60} {18, 30, 61} {18, 30, 62} {18, 30, 63} {18, 30, 64} {18, 30, 65} {18, 30, 66} {18, 31, 32}
{18, 31, 33} {18, 31, 34} {18, 31, 35} {18, 31, 36} {18, 31, 37} {18, 31, 38} {18, 31, 39} {18, 31, 40} {18, 31, 41}
{18, 31, 42} {18, 31, 43} {18, 31, 44} {18, 31, 45} {18, 31, 46} {18, 31, 47} {18, 31, 48} {18, 31, 49} {18, 31, 50}
{18, 31, 51} {18, 31, 52} {18, 31, 53} {18, 31, 54} {18, 31, 55} {18, 31, 56} {18, 31, 57} {18, 31, 58} {18, 31, 59}
{18, 31, 60} {18, 31, 61} {18, 31, 62} {18, 31, 63} {18, 31, 64} {18, 31, 65} {18, 31, 66} {18, 32, 33} {18, 32, 34}
{18, 32, 35} {18, 32, 36} {18, 32, 37} {18, 32, 38} {18, 32, 39} {18, 32, 40} {18, 32, 41} {18, 32, 42} {18, 32, 43}
{18, 32, 44} {18, 32, 45} {18, 32, 46} {18, 32, 47} {18, 32, 48} {18, 32, 49} {18, 32, 50} {18, 32, 51} {18, 32, 52}
{18, 32, 53} {18, 32, 54} {18, 32, 55} {18, 32, 56} {18, 32, 57} {18, 32, 58} {18, 32, 59} {18, 32, 60} {18, 32, 61}
{18, 32, 62} {18, 32, 63} {18, 32, 64} {18, 32, 65} {18, 32, 66} {18, 33, 34} {18, 33, 35} {18, 33, 36} {18, 33, 37}
{18, 33, 38} {18, 33, 39} {18, 33, 40} {18, 33, 41} {18, 33, 42} {18, 33, 43} {18, 33, 44} {18, 33, 45} {18, 33, 46}
{18, 33, 47} {18, 33, 48} {18, 33, 49} {18, 33, 50} {18, 33, 51} {18, 33, 52} {18, 33, 53} {18, 33, 54} {18, 33, 55}
{18, 33, 56} {18, 33, 57} {18, 33, 58} {18, 33, 59} {18, 33, 60} {18, 33, 61} {18, 33, 62} {18, 33, 63} {18, 33, 64}
{18, 33, 65} {18, 33, 66} {18, 34, 35} {18, 34, 36} {18, 34, 37} {18, 34, 38} {18, 34, 39} {18, 34, 40} {18, 34, 41}
{18, 34, 42} {18, 34, 43} {18, 34, 44} {18, 34, 45} {18, 34, 46} {18, 34, 47} {18, 34, 48} {18, 34, 49} {18, 34, 50}
{18, 34, 51} {18, 34, 52} {18, 34, 53} {18, 34, 54} {18, 34, 55} {18, 34, 56} {18, 34, 57} {18, 34, 58} {18, 34, 59}
{18, 34, 60} {18, 34, 61} {18, 34, 62} {18, 34, 63} {18, 34, 64} {18, 34, 65} {18, 34, 66} {18, 35, 36} {18, 35, 37}
{18, 35, 38} {18, 35, 39} {18, 35, 40} {18, 35, 41} {18, 35, 42} {18, 35, 43} {18, 35, 44} {18, 35, 45} {18, 35, 46}
{18, 35, 47} {18, 35, 48} {18, 35, 49} {18, 35, 50} {18, 35, 51} {18, 35, 52} {18, 35, 53} {18, 35, 54} {18, 35, 55}
{18, 35, 56} {18, 35, 57} {18, 35, 58} {18, 35, 59} {18, 35, 60} {18, 35, 61} {18, 35, 62} {18, 35, 63} {18, 35, 64}
{18, 35, 65} {18, 35, 66} {18, 36, 37} {18, 36, 38} {18, 36, 39} {18, 36, 40} {18, 36, 41} {18, 36, 42} {18, 36, 43}
{18, 36, 44} {18, 36, 45} {18, 36, 46} {18, 36, 47} {18, 36, 48} {18, 36, 49} {18, 36, 50} {18, 36, 51} {18, 36, 52}
{18, 36, 53} {18, 36, 54} {18, 36, 55} {18, 36, 56} {18, 36, 57} {18, 36, 58} {18, 36, 59} {18, 36, 60} {18, 36, 61}
{18, 36, 62} {18, 36, 63} {18, 36, 64} {18, 36, 65} {18, 36, 66} {18, 37, 38} {18, 37, 39} {18, 37, 40} {18, 37, 41}
{18, 37, 42} {18, 37, 43} {18, 37, 44} {18, 37, 45} {18, 37, 46} {18, 37, 47} {18, 37, 48} {18, 37, 49} {18, 37, 50}
{18, 37, 51} {18, 37, 52} {18, 37, 53} {18, 37, 54} {18, 37, 55} {18, 37, 56} {18, 37, 57} {18, 37, 58} {18, 37, 59}
{18, 37, 60} {18, 37, 61} {18, 37, 62} {18, 37, 63} {18, 37, 64} {18, 37, 65} {18, 37, 66} {18, 38, 39} {18, 38, 40}
{18, 38, 41} {18, 38, 42} {18, 38, 43} {18, 38, 44} {18, 38, 45} {18, 38, 46} {18, 38, 47} {18, 38, 48} {18, 38, 49}
{18, 38, 50} {18, 38, 51} {18, 38, 52} {18, 38, 53} {18, 38, 54} {18, 38, 55} {18, 38, 56} {18, 38, 57} {18, 38, 58}
{18, 38, 59} {18, 38, 60} {18, 38, 61} {18, 38, 62} {18, 38, 63} {18, 38, 64} {18, 38, 65} {18, 38, 66} {18, 39, 40}
{18, 39, 41} {18, 39, 42} {18, 39, 43} {18, 39, 44} {18, 39, 45} {18, 39, 46} {18, 39, 47} {18, 39, 48} {18, 39, 49}
{18, 39, 50} {18, 39, 51} {18, 39, 52} {18, 39, 53} {18, 39, 54} {18, 39, 55} {18, 39, 56} {18, 39, 57} {18, 39, 58}
{18, 39, 59} {18, 39, 60} {18, 39, 61} {18, 39, 62} {18, 39, 63} {18, 39, 64} {18, 39, 65} {18, 39, 66} {18, 40, 41}
{18, 40, 42} {18, 40, 43} {18, 40, 44} {18, 40, 45} {18, 40, 46} {18, 40, 47} {18, 40, 48} {18, 40, 49} {18, 40, 50}
{18, 40, 51} {18, 40, 52} {18, 40, 53} {18, 40, 54} {18, 40, 55} {18, 40, 56} {18, 40, 57} {18, 40, 58} {18, 40, 59}
{18, 40, 60} {18, 40, 61} {18, 40, 62} {18, 40, 63} {18, 40, 64} {18, 40, 65} {18, 40, 66} {18, 41, 42} {18, 41, 43}
{18, 41, 44} {18, 41, 45} {18, 41, 46} {18, 41, 47} {18, 41, 48} {18, 41, 49} {18, 41, 50} {18, 41, 51} {18, 41, 52}
{18, 41, 53} {18, 41, 54} {18, 41, 55} {18, 41, 56} {18, 41, 57} {18, 41, 58} {18, 41, 59} {18, 41, 60} {18, 41, 61}
{18, 41, 62} {18, 41, 63} {18, 41, 64} {18, 41, 65} {18, 41, 66} {18, 42, 43} {18, 42, 44} {18, 42, 45} {18, 42, 46}
{18, 42, 47} {18, 42, 48} {18, 42, 49} {18, 42, 50} {18, 42, 51} {18, 42, 52} {18, 42, 53} {18, 42, 54} {18, 42, 55}
{18, 42, 56} {18, 42, 57} {18, 42, 58} {18, 42, 59} {18, 42, 60} {18, 42, 61} {18, 42, 62} {18, 42, 63} {18, 42, 64}
{18, 42, 65} {18, 42, 66} {18, 43, 44} {18, 43, 45} {18, 43, 46} {18, 43, 47} {18, 43, 48} {18, 43, 49} {18, 43, 50}
{18, 43, 51} {18, 43, 52} {18, 43, 53} {18, 43, 54} {18, 43, 55} {18, 43, 56} {18, 43, 57} {18, 43, 58} {18, 43, 59}
{18, 43, 60} {18, 43, 61} {18, 43, 62} {18, 43, 63} {18, 43, 64} {18, 43, 65} {18, 43, 66} {18, 44, 45} {18, 44, 46}
{18, 44, 47} {18, 44, 48} {18, 44, 49} {18, 44, 50} {18, 44, 51} {18, 44, 52} {18, 44, 53} {18, 44, 54} {18, 44, 55}
{18, 44, 56} {18, 44, 57} {18, 44, 58} {18, 44, 59} {18, 44, 60} {18, 44, 61} {18, 44, 62} {18, 44, 63} {18, 44, 64}
{18, 44, 65} {18, 44, 66} {18, 45, 46} {18, 45, 47} {18, 45, 48} {18, 45, 49} {18, 45, 50} {18, 45, 51} {18, 45, 52}
{18, 45, 53} {18, 45, 54} {18, 45, 55} {18, 45, 56} {18, 45, 57} {18, 45, 58} {18, 45, 59} {18, 45, 60} {18, 45, 61}
{18, 45, 62} {18, 45, 63} {18, 45, 64} {18, 45, 65} {18, 46, 47} {18, 46, 48} {18, 46, 49} {18, 46, 50}
{18, 46, 51} {18, 46, 52} {18, 46, 53} {18, 46, 54} {18, 46, 55} {18, 46, 56} {18, 46, 57} {18, 46, 58} {18, 46, 59}
{18, 46, 60} {18, 46, 61} {18, 46, 62} {18, 46, 63} {18, 46, 64} {18, 46, 65} {18, 46, 66} {18, 47, 48} {18, 47, 49}
{18, 47, 50} {18, 47, 51} {18, 47, 52} {18, 47, 53} {18, 47, 54} {18, 47, 55} {18, 47, 56} {18, 47, 57} {18, 47, 58}
{18, 47, 59} {18, 47, 60} {18, 47, 61} {18, 47, 62} {18, 47, 63} {18, 47, 64} {18, 47, 65} {18, 47, 66} {18, 48, 49}
{18, 48, 50} {18, 48, 51} {18, 48, 52} {18, 48, 53} {18, 48, 54} {18, 48, 55} {18, 48, 56} {18, 48, 57} {18, 48, 58}

TABLE 3A-continued

{18, 48, 59} {18, 48, 60} {18, 48, 61} {18, 48, 62} {18, 48, 63} {18, 48, 64} {18, 48, 65} {18, 48, 66} {18, 49, 50}
{18, 49, 51} {18, 49, 52} {18, 49, 53} {18, 49, 54} {18, 49, 55} {18, 49, 56} {18, 49, 57} {18, 49, 58} {18, 49, 59}
{18, 49, 60} {18, 49, 61} {18, 49, 62} {18, 49, 63} {18, 49, 64} {18, 49, 65} {18, 49, 66} {18, 50, 51} {18, 50, 52}
{18, 50, 53} {18, 50, 54} {18, 50, 55} {18, 50, 56} {18, 50, 57} {18, 50, 58} {18, 50, 59} {18, 50, 60} {18, 50, 61}
{18, 50, 62} {18, 50, 63} {18, 50, 64} {18, 50, 65} {18, 50, 66} {18, 51, 52} {18, 51, 53} {18, 51, 54} {18, 51, 55}
{18, 51, 56} {18, 51, 57} {18, 51, 58} {18, 51, 59} {18, 51, 60} {18, 51, 61} {18, 51, 62} {18, 51, 63} {18, 51, 64}
{18, 51, 65} {18, 51, 66} {18, 52, 53} {18, 52, 54} {18, 52, 55} {18, 52, 56} {18, 52, 57} {18, 52, 58} {18, 52, 59}
{18, 52, 60} {18, 52, 61} {18, 52, 62} {18, 52, 63} {18, 52, 64} {18, 52, 65} {18, 52, 66} {18, 53, 54} {18, 53, 55}
{18, 53, 56} {18, 53, 57} {18, 53, 58} {18, 53, 59} {18, 53, 60} {18, 53, 61} {18, 53, 62} {18, 53, 63} {18, 53, 64}
{18, 53, 65} {18, 53, 66} {18, 54, 55} {18, 54, 56} {18, 54, 57} {18, 54, 58} {18, 54, 59} {18, 54, 60} {18, 54, 61}
{18, 54, 62} {18, 54, 63} {18, 54, 64} {18, 54, 65} {18, 54, 66} {18, 55, 56} {18, 55, 57} {18, 55, 58} {18, 55, 59}
{18, 55, 60} {18, 55, 61} {18, 55, 62} {18, 55, 63} {18, 55, 64} {18, 55, 65} {18, 55, 66} {18, 56, 57} {18, 56, 58}
{18, 56, 59} {18, 56, 60} {18, 56, 61} {18, 56, 62} {18, 56, 63} {18, 56, 64} {18, 56, 65} {18, 56, 66} {18, 57, 58}
{18, 57, 59} {18, 57, 60} {18, 57, 61} {18, 57, 62} {18, 57, 63} {18, 57, 64} {18, 57, 65} {18, 57, 66} {18, 58, 59}
{18, 58, 60} {18, 58, 61} {18, 58, 62} {18, 58, 63} {18, 58, 64} {18, 58, 65} {18, 58, 66} {18, 59, 60} {18, 59, 61}
{18, 59, 62} {18, 59, 63} {18, 59, 64} {18, 59, 65} {18, 59, 66} {18, 60, 61} {18, 60, 62} {18, 60, 63} {18, 60, 64}
{18, 60, 65} {18, 60, 66} {18, 61, 62} {18, 61, 63} {18, 61, 64} {18, 61, 65} {18, 61, 66} {18, 62, 63} {18, 62, 64}
{18, 62, 65} {18, 62, 66} {18, 63, 64} {18, 63, 65} {18, 63, 66} {18, 64, 65} {18, 64, 66} {18, 65, 66} {19, 20, 21}
{19, 20, 22} {19, 20, 23} {19, 20, 24} {19, 20, 25} {19, 20, 26} {19, 20, 27} {19, 20, 28} {19, 20, 29} {19, 20, 30}
{19, 20, 31} {19, 20, 32} {19, 20, 33} {19, 20, 34} {19, 20, 35} {19, 20, 36} {19, 20, 37} {19, 20, 38} {19, 20, 39}
{19, 20, 40} {19, 20, 41} {19, 20, 42} {19, 20, 43} {19, 20, 44} {19, 20, 45} {19, 20, 46} {19, 20, 47} {19, 20, 48}
{19, 20, 49} {19, 20, 50} {19, 20, 51} {19, 20, 52} {19, 20, 53} {19, 20, 54} {19, 20, 55} {19, 20, 56} {19, 20, 57}
{19, 20, 58} {19, 20, 59} {19, 20, 60} {19, 20, 61} {19, 20, 62} {19, 20, 63} {19, 20, 64} {19, 20, 65} {19, 20, 66}
{19, 21, 22} {19, 21, 23} {19, 21, 24} {19, 21, 25} {19, 21, 26} {19, 21, 27} {19, 21, 28} {19, 21, 29} {19, 21, 30}
{19, 21, 31} {19, 21, 32} {19, 21, 33} {19, 21, 34} {19, 21, 35} {19, 21, 36} {19, 21, 37} {19, 21, 38} {19, 21, 39}
{19, 21, 40} {19, 21, 41} {19, 21, 42} {19, 21, 43} {19, 21, 44} {19, 21, 45} {19, 21, 46} {19, 21, 47} {19, 21, 48}
{19, 21, 49} {19, 21, 50} {19, 21, 51} {19, 21, 52} {19, 21, 53} {19, 21, 54} {19, 21, 55} {19, 21, 56} {19, 21, 57}
{19, 21, 58} {19, 21, 59} {19, 21, 60} {19, 21, 61} {19, 21, 62} {19, 21, 63} {19, 21, 64} {19, 21, 65} {19, 21, 66}
{19, 22, 23} {19, 22, 24} {19, 22, 25} {19, 22, 26} {19, 22, 27} {19, 22, 28} {19, 22, 29} {19, 22, 30} {19, 22, 31}
{19, 22, 32} {19, 22, 33} {19, 22, 34} {19, 22, 35} {19, 22, 36} {19, 22, 37} {19, 22, 38} {19, 22, 39} {19, 22, 40}
{19, 22, 41} {19, 22, 42} {19, 22, 43} {19, 22, 44} {19, 22, 45} {19, 22, 46} {19, 22, 47} {19, 22, 48} {19, 22, 49}
{19, 22, 50} {19, 22, 51} {19, 22, 52} {19, 22, 53} {19, 22, 54} {19, 22, 55} {19, 22, 56} {19, 22, 57} {19, 22, 58}
{19, 22, 59} {19, 22, 60} {19, 22, 61} {19, 22, 62} {19, 22, 63} {19, 22, 64} {19, 22, 65} {19, 22, 66} {19, 23, 24}
{19, 23, 25} {19, 23, 26} {19, 23, 27} {19, 23, 28} {19, 23, 29} {19, 23, 30} {19, 23, 31} {19, 23, 32} {19, 23, 33}
{19, 23, 34} {19, 23, 35} {19, 23, 36} {19, 23, 37} {19, 23, 38} {19, 23, 39} {19, 23, 40} {19, 23, 41} {19, 23, 42}
{19, 23, 43} {19, 23, 44} {19, 23, 45} {19, 23, 46} {19, 23, 47} {19, 23, 48} {19, 23, 49} {19, 23, 50} {19, 23, 51}
{19, 23, 52} {19, 23, 53} {19, 23, 54} {19, 23, 55} {19, 23, 56} {19, 23, 57} {19, 23, 58} {19, 23, 59} {19, 23, 60}
{19, 23, 61} {19, 23, 62} {19, 23, 63} {19, 23, 64} {19, 23, 65} {19, 23, 66} {19, 24, 25} {19, 24, 26} {19, 24, 27}
{19, 24, 28} {19, 24, 29} {19, 24, 30} {19, 24, 31} {19, 24, 32} {19, 24, 33} {19, 24, 34} {19, 24, 35} {19, 24, 36}
{19, 24, 37} {19, 24, 38} {19, 24, 39} {19, 24, 40} {19, 24, 41} {19, 24, 42} {19, 24, 43} {19, 24, 44} {19, 24, 45}
{19, 24, 46} {19, 24, 47} {19, 24, 48} {19, 24, 49} {19, 24, 50} {19, 24, 51} {19, 24, 52} {19, 24, 53} {19, 24, 54}
{19, 24, 55} {19, 24, 56} {19, 24, 57} {19, 24, 58} {19, 24, 59} {19, 24, 60} {19, 24, 61} {19, 24, 62} {19, 24, 63}
{19, 24, 64} {19, 24, 65} {19, 24, 66} {19, 25, 26} {19, 25, 27} {19, 25, 28} {19, 25, 29} {19, 25, 30} {19, 25, 31}
{19, 25, 32} {19, 25, 33} {19, 25, 34} {19, 25, 35} {19, 25, 36} {19, 25, 37} {19, 25, 38} {19, 25, 39} {19, 25, 40}
{19, 25, 41} {19, 25, 42} {19, 25, 43} {19, 25, 44} {19, 25, 45} {19, 25, 46} {19, 25, 47} {19, 25, 48} {19, 25, 49}
{19, 25, 50} {19, 25, 51} {19, 25, 52} {19, 25, 53} {19, 25, 54} {19, 25, 55} {19, 25, 56} {19, 25, 57} {19, 25, 58}
{19, 25, 59} {19, 25, 60} {19, 25, 61} {19, 25, 62} {19, 25, 63} {19, 25, 64} {19, 25, 65} {19, 25, 66} {19, 26, 27}
{19, 26, 28} {19, 26, 29} {19, 26, 30} {19, 26, 31} {19, 26, 32} {19, 26, 33} {19, 26, 34} {19, 26, 35} {19, 26, 36}
{19, 26, 37} {19, 26, 38} {19, 26, 39} {19, 26, 40} {19, 26, 41} {19, 26, 42} {19, 26, 43} {19, 26, 44} {19, 26, 45}
{19, 26, 46} {19, 26, 47} {19, 26, 48} {19, 26, 49} {19, 26, 50} {19, 26, 51} {19, 26, 52} {19, 26, 53} {19, 26, 54}
{19, 26, 55} {19, 26, 56} {19, 26, 57} {19, 26, 58} {19, 26, 59} {19, 26, 60} {19, 26, 61} {19, 26, 62} {19, 26, 63}
{19, 26, 64} {19, 26, 65} {19, 26, 66} {19, 27, 28} {19, 27, 29} {19, 27, 30} {19, 27, 31} {19, 27, 32} {19, 27, 33}
{19, 27, 34} {19, 27, 35} {19, 27, 36} {19, 27, 37} {19, 27, 38} {19, 27, 39} {19, 27, 40} {19, 27, 41} {19, 27, 42}
{19, 27, 43} {19, 27, 44} {19, 27, 45} {19, 27, 46} {19, 27, 47} {19, 27, 48} {19, 27, 49} {19, 27, 50} {19, 27, 51}
{19, 27, 52} {19, 27, 53} {19, 27, 54} {19, 27, 55} {19, 27, 56} {19, 27, 57} {19, 27, 58} {19, 27, 59} {19, 27, 60}
{19, 27, 61} {19, 27, 62} {19, 27, 63} {19, 27, 64} {19, 27, 65} {19, 27, 66} {19, 28, 29} {19, 28, 30} {19, 28, 31}
{19, 28, 32} {19, 28, 33} {19, 28, 34} {19, 28, 35} {19, 28, 36} {19, 28, 37} {19, 28, 38} {19, 28, 39} {19, 28, 40}
{19, 28, 41} {19, 28, 42} {19, 28, 43} {19, 28, 44} {19, 28, 45} {19, 28, 46} {19, 28, 47} {19, 28, 48} {19, 28, 49}
{19, 28, 50} {19, 28, 51} {19, 28, 52} {19, 28, 53} {19, 28, 54} {19, 28, 55} {19, 28, 56} {19, 28, 57} {19, 28, 58}
{19, 28, 59} {19, 28, 60} {19, 28, 61} {19, 28, 62} {19, 28, 63} {19, 28, 64} {19, 28, 65} {19, 28, 66} {19, 29, 30}
{19, 29, 31} {19, 29, 32} {19, 29, 33} {19, 29, 34} {19, 29, 35} {19, 29, 36} {19, 29, 37} {19, 29, 38} {19, 29, 39}
{19, 29, 40} {19, 29, 41} {19, 29, 42} {19, 29, 43} {19, 29, 44} {19, 29, 45} {19, 29, 46} {19, 29, 47} {19, 29, 48}
{19, 29, 49} {19, 29, 50} {19, 29, 51} {19, 29, 52} {19, 29, 53} {19, 29, 54} {19, 29, 55} {19, 29, 56} {19, 29, 57}
{19, 29, 58} {19, 29, 59} {19, 29, 60} {19, 29, 61} {19, 29, 62} {19, 29, 63} {19, 29, 64} {19, 29, 65} {19, 29, 66}
{19, 30, 31} {19, 30, 32} {19, 30, 33} {19, 30, 34} {19, 30, 35} {19, 30, 36} {19, 30, 37} {19, 30, 38} {19, 30, 39}
{19, 30, 40} {19, 30, 41} {19, 30, 42} {19, 30, 43} {19, 30, 44} {19, 30, 45} {19, 30, 46} {19, 30, 47} {19, 30, 48}
{19, 30, 49} {19, 30, 50} {19, 30, 51} {19, 30, 52} {19, 30, 53} {19, 30, 54} {19, 30, 55} {19, 30, 56} {19, 30, 57}
{19, 30, 58} {19, 30, 59} {19, 30, 60} {19, 30, 61} {19, 30, 62} {19, 30, 63} {19, 30, 64} {19, 30, 65} {19, 30, 66}
{19, 31, 32} {19, 31, 33} {19, 31, 34} {19, 31, 35} {19, 31, 36} {19, 31, 37} {19, 31, 38} {19, 31, 39} {19, 31, 40}
{19, 31, 41} {19, 31, 42} {19, 31, 43} {19, 31, 44} {19, 31, 45} {19, 31, 46} {19, 31, 47} {19, 31, 48} {19, 31, 49}
{19, 31, 50} {19, 31, 51} {19, 31, 52} {19, 31, 53} {19, 31, 54} {19, 31, 55} {19, 31, 56} {19, 31, 57} {19, 31, 58}
{19, 31, 59} {19, 31, 60} {19, 31, 61} {19, 31, 62} {19, 31, 63} {19, 31, 64} {19, 31, 65} {19, 31, 66} {19, 32, 33}
{19, 32, 34} {19, 32, 35} {19, 32, 36} {19, 32, 37} {19, 32, 38} {19, 32, 39} {19, 32, 40} {19, 32, 41} {19, 32, 42}
{19, 32, 43} {19, 32, 44} {19, 32, 45} {19, 32, 46} {19, 32, 47} {19, 32, 48} {19, 32, 49} {19, 32, 50} {19, 32, 51}
{19, 32, 52} {19, 32, 53} {19, 32, 54} {19, 32, 55} {19, 32, 56} {19, 32, 57} {19, 32, 58} {19, 32, 59} {19, 32, 60}
{19, 32, 61} {19, 32, 62} {19, 32, 63} {19, 32, 64} {19, 32, 65} {19, 32, 66} {19, 33, 34} {19, 33, 35} {19, 33, 36}
{19, 33, 37} {19, 33, 38} {19, 33, 39} {19, 33, 40} {19, 33, 41} {19, 33, 42} {19, 33, 43} {19, 33, 44} {19, 33, 45}
{19, 33, 46} {19, 33, 47} {19, 33, 48} {19, 33, 49} {19, 33, 50} {19, 33, 51} {19, 33, 52} {19, 33, 53} {19, 33, 54}
{19, 33, 55} {19, 33, 56} {19, 33, 57} {19, 33, 58} {19, 33, 59} {19, 33, 60} {19, 33, 61} {19, 33, 62} {19, 33, 63}
{19, 33, 64} {19, 33, 65} {19, 33, 66} {19, 34, 35} {19, 34, 36} {19, 34, 37} {19, 34, 38} {19, 34, 39} {19, 34, 40}

TABLE 3A-continued

{19, 34, 41} {19, 34, 42} {19, 34, 43} {19, 34, 44} {19, 34, 45} {19, 34, 46} {19, 34, 47} {19, 34, 48} {19, 34, 49}
{19, 34, 50} {19, 34, 51} {19, 34, 52} {19, 34, 53} {19, 34, 54} {19, 34, 55} {19, 34, 56} {19, 34, 57} {19, 34, 58}
{19, 34, 59} {19, 34, 60} {19, 34, 61} {19, 34, 62} {19, 34, 63} {19, 34, 64} {19, 34, 65} {19, 34, 66} {19, 35, 36}
{19, 35, 37} {19, 35, 38} {19, 35, 39} {19, 35, 40} {19, 35, 41} {19, 35, 42} {19, 35, 43} {19, 35, 44} {19, 35, 45}
{19, 35, 46} {19, 35, 47} {19, 35, 48} {19, 35, 49} {19, 35, 50} {19, 35, 51} {19, 35, 52} {19, 35, 53} {19, 35, 54}
{19, 35, 55} {19, 35, 56} {19, 35, 57} {19, 35, 58} {19, 35, 59} {19, 35, 60} {19, 35, 61} {19, 35, 62} {19, 35, 63}
{19, 35, 64} {19, 35, 65} {19, 35, 66} {19, 36, 37} {19, 36, 38} {19, 36, 39} {19, 36, 40} {19, 36, 41} {19, 36, 42}
{19, 36, 43} {19, 36, 44} {19, 36, 45} {19, 36, 46} {19, 36, 47} {19, 36, 48} {19, 36, 49} {19, 36, 50} {19, 36, 51}
{19, 36, 52} {19, 36, 53} {19, 36, 54} {19, 36, 55} {19, 36, 56} {19, 36, 57} {19, 36, 58} {19, 36, 59} {19, 36, 60}
{19, 36, 61} {19, 36, 62} {19, 36, 63} {19, 36, 64} {19, 36, 65} {19, 36, 66} {19, 37, 38} {19, 37, 39} {19, 37, 40}
{19, 37, 41} {19, 37, 42} {19, 37, 43} {19, 37, 44} {19, 37, 45} {19, 37, 46} {19, 37, 47} {19, 37, 48} {19, 37, 49}
{19, 37, 50} {19, 37, 51} {19, 37, 52} {19, 37, 53} {19, 37, 54} {19, 37, 55} {19, 37, 56} {19, 37, 57} {19, 37, 58}
{19, 37, 59} {19, 37, 60} {19, 37, 61} {19, 37, 62} {19, 37, 63} {19, 37, 64} {19, 37, 65} {19, 37, 66} {19, 38, 39}
{19, 38, 40} {19, 38, 41} {19, 38, 42} {19, 38, 43} {19, 38, 44} {19, 38, 45} {19, 38, 46} {19, 38, 47} {19, 38, 48}
{19, 38, 49} {19, 38, 50} {19, 38, 51} {19, 38, 52} {19, 38, 53} {19, 38, 54} {19, 38, 55} {19, 38, 56} {19, 38, 57}
{19, 38, 58} {19, 38, 59} {19, 38, 60} {19, 38, 61} {19, 38, 62} {19, 38, 63} {19, 38, 64} {19, 38, 65} {19, 38, 66}
{19, 39, 40} {19, 39, 41} {19, 39, 42} {19, 39, 43} {19, 39, 44} {19, 39, 45} {19, 39, 46} {19, 39, 47} {19, 39, 48}
{19, 39, 49} {19, 39, 50} {19, 39, 51} {19, 39, 52} {19, 39, 53} {19, 39, 54} {19, 39, 55} {19, 39, 56} {19, 39, 57}
{19, 39, 58} {19, 39, 59} {19, 39, 60} {19, 39, 61} {19, 39, 62} {19, 39, 63} {19, 39, 64} {19, 39, 65} {19, 39, 66}
{19, 40, 41} {19, 40, 42} {19, 40, 43} {19, 40, 44} {19, 40, 45} {19, 40, 46} {19, 40, 47} {19, 40, 48} {19, 40, 49}
{19, 40, 50} {19, 40, 51} {19, 40, 52} {19, 40, 53} {19, 40, 54} {19, 40, 55} {19, 40, 56} {19, 40, 57} {19, 40, 58}
{19, 40, 59} {19, 40, 60} {19, 40, 61} {19, 40, 62} {19, 40, 63} {19, 40, 64} {19, 40, 65} {19, 40, 66} {19, 41, 42}
{19, 41, 43} {19, 41, 44} {19, 41, 45} {19, 41, 46} {19, 41, 47} {19, 41, 48} {19, 41, 49} {19, 41, 50} {19, 41, 51}
{19, 41, 52} {19, 41, 53} {19, 41, 54} {19, 41, 55} {19, 41, 56} {19, 41, 57} {19, 41, 58} {19, 41, 59} {19, 41, 60}
{19, 41, 61} {19, 41, 62} {19, 41, 63} {19, 41, 64} {19, 41, 65} {19, 41, 66} {19, 42, 43} {19, 42, 44} {19, 42, 45}
{19, 42, 46} {19, 42, 47} {19, 42, 48} {19, 42, 49} {19, 42, 50} {19, 42, 51} {19, 42, 52} {19, 42, 53} {19, 42, 54}
{19, 42, 55} {19, 42, 56} {19, 42, 57} {19, 42, 58} {19, 42, 59} {19, 42, 60} {19, 42, 61} {19, 42, 62} {19, 42, 63}
{19, 42, 64} {19, 42, 65} {19, 42, 66} {19, 43, 44} {19, 43, 45} {19, 43, 46} {19, 43, 47} {19, 43, 48} {19, 43, 49}
{19, 43, 50} {19, 43, 51} {19, 43, 52} {19, 43, 53} {19, 43, 54} {19, 43, 55} {19, 43, 56} {19, 43, 57} {19, 43, 58}
{19, 43, 59} {19, 43, 60} {19, 43, 61} {19, 43, 62} {19, 43, 63} {19, 43, 64} {19, 43, 65} {19, 43, 66} {19, 44, 45}
{19, 44, 46} {19, 44, 47} {19, 44, 48} {19, 44, 49} {19, 44, 50} {19, 44, 51} {19, 44, 52} {19, 44, 53} {19, 44, 54}
{19, 44, 55} {19, 44, 56} {19, 44, 57} {19, 44, 58} {19, 44, 59} {19, 44, 60} {19, 44, 61} {19, 44, 62} {19, 44, 63}
{19, 44, 64} {19, 44, 65} {19, 44, 66} {19, 45, 46} {19, 45, 47} {19, 45, 48} {19, 45, 49} {19, 45, 50} {19, 45, 51}
{19, 45, 52} {19, 45, 53} {19, 45, 54} {19, 45, 55} {19, 45, 56} {19, 45, 57} {19, 45, 58} {19, 45, 59} {19, 45, 60}
{19, 45, 61} {19, 45, 62} {19, 45, 63} {19, 45, 64} {19, 45, 65} {19, 45, 66} {19, 46, 47} {19, 46, 48} {19, 46, 49}
{19, 46, 50} {19, 46, 51} {19, 46, 52} {19, 46, 53} {19, 46, 54} {19, 46, 55} {19, 46, 56} {19, 46, 57} {19, 46, 58}
{19, 46, 59} {19, 46, 60} {19, 46, 61} {19, 46, 62} {19, 46, 63} {19, 46, 64} {19, 46, 65} {19, 46, 66} {19, 47, 48}
{19, 47, 49} {19, 47, 50} {19, 47, 51} {19, 47, 52} {19, 47, 53} {19, 47, 54} {19, 47, 55} {19, 47, 56} {19, 47, 57}
{19, 47, 58} {19, 47, 59} {19, 47, 60} {19, 47, 61} {19, 47, 62} {19, 47, 63} {19, 47, 64} {19, 47, 65} {19, 47, 66}
{19, 48, 49} {19, 48, 50} {19, 48, 51} {19, 48, 52} {19, 48, 53} {19, 48, 54} {19, 48, 55} {19, 48, 56} {19, 48, 57}
{19, 48, 58} {19, 48, 59} {19, 48, 60} {19, 48, 61} {19, 48, 62} {19, 48, 63} {19, 48, 64} {19, 48, 65} {19, 48, 66}
{19, 49, 50} {19, 49, 51} {19, 49, 52} {19, 49, 53} {19, 49, 54} {19, 49, 55} {19, 49, 56} {19, 49, 57} {19, 49, 58}
{19, 49, 59} {19, 49, 60} {19, 49, 61} {19, 49, 62} {19, 49, 63} {19, 49, 64} {19, 49, 65} {19, 49, 66} {19, 50, 51}
{19, 50, 52} {19, 50, 53} {19, 50, 54} {19, 50, 55} {19, 50, 56} {19, 50, 57} {19, 50, 58} {19, 50, 59} {19, 50, 60}
{19, 50, 61} {19, 50, 62} {19, 50, 63} {19, 50, 64} {19, 50, 65} {19, 50, 66} {19, 51, 52} {19, 51, 53} {19, 51, 54}
{19, 51, 55} {19, 51, 56} {19, 51, 57} {19, 51, 58} {19, 51, 59} {19, 51, 60} {19, 51, 61} {19, 51, 62} {19, 51, 63}
{19, 51, 64} {19, 51, 65} {19, 51, 66} {19, 52, 53} {19, 52, 54} {19, 52, 55} {19, 52, 56} {19, 52, 57} {19, 52, 58}
{19, 52, 59} {19, 52, 60} {19, 52, 61} {19, 52, 62} {19, 52, 63} {19, 52, 64} {19, 52, 65} {19, 52, 66} {19, 53, 54}
{19, 53, 55} {19, 53, 56} {19, 53, 57} {19, 53, 58} {19, 53, 59} {19, 53, 60} {19, 53, 61} {19, 53, 62} {19, 53, 63}
{19, 53, 64} {19, 53, 65} {19, 53, 66} {19, 54, 55} {19, 54, 56} {19, 54, 57} {19, 54, 58} {19, 54, 59} {19, 54, 60}
{19, 54, 61} {19, 54, 62} {19, 54, 63} {19, 54, 64} {19, 54, 65} {19, 54, 66} {19, 55, 56} {19, 55, 57} {19, 55, 58}
{19, 55, 59} {19, 55, 60} {19, 55, 61} {19, 55, 62} {19, 55, 63} {19, 55, 64} {19, 55, 65} {19, 55, 66} {19, 56, 57}
{19, 56, 58} {19, 56, 59} {19, 56, 60} {19, 56, 61} {19, 56, 62} {19, 56, 63} {19, 56, 64} {19, 56, 65} {19, 56, 66}
{19, 57, 58} {19, 57, 59} {19, 57, 60} {19, 57, 61} {19, 57, 62} {19, 57, 63} {19, 57, 64} {19, 57, 65} {19, 57, 66}
{19, 58, 59} {19, 58, 60} {19, 58, 61} {19, 58, 62} {19, 58, 63} {19, 58, 64} {19, 58, 65} {19, 58, 66} {19, 59, 60}
{19, 59, 61} {19, 59, 62} {19, 59, 63} {19, 59, 64} {19, 59, 65} {19, 59, 66} {19, 60, 61} {19, 60, 62} {19, 60, 63}
{19, 60, 64} {19, 60, 65} {19, 60, 66} {19, 61, 62} {19, 61, 63} {19, 61, 64} {19, 61, 65} {19, 61, 66} {19, 62, 63}
{19, 62, 64} {19, 62, 65} {19, 62, 66} {19, 63, 64} {19, 63, 65} {19, 63, 66} {19, 64, 65} {19, 64, 66} {19, 65, 66}
{20, 21, 22} {20, 21, 23} {20, 21, 24} {20, 21, 25} {20, 21, 26} {20, 21, 27} {20, 21, 28} {20, 21, 29} {20, 21, 30}
{20, 21, 31} {20, 21, 32} {20, 21, 33} {20, 21, 34} {20, 21, 35} {20, 21, 36} {20, 21, 37} {20, 21, 38} {20, 21, 39}
{20, 21, 40} {20, 21, 41} {20, 21, 42} {20, 21, 43} {20, 21, 44} {20, 21, 45} {20, 21, 46} {20, 21, 47} {20, 21, 48}
{20, 21, 49} {20, 21, 50} {20, 21, 51} {20, 21, 52} {20, 21, 53} {20, 21, 54} {20, 21, 55} {20, 21, 56} {20, 21, 57}
{20, 21, 58} {20, 21, 59} {20, 21, 60} {20, 21, 61} {20, 21, 62} {20, 21, 63} {20, 21, 64} {20, 21, 65} {20, 21, 66}
{20, 22, 23} {20, 22, 24} {20, 22, 25} {20, 22, 26} {20, 22, 27} {20, 22, 28} {20, 22, 29} {20, 22, 30} {20, 22, 31}
{20, 22, 32} {20, 22, 33} {20, 22, 34} {20, 22, 35} {20, 22, 36} {20, 22, 37} {20, 22, 38} {20, 22, 39} {20, 22, 40}
{20, 22, 41} {20, 22, 42} {20, 22, 43} {20, 22, 44} {20, 22, 45} {20, 22, 46} {20, 22, 47} {20, 22, 48} {20, 22, 49}
{20, 22, 50} {20, 22, 51} {20, 22, 52} {20, 22, 53} {20, 22, 54} {20, 22, 55} {20, 22, 56} {20, 22, 57} {20, 22, 58}
{20, 22, 59} {20, 22, 60} {20, 22, 61} {20, 22, 62} {20, 22, 63} {20, 22, 64} {20, 22, 65} {20, 22, 66} {20, 23, 24}
{20, 23, 25} {20, 23, 26} {20, 23, 27} {20, 23, 28} {20, 23, 29} {20, 23, 30} {20, 23, 31} {20, 23, 32} {20, 23, 33}
{20, 23, 34} {20, 23, 35} {20, 23, 36} {20, 23, 37} {20, 23, 38} {20, 23, 39} {20, 23, 40} {20, 23, 41} {20, 23, 42}
{20, 23, 43} {20, 23, 44} {20, 23, 45} {20, 23, 46} {20, 23, 47} {20, 23, 48} {20, 23, 49} {20, 23, 50} {20, 23, 51}
{20, 23, 52} {20, 23, 53} {20, 23, 54} {20, 23, 55} {20, 23, 56} {20, 23, 57} {20, 23, 58} {20, 23, 59} {20, 23, 60}
{20, 23, 61} {20, 23, 62} {20, 23, 63} {20, 23, 64} {20, 23, 65} {20, 23, 66} {20, 24, 25} {20, 24, 26} {20, 24, 27}
{20, 24, 28} {20, 24, 29} {20, 24, 30} {20, 24, 31} {20, 24, 32} {20, 24, 33} {20, 24, 34} {20, 24, 35} {20, 24, 36}
{20, 24, 37} {20, 24, 38} {20, 24, 39} {20, 24, 40} {20, 24, 41} {20, 24, 42} {20, 24, 43} {20, 24, 44} {20, 24, 45}
{20, 24, 46} {20, 24, 47} {20, 24, 48} {20, 24, 49} {20, 24, 50} {20, 24, 51} {20, 24, 52} {20, 24, 53} {20, 24, 54}
{20, 24, 55} {20, 24, 56} {20, 24, 57} {20, 24, 58} {20, 24, 59} {20, 24, 60} {20, 24, 61} {20, 24, 62} {20, 24, 63}
{20, 24, 64} {20, 24, 65} {20, 24, 66} {20, 25, 26} {20, 25, 27} {20, 25, 28} {20, 25, 29} {20, 25, 30} {20, 25, 31}
{20, 25, 32} {20, 25, 33} {20, 25, 34} {20, 25, 35} {20, 25, 36} {20, 25, 37} {20, 25, 38} {20, 25, 39} {20, 25, 40}
{20, 25, 41} {20, 25, 42} {20, 25, 43} {20, 25, 44} {20, 25, 45} {20, 25, 46} {20, 25, 47} {20, 25, 48} {20, 25, 49}

TABLE 3A-continued

{20, 25, 50} {20, 25, 51} {20, 25, 52} {20, 25, 53} {20, 25, 54} {20, 25, 55} {20, 25, 56} {20, 25, 57} {20, 25, 58}
{20, 25, 59} {20, 25, 60} {20, 25, 61} {20, 25, 62} {20, 25, 63} {20, 25, 64} {20, 25, 65} {20, 25, 66} {20, 26, 27}
{20, 26, 28} {20, 26, 29} {20, 26, 30} {20, 26, 31} {20, 26, 32} {20, 26, 33} {20, 26, 34} {20, 26, 35} {20, 26, 36}
{20, 26, 37} {20, 26, 38} {20, 26, 39} {20, 26, 40} {20, 26, 41} {20, 26, 42} {20, 26, 43} {20, 26, 44} {20, 26, 45}
{20, 26, 46} {20, 26, 47} {20, 26, 48} {20, 26, 49} {20, 26, 50} {20, 26, 51} {20, 26, 52} {20, 26, 53} {20, 26, 54}
{20, 26, 55} {20, 26, 56} {20, 26, 57} {20, 26, 58} {20, 26, 59} {20, 26, 60} {20, 26, 61} {20, 26, 62} {20, 26, 63}
{20, 26, 64} {20, 26, 65} {20, 26, 66} {20, 27, 28} {20, 27, 29} {20, 27, 30} {20, 27, 31} {20, 27, 32} {20, 27, 33}
{20, 27, 34} {20, 27, 35} {20, 27, 36} {20, 27, 37} {20, 27, 38} {20, 27, 39} {20, 27, 40} {20, 27, 41} {20, 27, 42}
{20, 27, 43} {20, 27, 44} {20, 27, 45} {20, 27, 46} {20, 27, 47} {20, 27, 48} {20, 27, 49} {20, 27, 50} {20, 27, 51}
{20, 27, 52} {20, 27, 53} {20, 27, 54} {20, 27, 55} {20, 27, 56} {20, 27, 57} {20, 27, 58} {20, 27, 59} {20, 27, 60}
{20, 27, 61} {20, 27, 62} {20, 27, 63} {20, 27, 64} {20, 27, 65} {20, 27, 66} {20, 28, 29} {20, 28, 30} {20, 28, 31}
{20, 28, 32} {20, 28, 33} {20, 28, 34} {20, 28, 35} {20, 28, 36} {20, 28, 37} {20, 28, 38} {20, 28, 39} {20, 28, 40}
{20, 28, 41} {20, 28, 42} {20, 28, 43} {20, 28, 44} {20, 28, 45} {20, 28, 46} {20, 28, 47} {20, 28, 48} {20, 28, 49}
{20, 28, 50} {20, 28, 51} {20, 28, 52} {20, 28, 53} {20, 28, 54} {20, 28, 55} {20, 28, 56} {20, 28, 57} {20, 28, 58}
{20, 28, 59} {20, 28, 60} {20, 28, 61} {20, 28, 62} {20, 28, 63} {20, 28, 64} {20, 28, 65} {20, 28, 66} {20, 29, 30}
{20, 29, 31} {20, 29, 32} {20, 29, 33} {20, 29, 34} {20, 29, 35} {20, 29, 36} {20, 29, 37} {20, 29, 38} {20, 29, 39}
{20, 29, 40} {20, 29, 41} {20, 29, 42} {20, 29, 43} {20, 29, 44} {20, 29, 45} {20, 29, 46} {20, 29, 47} {20, 29, 48}
{20, 29, 49} {20, 29, 50} {20, 29, 51} {20, 29, 52} {20, 29, 53} {20, 29, 54} {20, 29, 55} {20, 29, 56} {20, 29, 57}
{20, 29, 58} {20, 29, 59} {20, 29, 60} {20, 29, 61} {20, 29, 62} {20, 29, 63} {20, 29, 64} {20, 29, 65} {20, 29, 66}
{20, 30, 31} {20, 30, 32} {20, 30, 33} {20, 30, 34} {20, 30, 35} {20, 30, 36} {20, 30, 37} {20, 30, 38} {20, 30, 39}
{20, 30, 40} {20, 30, 41} {20, 30, 42} {20, 30, 43} {20, 30, 44} {20, 30, 45} {20, 30, 46} {20, 30, 47} {20, 30, 48}
{20, 30, 49} {20, 30, 50} {20, 30, 51} {20, 30, 52} {20, 30, 53} {20, 30, 54} {20, 30, 55} {20, 30, 56} {20, 30, 57}
{20, 30, 58} {20, 30, 59} {20, 30, 60} {20, 30, 61} {20, 30, 62} {20, 30, 63} {20, 30, 64} {20, 30, 65} {20, 30, 66}
{20, 31, 32} {20, 31, 33} {20, 31, 34} {20, 31, 35} {20, 31, 36} {20, 31, 37} {20, 31, 38} {20, 31, 39} {20, 31, 40}
{20, 31, 41} {20, 31, 42} {20, 31, 43} {20, 31, 44} {20, 31, 45} {20, 31, 46} {20, 31, 47} {20, 31, 48} {20, 31, 49}
{20, 31, 50} {20, 31, 51} {20, 31, 52} {20, 31, 53} {20, 31, 54} {20, 31, 55} {20, 31, 56} {20, 31, 57} {20, 31, 58}
{20, 31, 59} {20, 31, 60} {20, 31, 61} {20, 31, 62} {20, 31, 63} {20, 31, 64} {20, 31, 65} {20, 31, 66} {20, 32, 33}
{20, 32, 34} {20, 32, 35} {20, 32, 36} {20, 32, 37} {20, 32, 38} {20, 32, 39} {20, 32, 40} {20, 32, 41} {20, 32, 42}
{20, 32, 43} {20, 32, 44} {20, 32, 45} {20, 32, 46} {20, 32, 47} {20, 32, 48} {20, 32, 49} {20, 32, 50} {20, 32, 51}
{20, 32, 52} {20, 32, 53} {20, 32, 54} {20, 32, 55} {20, 32, 56} {20, 32, 57} {20, 32, 58} {20, 32, 59} {20, 32, 60}
{20, 32, 61} {20, 32, 62} {20, 32, 63} {20, 32, 64} {20, 32, 65} {20, 32, 66} {20, 33, 34} {20, 33, 35} {20, 33, 36}
{20, 33, 37} {20, 33, 38} {20, 33, 39} {20, 33, 40} {20, 33, 41} {20, 33, 42} {20, 33, 43} {20, 33, 44} {20, 33, 45}
{20, 33, 46} {20, 33, 47} {20, 33, 48} {20, 33, 49} {20, 33, 50} {20, 33, 51} {20, 33, 52} {20, 33, 53} {20, 33, 54}
{20, 33, 55} {20, 33, 56} {20, 33, 57} {20, 33, 58} {20, 33, 59} {20, 33, 60} {20, 33, 61} {20, 33, 62} {20, 33, 63}
{20, 33, 64} {20, 33, 65} {20, 33, 66} {20, 34, 35} {20, 34, 36} {20, 34, 37} {20, 34, 38} {20, 34, 39} {20, 34, 40}
{20, 34, 41} {20, 34, 42} {20, 34, 43} {20, 34, 44} {20, 34, 45} {20, 34, 46} {20, 34, 47} {20, 34, 48} {20, 34, 49}
{20, 34, 50} {20, 34, 51} {20, 34, 52} {20, 34, 53} {20, 34, 54} {20, 34, 55} {20, 34, 56} {20, 34, 57} {20, 34, 58}
{20, 34, 59} {20, 34, 60} {20, 34, 61} {20, 34, 62} {20, 34, 63} {20, 34, 64} {20, 34, 65} {20, 34, 66} {20, 35, 36}
{20, 35, 37} {20, 35, 38} {20, 35, 39} {20, 35, 40} {20, 35, 41} {20, 35, 42} {20, 35, 43} {20, 35, 44} {20, 35, 45}
{20, 35, 46} {20, 35, 47} {20, 35, 48} {20, 35, 49} {20, 35, 50} {20, 35, 51} {20, 35, 52} {20, 35, 53} {20, 35, 54}
{20, 35, 55} {20, 35, 56} {20, 35, 57} {20, 35, 58} {20, 35, 59} {20, 35, 60} {20, 35, 61} {20, 35, 62} {20, 35, 63}
{20, 35, 64} {20, 35, 65} {20, 35, 66} {20, 36, 37} {20, 36, 38} {20, 36, 39} {20, 36, 40} {20, 36, 41} {20, 36, 42}
{20, 36, 43} {20, 36, 44} {20, 36, 45} {20, 36, 46} {20, 36, 47} {20, 36, 48} {20, 36, 49} {20, 36, 50} {20, 36, 51}
{20, 36, 52} {20, 36, 53} {20, 36, 54} {20, 36, 55} {20, 36, 56} {20, 36, 57} {20, 36, 58} {20, 36, 59} {20, 36, 60}
{20, 36, 61} {20, 36, 62} {20, 36, 63} {20, 36, 64} {20, 36, 65} {20, 36, 66} {20, 37, 38} {20, 37, 39} {20, 37, 40}
{20, 37, 41} {20, 37, 42} {20, 37, 43} {20, 37, 44} {20, 37, 45} {20, 37, 46} {20, 37, 47} {20, 37, 48} {20, 37, 49}
{20, 37, 50} {20, 37, 51} {20, 37, 52} {20, 37, 53} {20, 37, 54} {20, 37, 55} {20, 37, 56} {20, 37, 57} {20, 37, 58}
{20, 37, 59} {20, 37, 60} {20, 37, 61} {20, 37, 62} {20, 37, 63} {20, 37, 64} {20, 37, 65} {20, 37, 66} {20, 38, 39}
{20, 38, 40} {20, 38, 41} {20, 38, 42} {20, 38, 43} {20, 38, 44} {20, 38, 45} {20, 38, 46} {20, 38, 47} {20, 38, 48}
{20, 38, 49} {20, 38, 50} {20, 38, 51} {20, 38, 52} {20, 38, 53} {20, 38, 54} {20, 38, 55} {20, 38, 56} {20, 38, 57}
{20, 38, 58} {20, 38, 59} {20, 38, 60} {20, 38, 61} {20, 38, 62} {20, 38, 63} {20, 38, 64} {20, 38, 65} {20, 38, 66}
{20, 39, 40} {20, 39, 41} {20, 39, 42} {20, 39, 43} {20, 39, 44} {20, 39, 45} {20, 39, 46} {20, 39, 47} {20, 39, 48}
{20, 39, 49} {20, 39, 50} {20, 39, 51} {20, 39, 52} {20, 39, 53} {20, 39, 54} {20, 39, 55} {20, 39, 56} {20, 39, 57}
{20, 39, 58} {20, 39, 59} {20, 39, 60} {20, 39, 61} {20, 39, 62} {20, 39, 63} {20, 39, 64} {20, 39, 65} {20, 39, 66}
{20, 40, 41} {20, 40, 42} {20, 40, 43} {20, 40, 44} {20, 40, 45} {20, 40, 46} {20, 40, 47} {20, 40, 48} {20, 40, 49}
{20, 40, 50} {20, 40, 51} {20, 40, 52} {20, 40, 53} {20, 40, 54} {20, 40, 55} {20, 40, 56} {20, 40, 57} {20, 40, 58}
{20, 40, 59} {20, 40, 60} {20, 40, 61} {20, 40, 62} {20, 40, 63} {20, 40, 64} {20, 40, 65} {20, 40, 66} {20, 41, 42}
{20, 41, 43} {20, 41, 44} {20, 41, 45} {20, 41, 46} {20, 41, 47} {20, 41, 48} {20, 41, 49} {20, 41, 50} {20, 41, 51}
{20, 41, 52} {20, 41, 53} {20, 41, 54} {20, 41, 55} {20, 41, 56} {20, 41, 57} {20, 41, 58} {20, 41, 59} {20, 41, 60}
{20, 41, 61} {20, 41, 62} {20, 41, 63} {20, 41, 64} {20, 41, 65} {20, 41, 66} {20, 42, 43} {20, 42, 44} {20, 42, 45}
{20, 42, 46} {20, 42, 47} {20, 42, 48} {20, 42, 49} {20, 42, 50} {20, 42, 51} {20, 42, 52} {20, 42, 53} {20, 42, 54}
{20, 42, 55} {20, 42, 56} {20, 42, 57} {20, 42, 58} {20, 42, 59} {20, 42, 60} {20, 42, 61} {20, 42, 62} {20, 42, 63}
{20, 42, 64} {20, 42, 65} {20, 42, 66} {20, 43, 44} {20, 43, 45} {20, 43, 46} {20, 43, 47} {20, 43, 48} {20, 43, 49}
{20, 43, 50} {20, 43, 51} {20, 43, 52} {20, 43, 53} {20, 43, 54} {20, 43, 55} {20, 43, 56} {20, 43, 57} {20, 43, 58}
{20, 43, 59} {20, 43, 60} {20, 43, 61} {20, 43, 62} {20, 43, 63} {20, 43, 64} {20, 43, 65} {20, 43, 66} {20, 44, 45}
{20, 44, 46} {20, 44, 47} {20, 44, 48} {20, 44, 49} {20, 44, 50} {20, 44, 51} {20, 44, 52} {20, 44, 53} {20, 44, 54}
{20, 44, 55} {20, 44, 56} {20, 44, 57} {20, 44, 58} {20, 44, 59} {20, 44, 60} {20, 44, 61} {20, 44, 62} {20, 44, 63}
{20, 44, 64} {20, 44, 65} {20, 44, 66} {20, 45, 46} {20, 45, 47} {20, 45, 48} {20, 45, 49} {20, 45, 50} {20, 45, 51}
{20, 45, 52} {20, 45, 53} {20, 45, 54} {20, 45, 55} {20, 45, 56} {20, 45, 57} {20, 45, 58} {20, 45, 59} {20, 45, 60}
{20, 45, 61} {20, 45, 62} {20, 45, 63} {20, 45, 64} {20, 45, 65} {20, 45, 66} {20, 46, 47} {20, 46, 48} {20, 46, 49}
{20, 46, 50} {20, 46, 51} {20, 46, 52} {20, 46, 53} {20, 46, 54} {20, 46, 55} {20, 46, 56} {20, 46, 57} {20, 46, 58}
{20, 46, 59} {20, 46, 60} {20, 46, 61} {20, 46, 62} {20, 46, 63} {20, 46, 64} {20, 46, 65} {20, 46, 66} {20, 47, 48}
{20, 47, 49} {20, 47, 50} {20, 47, 51} {20, 47, 52} {20, 47, 53} {20, 47, 54} {20, 47, 55} {20, 47, 56} {20, 47, 57}
{20, 47, 58} {20, 47, 59} {20, 47, 60} {20, 47, 61} {20, 47, 62} {20, 47, 63} {20, 47, 64} {20, 47, 65} {20, 47, 66}
{20, 48, 49} {20, 48, 50} {20, 48, 51} {20, 48, 52} {20, 48, 53} {20, 48, 54} {20, 48, 55} {20, 48, 56} {20, 48, 57}
{20, 48, 58} {20, 48, 59} {20, 48, 60} {20, 48, 61} {20, 48, 62} {20, 48, 63} {20, 48, 64} {20, 48, 65} {20, 48, 66}
{20, 49, 50} {20, 49, 51} {20, 49, 52} {20, 49, 53} {20, 49, 54} {20, 49, 55} {20, 49, 56} {20, 49, 57} {20, 49, 58}
{20, 49, 59} {20, 49, 60} {20, 49, 61} {20, 49, 62} {20, 49, 63} {20, 49, 64} {20, 49, 65} {20, 49, 66} {20, 50, 51}
{20, 50, 52} {20, 50, 53} {20, 50, 54} {20, 50, 55} {20, 50, 56} {20, 50, 57} {20, 50, 58} {20, 50, 59} {20, 50, 60}
{20, 50, 61} {20, 50, 62} {20, 50, 63} {20, 50, 64} {20, 50, 65} {20, 50, 66} {20, 51, 52} {20, 51, 53} {20, 51, 54}

TABLE 3A-continued

{20, 51, 55} {20, 51, 56} {20, 51, 57} {20, 51, 58} {20, 51, 59} {20, 51, 60} {20, 51, 61} {20, 51, 62} {20, 51, 63}
{20, 51, 64} {20, 51, 65} {20, 51, 66} {20, 52, 53} {20, 52, 54} {20, 52, 55} {20, 52, 56} {20, 52, 57} {20, 52, 58}
{20, 52, 59} {20, 52, 60} {20, 52, 61} {20, 52, 62} {20, 52, 63} {20, 52, 64} {20, 52, 65} {20, 52, 66} {20, 53, 54}
{20, 53, 55} {20, 53, 56} {20, 53, 57} {20, 53, 58} {20, 53, 59} {20, 53, 60} {20, 53, 61} {20, 53, 62} {20, 53, 63}
{20, 53, 64} {20, 53, 65} {20, 53, 66} {20, 54, 55} {20, 54, 56} {20, 54, 57} {20, 54, 58} {20, 54, 59} {20, 54, 60}
{20, 54, 61} {20, 54, 62} {20, 54, 63} {20, 54, 64} {20, 54, 65} {20, 54, 66} {20, 55, 56} {20, 55, 57} {20, 55, 58}
{20, 55, 59} {20, 55, 60} {20, 55, 61} {20, 55, 62} {20, 55, 63} {20, 55, 64} {20, 55, 65} {20, 55, 66} {20, 56, 57}
{20, 56, 58} {20, 56, 59} {20, 56, 60} {20, 56, 61} {20, 56, 62} {20, 56, 63} {20, 56, 64} {20, 56, 65} {20, 56, 66}
{20, 57, 58} {20, 57, 59} {20, 57, 60} {20, 57, 61} {20, 57, 62} {20, 57, 63} {20, 57, 64} {20, 57, 65} {20, 57, 66}
{20, 58, 59} {20, 58, 60} {20, 58, 61} {20, 58, 62} {20, 58, 63} {20, 58, 64} {20, 58, 65} {20, 58, 66} {20, 59, 60}
{20, 59, 61} {20, 59, 62} {20, 59, 63} {20, 59, 64} {20, 59, 65} {20, 59, 66} {20, 60, 61} {20, 60, 62} {20, 60, 63}
{20, 60, 64} {20, 60, 65} {20, 60, 66} {20, 61, 62} {20, 61, 63} {20, 61, 64} {20, 61, 65} {20, 61, 66} {20, 62, 63}
{20, 62, 64} {20, 62, 65} {20, 62, 66} {20, 63, 64} {20, 63, 65} {20, 63, 66} {20, 64, 65} {20, 64, 66} {20, 65, 66}
{21, 22, 23} {21, 22, 24} {21, 22, 25} {21, 22, 26} {21, 22, 27} {21, 22, 28} {21, 22, 29} {21, 22, 30} {21, 22, 31}
{21, 22, 32} {21, 22, 33} {21, 22, 34} {21, 22, 35} {21, 22, 36} {21, 22, 37} {21, 22, 38} {21, 22, 39} {21, 22, 40}
{21, 22, 41} {21, 22, 42} {21, 22, 43} {21, 22, 44} {21, 22, 45} {21, 22, 46} {21, 22, 47} {21, 22, 48} {21, 22, 49}
{21, 22, 50} {21, 22, 51} {21, 22, 52} {21, 22, 53} {21, 22, 54} {21, 22, 55} {21, 22, 56} {21, 22, 57} {21, 22, 58}
{21, 22, 59} {21, 22, 60} {21, 22, 61} {21, 22, 62} {21, 22, 63} {21, 22, 64} {21, 22, 65} {21, 22, 66} {21, 23, 24}
{21, 23, 25} {21, 23, 26} {21, 23, 27} {21, 23, 28} {21, 23, 29} {21, 23, 30} {21, 23, 31} {21, 23, 32} {21, 23, 33}
{21, 23, 34} {21, 23, 35} {21, 23, 36} {21, 23, 37} {21, 23, 38} {21, 23, 39} {21, 23, 40} {21, 23, 41} {21, 23, 42}
{21, 23, 43} {21, 23, 44} {21, 23, 45} {21, 23, 46} {21, 23, 47} {21, 23, 48} {21, 23, 49} {21, 23, 50} {21, 23, 51}
{21, 23, 52} {21, 23, 53} {21, 23, 54} {21, 23, 55} {21, 23, 56} {21, 23, 57} {21, 23, 58} {21, 23, 59} {21, 23, 60}
{21, 23, 61} {21, 23, 62} {21, 23, 63} {21, 23, 64} {21, 23, 65} {21, 23, 66} {21, 24, 25} {21, 24, 26} {21, 24, 27}
{21, 24, 28} {21, 24, 29} {21, 24, 30} {21, 24, 31} {21, 24, 32} {21, 24, 33} {21, 24, 34} {21, 24, 35} {21, 24, 36}
{21, 24, 37} {21, 24, 38} {21, 24, 39} {21, 24, 40} {21, 24, 41} {21, 24, 42} {21, 24, 43} {21, 24, 44} {21, 24, 45}
{21, 24, 46} {21, 24, 47} {21, 24, 48} {21, 24, 49} {21, 24, 50} {21, 24, 51} {21, 24, 52} {21, 24, 53} {21, 24, 54}
{21, 24, 55} {21, 24, 56} {21, 24, 57} {21, 24, 58} {21, 24, 59} {21, 24, 60} {21, 24, 61} {21, 24, 62} {21, 24, 63}
{21, 24, 64} {21, 24, 65} {21, 24, 66} {21, 25, 26} {21, 25, 27} {21, 25, 28} {21, 25, 29} {21, 25, 30} {21, 25, 31}
{21, 25, 32} {21, 25, 33} {21, 25, 34} {21, 25, 35} {21, 25, 36} {21, 25, 37} {21, 25, 38} {21, 25, 39} {21, 25, 40}
{21, 25, 41} {21, 25, 42} {21, 25, 43} {21, 25, 44} {21, 25, 45} {21, 25, 46} {21, 25, 47} {21, 25, 48} {21, 25, 49}
{21, 25, 50} {21, 25, 51} {21, 25, 52} {21, 25, 53} {21, 25, 54} {21, 25, 55} {21, 25, 56} {21, 25, 57} {21, 25, 58}
{21, 25, 59} {21, 25, 60} {21, 25, 61} {21, 25, 62} {21, 25, 63} {21, 25, 64} {21, 25, 65} {21, 25, 66} {21, 26, 27}
{21, 26, 28} {21, 26, 29} {21, 26, 30} {21, 26, 31} {21, 26, 32} {21, 26, 33} {21, 26, 34} {21, 26, 35} {21, 26, 36}
{21, 26, 37} {21, 26, 38} {21, 26, 39} {21, 26, 40} {21, 26, 41} {21, 26, 42} {21, 26, 43} {21, 26, 44} {21, 26, 45}
{21, 26, 46} {21, 26, 47} {21, 26, 48} {21, 26, 49} {21, 26, 50} {21, 26, 51} {21, 26, 52} {21, 26, 53} {21, 26, 54}
{21, 26, 55} {21, 26, 56} {21, 26, 57} {21, 26, 58} {21, 26, 59} {21, 26, 60} {21, 26, 61} {21, 26, 62} {21, 26, 63}
{21, 26, 64} {21, 26, 65} {21, 26, 66} {21, 27, 28} {21, 27, 29} {21, 27, 30} {21, 27, 31} {21, 27, 32} {21, 27, 33}
{21, 27, 34} {21, 27, 35} {21, 27, 36} {21, 27, 37} {21, 27, 38} {21, 27, 39} {21, 27, 40} {21, 27, 41} {21, 27, 42}
{21, 27, 43} {21, 27, 44} {21, 27, 45} {21, 27, 46} {21, 27, 47} {21, 27, 48} {21, 27, 49} {21, 27, 50} {21, 27, 51}
{21, 27, 52} {21, 27, 53} {21, 27, 54} {21, 27, 55} {21, 27, 56} {21, 27, 57} {21, 27, 58} {21, 27, 59} {21, 27, 60}
{21, 27, 61} {21, 27, 62} {21, 27, 63} {21, 27, 64} {21, 27, 65} {21, 27, 66} {21, 28, 29} {21, 28, 30} {21, 28, 31}
{21, 28, 32} {21, 28, 33} {21, 28, 34} {21, 28, 35} {21, 28, 36} {21, 28, 37} {21, 28, 38} {21, 28, 39} {21, 28, 40}
{21, 28, 41} {21, 28, 42} {21, 28, 43} {21, 28, 44} {21, 28, 45} {21, 28, 46} {21, 28, 47} {21, 28, 48} {21, 28, 49}
{21, 28, 50} {21, 28, 51} {21, 28, 52} {21, 28, 53} {21, 28, 54} {21, 28, 55} {21, 28, 56} {21, 28, 57} {21, 28, 58}
{21, 28, 59} {21, 28, 60} {21, 28, 61} {21, 28, 62} {21, 28, 63} {21, 28, 64} {21, 28, 65} {21, 28, 66} {21, 29, 30}
{21, 29, 31} {21, 29, 32} {21, 29, 33} {21, 29, 34} {21, 29, 35} {21, 29, 36} {21, 29, 37} {21, 29, 38} {21, 29, 39}
{21, 29, 40} {21, 29, 41} {21, 29, 42} {21, 29, 43} {21, 29, 44} {21, 29, 45} {21, 29, 46} {21, 29, 47} {21, 29, 48}
{21, 29, 49} {21, 29, 50} {21, 29, 51} {21, 29, 52} {21, 29, 53} {21, 29, 54} {21, 29, 55} {21, 29, 56} {21, 29, 57}
{21, 29, 58} {21, 29, 59} {21, 29, 60} {21, 29, 61} {21, 29, 62} {21, 29, 63} {21, 29, 64} {21, 29, 65} {21, 29, 66}
{21, 30, 31} {21, 30, 32} {21, 30, 33} {21, 30, 34} {21, 30, 35} {21, 30, 36} {21, 30, 37} {21, 30, 38} {21, 30, 39}
{21, 30, 40} {21, 30, 41} {21, 30, 42} {21, 30, 43} {21, 30, 44} {21, 30, 45} {21, 30, 46} {21, 30, 47} {21, 30, 48}
{21, 30, 49} {21, 30, 50} {21, 30, 51} {21, 30, 52} {21, 30, 53} {21, 30, 54} {21, 30, 55} {21, 30, 56} {21, 30, 57}
{21, 30, 58} {21, 30, 59} {21, 30, 60} {21, 30, 61} {21, 30, 62} {21, 30, 63} {21, 30, 64} {21, 30, 65} {21, 30, 66}
{21, 31, 32} {21, 31, 33} {21, 31, 34} {21, 31, 35} {21, 31, 36} {21, 31, 37} {21, 31, 38} {21, 31, 39} {21, 31, 40}
{21, 31, 41} {21, 31, 42} {21, 31, 43} {21, 31, 44} {21, 31, 45} {21, 31, 46} {21, 31, 47} {21, 31, 48} {21, 31, 49}
{21, 31, 50} {21, 31, 51} {21, 31, 52} {21, 31, 53} {21, 31, 54} {21, 31, 55} {21, 31, 56} {21, 31, 57} {21, 31, 58}
{21, 31, 59} {21, 31, 60} {21, 31, 61} {21, 31, 62} {21, 31, 63} {21, 31, 64} {21, 31, 65} {21, 31, 66} {21, 32, 33}
{21, 32, 34} {21, 32, 35} {21, 32, 36} {21, 32, 37} {21, 32, 38} {21, 32, 39} {21, 32, 40} {21, 32, 41} {21, 32, 42}
{21, 32, 43} {21, 32, 44} {21, 32, 45} {21, 32, 46} {21, 32, 47} {21, 32, 48} {21, 32, 49} {21, 32, 50} {21, 32, 51}
{21, 32, 52} {21, 32, 53} {21, 32, 54} {21, 32, 55} {21, 32, 56} {21, 32, 57} {21, 32, 58} {21, 32, 59} {21, 32, 60}
{21, 32, 61} {21, 32, 62} {21, 32, 63} {21, 32, 64} {21, 32, 65} {21, 32, 66} {21, 33, 34} {21, 33, 35} {21, 33, 36}
{21, 33, 37} {21, 33, 38} {21, 33, 39} {21, 33, 40} {21, 33, 41} {21, 33, 42} {21, 33, 43} {21, 33, 44} {21, 33, 45}
{21, 33, 46} {21, 33, 47} {21, 33, 48} {21, 33, 49} {21, 33, 50} {21, 33, 51} {21, 33, 52} {21, 33, 53} {21, 33, 54}
{21, 33, 55} {21, 33, 56} {21, 33, 57} {21, 33, 58} {21, 33, 59} {21, 33, 60} {21, 33, 61} {21, 33, 62} {21, 33, 63}
{21, 33, 64} {21, 33, 65} {21, 33, 66} {21, 34, 35} {21, 34, 36} {21, 34, 37} {21, 34, 38} {21, 34, 39} {21, 34, 40}
{21, 34, 41} {21, 34, 42} {21, 34, 43} {21, 34, 44} {21, 34, 45} {21, 34, 46} {21, 34, 47} {21, 34, 48} {21, 34, 49}
{21, 34, 50} {21, 34, 51} {21, 34, 52} {21, 34, 53} {21, 34, 54} {21, 34, 55} {21, 34, 56} {21, 34, 57} {21, 34, 58}
{21, 34, 59} {21, 34, 60} {21, 34, 61} {21, 34, 62} {21, 34, 63} {21, 34, 64} {21, 34, 65} {21, 34, 66} {21, 35, 36}
{21, 35, 37} {21, 35, 38} {21, 35, 39} {21, 35, 40} {21, 35, 41} {21, 35, 42} {21, 35, 43} {21, 35, 44} {21, 35, 45}
{21, 35, 46} {21, 35, 47} {21, 35, 48} {21, 35, 49} {21, 35, 50} {21, 35, 51} {21, 35, 52} {21, 35, 53} {21, 35, 54}
{21, 35, 55} {21, 35, 56} {21, 35, 57} {21, 35, 58} {21, 35, 59} {21, 35, 60} {21, 35, 61} {21, 35, 62} {21, 35, 63}
{21, 35, 64} {21, 35, 65} {21, 35, 66} {21, 36, 37} {21, 36, 38} {21, 36, 39} {21, 36, 40} {21, 36, 41} {21, 36, 42}
{21, 36, 43} {21, 36, 44} {21, 36, 45} {21, 36, 46} {21, 36, 47} {21, 36, 48} {21, 36, 49} {21, 36, 50} {21, 36, 51}
{21, 36, 52} {21, 36, 53} {21, 36, 54} {21, 36, 55} {21, 36, 56} {21, 36, 57} {21, 36, 58} {21, 36, 59} {21, 36, 60}
{21, 36, 61} {21, 36, 62} {21, 36, 63} {21, 36, 64} {21, 36, 65} {21, 36, 66} {21, 37, 38} {21, 37, 39} {21, 37, 40}
{21, 37, 41} {21, 37, 42} {21, 37, 43} {21, 37, 44} {21, 37, 45} {21, 37, 46} {21, 37, 47} {21, 37, 48} {21, 37, 49}
{21, 37, 50} {21, 37, 51} {21, 37, 52} {21, 37, 53} {21, 37, 54} {21, 37, 55} {21, 37, 56} {21, 37, 57} {21, 37, 58}
{21, 37, 59} {21, 37, 60} {21, 37, 61} {21, 37, 62} {21, 37, 63} {21, 37, 64} {21, 37, 65} {21, 37, 66} {21, 38, 39}
{21, 38, 40} {21, 38, 41} {21, 38, 42} {21, 38, 43} {21, 38, 44} {21, 38, 45} {21, 38, 46} {21, 38, 47} {21, 38, 48}
{21, 38, 49} {21, 38, 50} {21, 38, 51} {21, 38, 52} {21, 38, 53} {21, 38, 54} {21, 38, 55} {21, 38, 56} {21, 38, 57}

TABLE 3A-continued

| | | | | | | | | |
|---|---|---|---|---|---|---|---|---|
| {21, 38, 58} | {21, 38, 59} | {21, 38, 60} | {21, 38, 61} | {21, 38, 62} | {21, 38, 63} | {21, 38, 64} | {21, 38, 65} | {21, 38, 66} |
| {21, 39, 40} | {21, 39, 41} | {21, 39, 42} | {21, 39, 43} | {21, 39, 44} | {21, 39, 45} | {21, 39, 46} | {21, 39, 47} | {21, 39, 48} |
| {21, 39, 49} | {21, 39, 50} | {21, 39, 51} | {21, 39, 52} | {21, 39, 53} | {21, 39, 54} | {21, 39, 55} | {21, 39, 56} | {21, 39, 57} |
| {21, 39, 58} | {21, 39, 59} | {21, 39, 60} | {21, 39, 61} | {21, 39, 62} | {21, 39, 63} | {21, 39, 64} | {21, 39, 65} | {21, 39, 66} |
| {21, 40, 41} | {21, 40, 42} | {21, 40, 43} | {21, 40, 44} | {21, 40, 45} | {21, 40, 46} | {21, 40, 47} | {21, 40, 48} | {21, 40, 49} |
| {21, 40, 50} | {21, 40, 51} | {21, 40, 52} | {21, 40, 53} | {21, 40, 54} | {21, 40, 55} | {21, 40, 56} | {21, 40, 57} | {21, 40, 58} |
| {21, 40, 59} | {21, 40, 60} | {21, 40, 61} | {21, 40, 62} | {21, 40, 63} | {21, 40, 64} | {21, 40, 65} | {21, 40, 66} | {21, 41, 42} |
| {21, 41, 43} | {21, 41, 44} | {21, 41, 45} | {21, 41, 46} | {21, 41, 47} | {21, 41, 48} | {21, 41, 49} | {21, 41, 50} | {21, 41, 51} |
| {21, 41, 52} | {21, 41, 53} | {21, 41, 54} | {21, 41, 55} | {21, 41, 56} | {21, 41, 57} | {21, 41, 58} | {21, 41, 59} | {21, 41, 60} |
| {21, 41, 61} | {21, 41, 62} | {21, 41, 63} | {21, 41, 64} | {21, 41, 65} | {21, 41, 66} | {21, 42, 43} | {21, 42, 44} | {21, 42, 45} |
| {21, 42, 46} | {21, 42, 47} | {21, 42, 48} | {21, 42, 49} | {21, 42, 50} | {21, 42, 51} | {21, 42, 52} | {21, 42, 53} | {21, 42, 54} |
| {21, 42, 55} | {21, 42, 56} | {21, 42, 57} | {21, 42, 58} | {21, 42, 59} | {21, 42, 60} | {21, 42, 61} | {21, 42, 62} | {21, 42, 63} |
| {21, 42, 64} | {21, 42, 65} | {21, 42, 66} | {21, 43, 44} | {21, 43, 45} | {21, 43, 46} | {21, 43, 47} | {21, 43, 48} | {21, 43, 49} |
| {21, 43, 50} | {21, 43, 51} | {21, 43, 52} | {21, 43, 53} | {21, 43, 54} | {21, 43, 55} | {21, 43, 56} | {21, 43, 57} | {21, 43, 58} |
| {21, 43, 59} | {21, 43, 60} | {21, 43, 61} | {21, 43, 62} | {21, 43, 63} | {21, 43, 64} | {21, 43, 65} | {21, 43, 66} | {21, 44, 45} |
| {21, 44, 46} | {21, 44, 47} | {21, 44, 48} | {21, 44, 49} | {21, 44, 50} | {21, 44, 51} | {21, 44, 52} | {21, 44, 53} | {21, 44, 54} |
| {21, 44, 55} | {21, 44, 56} | {21, 44, 57} | {21, 44, 58} | {21, 44, 59} | {21, 44, 60} | {21, 44, 61} | {21, 44, 62} | {21, 44, 63} |
| {21, 44, 64} | {21, 44, 65} | {21, 44, 66} | {21, 45, 46} | {21, 45, 47} | {21, 45, 48} | {21, 45, 49} | {21, 45, 50} | {21, 45, 51} |
| {21, 45, 52} | {21, 45, 53} | {21, 45, 54} | {21, 45, 55} | {21, 45, 56} | {21, 45, 57} | {21, 45, 58} | {21, 45, 59} | {21, 45, 60} |
| {21, 45, 61} | {21, 45, 62} | {21, 45, 63} | {21, 45, 64} | {21, 45, 65} | {21, 45, 66} | {21, 46, 47} | {21, 46, 48} | {21, 46, 49} |
| {21, 46, 50} | {21, 46, 51} | {21, 46, 52} | {21, 46, 53} | {21, 46, 54} | {21, 46, 55} | {21, 46, 56} | {21, 46, 57} | {21, 46, 58} |
| {21, 46, 59} | {21, 46, 60} | {21, 46, 61} | {21, 46, 62} | {21, 46, 63} | {21, 46, 64} | {21, 46, 65} | {21, 46, 66} | {21, 47, 48} |
| {21, 47, 49} | {21, 47, 50} | {21, 47, 51} | {21, 47, 52} | {21, 47, 53} | {21, 47, 54} | {21, 47, 55} | {21, 47, 56} | {21, 47, 57} |
| {21, 47, 58} | {21, 47, 59} | {21, 47, 60} | {21, 47, 61} | {21, 47, 62} | {21, 47, 63} | {21, 47, 64} | {21, 47, 65} | {21, 47, 66} |
| {21, 48, 49} | {21, 48, 50} | {21, 48, 51} | {21, 48, 52} | {21, 48, 53} | {21, 48, 54} | {21, 48, 55} | {21, 48, 56} | {21, 48, 57} |
| {21, 48, 58} | {21, 48, 59} | {21, 48, 60} | {21, 48, 61} | {21, 48, 62} | {21, 48, 63} | {21, 48, 64} | {21, 48, 65} | {21, 48, 66} |
| {21, 49, 50} | {21, 49, 51} | {21, 49, 52} | {21, 49, 53} | {21, 49, 54} | {21, 49, 55} | {21, 49, 56} | {21, 49, 57} | {21, 49, 58} |
| {21, 49, 59} | {21, 49, 60} | {21, 49, 61} | {21, 49, 62} | {21, 49, 63} | {21, 49, 64} | {21, 49, 65} | {21, 49, 66} | {21, 50, 51} |
| {21, 50, 52} | {21, 50, 53} | {21, 50, 54} | {21, 50, 55} | {21, 50, 56} | {21, 50, 57} | {21, 50, 58} | {21, 50, 59} | {21, 50, 60} |
| {21, 50, 61} | {21, 50, 62} | {21, 50, 63} | {21, 50, 64} | {21, 50, 65} | {21, 50, 66} | {21, 51, 52} | {21, 51, 53} | {21, 51, 54} |
| {21, 51, 55} | {21, 51, 56} | {21, 51, 57} | {21, 51, 58} | {21, 51, 59} | {21, 51, 60} | {21, 51, 61} | {21, 51, 62} | {21, 51, 63} |
| {21, 51, 64} | {21, 51, 65} | {21, 51, 66} | {21, 52, 53} | {21, 52, 54} | {21, 52, 55} | {21, 52, 56} | {21, 52, 57} | {21, 52, 58} |
| {21, 52, 59} | {21, 52, 60} | {21, 52, 61} | {21, 52, 62} | {21, 52, 63} | {21, 52, 64} | {21, 52, 65} | {21, 52, 66} | {21, 53, 54} |
| {21, 53, 55} | {21, 53, 56} | {21, 53, 57} | {21, 53, 58} | {21, 53, 59} | {21, 53, 60} | {21, 53, 61} | {21, 53, 62} | {21, 53, 63} |
| {21, 53, 64} | {21, 53, 65} | {21, 53, 66} | {21, 54, 55} | {21, 54, 56} | {21, 54, 57} | {21, 54, 58} | {21, 54, 59} | {21, 54, 60} |
| {21, 54, 61} | {21, 54, 62} | {21, 54, 63} | {21, 54, 64} | {21, 54, 65} | {21, 54, 66} | {21, 55, 56} | {21, 55, 57} | {21, 55, 58} |
| {21, 55, 59} | {21, 55, 60} | {21, 55, 61} | {21, 55, 62} | {21, 55, 63} | {21, 55, 64} | {21, 55, 65} | {21, 55, 66} | {21, 56, 57} |
| {21, 56, 58} | {21, 56, 59} | {21, 56, 60} | {21, 56, 61} | {21, 56, 62} | {21, 56, 63} | {21, 56, 64} | {21, 56, 65} | {21, 56, 66} |
| {21, 57, 58} | {21, 57, 59} | {21, 57, 60} | {21, 57, 61} | {21, 57, 62} | {21, 57, 63} | {21, 57, 64} | {21, 57, 65} | {21, 57, 66} |
| {21, 58, 59} | {21, 58, 60} | {21, 58, 61} | {21, 58, 62} | {21, 58, 63} | {21, 58, 64} | {21, 58, 65} | {21, 58, 66} | {21, 59, 60} |
| {21, 59, 61} | {21, 59, 62} | {21, 59, 63} | {21, 59, 64} | {21, 59, 65} | {21, 59, 66} | {21, 60, 61} | {21, 60, 62} | {21, 60, 63} |
| {21, 60, 64} | {21, 60, 65} | {21, 60, 66} | {21, 61, 62} | {21, 61, 63} | {21, 61, 64} | {21, 61, 65} | {21, 61, 66} | {21, 62, 63} |
| {21, 62, 64} | {21, 62, 65} | {21, 62, 66} | {21, 63, 64} | {21, 63, 65} | {21, 63, 66} | {21, 64, 65} | {21, 64, 66} | {21, 65, 66} |
| {22, 23, 24} | {22, 23, 25} | {22, 23, 26} | {22, 23, 27} | {22, 23, 28} | {22, 23, 29} | {22, 23, 30} | {22, 23, 31} | {22, 23, 32} |
| {22, 23, 33} | {22, 23, 34} | {22, 23, 35} | {22, 23, 36} | {22, 23, 37} | {22, 23, 38} | {22, 23, 39} | {22, 23, 40} | {22, 23, 41} |
| {22, 23, 42} | {22, 23, 43} | {22, 23, 44} | {22, 23, 45} | {22, 23, 46} | {22, 23, 47} | {22, 23, 48} | {22, 23, 49} | {22, 23, 50} |
| {22, 23, 51} | {22, 23, 52} | {22, 23, 53} | {22, 23, 54} | {22, 23, 55} | {22, 23, 56} | {22, 23, 57} | {22, 23, 58} | {22, 23, 59} |
| {22, 23, 60} | {22, 23, 61} | {22, 23, 62} | {22, 23, 63} | {22, 23, 64} | {22, 23, 65} | {22, 23, 66} | {22, 24, 25} | {22, 24, 26} |
| {22, 24, 27} | {22, 24, 28} | {22, 24, 29} | {22, 24, 30} | {22, 24, 31} | {22, 24, 32} | {22, 24, 33} | {22, 24, 34} | {22, 24, 35} |
| {22, 24, 36} | {22, 24, 37} | {22, 24, 38} | {22, 24, 39} | {22, 24, 40} | {22, 24, 41} | {22, 24, 42} | {22, 24, 43} | {22, 24, 44} |
| {22, 24, 45} | {22, 24, 46} | {22, 24, 47} | {22, 24, 48} | {22, 24, 49} | {22, 24, 50} | {22, 24, 51} | {22, 24, 52} | {22, 24, 53} |
| {22, 24, 54} | {22, 24, 55} | {22, 24, 56} | {22, 24, 57} | {22, 24, 58} | {22, 24, 59} | {22, 24, 60} | {22, 24, 61} | {22, 24, 62} |
| {22, 24, 63} | {22, 24, 64} | {22, 24, 65} | {22, 24, 66} | {22, 25, 26} | {22, 25, 27} | {22, 25, 28} | {22, 25, 29} | {22, 25, 30} |
| {22, 25, 31} | {22, 25, 32} | {22, 25, 33} | {22, 25, 34} | {22, 25, 35} | {22, 25, 36} | {22, 25, 37} | {22, 25, 38} | {22, 25, 39} |
| {22, 25, 40} | {22, 25, 41} | {22, 25, 42} | {22, 25, 43} | {22, 25, 44} | {22, 25, 45} | {22, 25, 46} | {22, 25, 47} | {22, 25, 48} |
| {22, 25, 49} | {22, 25, 50} | {22, 25, 51} | {22, 25, 52} | {22, 25, 53} | {22, 25, 54} | {22, 25, 55} | {22, 25, 56} | {22, 25, 57} |
| {22, 25, 58} | {22, 25, 59} | {22, 25, 60} | {22, 25, 61} | {22, 25, 62} | {22, 25, 63} | {22, 25, 64} | {22, 25, 65} | {22, 25, 66} |
| {22, 26, 27} | {22, 26, 28} | {22, 26, 29} | {22, 26, 30} | {22, 26, 31} | {22, 26, 32} | {22, 26, 33} | {22, 26, 34} | {22, 26, 35} |
| {22, 26, 36} | {22, 26, 37} | {22, 26, 38} | {22, 26, 39} | {22, 26, 40} | {22, 26, 41} | {22, 26, 42} | {22, 26, 43} | {22, 26, 44} |
| {22, 26, 45} | {22, 26, 46} | {22, 26, 47} | {22, 26, 48} | {22, 26, 49} | {22, 26, 50} | {22, 26, 51} | {22, 26, 52} | {22, 26, 53} |
| {22, 26, 54} | {22, 26, 55} | {22, 26, 56} | {22, 26, 57} | {22, 26, 58} | {22, 26, 59} | {22, 26, 60} | {22, 26, 61} | {22, 26, 62} |
| {22, 26, 63} | {22, 26, 64} | {22, 26, 65} | {22, 26, 66} | {22, 27, 28} | {22, 27, 29} | {22, 27, 30} | {22, 27, 31} | {22, 27, 32} |
| {22, 27, 33} | {22, 27, 34} | {22, 27, 35} | {22, 27, 36} | {22, 27, 37} | {22, 27, 38} | {22, 27, 39} | {22, 27, 40} | {22, 27, 41} |
| {22, 27, 42} | {22, 27, 43} | {22, 27, 44} | {22, 27, 45} | {22, 27, 46} | {22, 27, 47} | {22, 27, 48} | {22, 27, 49} | {22, 27, 50} |
| {22, 27, 51} | {22, 27, 52} | {22, 27, 53} | {22, 27, 54} | {22, 27, 55} | {22, 27, 56} | {22, 27, 57} | {22, 27, 58} | {22, 27, 59} |
| {22, 27, 60} | {22, 27, 61} | {22, 27, 62} | {22, 27, 63} | {22, 27, 64} | {22, 27, 65} | {22, 27, 66} | {22, 28, 29} | {22, 28, 30} |
| {22, 28, 31} | {22, 28, 32} | {22, 28, 33} | {22, 28, 34} | {22, 28, 35} | {22, 28, 36} | {22, 28, 37} | {22, 28, 38} | {22, 28, 39} |
| {22, 28, 40} | {22, 28, 41} | {22, 28, 42} | {22, 28, 43} | {22, 28, 44} | {22, 28, 45} | {22, 28, 46} | {22, 28, 47} | {22, 28, 48} |
| {22, 28, 49} | {22, 28, 50} | {22, 28, 51} | {22, 28, 52} | {22, 28, 53} | {22, 28, 54} | {22, 28, 55} | {22, 28, 56} | {22, 28, 57} |
| {22, 28, 58} | {22, 28, 59} | {22, 28, 60} | {22, 28, 61} | {22, 28, 62} | {22, 28, 63} | {22, 28, 64} | {22, 28, 65} | {22, 28, 66} |
| {22, 29, 30} | {22, 29, 31} | {22, 29, 32} | {22, 29, 33} | {22, 29, 34} | {22, 29, 35} | {22, 29, 36} | {22, 29, 37} | {22, 29, 38} |
| {22, 29, 39} | {22, 29, 40} | {22, 29, 41} | {22, 29, 42} | {22, 29, 43} | {22, 29, 44} | {22, 29, 45} | {22, 29, 46} | {22, 29, 47} |
| {22, 29, 48} | {22, 29, 49} | {22, 29, 50} | {22, 29, 51} | {22, 29, 52} | {22, 29, 53} | {22, 29, 54} | {22, 29, 55} | {22, 29, 56} |
| {22, 29, 57} | {22, 29, 58} | {22, 29, 59} | {22, 29, 60} | {22, 29, 61} | {22, 29, 62} | {22, 29, 63} | {22, 29, 64} | {22, 29, 65} |
| {22, 29, 66} | {22, 30, 31} | {22, 30, 32} | {22, 30, 33} | {22, 30, 34} | {22, 30, 35} | {22, 30, 36} | {22, 30, 37} | {22, 30, 38} |
| {22, 30, 39} | {22, 30, 40} | {22, 30, 41} | {22, 30, 42} | {22, 30, 43} | {22, 30, 44} | {22, 30, 45} | {22, 30, 46} | {22, 30, 47} |
| {22, 30, 48} | {22, 30, 49} | {22, 30, 50} | {22, 30, 51} | {22, 30, 52} | {22, 30, 53} | {22, 30, 54} | {22, 30, 55} | {22, 30, 56} |
| {22, 30, 57} | {22, 30, 58} | {22, 30, 59} | {22, 30, 60} | {22, 30, 61} | {22, 30, 62} | {22, 30, 63} | {22, 30, 64} | {22, 30, 65} |
| {22, 30, 66} | {22, 31, 32} | {22, 31, 33} | {22, 31, 34} | {22, 31, 35} | {22, 31, 36} | {22, 31, 37} | {22, 31, 38} | {22, 31, 39} |
| {22, 31, 40} | {22, 31, 41} | {22, 31, 42} | {22, 31, 43} | {22, 31, 44} | {22, 31, 45} | {22, 31, 46} | {22, 31, 47} | {22, 31, 48} |

TABLE 3A-continued

| | | | | | | | |
|---|---|---|---|---|---|---|---|
| {22, 31, 49} | {22, 31, 50} | {22, 31, 51} | {22, 31, 52} | {22, 31, 53} | {22, 31, 54} | {22, 31, 55} | {22, 31, 56} | {22, 31, 57} |
| {22, 31, 58} | {22, 31, 59} | {22, 31, 60} | {22, 31, 61} | {22, 31, 62} | {22, 31, 63} | {22, 31, 64} | {22, 31, 65} | {22, 31, 66} |
| {22, 32, 33} | {22, 32, 34} | {22, 32, 35} | {22, 32, 36} | {22, 32, 37} | {22, 32, 38} | {22, 32, 39} | {22, 32, 40} | {22, 32, 41} |
| {22, 32, 42} | {22, 32, 43} | {22, 32, 44} | {22, 32, 45} | {22, 32, 46} | {22, 32, 47} | {22, 32, 48} | {22, 32, 49} | {22, 32, 50} |
| {22, 32, 51} | {22, 32, 52} | {22, 32, 53} | {22, 32, 54} | {22, 32, 55} | {22, 32, 56} | {22, 32, 57} | {22, 32, 58} | {22, 32, 59} |
| {22, 32, 60} | {22, 32, 61} | {22, 32, 62} | {22, 32, 63} | {22, 32, 64} | {22, 32, 65} | {22, 32, 66} | {22, 33, 34} | {22, 33, 35} |
| {22, 33, 36} | {22, 33, 37} | {22, 33, 38} | {22, 33, 39} | {22, 33, 40} | {22, 33, 41} | {22, 33, 42} | {22, 33, 43} | {22, 33, 44} |
| {22, 33, 45} | {22, 33, 46} | {22, 33, 47} | {22, 33, 48} | {22, 33, 49} | {22, 33, 50} | {22, 33, 51} | {22, 33, 52} | {22, 33, 53} |
| {22, 33, 54} | {22, 33, 55} | {22, 33, 56} | {22, 33, 57} | {22, 33, 58} | {22, 33, 59} | {22, 33, 60} | {22, 33, 61} | {22, 33, 62} |
| {22, 33, 63} | {22, 33, 64} | {22, 33, 65} | {22, 33, 66} | {22, 34, 35} | {22, 34, 36} | {22, 34, 37} | {22, 34, 38} | {22, 34, 39} |
| {22, 34, 40} | {22, 34, 41} | {22, 34, 42} | {22, 34, 43} | {22, 34, 44} | {22, 34, 45} | {22, 34, 46} | {22, 34, 47} | {22, 34, 48} |
| {22, 34, 49} | {22, 34, 50} | {22, 34, 51} | {22, 34, 52} | {22, 34, 53} | {22, 34, 54} | {22, 34, 55} | {22, 34, 56} | {22, 34, 57} |
| {22, 34, 58} | {22, 34, 59} | {22, 34, 60} | {22, 34, 61} | {22, 34, 62} | {22, 34, 63} | {22, 34, 64} | {22, 34, 65} | {22, 34, 66} |
| {22, 35, 36} | {22, 35, 37} | {22, 35, 38} | {22, 35, 39} | {22, 35, 40} | {22, 35, 41} | {22, 35, 42} | {22, 35, 43} | {22, 35, 44} |
| {22, 35, 45} | {22, 35, 46} | {22, 35, 47} | {22, 35, 48} | {22, 35, 49} | {22, 35, 50} | {22, 35, 51} | {22, 35, 52} | {22, 35, 53} |
| {22, 35, 54} | {22, 35, 55} | {22, 35, 56} | {22, 35, 57} | {22, 35, 58} | {22, 35, 59} | {22, 35, 60} | {22, 35, 61} | {22, 35, 62} |
| {22, 35, 63} | {22, 35, 64} | {22, 35, 65} | {22, 35, 66} | {22, 36, 37} | {22, 36, 38} | {22, 36, 39} | {22, 36, 40} | {22, 36, 41} |
| {22, 36, 42} | {22, 36, 43} | {22, 36, 44} | {22, 36, 45} | {22, 36, 46} | {22, 36, 47} | {22, 36, 48} | {22, 36, 49} | {22, 36, 50} |
| {22, 36, 51} | {22, 36, 52} | {22, 36, 53} | {22, 36, 54} | {22, 36, 55} | {22, 36, 56} | {22, 36, 57} | {22, 36, 58} | {22, 36, 59} |
| {22, 36, 60} | {22, 36, 61} | {22, 36, 62} | {22, 36, 63} | {22, 36, 64} | {22, 36, 65} | {22, 36, 66} | {22, 37, 38} | {22, 37, 39} |
| {22, 37, 40} | {22, 37, 41} | {22, 37, 42} | {22, 37, 43} | {22, 37, 44} | {22, 37, 45} | {22, 37, 46} | {22, 37, 47} | {22, 37, 48} |
| {22, 37, 49} | {22, 37, 50} | {22, 37, 51} | {22, 37, 52} | {22, 37, 53} | {22, 37, 54} | {22, 37, 55} | {22, 37, 56} | {22, 37, 57} |
| {22, 37, 58} | {22, 37, 59} | {22, 37, 60} | {22, 37, 61} | {22, 37, 62} | {22, 37, 63} | {22, 37, 64} | {22, 37, 65} | {22, 37, 66} |
| {22, 38, 39} | {22, 38, 40} | {22, 38, 41} | {22, 38, 42} | {22, 38, 43} | {22, 38, 44} | {22, 38, 45} | {22, 38, 46} | {22, 38, 47} |
| {22, 38, 48} | {22, 38, 49} | {22, 38, 50} | {22, 38, 51} | {22, 38, 52} | {22, 38, 53} | {22, 38, 54} | {22, 38, 55} | {22, 38, 56} |
| {22, 38, 57} | {22, 38, 58} | {22, 38, 59} | {22, 38, 60} | {22, 38, 61} | {22, 38, 62} | {22, 38, 63} | {22, 38, 64} | {22, 38, 65} |
| {22, 38, 66} | {22, 39, 40} | {22, 39, 41} | {22, 39, 42} | {22, 39, 43} | {22, 39, 44} | {22, 39, 45} | {22, 39, 46} | {22, 39, 47} |
| {22, 39, 48} | {22, 39, 49} | {22, 39, 50} | {22, 39, 51} | {22, 39, 52} | {22, 39, 53} | {22, 39, 54} | {22, 39, 55} | {22, 39, 56} |
| {22, 39, 57} | {22, 39, 58} | {22, 39, 59} | {22, 39, 60} | {22, 39, 61} | {22, 39, 62} | {22, 39, 63} | {22, 39, 64} | {22, 39, 65} |
| {22, 39, 66} | {22, 40, 41} | {22, 40, 42} | {22, 40, 43} | {22, 40, 44} | {22, 40, 45} | {22, 40, 46} | {22, 40, 47} | {22, 40, 48} |
| {22, 40, 49} | {22, 40, 50} | {22, 40, 51} | {22, 40, 52} | {22, 40, 53} | {22, 40, 54} | {22, 40, 55} | {22, 40, 56} | {22, 40, 57} |
| {22, 40, 58} | {22, 40, 59} | {22, 40, 60} | {22, 40, 61} | {22, 40, 62} | {22, 40, 63} | {22, 40, 64} | {22, 40, 65} | {22, 40, 66} |
| {22, 41, 42} | {22, 41, 43} | {22, 41, 44} | {22, 41, 45} | {22, 41, 46} | {22, 41, 47} | {22, 41, 48} | {22, 41, 49} | {22, 41, 50} |
| {22, 41, 51} | {22, 41, 52} | {22, 41, 53} | {22, 41, 54} | {22, 41, 55} | {22, 41, 56} | {22, 41, 57} | {22, 41, 58} | {22, 41, 59} |
| {22, 41, 60} | {22, 41, 61} | {22, 41, 62} | {22, 41, 63} | {22, 41, 64} | {22, 41, 65} | {22, 41, 66} | {22, 42, 43} | {22, 42, 44} |
| {22, 42, 45} | {22, 42, 46} | {22, 42, 47} | {22, 42, 48} | {22, 42, 49} | {22, 42, 50} | {22, 42, 51} | {22, 42, 52} | {22, 42, 53} |
| {22, 42, 54} | {22, 42, 55} | {22, 42, 56} | {22, 42, 57} | {22, 42, 58} | {22, 42, 59} | {22, 42, 60} | {22, 42, 61} | {22, 42, 62} |
| {22, 42, 63} | {22, 42, 64} | {22, 42, 65} | {22, 42, 66} | {22, 43, 44} | {22, 43, 45} | {22, 43, 46} | {22, 43, 47} | {22, 43, 48} |
| {22, 43, 49} | {22, 43, 50} | {22, 43, 51} | {22, 43, 52} | {22, 43, 53} | {22, 43, 54} | {22, 43, 55} | {22, 43, 56} | {22, 43, 57} |
| {22, 43, 58} | {22, 43, 59} | {22, 43, 60} | {22, 43, 61} | {22, 43, 62} | {22, 43, 63} | {22, 43, 64} | {22, 43, 65} | {22, 43, 66} |
| {22, 44, 45} | {22, 44, 46} | {22, 44, 47} | {22, 44, 48} | {22, 44, 49} | {22, 44, 50} | {22, 44, 51} | {22, 44, 52} | {22, 44, 53} |
| {22, 44, 54} | {22, 44, 55} | {22, 44, 56} | {22, 44, 57} | {22, 44, 58} | {22, 44, 59} | {22, 44, 60} | {22, 44, 61} | {22, 44, 62} |
| {22, 44, 63} | {22, 44, 64} | {22, 44, 65} | {22, 44, 66} | {22, 45, 46} | {22, 45, 47} | {22, 45, 48} | {22, 45, 49} | {22, 45, 50} |
| {22, 45, 51} | {22, 45, 52} | {22, 45, 53} | {22, 45, 54} | {22, 45, 55} | {22, 45, 56} | {22, 45, 57} | {22, 45, 58} | {22, 45, 59} |
| {22, 45, 60} | {22, 45, 61} | {22, 45, 62} | {22, 45, 63} | {22, 45, 64} | {22, 45, 65} | {22, 45, 66} | {22, 46, 47} | {22, 46, 48} |
| {22, 46, 49} | {22, 46, 50} | {22, 46, 51} | {22, 46, 52} | {22, 46, 53} | {22, 46, 54} | {22, 46, 55} | {22, 46, 56} | {22, 46, 57} |
| {22, 46, 58} | {22, 46, 59} | {22, 46, 60} | {22, 46, 61} | {22, 46, 62} | {22, 46, 63} | {22, 46, 64} | {22, 46, 65} | {22, 46, 66} |
| {22, 47, 48} | {22, 47, 49} | {22, 47, 50} | {22, 47, 51} | {22, 47, 52} | {22, 47, 53} | {22, 47, 54} | {22, 47, 55} | {22, 47, 56} |
| {22, 47, 57} | {22, 47, 58} | {22, 47, 59} | {22, 47, 60} | {22, 47, 61} | {22, 47, 62} | {22, 47, 63} | {22, 47, 64} | {22, 47, 65} |
| {22, 47, 66} | {22, 48, 49} | {22, 48, 50} | {22, 48, 51} | {22, 48, 52} | {22, 48, 53} | {22, 48, 54} | {22, 48, 55} | {22, 48, 56} |
| {22, 48, 57} | {22, 48, 58} | {22, 48, 59} | {22, 48, 60} | {22, 48, 61} | {22, 48, 62} | {22, 48, 63} | {22, 48, 64} | {22, 48, 65} |
| {22, 48, 66} | {22, 49, 50} | {22, 49, 51} | {22, 49, 52} | {22, 49, 53} | {22, 49, 54} | {22, 49, 55} | {22, 49, 56} | {22, 49, 57} |
| {22, 49, 58} | {22, 49, 59} | {22, 49, 60} | {22, 49, 61} | {22, 49, 62} | {22, 49, 63} | {22, 49, 64} | {22, 49, 65} | {22, 49, 66} |
| {22, 50, 51} | {22, 50, 52} | {22, 50, 53} | {22, 50, 54} | {22, 50, 55} | {22, 50, 56} | {22, 50, 57} | {22, 50, 58} | {22, 50, 59} |
| {22, 50, 60} | {22, 50, 61} | {22, 50, 62} | {22, 50, 63} | {22, 50, 64} | {22, 50, 65} | {22, 50, 66} | {22, 51, 52} | {22, 51, 53} |
| {22, 51, 54} | {22, 51, 55} | {22, 51, 56} | {22, 51, 57} | {22, 51, 58} | {22, 51, 59} | {22, 51, 60} | {22, 51, 61} | {22, 51, 62} |
| {22, 51, 63} | {22, 51, 64} | {22, 51, 65} | {22, 51, 66} | {22, 52, 53} | {22, 52, 54} | {22, 52, 55} | {22, 52, 56} | {22, 52, 57} |
| {22, 52, 58} | {22, 52, 59} | {22, 52, 60} | {22, 52, 61} | {22, 52, 62} | {22, 52, 63} | {22, 52, 64} | {22, 52, 65} | {22, 52, 66} |
| {22, 53, 54} | {22, 53, 55} | {22, 53, 56} | {22, 53, 57} | {22, 53, 58} | {22, 53, 59} | {22, 53, 60} | {22, 53, 61} | {22, 53, 62} |
| {22, 53, 63} | {22, 53, 64} | {22, 53, 65} | {22, 53, 66} | {22, 54, 55} | {22, 54, 56} | {22, 54, 57} | {22, 54, 58} | {22, 54, 59} |
| {22, 54, 60} | {22, 54, 61} | {22, 54, 62} | {22, 54, 63} | {22, 54, 64} | {22, 54, 65} | {22, 54, 66} | {22, 55, 56} | {22, 55, 57} |
| {22, 55, 58} | {22, 55, 59} | {22, 55, 60} | {22, 55, 61} | {22, 55, 62} | {22, 55, 63} | {22, 55, 64} | {22, 55, 65} | {22, 55, 66} |
| {22, 56, 57} | {22, 56, 58} | {22, 56, 59} | {22, 56, 60} | {22, 56, 61} | {22, 56, 62} | {22, 56, 63} | {22, 56, 64} | {22, 56, 65} |
| {22, 56, 66} | {22, 57, 58} | {22, 57, 59} | {22, 57, 60} | {22, 57, 61} | {22, 57, 62} | {22, 57, 63} | {22, 57, 64} | {22, 57, 65} |
| {22, 57, 66} | {22, 58, 59} | {22, 58, 60} | {22, 58, 61} | {22, 58, 62} | {22, 58, 63} | {22, 58, 64} | {22, 58, 65} | {22, 58, 66} |
| {22, 59, 60} | {22, 59, 61} | {22, 59, 62} | {22, 59, 63} | {22, 59, 64} | {22, 59, 65} | {22, 59, 66} | {22, 60, 61} | {22, 60, 62} |
| {22, 60, 63} | {22, 60, 64} | {22, 60, 65} | {22, 60, 66} | {22, 61, 62} | {22, 61, 63} | {22, 61, 64} | {22, 61, 65} | {22, 61, 66} |
| {22, 62, 63} | {22, 62, 64} | {22, 62, 65} | {22, 62, 66} | {22, 63, 64} | {22, 63, 65} | {22, 63, 66} | {22, 64, 65} | {22, 64, 66} |
| {22, 65, 66} | {23, 24, 25} | {23, 24, 26} | {23, 24, 27} | {23, 24, 28} | {23, 24, 29} | {23, 24, 30} | {23, 24, 31} | {23, 24, 32} |
| {23, 24, 33} | {23, 24, 34} | {23, 24, 35} | {23, 24, 36} | {23, 24, 37} | {23, 24, 38} | {23, 24, 39} | {23, 24, 40} | {23, 24, 41} |
| {23, 24, 42} | {23, 24, 43} | {23, 24, 44} | {23, 24, 45} | {23, 24, 46} | {23, 24, 47} | {23, 24, 48} | {23, 24, 49} | {23, 24, 50} |
| {23, 24, 51} | {23, 24, 52} | {23, 24, 53} | {23, 24, 54} | {23, 24, 55} | {23, 24, 56} | {23, 24, 57} | {23, 24, 58} | {23, 24, 59} |
| {23, 24, 60} | {23, 24, 61} | {23, 24, 62} | {23, 24, 63} | {23, 24, 64} | {23, 24, 65} | {23, 24, 66} | {23, 25, 26} | {23, 25, 27} |
| {23, 25, 28} | {23, 25, 29} | {23, 25, 30} | {23, 25, 31} | {23, 25, 32} | {23, 25, 33} | {23, 25, 34} | {23, 25, 35} | {23, 25, 36} |
| {23, 25, 37} | {23, 25, 38} | {23, 25, 39} | {23, 25, 40} | {23, 25, 41} | {23, 25, 42} | {23, 25, 43} | {23, 25, 44} | {23, 25, 45} |
| {23, 25, 46} | {23, 25, 47} | {23, 25, 48} | {23, 25, 49} | {23, 25, 50} | {23, 25, 51} | {23, 25, 52} | {23, 25, 53} | {23, 25, 54} |
| {23, 25, 55} | {23, 25, 56} | {23, 25, 57} | {23, 25, 58} | {23, 25, 59} | {23, 25, 60} | {23, 25, 61} | {23, 25, 62} | {23, 25, 63} |
| {23, 25, 64} | {23, 25, 65} | {23, 25, 66} | {23, 26, 27} | {23, 26, 28} | {23, 26, 29} | {23, 26, 30} | {23, 26, 31} | {23, 26, 32} |
| {23, 26, 33} | {23, 26, 34} | {23, 26, 35} | {23, 26, 36} | {23, 26, 37} | {23, 26, 38} | {23, 26, 39} | {23, 26, 40} | {23, 26, 41} |
| {23, 26, 42} | {23, 26, 43} | {23, 26, 44} | {23, 26, 45} | {23, 26, 46} | {23, 26, 47} | {23, 26, 48} | {23, 26, 49} | {23, 26, 50} |

TABLE 3A-continued

{23, 26, 51} {23, 26, 52} {23, 26, 53} {23, 26, 54} {23, 26, 55} {23, 26, 56} {23, 26, 57} {23, 26, 58} {23, 26, 59}
{23, 26, 60} {23, 26, 61} {23, 26, 62} {23, 26, 63} {23, 26, 64} {23, 26, 65} {23, 26, 66} {23, 27, 28} {23, 27, 29}
{23, 27, 30} {23, 27, 31} {23, 27, 32} {23, 27, 33} {23, 27, 34} {23, 27, 35} {23, 27, 36} {23, 27, 37} {23, 27, 38}
{23, 27, 39} {23, 27, 40} {23, 27, 41} {23, 27, 42} {23, 27, 43} {23, 27, 44} {23, 27, 45} {23, 27, 46} {23, 27, 47}
{23, 27, 48} {23, 27, 49} {23, 27, 50} {23, 27, 51} {23, 27, 52} {23, 27, 53} {23, 27, 54} {23, 27, 55} {23, 27, 56}
{23, 27, 57} {23, 27, 58} {23, 27, 59} {23, 27, 60} {23, 27, 61} {23, 27, 62} {23, 27, 63} {23, 27, 64} {23, 27, 65}
{23, 27, 66} {23, 28, 29} {23, 28, 30} {23, 28, 31} {23, 28, 32} {23, 28, 33} {23, 28, 34} {23, 28, 35} {23, 28, 36}
{23, 28, 37} {23, 28, 38} {23, 28, 39} {23, 28, 40} {23, 28, 41} {23, 28, 42} {23, 28, 43} {23, 28, 44} {23, 28, 45}
{23, 28, 46} {23, 28, 47} {23, 28, 48} {23, 28, 49} {23, 28, 50} {23, 28, 51} {23, 28, 52} {23, 28, 53} {23, 28, 54}
{23, 28, 55} {23, 28, 56} {23, 28, 57} {23, 28, 58} {23, 28, 59} {23, 28, 60} {23, 28, 61} {23, 28, 62} {23, 28, 63}
{23, 28, 64} {23, 28, 65} {23, 28, 66} {23, 29, 30} {23, 29, 31} {23, 29, 32} {23, 29, 33} {23, 29, 34} {23, 29, 35}
{23, 29, 36} {23, 29, 37} {23, 29, 38} {23, 29, 39} {23, 29, 40} {23, 29, 41} {23, 29, 42} {23, 29, 43} {23, 29, 44}
{23, 29, 45} {23, 29, 46} {23, 29, 47} {23, 29, 48} {23, 29, 49} {23, 29, 50} {23, 29, 51} {23, 29, 52} {23, 29, 53}
{23, 29, 54} {23, 29, 55} {23, 29, 56} {23, 29, 57} {23, 29, 58} {23, 29, 59} {23, 29, 60} {23, 29, 61} {23, 29, 62}
{23, 29, 63} {23, 29, 64} {23, 29, 65} {23, 29, 66} {23, 30, 31} {23, 30, 32} {23, 30, 33} {23, 30, 34} {23, 30, 35}
{23, 30, 36} {23, 30, 37} {23, 30, 38} {23, 30, 39} {23, 30, 40} {23, 30, 41} {23, 30, 42} {23, 30, 43} {23, 30, 44}
{23, 30, 45} {23, 30, 46} {23, 30, 47} {23, 30, 48} {23, 30, 49} {23, 30, 50} {23, 30, 51} {23, 30, 52} {23, 30, 53}
{23, 30, 54} {23, 30, 55} {23, 30, 56} {23, 30, 57} {23, 30, 58} {23, 30, 59} {23, 30, 60} {23, 30, 61} {23, 30, 62}
{23, 30, 63} {23, 30, 64} {23, 30, 65} {23, 30, 66} {23, 31, 32} {23, 31, 33} {23, 31, 34} {23, 31, 35} {23, 31, 36}
{23, 31, 37} {23, 31, 38} {23, 31, 39} {23, 31, 40} {23, 31, 41} {23, 31, 42} {23, 31, 43} {23, 31, 44} {23, 31, 45}
{23, 31, 46} {23, 31, 47} {23, 31, 48} {23, 31, 49} {23, 31, 50} {23, 31, 51} {23, 31, 52} {23, 31, 53} {23, 31, 54}
{23, 31, 55} {23, 31, 56} {23, 31, 57} {23, 31, 58} {23, 31, 59} {23, 31, 60} {23, 31, 61} {23, 31, 62} {23, 31, 63}
{23, 31, 64} {23, 31, 65} {23, 31, 66} {23, 32, 33} {23, 32, 34} {23, 32, 35} {23, 32, 36} {23, 32, 37} {23, 32, 38}
{23, 32, 39} {23, 32, 40} {23, 32, 41} {23, 32, 42} {23, 32, 43} {23, 32, 44} {23, 32, 45} {23, 32, 46} {23, 32, 47}
{23, 32, 48} {23, 32, 49} {23, 32, 50} {23, 32, 51} {23, 32, 52} {23, 32, 53} {23, 32, 54} {23, 32, 55} {23, 32, 56}
{23, 32, 57} {23, 32, 58} {23, 32, 59} {23, 32, 60} {23, 32, 61} {23, 32, 62} {23, 32, 63} {23, 32, 64} {23, 32, 65}
{23, 32, 66} {23, 33, 34} {23, 33, 35} {23, 33, 36} {23, 33, 37} {23, 33, 38} {23, 33, 39} {23, 33, 40} {23, 33, 41}
{23, 33, 42} {23, 33, 43} {23, 33, 44} {23, 33, 45} {23, 33, 46} {23, 33, 47} {23, 33, 48} {23, 33, 49} {23, 33, 50}
{23, 33, 51} {23, 33, 52} {23, 33, 53} {23, 33, 54} {23, 33, 55} {23, 33, 56} {23, 33, 57} {23, 33, 58} {23, 33, 59}
{23, 33, 60} {23, 33, 61} {23, 33, 62} {23, 33, 63} {23, 33, 64} {23, 33, 65} {23, 33, 66} {23, 34, 35} {23, 34, 36}
{23, 34, 37} {23, 34, 38} {23, 34, 39} {23, 34, 40} {23, 34, 41} {23, 34, 42} {23, 34, 43} {23, 34, 44} {23, 34, 45}
{23, 34, 46} {23, 34, 47} {23, 34, 48} {23, 34, 49} {23, 34, 50} {23, 34, 51} {23, 34, 52} {23, 34, 53} {23, 34, 54}
{23, 34, 55} {23, 34, 56} {23, 34, 57} {23, 34, 58} {23, 34, 59} {23, 34, 60} {23, 34, 61} {23, 34, 62} {23, 34, 63}
{23, 34, 64} {23, 34, 65} {23, 34, 66} {23, 35, 36} {23, 35, 37} {23, 35, 38} {23, 35, 39} {23, 35, 40} {23, 35, 41}
{23, 35, 42} {23, 35, 43} {23, 35, 44} {23, 35, 45} {23, 35, 46} {23, 35, 47} {23, 35, 48} {23, 35, 49} {23, 35, 50}
{23, 35, 51} {23, 35, 52} {23, 35, 53} {23, 35, 54} {23, 35, 55} {23, 35, 56} {23, 35, 57} {23, 35, 58} {23, 35, 59}
{23, 35, 60} {23, 35, 61} {23, 35, 62} {23, 35, 63} {23, 35, 64} {23, 35, 65} {23, 35, 66} {23, 36, 37} {23, 36, 38}
{23, 36, 39} {23, 36, 40} {23, 36, 41} {23, 36, 42} {23, 36, 43} {23, 36, 44} {23, 36, 45} {23, 36, 46} {23, 36, 47}
{23, 36, 48} {23, 36, 49} {23, 36, 50} {23, 36, 51} {23, 36, 52} {23, 36, 53} {23, 36, 54} {23, 36, 55} {23, 36, 56}
{23, 36, 57} {23, 36, 58} {23, 36, 59} {23, 36, 60} {23, 36, 61} {23, 36, 62} {23, 36, 63} {23, 36, 64} {23, 36, 65}
{23, 36, 66} {23, 37, 38} {23, 37, 39} {23, 37, 40} {23, 37, 41} {23, 37, 42} {23, 37, 43} {23, 37, 44} {23, 37, 45}
{23, 37, 46} {23, 37, 47} {23, 37, 48} {23, 37, 49} {23, 37, 50} {23, 37, 51} {23, 37, 52} {23, 37, 53} {23, 37, 54}
{23, 37, 55} {23, 37, 56} {23, 37, 57} {23, 37, 58} {23, 37, 59} {23, 37, 60} {23, 37, 61} {23, 37, 62} {23, 37, 63}
{23, 37, 64} {23, 37, 65} {23, 37, 66} {23, 38, 39} {23, 38, 40} {23, 38, 41} {23, 38, 42} {23, 38, 43} {23, 38, 44}
{23, 38, 45} {23, 38, 46} {23, 38, 47} {23, 38, 48} {23, 38, 49} {23, 38, 50} {23, 38, 51} {23, 38, 52} {23, 38, 53}
{23, 38, 54} {23, 38, 55} {23, 38, 56} {23, 38, 57} {23, 38, 58} {23, 38, 59} {23, 38, 60} {23, 38, 61} {23, 38, 62}
{23, 38, 63} {23, 38, 64} {23, 38, 65} {23, 38, 66} {23, 39, 40} {23, 39, 41} {23, 39, 42} {23, 39, 43} {23, 39, 44}
{23, 39, 45} {23, 39, 46} {23, 39, 47} {23, 39, 48} {23, 39, 49} {23, 39, 50} {23, 39, 51} {23, 39, 52} {23, 39, 53}
{23, 39, 54} {23, 39, 55} {23, 39, 56} {23, 39, 57} {23, 39, 58} {23, 39, 59} {23, 39, 60} {23, 39, 61} {23, 39, 62}
{23, 39, 63} {23, 39, 64} {23, 39, 65} {23, 39, 66} {23, 40, 41} {23, 40, 42} {23, 40, 43} {23, 40, 44} {23, 40, 45}
{23, 40, 46} {23, 40, 47} {23, 40, 48} {23, 40, 49} {23, 40, 50} {23, 40, 51} {23, 40, 52} {23, 40, 53} {23, 40, 54}
{23, 40, 55} {23, 40, 56} {23, 40, 57} {23, 40, 58} {23, 40, 59} {23, 40, 60} {23, 40, 61} {23, 40, 62} {23, 40, 63}
{23, 40, 64} {23, 40, 65} {23, 40, 66} {23, 41, 42} {23, 41, 43} {23, 41, 44} {23, 41, 45} {23, 41, 46} {23, 41, 47}
{23, 41, 48} {23, 41, 49} {23, 41, 50} {23, 41, 51} {23, 41, 52} {23, 41, 53} {23, 41, 54} {23, 41, 55} {23, 41, 56}
{23, 41, 57} {23, 41, 58} {23, 41, 59} {23, 41, 60} {23, 41, 61} {23, 41, 62} {23, 41, 63} {23, 41, 64} {23, 41, 65}
{23, 41, 66} {23, 42, 43} {23, 42, 44} {23, 42, 45} {23, 42, 46} {23, 42, 47} {23, 42, 48} {23, 42, 49} {23, 42, 50}
{23, 42, 51} {23, 42, 52} {23, 42, 53} {23, 42, 54} {23, 42, 55} {23, 42, 56} {23, 42, 57} {23, 42, 58} {23, 42, 59}
{23, 42, 60} {23, 42, 61} {23, 42, 62} {23, 42, 63} {23, 42, 64} {23, 42, 65} {23, 42, 66} {23, 43, 44} {23, 43, 45}
{23, 43, 46} {23, 43, 47} {23, 43, 48} {23, 43, 49} {23, 43, 50} {23, 43, 51} {23, 43, 52} {23, 43, 53} {23, 43, 54}
{23, 43, 55} {23, 43, 56} {23, 43, 57} {23, 43, 58} {23, 43, 59} {23, 43, 60} {23, 43, 61} {23, 43, 62} {23, 43, 63}
{23, 43, 64} {23, 43, 65} {23, 43, 66} {23, 44, 45} {23, 44, 46} {23, 44, 47} {23, 44, 48} {23, 44, 49} {23, 44, 50}
{23, 44, 51} {23, 44, 52} {23, 44, 53} {23, 44, 54} {23, 44, 55} {23, 44, 56} {23, 44, 57} {23, 44, 58} {23, 44, 59}
{23, 44, 60} {23, 44, 61} {23, 44, 62} {23, 44, 63} {23, 44, 64} {23, 44, 65} {23, 44, 66} {23, 45, 46} {23, 45, 47}
{23, 45, 48} {23, 45, 49} {23, 45, 50} {23, 45, 51} {23, 45, 52} {23, 45, 53} {23, 45, 54} {23, 45, 55} {23, 45, 56}
{23, 45, 57} {23, 45, 58} {23, 45, 59} {23, 45, 60} {23, 45, 61} {23, 45, 62} {23, 45, 63} {23, 45, 64} {23, 45, 65}
{23, 45, 66} {23, 46, 47} {23, 46, 48} {23, 46, 49} {23, 46, 50} {23, 46, 51} {23, 46, 52} {23, 46, 53} {23, 46, 54}
{23, 46, 55} {23, 46, 56} {23, 46, 57} {23, 46, 58} {23, 46, 59} {23, 46, 60} {23, 46, 61} {23, 46, 62} {23, 46, 63}
{23, 46, 64} {23, 46, 65} {23, 46, 66} {23, 47, 48} {23, 47, 49} {23, 47, 50} {23, 47, 51} {23, 47, 52} {23, 47, 53}
{23, 47, 54} {23, 47, 55} {23, 47, 56} {23, 47, 57} {23, 47, 58} {23, 47, 59} {23, 47, 60} {23, 47, 61} {23, 47, 62}
{23, 47, 63} {23, 47, 64} {23, 47, 65} {23, 47, 66} {23, 48, 49} {23, 48, 50} {23, 48, 51} {23, 48, 52} {23, 48, 53}
{23, 48, 54} {23, 48, 55} {23, 48, 56} {23, 48, 57} {23, 48, 58} {23, 48, 59} {23, 48, 60} {23, 48, 61} {23, 48, 62}
{23, 48, 63} {23, 48, 64} {23, 48, 65} {23, 48, 66} {23, 49, 50} {23, 49, 51} {23, 49, 52} {23, 49, 53} {23, 49, 54}
{23, 49, 55} {23, 49, 56} {23, 49, 57} {23, 49, 58} {23, 49, 59} {23, 49, 60} {23, 49, 61} {23, 49, 62} {23, 49, 63}
{23, 49, 64} {23, 49, 65} {23, 49, 66} {23, 50, 51} {23, 50, 52} {23, 50, 53} {23, 50, 54} {23, 50, 55} {23, 50, 56}
{23, 50, 57} {23, 50, 58} {23, 50, 59} {23, 50, 60} {23, 50, 61} {23, 50, 62} {23, 50, 63} {23, 50, 64} {23, 50, 65}
{23, 50, 66} {23, 51, 52} {23, 51, 53} {23, 51, 54} {23, 51, 55} {23, 51, 56} {23, 51, 57} {23, 51, 58} {23, 51, 59}
{23, 51, 60} {23, 51, 61} {23, 51, 62} {23, 51, 63} {23, 51, 64} {23, 51, 65} {23, 51, 66} {23, 52, 53} {23, 52, 54}
{23, 52, 55} {23, 52, 56} {23, 52, 57} {23, 52, 58} {23, 52, 59} {23, 52, 60} {23, 52, 61} {23, 52, 62} {23, 52, 63}
{23, 52, 64} {23, 52, 65} {23, 52, 66} {23, 53, 54} {23, 53, 55} {23, 53, 56} {23, 53, 57} {23, 53, 58} {23, 53, 59}
{23, 53, 60} {23, 53, 61} {23, 53, 62} {23, 53, 63} {23, 53, 64} {23, 53, 65} {23, 53, 66} {23, 54, 55} {23, 54, 56}

TABLE 3A-continued

{23, 54, 57} {23, 54, 58} {23, 54, 59} {23, 54, 60} {23, 54, 61} {23, 54, 62} {23, 54, 63} {23, 54, 64} {23, 54, 65}
{23, 54, 66} {23, 55, 56} {23, 55, 57} {23, 55, 58} {23, 55, 59} {23, 55, 60} {23, 55, 61} {23, 55, 62} {23, 55, 63}
{23, 55, 64} {23, 55, 65} {23, 55, 66} {23, 56, 57} {23, 56, 58} {23, 56, 59} {23, 56, 60} {23, 56, 61} {23, 56, 62}
{23, 56, 63} {23, 56, 64} {23, 56, 65} {23, 56, 66} {23, 57, 58} {23, 57, 59} {23, 57, 60} {23, 57, 61} {23, 57, 62}
{23, 57, 63} {23, 57, 64} {23, 57, 65} {23, 57, 66} {23, 58, 59} {23, 58, 60} {23, 58, 61} {23, 58, 62} {23, 58, 63}
{23, 58, 64} {23, 58, 65} {23, 58, 66} {23, 59, 60} {23, 59, 61} {23, 59, 62} {23, 59, 63} {23, 59, 64} {23, 59, 65}
{23, 59, 66} {23, 60, 61} {23, 60, 62} {23, 60, 63} {23, 60, 64} {23, 60, 65} {23, 60, 66} {23, 61, 62} {23, 61, 63}
{23, 61, 64} {23, 61, 65} {23, 61, 66} {23, 62, 63} {23, 62, 64} {23, 62, 65} {23, 62, 66} {23, 63, 64} {23, 63, 65}
{23, 63, 66} {23, 64, 65} {23, 64, 66} {23, 65, 66} {24, 25, 26} {24, 25, 27} {24, 25, 28} {24, 25, 29} {24, 25, 30}
{24, 25, 31} {24, 25, 32} {24, 25, 33} {24, 25, 34} {24, 25, 35} {24, 25, 36} {24, 25, 37} {24, 25, 38} {24, 25, 39}
{24, 25, 40} {24, 25, 41} {24, 25, 42} {24, 25, 43} {24, 25, 44} {24, 25, 45} {24, 25, 46} {24, 25, 47} {24, 25, 48}
{24, 25, 49} {24, 25, 50} {24, 25, 51} {24, 25, 52} {24, 25, 53} {24, 25, 54} {24, 25, 55} {24, 25, 56} {24, 25, 57}
{24, 25, 58} {24, 25, 59} {24, 25, 60} {24, 25, 61} {24, 25, 62} {24, 25, 63} {24, 25, 64} {24, 25, 65} {24, 25, 66}
{24, 26, 27} {24, 26, 28} {24, 26, 29} {24, 26, 30} {24, 26, 31} {24, 26, 32} {24, 26, 33} {24, 26, 34} {24, 26, 35}
{24, 26, 36} {24, 26, 37} {24, 26, 38} {24, 26, 39} {24, 26, 40} {24, 26, 41} {24, 26, 42} {24, 26, 43} {24, 26, 44}
{24, 26, 45} {24, 26, 46} {24, 26, 47} {24, 26, 48} {24, 26, 49} {24, 26, 50} {24, 26, 51} {24, 26, 52} {24, 26, 53}
{24, 26, 54} {24, 26, 55} {24, 26, 56} {24, 26, 57} {24, 26, 58} {24, 26, 59} {24, 26, 60} {24, 26, 61} {24, 26, 62}
{24, 26, 63} {24, 26, 64} {24, 26, 65} {24, 26, 66} {24, 27, 28} {24, 27, 29} {24, 27, 30} {24, 27, 31} {24, 27, 32}
{24, 27, 33} {24, 27, 34} {24, 27, 35} {24, 27, 36} {24, 27, 37} {24, 27, 38} {24, 27, 39} {24, 27, 40} {24, 27, 41}
{24, 27, 42} {24, 27, 43} {24, 27, 44} {24, 27, 45} {24, 27, 46} {24, 27, 47} {24, 27, 48} {24, 27, 49} {24, 27, 50}
{24, 27, 51} {24, 27, 52} {24, 27, 53} {24, 27, 54} {24, 27, 55} {24, 27, 56} {24, 27, 57} {24, 27, 58} {24, 27, 59}
{24, 27, 60} {24, 27, 61} {24, 27, 62} {24, 27, 63} {24, 27, 64} {24, 27, 65} {24, 27, 66} {24, 28, 29} {24, 28, 30}
{24, 28, 31} {24, 28, 32} {24, 28, 33} {24, 28, 34} {24, 28, 35} {24, 28, 36} {24, 28, 37} {24, 28, 38} {24, 28, 39}
{24, 28, 40} {24, 28, 41} {24, 28, 42} {24, 28, 43} {24, 28, 44} {24, 28, 45} {24, 28, 46} {24, 28, 47} {24, 28, 48}
{24, 28, 49} {24, 28, 50} {24, 28, 51} {24, 28, 52} {24, 28, 53} {24, 28, 54} {24, 28, 55} {24, 28, 56} {24, 28, 57}
{24, 28, 58} {24, 28, 59} {24, 28, 60} {24, 28, 61} {24, 28, 62} {24, 28, 63} {24, 28, 64} {24, 28, 65} {24, 28, 66}
{24, 29, 30} {24, 29, 31} {24, 29, 32} {24, 29, 33} {24, 29, 34} {24, 29, 35} {24, 29, 36} {24, 29, 37} {24, 29, 38}
{24, 29, 39} {24, 29, 40} {24, 29, 41} {24, 29, 42} {24, 29, 43} {24, 29, 44} {24, 29, 45} {24, 29, 46} {24, 29, 47}
{24, 29, 48} {24, 29, 49} {24, 29, 50} {24, 29, 51} {24, 29, 52} {24, 29, 53} {24, 29, 54} {24, 29, 55} {24, 29, 56}
{24, 29, 57} {24, 29, 58} {24, 29, 59} {24, 29, 60} {24, 29, 61} {24, 29, 62} {24, 29, 63} {24, 29, 64} {24, 29, 65}
{24, 29, 66} {24, 30, 31} {24, 30, 32} {24, 30, 33} {24, 30, 34} {24, 30, 35} {24, 30, 36} {24, 30, 37} {24, 30, 38}
{24, 30, 39} {24, 30, 40} {24, 30, 41} {24, 30, 42} {24, 30, 43} {24, 30, 44} {24, 30, 45} {24, 30, 46} {24, 30, 47}
{24, 30, 48} {24, 30, 49} {24, 30, 50} {24, 30, 51} {24, 30, 52} {24, 30, 53} {24, 30, 54} {24, 30, 55} {24, 30, 56}
{24, 30, 57} {24, 30, 58} {24, 30, 59} {24, 30, 60} {24, 30, 61} {24, 30, 62} {24, 30, 63} {24, 30, 64} {24, 30, 65}
{24, 30, 66} {24, 31, 32} {24, 31, 33} {24, 31, 34} {24, 31, 35} {24, 31, 36} {24, 31, 37} {24, 31, 38} {24, 31, 39}
{24, 31, 40} {24, 31, 41} {24, 31, 42} {24, 31, 43} {24, 31, 44} {24, 31, 45} {24, 31, 46} {24, 31, 47} {24, 31, 48}
{24, 31, 49} {24, 31, 50} {24, 31, 51} {24, 31, 52} {24, 31, 53} {24, 31, 54} {24, 31, 55} {24, 31, 56} {24, 31, 57}
{24, 31, 58} {24, 31, 59} {24, 31, 60} {24, 31, 61} {24, 31, 62} {24, 31, 63} {24, 31, 64} {24, 31, 65} {24, 31, 66}
{24, 32, 33} {24, 32, 34} {24, 32, 35} {24, 32, 36} {24, 32, 37} {24, 32, 38} {24, 32, 39} {24, 32, 40} {24, 32, 41}
{24, 32, 42} {24, 32, 43} {24, 32, 44} {24, 32, 45} {24, 32, 46} {24, 32, 47} {24, 32, 48} {24, 32, 49} {24, 32, 50}
{24, 32, 51} {24, 32, 52} {24, 32, 53} {24, 32, 54} {24, 32, 55} {24, 32, 56} {24, 32, 57} {24, 32, 58} {24, 32, 59}
{24, 32, 60} {24, 32, 61} {24, 32, 62} {24, 32, 63} {24, 32, 64} {24, 32, 65} {24, 32, 66} {24, 33, 34} {24, 33, 35}
{24, 33, 36} {24, 33, 37} {24, 33, 38} {24, 33, 39} {24, 33, 40} {24, 33, 41} {24, 33, 42} {24, 33, 43} {24, 33, 44}
{24, 33, 45} {24, 33, 46} {24, 33, 47} {24, 33, 48} {24, 33, 49} {24, 33, 50} {24, 33, 51} {24, 33, 52} {24, 33, 53}
{24, 33, 54} {24, 33, 55} {24, 33, 56} {24, 33, 57} {24, 33, 58} {24, 33, 59} {24, 33, 60} {24, 33, 61} {24, 33, 62}
{24, 33, 63} {24, 33, 64} {24, 33, 65} {24, 33, 66} {24, 34, 35} {24, 34, 36} {24, 34, 37} {24, 34, 38} {24, 34, 39}
{24, 34, 40} {24, 34, 41} {24, 34, 42} {24, 34, 43} {24, 34, 44} {24, 34, 45} {24, 34, 46} {24, 34, 47} {24, 34, 48}
{24, 34, 49} {24, 34, 50} {24, 34, 51} {24, 34, 52} {24, 34, 53} {24, 34, 54} {24, 34, 55} {24, 34, 56} {24, 34, 57}
{24, 34, 58} {24, 34, 59} {24, 34, 60} {24, 34, 61} {24, 34, 62} {24, 34, 63} {24, 34, 64} {24, 34, 65} {24, 34, 66}
{24, 35, 36} {24, 35, 37} {24, 35, 38} {24, 35, 39} {24, 35, 40} {24, 35, 41} {24, 35, 42} {24, 35, 43} {24, 35, 44}
{24, 35, 45} {24, 35, 46} {24, 35, 47} {24, 35, 48} {24, 35, 49} {24, 35, 50} {24, 35, 51} {24, 35, 52} {24, 35, 53}
{24, 35, 54} {24, 35, 55} {24, 35, 56} {24, 35, 57} {24, 35, 58} {24, 35, 59} {24, 35, 60} {24, 35, 61} {24, 35, 62}
{24, 35, 63} {24, 35, 64} {24, 35, 65} {24, 35, 66} {24, 36, 37} {24, 36, 38} {24, 36, 39} {24, 36, 40} {24, 36, 41}
{24, 36, 42} {24, 36, 43} {24, 36, 44} {24, 36, 45} {24, 36, 46} {24, 36, 47} {24, 36, 48} {24, 36, 49} {24, 36, 50}
{24, 36, 51} {24, 36, 52} {24, 36, 53} {24, 36, 54} {24, 36, 55} {24, 36, 56} {24, 36, 57} {24, 36, 58} {24, 36, 59}
{24, 36, 60} {24, 36, 61} {24, 36, 62} {24, 36, 63} {24, 36, 64} {24, 36, 65} {24, 36, 66} {24, 37, 38} {24, 37, 39}
{24, 37, 40} {24, 37, 41} {24, 37, 42} {24, 37, 43} {24, 37, 44} {24, 37, 45} {24, 37, 46} {24, 37, 47} {24, 37, 48}
{24, 37, 49} {24, 37, 50} {24, 37, 51} {24, 37, 52} {24, 37, 53} {24, 37, 54} {24, 37, 55} {24, 37, 56} {24, 37, 57}
{24, 37, 58} {24, 37, 59} {24, 37, 60} {24, 37, 61} {24, 37, 62} {24, 37, 63} {24, 37, 64} {24, 37, 65} {24, 37, 66}
{24, 38, 39} {24, 38, 40} {24, 38, 41} {24, 38, 42} {24, 38, 43} {24, 38, 44} {24, 38, 45} {24, 38, 46} {24, 38, 47}
{24, 38, 48} {24, 38, 49} {24, 38, 50} {24, 38, 51} {24, 38, 52} {24, 38, 53} {24, 38, 54} {24, 38, 55} {24, 38, 56}
{24, 38, 57} {24, 38, 58} {24, 38, 59} {24, 38, 60} {24, 38, 61} {24, 38, 62} {24, 38, 63} {24, 38, 64} {24, 38, 65}
{24, 38, 66} {24, 39, 40} {24, 39, 41} {24, 39, 42} {24, 39, 43} {24, 39, 44} {24, 39, 45} {24, 39, 46} {24, 39, 47}
{24, 39, 48} {24, 39, 49} {24, 39, 50} {24, 39, 51} {24, 39, 52} {24, 39, 53} {24, 39, 54} {24, 39, 55} {24, 39, 56}
{24, 39, 57} {24, 39, 58} {24, 39, 59} {24, 39, 60} {24, 39, 61} {24, 39, 62} {24, 39, 63} {24, 39, 64} {24, 39, 65}
{24, 39, 66} {24, 40, 41} {24, 40, 42} {24, 40, 43} {24, 40, 44} {24, 40, 45} {24, 40, 46} {24, 40, 47} {24, 40, 48}
{24, 40, 49} {24, 40, 50} {24, 40, 51} {24, 40, 52} {24, 40, 53} {24, 40, 54} {24, 40, 55} {24, 40, 56} {24, 40, 57}
{24, 40, 58} {24, 40, 59} {24, 40, 60} {24, 40, 61} {24, 40, 62} {24, 40, 63} {24, 40, 64} {24, 40, 65} {24, 40, 66}
{24, 41, 42} {24, 41, 43} {24, 41, 44} {24, 41, 45} {24, 41, 46} {24, 41, 47} {24, 41, 48} {24, 41, 49} {24, 41, 50}
{24, 41, 51} {24, 41, 52} {24, 41, 53} {24, 41, 54} {24, 41, 55} {24, 41, 56} {24, 41, 57} {24, 41, 58} {24, 41, 59}
{24, 41, 60} {24, 41, 61} {24, 41, 62} {24, 41, 63} {24, 41, 64} {24, 41, 65} {24, 41, 66} {24, 42, 43} {24, 42, 44}
{24, 42, 45} {24, 42, 46} {24, 42, 47} {24, 42, 48} {24, 42, 49} {24, 42, 50} {24, 42, 51} {24, 42, 52} {24, 42, 53}
{24, 42, 54} {24, 42, 55} {24, 42, 56} {24, 42, 57} {24, 42, 58} {24, 42, 59} {24, 42, 60} {24, 42, 61} {24, 42, 62}
{24, 42, 63} {24, 42, 64} {24, 42, 65} {24, 42, 66} {24, 43, 44} {24, 43, 45} {24, 43, 46} {24, 43, 47} {24, 43, 48}
{24, 43, 49} {24, 43, 50} {24, 43, 51} {24, 43, 52} {24, 43, 53} {24, 43, 54} {24, 43, 55} {24, 43, 56} {24, 43, 57}
{24, 43, 58} {24, 43, 59} {24, 43, 60} {24, 43, 61} {24, 43, 62} {24, 43, 63} {24, 43, 64} {24, 43, 65} {24, 43, 66}
{24, 44, 45} {24, 44, 46} {24, 44, 47} {24, 44, 48} {24, 44, 49} {24, 44, 50} {24, 44, 51} {24, 44, 52} {24, 44, 53}
{24, 44, 54} {24, 44, 55} {24, 44, 56} {24, 44, 57} {24, 44, 58} {24, 44, 59} {24, 44, 60} {24, 44, 61} {24, 44, 62}
{24, 44, 63} {24, 44, 64} {24, 44, 65} {24, 44, 66} {24, 45, 46} {24, 45, 47} {24, 45, 48} {24, 45, 49} {24, 45, 50}
{24, 45, 51} {24, 45, 52} {24, 45, 53} {24, 45, 54} {24, 45, 55} {24, 45, 56} {24, 45, 57} {24, 45, 58} {24, 45, 59}

TABLE 3A-continued

| | | | | | | | | |
|---|---|---|---|---|---|---|---|---|
| {24, 45, 60} | {24, 45, 61} | {24, 45, 62} | {24, 45, 63} | {24, 45, 64} | {24, 45, 65} | {24, 45, 66} | {24, 46, 47} | {24, 46, 48} |
| {24, 46, 49} | {24, 46, 50} | {24, 46, 51} | {24, 46, 52} | {24, 46, 53} | {24, 46, 54} | {24, 46, 55} | {24, 46, 56} | {24, 46, 57} |
| {24, 46, 58} | {24, 46, 59} | {24, 46, 60} | {24, 46, 61} | {24, 46, 62} | {24, 46, 63} | {24, 46, 64} | {24, 46, 65} | {24, 46, 66} |
| {24, 47, 48} | {24, 47, 49} | {24, 47, 50} | {24, 47, 51} | {24, 47, 52} | {24, 47, 53} | {24, 47, 54} | {24, 47, 55} | {24, 47, 56} |
| {24, 47, 57} | {24, 47, 58} | {24, 47, 59} | {24, 47, 60} | {24, 47, 61} | {24, 47, 62} | {24, 47, 63} | {24, 47, 64} | {24, 47, 65} |
| {24, 47, 66} | {24, 48, 49} | {24, 48, 50} | {24, 48, 51} | {24, 48, 52} | {24, 48, 53} | {24, 48, 54} | {24, 48, 55} | {24, 48, 56} |
| {24, 48, 57} | {24, 48, 58} | {24, 48, 59} | {24, 48, 60} | {24, 48, 61} | {24, 48, 62} | {24, 48, 63} | {24, 48, 64} | {24, 48, 65} |
| {24, 48, 66} | {24, 49, 50} | {24, 49, 51} | {24, 49, 52} | {24, 49, 53} | {24, 49, 54} | {24, 49, 55} | {24, 49, 56} | {24, 49, 57} |
| {24, 49, 58} | {24, 49, 59} | {24, 49, 60} | {24, 49, 61} | {24, 49, 62} | {24, 49, 63} | {24, 49, 64} | {24, 49, 65} | {24, 49, 66} |
| {24, 50, 51} | {24, 50, 52} | {24, 50, 53} | {24, 50, 54} | {24, 50, 55} | {24, 50, 56} | {24, 50, 57} | {24, 50, 58} | {24, 50, 59} |
| {24, 50, 60} | {24, 50, 61} | {24, 50, 62} | {24, 50, 63} | {24, 50, 64} | {24, 50, 65} | {24, 50, 66} | {24, 51, 52} | {24, 51, 53} |
| {24, 51, 54} | {24, 51, 55} | {24, 51, 56} | {24, 51, 57} | {24, 51, 58} | {24, 51, 59} | {24, 51, 60} | {24, 51, 61} | {24, 51, 62} |
| {24, 51, 63} | {24, 51, 64} | {24, 51, 65} | {24, 51, 66} | {24, 52, 53} | {24, 52, 54} | {24, 52, 55} | {24, 52, 56} | {24, 52, 57} |
| {24, 52, 58} | {24, 52, 59} | {24, 52, 60} | {24, 52, 61} | {24, 52, 62} | {24, 52, 63} | {24, 52, 64} | {24, 52, 65} | {24, 52, 66} |
| {24, 53, 54} | {24, 53, 55} | {24, 53, 56} | {24, 53, 57} | {24, 53, 58} | {24, 53, 59} | {24, 53, 60} | {24, 53, 61} | {24, 53, 62} |
| {24, 53, 63} | {24, 53, 64} | {24, 53, 65} | {24, 53, 66} | {24, 54, 55} | {24, 54, 56} | {24, 54, 57} | {24, 54, 58} | {24, 54, 59} |
| {24, 54, 60} | {24, 54, 61} | {24, 54, 62} | {24, 54, 63} | {24, 54, 64} | {24, 54, 65} | {24, 54, 66} | {24, 55, 56} | {24, 55, 57} |
| {24, 55, 58} | {24, 55, 59} | {24, 55, 60} | {24, 55, 61} | {24, 55, 62} | {24, 55, 63} | {24, 55, 64} | {24, 55, 65} | {24, 55, 66} |
| {24, 56, 57} | {24, 56, 58} | {24, 56, 59} | {24, 56, 60} | {24, 56, 61} | {24, 56, 62} | {24, 56, 63} | {24, 56, 64} | {24, 56, 65} |
| {24, 56, 66} | {24, 57, 58} | {24, 57, 59} | {24, 57, 60} | {24, 57, 61} | {24, 57, 62} | {24, 57, 63} | {24, 57, 64} | {24, 57, 65} |
| {24, 57, 66} | {24, 58, 59} | {24, 58, 60} | {24, 58, 61} | {24, 58, 62} | {24, 58, 63} | {24, 58, 64} | {24, 58, 65} | {24, 58, 66} |
| {24, 59, 60} | {24, 59, 61} | {24, 59, 62} | {24, 59, 63} | {24, 59, 64} | {24, 59, 65} | {24, 59, 66} | {24, 60, 61} | {24, 60, 62} |
| {24, 60, 63} | {24, 60, 64} | {24, 60, 65} | {24, 60, 66} | {24, 61, 62} | {24, 61, 63} | {24, 61, 64} | {24, 61, 65} | {24, 61, 66} |
| {24, 62, 63} | {24, 62, 64} | {24, 62, 65} | {24, 62, 66} | {24, 63, 64} | {24, 63, 65} | {24, 63, 66} | {24, 64, 65} | {24, 64, 66} |
| {24, 65, 66} | {25, 26, 27} | {25, 26, 28} | {25, 26, 29} | {25, 26, 30} | {25, 26, 31} | {25, 26, 32} | {25, 26, 33} | {25, 26, 34} |
| {25, 26, 35} | {25, 26, 36} | {25, 26, 37} | {25, 26, 38} | {25, 26, 39} | {25, 26, 40} | {25, 26, 41} | {25, 26, 42} | {25, 26, 43} |
| {25, 26, 44} | {25, 26, 45} | {25, 26, 46} | {25, 26, 47} | {25, 26, 48} | {25, 26, 49} | {25, 26, 50} | {25, 26, 51} | {25, 26, 52} |
| {25, 26, 53} | {25, 26, 54} | {25, 26, 55} | {25, 26, 56} | {25, 26, 57} | {25, 26, 58} | {25, 26, 59} | {25, 26, 60} | {25, 26, 61} |
| {25, 26, 62} | {25, 26, 63} | {25, 26, 64} | {25, 26, 65} | {25, 26, 66} | {25, 27, 28} | {25, 27, 29} | {25, 27, 30} | {25, 27, 31} |
| {25, 27, 32} | {25, 27, 33} | {25, 27, 34} | {25, 27, 35} | {25, 27, 36} | {25, 27, 37} | {25, 27, 38} | {25, 27, 39} | {25, 27, 40} |
| {25, 27, 41} | {25, 27, 42} | {25, 27, 43} | {25, 27, 44} | {25, 27, 45} | {25, 27, 46} | {25, 27, 47} | {25, 27, 48} | {25, 27, 49} |
| {25, 27, 50} | {25, 27, 51} | {25, 27, 52} | {25, 27, 53} | {25, 27, 54} | {25, 27, 55} | {25, 27, 56} | {25, 27, 57} | {25, 27, 58} |
| {25, 27, 59} | {25, 27, 60} | {25, 27, 61} | {25, 27, 62} | {25, 27, 63} | {25, 27, 64} | {25, 27, 65} | {25, 27, 66} | {25, 28, 29} |
| {25, 28, 30} | {25, 28, 31} | {25, 28, 32} | {25, 28, 33} | {25, 28, 34} | {25, 28, 35} | {25, 28, 36} | {25, 28, 37} | {25, 28, 38} |
| {25, 28, 39} | {25, 28, 40} | {25, 28, 41} | {25, 28, 42} | {25, 28, 43} | {25, 28, 44} | {25, 28, 45} | {25, 28, 46} | {25, 28, 47} |
| {25, 28, 48} | {25, 28, 49} | {25, 28, 50} | {25, 28, 51} | {25, 28, 52} | {25, 28, 53} | {25, 28, 54} | {25, 28, 55} | {25, 28, 56} |
| {25, 28, 57} | {25, 28, 58} | {25, 28, 59} | {25, 28, 60} | {25, 28, 61} | {25, 28, 62} | {25, 28, 63} | {25, 28, 64} | {25, 28, 65} |
| {25, 28, 66} | {25, 29, 30} | {25, 29, 31} | {25, 29, 32} | {25, 29, 33} | {25, 29, 34} | {25, 29, 35} | {25, 29, 36} | {25, 29, 37} |
| {25, 29, 38} | {25, 29, 39} | {25, 29, 40} | {25, 29, 41} | {25, 29, 42} | {25, 29, 43} | {25, 29, 44} | {25, 29, 45} | {25, 29, 46} |
| {25, 29, 47} | {25, 29, 48} | {25, 29, 49} | {25, 29, 50} | {25, 29, 51} | {25, 29, 52} | {25, 29, 53} | {25, 29, 54} | {25, 29, 55} |
| {25, 29, 56} | {25, 29, 57} | {25, 29, 58} | {25, 29, 59} | {25, 29, 60} | {25, 29, 61} | {25, 29, 62} | {25, 29, 63} | {25, 29, 64} |
| {25, 29, 65} | {25, 29, 66} | {25, 30, 31} | {25, 30, 32} | {25, 30, 33} | {25, 30, 34} | {25, 30, 35} | {25, 30, 36} | {25, 30, 37} |
| {25, 30, 38} | {25, 30, 39} | {25, 30, 40} | {25, 30, 41} | {25, 30, 42} | {25, 30, 43} | {25, 30, 44} | {25, 30, 45} | {25, 30, 46} |
| {25, 30, 47} | {25, 30, 48} | {25, 30, 49} | {25, 30, 50} | {25, 30, 51} | {25, 30, 52} | {25, 30, 53} | {25, 30, 54} | {25, 30, 55} |
| {25, 30, 56} | {25, 30, 57} | {25, 30, 58} | {25, 30, 59} | {25, 30, 60} | {25, 30, 61} | {25, 30, 62} | {25, 30, 63} | {25, 30, 64} |
| {25, 30, 65} | {25, 30, 66} | {25, 31, 32} | {25, 31, 33} | {25, 31, 34} | {25, 31, 35} | {25, 31, 36} | {25, 31, 37} | {25, 31, 38} |
| {25, 31, 39} | {25, 31, 40} | {25, 31, 41} | {25, 31, 42} | {25, 31, 43} | {25, 31, 44} | {25, 31, 45} | {25, 31, 46} | {25, 31, 47} |
| {25, 31, 48} | {25, 31, 49} | {25, 31, 50} | {25, 31, 51} | {25, 31, 52} | {25, 31, 53} | {25, 31, 54} | {25, 31, 55} | {25, 31, 56} |
| {25, 31, 57} | {25, 31, 58} | {25, 31, 59} | {25, 31, 60} | {25, 31, 61} | {25, 31, 62} | {25, 31, 63} | {25, 31, 64} | {25, 31, 65} |
| {25, 31, 66} | {25, 32, 33} | {25, 32, 34} | {25, 32, 35} | {25, 32, 36} | {25, 32, 37} | {25, 32, 38} | {25, 32, 39} | {25, 32, 40} |
| {25, 32, 41} | {25, 32, 42} | {25, 32, 43} | {25, 32, 44} | {25, 32, 45} | {25, 32, 46} | {25, 32, 47} | {25, 32, 48} | {25, 32, 49} |
| {25, 32, 50} | {25, 32, 51} | {25, 32, 52} | {25, 32, 53} | {25, 32, 54} | {25, 32, 55} | {25, 32, 56} | {25, 32, 57} | {25, 32, 58} |
| {25, 32, 59} | {25, 32, 60} | {25, 32, 61} | {25, 32, 62} | {25, 32, 63} | {25, 32, 64} | {25, 32, 65} | {25, 32, 66} | {25, 33, 34} |
| {25, 33, 35} | {25, 33, 36} | {25, 33, 37} | {25, 33, 38} | {25, 33, 39} | {25, 33, 40} | {25, 33, 41} | {25, 33, 42} | {25, 33, 43} |
| {25, 33, 44} | {25, 33, 45} | {25, 33, 46} | {25, 33, 47} | {25, 33, 48} | {25, 33, 49} | {25, 33, 50} | {25, 33, 51} | {25, 33, 52} |
| {25, 33, 53} | {25, 33, 54} | {25, 33, 55} | {25, 33, 56} | {25, 33, 57} | {25, 33, 58} | {25, 33, 59} | {25, 33, 60} | {25, 33, 61} |
| {25, 33, 62} | {25, 33, 63} | {25, 33, 64} | {25, 33, 65} | {25, 33, 66} | {25, 34, 35} | {25, 34, 36} | {25, 34, 37} | {25, 34, 38} |
| {25, 34, 39} | {25, 34, 40} | {25, 34, 41} | {25, 34, 42} | {25, 34, 43} | {25, 34, 44} | {25, 34, 45} | {25, 34, 46} | {25, 34, 47} |
| {25, 34, 48} | {25, 34, 49} | {25, 34, 50} | {25, 34, 51} | {25, 34, 52} | {25, 34, 53} | {25, 34, 54} | {25, 34, 55} | {25, 34, 56} |
| {25, 34, 57} | {25, 34, 58} | {25, 34, 59} | {25, 34, 60} | {25, 34, 61} | {25, 34, 62} | {25, 34, 63} | {25, 34, 64} | {25, 34, 65} |
| {25, 34, 66} | {25, 35, 36} | {25, 35, 37} | {25, 35, 38} | {25, 35, 39} | {25, 35, 40} | {25, 35, 41} | {25, 35, 42} | {25, 35, 43} |
| {25, 35, 44} | {25, 35, 45} | {25, 35, 46} | {25, 35, 47} | {25, 35, 48} | {25, 35, 49} | {25, 35, 50} | {25, 35, 51} | {25, 35, 52} |
| {25, 35, 53} | {25, 35, 54} | {25, 35, 55} | {25, 35, 56} | {25, 35, 57} | {25, 35, 58} | {25, 35, 59} | {25, 35, 60} | {25, 35, 61} |
| {25, 35, 62} | {25, 35, 63} | {25, 35, 64} | {25, 35, 65} | {25, 35, 66} | {25, 36, 37} | {25, 36, 38} | {25, 36, 39} | {25, 36, 40} |
| {25, 36, 41} | {25, 36, 42} | {25, 36, 43} | {25, 36, 44} | {25, 36, 45} | {25, 36, 46} | {25, 36, 47} | {25, 36, 48} | {25, 36, 49} |
| {25, 36, 50} | {25, 36, 51} | {25, 36, 52} | {25, 36, 53} | {25, 36, 54} | {25, 36, 55} | {25, 36, 56} | {25, 36, 57} | {25, 36, 58} |
| {25, 36, 59} | {25, 36, 60} | {25, 36, 61} | {25, 36, 62} | {25, 36, 63} | {25, 36, 64} | {25, 36, 65} | {25, 36, 66} | {25, 37, 38} |
| {25, 37, 39} | {25, 37, 40} | {25, 37, 41} | {25, 37, 42} | {25, 37, 43} | {25, 37, 44} | {25, 37, 45} | {25, 37, 46} | {25, 37, 47} |
| {25, 37, 48} | {25, 37, 49} | {25, 37, 50} | {25, 37, 51} | {25, 37, 52} | {25, 37, 53} | {25, 37, 54} | {25, 37, 55} | {25, 37, 56} |
| {25, 37, 57} | {25, 37, 58} | {25, 37, 59} | {25, 37, 60} | {25, 37, 61} | {25, 37, 62} | {25, 37, 63} | {25, 37, 64} | {25, 37, 65} |
| {25, 37, 66} | {25, 38, 39} | {25, 38, 40} | {25, 38, 41} | {25, 38, 42} | {25, 38, 43} | {25, 38, 44} | {25, 38, 45} | {25, 38, 46} |
| {25, 38, 47} | {25, 38, 48} | {25, 38, 49} | {25, 38, 50} | {25, 38, 51} | {25, 38, 52} | {25, 38, 53} | {25, 38, 54} | {25, 38, 55} |
| {25, 38, 56} | {25, 38, 57} | {25, 38, 58} | {25, 38, 59} | {25, 38, 60} | {25, 38, 61} | {25, 38, 62} | {25, 38, 63} | {25, 38, 64} |
| {25, 38, 65} | {25, 38, 66} | {25, 39, 40} | {25, 39, 41} | {25, 39, 42} | {25, 39, 43} | {25, 39, 44} | {25, 39, 45} | {25, 39, 46} |
| {25, 39, 47} | {25, 39, 48} | {25, 39, 49} | {25, 39, 50} | {25, 39, 51} | {25, 39, 52} | {25, 39, 53} | {25, 39, 54} | {25, 39, 55} |
| {25, 39, 56} | {25, 39, 57} | {25, 39, 58} | {25, 39, 59} | {25, 39, 60} | {25, 39, 61} | {25, 39, 62} | {25, 39, 63} | {25, 39, 64} |
| {25, 39, 65} | {25, 39, 66} | {25, 40, 41} | {25, 40, 42} | {25, 40, 43} | {25, 40, 44} | {25, 40, 45} | {25, 40, 46} | {25, 40, 47} |
| {25, 40, 48} | {25, 40, 49} | {25, 40, 50} | {25, 40, 51} | {25, 40, 52} | {25, 40, 53} | {25, 40, 54} | {25, 40, 55} | {25, 40, 56} |
| {25, 40, 57} | {25, 40, 58} | {25, 40, 59} | {25, 40, 60} | {25, 40, 61} | {25, 40, 62} | {25, 40, 63} | {25, 40, 64} | {25, 40, 65} |
| {25, 40, 66} | {25, 41, 42} | {25, 41, 43} | {25, 41, 44} | {25, 41, 45} | {25, 41, 46} | {25, 41, 47} | {25, 41, 48} | {25, 41, 49} |

TABLE 3A-continued

{25, 41, 50} {25, 41, 51} {25, 41, 52} {25, 41, 53} {25, 41, 54} {25, 41, 55} {25, 41, 56} {25, 41, 57} {25, 41, 58}
{25, 41, 59} {25, 41, 60} {25, 41, 61} {25, 41, 62} {25, 41, 63} {25, 41, 64} {25, 41, 65} {25, 41, 66} {25, 42, 43}
{25, 42, 44} {25, 42, 45} {25, 42, 46} {25, 42, 47} {25, 42, 48} {25, 42, 49} {25, 42, 50} {25, 42, 51} {25, 42, 52}
{25, 42, 53} {25, 42, 54} {25, 42, 55} {25, 42, 56} {25, 42, 57} {25, 42, 58} {25, 42, 59} {25, 42, 60} {25, 42, 61}
{25, 42, 62} {25, 42, 63} {25, 42, 64} {25, 42, 65} {25, 42, 66} {25, 43, 44} {25, 43, 45} {25, 43, 46} {25, 43, 47}
{25, 43, 48} {25, 43, 49} {25, 43, 50} {25, 43, 51} {25, 43, 52} {25, 43, 53} {25, 43, 54} {25, 43, 55} {25, 43, 56}
{25, 43, 57} {25, 43, 58} {25, 43, 59} {25, 43, 60} {25, 43, 61} {25, 43, 62} {25, 43, 63} {25, 43, 64} {25, 43, 65}
{25, 43, 66} {25, 44, 45} {25, 44, 46} {25, 44, 47} {25, 44, 48} {25, 44, 49} {25, 44, 50} {25, 44, 51} {25, 44, 52}
{25, 44, 53} {25, 44, 54} {25, 44, 55} {25, 44, 56} {25, 44, 57} {25, 44, 58} {25, 44, 59} {25, 44, 60} {25, 44, 61}
{25, 44, 62} {25, 44, 63} {25, 44, 64} {25, 44, 65} {25, 44, 66} {25, 45, 46} {25, 45, 47} {25, 45, 48} {25, 45, 49}
{25, 45, 50} {25, 45, 51} {25, 45, 52} {25, 45, 53} {25, 45, 54} {25, 45, 55} {25, 45, 56} {25, 45, 57} {25, 45, 58}
{25, 45, 59} {25, 45, 60} {25, 45, 61} {25, 45, 62} {25, 45, 63} {25, 45, 64} {25, 45, 65} {25, 45, 66} {25, 46, 47}
{25, 46, 48} {25, 46, 49} {25, 46, 50} {25, 46, 51} {25, 46, 52} {25, 46, 53} {25, 46, 54} {25, 46, 55} {25, 46, 56}
{25, 46, 57} {25, 46, 58} {25, 46, 59} {25, 46, 60} {25, 46, 61} {25, 46, 62} {25, 46, 63} {25, 46, 64} {25, 46, 65}
{25, 46, 66} {25, 47, 48} {25, 47, 49} {25, 47, 50} {25, 47, 51} {25, 47, 52} {25, 47, 53} {25, 47, 54} {25, 47, 55}
{25, 47, 56} {25, 47, 57} {25, 47, 58} {25, 47, 59} {25, 47, 60} {25, 47, 61} {25, 47, 62} {25, 47, 63} {25, 47, 64}
{25, 47, 65} {25, 47, 66} {25, 48, 49} {25, 48, 50} {25, 48, 51} {25, 48, 52} {25, 48, 53} {25, 48, 54} {25, 48, 55}
{25, 48, 56} {25, 48, 57} {25, 48, 58} {25, 48, 59} {25, 48, 60} {25, 48, 61} {25, 48, 62} {25, 48, 63} {25, 48, 64}
{25, 48, 65} {25, 48, 66} {25, 49, 50} {25, 49, 51} {25, 49, 52} {25, 49, 53} {25, 49, 54} {25, 49, 55} {25, 49, 56}
{25, 49, 57} {25, 49, 58} {25, 49, 59} {25, 49, 60} {25, 49, 61} {25, 49, 62} {25, 49, 63} {25, 49, 64} {25, 49, 65}
{25, 49, 66} {25, 50, 51} {25, 50, 52} {25, 50, 53} {25, 50, 54} {25, 50, 55} {25, 50, 56} {25, 50, 57} {25, 50, 58}
{25, 50, 59} {25, 50, 60} {25, 50, 61} {25, 50, 62} {25, 50, 63} {25, 50, 64} {25, 50, 65} {25, 50, 66} {25, 51, 52}
{25, 51, 53} {25, 51, 54} {25, 51, 55} {25, 51, 56} {25, 51, 57} {25, 51, 58} {25, 51, 59} {25, 51, 60} {25, 51, 61}
{25, 51, 62} {25, 51, 63} {25, 51, 64} {25, 51, 65} {25, 51, 66} {25, 52, 53} {25, 52, 54} {25, 52, 55} {25, 52, 56}
{25, 52, 57} {25, 52, 58} {25, 52, 59} {25, 52, 60} {25, 52, 61} {25, 52, 62} {25, 52, 63} {25, 52, 64} {25, 52, 65}
{25, 52, 66} {25, 53, 54} {25, 53, 55} {25, 53, 56} {25, 53, 57} {25, 53, 58} {25, 53, 59} {25, 53, 60} {25, 53, 61}
{25, 53, 62} {25, 53, 63} {25, 53, 64} {25, 53, 65} {25, 53, 66} {25, 54, 55} {25, 54, 56} {25, 54, 57} {25, 54, 58}
{25, 54, 59} {25, 54, 60} {25, 54, 61} {25, 54, 62} {25, 54, 63} {25, 54, 64} {25, 54, 65} {25, 54, 66} {25, 55, 56}
{25, 55, 57} {25, 55, 58} {25, 55, 59} {25, 55, 60} {25, 55, 61} {25, 55, 62} {25, 55, 63} {25, 55, 64} {25, 55, 65}
{25, 55, 66} {25, 56, 57} {25, 56, 58} {25, 56, 59} {25, 56, 60} {25, 56, 61} {25, 56, 62} {25, 56, 63} {25, 56, 64}
{25, 56, 65} {25, 56, 66} {25, 57, 58} {25, 57, 59} {25, 57, 60} {25, 57, 61} {25, 57, 62} {25, 57, 63} {25, 57, 64}
{25, 57, 65} {25, 57, 66} {25, 58, 59} {25, 58, 60} {25, 58, 61} {25, 58, 62} {25, 58, 63} {25, 58, 64} {25, 58, 65}
{25, 58, 66} {25, 59, 60} {25, 59, 61} {25, 59, 62} {25, 59, 63} {25, 59, 64} {25, 59, 65} {25, 59, 66} {25, 60, 61}
{25, 60, 62} {25, 60, 63} {25, 60, 64} {25, 60, 65} {25, 60, 66} {25, 61, 62} {25, 61, 63} {25, 61, 64} {25, 61, 65}
{25, 61, 66} {25, 62, 63} {25, 62, 64} {25, 62, 65} {25, 62, 66} {25, 63, 64} {25, 63, 65} {25, 63, 66} {25, 64, 65}
{25, 64, 66} {25, 65, 66} {26, 27, 28} {26, 27, 29} {26, 27, 30} {26, 27, 31} {26, 27, 32} {26, 27, 33} {26, 27, 34}
{26, 27, 35} {26, 27, 36} {26, 27, 37} {26, 27, 38} {26, 27, 39} {26, 27, 40} {26, 27, 41} {26, 27, 42} {26, 27, 43}
{26, 27, 44} {26, 27, 45} {26, 27, 46} {26, 27, 47} {26, 27, 48} {26, 27, 49} {26, 27, 50} {26, 27, 51} {26, 27, 52}
{26, 27, 53} {26, 27, 54} {26, 27, 55} {26, 27, 56} {26, 27, 57} {26, 27, 58} {26, 27, 59} {26, 27, 60} {26, 27, 61}
{26, 27, 62} {26, 27, 63} {26, 27, 64} {26, 27, 65} {26, 27, 66} {26, 28, 29} {26, 28, 30} {26, 28, 31} {26, 28, 32}
{26, 28, 33} {26, 28, 34} {26, 28, 35} {26, 28, 36} {26, 28, 37} {26, 28, 38} {26, 28, 39} {26, 28, 40} {26, 28, 41}
{26, 28, 42} {26, 28, 43} {26, 28, 44} {26, 28, 45} {26, 28, 46} {26, 28, 47} {26, 28, 48} {26, 28, 49} {26, 28, 50}
{26, 28, 51} {26, 28, 52} {26, 28, 53} {26, 28, 54} {26, 28, 55} {26, 28, 56} {26, 28, 57} {26, 28, 58} {26, 28, 59}
{26, 28, 60} {26, 28, 61} {26, 28, 62} {26, 28, 63} {26, 28, 64} {26, 28, 65} {26, 28, 66} {26, 29, 30} {26, 29, 31}
{26, 29, 32} {26, 29, 33} {26, 29, 34} {26, 29, 35} {26, 29, 36} {26, 29, 37} {26, 29, 38} {26, 29, 39} {26, 29, 40}
{26, 29, 41} {26, 29, 42} {26, 29, 43} {26, 29, 44} {26, 29, 45} {26, 29, 46} {26, 29, 47} {26, 29, 48} {26, 29, 49}
{26, 29, 50} {26, 29, 51} {26, 29, 52} {26, 29, 53} {26, 29, 54} {26, 29, 55} {26, 29, 56} {26, 29, 57} {26, 29, 58}
{26, 29, 59} {26, 29, 60} {26, 29, 61} {26, 29, 62} {26, 29, 63} {26, 29, 64} {26, 29, 65} {26, 29, 66} {26, 30, 31}
{26, 30, 32} {26, 30, 33} {26, 30, 34} {26, 30, 35} {26, 30, 36} {26, 30, 37} {26, 30, 38} {26, 30, 39} {26, 30, 40}
{26, 30, 41} {26, 30, 42} {26, 30, 43} {26, 30, 44} {26, 30, 45} {26, 30, 46} {26, 30, 47} {26, 30, 48} {26, 30, 49}
{26, 30, 50} {26, 30, 51} {26, 30, 52} {26, 30, 53} {26, 30, 54} {26, 30, 55} {26, 30, 56} {26, 30, 57} {26, 30, 58}
{26, 30, 59} {26, 30, 60} {26, 30, 61} {26, 30, 62} {26, 30, 63} {26, 30, 64} {26, 30, 65} {26, 30, 66} {26, 31, 32}
{26, 31, 33} {26, 31, 34} {26, 31, 35} {26, 31, 36} {26, 31, 37} {26, 31, 38} {26, 31, 39} {26, 31, 40} {26, 31, 41}
{26, 31, 42} {26, 31, 43} {26, 31, 44} {26, 31, 45} {26, 31, 46} {26, 31, 47} {26, 31, 48} {26, 31, 49} {26, 31, 50}
{26, 31, 51} {26, 31, 52} {26, 31, 53} {26, 31, 54} {26, 31, 55} {26, 31, 56} {26, 31, 57} {26, 31, 58} {26, 31, 59}
{26, 31, 60} {26, 31, 61} {26, 31, 62} {26, 31, 63} {26, 31, 64} {26, 31, 65} {26, 31, 66} {26, 32, 33} {26, 32, 34}
{26, 32, 35} {26, 32, 36} {26, 32, 37} {26, 32, 38} {26, 32, 39} {26, 32, 40} {26, 32, 41} {26, 32, 42} {26, 32, 43}
{26, 32, 44} {26, 32, 45} {26, 32, 46} {26, 32, 47} {26, 32, 48} {26, 32, 49} {26, 32, 50} {26, 32, 51} {26, 32, 52}
{26, 32, 53} {26, 32, 54} {26, 32, 55} {26, 32, 56} {26, 32, 57} {26, 32, 58} {26, 32, 59} {26, 32, 60} {26, 32, 61}
{26, 32, 62} {26, 32, 63} {26, 32, 64} {26, 32, 65} {26, 32, 66} {26, 33, 34} {26, 33, 35} {26, 33, 36} {26, 33, 37}
{26, 33, 38} {26, 33, 39} {26, 33, 40} {26, 33, 41} {26, 33, 42} {26, 33, 43} {26, 33, 44} {26, 33, 45} {26, 33, 46}
{26, 33, 47} {26, 33, 48} {26, 33, 49} {26, 33, 50} {26, 33, 51} {26, 33, 52} {26, 33, 53} {26, 33, 54} {26, 33, 55}
{26, 33, 56} {26, 33, 57} {26, 33, 58} {26, 33, 59} {26, 33, 60} {26, 33, 61} {26, 33, 62} {26, 33, 63} {26, 33, 64}
{26, 33, 65} {26, 33, 66} {26, 34, 35} {26, 34, 36} {26, 34, 37} {26, 34, 38} {26, 34, 39} {26, 34, 40} {26, 34, 41}
{26, 34, 42} {26, 34, 43} {26, 34, 44} {26, 34, 45} {26, 34, 46} {26, 34, 47} {26, 34, 48} {26, 34, 49} {26, 34, 50}
{26, 34, 51} {26, 34, 52} {26, 34, 53} {26, 34, 54} {26, 34, 55} {26, 34, 56} {26, 34, 57} {26, 34, 58} {26, 34, 59}
{26, 34, 60} {26, 34, 61} {26, 34, 62} {26, 34, 63} {26, 34, 64} {26, 34, 65} {26, 34, 66} {26, 35, 36} {26, 35, 37}
{26, 35, 38} {26, 35, 39} {26, 35, 40} {26, 35, 41} {26, 35, 42} {26, 35, 43} {26, 35, 44} {26, 35, 45} {26, 35, 46}
{26, 35, 47} {26, 35, 48} {26, 35, 49} {26, 35, 50} {26, 35, 51} {26, 35, 52} {26, 35, 53} {26, 35, 54} {26, 35, 55}
{26, 35, 56} {26, 35, 57} {26, 35, 58} {26, 35, 59} {26, 35, 60} {26, 35, 61} {26, 35, 62} {26, 35, 63} {26, 35, 64}
{26, 35, 65} {26, 35, 66} {26, 36, 37} {26, 36, 38} {26, 36, 39} {26, 36, 40} {26, 36, 41} {26, 36, 42} {26, 36, 43}
{26, 36, 44} {26, 36, 45} {26, 36, 46} {26, 36, 47} {26, 36, 48} {26, 36, 49} {26, 36, 50} {26, 36, 51} {26, 36, 52}
{26, 36, 53} {26, 36, 54} {26, 36, 55} {26, 36, 56} {26, 36, 57} {26, 36, 58} {26, 36, 59} {26, 36, 60} {26, 36, 61}
{26, 36, 62} {26, 36, 63} {26, 36, 64} {26, 36, 65} {26, 36, 66} {26, 37, 38} {26, 37, 39} {26, 37, 40} {26, 37, 41}
{26, 37, 42} {26, 37, 43} {26, 37, 44} {26, 37, 45} {26, 37, 46} {26, 37, 47} {26, 37, 48} {26, 37, 49} {26, 37, 50}
{26, 37, 51} {26, 37, 52} {26, 37, 53} {26, 37, 54} {26, 37, 55} {26, 37, 56} {26, 37, 57} {26, 37, 58} {26, 37, 59}
{26, 37, 60} {26, 37, 61} {26, 37, 62} {26, 37, 63} {26, 37, 64} {26, 37, 65} {26, 37, 66} {26, 38, 39} {26, 38, 40}
{26, 38, 41} {26, 38, 42} {26, 38, 43} {26, 38, 44} {26, 38, 45} {26, 38, 46} {26, 38, 47} {26, 38, 48} {26, 38, 49}
{26, 38, 50} {26, 38, 51} {26, 38, 52} {26, 38, 53} {26, 38, 54} {26, 38, 55} {26, 38, 56} {26, 38, 57} {26, 38, 58}
{26, 38, 59} {26, 38, 60} {26, 38, 61} {26, 38, 62} {26, 38, 63} {26, 38, 64} {26, 38, 65} {26, 38, 66} {26, 39, 40}

TABLE 3A-continued

{26, 39, 41} {26, 39, 42} {26, 39, 43} {26, 39, 44} {26, 39, 45} {26, 39, 46} {26, 39, 47} {26, 39, 48} {26, 39, 49}
{26, 39, 50} {26, 39, 51} {26, 39, 52} {26, 39, 53} {26, 39, 54} {26, 39, 55} {26, 39, 56} {26, 39, 57} {26, 39, 58}
{26, 39, 59} {26, 39, 60} {26, 39, 61} {26, 39, 62} {26, 39, 63} {26, 39, 64} {26, 39, 65} {26, 39, 66} {26, 40, 41}
{26, 40, 42} {26, 40, 43} {26, 40, 44} {26, 40, 45} {26, 40, 46} {26, 40, 47} {26, 40, 48} {26, 40, 49} {26, 40, 50}
{26, 40, 51} {26, 40, 52} {26, 40, 53} {26, 40, 54} {26, 40, 55} {26, 40, 56} {26, 40, 57} {26, 40, 58} {26, 40, 59}
{26, 40, 60} {26, 40, 61} {26, 40, 62} {26, 40, 63} {26, 40, 64} {26, 40, 65} {26, 40, 66} {26, 41, 42} {26, 41, 43}
{26, 41, 44} {26, 41, 45} {26, 41, 46} {26, 41, 47} {26, 41, 48} {26, 41, 49} {26, 41, 50} {26, 41, 51} {26, 41, 52}
{26, 41, 53} {26, 41, 54} {26, 41, 55} {26, 41, 56} {26, 41, 57} {26, 41, 58} {26, 41, 59} {26, 41, 60} {26, 41, 61}
{26, 41, 62} {26, 41, 63} {26, 41, 64} {26, 41, 65} {26, 41, 66} {26, 42, 43} {26, 42, 44} {26, 42, 45} {26, 42, 46}
{26, 42, 47} {26, 42, 48} {26, 42, 49} {26, 42, 50} {26, 42, 51} {26, 42, 52} {26, 42, 53} {26, 42, 54} {26, 42, 55}
{26, 42, 56} {26, 42, 57} {26, 42, 58} {26, 42, 59} {26, 42, 60} {26, 42, 61} {26, 42, 62} {26, 42, 63} {26, 42, 64}
{26, 42, 65} {26, 42, 66} {26, 43, 44} {26, 43, 45} {26, 43, 46} {26, 43, 47} {26, 43, 48} {26, 43, 49} {26, 43, 50}
{26, 43, 51} {26, 43, 52} {26, 43, 53} {26, 43, 54} {26, 43, 55} {26, 43, 56} {26, 43, 57} {26, 43, 58} {26, 43, 59}
{26, 43, 60} {26, 43, 61} {26, 43, 62} {26, 43, 63} {26, 43, 64} {26, 43, 65} {26, 43, 66} {26, 44, 45} {26, 44, 46}
{26, 44, 47} {26, 44, 48} {26, 44, 49} {26, 44, 50} {26, 44, 51} {26, 44, 52} {26, 44, 53} {26, 44, 54} {26, 44, 55}
{26, 44, 56} {26, 44, 57} {26, 44, 58} {26, 44, 59} {26, 44, 60} {26, 44, 61} {26, 44, 62} {26, 44, 63} {26, 44, 64}
{26, 44, 65} {26, 44, 66} {26, 45, 46} {26, 45, 47} {26, 45, 48} {26, 45, 49} {26, 45, 50} {26, 45, 51} {26, 45, 52}
{26, 45, 53} {26, 45, 54} {26, 45, 55} {26, 45, 56} {26, 45, 57} {26, 45, 58} {26, 45, 59} {26, 45, 60} {26, 45, 61}
{26, 45, 62} {26, 45, 63} {26, 45, 64} {26, 45, 65} {26, 45, 66} {26, 46, 47} {26, 46, 48} {26, 46, 49} {26, 46, 50}
{26, 46, 51} {26, 46, 52} {26, 46, 53} {26, 46, 54} {26, 46, 55} {26, 46, 56} {26, 46, 57} {26, 46, 58} {26, 46, 59}
{26, 46, 60} {26, 46, 61} {26, 46, 62} {26, 46, 63} {26, 46, 64} {26, 46, 65} {26, 46, 66} {26, 47, 48} {26, 47, 49}
{26, 47, 50} {26, 47, 51} {26, 47, 52} {26, 47, 53} {26, 47, 54} {26, 47, 55} {26, 47, 56} {26, 47, 57} {26, 47, 58}
{26, 47, 59} {26, 47, 60} {26, 47, 61} {26, 47, 62} {26, 47, 63} {26, 47, 64} {26, 47, 65} {26, 47, 66} {26, 48, 49}
{26, 48, 50} {26, 48, 51} {26, 48, 52} {26, 48, 53} {26, 48, 54} {26, 48, 55} {26, 48, 56} {26, 48, 57} {26, 48, 58}
{26, 48, 59} {26, 48, 60} {26, 48, 61} {26, 48, 62} {26, 48, 63} {26, 48, 64} {26, 48, 65} {26, 48, 66} {26, 49, 50}
{26, 49, 51} {26, 49, 52} {26, 49, 53} {26, 49, 54} {26, 49, 55} {26, 49, 56} {26, 49, 57} {26, 49, 58} {26, 49, 59}
{26, 49, 60} {26, 49, 61} {26, 49, 62} {26, 49, 63} {26, 49, 64} {26, 49, 65} {26, 49, 66} {26, 50, 51} {26, 50, 52}
{26, 50, 53} {26, 50, 54} {26, 50, 55} {26, 50, 56} {26, 50, 57} {26, 50, 58} {26, 50, 59} {26, 50, 60} {26, 50, 61}
{26, 50, 62} {26, 50, 63} {26, 50, 64} {26, 50, 65} {26, 50, 66} {26, 51, 52} {26, 51, 53} {26, 51, 54} {26, 51, 55}
{26, 51, 56} {26, 51, 57} {26, 51, 58} {26, 51, 59} {26, 51, 60} {26, 51, 61} {26, 51, 62} {26, 51, 63} {26, 51, 64}
{26, 51, 65} {26, 51, 66} {26, 52, 53} {26, 52, 54} {26, 52, 55} {26, 52, 56} {26, 52, 57} {26, 52, 58} {26, 52, 59}
{26, 52, 60} {26, 52, 61} {26, 52, 62} {26, 52, 63} {26, 52, 64} {26, 52, 65} {26, 52, 66} {26, 53, 54} {26, 53, 55}
{26, 53, 56} {26, 53, 57} {26, 53, 58} {26, 53, 59} {26, 53, 60} {26, 53, 61} {26, 53, 62} {26, 53, 63} {26, 53, 64}
{26, 53, 65} {26, 53, 66} {26, 54, 55} {26, 54, 56} {26, 54, 57} {26, 54, 58} {26, 54, 59} {26, 54, 60} {26, 54, 61}
{26, 54, 62} {26, 54, 63} {26, 54, 64} {26, 54, 65} {26, 54, 66} {26, 55, 56} {26, 55, 57} {26, 55, 58} {26, 55, 59}
{26, 55, 60} {26, 55, 61} {26, 55, 62} {26, 55, 63} {26, 55, 64} {26, 55, 65} {26, 55, 66} {26, 56, 57} {26, 56, 58}
{26, 56, 59} {26, 56, 60} {26, 56, 61} {26, 56, 62} {26, 56, 63} {26, 56, 64} {26, 56, 65} {26, 56, 66} {26, 57, 58}
{26, 57, 59} {26, 57, 60} {26, 57, 61} {26, 57, 62} {26, 57, 63} {26, 57, 64} {26, 57, 65} {26, 57, 66} {26, 58, 59}
{26, 58, 60} {26, 58, 61} {26, 58, 62} {26, 58, 63} {26, 58, 64} {26, 58, 65} {26, 58, 66} {26, 59, 60} {26, 59, 61}
{26, 59, 62} {26, 59, 63} {26, 59, 64} {26, 59, 65} {26, 59, 66} {26, 60, 61} {26, 60, 62} {26, 60, 63} {26, 60, 64}
{26, 60, 65} {26, 60, 66} {26, 61, 62} {26, 61, 63} {26, 61, 64} {26, 61, 65} {26, 61, 66} {26, 62, 63} {26, 62, 64}
{26, 62, 65} {26, 62, 66} {26, 63, 64} {26, 63, 65} {26, 63, 66} {26, 64, 65} {26, 64, 66} {26, 65, 66} {27, 28, 29}
{27, 28, 30} {27, 28, 31} {27, 28, 32} {27, 28, 33} {27, 28, 34} {27, 28, 35} {27, 28, 36} {27, 28, 37} {27, 28, 38}
{27, 28, 39} {27, 28, 40} {27, 28, 41} {27, 28, 42} {27, 28, 43} {27, 28, 44} {27, 28, 45} {27, 28, 46} {27, 28, 47}
{27, 28, 48} {27, 28, 49} {27, 28, 50} {27, 28, 51} {27, 28, 52} {27, 28, 53} {27, 28, 54} {27, 28, 55} {27, 28, 56}
{27, 28, 57} {27, 28, 58} {27, 28, 59} {27, 28, 60} {27, 28, 61} {27, 28, 62} {27, 28, 63} {27, 28, 64} {27, 28, 65}
{27, 28, 66} {27, 29, 30} {27, 29, 31} {27, 29, 32} {27, 29, 33} {27, 29, 34} {27, 29, 35} {27, 29, 36} {27, 29, 37}
{27, 29, 38} {27, 29, 39} {27, 29, 40} {27, 29, 41} {27, 29, 42} {27, 29, 43} {27, 29, 44} {27, 29, 45} {27, 29, 46}
{27, 29, 47} {27, 29, 48} {27, 29, 49} {27, 29, 50} {27, 29, 51} {27, 29, 52} {27, 29, 53} {27, 29, 54} {27, 29, 55}
{27, 29, 56} {27, 29, 57} {27, 29, 58} {27, 29, 59} {27, 29, 60} {27, 29, 61} {27, 29, 62} {27, 29, 63} {27, 29, 64}
{27, 29, 65} {27, 29, 66} {27, 30, 31} {27, 30, 32} {27, 30, 33} {27, 30, 34} {27, 30, 35} {27, 30, 36} {27, 30, 37}
{27, 30, 38} {27, 30, 39} {27, 30, 40} {27, 30, 41} {27, 30, 42} {27, 30, 43} {27, 30, 44} {27, 30, 45} {27, 30, 46}
{27, 30, 47} {27, 30, 48} {27, 30, 49} {27, 30, 50} {27, 30, 51} {27, 30, 52} {27, 30, 53} {27, 30, 54} {27, 30, 55}
{27, 30, 56} {27, 30, 57} {27, 30, 58} {27, 30, 59} {27, 30, 60} {27, 30, 61} {27, 30, 62} {27, 30, 63} {27, 30, 64}
{27, 30, 65} {27, 30, 66} {27, 31, 32} {27, 31, 33} {27, 31, 34} {27, 31, 35} {27, 31, 36} {27, 31, 37} {27, 31, 38}
{27, 31, 39} {27, 31, 40} {27, 31, 41} {27, 31, 42} {27, 31, 43} {27, 31, 44} {27, 31, 45} {27, 31, 46} {27, 31, 47}
{27, 31, 48} {27, 31, 49} {27, 31, 50} {27, 31, 51} {27, 31, 52} {27, 31, 53} {27, 31, 54} {27, 31, 55} {27, 31, 56}
{27, 31, 57} {27, 31, 58} {27, 31, 59} {27, 31, 60} {27, 31, 61} {27, 31, 62} {27, 31, 63} {27, 31, 64} {27, 31, 65}
{27, 31, 66} {27, 32, 33} {27, 32, 34} {27, 32, 35} {27, 32, 36} {27, 32, 37} {27, 32, 38} {27, 32, 39} {27, 32, 40}
{27, 32, 41} {27, 32, 42} {27, 32, 43} {27, 32, 44} {27, 32, 45} {27, 32, 46} {27, 32, 47} {27, 32, 48} {27, 32, 49}
{27, 32, 50} {27, 32, 51} {27, 32, 52} {27, 32, 53} {27, 32, 54} {27, 32, 55} {27, 32, 56} {27, 32, 57} {27, 32, 58}
{27, 32, 59} {27, 32, 60} {27, 32, 61} {27, 32, 62} {27, 32, 63} {27, 32, 64} {27, 32, 65} {27, 32, 66} {27, 33, 34}
{27, 33, 35} {27, 33, 36} {27, 33, 37} {27, 33, 38} {27, 33, 39} {27, 33, 40} {27, 33, 41} {27, 33, 42} {27, 33, 43}
{27, 33, 44} {27, 33, 45} {27, 33, 46} {27, 33, 47} {27, 33, 48} {27, 33, 49} {27, 33, 50} {27, 33, 51} {27, 33, 52}
{27, 33, 53} {27, 33, 54} {27, 33, 55} {27, 33, 56} {27, 33, 57} {27, 33, 58} {27, 33, 59} {27, 33, 60} {27, 33, 61}
{27, 33, 62} {27, 33, 63} {27, 33, 64} {27, 33, 65} {27, 33, 66} {27, 34, 35} {27, 34, 36} {27, 34, 37} {27, 34, 38}
{27, 34, 39} {27, 34, 40} {27, 34, 41} {27, 34, 42} {27, 34, 43} {27, 34, 44} {27, 34, 45} {27, 34, 46} {27, 34, 47}
{27, 34, 48} {27, 34, 49} {27, 34, 50} {27, 34, 51} {27, 34, 52} {27, 34, 53} {27, 34, 54} {27, 34, 55} {27, 34, 56}
{27, 34, 57} {27, 34, 58} {27, 34, 59} {27, 34, 60} {27, 34, 61} {27, 34, 62} {27, 34, 63} {27, 34, 64} {27, 34, 65}
{27, 34, 66} {27, 35, 36} {27, 35, 37} {27, 35, 38} {27, 35, 39} {27, 35, 40} {27, 35, 41} {27, 35, 42} {27, 35, 43}
{27, 35, 44} {27, 35, 45} {27, 35, 46} {27, 35, 47} {27, 35, 48} {27, 35, 49} {27, 35, 50} {27, 35, 51} {27, 35, 52}
{27, 35, 53} {27, 35, 54} {27, 35, 55} {27, 35, 56} {27, 35, 57} {27, 35, 58} {27, 35, 59} {27, 35, 60} {27, 35, 61}
{27, 35, 62} {27, 35, 63} {27, 35, 64} {27, 35, 65} {27, 35, 66} {27, 36, 37} {27, 36, 38} {27, 36, 39} {27, 36, 40}
{27, 36, 41} {27, 36, 42} {27, 36, 43} {27, 36, 44} {27, 36, 45} {27, 36, 46} {27, 36, 47} {27, 36, 48} {27, 36, 49}
{27, 36, 50} {27, 36, 51} {27, 36, 52} {27, 36, 53} {27, 36, 54} {27, 36, 55} {27, 36, 56} {27, 36, 57} {27, 36, 58}
{27, 36, 59} {27, 36, 60} {27, 36, 61} {27, 36, 62} {27, 36, 63} {27, 36, 64} {27, 36, 65} {27, 36, 66} {27, 37, 38}
{27, 37, 39} {27, 37, 40} {27, 37, 41} {27, 37, 42} {27, 37, 43} {27, 37, 44} {27, 37, 45} {27, 37, 46} {27, 37, 47}
{27, 37, 48} {27, 37, 49} {27, 37, 50} {27, 37, 51} {27, 37, 52} {27, 37, 53} {27, 37, 54} {27, 37, 55} {27, 37, 56}
{27, 37, 57} {27, 37, 58} {27, 37, 59} {27, 37, 60} {27, 37, 61} {27, 37, 62} {27, 37, 63} {27, 37, 64} {27, 37, 65}
{27, 37, 66} {27, 38, 39} {27, 38, 40} {27, 38, 41} {27, 38, 42} {27, 38, 43} {27, 38, 44} {27, 38, 45} {27, 38, 46}

TABLE 3A-continued

{27, 38, 47} {27, 38, 48} {27, 38, 49} {27, 38, 50} {27, 38, 51} {27, 38, 52} {27, 38, 53} {27, 38, 54} {27, 38, 55}
{27, 38, 56} {27, 38, 57} {27, 38, 58} {27, 38, 59} {27, 38, 60} {27, 38, 61} {27, 38, 62} {27, 38, 63} {27, 38, 64}
{27, 38, 65} {27, 38, 66} {27, 39, 40} {27, 39, 41} {27, 39, 42} {27, 39, 43} {27, 39, 44} {27, 39, 45} {27, 39, 46}
{27, 39, 47} {27, 39, 48} {27, 39, 49} {27, 39, 50} {27, 39, 51} {27, 39, 52} {27, 39, 53} {27, 39, 54} {27, 39, 55}
{27, 39, 56} {27, 39, 57} {27, 39, 58} {27, 39, 59} {27, 39, 60} {27, 39, 61} {27, 39, 62} {27, 39, 63} {27, 39, 64}
{27, 39, 65} {27, 39, 66} {27, 40, 41} {27, 40, 42} {27, 40, 43} {27, 40, 44} {27, 40, 45} {27, 40, 46} {27, 40, 47}
{27, 40, 48} {27, 40, 49} {27, 40, 50} {27, 40, 51} {27, 40, 52} {27, 40, 53} {27, 40, 54} {27, 40, 55} {27, 40, 56}
{27, 40, 57} {27, 40, 58} {27, 40, 59} {27, 40, 60} {27, 40, 61} {27, 40, 62} {27, 40, 63} {27, 40, 64} {27, 40, 65}
{27, 40, 66} {27, 41, 42} {27, 41, 43} {27, 41, 44} {27, 41, 45} {27, 41, 46} {27, 41, 47} {27, 41, 48} {27, 41, 49}
{27, 41, 50} {27, 41, 51} {27, 41, 52} {27, 41, 53} {27, 41, 54} {27, 41, 55} {27, 41, 56} {27, 41, 57} {27, 41, 58}
{27, 41, 59} {27, 41, 60} {27, 41, 61} {27, 41, 62} {27, 41, 63} {27, 41, 64} {27, 41, 65} {27, 41, 66} {27, 42, 43}
{27, 42, 44} {27, 42, 45} {27, 42, 46} {27, 42, 47} {27, 42, 48} {27, 42, 49} {27, 42, 50} {27, 42, 51} {27, 42, 52}
{27, 42, 53} {27, 42, 54} {27, 42, 55} {27, 42, 56} {27, 42, 57} {27, 42, 58} {27, 42, 59} {27, 42, 60} {27, 42, 61}
{27, 42, 62} {27, 42, 63} {27, 42, 64} {27, 42, 65} {27, 42, 66} {27, 43, 44} {27, 43, 45} {27, 43, 46} {27, 43, 47}
{27, 43, 48} {27, 43, 49} {27, 43, 50} {27, 43, 51} {27, 43, 52} {27, 43, 53} {27, 43, 54} {27, 43, 55} {27, 43, 56}
{27, 43, 57} {27, 43, 58} {27, 43, 59} {27, 43, 60} {27, 43, 61} {27, 43, 62} {27, 43, 63} {27, 43, 64} {27, 43, 65}
{27, 43, 66} {27, 44, 45} {27, 44, 46} {27, 44, 47} {27, 44, 48} {27, 44, 49} {27, 44, 50} {27, 44, 51} {27, 44, 52}
{27, 44, 53} {27, 44, 54} {27, 44, 55} {27, 44, 56} {27, 44, 57} {27, 44, 58} {27, 44, 59} {27, 44, 60} {27, 44, 61}
{27, 44, 62} {27, 44, 63} {27, 44, 64} {27, 44, 65} {27, 44, 66} {27, 45, 46} {27, 45, 47} {27, 45, 48} {27, 45, 49}
{27, 45, 50} {27, 45, 51} {27, 45, 52} {27, 45, 53} {27, 45, 54} {27, 45, 55} {27, 45, 56} {27, 45, 57} {27, 45, 58}
{27, 45, 59} {27, 45, 60} {27, 45, 61} {27, 45, 62} {27, 45, 63} {27, 45, 64} {27, 45, 65} {27, 45, 66} {27, 46, 47}
{27, 46, 48} {27, 46, 49} {27, 46, 50} {27, 46, 51} {27, 46, 52} {27, 46, 53} {27, 46, 54} {27, 46, 55} {27, 46, 56}
{27, 46, 57} {27, 46, 58} {27, 46, 59} {27, 46, 60} {27, 46, 61} {27, 46, 62} {27, 46, 63} {27, 46, 64} {27, 46, 65}
{27, 46, 66} {27, 47, 48} {27, 47, 49} {27, 47, 50} {27, 47, 51} {27, 47, 52} {27, 47, 53} {27, 47, 54} {27, 47, 55}
{27, 47, 56} {27, 47, 57} {27, 47, 58} {27, 47, 59} {27, 47, 60} {27, 47, 61} {27, 47, 62} {27, 47, 63} {27, 47, 64}
{27, 47, 65} {27, 47, 66} {27, 48, 49} {27, 48, 50} {27, 48, 51} {27, 48, 52} {27, 48, 53} {27, 48, 54} {27, 48, 55}
{27, 48, 56} {27, 48, 57} {27, 48, 58} {27, 48, 59} {27, 48, 60} {27, 48, 61} {27, 48, 62} {27, 48, 63} {27, 48, 64}
{27, 48, 65} {27, 48, 66} {27, 49, 50} {27, 49, 51} {27, 49, 52} {27, 49, 53} {27, 49, 54} {27, 49, 55} {27, 49, 56}
{27, 49, 57} {27, 49, 58} {27, 49, 59} {27, 49, 60} {27, 49, 61} {27, 49, 62} {27, 49, 63} {27, 49, 64} {27, 49, 65}
{27, 49, 66} {27, 50, 51} {27, 50, 52} {27, 50, 53} {27, 50, 54} {27, 50, 55} {27, 50, 56} {27, 50, 57} {27, 50, 58}
{27, 50, 59} {27, 50, 60} {27, 50, 61} {27, 50, 62} {27, 50, 63} {27, 50, 64} {27, 50, 65} {27, 50, 66} {27, 51, 52}
{27, 51, 53} {27, 51, 54} {27, 51, 55} {27, 51, 56} {27, 51, 57} {27, 51, 58} {27, 51, 59} {27, 51, 60} {27, 51, 61}
{27, 51, 62} {27, 51, 63} {27, 51, 64} {27, 51, 65} {27, 51, 66} {27, 52, 53} {27, 52, 54} {27, 52, 55} {27, 52, 56}
{27, 52, 57} {27, 52, 58} {27, 52, 59} {27, 52, 60} {27, 52, 61} {27, 52, 62} {27, 52, 63} {27, 52, 64} {27, 52, 65}
{27, 52, 66} {27, 53, 54} {27, 53, 55} {27, 53, 56} {27, 53, 57} {27, 53, 58} {27, 53, 59} {27, 53, 60} {27, 53, 61}
{27, 53, 62} {27, 53, 63} {27, 53, 64} {27, 53, 65} {27, 53, 66} {27, 54, 55} {27, 54, 56} {27, 54, 57} {27, 54, 58}
{27, 54, 59} {27, 54, 60} {27, 54, 61} {27, 54, 62} {27, 54, 63} {27, 54, 64} {27, 54, 65} {27, 54, 66} {27, 55, 56}
{27, 55, 57} {27, 55, 58} {27, 55, 59} {27, 55, 60} {27, 55, 61} {27, 55, 62} {27, 55, 63} {27, 55, 64} {27, 55, 65}
{27, 55, 66} {27, 56, 57} {27, 56, 58} {27, 56, 59} {27, 56, 60} {27, 56, 61} {27, 56, 62} {27, 56, 63} {27, 56, 64}
{27, 56, 65} {27, 56, 66} {27, 57, 58} {27, 57, 59} {27, 57, 60} {27, 57, 61} {27, 57, 62} {27, 57, 63} {27, 57, 64}
{27, 57, 65} {27, 57, 66} {27, 58, 59} {27, 58, 60} {27, 58, 61} {27, 58, 62} {27, 58, 63} {27, 58, 64} {27, 58, 65}
{27, 58, 66} {27, 59, 60} {27, 59, 61} {27, 59, 62} {27, 59, 63} {27, 59, 64} {27, 59, 65} {27, 59, 66} {27, 60, 61}
{27, 60, 62} {27, 60, 63} {27, 60, 64} {27, 60, 65} {27, 60, 66} {27, 61, 62} {27, 61, 63} {27, 61, 64} {27, 61, 65}
{27, 61, 66} {27, 62, 63} {27, 62, 64} {27, 62, 65} {27, 62, 66} {27, 63, 64} {27, 63, 65} {27, 63, 66} {27, 64, 65}
{27, 64, 66} {27, 65, 66} {28, 29, 30} {28, 29, 31} {28, 29, 32} {28, 29, 33} {28, 29, 34} {28, 29, 35} {28, 29, 36}
{28, 29, 37} {28, 29, 38} {28, 29, 39} {28, 29, 40} {28, 29, 41} {28, 29, 42} {28, 29, 43} {28, 29, 44} {28, 29, 45}
{28, 29, 46} {28, 29, 47} {28, 29, 48} {28, 29, 49} {28, 29, 50} {28, 29, 51} {28, 29, 52} {28, 29, 53} {28, 29, 54}
{28, 29, 55} {28, 29, 56} {28, 29, 57} {28, 29, 58} {28, 29, 59} {28, 29, 60} {28, 29, 61} {28, 29, 62} {28, 29, 63}
{28, 29, 64} {28, 29, 65} {28, 29, 66} {28, 30, 31} {28, 30, 32} {28, 30, 33} {28, 30, 34} {28, 30, 35} {28, 30, 36}
{28, 30, 37} {28, 30, 38} {28, 30, 39} {28, 30, 40} {28, 30, 41} {28, 30, 42} {28, 30, 43} {28, 30, 44} {28, 30, 45}
{28, 30, 46} {28, 30, 47} {28, 30, 48} {28, 30, 49} {28, 30, 50} {28, 30, 51} {28, 30, 52} {28, 30, 53} {28, 30, 54}
{28, 30, 55} {28, 30, 56} {28, 30, 57} {28, 30, 58} {28, 30, 59} {28, 30, 60} {28, 30, 61} {28, 30, 62} {28, 30, 63}
{28, 30, 64} {28, 30, 65} {28, 30, 66} {28, 31, 32} {28, 31, 33} {28, 31, 34} {28, 31, 35} {28, 31, 36} {28, 31, 37}
{28, 31, 38} {28, 31, 39} {28, 31, 40} {28, 31, 41} {28, 31, 42} {28, 31, 43} {28, 31, 44} {28, 31, 45} {28, 31, 46}
{28, 31, 47} {28, 31, 48} {28, 31, 49} {28, 31, 50} {28, 31, 51} {28, 31, 52} {28, 31, 53} {28, 31, 54} {28, 31, 55}
{28, 31, 56} {28, 31, 57} {28, 31, 58} {28, 31, 59} {28, 31, 60} {28, 31, 61} {28, 31, 62} {28, 31, 63} {28, 31, 64}
{28, 31, 65} {28, 31, 66} {28, 32, 33} {28, 32, 34} {28, 32, 35} {28, 32, 36} {28, 32, 37} {28, 32, 38} {28, 32, 39}
{28, 32, 40} {28, 32, 41} {28, 32, 42} {28, 32, 43} {28, 32, 44} {28, 32, 45} {28, 32, 46} {28, 32, 47} {28, 32, 48}
{28, 32, 49} {28, 32, 50} {28, 32, 51} {28, 32, 52} {28, 32, 53} {28, 32, 54} {28, 32, 55} {28, 32, 56} {28, 32, 57}
{28, 32, 58} {28, 32, 59} {28, 32, 60} {28, 32, 61} {28, 32, 62} {28, 32, 63} {28, 32, 64} {28, 32, 65} {28, 32, 66}
{28, 33, 34} {28, 33, 35} {28, 33, 36} {28, 33, 37} {28, 33, 38} {28, 33, 39} {28, 33, 40} {28, 33, 41} {28, 33, 42}
{28, 33, 43} {28, 33, 44} {28, 33, 45} {28, 33, 46} {28, 33, 47} {28, 33, 48} {28, 33, 49} {28, 33, 50} {28, 33, 51}
{28, 33, 52} {28, 33, 53} {28, 33, 54} {28, 33, 55} {28, 33, 56} {28, 33, 57} {28, 33, 58} {28, 33, 59} {28, 33, 60}
{28, 33, 61} {28, 33, 62} {28, 33, 63} {28, 33, 64} {28, 33, 65} {28, 33, 66} {28, 34, 35} {28, 34, 36} {28, 34, 37}
{28, 34, 38} {28, 34, 39} {28, 34, 40} {28, 34, 41} {28, 34, 42} {28, 34, 43} {28, 34, 44} {28, 34, 45} {28, 34, 46}
{28, 34, 47} {28, 34, 48} {28, 34, 49} {28, 34, 50} {28, 34, 51} {28, 34, 52} {28, 34, 53} {28, 34, 54} {28, 34, 55}
{28, 34, 56} {28, 34, 57} {28, 34, 58} {28, 34, 59} {28, 34, 60} {28, 34, 61} {28, 34, 62} {28, 34, 63} {28, 34, 64}
{28, 34, 65} {28, 34, 66} {28, 35, 36} {28, 35, 37} {28, 35, 38} {28, 35, 39} {28, 35, 40} {28, 35, 41} {28, 35, 42}
{28, 35, 43} {28, 35, 44} {28, 35, 45} {28, 35, 46} {28, 35, 47} {28, 35, 48} {28, 35, 49} {28, 35, 50} {28, 35, 51}
{28, 35, 52} {28, 35, 53} {28, 35, 54} {28, 35, 55} {28, 35, 56} {28, 35, 57} {28, 35, 58} {28, 35, 59} {28, 35, 60}
{28, 35, 61} {28, 35, 62} {28, 35, 63} {28, 35, 64} {28, 35, 65} {28, 35, 66} {28, 36, 37} {28, 36, 38} {28, 36, 39}
{28, 36, 40} {28, 36, 41} {28, 36, 42} {28, 36, 43} {28, 36, 44} {28, 36, 45} {28, 36, 46} {28, 36, 47} {28, 36, 48}
{28, 36, 49} {28, 36, 50} {28, 36, 51} {28, 36, 52} {28, 36, 53} {28, 36, 54} {28, 36, 55} {28, 36, 56} {28, 36, 57}
{28, 36, 58} {28, 36, 59} {28, 36, 60} {28, 36, 61} {28, 36, 62} {28, 36, 63} {28, 36, 64} {28, 36, 65} {28, 36, 66}
{28, 37, 38} {28, 37, 39} {28, 37, 40} {28, 37, 41} {28, 37, 42} {28, 37, 43} {28, 37, 44} {28, 37, 45} {28, 37, 46}
{28, 37, 47} {28, 37, 48} {28, 37, 49} {28, 37, 50} {28, 37, 51} {28, 37, 52} {28, 37, 53} {28, 37, 54} {28, 37, 55}
{28, 37, 56} {28, 37, 57} {28, 37, 58} {28, 37, 59} {28, 37, 60} {28, 37, 61} {28, 37, 62} {28, 37, 63} {28, 37, 64}
{28, 37, 65} {28, 37, 66} {28, 38, 39} {28, 38, 40} {28, 38, 41} {28, 38, 42} {28, 38, 43} {28, 38, 44} {28, 38, 45}
{28, 38, 46} {28, 38, 47} {28, 38, 48} {28, 38, 49} {28, 38, 50} {28, 38, 51} {28, 38, 52} {28, 38, 53} {28, 38, 54}
{28, 38, 55} {28, 38, 56} {28, 38, 57} {28, 38, 58} {28, 38, 59} {28, 38, 60} {28, 38, 61} {28, 38, 62} {28, 38, 63}

TABLE 3A-continued

| | | | | | | | | |
|---|---|---|---|---|---|---|---|---|
| {28, 38, 64} | {28, 38, 65} | {28, 38, 66} | {28, 39, 40} | {28, 39, 41} | {28, 39, 42} | {28, 39, 43} | {28, 39, 44} | {28, 39, 45} |
| {28, 39, 46} | {28, 39, 47} | {28, 39, 48} | {28, 39, 49} | {28, 39, 50} | {28, 39, 51} | {28, 39, 52} | {28, 39, 53} | {28, 39, 54} |
| {28, 39, 55} | {28, 39, 56} | {28, 39, 57} | {28, 39, 58} | {28, 39, 59} | {28, 39, 60} | {28, 39, 61} | {28, 39, 62} | {28, 39, 63} |
| {28, 39, 64} | {28, 39, 65} | {28, 39, 66} | {28, 40, 41} | {28, 40, 42} | {28, 40, 43} | {28, 40, 44} | {28, 40, 45} | {28, 40, 46} |
| {28, 40, 47} | {28, 40, 48} | {28, 40, 49} | {28, 40, 50} | {28, 40, 51} | {28, 40, 52} | {28, 40, 53} | {28, 40, 54} | {28, 40, 55} |
| {28, 40, 56} | {28, 40, 57} | {28, 40, 58} | {28, 40, 59} | {28, 40, 60} | {28, 40, 61} | {28, 40, 62} | {28, 40, 63} | {28, 40, 64} |
| {28, 40, 65} | {28, 40, 66} | {28, 41, 42} | {28, 41, 43} | {28, 41, 44} | {28, 41, 45} | {28, 41, 46} | {28, 41, 47} | {28, 41, 48} |
| {28, 41, 49} | {28, 41, 50} | {28, 41, 51} | {28, 41, 52} | {28, 41, 53} | {28, 41, 54} | {28, 41, 55} | {28, 41, 56} | {28, 41, 57} |
| {28, 41, 58} | {28, 41, 59} | {28, 41, 60} | {28, 41, 61} | {28, 41, 62} | {28, 41, 63} | {28, 41, 64} | {28, 41, 65} | {28, 41, 66} |
| {28, 42, 43} | {28, 42, 44} | {28, 42, 45} | {28, 42, 46} | {28, 42, 47} | {28, 42, 48} | {28, 42, 49} | {28, 42, 50} | {28, 42, 51} |
| {28, 42, 52} | {28, 42, 53} | {28, 42, 54} | {28, 42, 55} | {28, 42, 56} | {28, 42, 57} | {28, 42, 58} | {28, 42, 59} | {28, 42, 60} |
| {28, 42, 61} | {28, 42, 62} | {28, 42, 63} | {28, 42, 64} | {28, 42, 65} | {28, 42, 66} | {28, 43, 44} | {28, 43, 45} | {28, 43, 46} |
| {28, 43, 47} | {28, 43, 48} | {28, 43, 49} | {28, 43, 50} | {28, 43, 51} | {28, 43, 52} | {28, 43, 53} | {28, 43, 54} | {28, 43, 55} |
| {28, 43, 56} | {28, 43, 57} | {28, 43, 58} | {28, 43, 59} | {28, 43, 60} | {28, 43, 61} | {28, 43, 62} | {28, 43, 63} | {28, 43, 64} |
| {28, 43, 65} | {28, 43, 66} | {28, 44, 45} | {28, 44, 46} | {28, 44, 47} | {28, 44, 48} | {28, 44, 49} | {28, 44, 50} | {28, 44, 51} |
| {28, 44, 52} | {28, 44, 53} | {28, 44, 54} | {28, 44, 55} | {28, 44, 56} | {28, 44, 57} | {28, 44, 58} | {28, 44, 59} | {28, 44, 60} |
| {28, 44, 61} | {28, 44, 62} | {28, 44, 63} | {28, 44, 64} | {28, 44, 65} | {28, 44, 66} | {28, 45, 46} | {28, 45, 47} | {28, 45, 48} |
| {28, 45, 49} | {28, 45, 50} | {28, 45, 51} | {28, 45, 52} | {28, 45, 53} | {28, 45, 54} | {28, 45, 55} | {28, 45, 56} | {28, 45, 57} |
| {28, 45, 58} | {28, 45, 59} | {28, 45, 60} | {28, 45, 61} | {28, 45, 62} | {28, 45, 63} | {28, 45, 64} | {28, 45, 65} | {28, 45, 66} |
| {28, 46, 47} | {28, 46, 48} | {28, 46, 49} | {28, 46, 50} | {28, 46, 51} | {28, 46, 52} | {28, 46, 53} | {28, 46, 54} | {28, 46, 55} |
| {28, 46, 56} | {28, 46, 57} | {28, 46, 58} | {28, 46, 59} | {28, 46, 60} | {28, 46, 61} | {28, 46, 62} | {28, 46, 63} | {28, 46, 64} |
| {28, 46, 65} | {28, 46, 66} | {28, 47, 48} | {28, 47, 49} | {28, 47, 50} | {28, 47, 51} | {28, 47, 52} | {28, 47, 53} | {28, 47, 54} |
| {28, 47, 55} | {28, 47, 56} | {28, 47, 57} | {28, 47, 58} | {28, 47, 59} | {28, 47, 60} | {28, 47, 61} | {28, 47, 62} | {28, 47, 63} |
| {28, 47, 64} | {28, 47, 65} | {28, 47, 66} | {28, 48, 49} | {28, 48, 50} | {28, 48, 51} | {28, 48, 52} | {28, 48, 53} | {28, 48, 54} |
| {28, 48, 55} | {28, 48, 56} | {28, 48, 57} | {28, 48, 58} | {28, 48, 59} | {28, 48, 60} | {28, 48, 61} | {28, 48, 62} | {28, 48, 63} |
| {28, 48, 64} | {28, 48, 65} | {28, 48, 66} | {28, 49, 50} | {28, 49, 51} | {28, 49, 52} | {28, 49, 53} | {28, 49, 54} | {28, 49, 55} |
| {28, 49, 56} | {28, 49, 57} | {28, 49, 58} | {28, 49, 59} | {28, 49, 60} | {28, 49, 61} | {28, 49, 62} | {28, 49, 63} | {28, 49, 64} |
| {28, 49, 65} | {28, 49, 66} | {28, 50, 51} | {28, 50, 52} | {28, 50, 53} | {28, 50, 54} | {28, 50, 55} | {28, 50, 56} | {28, 50, 57} |
| {28, 50, 58} | {28, 50, 59} | {28, 50, 60} | {28, 50, 61} | {28, 50, 62} | {28, 50, 63} | {28, 50, 64} | {28, 50, 65} | {28, 50, 66} |
| {28, 51, 52} | {28, 51, 53} | {28, 51, 54} | {28, 51, 55} | {28, 51, 56} | {28, 51, 57} | {28, 51, 58} | {28, 51, 59} | {28, 51, 60} |
| {28, 51, 61} | {28, 51, 62} | {28, 51, 63} | {28, 51, 64} | {28, 51, 65} | {28, 51, 66} | {28, 52, 53} | {28, 52, 54} | {28, 52, 55} |
| {28, 52, 56} | {28, 52, 57} | {28, 52, 58} | {28, 52, 59} | {28, 52, 60} | {28, 52, 61} | {28, 52, 62} | {28, 52, 63} | {28, 52, 64} |
| {28, 52, 65} | {28, 52, 66} | {28, 53, 54} | {28, 53, 55} | {28, 53, 56} | {28, 53, 57} | {28, 53, 58} | {28, 53, 59} | {28, 53, 60} |
| {28, 53, 61} | {28, 53, 62} | {28, 53, 63} | {28, 53, 64} | {28, 53, 65} | {28, 53, 66} | {28, 54, 55} | {28, 54, 56} | {28, 54, 57} |
| {28, 54, 58} | {28, 54, 59} | {28, 54, 60} | {28, 54, 61} | {28, 54, 62} | {28, 54, 63} | {28, 54, 64} | {28, 54, 65} | {28, 54, 66} |
| {28, 55, 56} | {28, 55, 57} | {28, 55, 58} | {28, 55, 59} | {28, 55, 60} | {28, 55, 61} | {28, 55, 62} | {28, 55, 63} | {28, 55, 64} |
| {28, 55, 65} | {28, 55, 66} | {28, 56, 57} | {28, 56, 58} | {28, 56, 59} | {28, 56, 60} | {28, 56, 61} | {28, 56, 62} | {28, 56, 63} |
| {28, 56, 64} | {28, 56, 65} | {28, 56, 66} | {28, 57, 58} | {28, 57, 59} | {28, 57, 60} | {28, 57, 61} | {28, 57, 62} | {28, 57, 63} |
| {28, 57, 64} | {28, 57, 65} | {28, 57, 66} | {28, 58, 59} | {28, 58, 60} | {28, 58, 61} | {28, 58, 62} | {28, 58, 63} | {28, 58, 64} |
| {28, 58, 65} | {28, 58, 66} | {28, 59, 60} | {28, 59, 61} | {28, 59, 62} | {28, 59, 63} | {28, 59, 64} | {28, 59, 65} | {28, 59, 66} |
| {28, 60, 61} | {28, 60, 62} | {28, 60, 63} | {28, 60, 64} | {28, 60, 65} | {28, 60, 66} | {28, 61, 62} | {28, 61, 63} | {28, 61, 64} |
| {28, 61, 65} | {28, 61, 66} | {28, 62, 63} | {28, 62, 64} | {28, 62, 65} | {28, 62, 66} | {28, 63, 64} | {28, 63, 65} | {28, 63, 66} |
| {28, 64, 65} | {28, 64, 66} | {28, 65, 66} | {29, 30, 31} | {29, 30, 32} | {29, 30, 33} | {29, 30, 34} | {29, 30, 35} | {29, 30, 36} |
| {29, 30, 37} | {29, 30, 38} | {29, 30, 39} | {29, 30, 40} | {29, 30, 41} | {29, 30, 42} | {29, 30, 43} | {29, 30, 44} | {29, 30, 45} |
| {29, 30, 46} | {29, 30, 47} | {29, 30, 48} | {29, 30, 49} | {29, 30, 50} | {29, 30, 51} | {29, 30, 52} | {29, 30, 53} | {29, 30, 54} |
| {29, 30, 55} | {29, 30, 56} | {29, 30, 57} | {29, 30, 58} | {29, 30, 59} | {29, 30, 60} | {29, 30, 61} | {29, 30, 62} | {29, 30, 63} |
| {29, 30, 64} | {29, 30, 65} | {29, 30, 66} | {29, 31, 32} | {29, 31, 33} | {29, 31, 34} | {29, 31, 35} | {29, 31, 36} | {29, 31, 37} |
| {29, 31, 38} | {29, 31, 39} | {29, 31, 40} | {29, 31, 41} | {29, 31, 42} | {29, 31, 43} | {29, 31, 44} | {29, 31, 45} | {29, 31, 46} |
| {29, 31, 47} | {29, 31, 48} | {29, 31, 49} | {29, 31, 50} | {29, 31, 51} | {29, 31, 52} | {29, 31, 53} | {29, 31, 54} | {29, 31, 55} |
| {29, 31, 56} | {29, 31, 57} | {29, 31, 58} | {29, 31, 59} | {29, 31, 60} | {29, 31, 61} | {29, 31, 62} | {29, 31, 63} | {29, 31, 64} |
| {29, 31, 65} | {29, 31, 66} | {29, 32, 33} | {29, 32, 34} | {29, 32, 35} | {29, 32, 36} | {29, 32, 37} | {29, 32, 38} | {29, 32, 39} |
| {29, 32, 40} | {29, 32, 41} | {29, 32, 42} | {29, 32, 43} | {29, 32, 44} | {29, 32, 45} | {29, 32, 46} | {29, 32, 47} | {29, 32, 48} |
| {29, 32, 49} | {29, 32, 50} | {29, 32, 51} | {29, 32, 52} | {29, 32, 53} | {29, 32, 54} | {29, 32, 55} | {29, 32, 56} | {29, 32, 57} |
| {29, 32, 58} | {29, 32, 59} | {29, 32, 60} | {29, 32, 61} | {29, 32, 62} | {29, 32, 63} | {29, 32, 64} | {29, 32, 65} | {29, 32, 66} |
| {29, 33, 34} | {29, 33, 35} | {29, 33, 36} | {29, 33, 37} | {29, 33, 38} | {29, 33, 39} | {29, 33, 40} | {29, 33, 41} | {29, 33, 42} |
| {29, 33, 43} | {29, 33, 44} | {29, 33, 45} | {29, 33, 46} | {29, 33, 47} | {29, 33, 48} | {29, 33, 49} | {29, 33, 50} | {29, 33, 51} |
| {29, 33, 52} | {29, 33, 53} | {29, 33, 54} | {29, 33, 55} | {29, 33, 56} | {29, 33, 57} | {29, 33, 58} | {29, 33, 59} | {29, 33, 60} |
| {29, 33, 61} | {29, 33, 62} | {29, 33, 63} | {29, 33, 64} | {29, 33, 65} | {29, 33, 66} | {29, 34, 35} | {29, 34, 36} | {29, 34, 37} |
| {29, 34, 38} | {29, 34, 39} | {29, 34, 40} | {29, 34, 41} | {29, 34, 42} | {29, 34, 43} | {29, 34, 44} | {29, 34, 45} | {29, 34, 46} |
| {29, 34, 47} | {29, 34, 48} | {29, 34, 49} | {29, 34, 50} | {29, 34, 51} | {29, 34, 52} | {29, 34, 53} | {29, 34, 54} | {29, 34, 55} |
| {29, 34, 56} | {29, 34, 57} | {29, 34, 58} | {29, 34, 59} | {29, 34, 60} | {29, 34, 61} | {29, 34, 62} | {29, 34, 63} | {29, 34, 64} |
| {29, 34, 65} | {29, 34, 66} | {29, 35, 36} | {29, 35, 37} | {29, 35, 38} | {29, 35, 39} | {29, 35, 40} | {29, 35, 41} | {29, 35, 42} |
| {29, 35, 43} | {29, 35, 44} | {29, 35, 45} | {29, 35, 46} | {29, 35, 47} | {29, 35, 48} | {29, 35, 49} | {29, 35, 50} | {29, 35, 51} |
| {29, 35, 52} | {29, 35, 53} | {29, 35, 54} | {29, 35, 55} | {29, 35, 56} | {29, 35, 57} | {29, 35, 58} | {29, 35, 59} | {29, 35, 60} |
| {29, 35, 61} | {29, 35, 62} | {29, 35, 63} | {29, 35, 64} | {29, 35, 65} | {29, 35, 66} | {29, 36, 37} | {29, 36, 38} | {29, 36, 39} |
| {29, 36, 40} | {29, 36, 41} | {29, 36, 42} | {29, 36, 43} | {29, 36, 44} | {29, 36, 45} | {29, 36, 46} | {29, 36, 47} | {29, 36, 48} |
| {29, 36, 49} | {29, 36, 50} | {29, 36, 51} | {29, 36, 52} | {29, 36, 53} | {29, 36, 54} | {29, 36, 55} | {29, 36, 56} | {29, 36, 57} |
| {29, 36, 58} | {29, 36, 59} | {29, 36, 60} | {29, 36, 61} | {29, 36, 62} | {29, 36, 63} | {29, 36, 64} | {29, 36, 65} | {29, 36, 66} |
| {29, 37, 38} | {29, 37, 39} | {29, 37, 40} | {29, 37, 41} | {29, 37, 42} | {29, 37, 43} | {29, 37, 44} | {29, 37, 45} | {29, 37, 46} |
| {29, 37, 47} | {29, 37, 48} | {29, 37, 49} | {29, 37, 50} | {29, 37, 51} | {29, 37, 52} | {29, 37, 53} | {29, 37, 54} | {29, 37, 55} |
| {29, 37, 56} | {29, 37, 57} | {29, 37, 58} | {29, 37, 59} | {29, 37, 60} | {29, 37, 61} | {29, 37, 62} | {29, 37, 63} | {29, 37, 64} |
| {29, 37, 65} | {29, 37, 66} | {29, 38, 39} | {29, 38, 40} | {29, 38, 41} | {29, 38, 42} | {29, 38, 43} | {29, 38, 44} | {29, 38, 45} |
| {29, 38, 46} | {29, 38, 47} | {29, 38, 48} | {29, 38, 49} | {29, 38, 50} | {29, 38, 51} | {29, 38, 52} | {29, 38, 53} | {29, 38, 54} |
| {29, 38, 55} | {29, 38, 56} | {29, 38, 57} | {29, 38, 58} | {29, 38, 59} | {29, 38, 60} | {29, 38, 61} | {29, 38, 62} | {29, 38, 63} |
| {29, 38, 64} | {29, 38, 65} | {29, 38, 66} | {29, 39, 40} | {29, 39, 41} | {29, 39, 42} | {29, 39, 43} | {29, 39, 44} | {29, 39, 45} |
| {29, 39, 46} | {29, 39, 47} | {29, 39, 48} | {29, 39, 49} | {29, 39, 50} | {29, 39, 51} | {29, 39, 52} | {29, 39, 53} | {29, 39, 54} |
| {29, 39, 55} | {29, 39, 56} | {29, 39, 57} | {29, 39, 58} | {29, 39, 59} | {29, 39, 60} | {29, 39, 61} | {29, 39, 62} | {29, 39, 63} |
| {29, 39, 64} | {29, 39, 65} | {29, 39, 66} | {29, 40, 41} | {29, 40, 42} | {29, 40, 43} | {29, 40, 44} | {29, 40, 45} | {29, 40, 46} |
| {29, 40, 47} | {29, 40, 48} | {29, 40, 49} | {29, 40, 50} | {29, 40, 51} | {29, 40, 52} | {29, 40, 53} | {29, 40, 54} | {29, 40, 55} |
| {29, 40, 56} | {29, 40, 57} | {29, 40, 58} | {29, 40, 59} | {29, 40, 60} | {29, 40, 61} | {29, 40, 62} | {29, 40, 63} | {29, 40, 64} |

TABLE 3A-continued

{29, 40, 65} {29, 40, 66} {29, 41, 42} {29, 41, 43} {29, 41, 44} {29, 41, 45} {29, 41, 46} {29, 41, 47} {29, 41, 48}
{29, 41, 49} {29, 41, 50} {29, 41, 51} {29, 41, 52} {29, 41, 53} {29, 41, 54} {29, 41, 55} {29, 41, 56} {29, 41, 57}
{29, 41, 58} {29, 41, 59} {29, 41, 60} {29, 41, 61} {29, 41, 62} {29, 41, 63} {29, 41, 64} {29, 41, 65} {29, 41, 66}
{29, 42, 43} {29, 42, 44} {29, 42, 45} {29, 42, 46} {29, 42, 47} {29, 42, 48} {29, 42, 49} {29, 42, 50} {29, 42, 51}
{29, 42, 52} {29, 42, 53} {29, 42, 54} {29, 42, 55} {29, 42, 56} {29, 42, 57} {29, 42, 58} {29, 42, 59} {29, 42, 60}
{29, 42, 61} {29, 42, 62} {29, 42, 63} {29, 42, 64} {29, 42, 65} {29, 42, 66} {29, 43, 44} {29, 43, 45} {29, 43, 46}
{29, 43, 47} {29, 43, 48} {29, 43, 49} {29, 43, 50} {29, 43, 51} {29, 43, 52} {29, 43, 53} {29, 43, 54} {29, 43, 55}
{29, 43, 56} {29, 43, 57} {29, 43, 58} {29, 43, 59} {29, 43, 60} {29, 43, 61} {29, 43, 62} {29, 43, 63} {29, 43, 64}
{29, 43, 65} {29, 43, 66} {29, 44, 45} {29, 44, 46} {29, 44, 47} {29, 44, 48} {29, 44, 49} {29, 44, 50} {29, 44, 51}
{29, 44, 52} {29, 44, 53} {29, 44, 54} {29, 44, 55} {29, 44, 56} {29, 44, 57} {29, 44, 58} {29, 44, 59} {29, 44, 60}
{29, 44, 61} {29, 44, 62} {29, 44, 63} {29, 44, 64} {29, 44, 65} {29, 44, 66} {29, 45, 46} {29, 45, 47} {29, 45, 48}
{29, 45, 49} {29, 45, 50} {29, 45, 51} {29, 45, 52} {29, 45, 53} {29, 45, 54} {29, 45, 55} {29, 45, 56} {29, 45, 57}
{29, 45, 58} {29, 45, 59} {29, 45, 60} {29, 45, 61} {29, 45, 62} {29, 45, 63} {29, 45, 64} {29, 45, 65} {29, 45, 66}
{29, 46, 47} {29, 46, 48} {29, 46, 49} {29, 46, 50} {29, 46, 51} {29, 46, 52} {29, 46, 53} {29, 46, 54} {29, 46, 55}
{29, 46, 56} {29, 46, 57} {29, 46, 58} {29, 46, 59} {29, 46, 60} {29, 46, 61} {29, 46, 62} {29, 46, 63} {29, 46, 64}
{29, 46, 65} {29, 46, 66} {29, 47, 48} {29, 47, 49} {29, 47, 50} {29, 47, 51} {29, 47, 52} {29, 47, 53} {29, 47, 54}
{29, 47, 55} {29, 47, 56} {29, 47, 57} {29, 47, 58} {29, 47, 59} {29, 47, 60} {29, 47, 61} {29, 47, 62} {29, 47, 63}
{29, 47, 64} {29, 47, 65} {29, 47, 66} {29, 48, 49} {29, 48, 50} {29, 48, 51} {29, 48, 52} {29, 48, 53} {29, 48, 54}
{29, 48, 55} {29, 48, 56} {29, 48, 57} {29, 48, 58} {29, 48, 59} {29, 48, 60} {29, 48, 61} {29, 48, 62} {29, 48, 63}
{29, 48, 64} {29, 48, 65} {29, 48, 66} {29, 49, 50} {29, 49, 51} {29, 49, 52} {29, 49, 53} {29, 49, 54} {29, 49, 55}
{29, 49, 56} {29, 49, 57} {29, 49, 58} {29, 49, 59} {29, 49, 60} {29, 49, 61} {29, 49, 62} {29, 49, 63} {29, 49, 64}
{29, 49, 65} {29, 49, 66} {29, 50, 51} {29, 50, 52} {29, 50, 53} {29, 50, 54} {29, 50, 55} {29, 50, 56} {29, 50, 57}
{29, 50, 58} {29, 50, 59} {29, 50, 60} {29, 50, 61} {29, 50, 62} {29, 50, 63} {29, 50, 64} {29, 50, 65} {29, 50, 66}
{29, 51, 52} {29, 51, 53} {29, 51, 54} {29, 51, 55} {29, 51, 56} {29, 51, 57} {29, 51, 58} {29, 51, 59} {29, 51, 60}
{29, 51, 61} {29, 51, 62} {29, 51, 63} {29, 51, 64} {29, 51, 65} {29, 51, 66} {29, 52, 53} {29, 52, 54} {29, 52, 55}
{29, 52, 56} {29, 52, 57} {29, 52, 58} {29, 52, 59} {29, 52, 60} {29, 52, 61} {29, 52, 62} {29, 52, 63} {29, 52, 64}
{29, 52, 65} {29, 52, 66} {29, 53, 54} {29, 53, 55} {29, 53, 56} {29, 53, 57} {29, 53, 58} {29, 53, 59} {29, 53, 60}
{29, 53, 61} {29, 53, 62} {29, 53, 63} {29, 53, 64} {29, 53, 65} {29, 53, 66} {29, 54, 55} {29, 54, 56} {29, 54, 57}
{29, 54, 58} {29, 54, 59} {29, 54, 60} {29, 54, 61} {29, 54, 62} {29, 54, 63} {29, 54, 64} {29, 54, 65} {29, 54, 66}
{29, 55, 56} {29, 55, 57} {29, 55, 58} {29, 55, 59} {29, 55, 60} {29, 55, 61} {29, 55, 62} {29, 55, 63} {29, 55, 64}
{29, 55, 65} {29, 55, 66} {29, 56, 57} {29, 56, 58} {29, 56, 59} {29, 56, 60} {29, 56, 61} {29, 56, 62} {29, 56, 63}
{29, 56, 64} {29, 56, 65} {29, 56, 66} {29, 57, 58} {29, 57, 59} {29, 57, 60} {29, 57, 61} {29, 57, 62} {29, 57, 63}
{29, 57, 64} {29, 57, 65} {29, 57, 66} {29, 58, 59} {29, 58, 60} {29, 58, 61} {29, 58, 62} {29, 58, 63} {29, 58, 64}
{29, 58, 65} {29, 58, 66} {29, 59, 60} {29, 59, 61} {29, 59, 62} {29, 59, 63} {29, 59, 64} {29, 59, 65} {29, 59, 66}
{29, 60, 61} {29, 60, 62} {29, 60, 63} {29, 60, 64} {29, 60, 65} {29, 60, 66} {29, 61, 62} {29, 61, 63} {29, 61, 64}
{29, 61, 65} {29, 61, 66} {29, 62, 63} {29, 62, 64} {29, 62, 65} {29, 62, 66} {29, 63, 64} {29, 63, 65} {29, 63, 66}
{29, 64, 65} {29, 64, 66} {29, 65, 66} {30, 31, 32} {30, 31, 33} {30, 31, 34} {30, 31, 35} {30, 31, 36} {30, 31, 37}
{30, 31, 38} {30, 31, 39} {30, 31, 40} {30, 31, 41} {30, 31, 42} {30, 31, 43} {30, 31, 44} {30, 31, 45} {30, 31, 46}
{30, 31, 47} {30, 31, 48} {30, 31, 49} {30, 31, 50} {30, 31, 51} {30, 31, 52} {30, 31, 53} {30, 31, 54} {30, 31, 55}
{30, 31, 56} {30, 31, 57} {30, 31, 58} {30, 31, 59} {30, 31, 60} {30, 31, 61} {30, 31, 62} {30, 31, 63} {30, 31, 64}
{30, 31, 65} {30, 31, 66} {30, 32, 33} {30, 32, 34} {30, 32, 35} {30, 32, 36} {30, 32, 37} {30, 32, 38} {30, 32, 39}
{30, 32, 40} {30, 32, 41} {30, 32, 42} {30, 32, 43} {30, 32, 44} {30, 32, 45} {30, 32, 46} {30, 32, 47} {30, 32, 48}
{30, 32, 49} {30, 32, 50} {30, 32, 51} {30, 32, 52} {30, 32, 53} {30, 32, 54} {30, 32, 55} {30, 32, 56} {30, 32, 57}
{30, 32, 58} {30, 32, 59} {30, 32, 60} {30, 32, 61} {30, 32, 62} {30, 32, 63} {30, 32, 64} {30, 32, 65} {30, 32, 66}
{30, 33, 34} {30, 33, 35} {30, 33, 36} {30, 33, 37} {30, 33, 38} {30, 33, 39} {30, 33, 40} {30, 33, 41} {30, 33, 42}
{30, 33, 43} {30, 33, 44} {30, 33, 45} {30, 33, 46} {30, 33, 47} {30, 33, 48} {30, 33, 49} {30, 33, 50} {30, 33, 51}
{30, 33, 52} {30, 33, 53} {30, 33, 54} {30, 33, 55} {30, 33, 56} {30, 33, 57} {30, 33, 58} {30, 33, 59} {30, 33, 60}
{30, 33, 61} {30, 33, 62} {30, 33, 63} {30, 33, 64} {30, 33, 65} {30, 33, 66} {30, 34, 35} {30, 34, 36} {30, 34, 37}
{30, 34, 38} {30, 34, 39} {30, 34, 40} {30, 34, 41} {30, 34, 42} {30, 34, 43} {30, 34, 44} {30, 34, 45} {30, 34, 46}
{30, 34, 47} {30, 34, 48} {30, 34, 49} {30, 34, 50} {30, 34, 51} {30, 34, 52} {30, 34, 53} {30, 34, 54} {30, 34, 55}
{30, 34, 56} {30, 34, 57} {30, 34, 58} {30, 34, 59} {30, 34, 60} {30, 34, 61} {30, 34, 62} {30, 34, 63} {30, 34, 64}
{30, 34, 65} {30, 34, 66} {30, 35, 36} {30, 35, 37} {30, 35, 38} {30, 35, 39} {30, 35, 40} {30, 35, 41} {30, 35, 42}
{30, 35, 43} {30, 35, 44} {30, 35, 45} {30, 35, 46} {30, 35, 47} {30, 35, 48} {30, 35, 49} {30, 35, 50} {30, 35, 51}
{30, 35, 52} {30, 35, 53} {30, 35, 54} {30, 35, 55} {30, 35, 56} {30, 35, 57} {30, 35, 58} {30, 35, 59} {30, 35, 60}
{30, 35, 61} {30, 35, 62} {30, 35, 63} {30, 35, 64} {30, 35, 65} {30, 35, 66} {30, 36, 37} {30, 36, 38} {30, 36, 39}
{30, 36, 40} {30, 36, 41} {30, 36, 42} {30, 36, 43} {30, 36, 44} {30, 36, 45} {30, 36, 46} {30, 36, 47} {30, 36, 48}
{30, 36, 49} {30, 36, 50} {30, 36, 51} {30, 36, 52} {30, 36, 53} {30, 36, 54} {30, 36, 55} {30, 36, 56} {30, 36, 57}
{30, 36, 58} {30, 36, 59} {30, 36, 60} {30, 36, 61} {30, 36, 62} {30, 36, 63} {30, 36, 64} {30, 36, 65} {30, 36, 66}
{30, 37, 38} {30, 37, 39} {30, 37, 40} {30, 37, 41} {30, 37, 42} {30, 37, 43} {30, 37, 44} {30, 37, 45} {30, 37, 46}
{30, 37, 47} {30, 37, 48} {30, 37, 49} {30, 37, 50} {30, 37, 51} {30, 37, 52} {30, 37, 53} {30, 37, 54} {30, 37, 55}
{30, 37, 56} {30, 37, 57} {30, 37, 58} {30, 37, 59} {30, 37, 60} {30, 37, 61} {30, 37, 62} {30, 37, 63} {30, 37, 64}
{30, 37, 65} {30, 37, 66} {30, 38, 39} {30, 38, 40} {30, 38, 41} {30, 38, 42} {30, 38, 43} {30, 38, 44} {30, 38, 45}
{30, 38, 46} {30, 38, 47} {30, 38, 48} {30, 38, 49} {30, 38, 50} {30, 38, 51} {30, 38, 52} {30, 38, 53} {30, 38, 54}
{30, 38, 55} {30, 38, 56} {30, 38, 57} {30, 38, 58} {30, 38, 59} {30, 38, 60} {30, 38, 61} {30, 38, 62} {30, 38, 63}
{30, 38, 64} {30, 38, 65} {30, 38, 66} {30, 39, 40} {30, 39, 41} {30, 39, 42} {30, 39, 43} {30, 39, 44} {30, 39, 45}
{30, 39, 46} {30, 39, 47} {30, 39, 48} {30, 39, 49} {30, 39, 50} {30, 39, 51} {30, 39, 52} {30, 39, 53} {30, 39, 54}
{30, 39, 55} {30, 39, 56} {30, 39, 57} {30, 39, 58} {30, 39, 59} {30, 39, 60} {30, 39, 61} {30, 39, 62} {30, 39, 63}
{30, 39, 64} {30, 39, 65} {30, 39, 66} {30, 40, 41} {30, 40, 42} {30, 40, 43} {30, 40, 44} {30, 40, 45} {30, 40, 46}
{30, 40, 47} {30, 40, 48} {30, 40, 49} {30, 40, 50} {30, 40, 51} {30, 40, 52} {30, 40, 53} {30, 40, 54} {30, 40, 55}
{30, 40, 56} {30, 40, 57} {30, 40, 58} {30, 40, 59} {30, 40, 60} {30, 40, 61} {30, 40, 62} {30, 40, 63} {30, 40, 64}
{30, 40, 65} {30, 40, 66} {30, 41, 42} {30, 41, 43} {30, 41, 44} {30, 41, 45} {30, 41, 46} {30, 41, 47} {30, 41, 48}
{30, 41, 49} {30, 41, 50} {30, 41, 51} {30, 41, 52} {30, 41, 53} {30, 41, 54} {30, 41, 55} {30, 41, 56} {30, 41, 57}
{30, 41, 58} {30, 41, 59} {30, 41, 60} {30, 41, 61} {30, 41, 62} {30, 41, 63} {30, 41, 64} {30, 41, 65} {30, 41, 66}
{30, 42, 43} {30, 42, 44} {30, 42, 45} {30, 42, 46} {30, 42, 47} {30, 42, 48} {30, 42, 49} {30, 42, 50} {30, 42, 51}
{30, 42, 52} {30, 42, 53} {30, 42, 54} {30, 42, 55} {30, 42, 56} {30, 42, 57} {30, 42, 58} {30, 42, 59} {30, 42, 60}
{30, 42, 61} {30, 42, 62} {30, 42, 63} {30, 42, 64} {30, 42, 65} {30, 42, 66} {30, 43, 44} {30, 43, 45} {30, 43, 46}
{30, 43, 47} {30, 43, 48} {30, 43, 49} {30, 43, 50} {30, 43, 51} {30, 43, 52} {30, 43, 53} {30, 43, 54} {30, 43, 55}
{30, 43, 56} {30, 43, 57} {30, 43, 58} {30, 43, 59} {30, 43, 60} {30, 43, 61} {30, 43, 62} {30, 43, 63} {30, 43, 64}
{30, 43, 65} {30, 43, 66} {30, 44, 45} {30, 44, 46} {30, 44, 47} {30, 44, 48} {30, 44, 49} {30, 44, 50} {30, 44, 51}
{30, 44, 52} {30, 44, 53} {30, 44, 54} {30, 44, 55} {30, 44, 56} {30, 44, 57} {30, 44, 58} {30, 44, 59} {30, 44, 60}

TABLE 3A-continued

{30, 44, 61} {30, 44, 62} {30, 44, 63} {30, 44, 64} {30, 44, 65} {30, 44, 66} {30, 45, 46} {30, 45, 47} {30, 45, 48}
{30, 45, 49} {30, 45, 50} {30, 45, 51} {30, 45, 52} {30, 45, 53} {30, 45, 54} {30, 45, 55} {30, 45, 56} {30, 45, 57}
{30, 45, 58} {30, 45, 59} {30, 45, 60} {30, 45, 61} {30, 45, 62} {30, 45, 63} {30, 45, 64} {30, 45, 65} {30, 45, 66}
{30, 46, 47} {30, 46, 48} {30, 46, 49} {30, 46, 50} {30, 46, 51} {30, 46, 52} {30, 46, 53} {30, 46, 54} {30, 46, 55}
{30, 46, 56} {30, 46, 57} {30, 46, 58} {30, 46, 59} {30, 46, 60} {30, 46, 61} {30, 46, 62} {30, 46, 63} {30, 46, 64}
{30, 46, 65} {30, 46, 66} {30, 47, 48} {30, 47, 49} {30, 47, 50} {30, 47, 51} {30, 47, 52} {30, 47, 53} {30, 47, 54}
{30, 47, 55} {30, 47, 56} {30, 47, 57} {30, 47, 58} {30, 47, 59} {30, 47, 60} {30, 47, 61} {30, 47, 62} {30, 47, 63}
{30, 47, 64} {30, 47, 65} {30, 47, 66} {30, 48, 49} {30, 48, 50} {30, 48, 51} {30, 48, 52} {30, 48, 53} {30, 48, 54}
{30, 48, 55} {30, 48, 56} {30, 48, 57} {30, 48, 58} {30, 48, 59} {30, 48, 60} {30, 48, 61} {30, 48, 62} {30, 48, 63}
{30, 48, 64} {30, 48, 65} {30, 48, 66} {30, 49, 50} {30, 49, 51} {30, 49, 52} {30, 49, 53} {30, 49, 54} {30, 49, 55}
{30, 49, 56} {30, 49, 57} {30, 49, 58} {30, 49, 59} {30, 49, 60} {30, 49, 61} {30, 49, 62} {30, 49, 63} {30, 49, 64}
{30, 49, 65} {30, 49, 66} {30, 50, 51} {30, 50, 52} {30, 50, 53} {30, 50, 54} {30, 50, 55} {30, 50, 56} {30, 50, 57}
{30, 50, 58} {30, 50, 59} {30, 50, 60} {30, 50, 61} {30, 50, 62} {30, 50, 63} {30, 50, 64} {30, 50, 65} {30, 50, 66}
{30, 51, 52} {30, 51, 53} {30, 51, 54} {30, 51, 55} {30, 51, 56} {30, 51, 57} {30, 51, 58} {30, 51, 59} {30, 51, 60}
{30, 51, 61} {30, 51, 62} {30, 51, 63} {30, 51, 64} {30, 51, 65} {30, 51, 66} {30, 52, 53} {30, 52, 54} {30, 52, 55}
{30, 52, 56} {30, 52, 57} {30, 52, 58} {30, 52, 59} {30, 52, 60} {30, 52, 61} {30, 52, 62} {30, 52, 63} {30, 52, 64}
{30, 52, 65} {30, 52, 66} {30, 53, 54} {30, 53, 55} {30, 53, 56} {30, 53, 57} {30, 53, 58} {30, 53, 59} {30, 53, 60}
{30, 53, 61} {30, 53, 62} {30, 53, 63} {30, 53, 64} {30, 53, 65} {30, 53, 66} {30, 54, 55} {30, 54, 56} {30, 54, 57}
{30, 54, 58} {30, 54, 59} {30, 54, 60} {30, 54, 61} {30, 54, 62} {30, 54, 63} {30, 54, 64} {30, 54, 65} {30, 54, 66}
{30, 55, 56} {30, 55, 57} {30, 55, 58} {30, 55, 59} {30, 55, 60} {30, 55, 61} {30, 55, 62} {30, 55, 63} {30, 55, 64}
{30, 55, 65} {30, 55, 66} {30, 56, 57} {30, 56, 58} {30, 56, 59} {30, 56, 60} {30, 56, 61} {30, 56, 62} {30, 56, 63}
{30, 56, 64} {30, 56, 65} {30, 56, 66} {30, 57, 58} {30, 57, 59} {30, 57, 60} {30, 57, 61} {30, 57, 62} {30, 57, 63}
{30, 57, 64} {30, 57, 65} {30, 57, 66} {30, 58, 59} {30, 58, 60} {30, 58, 61} {30, 58, 62} {30, 58, 63} {30, 58, 64}
{30, 58, 65} {30, 58, 66} {30, 59, 60} {30, 59, 61} {30, 59, 62} {30, 59, 63} {30, 59, 64} {30, 59, 65} {30, 59, 66}
{30, 60, 61} {30, 60, 62} {30, 60, 63} {30, 60, 64} {30, 60, 65} {30, 60, 66} {30, 61, 62} {30, 61, 63} {30, 61, 64}
{30, 61, 65} {30, 61, 66} {30, 62, 63} {30, 62, 64} {30, 62, 65} {30, 62, 66} {30, 63, 64} {30, 63, 65} {30, 63, 66}
{30, 64, 65} {30, 64, 66} {30, 65, 66} {31, 32, 33} {31, 32, 34} {31, 32, 35} {31, 32, 36} {31, 32, 37} {31, 32, 38}
{31, 32, 39} {31, 32, 40} {31, 32, 41} {31, 32, 42} {31, 32, 43} {31, 32, 44} {31, 32, 45} {31, 32, 46} {31, 32, 47}
{31, 32, 48} {31, 32, 49} {31, 32, 50} {31, 32, 51} {31, 32, 52} {31, 32, 53} {31, 32, 54} {31, 32, 55} {31, 32, 56}
{31, 32, 57} {31, 32, 58} {31, 32, 59} {31, 32, 60} {31, 32, 61} {31, 32, 62} {31, 32, 63} {31, 32, 64} {31, 32, 65}
{31, 32, 66} {31, 33, 34} {31, 33, 35} {31, 33, 36} {31, 33, 37} {31, 33, 38} {31, 33, 39} {31, 33, 40} {31, 33, 41}
{31, 33, 42} {31, 33, 43} {31, 33, 44} {31, 33, 45} {31, 33, 46} {31, 33, 47} {31, 33, 48} {31, 33, 49} {31, 33, 50}
{31, 33, 51} {31, 33, 52} {31, 33, 53} {31, 33, 54} {31, 33, 55} {31, 33, 56} {31, 33, 57} {31, 33, 58} {31, 33, 59}
{31, 33, 60} {31, 33, 61} {31, 33, 62} {31, 33, 63} {31, 33, 64} {31, 33, 65} {31, 33, 66} {31, 34, 35} {31, 34, 36}
{31, 34, 37} {31, 34, 38} {31, 34, 39} {31, 34, 40} {31, 34, 41} {31, 34, 42} {31, 34, 43} {31, 34, 44} {31, 34, 45}
{31, 34, 46} {31, 34, 47} {31, 34, 48} {31, 34, 49} {31, 34, 50} {31, 34, 51} {31, 34, 52} {31, 34, 53} {31, 34, 54}
{31, 34, 55} {31, 34, 56} {31, 34, 57} {31, 34, 58} {31, 34, 59} {31, 34, 60} {31, 34, 61} {31, 34, 62} {31, 34, 63}
{31, 34, 64} {31, 34, 65} {31, 34, 66} {31, 35, 36} {31, 35, 37} {31, 35, 38} {31, 35, 39} {31, 35, 40} {31, 35, 41}
{31, 35, 42} {31, 35, 43} {31, 35, 44} {31, 35, 45} {31, 35, 46} {31, 35, 47} {31, 35, 48} {31, 35, 49} {31, 35, 50}
{31, 35, 51} {31, 35, 52} {31, 35, 53} {31, 35, 54} {31, 35, 55} {31, 35, 56} {31, 35, 57} {31, 35, 58} {31, 35, 59}
{31, 35, 60} {31, 35, 61} {31, 35, 62} {31, 35, 63} {31, 35, 64} {31, 35, 65} {31, 35, 66} {31, 36, 37} {31, 36, 38}
{31, 36, 39} {31, 36, 40} {31, 36, 41} {31, 36, 42} {31, 36, 43} {31, 36, 44} {31, 36, 45} {31, 36, 46} {31, 36, 47}
{31, 36, 48} {31, 36, 49} {31, 36, 50} {31, 36, 51} {31, 36, 52} {31, 36, 53} {31, 36, 54} {31, 36, 55} {31, 36, 56}
{31, 36, 57} {31, 36, 58} {31, 36, 59} {31, 36, 60} {31, 36, 61} {31, 36, 62} {31, 36, 63} {31, 36, 64} {31, 36, 65}
{31, 36, 66} {31, 37, 38} {31, 37, 39} {31, 37, 40} {31, 37, 41} {31, 37, 42} {31, 37, 43} {31, 37, 44} {31, 37, 45}
{31, 37, 46} {31, 37, 47} {31, 37, 48} {31, 37, 49} {31, 37, 50} {31, 37, 51} {31, 37, 52} {31, 37, 53} {31, 37, 54}
{31, 37, 55} {31, 37, 56} {31, 37, 57} {31, 37, 58} {31, 37, 59} {31, 37, 60} {31, 37, 61} {31, 37, 62} {31, 37, 63}
{31, 37, 64} {31, 37, 65} {31, 37, 66} {31, 38, 39} {31, 38, 40} {31, 38, 41} {31, 38, 42} {31, 38, 43} {31, 38, 44}
{31, 38, 45} {31, 38, 46} {31, 38, 47} {31, 38, 48} {31, 38, 49} {31, 38, 50} {31, 38, 51} {31, 38, 52} {31, 38, 53}
{31, 38, 54} {31, 38, 55} {31, 38, 56} {31, 38, 57} {31, 38, 58} {31, 38, 59} {31, 38, 60} {31, 38, 61} {31, 38, 62}
{31, 38, 63} {31, 38, 64} {31, 38, 65} {31, 38, 66} {31, 39, 40} {31, 39, 41} {31, 39, 42} {31, 39, 43} {31, 39, 44}
{31, 39, 45} {31, 39, 46} {31, 39, 47} {31, 39, 48} {31, 39, 49} {31, 39, 50} {31, 39, 51} {31, 39, 52} {31, 39, 53}
{31, 39, 54} {31, 39, 55} {31, 39, 56} {31, 39, 57} {31, 39, 58} {31, 39, 59} {31, 39, 60} {31, 39, 61} {31, 39, 62}
{31, 39, 63} {31, 39, 64} {31, 39, 65} {31, 39, 66} {31, 40, 41} {31, 40, 42} {31, 40, 43} {31, 40, 44} {31, 40, 45}
{31, 40, 46} {31, 40, 47} {31, 40, 48} {31, 40, 49} {31, 40, 50} {31, 40, 51} {31, 40, 52} {31, 40, 53} {31, 40, 54}
{31, 40, 55} {31, 40, 56} {31, 40, 57} {31, 40, 58} {31, 40, 59} {31, 40, 60} {31, 40, 61} {31, 40, 62} {31, 40, 63}
{31, 40, 64} {31, 40, 65} {31, 40, 66} {31, 41, 42} {31, 41, 43} {31, 41, 44} {31, 41, 45} {31, 41, 46} {31, 41, 47}
{31, 41, 48} {31, 41, 49} {31, 41, 50} {31, 41, 51} {31, 41, 52} {31, 41, 53} {31, 41, 54} {31, 41, 55} {31, 41, 56}
{31, 41, 57} {31, 41, 58} {31, 41, 59} {31, 41, 60} {31, 41, 61} {31, 41, 62} {31, 41, 63} {31, 41, 64} {31, 41, 65}
{31, 41, 66} {31, 42, 43} {31, 42, 44} {31, 42, 45} {31, 42, 46} {31, 42, 47} {31, 42, 48} {31, 42, 49} {31, 42, 50}
{31, 42, 51} {31, 42, 52} {31, 42, 53} {31, 42, 54} {31, 42, 55} {31, 42, 56} {31, 42, 57} {31, 42, 58} {31, 42, 59}
{31, 42, 60} {31, 42, 61} {31, 42, 62} {31, 42, 63} {31, 42, 64} {31, 42, 65} {31, 42, 66} {31, 43, 44} {31, 43, 45}
{31, 43, 46} {31, 43, 47} {31, 43, 48} {31, 43, 49} {31, 43, 50} {31, 43, 51} {31, 43, 52} {31, 43, 53} {31, 43, 54}
{31, 43, 55} {31, 43, 56} {31, 43, 57} {31, 43, 58} {31, 43, 59} {31, 43, 60} {31, 43, 61} {31, 43, 62} {31, 43, 63}
{31, 43, 64} {31, 43, 65} {31, 43, 66} {31, 44, 45} {31, 44, 46} {31, 44, 47} {31, 44, 48} {31, 44, 49} {31, 44, 50}
{31, 44, 51} {31, 44, 52} {31, 44, 53} {31, 44, 54} {31, 44, 55} {31, 44, 56} {31, 44, 57} {31, 44, 58} {31, 44, 59}
{31, 44, 60} {31, 44, 61} {31, 44, 62} {31, 44, 63} {31, 44, 64} {31, 44, 65} {31, 44, 66} {31, 45, 46} {31, 45, 47}
{31, 45, 48} {31, 45, 49} {31, 45, 50} {31, 45, 51} {31, 45, 52} {31, 45, 53} {31, 45, 54} {31, 45, 55} {31, 45, 56}
{31, 45, 57} {31, 45, 58} {31, 45, 59} {31, 45, 60} {31, 45, 61} {31, 45, 62} {31, 45, 63} {31, 45, 64} {31, 45, 65}
{31, 45, 66} {31, 46, 47} {31, 46, 48} {31, 46, 49} {31, 46, 50} {31, 46, 51} {31, 46, 52} {31, 46, 53} {31, 46, 54}
{31, 46, 55} {31, 46, 56} {31, 46, 57} {31, 46, 58} {31, 46, 59} {31, 46, 60} {31, 46, 61} {31, 46, 62} {31, 46, 63}
{31, 46, 64} {31, 46, 65} {31, 46, 66} {31, 47, 48} {31, 47, 49} {31, 47, 50} {31, 47, 51} {31, 47, 52} {31, 47, 53}
{31, 47, 54} {31, 47, 55} {31, 47, 56} {31, 47, 57} {31, 47, 58} {31, 47, 59} {31, 47, 60} {31, 47, 61} {31, 47, 62}
{31, 47, 63} {31, 47, 64} {31, 47, 65} {31, 47, 66} {31, 48, 49} {31, 48, 50} {31, 48, 51} {31, 48, 52} {31, 48, 53}
{31, 48, 54} {31, 48, 55} {31, 48, 56} {31, 48, 57} {31, 48, 58} {31, 48, 59} {31, 48, 60} {31, 48, 61} {31, 48, 62}
{31, 48, 63} {31, 48, 64} {31, 48, 65} {31, 48, 66} {31, 49, 50} {31, 49, 51} {31, 49, 52} {31, 49, 53} {31, 49, 54}
{31, 49, 55} {31, 49, 56} {31, 49, 57} {31, 49, 58} {31, 49, 59} {31, 49, 60} {31, 49, 61} {31, 49, 62} {31, 49, 63}
{31, 49, 64} {31, 49, 65} {31, 49, 66} {31, 50, 51} {31, 50, 52} {31, 50, 53} {31, 50, 54} {31, 50, 55} {31, 50, 56}
{31, 50, 57} {31, 50, 58} {31, 50, 59} {31, 50, 60} {31, 50, 61} {31, 50, 62} {31, 50, 63} {31, 50, 64} {31, 50, 65}
{31, 50, 66} {31, 51, 52} {31, 51, 53} {31, 51, 54} {31, 51, 55} {31, 51, 56} {31, 51, 57} {31, 51, 58} {31, 51, 59}

TABLE 3A-continued

{31, 51, 60} {31, 51, 61} {31, 51, 62} {31, 51, 63} {31, 51, 64} {31, 51, 65} {31, 51, 66} {31, 52, 53} {31, 52, 54}
{31, 52, 55} {31, 52, 56} {31, 52, 57} {31, 52, 58} {31, 52, 59} {31, 52, 60} {31, 52, 61} {31, 52, 62} {31, 52, 63}
{31, 52, 64} {31, 52, 65} {31, 52, 66} {31, 53, 54} {31, 53, 55} {31, 53, 56} {31, 53, 57} {31, 53, 58} {31, 53, 59}
{31, 53, 60} {31, 53, 61} {31, 53, 62} {31, 53, 63} {31, 53, 64} {31, 53, 65} {31, 53, 66} {31, 54, 55} {31, 54, 56}
{31, 54, 57} {31, 54, 58} {31, 54, 59} {31, 54, 60} {31, 54, 61} {31, 54, 62} {31, 54, 63} {31, 54, 64} {31, 54, 65}
{31, 54, 66} {31, 55, 56} {31, 55, 57} {31, 55, 58} {31, 55, 59} {31, 55, 60} {31, 55, 61} {31, 55, 62} {31, 55, 63}
{31, 55, 64} {31, 55, 65} {31, 55, 66} {31, 56, 57} {31, 56, 58} {31, 56, 59} {31, 56, 60} {31, 56, 61} {31, 56, 62}
{31, 56, 63} {31, 56, 64} {31, 56, 65} {31, 56, 66} {31, 57, 58} {31, 57, 59} {31, 57, 60} {31, 57, 61} {31, 57, 62}
{31, 57, 63} {31, 57, 64} {31, 57, 65} {31, 57, 66} {31, 58, 59} {31, 58, 60} {31, 58, 61} {31, 58, 62} {31, 58, 63}
{31, 58, 64} {31, 58, 65} {31, 58, 66} {31, 59, 60} {31, 59, 61} {31, 59, 62} {31, 59, 63} {31, 59, 64} {31, 59, 65}
{31, 59, 66} {31, 60, 61} {31, 60, 62} {31, 60, 63} {31, 60, 64} {31, 60, 65} {31, 60, 66} {31, 61, 62} {31, 61, 63}
{31, 61, 64} {31, 61, 65} {31, 61, 66} {31, 62, 63} {31, 62, 64} {31, 62, 65} {31, 62, 66} {31, 63, 64} {31, 63, 65}
{31, 63, 66} {31, 64, 65} {31, 64, 66} {31, 65, 66} {32, 33, 34} {32, 33, 35} {32, 33, 36} {32, 33, 37} {32, 33, 38}
{32, 33, 39} {32, 33, 40} {32, 33, 41} {32, 33, 42} {32, 33, 43} {32, 33, 44} {32, 33, 45} {32, 33, 46} {32, 33, 47}
{32, 33, 48} {32, 33, 49} {32, 33, 50} {32, 33, 51} {32, 33, 52} {32, 33, 53} {32, 33, 54} {32, 33, 55} {32, 33, 56}
{32, 33, 57} {32, 33, 58} {32, 33, 59} {32, 33, 60} {32, 33, 61} {32, 33, 62} {32, 33, 63} {32, 33, 64} {32, 33, 65}
{32, 33, 66} {32, 34, 35} {32, 34, 36} {32, 34, 37} {32, 34, 38} {32, 34, 39} {32, 34, 40} {32, 34, 41} {32, 34, 42}
{32, 34, 43} {32, 34, 44} {32, 34, 45} {32, 34, 46} {32, 34, 47} {32, 34, 48} {32, 34, 49} {32, 34, 50} {32, 34, 51}
{32, 34, 52} {32, 34, 53} {32, 34, 54} {32, 34, 55} {32, 34, 56} {32, 34, 57} {32, 34, 58} {32, 34, 59} {32, 34, 60}
{32, 34, 61} {32, 34, 62} {32, 34, 63} {32, 34, 64} {32, 34, 65} {32, 34, 66} {32, 35, 36} {32, 35, 37} {32, 35, 38}
{32, 35, 39} {32, 35, 40} {32, 35, 41} {32, 35, 42} {32, 35, 43} {32, 35, 44} {32, 35, 45} {32, 35, 46} {32, 35, 47}
{32, 35, 48} {32, 35, 49} {32, 35, 50} {32, 35, 51} {32, 35, 52} {32, 35, 53} {32, 35, 54} {32, 35, 55} {32, 35, 56}
{32, 35, 57} {32, 35, 58} {32, 35, 59} {32, 35, 60} {32, 35, 61} {32, 35, 62} {32, 35, 63} {32, 35, 64} {32, 35, 65}
{32, 35, 66} {32, 36, 37} {32, 36, 38} {32, 36, 39} {32, 36, 40} {32, 36, 41} {32, 36, 42} {32, 36, 43} {32, 36, 44}
{32, 36, 45} {32, 36, 46} {32, 36, 47} {32, 36, 48} {32, 36, 49} {32, 36, 50} {32, 36, 51} {32, 36, 52} {32, 36, 53}
{32, 36, 54} {32, 36, 55} {32, 36, 56} {32, 36, 57} {32, 36, 58} {32, 36, 59} {32, 36, 60} {32, 36, 61} {32, 36, 62}
{32, 36, 63} {32, 36, 64} {32, 36, 65} {32, 36, 66} {32, 37, 38} {32, 37, 39} {32, 37, 40} {32, 37, 41} {32, 37, 42}
{32, 37, 43} {32, 37, 44} {32, 37, 45} {32, 37, 46} {32, 37, 47} {32, 37, 48} {32, 37, 49} {32, 37, 50} {32, 37, 51}
{32, 37, 52} {32, 37, 53} {32, 37, 54} {32, 37, 55} {32, 37, 56} {32, 37, 57} {32, 37, 58} {32, 37, 59} {32, 37, 60}
{32, 37, 61} {32, 37, 62} {32, 37, 63} {32, 37, 64} {32, 37, 65} {32, 37, 66} {32, 38, 39} {32, 38, 40} {32, 38, 41}
{32, 38, 42} {32, 38, 43} {32, 38, 44} {32, 38, 45} {32, 38, 46} {32, 38, 47} {32, 38, 48} {32, 38, 49} {32, 38, 50}
{32, 38, 51} {32, 38, 52} {32, 38, 53} {32, 38, 54} {32, 38, 55} {32, 38, 56} {32, 38, 57} {32, 38, 58} {32, 38, 59}
{32, 38, 60} {32, 38, 61} {32, 38, 62} {32, 38, 63} {32, 38, 64} {32, 38, 65} {32, 38, 66} {32, 39, 40} {32, 39, 41}
{32, 39, 42} {32, 39, 43} {32, 39, 44} {32, 39, 45} {32, 39, 46} {32, 39, 47} {32, 39, 48} {32, 39, 49} {32, 39, 50}
{32, 39, 51} {32, 39, 52} {32, 39, 53} {32, 39, 54} {32, 39, 55} {32, 39, 56} {32, 39, 57} {32, 39, 58} {32, 39, 59}
{32, 39, 60} {32, 39, 61} {32, 39, 62} {32, 39, 63} {32, 39, 64} {32, 39, 65} {32, 39, 66} {32, 40, 41} {32, 40, 42}
{32, 40, 43} {32, 40, 44} {32, 40, 45} {32, 40, 46} {32, 40, 47} {32, 40, 48} {32, 40, 49} {32, 40, 50} {32, 40, 51}
{32, 40, 52} {32, 40, 53} {32, 40, 54} {32, 40, 55} {32, 40, 56} {32, 40, 57} {32, 40, 58} {32, 40, 59} {32, 40, 60}
{32, 40, 61} {32, 40, 62} {32, 40, 63} {32, 40, 64} {32, 40, 65} {32, 40, 66} {32, 41, 42} {32, 41, 43} {32, 41, 44}
{32, 41, 45} {32, 41, 46} {32, 41, 47} {32, 41, 48} {32, 41, 49} {32, 41, 50} {32, 41, 51} {32, 41, 52} {32, 41, 53}
{32, 41, 54} {32, 41, 55} {32, 41, 56} {32, 41, 57} {32, 41, 58} {32, 41, 59} {32, 41, 60} {32, 41, 61} {32, 41, 62}
{32, 41, 63} {32, 41, 64} {32, 41, 65} {32, 41, 66} {32, 42, 43} {32, 42, 44} {32, 42, 45} {32, 42, 46} {32, 42, 47}
{32, 42, 48} {32, 42, 49} {32, 42, 50} {32, 42, 51} {32, 42, 52} {32, 42, 53} {32, 42, 54} {32, 42, 55} {32, 42, 56}
{32, 42, 57} {32, 42, 58} {32, 42, 59} {32, 42, 60} {32, 42, 61} {32, 42, 62} {32, 42, 63} {32, 42, 64} {32, 42, 65}
{32, 42, 66} {32, 43, 44} {32, 43, 45} {32, 43, 46} {32, 43, 47} {32, 43, 48} {32, 43, 49} {32, 43, 50} {32, 43, 51}
{32, 43, 52} {32, 43, 53} {32, 43, 54} {32, 43, 55} {32, 43, 56} {32, 43, 57} {32, 43, 58} {32, 43, 59} {32, 43, 60}
{32, 43, 61} {32, 43, 62} {32, 43, 63} {32, 43, 64} {32, 43, 65} {32, 43, 66} {32, 44, 45} {32, 44, 46} {32, 44, 47}
{32, 44, 48} {32, 44, 49} {32, 44, 50} {32, 44, 51} {32, 44, 52} {32, 44, 53} {32, 44, 54} {32, 44, 55} {32, 44, 56}
{32, 44, 57} {32, 44, 58} {32, 44, 59} {32, 44, 60} {32, 44, 61} {32, 44, 62} {32, 44, 63} {32, 44, 64} {32, 44, 65}
{32, 44, 66} {32, 45, 46} {32, 45, 47} {32, 45, 48} {32, 45, 49} {32, 45, 50} {32, 45, 51} {32, 45, 52} {32, 45, 53}
{32, 45, 54} {32, 45, 55} {32, 45, 56} {32, 45, 57} {32, 45, 58} {32, 45, 59} {32, 45, 60} {32, 45, 61} {32, 45, 62}
{32, 45, 63} {32, 45, 64} {32, 45, 65} {32, 45, 66} {32, 46, 47} {32, 46, 48} {32, 46, 49} {32, 46, 50} {32, 46, 51}
{32, 46, 52} {32, 46, 53} {32, 46, 54} {32, 46, 55} {32, 46, 56} {32, 46, 57} {32, 46, 58} {32, 46, 59} {32, 46, 60}
{32, 46, 61} {32, 46, 62} {32, 46, 63} {32, 46, 64} {32, 46, 65} {32, 46, 66} {32, 47, 48} {32, 47, 49} {32, 47, 50}
{32, 47, 51} {32, 47, 52} {32, 47, 53} {32, 47, 54} {32, 47, 55} {32, 47, 56} {32, 47, 57} {32, 47, 58} {32, 47, 59}
{32, 47, 60} {32, 47, 61} {32, 47, 62} {32, 47, 63} {32, 47, 64} {32, 47, 65} {32, 47, 66} {32, 48, 49} {32, 48, 50}
{32, 48, 51} {32, 48, 52} {32, 48, 53} {32, 48, 54} {32, 48, 55} {32, 48, 56} {32, 48, 57} {32, 48, 58} {32, 48, 59}
{32, 48, 60} {32, 48, 61} {32, 48, 62} {32, 48, 63} {32, 48, 64} {32, 48, 65} {32, 48, 66} {32, 49, 50} {32, 49, 51}
{32, 49, 52} {32, 49, 53} {32, 49, 54} {32, 49, 55} {32, 49, 56} {32, 49, 57} {32, 49, 58} {32, 49, 59} {32, 49, 60}
{32, 49, 61} {32, 49, 62} {32, 49, 63} {32, 49, 64} {32, 49, 65} {32, 49, 66} {32, 50, 51} {32, 50, 52} {32, 50, 53}
{32, 50, 54} {32, 50, 55} {32, 50, 56} {32, 50, 57} {32, 50, 58} {32, 50, 59} {32, 50, 60} {32, 50, 61} {32, 50, 62}
{32, 50, 63} {32, 50, 64} {32, 50, 65} {32, 50, 66} {32, 51, 52} {32, 51, 53} {32, 51, 54} {32, 51, 55} {32, 51, 56}
{32, 51, 57} {32, 51, 58} {32, 51, 59} {32, 51, 60} {32, 51, 61} {32, 51, 62} {32, 51, 63} {32, 51, 64} {32, 51, 65}
{32, 51, 66} {32, 52, 53} {32, 52, 54} {32, 52, 55} {32, 52, 56} {32, 52, 57} {32, 52, 58} {32, 52, 59} {32, 52, 60}
{32, 52, 61} {32, 52, 62} {32, 52, 63} {32, 52, 64} {32, 52, 65} {32, 52, 66} {32, 53, 54} {32, 53, 55} {32, 53, 56}
{32, 53, 57} {32, 53, 58} {32, 53, 59} {32, 53, 60} {32, 53, 61} {32, 53, 62} {32, 53, 63} {32, 53, 64} {32, 53, 65}
{32, 53, 66} {32, 54, 55} {32, 54, 56} {32, 54, 57} {32, 54, 58} {32, 54, 59} {32, 54, 60} {32, 54, 61} {32, 54, 62}
{32, 54, 63} {32, 54, 64} {32, 54, 65} {32, 54, 66} {32, 55, 56} {32, 55, 57} {32, 55, 58} {32, 55, 59} {32, 55, 60}
{32, 55, 61} {32, 55, 62} {32, 55, 63} {32, 55, 64} {32, 55, 65} {32, 55, 66} {32, 56, 57} {32, 56, 58} {32, 56, 59}
{32, 56, 60} {32, 56, 61} {32, 56, 62} {32, 56, 63} {32, 56, 64} {32, 56, 65} {32, 56, 66} {32, 57, 58} {32, 57, 59}
{32, 57, 60} {32, 57, 61} {32, 57, 62} {32, 57, 63} {32, 57, 64} {32, 57, 65} {32, 57, 66} {32, 58, 59} {32, 58, 60}
{32, 58, 61} {32, 58, 62} {32, 58, 63} {32, 58, 64} {32, 58, 65} {32, 58, 66} {32, 59, 60} {32, 59, 61} {32, 59, 62}
{32, 59, 63} {32, 59, 64} {32, 59, 65} {32, 59, 66} {32, 60, 61} {32, 60, 62} {32, 60, 63} {32, 60, 64} {32, 60, 65}
{32, 60, 66} {32, 61, 62} {32, 61, 63} {32, 61, 64} {32, 61, 65} {32, 61, 66} {32, 62, 63} {32, 62, 64} {32, 62, 65}
{32, 62, 66} {32, 63, 64} {32, 63, 65} {32, 63, 66} {32, 64, 65} {32, 64, 66} {32, 65, 66} {33, 34, 35} {33, 34, 36}
{33, 34, 37} {33, 34, 38} {33, 34, 39} {33, 34, 40} {33, 34, 41} {33, 34, 42} {33, 34, 43} {33, 34, 44} {33, 34, 45}
{33, 34, 46} {33, 34, 47} {33, 34, 48} {33, 34, 49} {33, 34, 50} {33, 34, 51} {33, 34, 52} {33, 34, 53} {33, 34, 54}
{33, 34, 55} {33, 34, 56} {33, 34, 57} {33, 34, 58} {33, 34, 59} {33, 34, 60} {33, 34, 61} {33, 34, 62} {33, 34, 63}
{33, 34, 64} {33, 34, 65} {33, 34, 66} {33, 35, 36} {33, 35, 37} {33, 35, 38} {33, 35, 39} {33, 35, 40} {33, 35, 41}
{33, 35, 42} {33, 35, 43} {33, 35, 44} {33, 35, 45} {33, 35, 46} {33, 35, 47} {33, 35, 48} {33, 35, 49} {33, 35, 50}

TABLE 3A-continued

{33, 35, 51} {33, 35, 52} {33, 35, 53} {33, 35, 54} {33, 35, 55} {33, 35, 56} {33, 35, 57} {33, 35, 58} {33, 35, 59}
{33, 35, 60} {33, 35, 61} {33, 35, 62} {33, 35, 63} {33, 35, 64} {33, 35, 65} {33, 35, 66} {33, 36, 37} {33, 36, 38}
{33, 36, 39} {33, 36, 40} {33, 36, 41} {33, 36, 42} {33, 36, 43} {33, 36, 44} {33, 36, 45} {33, 36, 46} {33, 36, 47}
{33, 36, 48} {33, 36, 49} {33, 36, 50} {33, 36, 51} {33, 36, 52} {33, 36, 53} {33, 36, 54} {33, 36, 55} {33, 36, 56}
{33, 36, 57} {33, 36, 58} {33, 36, 59} {33, 36, 60} {33, 36, 61} {33, 36, 62} {33, 36, 63} {33, 36, 64} {33, 36, 65}
{33, 36, 66} {33, 37, 38} {33, 37, 39} {33, 37, 40} {33, 37, 41} {33, 37, 42} {33, 37, 43} {33, 37, 44} {33, 37, 45}
{33, 37, 46} {33, 37, 47} {33, 37, 48} {33, 37, 49} {33, 37, 50} {33, 37, 51} {33, 37, 52} {33, 37, 53} {33, 37, 54}
{33, 37, 55} {33, 37, 56} {33, 37, 57} {33, 37, 58} {33, 37, 59} {33, 37, 60} {33, 37, 61} {33, 37, 62} {33, 37, 63}
{33, 37, 64} {33, 37, 65} {33, 37, 66} {33, 38, 39} {33, 38, 40} {33, 38, 41} {33, 38, 42} {33, 38, 43} {33, 38, 44}
{33, 38, 45} {33, 38, 46} {33, 38, 47} {33, 38, 48} {33, 38, 49} {33, 38, 50} {33, 38, 51} {33, 38, 52} {33, 38, 53}
{33, 38, 54} {33, 38, 55} {33, 38, 56} {33, 38, 57} {33, 38, 58} {33, 38, 59} {33, 38, 60} {33, 38, 61} {33, 38, 62}
{33, 38, 63} {33, 38, 64} {33, 38, 65} {33, 38, 66} {33, 39, 40} {33, 39, 41} {33, 39, 42} {33, 39, 43} {33, 39, 44}
{33, 39, 45} {33, 39, 46} {33, 39, 47} {33, 39, 48} {33, 39, 49} {33, 39, 50} {33, 39, 51} {33, 39, 52} {33, 39, 53}
{33, 39, 54} {33, 39, 55} {33, 39, 56} {33, 39, 57} {33, 39, 58} {33, 39, 59} {33, 39, 60} {33, 39, 61} {33, 39, 62}
{33, 39, 63} {33, 39, 64} {33, 39, 65} {33, 39, 66} {33, 40, 41} {33, 40, 42} {33, 40, 43} {33, 40, 44} {33, 40, 45}
{33, 40, 46} {33, 40, 47} {33, 40, 48} {33, 40, 49} {33, 40, 50} {33, 40, 51} {33, 40, 52} {33, 40, 53} {33, 40, 54}
{33, 40, 55} {33, 40, 56} {33, 40, 57} {33, 40, 58} {33, 40, 59} {33, 40, 60} {33, 40, 61} {33, 40, 62} {33, 40, 63}
{33, 40, 64} {33, 40, 65} {33, 40, 66} {33, 41, 42} {33, 41, 43} {33, 41, 44} {33, 41, 45} {33, 41, 46} {33, 41, 47}
{33, 41, 48} {33, 41, 49} {33, 41, 50} {33, 41, 51} {33, 41, 52} {33, 41, 53} {33, 41, 54} {33, 41, 55} {33, 41, 56}
{33, 41, 57} {33, 41, 58} {33, 41, 59} {33, 41, 60} {33, 41, 61} {33, 41, 62} {33, 41, 63} {33, 41, 64} {33, 41, 65}
{33, 41, 66} {33, 42, 43} {33, 42, 44} {33, 42, 45} {33, 42, 46} {33, 42, 47} {33, 42, 48} {33, 42, 49} {33, 42, 50}
{33, 42, 51} {33, 42, 52} {33, 42, 53} {33, 42, 54} {33, 42, 55} {33, 42, 56} {33, 42, 57} {33, 42, 58} {33, 42, 59}
{33, 42, 60} {33, 42, 61} {33, 42, 62} {33, 42, 63} {33, 42, 64} {33, 42, 65} {33, 42, 66} {33, 43, 44} {33, 43, 45}
{33, 43, 46} {33, 43, 47} {33, 43, 48} {33, 43, 49} {33, 43, 50} {33, 43, 51} {33, 43, 52} {33, 43, 53} {33, 43, 54}
{33, 43, 55} {33, 43, 56} {33, 43, 57} {33, 43, 58} {33, 43, 59} {33, 43, 60} {33, 43, 61} {33, 43, 62} {33, 43, 63}
{33, 43, 64} {33, 43, 65} {33, 43, 66} {33, 44, 45} {33, 44, 46} {33, 44, 47} {33, 44, 48} {33, 44, 49} {33, 44, 50}
{33, 44, 51} {33, 44, 52} {33, 44, 53} {33, 44, 54} {33, 44, 55} {33, 44, 56} {33, 44, 57} {33, 44, 58} {33, 44, 59}
{33, 44, 60} {33, 44, 61} {33, 44, 62} {33, 44, 63} {33, 44, 64} {33, 44, 65} {33, 44, 66} {33, 45, 46} {33, 45, 47}
{33, 45, 48} {33, 45, 49} {33, 45, 50} {33, 45, 51} {33, 45, 52} {33, 45, 53} {33, 45, 54} {33, 45, 55} {33, 45, 56}
{33, 45, 57} {33, 45, 58} {33, 45, 59} {33, 45, 60} {33, 45, 61} {33, 45, 62} {33, 45, 63} {33, 45, 64} {33, 45, 65}
{33, 45, 66} {33, 46, 47} {33, 46, 48} {33, 46, 49} {33, 46, 50} {33, 46, 51} {33, 46, 52} {33, 46, 53} {33, 46, 54}
{33, 46, 55} {33, 46, 56} {33, 46, 57} {33, 46, 58} {33, 46, 59} {33, 46, 60} {33, 46, 61} {33, 46, 62} {33, 46, 63}
{33, 46, 64} {33, 46, 65} {33, 46, 66} {33, 47, 48} {33, 47, 49} {33, 47, 50} {33, 47, 51} {33, 47, 52} {33, 47, 53}
{33, 47, 54} {33, 47, 55} {33, 47, 56} {33, 47, 57} {33, 47, 58} {33, 47, 59} {33, 47, 60} {33, 47, 61} {33, 47, 62}
{33, 47, 63} {33, 47, 64} {33, 47, 65} {33, 47, 66} {33, 48, 49} {33, 48, 50} {33, 48, 51} {33, 48, 52} {33, 48, 53}
{33, 48, 54} {33, 48, 55} {33, 48, 56} {33, 48, 57} {33, 48, 58} {33, 48, 59} {33, 48, 60} {33, 48, 61} {33, 48, 62}
{33, 48, 63} {33, 48, 64} {33, 48, 65} {33, 48, 66} {33, 49, 50} {33, 49, 51} {33, 49, 52} {33, 49, 53} {33, 49, 54}
{33, 49, 55} {33, 49, 56} {33, 49, 57} {33, 49, 58} {33, 49, 59} {33, 49, 60} {33, 49, 61} {33, 49, 62} {33, 49, 63}
{33, 49, 64} {33, 49, 65} {33, 49, 66} {33, 50, 51} {33, 50, 52} {33, 50, 53} {33, 50, 54} {33, 50, 55} {33, 50, 56}
{33, 50, 57} {33, 50, 58} {33, 50, 59} {33, 50, 60} {33, 50, 61} {33, 50, 62} {33, 50, 63} {33, 50, 64} {33, 50, 65}
{33, 50, 66} {33, 51, 52} {33, 51, 53} {33, 51, 54} {33, 51, 55} {33, 51, 56} {33, 51, 57} {33, 51, 58} {33, 51, 59}
{33, 51, 60} {33, 51, 61} {33, 51, 62} {33, 51, 63} {33, 51, 64} {33, 51, 65} {33, 51, 66} {33, 52, 53} {33, 52, 54}
{33, 52, 55} {33, 52, 56} {33, 52, 57} {33, 52, 58} {33, 52, 59} {33, 52, 60} {33, 52, 61} {33, 52, 62} {33, 52, 63}
{33, 52, 64} {33, 52, 65} {33, 52, 66} {33, 53, 54} {33, 53, 55} {33, 53, 56} {33, 53, 57} {33, 53, 58} {33, 53, 59}
{33, 53, 60} {33, 53, 61} {33, 53, 62} {33, 53, 63} {33, 53, 64} {33, 53, 65} {33, 53, 66} {33, 54, 55} {33, 54, 56}
{33, 54, 57} {33, 54, 58} {33, 54, 59} {33, 54, 60} {33, 54, 61} {33, 54, 62} {33, 54, 63} {33, 54, 64} {33, 54, 65}
{33, 54, 66} {33, 55, 56} {33, 55, 57} {33, 55, 58} {33, 55, 59} {33, 55, 60} {33, 55, 61} {33, 55, 62} {33, 55, 63}
{33, 55, 64} {33, 55, 65} {33, 55, 66} {33, 56, 57} {33, 56, 58} {33, 56, 59} {33, 56, 60} {33, 56, 61} {33, 56, 62}
{33, 56, 63} {33, 56, 64} {33, 56, 65} {33, 56, 66} {33, 57, 58} {33, 57, 59} {33, 57, 60} {33, 57, 61} {33, 57, 62}
{33, 57, 63} {33, 57, 64} {33, 57, 65} {33, 57, 66} {33, 58, 59} {33, 58, 60} {33, 58, 61} {33, 58, 62} {33, 58, 63}
{33, 58, 64} {33, 58, 65} {33, 58, 66} {33, 59, 60} {33, 59, 61} {33, 59, 62} {33, 59, 63} {33, 59, 64} {33, 59, 65}
{33, 59, 66} {33, 60, 61} {33, 60, 62} {33, 60, 63} {33, 60, 64} {33, 60, 65} {33, 60, 66} {33, 61, 62} {33, 61, 63}
{33, 61, 64} {33, 61, 65} {33, 61, 66} {33, 62, 63} {33, 62, 64} {33, 62, 65} {33, 62, 66} {33, 63, 64} {33, 63, 65}
{33, 63, 66} {33, 64, 65} {33, 64, 66} {33, 65, 66} {34, 35, 36} {34, 35, 37} {34, 35, 38} {34, 35, 39} {34, 35, 40}
{34, 35, 41} {34, 35, 42} {34, 35, 43} {34, 35, 44} {34, 35, 45} {34, 35, 46} {34, 35, 47} {34, 35, 48} {34, 35, 49}
{34, 35, 50} {34, 35, 51} {34, 35, 52} {34, 35, 53} {34, 35, 54} {34, 35, 55} {34, 35, 56} {34, 35, 57} {34, 35, 58}
{34, 35, 59} {34, 35, 60} {34, 35, 61} {34, 35, 62} {34, 35, 63} {34, 35, 64} {34, 35, 65} {34, 35, 66} {34, 36, 37}
{34, 36, 38} {34, 36, 39} {34, 36, 40} {34, 36, 41} {34, 36, 42} {34, 36, 43} {34, 36, 44} {34, 36, 45} {34, 36, 46}
{34, 36, 47} {34, 36, 48} {34, 36, 49} {34, 36, 50} {34, 36, 51} {34, 36, 52} {34, 36, 53} {34, 36, 54} {34, 36, 55}
{34, 36, 56} {34, 36, 57} {34, 36, 58} {34, 36, 59} {34, 36, 60} {34, 36, 61} {34, 36, 62} {34, 36, 63} {34, 36, 64}
{34, 36, 65} {34, 36, 66} {34, 37, 38} {34, 37, 39} {34, 37, 40} {34, 37, 41} {34, 37, 42} {34, 37, 43} {34, 37, 44}
{34, 37, 45} {34, 37, 46} {34, 37, 47} {34, 37, 48} {34, 37, 49} {34, 37, 50} {34, 37, 51} {34, 37, 52} {34, 37, 53}
{34, 37, 54} {34, 37, 55} {34, 37, 56} {34, 37, 57} {34, 37, 58} {34, 37, 59} {34, 37, 60} {34, 37, 61} {34, 37, 62}
{34, 37, 63} {34, 37, 64} {34, 37, 65} {34, 37, 66} {34, 38, 39} {34, 38, 40} {34, 38, 41} {34, 38, 42} {34, 38, 43}
{34, 38, 44} {34, 38, 45} {34, 38, 46} {34, 38, 47} {34, 38, 48} {34, 38, 49} {34, 38, 50} {34, 38, 51} {34, 38, 52}
{34, 38, 53} {34, 38, 54} {34, 38, 55} {34, 38, 56} {34, 38, 57} {34, 38, 58} {34, 38, 59} {34, 38, 60} {34, 38, 61}
{34, 38, 62} {34, 38, 63} {34, 38, 64} {34, 38, 65} {34, 38, 66} {34, 39, 40} {34, 39, 41} {34, 39, 42} {34, 39, 43}
{34, 39, 44} {34, 39, 45} {34, 39, 46} {34, 39, 47} {34, 39, 48} {34, 39, 49} {34, 39, 50} {34, 39, 51} {34, 39, 52}
{34, 39, 53} {34, 39, 54} {34, 39, 55} {34, 39, 56} {34, 39, 57} {34, 39, 58} {34, 39, 59} {34, 39, 60} {34, 39, 61}
{34, 39, 62} {34, 39, 63} {34, 39, 64} {34, 39, 65} {34, 39, 66} {34, 40, 41} {34, 40, 42} {34, 40, 43} {34, 40, 44}
{34, 40, 45} {34, 40, 46} {34, 40, 47} {34, 40, 48} {34, 40, 49} {34, 40, 50} {34, 40, 51} {34, 40, 52} {34, 40, 53}
{34, 40, 54} {34, 40, 55} {34, 40, 56} {34, 40, 57} {34, 40, 58} {34, 40, 59} {34, 40, 60} {34, 40, 61} {34, 40, 62}
{34, 40, 63} {34, 40, 64} {34, 40, 65} {34, 40, 66} {34, 41, 42} {34, 41, 43} {34, 41, 44} {34, 41, 45} {34, 41, 46}
{34, 41, 47} {34, 41, 48} {34, 41, 49} {34, 41, 50} {34, 41, 51} {34, 41, 52} {34, 41, 53} {34, 41, 54} {34, 41, 55}
{34, 41, 56} {34, 41, 57} {34, 41, 58} {34, 41, 59} {34, 41, 60} {34, 41, 61} {34, 41, 62} {34, 41, 63} {34, 41, 64}
{34, 41, 65} {34, 41, 66} {34, 42, 43} {34, 42, 44} {34, 42, 45} {34, 42, 46} {34, 42, 47} {34, 42, 48} {34, 42, 49}
{34, 42, 50} {34, 42, 51} {34, 42, 52} {34, 42, 53} {34, 42, 54} {34, 42, 55} {34, 42, 56} {34, 42, 57} {34, 42, 58}
{34, 42, 59} {34, 42, 60} {34, 42, 61} {34, 42, 62} {34, 42, 63} {34, 42, 64} {34, 42, 65} {34, 42, 66} {34, 43, 44}
{34, 43, 45} {34, 43, 46} {34, 43, 47} {34, 43, 48} {34, 43, 49} {34, 43, 50} {34, 43, 51} {34, 43, 52} {34, 43, 53}
{34, 43, 54} {34, 43, 55} {34, 43, 56} {34, 43, 57} {34, 43, 58} {34, 43, 59} {34, 43, 60} {34, 43, 61} {34, 43, 62}

TABLE 3A-continued

{34, 43, 63} {34, 43, 64} {34, 43, 65} {34, 43, 66} {34, 44, 45} {34, 44, 46} {34, 44, 47} {34, 44, 48} {34, 44, 49}
{34, 44, 50} {34, 44, 51} {34, 44, 52} {34, 44, 53} {34, 44, 54} {34, 44, 55} {34, 44, 56} {34, 44, 57} {34, 44, 58}
{34, 44, 59} {34, 44, 60} {34, 44, 61} {34, 44, 62} {34, 44, 63} {34, 44, 64} {34, 44, 65} {34, 44, 66} {34, 45, 46}
{34, 45, 47} {34, 45, 48} {34, 45, 49} {34, 45, 50} {34, 45, 51} {34, 45, 52} {34, 45, 53} {34, 45, 54} {34, 45, 55}
{34, 45, 56} {34, 45, 57} {34, 45, 58} {34, 45, 59} {34, 45, 60} {34, 45, 61} {34, 45, 62} {34, 45, 63} {34, 45, 64}
{34, 45, 65} {34, 45, 66} {34, 46, 47} {34, 46, 48} {34, 46, 49} {34, 46, 50} {34, 46, 51} {34, 46, 52} {34, 46, 53}
{34, 46, 54} {34, 46, 55} {34, 46, 56} {34, 46, 57} {34, 46, 58} {34, 46, 59} {34, 46, 60} {34, 46, 61} {34, 46, 62}
{34, 46, 63} {34, 46, 64} {34, 46, 65} {34, 46, 66} {34, 47, 48} {34, 47, 49} {34, 47, 50} {34, 47, 51} {34, 47, 52}
{34, 47, 53} {34, 47, 54} {34, 47, 55} {34, 47, 56} {34, 47, 57} {34, 47, 58} {34, 47, 59} {34, 47, 60} {34, 47, 61}
{34, 47, 62} {34, 47, 63} {34, 47, 64} {34, 47, 65} {34, 47, 66} {34, 48, 49} {34, 48, 50} {34, 48, 51} {34, 48, 52}
{34, 48, 53} {34, 48, 54} {34, 48, 55} {34, 48, 56} {34, 48, 57} {34, 48, 58} {34, 48, 59} {34, 48, 60} {34, 48, 61}
{34, 48, 62} {34, 48, 63} {34, 48, 64} {34, 48, 65} {34, 48, 66} {34, 49, 50} {34, 49, 51} {34, 49, 52} {34, 49, 53}
{34, 49, 54} {34, 49, 55} {34, 49, 56} {34, 49, 57} {34, 49, 58} {34, 49, 59} {34, 49, 60} {34, 49, 61} {34, 49, 62}
{34, 49, 63} {34, 49, 64} {34, 49, 65} {34, 49, 66} {34, 50, 51} {34, 50, 52} {34, 50, 53} {34, 50, 54} {34, 50, 55}
{34, 50, 56} {34, 50, 57} {34, 50, 58} {34, 50, 59} {34, 50, 60} {34, 50, 61} {34, 50, 62} {34, 50, 63} {34, 50, 64}
{34, 50, 65} {34, 50, 66} {34, 51, 52} {34, 51, 53} {34, 51, 54} {34, 51, 55} {34, 51, 56} {34, 51, 57} {34, 51, 58}
{34, 51, 59} {34, 51, 60} {34, 51, 61} {34, 51, 62} {34, 51, 63} {34, 51, 64} {34, 51, 65} {34, 51, 66} {34, 52, 53}
{34, 52, 54} {34, 52, 55} {34, 52, 56} {34, 52, 57} {34, 52, 58} {34, 52, 59} {34, 52, 60} {34, 52, 61} {34, 52, 62}
{34, 52, 63} {34, 52, 64} {34, 52, 65} {34, 52, 66} {34, 53, 54} {34, 53, 55} {34, 53, 56} {34, 53, 57} {34, 53, 58}
{34, 53, 59} {34, 53, 60} {34, 53, 61} {34, 53, 62} {34, 53, 63} {34, 53, 64} {34, 53, 65} {34, 53, 66} {34, 54, 55}
{34, 54, 56} {34, 54, 57} {34, 54, 58} {34, 54, 59} {34, 54, 60} {34, 54, 61} {34, 54, 62} {34, 54, 63} {34, 54, 64}
{34, 54, 65} {34, 54, 66} {34, 55, 56} {34, 55, 57} {34, 55, 58} {34, 55, 59} {34, 55, 60} {34, 55, 61} {34, 55, 62}
{34, 55, 63} {34, 55, 64} {34, 55, 65} {34, 55, 66} {34, 56, 57} {34, 56, 58} {34, 56, 59} {34, 56, 60} {34, 56, 61}
{34, 56, 62} {34, 56, 63} {34, 56, 64} {34, 56, 65} {34, 56, 66} {34, 57, 58} {34, 57, 59} {34, 57, 60} {34, 57, 61}
{34, 57, 62} {34, 57, 63} {34, 57, 64} {34, 57, 65} {34, 57, 66} {34, 58, 59} {34, 58, 60} {34, 58, 61} {34, 58, 62}
{34, 58, 63} {34, 58, 64} {34, 58, 65} {34, 58, 66} {34, 59, 60} {34, 59, 61} {34, 59, 62} {34, 59, 63} {34, 59, 64}
{34, 59, 65} {34, 59, 66} {34, 60, 61} {34, 60, 62} {34, 60, 63} {34, 60, 64} {34, 60, 65} {34, 60, 66} {34, 61, 62}
{34, 61, 63} {34, 61, 64} {34, 61, 65} {34, 61, 66} {34, 62, 63} {34, 62, 64} {34, 62, 65} {34, 62, 66} {34, 63, 64}
{34, 63, 65} {34, 63, 66} {34, 64, 65} {34, 64, 66} {34, 65, 66} {35, 36, 37} {35, 36, 38} {35, 36, 39} {35, 36, 40}
{35, 36, 41} {35, 36, 42} {35, 36, 43} {35, 36, 44} {35, 36, 45} {35, 36, 46} {35, 36, 47} {35, 36, 48} {35, 36, 49}
{35, 36, 50} {35, 36, 51} {35, 36, 52} {35, 36, 53} {35, 36, 54} {35, 36, 55} {35, 36, 56} {35, 36, 57} {35, 36, 58}
{35, 36, 59} {35, 36, 60} {35, 36, 61} {35, 36, 62} {35, 36, 63} {35, 36, 64} {35, 36, 65} {35, 36, 66} {35, 37, 38}
{35, 37, 39} {35, 37, 40} {35, 37, 41} {35, 37, 42} {35, 37, 43} {35, 37, 44} {35, 37, 45} {35, 37, 46} {35, 37, 47}
{35, 37, 48} {35, 37, 49} {35, 37, 50} {35, 37, 51} {35, 37, 52} {35, 37, 53} {35, 37, 54} {35, 37, 55} {35, 37, 56}
{35, 37, 57} {35, 37, 58} {35, 37, 59} {35, 37, 60} {35, 37, 61} {35, 37, 62} {35, 37, 63} {35, 37, 64} {35, 37, 65}
{35, 37, 66} {35, 38, 39} {35, 38, 40} {35, 38, 41} {35, 38, 42} {35, 38, 43} {35, 38, 44} {35, 38, 45} {35, 38, 46}
{35, 38, 47} {35, 38, 48} {35, 38, 49} {35, 38, 50} {35, 38, 51} {35, 38, 52} {35, 38, 53} {35, 38, 54} {35, 38, 55}
{35, 38, 56} {35, 38, 57} {35, 38, 58} {35, 38, 59} {35, 38, 60} {35, 38, 61} {35, 38, 62} {35, 38, 63} {35, 38, 64}
{35, 38, 65} {35, 38, 66} {35, 39, 40} {35, 39, 41} {35, 39, 42} {35, 39, 43} {35, 39, 44} {35, 39, 45} {35, 39, 46}
{35, 39, 47} {35, 39, 48} {35, 39, 49} {35, 39, 50} {35, 39, 51} {35, 39, 52} {35, 39, 53} {35, 39, 54} {35, 39, 55}
{35, 39, 56} {35, 39, 57} {35, 39, 58} {35, 39, 59} {35, 39, 60} {35, 39, 61} {35, 39, 62} {35, 39, 63} {35, 39, 64}
{35, 39, 65} {35, 39, 66} {35, 40, 41} {35, 40, 42} {35, 40, 43} {35, 40, 44} {35, 40, 45} {35, 40, 46} {35, 40, 47}
{35, 40, 48} {35, 40, 49} {35, 40, 50} {35, 40, 51} {35, 40, 52} {35, 40, 53} {35, 40, 54} {35, 40, 55} {35, 40, 56}
{35, 40, 57} {35, 40, 58} {35, 40, 59} {35, 40, 60} {35, 40, 61} {35, 40, 62} {35, 40, 63} {35, 40, 64} {35, 40, 65}
{35, 40, 66} {35, 41, 42} {35, 41, 43} {35, 41, 44} {35, 41, 45} {35, 41, 46} {35, 41, 47} {35, 41, 48} {35, 41, 49}
{35, 41, 50} {35, 41, 51} {35, 41, 52} {35, 41, 53} {35, 41, 54} {35, 41, 55} {35, 41, 56} {35, 41, 57} {35, 41, 58}
{35, 41, 59} {35, 41, 60} {35, 41, 61} {35, 41, 62} {35, 41, 63} {35, 41, 64} {35, 41, 65} {35, 41, 66} {35, 42, 43}
{35, 42, 44} {35, 42, 45} {35, 42, 46} {35, 42, 47} {35, 42, 48} {35, 42, 49} {35, 42, 50} {35, 42, 51} {35, 42, 52}
{35, 42, 53} {35, 42, 54} {35, 42, 55} {35, 42, 56} {35, 42, 57} {35, 42, 58} {35, 42, 59} {35, 42, 60} {35, 42, 61}
{35, 42, 62} {35, 42, 63} {35, 42, 64} {35, 42, 65} {35, 42, 66} {35, 43, 44} {35, 43, 45} {35, 43, 46} {35, 43, 47}
{35, 43, 48} {35, 43, 49} {35, 43, 50} {35, 43, 51} {35, 43, 52} {35, 43, 53} {35, 43, 54} {35, 43, 55} {35, 43, 56}
{35, 43, 57} {35, 43, 58} {35, 43, 59} {35, 43, 60} {35, 43, 61} {35, 43, 62} {35, 43, 63} {35, 43, 64} {35, 43, 65}
{35, 43, 66} {35, 44, 45} {35, 44, 46} {35, 44, 47} {35, 44, 48} {35, 44, 49} {35, 44, 50} {35, 44, 51} {35, 44, 52}
{35, 44, 53} {35, 44, 54} {35, 44, 55} {35, 44, 56} {35, 44, 57} {35, 44, 58} {35, 44, 59} {35, 44, 60} {35, 44, 61}
{35, 44, 62} {35, 44, 63} {35, 44, 64} {35, 44, 65} {35, 44, 66} {35, 45, 46} {35, 45, 47} {35, 45, 48} {35, 45, 49}
{35, 45, 50} {35, 45, 51} {35, 45, 52} {35, 45, 53} {35, 45, 54} {35, 45, 55} {35, 45, 56} {35, 45, 57} {35, 45, 58}
{35, 45, 59} {35, 45, 60} {35, 45, 61} {35, 45, 62} {35, 45, 63} {35, 45, 64} {35, 45, 65} {35, 45, 66} {35, 46, 47}
{35, 46, 48} {35, 46, 49} {35, 46, 50} {35, 46, 51} {35, 46, 52} {35, 46, 53} {35, 46, 54} {35, 46, 55} {35, 46, 56}
{35, 46, 57} {35, 46, 58} {35, 46, 59} {35, 46, 60} {35, 46, 61} {35, 46, 62} {35, 46, 63} {35, 46, 64} {35, 46, 65}
{35, 46, 66} {35, 47, 48} {35, 47, 49} {35, 47, 50} {35, 47, 51} {35, 47, 52} {35, 47, 53} {35, 47, 54} {35, 47, 55}
{35, 47, 56} {35, 47, 57} {35, 47, 58} {35, 47, 59} {35, 47, 60} {35, 47, 61} {35, 47, 62} {35, 47, 63} {35, 47, 64}
{35, 47, 65} {35, 47, 66} {35, 48, 49} {35, 48, 50} {35, 48, 51} {35, 48, 52} {35, 48, 53} {35, 48, 54} {35, 48, 55}
{35, 48, 56} {35, 48, 57} {35, 48, 58} {35, 48, 59} {35, 48, 60} {35, 48, 61} {35, 48, 62} {35, 48, 63} {35, 48, 64}
{35, 48, 65} {35, 48, 66} {35, 49, 50} {35, 49, 51} {35, 49, 52} {35, 49, 53} {35, 49, 54} {35, 49, 55} {35, 49, 56}
{35, 49, 57} {35, 49, 58} {35, 49, 59} {35, 49, 60} {35, 49, 61} {35, 49, 62} {35, 49, 63} {35, 49, 64} {35, 49, 65}
{35, 49, 66} {35, 50, 51} {35, 50, 52} {35, 50, 53} {35, 50, 54} {35, 50, 55} {35, 50, 56} {35, 50, 57} {35, 50, 58}
{35, 50, 59} {35, 50, 60} {35, 50, 61} {35, 50, 62} {35, 50, 63} {35, 50, 64} {35, 50, 65} {35, 50, 66} {35, 51, 52}
{35, 51, 53} {35, 51, 54} {35, 51, 55} {35, 51, 56} {35, 51, 57} {35, 51, 58} {35, 51, 59} {35, 51, 60} {35, 51, 61}
{35, 51, 62} {35, 51, 63} {35, 51, 64} {35, 51, 65} {35, 51, 66} {35, 52, 53} {35, 52, 54} {35, 52, 55} {35, 52, 56}
{35, 52, 57} {35, 52, 58} {35, 52, 59} {35, 52, 60} {35, 52, 61} {35, 52, 62} {35, 52, 63} {35, 52, 64} {35, 52, 65}
{35, 52, 66} {35, 53, 54} {35, 53, 55} {35, 53, 56} {35, 53, 57} {35, 53, 58} {35, 53, 59} {35, 53, 60} {35, 53, 61}
{35, 53, 62} {35, 53, 63} {35, 53, 64} {35, 53, 65} {35, 53, 66} {35, 54, 55} {35, 54, 56} {35, 54, 57} {35, 54, 58}
{35, 54, 59} {35, 54, 60} {35, 54, 61} {35, 54, 62} {35, 54, 63} {35, 54, 64} {35, 54, 65} {35, 54, 66} {35, 55, 56}
{35, 55, 57} {35, 55, 58} {35, 55, 59} {35, 55, 60} {35, 55, 61} {35, 55, 62} {35, 55, 63} {35, 55, 64} {35, 55, 65}
{35, 55, 66} {35, 56, 57} {35, 56, 58} {35, 56, 59} {35, 56, 60} {35, 56, 61} {35, 56, 62} {35, 56, 63} {35, 56, 64}
{35, 56, 65} {35, 56, 66} {35, 57, 58} {35, 57, 59} {35, 57, 60} {35, 57, 61} {35, 57, 62} {35, 57, 63} {35, 57, 64}
{35, 57, 65} {35, 57, 66} {35, 58, 59} {35, 58, 60} {35, 58, 61} {35, 58, 62} {35, 58, 63} {35, 58, 64} {35, 58, 65}
{35, 58, 66} {35, 59, 60} {35, 59, 61} {35, 59, 62} {35, 59, 63} {35, 59, 64} {35, 59, 65} {35, 59, 66} {35, 60, 61}
{35, 60, 62} {35, 60, 63} {35, 60, 64} {35, 60, 65} {35, 60, 66} {35, 61, 62} {35, 61, 63} {35, 61, 64} {35, 61, 65}
{35, 61, 66} {35, 62, 63} {35, 62, 64} {35, 62, 65} {35, 62, 66} {35, 63, 64} {35, 63, 65} {35, 63, 66} {35, 64, 65}

TABLE 3A-continued

{35, 64, 66} {35, 65, 66} {36, 37, 38} {36, 37, 39} {36, 37, 40} {36, 37, 41} {36, 37, 42} {36, 37, 43} {36, 37, 44}
{36, 37, 45} {36, 37, 46} {36, 37, 47} {36, 37, 48} {36, 37, 49} {36, 37, 50} {36, 37, 51} {36, 37, 52} {36, 37, 53}
{36, 37, 54} {36, 37, 55} {36, 37, 56} {36, 37, 57} {36, 37, 58} {36, 37, 59} {36, 37, 60} {36, 37, 61} {36, 37, 62}
{36, 37, 63} {36, 37, 64} {36, 37, 65} {36, 37, 66} {36, 38, 40} {36, 38, 41} {36, 38, 42} {36, 38, 43}
{36, 38, 44} {36, 38, 45} {36, 38, 46} {36, 38, 47} {36, 38, 48} {36, 38, 49} {36, 38, 50} {36, 38, 51} {36, 38, 52}
{36, 38, 53} {36, 38, 54} {36, 38, 55} {36, 38, 56} {36, 38, 57} {36, 38, 58} {36, 38, 59} {36, 38, 60} {36, 38, 61}
{36, 38, 62} {36, 38, 63} {36, 38, 64} {36, 38, 65} {36, 38, 66} {36, 39, 40} {36, 39, 41} {36, 39, 42} {36, 39, 43}
{36, 39, 44} {36, 39, 45} {36, 39, 46} {36, 39, 47} {36, 39, 48} {36, 39, 49} {36, 39, 50} {36, 39, 51} {36, 39, 52}
{36, 39, 53} {36, 39, 54} {36, 39, 55} {36, 39, 56} {36, 39, 57} {36, 39, 58} {36, 39, 59} {36, 39, 60} {36, 39, 61}
{36, 39, 62} {36, 39, 63} {36, 39, 64} {36, 39, 65} {36, 39, 66} {36, 40, 41} {36, 40, 42} {36, 40, 43} {36, 40, 44}
{36, 40, 45} {36, 40, 46} {36, 40, 47} {36, 40, 48} {36, 40, 49} {36, 40, 50} {36, 40, 51} {36, 40, 52} {36, 40, 53}
{36, 40, 54} {36, 40, 55} {36, 40, 56} {36, 40, 57} {36, 40, 58} {36, 40, 59} {36, 40, 60} {36, 40, 61} {36, 40, 62}
{36, 40, 63} {36, 40, 64} {36, 40, 65} {36, 40, 66} {36, 41, 42} {36, 41, 43} {36, 41, 44} {36, 41, 45} {36, 41, 46}
{36, 41, 47} {36, 41, 48} {36, 41, 49} {36, 41, 50} {36, 41, 51} {36, 41, 52} {36, 41, 53} {36, 41, 54} {36, 41, 55}
{36, 41, 56} {36, 41, 57} {36, 41, 58} {36, 41, 59} {36, 41, 60} {36, 41, 61} {36, 41, 62} {36, 41, 63} {36, 41, 64}
{36, 41, 65} {36, 41, 66} {36, 42, 43} {36, 42, 44} {36, 42, 45} {36, 42, 46} {36, 42, 47} {36, 42, 48} {36, 42, 49}
{36, 42, 50} {36, 42, 51} {36, 42, 52} {36, 42, 53} {36, 42, 54} {36, 42, 55} {36, 42, 56} {36, 42, 57} {36, 42, 58}
{36, 42, 59} {36, 42, 60} {36, 42, 61} {36, 42, 62} {36, 42, 63} {36, 42, 64} {36, 42, 65} {36, 42, 66} {36, 43, 44}
{36, 43, 45} {36, 43, 46} {36, 43, 47} {36, 43, 48} {36, 43, 49} {36, 43, 50} {36, 43, 51} {36, 43, 52} {36, 43, 53}
{36, 43, 54} {36, 43, 55} {36, 43, 56} {36, 43, 57} {36, 43, 58} {36, 43, 59} {36, 43, 60} {36, 43, 61} {36, 43, 62}
{36, 43, 63} {36, 43, 64} {36, 43, 65} {36, 43, 66} {36, 44, 45} {36, 44, 46} {36, 44, 47} {36, 44, 48} {36, 44, 49}
{36, 44, 50} {36, 44, 51} {36, 44, 52} {36, 44, 53} {36, 44, 54} {36, 44, 55} {36, 44, 56} {36, 44, 57} {36, 44, 58}
{36, 44, 59} {36, 44, 60} {36, 44, 61} {36, 44, 62} {36, 44, 63} {36, 44, 64} {36, 44, 65} {36, 44, 66} {36, 45, 46}
{36, 45, 47} {36, 45, 48} {36, 45, 49} {36, 45, 50} {36, 45, 51} {36, 45, 52} {36, 45, 53} {36, 45, 54} {36, 45, 55}
{36, 45, 56} {36, 45, 57} {36, 45, 58} {36, 45, 59} {36, 45, 60} {36, 45, 61} {36, 45, 62} {36, 45, 63} {36, 45, 64}
{36, 45, 65} {36, 45, 66} {36, 46, 47} {36, 46, 48} {36, 46, 49} {36, 46, 50} {36, 46, 51} {36, 46, 52} {36, 46, 53}
{36, 46, 54} {36, 46, 55} {36, 46, 56} {36, 46, 57} {36, 46, 58} {36, 46, 59} {36, 46, 60} {36, 46, 61} {36, 46, 62}
{36, 46, 63} {36, 46, 64} {36, 46, 65} {36, 46, 66} {36, 47, 48} {36, 47, 49} {36, 47, 50} {36, 47, 51} {36, 47, 52}
{36, 47, 53} {36, 47, 54} {36, 47, 55} {36, 47, 56} {36, 47, 57} {36, 47, 58} {36, 47, 59} {36, 47, 60} {36, 47, 61}
{36, 47, 62} {36, 47, 63} {36, 47, 64} {36, 47, 65} {36, 47, 66} {36, 48, 49} {36, 48, 50} {36, 48, 51} {36, 48, 52}
{36, 48, 53} {36, 48, 54} {36, 48, 55} {36, 48, 56} {36, 48, 57} {36, 48, 58} {36, 48, 59} {36, 48, 60} {36, 48, 61}
{36, 48, 62} {36, 48, 63} {36, 48, 64} {36, 48, 65} {36, 48, 66} {36, 49, 50} {36, 49, 51} {36, 49, 52} {36, 49, 53}
{36, 49, 54} {36, 49, 55} {36, 49, 56} {36, 49, 57} {36, 49, 58} {36, 49, 59} {36, 49, 60} {36, 49, 61} {36, 49, 62}
{36, 49, 63} {36, 49, 64} {36, 49, 65} {36, 49, 66} {36, 50, 51} {36, 50, 52} {36, 50, 53} {36, 50, 54} {36, 50, 55}
{36, 50, 56} {36, 50, 57} {36, 50, 58} {36, 50, 59} {36, 50, 60} {36, 50, 61} {36, 50, 62} {36, 50, 63} {36, 50, 64}
{36, 50, 65} {36, 50, 66} {36, 51, 52} {36, 51, 53} {36, 51, 54} {36, 51, 55} {36, 51, 56} {36, 51, 57} {36, 51, 58}
{36, 51, 59} {36, 51, 60} {36, 51, 61} {36, 51, 62} {36, 51, 63} {36, 51, 64} {36, 51, 65} {36, 51, 66} {36, 52, 53}
{36, 52, 54} {36, 52, 55} {36, 52, 56} {36, 52, 57} {36, 52, 58} {36, 52, 59} {36, 52, 60} {36, 52, 61} {36, 52, 62}
{36, 52, 63} {36, 52, 64} {36, 52, 65} {36, 52, 66} {36, 53, 54} {36, 53, 55} {36, 53, 56} {36, 53, 57} {36, 53, 58}
{36, 53, 59} {36, 53, 60} {36, 53, 61} {36, 53, 62} {36, 53, 63} {36, 53, 64} {36, 53, 65} {36, 53, 66} {36, 54, 55}
{36, 54, 56} {36, 54, 57} {36, 54, 58} {36, 54, 59} {36, 54, 60} {36, 54, 61} {36, 54, 62} {36, 54, 63} {36, 54, 64}
{36, 54, 65} {36, 54, 66} {36, 55, 56} {36, 55, 57} {36, 55, 58} {36, 55, 59} {36, 55, 60} {36, 55, 61} {36, 55, 62}
{36, 55, 63} {36, 55, 64} {36, 55, 65} {36, 55, 66} {36, 56, 57} {36, 56, 58} {36, 56, 59} {36, 56, 60} {36, 56, 61}
{36, 56, 62} {36, 56, 63} {36, 56, 64} {36, 56, 65} {36, 56, 66} {36, 57, 58} {36, 57, 59} {36, 57, 60} {36, 57, 61}
{36, 57, 62} {36, 57, 63} {36, 57, 64} {36, 57, 65} {36, 57, 66} {36, 58, 59} {36, 58, 60} {36, 58, 61} {36, 58, 62}
{36, 58, 63} {36, 58, 64} {36, 58, 65} {36, 58, 66} {36, 59, 60} {36, 59, 61} {36, 59, 62} {36, 59, 63} {36, 59, 64}
{36, 59, 65} {36, 59, 66} {36, 60, 61} {36, 60, 62} {36, 60, 63} {36, 60, 64} {36, 60, 65} {36, 60, 66} {36, 61, 62}
{36, 61, 63} {36, 61, 64} {36, 61, 65} {36, 61, 66} {36, 62, 63} {36, 62, 64} {36, 62, 65} {36, 62, 66} {36, 63, 64}
{36, 63, 65} {36, 63, 66} {36, 64, 65} {36, 64, 66} {36, 65, 66} {37, 38, 39} {37, 38, 40} {37, 38, 41} {37, 38, 42}
{37, 38, 43} {37, 38, 44} {37, 38, 45} {37, 38, 46} {37, 38, 47} {37, 38, 48} {37, 38, 49} {37, 38, 50} {37, 38, 51}
{37, 38, 52} {37, 38, 53} {37, 38, 54} {37, 38, 55} {37, 38, 56} {37, 38, 57} {37, 38, 58} {37, 38, 59} {37, 38, 60}
{37, 38, 61} {37, 38, 62} {37, 38, 63} {37, 38, 64} {37, 38, 65} {37, 38, 66} {37, 39, 40} {37, 39, 41} {37, 39, 42}
{37, 39, 43} {37, 39, 44} {37, 39, 45} {37, 39, 46} {37, 39, 47} {37, 39, 48} {37, 39, 49} {37, 39, 50} {37, 39, 51}
{37, 39, 52} {37, 39, 53} {37, 39, 54} {37, 39, 55} {37, 39, 56} {37, 39, 57} {37, 39, 58} {37, 39, 59} {37, 39, 60}
{37, 39, 61} {37, 39, 62} {37, 39, 63} {37, 39, 64} {37, 39, 65} {37, 39, 66} {37, 40, 41} {37, 40, 42} {37, 40, 43}
{37, 40, 44} {37, 40, 45} {37, 40, 46} {37, 40, 47} {37, 40, 48} {37, 40, 49} {37, 40, 50} {37, 40, 51} {37, 40, 52}
{37, 40, 53} {37, 40, 54} {37, 40, 55} {37, 40, 56} {37, 40, 57} {37, 40, 58} {37, 40, 59} {37, 40, 60} {37, 40, 61}
{37, 40, 62} {37, 40, 63} {37, 40, 64} {37, 40, 65} {37, 41, 42} {37, 41, 43} {37, 41, 44} {37, 41, 45}
{37, 41, 46} {37, 41, 47} {37, 41, 48} {37, 41, 49} {37, 41, 50} {37, 41, 51} {37, 41, 52} {37, 41, 53} {37, 41, 54}
{37, 41, 55} {37, 41, 56} {37, 41, 57} {37, 41, 58} {37, 41, 59} {37, 41, 60} {37, 41, 61} {37, 41, 62} {37, 41, 63}
{37, 41, 64} {37, 41, 65} {37, 41, 66} {37, 42, 43} {37, 42, 44} {37, 42, 45} {37, 42, 46} {37, 42, 47} {37, 42, 48}
{37, 42, 49} {37, 42, 50} {37, 42, 51} {37, 42, 52} {37, 42, 53} {37, 42, 54} {37, 42, 55} {37, 42, 56} {37, 42, 57}
{37, 42, 58} {37, 42, 59} {37, 42, 60} {37, 42, 61} {37, 42, 62} {37, 42, 63} {37, 42, 64} {37, 42, 65} {37, 42, 66}
{37, 43, 44} {37, 43, 45} {37, 43, 46} {37, 43, 47} {37, 43, 48} {37, 43, 49} {37, 43, 50} {37, 43, 51} {37, 43, 52}
{37, 43, 53} {37, 43, 54} {37, 43, 55} {37, 43, 56} {37, 43, 57} {37, 43, 58} {37, 43, 59} {37, 43, 60} {37, 43, 61}
{37, 43, 62} {37, 43, 63} {37, 43, 64} {37, 43, 65} {37, 43, 66} {37, 44, 45} {37, 44, 46} {37, 44, 47} {37, 44, 48}
{37, 44, 49} {37, 44, 50} {37, 44, 51} {37, 44, 52} {37, 44, 53} {37, 44, 54} {37, 44, 55} {37, 44, 56} {37, 44, 57}
{37, 44, 58} {37, 44, 59} {37, 44, 60} {37, 44, 61} {37, 44, 62} {37, 44, 63} {37, 44, 64} {37, 44, 65} {37, 44, 66}
{37, 45, 46} {37, 45, 47} {37, 45, 48} {37, 45, 49} {37, 45, 50} {37, 45, 51} {37, 45, 52} {37, 45, 53} {37, 45, 54}
{37, 45, 55} {37, 45, 56} {37, 45, 57} {37, 45, 58} {37, 45, 59} {37, 45, 60} {37, 45, 61} {37, 45, 62} {37, 45, 63}
{37, 45, 64} {37, 45, 65} {37, 45, 66} {37, 46, 47} {37, 46, 48} {37, 46, 49} {37, 46, 50} {37, 46, 51} {37, 46, 52}
{37, 46, 53} {37, 46, 54} {37, 46, 55} {37, 46, 56} {37, 46, 57} {37, 46, 58} {37, 46, 59} {37, 46, 60} {37, 46, 61}
{37, 46, 62} {37, 46, 63} {37, 46, 64} {37, 46, 65} {37, 46, 66} {37, 47, 48} {37, 47, 49} {37, 47, 50} {37, 47, 51}
{37, 47, 52} {37, 47, 53} {37, 47, 54} {37, 47, 55} {37, 47, 56} {37, 47, 57} {37, 47, 58} {37, 47, 59} {37, 47, 60}
{37, 47, 61} {37, 47, 62} {37, 47, 63} {37, 47, 64} {37, 47, 65} {37, 47, 66} {37, 48, 49} {37, 48, 50} {37, 48, 51}
{37, 48, 52} {37, 48, 53} {37, 48, 54} {37, 48, 55} {37, 48, 56} {37, 48, 57} {37, 48, 58} {37, 48, 59} {37, 48, 60}
{37, 48, 61} {37, 48, 62} {37, 48, 63} {37, 48, 64} {37, 48, 65} {37, 48, 66} {37, 49, 50} {37, 49, 51} {37, 49, 52}
{37, 49, 53} {37, 49, 54} {37, 49, 55} {37, 49, 56} {37, 49, 57} {37, 49, 58} {37, 49, 59} {37, 49, 60} {37, 49, 61}
{37, 49, 62} {37, 49, 63} {37, 49, 64} {37, 49, 65} {37, 49, 66} {37, 50, 51} {37, 50, 52} {37, 50, 53} {37, 50, 54}
{37, 50, 55} {37, 50, 56} {37, 50, 57} {37, 50, 58} {37, 50, 59} {37, 50, 60} {37, 50, 61} {37, 50, 62} {37, 50, 63}

TABLE 3A-continued

| | | | | | | | |
|---|---|---|---|---|---|---|---|
| {37, 50, 64} | {37, 50, 65} | {37, 50, 66} | {37, 51, 52} | {37, 51, 53} | {37, 51, 54} | {37, 51, 55} | {37, 51, 56} | {37, 51, 57} |
| {37, 51, 58} | {37, 51, 59} | {37, 51, 60} | {37, 51, 61} | {37, 51, 62} | {37, 51, 63} | {37, 51, 64} | {37, 51, 65} | {37, 51, 66} |
| {37, 52, 53} | {37, 52, 54} | {37, 52, 55} | {37, 52, 56} | {37, 52, 57} | {37, 52, 58} | {37, 52, 59} | {37, 52, 60} | {37, 52, 61} |
| {37, 52, 62} | {37, 52, 63} | {37, 52, 64} | {37, 52, 65} | {37, 52, 66} | {37, 53, 54} | {37, 53, 55} | {37, 53, 56} | {37, 53, 57} |
| {37, 53, 58} | {37, 53, 59} | {37, 53, 60} | {37, 53, 61} | {37, 53, 62} | {37, 53, 63} | {37, 53, 64} | {37, 53, 65} | {37, 53, 66} |
| {37, 54, 55} | {37, 54, 56} | {37, 54, 57} | {37, 54, 58} | {37, 54, 59} | {37, 54, 60} | {37, 54, 61} | {37, 54, 62} | {37, 54, 63} |
| {37, 54, 64} | {37, 54, 65} | {37, 54, 66} | {37, 55, 56} | {37, 55, 57} | {37, 55, 58} | {37, 55, 59} | {37, 55, 60} | {37, 55, 61} |
| {37, 55, 62} | {37, 55, 63} | {37, 55, 64} | {37, 55, 65} | {37, 55, 66} | {37, 56, 57} | {37, 56, 58} | {37, 56, 59} | {37, 56, 60} |
| {37, 56, 61} | {37, 56, 62} | {37, 56, 63} | {37, 56, 64} | {37, 56, 65} | {37, 56, 66} | {37, 57, 58} | {37, 57, 59} | {37, 57, 60} |
| {37, 57, 61} | {37, 57, 62} | {37, 57, 63} | {37, 57, 64} | {37, 57, 65} | {37, 57, 66} | {37, 58, 59} | {37, 58, 60} | {37, 58, 61} |
| {37, 58, 62} | {37, 58, 63} | {37, 58, 64} | {37, 58, 65} | {37, 58, 66} | {37, 59, 60} | {37, 59, 61} | {37, 59, 62} | {37, 59, 63} |
| {37, 59, 64} | {37, 59, 65} | {37, 59, 66} | {37, 60, 61} | {37, 60, 62} | {37, 60, 63} | {37, 60, 64} | {37, 60, 65} | {37, 60, 66} |
| {37, 61, 62} | {37, 61, 63} | {37, 61, 64} | {37, 61, 65} | {37, 61, 66} | {37, 62, 63} | {37, 62, 64} | {37, 62, 65} | {37, 62, 66} |
| {37, 63, 64} | {37, 63, 65} | {37, 63, 66} | {37, 64, 65} | {37, 64, 66} | {37, 65, 66} | {38, 39, 40} | {38, 39, 41} | {38, 39, 42} |
| {38, 39, 43} | {38, 39, 44} | {38, 39, 45} | {38, 39, 46} | {38, 39, 47} | {38, 39, 48} | {38, 39, 49} | {38, 39, 50} | {38, 39, 51} |
| {38, 39, 52} | {38, 39, 53} | {38, 39, 54} | {38, 39, 55} | {38, 39, 56} | {38, 39, 57} | {38, 39, 58} | {38, 39, 59} | {38, 39, 60} |
| {38, 39, 61} | {38, 39, 62} | {38, 39, 63} | {38, 39, 64} | {38, 39, 65} | {38, 39, 66} | {38, 40, 41} | {38, 40, 42} | {38, 40, 43} |
| {38, 40, 44} | {38, 40, 45} | {38, 40, 46} | {38, 40, 47} | {38, 40, 48} | {38, 40, 49} | {38, 40, 50} | {38, 40, 51} | {38, 40, 52} |
| {38, 40, 53} | {38, 40, 54} | {38, 40, 55} | {38, 40, 56} | {38, 40, 57} | {38, 40, 58} | {38, 40, 59} | {38, 40, 60} | {38, 40, 61} |
| {38, 40, 62} | {38, 40, 63} | {38, 40, 64} | {38, 40, 65} | {38, 40, 66} | {38, 41, 42} | {38, 41, 43} | {38, 41, 44} | {38, 41, 45} |
| {38, 41, 46} | {38, 41, 47} | {38, 41, 48} | {38, 41, 49} | {38, 41, 50} | {38, 41, 51} | {38, 41, 52} | {38, 41, 53} | {38, 41, 54} |
| {38, 41, 55} | {38, 41, 56} | {38, 41, 57} | {38, 41, 58} | {38, 41, 59} | {38, 41, 60} | {38, 41, 61} | {38, 41, 62} | {38, 41, 63} |
| {38, 41, 64} | {38, 41, 65} | {38, 41, 66} | {38, 42, 43} | {38, 42, 44} | {38, 42, 45} | {38, 42, 46} | {38, 42, 47} | {38, 42, 48} |
| {38, 42, 49} | {38, 42, 50} | {38, 42, 51} | {38, 42, 52} | {38, 42, 53} | {38, 42, 54} | {38, 42, 55} | {38, 42, 56} | {38, 42, 57} |
| {38, 42, 58} | {38, 42, 59} | {38, 42, 60} | {38, 42, 61} | {38, 42, 62} | {38, 42, 63} | {38, 42, 64} | {38, 42, 65} | {38, 42, 66} |
| {38, 43, 44} | {38, 43, 45} | {38, 43, 46} | {38, 43, 47} | {38, 43, 48} | {38, 43, 49} | {38, 43, 50} | {38, 43, 51} | {38, 43, 52} |
| {38, 43, 53} | {38, 43, 54} | {38, 43, 55} | {38, 43, 56} | {38, 43, 57} | {38, 43, 58} | {38, 43, 59} | {38, 43, 60} | {38, 43, 61} |
| {38, 43, 62} | {38, 43, 63} | {38, 43, 64} | {38, 43, 65} | {38, 43, 66} | {38, 44, 45} | {38, 44, 46} | {38, 44, 47} | {38, 44, 48} |
| {38, 44, 49} | {38, 44, 50} | {38, 44, 51} | {38, 44, 52} | {38, 44, 53} | {38, 44, 54} | {38, 44, 55} | {38, 44, 56} | {38, 44, 57} |
| {38, 44, 58} | {38, 44, 59} | {38, 44, 60} | {38, 44, 61} | {38, 44, 62} | {38, 44, 63} | {38, 44, 64} | {38, 44, 65} | {38, 44, 66} |
| {38, 45, 46} | {38, 45, 47} | {38, 45, 48} | {38, 45, 49} | {38, 45, 50} | {38, 45, 51} | {38, 45, 52} | {38, 45, 53} | {38, 45, 54} |
| {38, 45, 55} | {38, 45, 56} | {38, 45, 57} | {38, 45, 58} | {38, 45, 59} | {38, 45, 60} | {38, 45, 61} | {38, 45, 62} | {38, 45, 63} |
| {38, 45, 64} | {38, 45, 65} | {38, 45, 66} | {38, 46, 47} | {38, 46, 48} | {38, 46, 49} | {38, 46, 50} | {38, 46, 51} | {38, 46, 52} |
| {38, 46, 53} | {38, 46, 54} | {38, 46, 55} | {38, 46, 56} | {38, 46, 57} | {38, 46, 58} | {38, 46, 59} | {38, 46, 60} | {38, 46, 61} |
| {38, 46, 62} | {38, 46, 63} | {38, 46, 64} | {38, 46, 65} | {38, 46, 66} | {38, 47, 48} | {38, 47, 49} | {38, 47, 50} | {38, 47, 51} |
| {38, 47, 52} | {38, 47, 53} | {38, 47, 54} | {38, 47, 55} | {38, 47, 56} | {38, 47, 57} | {38, 47, 58} | {38, 47, 59} | {38, 47, 60} |
| {38, 47, 61} | {38, 47, 62} | {38, 47, 63} | {38, 47, 64} | {38, 47, 65} | {38, 47, 66} | {38, 48, 49} | {38, 48, 50} | {38, 48, 51} |
| {38, 48, 52} | {38, 48, 53} | {38, 48, 54} | {38, 48, 55} | {38, 48, 56} | {38, 48, 57} | {38, 48, 58} | {38, 48, 59} | {38, 48, 60} |
| {38, 48, 61} | {38, 48, 62} | {38, 48, 63} | {38, 48, 64} | {38, 48, 65} | {38, 48, 66} | {38, 49, 50} | {38, 49, 51} | {38, 49, 52} |
| {38, 49, 53} | {38, 49, 54} | {38, 49, 55} | {38, 49, 56} | {38, 49, 57} | {38, 49, 58} | {38, 49, 59} | {38, 49, 60} | {38, 49, 61} |
| {38, 49, 62} | {38, 49, 63} | {38, 49, 64} | {38, 49, 65} | {38, 49, 66} | {38, 50, 51} | {38, 50, 52} | {38, 50, 53} | {38, 50, 54} |
| {38, 50, 55} | {38, 50, 56} | {38, 50, 57} | {38, 50, 58} | {38, 50, 59} | {38, 50, 60} | {38, 50, 61} | {38, 50, 62} | {38, 50, 63} |
| {38, 50, 64} | {38, 50, 65} | {38, 50, 66} | {38, 51, 52} | {38, 51, 53} | {38, 51, 54} | {38, 51, 55} | {38, 51, 56} | {38, 51, 57} |
| {38, 51, 58} | {38, 51, 59} | {38, 51, 60} | {38, 51, 61} | {38, 51, 62} | {38, 51, 63} | {38, 51, 64} | {38, 51, 65} | {38, 51, 66} |
| {38, 52, 53} | {38, 52, 54} | {38, 52, 55} | {38, 52, 56} | {38, 52, 57} | {38, 52, 58} | {38, 52, 59} | {38, 52, 60} | {38, 52, 61} |
| {38, 52, 62} | {38, 52, 63} | {38, 52, 64} | {38, 52, 65} | {38, 52, 66} | {38, 53, 54} | {38, 53, 55} | {38, 53, 56} | {38, 53, 57} |
| {38, 53, 58} | {38, 53, 59} | {38, 53, 60} | {38, 53, 61} | {38, 53, 62} | {38, 53, 63} | {38, 53, 64} | {38, 53, 65} | {38, 53, 66} |
| {38, 54, 55} | {38, 54, 56} | {38, 54, 57} | {38, 54, 58} | {38, 54, 59} | {38, 54, 60} | {38, 54, 61} | {38, 54, 62} | {38, 54, 63} |
| {38, 54, 64} | {38, 54, 65} | {38, 54, 66} | {38, 55, 56} | {38, 55, 57} | {38, 55, 58} | {38, 55, 59} | {38, 55, 60} | {38, 55, 61} |
| {38, 55, 62} | {38, 55, 63} | {38, 55, 64} | {38, 55, 65} | {38, 55, 66} | {38, 56, 57} | {38, 56, 58} | {38, 56, 59} | {38, 56, 60} |
| {38, 56, 61} | {38, 56, 62} | {38, 56, 63} | {38, 56, 64} | {38, 56, 65} | {38, 56, 66} | {38, 57, 58} | {38, 57, 59} | {38, 57, 60} |
| {38, 57, 61} | {38, 57, 62} | {38, 57, 63} | {38, 57, 64} | {38, 57, 65} | {38, 57, 66} | {38, 58, 59} | {38, 58, 60} | {38, 58, 61} |
| {38, 58, 62} | {38, 58, 63} | {38, 58, 64} | {38, 58, 65} | {38, 58, 66} | {38, 59, 60} | {38, 59, 61} | {38, 59, 62} | {38, 59, 63} |
| {38, 59, 64} | {38, 59, 65} | {38, 59, 66} | {38, 60, 61} | {38, 60, 62} | {38, 60, 63} | {38, 60, 64} | {38, 60, 65} | {38, 60, 66} |
| {38, 61, 62} | {38, 61, 63} | {38, 61, 64} | {38, 61, 65} | {38, 61, 66} | {38, 62, 63} | {38, 62, 64} | {38, 62, 65} | {38, 62, 66} |
| {38, 63, 64} | {38, 63, 65} | {38, 63, 66} | {38, 64, 65} | {38, 64, 66} | {38, 65, 66} | {39, 40, 41} | {39, 40, 42} | {39, 40, 43} |
| {39, 40, 44} | {39, 40, 45} | {39, 40, 46} | {39, 40, 47} | {39, 40, 48} | {39, 40, 49} | {39, 40, 50} | {39, 40, 51} | {39, 40, 52} |
| {39, 40, 53} | {39, 40, 54} | {39, 40, 55} | {39, 40, 56} | {39, 40, 57} | {39, 40, 58} | {39, 40, 59} | {39, 40, 60} | {39, 40, 61} |
| {39, 40, 62} | {39, 40, 63} | {39, 40, 64} | {39, 40, 65} | {39, 40, 66} | {39, 41, 42} | {39, 41, 43} | {39, 41, 44} | {39, 41, 45} |
| {39, 41, 46} | {39, 41, 47} | {39, 41, 48} | {39, 41, 49} | {39, 41, 50} | {39, 41, 51} | {39, 41, 52} | {39, 41, 53} | {39, 41, 54} |
| {39, 41, 55} | {39, 41, 56} | {39, 41, 57} | {39, 41, 58} | {39, 41, 59} | {39, 41, 60} | {39, 41, 61} | {39, 41, 62} | {39, 41, 63} |
| {39, 41, 64} | {39, 41, 65} | {39, 41, 66} | {39, 42, 43} | {39, 42, 44} | {39, 42, 45} | {39, 42, 46} | {39, 42, 47} | {39, 42, 48} |
| {39, 42, 49} | {39, 42, 50} | {39, 42, 51} | {39, 42, 52} | {39, 42, 53} | {39, 42, 54} | {39, 42, 55} | {39, 42, 56} | {39, 42, 57} |
| {39, 42, 58} | {39, 42, 59} | {39, 42, 60} | {39, 42, 61} | {39, 42, 62} | {39, 42, 63} | {39, 42, 64} | {39, 42, 65} | {39, 42, 66} |
| {39, 43, 44} | {39, 43, 45} | {39, 43, 46} | {39, 43, 47} | {39, 43, 48} | {39, 43, 49} | {39, 43, 50} | {39, 43, 51} | {39, 43, 52} |
| {39, 43, 53} | {39, 43, 54} | {39, 43, 55} | {39, 43, 56} | {39, 43, 57} | {39, 43, 58} | {39, 43, 59} | {39, 43, 60} | {39, 43, 61} |
| {39, 43, 62} | {39, 43, 63} | {39, 43, 64} | {39, 43, 65} | {39, 43, 66} | {39, 44, 45} | {39, 44, 46} | {39, 44, 47} | {39, 44, 48} |
| {39, 44, 49} | {39, 44, 50} | {39, 44, 51} | {39, 44, 52} | {39, 44, 53} | {39, 44, 54} | {39, 44, 55} | {39, 44, 56} | {39, 44, 57} |
| {39, 44, 58} | {39, 44, 59} | {39, 44, 60} | {39, 44, 61} | {39, 44, 62} | {39, 44, 63} | {39, 44, 64} | {39, 44, 65} | {39, 44, 66} |
| {39, 45, 46} | {39, 45, 47} | {39, 45, 48} | {39, 45, 49} | {39, 45, 50} | {39, 45, 51} | {39, 45, 52} | {39, 45, 53} | {39, 45, 54} |
| {39, 45, 55} | {39, 45, 56} | {39, 45, 57} | {39, 45, 58} | {39, 45, 59} | {39, 45, 60} | {39, 45, 61} | {39, 45, 62} | {39, 45, 63} |
| {39, 45, 64} | {39, 45, 65} | {39, 45, 66} | {39, 46, 47} | {39, 46, 48} | {39, 46, 49} | {39, 46, 50} | {39, 46, 51} | {39, 46, 52} |
| {39, 46, 53} | {39, 46, 54} | {39, 46, 55} | {39, 46, 56} | {39, 46, 57} | {39, 46, 58} | {39, 46, 59} | {39, 46, 60} | {39, 46, 61} |
| {39, 46, 62} | {39, 46, 63} | {39, 46, 64} | {39, 46, 65} | {39, 46, 66} | {39, 47, 48} | {39, 47, 49} | {39, 47, 50} | {39, 47, 51} |
| {39, 47, 52} | {39, 47, 53} | {39, 47, 54} | {39, 47, 55} | {39, 47, 56} | {39, 47, 57} | {39, 47, 58} | {39, 47, 59} | {39, 47, 60} |
| {39, 47, 61} | {39, 47, 62} | {39, 47, 63} | {39, 47, 64} | {39, 47, 65} | {39, 47, 66} | {39, 48, 49} | {39, 48, 50} | {39, 48, 51} |
| {39, 48, 52} | {39, 48, 53} | {39, 48, 54} | {39, 48, 55} | {39, 48, 56} | {39, 48, 57} | {39, 48, 58} | {39, 48, 59} | {39, 48, 60} |
| {39, 48, 61} | {39, 48, 62} | {39, 48, 63} | {39, 48, 64} | {39, 48, 65} | {39, 48, 66} | {39, 49, 50} | {39, 49, 51} | {39, 49, 52} |
| {39, 49, 53} | {39, 49, 54} | {39, 49, 55} | {39, 49, 56} | {39, 49, 57} | {39, 49, 58} | {39, 49, 59} | {39, 49, 60} | {39, 49, 61} |
| {39, 49, 62} | {39, 49, 63} | {39, 49, 64} | {39, 49, 65} | {39, 49, 66} | {39, 50, 51} | {39, 50, 52} | {39, 50, 53} | {39, 50, 54} |

TABLE 3A-continued

{39, 50, 55} {39, 50, 56} {39, 50, 57} {39, 50, 58} {39, 50, 59} {39, 50, 60} {39, 50, 61} {39, 50, 62} {39, 50, 63}
{39, 50, 64} {39, 50, 65} {39, 50, 66} {39, 51, 52} {39, 51, 53} {39, 51, 54} {39, 51, 55} {39, 51, 56} {39, 51, 57}
{39, 51, 58} {39, 51, 59} {39, 51, 60} {39, 51, 61} {39, 51, 62} {39, 51, 63} {39, 51, 64} {39, 51, 65} {39, 51, 66}
{39, 52, 53} {39, 52, 54} {39, 52, 55} {39, 52, 56} {39, 52, 57} {39, 52, 58} {39, 52, 59} {39, 52, 60} {39, 52, 61}
{39, 52, 62} {39, 52, 63} {39, 52, 64} {39, 52, 65} {39, 52, 66} {39, 53, 54} {39, 53, 55} {39, 53, 56} {39, 53, 57}
{39, 53, 58} {39, 53, 59} {39, 53, 60} {39, 53, 61} {39, 53, 62} {39, 53, 63} {39, 53, 64} {39, 53, 65} {39, 53, 66}
{39, 54, 55} {39, 54, 56} {39, 54, 57} {39, 54, 58} {39, 54, 59} {39, 54, 60} {39, 54, 61} {39, 54, 62} {39, 54, 63}
{39, 54, 64} {39, 54, 65} {39, 54, 66} {39, 55, 56} {39, 55, 57} {39, 55, 58} {39, 55, 59} {39, 55, 60} {39, 55, 61}
{39, 55, 62} {39, 55, 63} {39, 55, 64} {39, 55, 65} {39, 55, 66} {39, 56, 57} {39, 56, 58} {39, 56, 59} {39, 56, 60}
{39, 56, 61} {39, 56, 62} {39, 56, 63} {39, 56, 64} {39, 56, 65} {39, 56, 66} {39, 57, 58} {39, 57, 59} {39, 57, 60}
{39, 57, 61} {39, 57, 62} {39, 57, 63} {39, 57, 64} {39, 57, 65} {39, 57, 66} {39, 58, 59} {39, 58, 60} {39, 58, 61}
{39, 58, 62} {39, 58, 63} {39, 58, 64} {39, 58, 65} {39, 58, 66} {39, 59, 60} {39, 59, 61} {39, 59, 62} {39, 59, 63}
{39, 59, 64} {39, 59, 65} {39, 59, 66} {39, 60, 61} {39, 60, 62} {39, 60, 63} {39, 60, 64} {39, 60, 65} {39, 60, 66}
{39, 61, 62} {39, 61, 63} {39, 61, 64} {39, 61, 65} {39, 61, 66} {39, 62, 63} {39, 62, 64} {39, 62, 65} {39, 62, 66}
{39, 63, 64} {39, 63, 65} {39, 63, 66} {39, 64, 65} {39, 64, 66} {39, 65, 66} {40, 41, 42} {40, 41, 43} {40, 41, 44}
{40, 41, 45} {40, 41, 46} {40, 41, 47} {40, 41, 48} {40, 41, 49} {40, 41, 50} {40, 41, 51} {40, 41, 52} {40, 41, 53}
{40, 41, 54} {40, 41, 55} {40, 41, 56} {40, 41, 57} {40, 41, 58} {40, 41, 59} {40, 41, 60} {40, 41, 61} {40, 41, 62}
{40, 41, 63} {40, 41, 64} {40, 41, 65} {40, 41, 66} {40, 42, 43} {40, 42, 44} {40, 42, 45} {40, 42, 46} {40, 42, 47}
{40, 42, 48} {40, 42, 49} {40, 42, 50} {40, 42, 51} {40, 42, 52} {40, 42, 53} {40, 42, 54} {40, 42, 55} {40, 42, 56}
{40, 42, 57} {40, 42, 58} {40, 42, 59} {40, 42, 60} {40, 42, 61} {40, 42, 62} {40, 42, 63} {40, 42, 64} {40, 42, 65}
{40, 42, 66} {40, 43, 44} {40, 43, 45} {40, 43, 46} {40, 43, 47} {40, 43, 48} {40, 43, 49} {40, 43, 50} {40, 43, 51}
{40, 43, 52} {40, 43, 53} {40, 43, 54} {40, 43, 55} {40, 43, 56} {40, 43, 57} {40, 43, 58} {40, 43, 59} {40, 43, 60}
{40, 43, 61} {40, 43, 62} {40, 43, 63} {40, 43, 64} {40, 43, 65} {40, 43, 66} {40, 44, 45} {40, 44, 46} {40, 44, 47}
{40, 44, 48} {40, 44, 49} {40, 44, 50} {40, 44, 51} {40, 44, 52} {40, 44, 53} {40, 44, 54} {40, 44, 55} {40, 44, 56}
{40, 44, 57} {40, 44, 58} {40, 44, 59} {40, 44, 60} {40, 44, 61} {40, 44, 62} {40, 44, 63} {40, 44, 64} {40, 44, 65}
{40, 44, 66} {40, 45, 46} {40, 45, 47} {40, 45, 48} {40, 45, 49} {40, 45, 50} {40, 45, 51} {40, 45, 52} {40, 45, 53}
{40, 45, 54} {40, 45, 55} {40, 45, 56} {40, 45, 57} {40, 45, 58} {40, 45, 59} {40, 45, 60} {40, 45, 61} {40, 45, 62}
{40, 45, 63} {40, 45, 64} {40, 45, 65} {40, 45, 66} {40, 46, 47} {40, 46, 48} {40, 46, 49} {40, 46, 50} {40, 46, 51}
{40, 46, 52} {40, 46, 53} {40, 46, 54} {40, 46, 55} {40, 46, 56} {40, 46, 57} {40, 46, 58} {40, 46, 59} {40, 46, 60}
{40, 46, 61} {40, 46, 62} {40, 46, 63} {40, 46, 64} {40, 46, 65} {40, 46, 66} {40, 47, 48} {40, 47, 49} {40, 47, 50}
{40, 47, 51} {40, 47, 52} {40, 47, 53} {40, 47, 54} {40, 47, 55} {40, 47, 56} {40, 47, 57} {40, 47, 58} {40, 47, 59}
{40, 47, 60} {40, 47, 61} {40, 47, 62} {40, 47, 63} {40, 47, 64} {40, 47, 65} {40, 47, 66} {40, 48, 49} {40, 48, 50}
{40, 48, 51} {40, 48, 52} {40, 48, 53} {40, 48, 54} {40, 48, 55} {40, 48, 56} {40, 48, 57} {40, 48, 58} {40, 48, 59}
{40, 48, 60} {40, 48, 61} {40, 48, 62} {40, 48, 63} {40, 48, 64} {40, 48, 65} {40, 48, 66} {40, 49, 50} {40, 49, 51}
{40, 49, 52} {40, 49, 53} {40, 49, 54} {40, 49, 55} {40, 49, 56} {40, 49, 57} {40, 49, 58} {40, 49, 59} {40, 49, 60}
{40, 49, 61} {40, 49, 62} {40, 49, 63} {40, 49, 64} {40, 49, 65} {40, 49, 66} {40, 50, 51} {40, 50, 52} {40, 50, 53}
{40, 50, 54} {40, 50, 55} {40, 50, 56} {40, 50, 57} {40, 50, 58} {40, 50, 59} {40, 50, 60} {40, 50, 61} {40, 50, 62}
{40, 50, 63} {40, 50, 64} {40, 50, 65} {40, 50, 66} {40, 51, 52} {40, 51, 53} {40, 51, 54} {40, 51, 55} {40, 51, 56}
{40, 51, 57} {40, 51, 58} {40, 51, 59} {40, 51, 60} {40, 51, 61} {40, 51, 62} {40, 51, 63} {40, 51, 64} {40, 51, 65}
{40, 51, 66} {40, 52, 53} {40, 52, 54} {40, 52, 55} {40, 52, 56} {40, 52, 57} {40, 52, 58} {40, 52, 59} {40, 52, 60}
{40, 52, 61} {40, 52, 62} {40, 52, 63} {40, 52, 64} {40, 52, 65} {40, 52, 66} {40, 53, 54} {40, 53, 55} {40, 53, 56}
{40, 53, 57} {40, 53, 58} {40, 53, 59} {40, 53, 60} {40, 53, 61} {40, 53, 62} {40, 53, 63} {40, 53, 64} {40, 53, 65}
{40, 53, 66} {40, 54, 55} {40, 54, 56} {40, 54, 57} {40, 54, 58} {40, 54, 59} {40, 54, 60} {40, 54, 61} {40, 54, 62}
{40, 54, 63} {40, 54, 64} {40, 54, 65} {40, 54, 66} {40, 55, 56} {40, 55, 57} {40, 55, 58} {40, 55, 59} {40, 55, 60}
{40, 55, 61} {40, 55, 62} {40, 55, 63} {40, 55, 64} {40, 55, 65} {40, 55, 66} {40, 56, 57} {40, 56, 58} {40, 56, 59}
{40, 56, 60} {40, 56, 61} {40, 56, 62} {40, 56, 63} {40, 56, 64} {40, 56, 65} {40, 56, 66} {40, 57, 58} {40, 57, 59}
{40, 57, 60} {40, 57, 61} {40, 57, 62} {40, 57, 63} {40, 57, 64} {40, 57, 65} {40, 57, 66} {40, 58, 59} {40, 58, 60}
{40, 58, 61} {40, 58, 62} {40, 58, 63} {40, 58, 64} {40, 58, 65} {40, 58, 66} {40, 59, 60} {40, 59, 61} {40, 59, 62}
{40, 59, 63} {40, 59, 64} {40, 59, 65} {40, 59, 66} {40, 60, 61} {40, 60, 62} {40, 60, 63} {40, 60, 64} {40, 60, 65}
{40, 60, 66} {40, 61, 62} {40, 61, 63} {40, 61, 64} {40, 61, 65} {40, 61, 66} {40, 62, 63} {40, 62, 64} {40, 62, 65}
{40, 62, 66} {40, 63, 64} {40, 63, 65} {40, 63, 66} {40, 64, 65} {40, 64, 66} {40, 65, 66} {41, 42, 43} {41, 42, 44}
{41, 42, 45} {41, 42, 46} {41, 42, 47} {41, 42, 48} {41, 42, 49} {41, 42, 50} {41, 42, 51} {41, 42, 52} {41, 42, 53}
{41, 42, 54} {41, 42, 55} {41, 42, 56} {41, 42, 57} {41, 42, 58} {41, 42, 59} {41, 42, 60} {41, 42, 61} {41, 42, 62}
{41, 42, 63} {41, 42, 64} {41, 42, 65} {41, 42, 66} {41, 43, 44} {41, 43, 45} {41, 43, 46} {41, 43, 47} {41, 43, 48}
{41, 43, 49} {41, 43, 50} {41, 43, 51} {41, 43, 52} {41, 43, 53} {41, 43, 54} {41, 43, 55} {41, 43, 56} {41, 43, 57}
{41, 43, 58} {41, 43, 59} {41, 43, 60} {41, 43, 61} {41, 43, 62} {41, 43, 63} {41, 43, 64} {41, 43, 65} {41, 43, 66}
{41, 44, 45} {41, 44, 46} {41, 44, 47} {41, 44, 48} {41, 44, 49} {41, 44, 50} {41, 44, 51} {41, 44, 52} {41, 44, 53}
{41, 44, 54} {41, 44, 55} {41, 44, 56} {41, 44, 57} {41, 44, 58} {41, 44, 59} {41, 44, 60} {41, 44, 61} {41, 44, 62}
{41, 44, 63} {41, 44, 64} {41, 44, 65} {41, 44, 66} {41, 45, 46} {41, 45, 47} {41, 45, 48} {41, 45, 49} {41, 45, 50}
{41, 45, 51} {41, 45, 52} {41, 45, 53} {41, 45, 54} {41, 45, 55} {41, 45, 56} {41, 45, 57} {41, 45, 58} {41, 45, 59}
{41, 45, 60} {41, 45, 61} {41, 45, 62} {41, 45, 63} {41, 45, 64} {41, 45, 65} {41, 45, 66} {41, 46, 47} {41, 46, 48}
{41, 46, 49} {41, 46, 50} {41, 46, 51} {41, 46, 52} {41, 46, 53} {41, 46, 54} {41, 46, 55} {41, 46, 56} {41, 46, 57}
{41, 46, 58} {41, 46, 59} {41, 46, 60} {41, 46, 61} {41, 46, 62} {41, 46, 63} {41, 46, 64} {41, 46, 65} {41, 46, 66}
{41, 47, 48} {41, 47, 49} {41, 47, 50} {41, 47, 51} {41, 47, 52} {41, 47, 53} {41, 47, 54} {41, 47, 55} {41, 47, 56}
{41, 47, 57} {41, 47, 58} {41, 47, 59} {41, 47, 60} {41, 47, 61} {41, 47, 62} {41, 47, 63} {41, 47, 64} {41, 47, 65}
{41, 47, 66} {41, 48, 49} {41, 48, 50} {41, 48, 51} {41, 48, 52} {41, 48, 53} {41, 48, 54} {41, 48, 55} {41, 48, 56}
{41, 48, 57} {41, 48, 58} {41, 48, 59} {41, 48, 60} {41, 48, 61} {41, 48, 62} {41, 48, 63} {41, 48, 64} {41, 48, 65}
{41, 48, 66} {41, 49, 50} {41, 49, 51} {41, 49, 52} {41, 49, 53} {41, 49, 54} {41, 49, 55} {41, 49, 56} {41, 49, 57}
{41, 49, 58} {41, 49, 59} {41, 49, 60} {41, 49, 61} {41, 49, 62} {41, 49, 63} {41, 49, 64} {41, 49, 65} {41, 49, 66}
{41, 50, 51} {41, 50, 52} {41, 50, 53} {41, 50, 54} {41, 50, 55} {41, 50, 56} {41, 50, 57} {41, 50, 58} {41, 50, 59}
{41, 50, 60} {41, 50, 61} {41, 50, 62} {41, 50, 63} {41, 50, 64} {41, 50, 65} {41, 50, 66} {41, 51, 52} {41, 51, 53}
{41, 51, 54} {41, 51, 55} {41, 51, 56} {41, 51, 57} {41, 51, 58} {41, 51, 59} {41, 51, 60} {41, 51, 61} {41, 51, 62}
{41, 51, 63} {41, 51, 64} {41, 51, 65} {41, 51, 66} {41, 52, 53} {41, 52, 54} {41, 52, 55} {41, 52, 56} {41, 52, 57}
{41, 52, 58} {41, 52, 59} {41, 52, 60} {41, 52, 61} {41, 52, 62} {41, 52, 63} {41, 52, 64} {41, 52, 65} {41, 52, 66}
{41, 53, 54} {41, 53, 55} {41, 53, 56} {41, 53, 57} {41, 53, 58} {41, 53, 59} {41, 53, 60} {41, 53, 61} {41, 53, 62}
{41, 53, 63} {41, 53, 64} {41, 53, 65} {41, 53, 66} {41, 54, 55} {41, 54, 56} {41, 54, 57} {41, 54, 58} {41, 54, 59}
{41, 54, 60} {41, 54, 61} {41, 54, 62} {41, 54, 63} {41, 54, 64} {41, 54, 65} {41, 54, 66} {41, 55, 56} {41, 55, 57}
{41, 55, 58} {41, 55, 59} {41, 55, 60} {41, 55, 61} {41, 55, 62} {41, 55, 63} {41, 55, 64} {41, 55, 65} {41, 55, 66}
{41, 56, 57} {41, 56, 58} {41, 56, 59} {41, 56, 60} {41, 56, 61} {41, 56, 62} {41, 56, 63} {41, 56, 64} {41, 56, 65}
{41, 56, 66} {41, 57, 58} {41, 57, 59} {41, 57, 60} {41, 57, 61} {41, 57, 62} {41, 57, 63} {41, 57, 64} {41, 57, 65}

TABLE 3A-continued

{41, 57, 66} {41, 58, 59} {41, 58, 60} {41, 58, 61} {41, 58, 62} {41, 58, 63} {41, 58, 64} {41, 58, 65} {41, 58, 66}
{41, 59, 60} {41, 59, 61} {41, 59, 62} {41, 59, 63} {41, 59, 64} {41, 59, 65} {41, 59, 66} {41, 60, 61} {41, 60, 62}
{41, 60, 63} {41, 60, 64} {41, 60, 65} {41, 60, 66} {41, 61, 62} {41, 61, 63} {41, 61, 64} {41, 61, 65} {41, 61, 66}
{41, 62, 63} {41, 62, 64} {41, 62, 65} {41, 62, 66} {41, 63, 64} {41, 63, 65} {41, 63, 66} {41, 64, 65} {41, 64, 66}
{41, 65, 66} {42, 43, 44} {42, 43, 45} {42, 43, 46} {42, 43, 47} {42, 43, 48} {42, 43, 49} {42, 43, 50} {42, 43, 51}
{42, 43, 52} {42, 43, 53} {42, 43, 54} {42, 43, 55} {42, 43, 56} {42, 43, 57} {42, 43, 58} {42, 43, 59} {42, 43, 60}
{42, 43, 61} {42, 43, 62} {42, 43, 63} {42, 43, 64} {42, 43, 65} {42, 43, 66} {42, 44, 45} {42, 44, 46} {42, 44, 47}
{42, 44, 48} {42, 44, 49} {42, 44, 50} {42, 44, 51} {42, 44, 52} {42, 44, 53} {42, 44, 54} {42, 44, 55} {42, 44, 56}
{42, 44, 57} {42, 44, 58} {42, 44, 59} {42, 44, 60} {42, 44, 61} {42, 44, 62} {42, 44, 63} {42, 44, 64} {42, 44, 65}
{42, 44, 66} {42, 45, 46} {42, 45, 47} {42, 45, 48} {42, 45, 49} {42, 45, 50} {42, 45, 51} {42, 45, 52} {42, 45, 53}
{42, 45, 54} {42, 45, 55} {42, 45, 56} {42, 45, 57} {42, 45, 58} {42, 45, 59} {42, 45, 60} {42, 45, 61} {42, 45, 62}
{42, 45, 63} {42, 45, 64} {42, 45, 65} {42, 45, 66} {42, 46, 47} {42, 46, 48} {42, 46, 49} {42, 46, 50} {42, 46, 51}
{42, 46, 52} {42, 46, 53} {42, 46, 54} {42, 46, 55} {42, 46, 56} {42, 46, 57} {42, 46, 58} {42, 46, 59} {42, 46, 60}
{42, 46, 61} {42, 46, 62} {42, 46, 63} {42, 46, 64} {42, 46, 65} {42, 46, 66} {42, 47, 48} {42, 47, 49} {42, 47, 50}
{42, 47, 51} {42, 47, 52} {42, 47, 53} {42, 47, 54} {42, 47, 55} {42, 47, 56} {42, 47, 57} {42, 47, 58} {42, 47, 59}
{42, 47, 60} {42, 47, 61} {42, 47, 62} {42, 47, 63} {42, 47, 64} {42, 47, 65} {42, 47, 66} {42, 48, 49} {42, 48, 50}
{42, 48, 51} {42, 48, 52} {42, 48, 53} {42, 48, 54} {42, 48, 55} {42, 48, 56} {42, 48, 57} {42, 48, 58} {42, 48, 59}
{42, 48, 60} {42, 48, 61} {42, 48, 62} {42, 48, 63} {42, 48, 64} {42, 48, 65} {42, 48, 66} {42, 49, 50} {42, 49, 51}
{42, 49, 52} {42, 49, 53} {42, 49, 54} {42, 49, 55} {42, 49, 56} {42, 49, 57} {42, 49, 58} {42, 49, 59} {42, 49, 60}
{42, 49, 61} {42, 49, 62} {42, 49, 63} {42, 49, 64} {42, 49, 65} {42, 49, 66} {42, 50, 51} {42, 50, 52} {42, 50, 53}
{42, 50, 54} {42, 50, 55} {42, 50, 56} {42, 50, 57} {42, 50, 58} {42, 50, 59} {42, 50, 60} {42, 50, 61} {42, 50, 62}
{42, 50, 63} {42, 50, 64} {42, 50, 65} {42, 50, 66} {42, 51, 52} {42, 51, 53} {42, 51, 54} {42, 51, 55} {42, 51, 56}
{42, 51, 57} {42, 51, 58} {42, 51, 59} {42, 51, 60} {42, 51, 61} {42, 51, 62} {42, 51, 63} {42, 51, 64} {42, 51, 65}
{42, 51, 66} {42, 52, 53} {42, 52, 54} {42, 52, 55} {42, 52, 56} {42, 52, 57} {42, 52, 58} {42, 52, 59} {42, 52, 60}
{42, 52, 61} {42, 52, 62} {42, 52, 63} {42, 52, 64} {42, 52, 65} {42, 52, 66} {42, 53, 54} {42, 53, 55} {42, 53, 56}
{42, 53, 57} {42, 53, 58} {42, 53, 59} {42, 53, 60} {42, 53, 61} {42, 53, 62} {42, 53, 63} {42, 53, 64} {42, 53, 65}
{42, 53, 66} {42, 54, 55} {42, 54, 56} {42, 54, 57} {42, 54, 58} {42, 54, 59} {42, 54, 60} {42, 54, 61} {42, 54, 62}
{42, 54, 63} {42, 54, 64} {42, 54, 65} {42, 54, 66} {42, 55, 56} {42, 55, 57} {42, 55, 58} {42, 55, 59} {42, 55, 60}
{42, 55, 61} {42, 55, 62} {42, 55, 63} {42, 55, 64} {42, 55, 65} {42, 55, 66} {42, 56, 57} {42, 56, 58} {42, 56, 59}
{42, 56, 60} {42, 56, 61} {42, 56, 62} {42, 56, 63} {42, 56, 64} {42, 56, 65} {42, 56, 66} {42, 57, 58} {42, 57, 59}
{42, 57, 60} {42, 57, 61} {42, 57, 62} {42, 57, 63} {42, 57, 64} {42, 57, 65} {42, 57, 66} {42, 58, 59} {42, 58, 60}
{42, 58, 61} {42, 58, 62} {42, 58, 63} {42, 58, 64} {42, 58, 65} {42, 58, 66} {42, 59, 60} {42, 59, 61} {42, 59, 62}
{42, 59, 63} {42, 59, 64} {42, 59, 65} {42, 59, 66} {42, 60, 61} {42, 60, 62} {42, 60, 63} {42, 60, 64} {42, 60, 65}
{42, 60, 66} {42, 61, 62} {42, 61, 63} {42, 61, 64} {42, 61, 65} {42, 61, 66} {42, 62, 63} {42, 62, 64} {42, 62, 65}
{42, 62, 66} {42, 63, 64} {42, 63, 65} {42, 63, 66} {42, 64, 65} {42, 64, 66} {42, 65, 66} {43, 44, 45} {43, 44, 46}
{43, 44, 47} {43, 44, 48} {43, 44, 49} {43, 44, 50} {43, 44, 51} {43, 44, 52} {43, 44, 53} {43, 44, 54} {43, 44, 55}
{43, 44, 56} {43, 44, 57} {43, 44, 58} {43, 44, 59} {43, 44, 60} {43, 44, 61} {43, 44, 62} {43, 44, 63} {43, 44, 64}
{43, 44, 65} {43, 44, 66} {43, 45, 46} {43, 45, 47} {43, 45, 48} {43, 45, 49} {43, 45, 50} {43, 45, 51} {43, 45, 52}
{43, 45, 53} {43, 45, 54} {43, 45, 55} {43, 45, 56} {43, 45, 57} {43, 45, 58} {43, 45, 59} {43, 45, 60} {43, 45, 61}
{43, 45, 62} {43, 45, 63} {43, 45, 64} {43, 45, 65} {43, 45, 66} {43, 46, 47} {43, 46, 48} {43, 46, 49} {43, 46, 50}
{43, 46, 51} {43, 46, 52} {43, 46, 53} {43, 46, 54} {43, 46, 55} {43, 46, 56} {43, 46, 57} {43, 46, 58} {43, 46, 59}
{43, 46, 60} {43, 46, 61} {43, 46, 62} {43, 46, 63} {43, 46, 64} {43, 46, 65} {43, 46, 66} {43, 47, 48} {43, 47, 49}
{43, 47, 50} {43, 47, 51} {43, 47, 52} {43, 47, 53} {43, 47, 54} {43, 47, 55} {43, 47, 56} {43, 47, 57} {43, 47, 58}
{43, 47, 59} {43, 47, 60} {43, 47, 61} {43, 47, 62} {43, 47, 63} {43, 47, 64} {43, 47, 65} {43, 47, 66} {43, 48, 49}
{43, 48, 50} {43, 48, 51} {43, 48, 52} {43, 48, 53} {43, 48, 54} {43, 48, 55} {43, 48, 56} {43, 48, 57} {43, 48, 58}
{43, 48, 59} {43, 48, 60} {43, 48, 61} {43, 48, 62} {43, 48, 63} {43, 48, 64} {43, 48, 65} {43, 48, 66} {43, 49, 50}
{43, 49, 51} {43, 49, 52} {43, 49, 53} {43, 49, 54} {43, 49, 55} {43, 49, 56} {43, 49, 57} {43, 49, 58} {43, 49, 59}
{43, 49, 60} {43, 49, 61} {43, 49, 62} {43, 49, 63} {43, 49, 64} {43, 49, 65} {43, 49, 66} {43, 50, 51} {43, 50, 52}
{43, 50, 53} {43, 50, 54} {43, 50, 55} {43, 50, 56} {43, 50, 57} {43, 50, 58} {43, 50, 59} {43, 50, 60} {43, 50, 61}
{43, 50, 62} {43, 50, 63} {43, 50, 64} {43, 50, 65} {43, 50, 66} {43, 51, 52} {43, 51, 53} {43, 51, 54} {43, 51, 55}
{43, 51, 56} {43, 51, 57} {43, 51, 58} {43, 51, 59} {43, 51, 60} {43, 51, 61} {43, 51, 62} {43, 51, 63} {43, 51, 64}
{43, 51, 65} {43, 51, 66} {43, 52, 53} {43, 52, 54} {43, 52, 55} {43, 52, 56} {43, 52, 57} {43, 52, 58} {43, 52, 59}
{43, 52, 60} {43, 52, 61} {43, 52, 62} {43, 52, 63} {43, 52, 64} {43, 52, 65} {43, 52, 66} {43, 53, 54} {43, 53, 55}
{43, 53, 56} {43, 53, 57} {43, 53, 58} {43, 53, 59} {43, 53, 60} {43, 53, 61} {43, 53, 62} {43, 53, 63} {43, 53, 64}
{43, 53, 65} {43, 53, 66} {43, 54, 55} {43, 54, 56} {43, 54, 57} {43, 54, 58} {43, 54, 59} {43, 54, 60} {43, 54, 61}
{43, 54, 62} {43, 54, 63} {43, 54, 64} {43, 54, 65} {43, 54, 66} {43, 55, 56} {43, 55, 57} {43, 55, 58} {43, 55, 59}
{43, 55, 60} {43, 55, 61} {43, 55, 62} {43, 55, 63} {43, 55, 64} {43, 55, 65} {43, 55, 66} {43, 56, 57} {43, 56, 58}
{43, 56, 59} {43, 56, 60} {43, 56, 61} {43, 56, 62} {43, 56, 63} {43, 56, 64} {43, 56, 65} {43, 56, 66} {43, 57, 58}
{43, 57, 59} {43, 57, 60} {43, 57, 61} {43, 57, 62} {43, 57, 63} {43, 57, 64} {43, 57, 65} {43, 57, 66} {43, 58, 59}
{43, 58, 60} {43, 58, 61} {43, 58, 62} {43, 58, 63} {43, 58, 64} {43, 58, 65} {43, 58, 66} {43, 59, 60} {43, 59, 61}
{43, 59, 62} {43, 59, 63} {43, 59, 64} {43, 59, 65} {43, 59, 66} {43, 60, 61} {43, 60, 62} {43, 60, 63} {43, 60, 64}
{43, 60, 65} {43, 60, 66} {43, 61, 62} {43, 61, 63} {43, 61, 64} {43, 61, 65} {43, 61, 66} {43, 62, 63} {43, 62, 64}
{43, 62, 65} {43, 62, 66} {43, 63, 64} {43, 63, 65} {43, 63, 66} {43, 64, 65} {43, 64, 66} {43, 65, 66} {44, 45, 46}
{44, 45, 47} {44, 45, 48} {44, 45, 49} {44, 45, 50} {44, 45, 51} {44, 45, 52} {44, 45, 53} {44, 45, 54} {44, 45, 55}
{44, 45, 56} {44, 45, 57} {44, 45, 58} {44, 45, 59} {44, 45, 60} {44, 45, 61} {44, 45, 62} {44, 45, 63} {44, 45, 64}
{44, 45, 65} {44, 45, 66} {44, 46, 47} {44, 46, 48} {44, 46, 49} {44, 46, 50} {44, 46, 51} {44, 46, 52} {44, 46, 53}
{44, 46, 54} {44, 46, 55} {44, 46, 56} {44, 46, 57} {44, 46, 58} {44, 46, 59} {44, 46, 60} {44, 46, 61} {44, 46, 62}
{44, 46, 63} {44, 46, 64} {44, 46, 65} {44, 46, 66} {44, 47, 48} {44, 47, 49} {44, 47, 50} {44, 47, 51} {44, 47, 52}
{44, 47, 53} {44, 47, 54} {44, 47, 55} {44, 47, 56} {44, 47, 57} {44, 47, 58} {44, 47, 59} {44, 47, 60} {44, 47, 61}
{44, 47, 62} {44, 47, 63} {44, 47, 64} {44, 47, 65} {44, 47, 66} {44, 48, 49} {44, 48, 50} {44, 48, 51} {44, 48, 52}
{44, 48, 53} {44, 48, 54} {44, 48, 55} {44, 48, 56} {44, 48, 57} {44, 48, 58} {44, 48, 59} {44, 48, 60} {44, 48, 61}
{44, 48, 62} {44, 48, 63} {44, 48, 64} {44, 48, 65} {44, 48, 66} {44, 49, 50} {44, 49, 51} {44, 49, 52} {44, 49, 53}
{44, 49, 54} {44, 49, 55} {44, 49, 56} {44, 49, 57} {44, 49, 58} {44, 49, 59} {44, 49, 60} {44, 49, 61} {44, 49, 62}
{44, 49, 63} {44, 49, 64} {44, 49, 65} {44, 49, 66} {44, 50, 51} {44, 50, 52} {44, 50, 53} {44, 50, 54} {44, 50, 55}
{44, 50, 56} {44, 50, 57} {44, 50, 58} {44, 50, 59} {44, 50, 60} {44, 50, 61} {44, 50, 62} {44, 50, 63} {44, 50, 64}
{44, 50, 65} {44, 50, 66} {44, 51, 52} {44, 51, 53} {44, 51, 54} {44, 51, 55} {44, 51, 56} {44, 51, 57} {44, 51, 58}
{44, 51, 59} {44, 51, 60} {44, 51, 61} {44, 51, 62} {44, 51, 63} {44, 51, 64} {44, 51, 65} {44, 51, 66} {44, 52, 53}
{44, 52, 54} {44, 52, 55} {44, 52, 56} {44, 52, 57} {44, 52, 58} {44, 52, 59} {44, 52, 60} {44, 52, 61} {44, 52, 62}
{44, 52, 63} {44, 52, 64} {44, 52, 65} {44, 52, 66} {44, 53, 54} {44, 53, 55} {44, 53, 56} {44, 53, 57} {44, 53, 58}
{44, 53, 59} {44, 53, 60} {44, 53, 61} {44, 53, 62} {44, 53, 63} {44, 53, 64} {44, 53, 65} {44, 53, 66} {44, 54, 55}

TABLE 3A-continued

{44, 54, 56} {44, 54, 57} {44, 54, 58} {44, 54, 59} {44, 54, 60} {44, 54, 61} {44, 54, 62} {44, 54, 63} {44, 54, 64}
{44, 54, 65} {44, 54, 66} {44, 55, 56} {44, 55, 57} {44, 55, 58} {44, 55, 59} {44, 55, 60} {44, 55, 61} {44, 55, 62}
{44, 55, 63} {44, 55, 64} {44, 55, 65} {44, 55, 66} {44, 56, 57} {44, 56, 58} {44, 56, 59} {44, 56, 60} {44, 56, 61}
{44, 56, 62} {44, 56, 63} {44, 56, 64} {44, 56, 65} {44, 56, 66} {44, 57, 58} {44, 57, 59} {44, 57, 60} {44, 57, 61}
{44, 57, 62} {44, 57, 63} {44, 57, 64} {44, 57, 65} {44, 57, 66} {44, 58, 59} {44, 58, 60} {44, 58, 61} {44, 58, 62}
{44, 58, 63} {44, 58, 64} {44, 58, 65} {44, 58, 66} {44, 59, 60} {44, 59, 61} {44, 59, 62} {44, 59, 63} {44, 59, 64}
{44, 59, 65} {44, 59, 66} {44, 60, 61} {44, 60, 62} {44, 60, 63} {44, 60, 64} {44, 60, 65} {44, 60, 66} {44, 61, 62}
{44, 61, 63} {44, 61, 64} {44, 61, 65} {44, 61, 66} {44, 62, 63} {44, 62, 64} {44, 62, 65} {44, 62, 66} {44, 63, 64}
{44, 63, 65} {44, 63, 66} {44, 64, 65} {44, 64, 66} {44, 65, 66} {45, 46, 47} {45, 46, 48} {45, 46, 49} {45, 46, 50}
{45, 46, 51} {45, 46, 52} {45, 46, 53} {45, 46, 54} {45, 46, 55} {45, 46, 56} {45, 46, 57} {45, 46, 58} {45, 46, 59}
{45, 46, 60} {45, 46, 61} {45, 46, 62} {45, 46, 63} {45, 46, 64} {45, 46, 65} {45, 46, 66} {45, 47, 48} {45, 47, 49}
{45, 47, 50} {45, 47, 51} {45, 47, 52} {45, 47, 53} {45, 47, 54} {45, 47, 55} {45, 47, 56} {45, 47, 57} {45, 47, 58}
{45, 47, 59} {45, 47, 60} {45, 47, 61} {45, 47, 62} {45, 47, 63} {45, 47, 64} {45, 47, 65} {45, 47, 66} {45, 48, 49}
{45, 48, 50} {45, 48, 51} {45, 48, 52} {45, 48, 53} {45, 48, 54} {45, 48, 55} {45, 48, 56} {45, 48, 57} {45, 48, 58}
{45, 48, 59} {45, 48, 60} {45, 48, 61} {45, 48, 62} {45, 48, 63} {45, 48, 64} {45, 48, 65} {45, 48, 66} {45, 49, 50}
{45, 49, 51} {45, 49, 52} {45, 49, 53} {45, 49, 54} {45, 49, 55} {45, 49, 56} {45, 49, 57} {45, 49, 58} {45, 49, 59}
{45, 49, 60} {45, 49, 61} {45, 49, 62} {45, 49, 63} {45, 49, 64} {45, 49, 65} {45, 49, 66} {45, 50, 51} {45, 50, 52}
{45, 50, 53} {45, 50, 54} {45, 50, 55} {45, 50, 56} {45, 50, 57} {45, 50, 58} {45, 50, 59} {45, 50, 60} {45, 50, 61}
{45, 50, 62} {45, 50, 63} {45, 50, 64} {45, 50, 65} {45, 50, 66} {45, 51, 52} {45, 51, 53} {45, 51, 54} {45, 51, 55}
{45, 51, 56} {45, 51, 57} {45, 51, 58} {45, 51, 59} {45, 51, 60} {45, 51, 61} {45, 51, 62} {45, 51, 63} {45, 51, 64}
{45, 51, 65} {45, 51, 66} {45, 52, 53} {45, 52, 54} {45, 52, 55} {45, 52, 56} {45, 52, 57} {45, 52, 58} {45, 52, 59}
{45, 52, 60} {45, 52, 61} {45, 52, 62} {45, 52, 63} {45, 52, 64} {45, 52, 65} {45, 52, 66} {45, 53, 54} {45, 53, 55}
{45, 53, 56} {45, 53, 57} {45, 53, 58} {45, 53, 59} {45, 53, 60} {45, 53, 61} {45, 53, 62} {45, 53, 63} {45, 53, 64}
{45, 53, 65} {45, 53, 66} {45, 54, 55} {45, 54, 56} {45, 54, 57} {45, 54, 58} {45, 54, 59} {45, 54, 60} {45, 54, 61}
{45, 54, 62} {45, 54, 63} {45, 54, 64} {45, 54, 65} {45, 54, 66} {45, 55, 56} {45, 55, 57} {45, 55, 58} {45, 55, 59}
{45, 55, 60} {45, 55, 61} {45, 55, 62} {45, 55, 63} {45, 55, 64} {45, 55, 65} {45, 55, 66} {45, 56, 57} {45, 56, 58}
{45, 56, 59} {45, 56, 60} {45, 56, 61} {45, 56, 62} {45, 56, 63} {45, 56, 64} {45, 56, 65} {45, 56, 66} {45, 57, 58}
{45, 57, 59} {45, 57, 60} {45, 57, 61} {45, 57, 62} {45, 57, 63} {45, 57, 64} {45, 57, 65} {45, 57, 66} {45, 58, 59}
{45, 58, 60} {45, 58, 61} {45, 58, 62} {45, 58, 63} {45, 58, 64} {45, 58, 65} {45, 58, 66} {45, 59, 60} {45, 59, 61}
{45, 59, 62} {45, 59, 63} {45, 59, 64} {45, 59, 65} {45, 59, 66} {45, 60, 61} {45, 60, 62} {45, 60, 63} {45, 60, 64}
{45, 60, 65} {45, 60, 66} {45, 61, 62} {45, 61, 63} {45, 61, 64} {45, 61, 65} {45, 61, 66} {45, 62, 63} {45, 62, 64}
{45, 62, 65} {45, 62, 66} {45, 63, 64} {45, 63, 65} {45, 63, 66} {45, 64, 65} {45, 64, 66} {45, 65, 66} {46, 47, 48}
{46, 47, 49} {46, 47, 50} {46, 47, 51} {46, 47, 52} {46, 47, 53} {46, 47, 54} {46, 47, 55} {46, 47, 56} {46, 47, 57}
{46, 47, 58} {46, 47, 59} {46, 47, 60} {46, 47, 61} {46, 47, 62} {46, 47, 63} {46, 47, 64} {46, 47, 65} {46, 47, 66}
{46, 48, 49} {46, 48, 50} {46, 48, 51} {46, 48, 52} {46, 48, 53} {46, 48, 54} {46, 48, 55} {46, 48, 56} {46, 48, 57}
{46, 48, 58} {46, 48, 59} {46, 48, 60} {46, 48, 61} {46, 48, 62} {46, 48, 63} {46, 48, 64} {46, 48, 65} {46, 48, 66}
{46, 49, 50} {46, 49, 51} {46, 49, 52} {46, 49, 53} {46, 49, 54} {46, 49, 55} {46, 49, 56} {46, 49, 57} {46, 49, 58}
{46, 49, 59} {46, 49, 60} {46, 49, 61} {46, 49, 62} {46, 49, 63} {46, 49, 64} {46, 49, 65} {46, 49, 66} {46, 50, 51}
{46, 50, 52} {46, 50, 53} {46, 50, 54} {46, 50, 55} {46, 50, 56} {46, 50, 57} {46, 50, 58} {46, 50, 59} {46, 50, 60}
{46, 50, 61} {46, 50, 62} {46, 50, 63} {46, 50, 64} {46, 50, 65} {46, 50, 66} {46, 51, 52} {46, 51, 53} {46, 51, 54}
{46, 51, 55} {46, 51, 56} {46, 51, 57} {46, 51, 58} {46, 51, 59} {46, 51, 60} {46, 51, 61} {46, 51, 62} {46, 51, 63}
{46, 51, 64} {46, 51, 65} {46, 51, 66} {46, 52, 53} {46, 52, 54} {46, 52, 55} {46, 52, 56} {46, 52, 57} {46, 52, 58}
{46, 52, 59} {46, 52, 60} {46, 52, 61} {46, 52, 62} {46, 52, 63} {46, 52, 64} {46, 52, 65} {46, 52, 66} {46, 53, 54}
{46, 53, 55} {46, 53, 56} {46, 53, 57} {46, 53, 58} {46, 53, 59} {46, 53, 60} {46, 53, 61} {46, 53, 62} {46, 53, 63}
{46, 53, 64} {46, 53, 65} {46, 53, 66} {46, 54, 55} {46, 54, 56} {46, 54, 57} {46, 54, 58} {46, 54, 59} {46, 54, 60}
{46, 54, 61} {46, 54, 62} {46, 54, 63} {46, 54, 64} {46, 54, 65} {46, 54, 66} {46, 55, 56} {46, 55, 57} {46, 55, 58}
{46, 55, 59} {46, 55, 60} {46, 55, 61} {46, 55, 62} {46, 55, 63} {46, 55, 64} {46, 55, 65} {46, 55, 66} {46, 56, 57}
{46, 56, 58} {46, 56, 59} {46, 56, 60} {46, 56, 61} {46, 56, 62} {46, 56, 63} {46, 56, 64} {46, 56, 65} {46, 56, 66}
{46, 57, 58} {46, 57, 59} {46, 57, 60} {46, 57, 61} {46, 57, 62} {46, 57, 63} {46, 57, 64} {46, 57, 65} {46, 57, 66}
{46, 58, 59} {46, 58, 60} {46, 58, 61} {46, 58, 62} {46, 58, 63} {46, 58, 64} {46, 58, 65} {46, 58, 66} {46, 59, 60}
{46, 59, 61} {46, 59, 62} {46, 59, 63} {46, 59, 64} {46, 59, 65} {46, 59, 66} {46, 60, 61} {46, 60, 62} {46, 60, 63}
{46, 60, 64} {46, 60, 65} {46, 60, 66} {46, 61, 62} {46, 61, 63} {46, 61, 64} {46, 61, 65} {46, 61, 66} {46, 62, 63}
{46, 62, 64} {46, 62, 65} {46, 62, 66} {46, 63, 64} {46, 63, 65} {46, 63, 66} {46, 64, 65} {46, 64, 66} {46, 65, 66}
{47, 48, 49} {47, 48, 50} {47, 48, 51} {47, 48, 52} {47, 48, 53} {47, 48, 54} {47, 48, 55} {47, 48, 56} {47, 48, 57}
{47, 48, 58} {47, 48, 59} {47, 48, 60} {47, 48, 61} {47, 48, 62} {47, 48, 63} {47, 48, 64} {47, 48, 65} {47, 48, 66}
{47, 49, 50} {47, 49, 51} {47, 49, 52} {47, 49, 53} {47, 49, 54} {47, 49, 55} {47, 49, 56} {47, 49, 57} {47, 49, 58}
{47, 49, 59} {47, 49, 60} {47, 49, 61} {47, 49, 62} {47, 49, 63} {47, 49, 64} {47, 49, 65} {47, 49, 66} {47, 50, 51}
{47, 50, 52} {47, 50, 53} {47, 50, 54} {47, 50, 55} {47, 50, 56} {47, 50, 57} {47, 50, 58} {47, 50, 59} {47, 50, 60}
{47, 50, 61} {47, 50, 62} {47, 50, 63} {47, 50, 64} {47, 50, 65} {47, 50, 66} {47, 51, 52} {47, 51, 53} {47, 51, 54}
{47, 51, 55} {47, 51, 56} {47, 51, 57} {47, 51, 58} {47, 51, 59} {47, 51, 60} {47, 51, 61} {47, 51, 62} {47, 51, 63}
{47, 51, 64} {47, 51, 65} {47, 51, 66} {47, 52, 53} {47, 52, 54} {47, 52, 55} {47, 52, 56} {47, 52, 57} {47, 52, 58}
{47, 52, 59} {47, 52, 60} {47, 52, 61} {47, 52, 62} {47, 52, 63} {47, 52, 64} {47, 52, 65} {47, 52, 66} {47, 53, 54}
{47, 53, 55} {47, 53, 56} {47, 53, 57} {47, 53, 58} {47, 53, 59} {47, 53, 60} {47, 53, 61} {47, 53, 62} {47, 53, 63}
{47, 53, 64} {47, 53, 65} {47, 53, 66} {47, 54, 55} {47, 54, 56} {47, 54, 57} {47, 54, 58} {47, 54, 59} {47, 54, 60}
{47, 54, 61} {47, 54, 62} {47, 54, 63} {47, 54, 64} {47, 54, 65} {47, 54, 66} {47, 55, 56} {47, 55, 57} {47, 55, 58}
{47, 55, 59} {47, 55, 60} {47, 55, 61} {47, 55, 62} {47, 55, 63} {47, 55, 64} {47, 55, 65} {47, 55, 66} {47, 56, 57}
{47, 56, 58} {47, 56, 59} {47, 56, 60} {47, 56, 61} {47, 56, 62} {47, 56, 63} {47, 56, 64} {47, 56, 65} {47, 56, 66}
{47, 57, 58} {47, 57, 59} {47, 57, 60} {47, 57, 61} {47, 57, 62} {47, 57, 63} {47, 57, 64} {47, 57, 65} {47, 57, 66}
{47, 58, 59} {47, 58, 60} {47, 58, 61} {47, 58, 62} {47, 58, 63} {47, 58, 64} {47, 58, 65} {47, 58, 66} {47, 59, 60}
{47, 59, 61} {47, 59, 62} {47, 59, 63} {47, 59, 64} {47, 59, 65} {47, 59, 66} {47, 60, 61} {47, 60, 62} {47, 60, 63}
{47, 60, 64} {47, 60, 65} {47, 60, 66} {47, 61, 62} {47, 61, 63} {47, 61, 64} {47, 61, 65} {47, 61, 66} {47, 62, 63}
{47, 62, 64} {47, 62, 65} {47, 62, 66} {47, 63, 64} {47, 63, 65} {47, 63, 66} {47, 64, 65} {47, 64, 66} {47, 65, 66}
{48, 49, 50} {48, 49, 51} {48, 49, 52} {48, 49, 53} {48, 49, 54} {48, 49, 55} {48, 49, 56} {48, 49, 57} {48, 49, 58}
{48, 49, 59} {48, 49, 60} {48, 49, 61} {48, 49, 62} {48, 49, 63} {48, 49, 64} {48, 49, 65} {48, 49, 66} {48, 50, 51}
{48, 50, 52} {48, 50, 53} {48, 50, 54} {48, 50, 55} {48, 50, 56} {48, 50, 57} {48, 50, 58} {48, 50, 59} {48, 50, 60}
{48, 50, 61} {48, 50, 62} {48, 50, 63} {48, 50, 64} {48, 50, 65} {48, 50, 66} {48, 51, 52} {48, 51, 53} {48, 51, 54}
{48, 51, 55} {48, 51, 56} {48, 51, 57} {48, 51, 58} {48, 51, 59} {48, 51, 60} {48, 51, 61} {48, 51, 62} {48, 51, 63}
{48, 51, 64} {48, 51, 65} {48, 51, 66} {48, 52, 53} {48, 52, 54} {48, 52, 55} {48, 52, 56} {48, 52, 57} {48, 52, 58}
{48, 52, 59} {48, 52, 60} {48, 52, 61} {48, 52, 62} {48, 52, 63} {48, 52, 64} {48, 52, 65} {48, 52, 66} {48, 53, 54}
{48, 53, 55} {48, 53, 56} {48, 53, 57} {48, 53, 58} {48, 53, 59} {48, 53, 60} {48, 53, 61} {48, 53, 62} {48, 53, 63}

TABLE 3A-continued

{48, 53, 64} {48, 53, 65} {48, 53, 66} {48, 54, 55} {48, 54, 56} {48, 54, 57} {48, 54, 58} {48, 54, 59} {48, 54, 60}
{48, 54, 61} {48, 54, 62} {48, 54, 63} {48, 54, 64} {48, 54, 65} {48, 54, 66} {48, 55, 56} {48, 55, 57} {48, 55, 58}
{48, 55, 59} {48, 55, 60} {48, 55, 61} {48, 55, 62} {48, 55, 63} {48, 55, 64} {48, 55, 65} {48, 55, 66} {48, 56, 57}
{48, 56, 58} {48, 56, 59} {48, 56, 60} {48, 56, 61} {48, 56, 62} {48, 56, 63} {48, 56, 64} {48, 56, 65} {48, 56, 66}
{48, 57, 58} {48, 57, 59} {48, 57, 60} {48, 57, 61} {48, 57, 62} {48, 57, 63} {48, 57, 64} {48, 57, 65} {48, 57, 66}
{48, 58, 59} {48, 58, 60} {48, 58, 61} {48, 58, 62} {48, 58, 63} {48, 58, 64} {48, 58, 65} {48, 58, 66} {48, 59, 60}
{48, 59, 61} {48, 59, 62} {48, 59, 63} {48, 59, 64} {48, 59, 65} {48, 59, 66} {48, 60, 61} {48, 60, 62} {48, 60, 63}
{48, 60, 64} {48, 60, 65} {48, 60, 66} {48, 61, 62} {48, 61, 63} {48, 61, 64} {48, 61, 65} {48, 61, 66} {48, 62, 63}
{48, 62, 64} {48, 62, 65} {48, 62, 66} {48, 63, 64} {48, 63, 65} {48, 63, 66} {48, 64, 65} {48, 64, 66} {48, 65, 66}
{49, 50, 51} {49, 50, 52} {49, 50, 53} {49, 50, 54} {49, 50, 55} {49, 50, 56} {49, 50, 57} {49, 50, 58} {49, 50, 59}
{49, 50, 60} {49, 50, 61} {49, 50, 62} {49, 50, 63} {49, 50, 64} {49, 50, 65} {49, 50, 66} {49, 51, 52} {49, 51, 53}
{49, 51, 54} {49, 51, 55} {49, 51, 56} {49, 51, 57} {49, 51, 58} {49, 51, 59} {49, 51, 60} {49, 51, 61} {49, 51, 62}
{49, 51, 63} {49, 51, 64} {49, 51, 65} {49, 51, 66} {49, 52, 53} {49, 52, 54} {49, 52, 55} {49, 52, 56} {49, 52, 57}
{49, 52, 58} {49, 52, 59} {49, 52, 60} {49, 52, 61} {49, 52, 62} {49, 52, 63} {49, 52, 64} {49, 52, 65} {49, 52, 66}
{49, 53, 54} {49, 53, 55} {49, 53, 56} {49, 53, 57} {49, 53, 58} {49, 53, 59} {49, 53, 60} {49, 53, 61} {49, 53, 62}
{49, 53, 63} {49, 53, 64} {49, 53, 65} {49, 53, 66} {49, 54, 55} {49, 54, 56} {49, 54, 57} {49, 54, 58} {49, 54, 59}
{49, 54, 60} {49, 54, 61} {49, 54, 62} {49, 54, 63} {49, 54, 64} {49, 54, 65} {49, 54, 66} {49, 55, 56} {49, 55, 57}
{49, 55, 58} {49, 55, 59} {49, 55, 60} {49, 55, 61} {49, 55, 62} {49, 55, 63} {49, 55, 64} {49, 55, 65} {49, 55, 66}
{49, 56, 57} {49, 56, 58} {49, 56, 59} {49, 56, 60} {49, 56, 61} {49, 56, 62} {49, 56, 63} {49, 56, 64} {49, 56, 65}
{49, 56, 66} {49, 57, 58} {49, 57, 59} {49, 57, 60} {49, 57, 61} {49, 57, 62} {49, 57, 63} {49, 57, 64} {49, 57, 65}
{49, 57, 66} {49, 58, 59} {49, 58, 60} {49, 58, 61} {49, 58, 62} {49, 58, 63} {49, 58, 64} {49, 58, 65} {49, 58, 66}
{49, 59, 60} {49, 59, 61} {49, 59, 62} {49, 59, 63} {49, 59, 64} {49, 59, 65} {49, 59, 66} {49, 60, 61} {49, 60, 62}
{49, 60, 63} {49, 60, 64} {49, 60, 65} {49, 60, 66} {49, 61, 62} {49, 61, 63} {49, 61, 64} {49, 61, 65} {49, 61, 66}
{49, 62, 63} {49, 62, 64} {49, 62, 65} {49, 62, 66} {49, 63, 64} {49, 63, 65} {49, 63, 66} {49, 64, 65} {49, 64, 66}
{49, 65, 66} {50, 51, 52} {50, 51, 53} {50, 51, 54} {50, 51, 55} {50, 51, 56} {50, 51, 57} {50, 51, 58} {50, 51, 59}
{50, 51, 60} {50, 51, 61} {50, 51, 62} {50, 51, 63} {50, 51, 64} {50, 51, 65} {50, 51, 66} {50, 52, 53} {50, 52, 54}
{50, 52, 55} {50, 52, 56} {50, 52, 57} {50, 52, 58} {50, 52, 59} {50, 52, 60} {50, 52, 61} {50, 52, 62} {50, 52, 63}
{50, 52, 64} {50, 52, 65} {50, 52, 66} {50, 53, 54} {50, 53, 55} {50, 53, 56} {50, 53, 57} {50, 53, 58} {50, 53, 59}
{50, 53, 60} {50, 53, 61} {50, 53, 62} {50, 53, 63} {50, 53, 64} {50, 53, 65} {50, 53, 66} {50, 54, 55} {50, 54, 56}
{50, 54, 57} {50, 54, 58} {50, 54, 59} {50, 54, 60} {50, 54, 61} {50, 54, 62} {50, 54, 63} {50, 54, 64} {50, 54, 65}
{50, 54, 66} {50, 55, 56} {50, 55, 57} {50, 55, 58} {50, 55, 59} {50, 55, 60} {50, 55, 61} {50, 55, 62} {50, 55, 63}
{50, 55, 64} {50, 55, 65} {50, 55, 66} {50, 56, 57} {50, 56, 58} {50, 56, 59} {50, 56, 60} {50, 56, 61} {50, 56, 62}
{50, 56, 63} {50, 56, 64} {50, 56, 65} {50, 56, 66} {50, 57, 58} {50, 57, 59} {50, 57, 60} {50, 57, 61} {50, 57, 62}
{50, 57, 63} {50, 57, 64} {50, 57, 65} {50, 57, 66} {50, 58, 59} {50, 58, 60} {50, 58, 61} {50, 58, 62} {50, 58, 63}
{50, 58, 64} {50, 58, 65} {50, 58, 66} {50, 59, 60} {50, 59, 61} {50, 59, 62} {50, 59, 63} {50, 59, 64} {50, 59, 65}
{50, 59, 66} {50, 60, 61} {50, 60, 62} {50, 60, 63} {50, 60, 64} {50, 60, 65} {50, 60, 66} {50, 61, 62} {50, 61, 63}
{50, 61, 64} {50, 61, 65} {50, 61, 66} {50, 62, 63} {50, 62, 64} {50, 62, 65} {50, 62, 66} {50, 63, 64} {50, 63, 65}
{50, 63, 66} {50, 64, 65} {50, 64, 66} {50, 65, 66} {51, 52, 53} {51, 52, 54} {51, 52, 55} {51, 52, 56} {51, 52, 57}
{51, 52, 58} {51, 52, 59} {51, 52, 60} {51, 52, 61} {51, 52, 62} {51, 52, 63} {51, 52, 64} {51, 52, 65} {51, 52, 66}
{51, 53, 54} {51, 53, 55} {51, 53, 56} {51, 53, 57} {51, 53, 58} {51, 53, 59} {51, 53, 60} {51, 53, 61} {51, 53, 62}
{51, 53, 63} {51, 53, 64} {51, 53, 65} {51, 53, 66} {51, 54, 55} {51, 54, 56} {51, 54, 57} {51, 54, 58} {51, 54, 59}
{51, 54, 60} {51, 54, 61} {51, 54, 62} {51, 54, 63} {51, 54, 64} {51, 54, 65} {51, 54, 66} {51, 55, 56} {51, 55, 57}
{51, 55, 58} {51, 55, 59} {51, 55, 60} {51, 55, 61} {51, 55, 62} {51, 55, 63} {51, 55, 64} {51, 55, 65} {51, 55, 66}
{51, 56, 57} {51, 56, 58} {51, 56, 59} {51, 56, 60} {51, 56, 61} {51, 56, 62} {51, 56, 63} {51, 56, 64} {51, 56, 65}
{51, 56, 66} {51, 57, 58} {51, 57, 59} {51, 57, 60} {51, 57, 61} {51, 57, 62} {51, 57, 63} {51, 57, 64} {51, 57, 65}
{51, 57, 66} {51, 58, 59} {51, 58, 60} {51, 58, 61} {51, 58, 62} {51, 58, 63} {51, 58, 64} {51, 58, 65} {51, 58, 66}
{51, 59, 60} {51, 59, 61} {51, 59, 62} {51, 59, 63} {51, 59, 64} {51, 59, 65} {51, 59, 66} {51, 60, 61} {51, 60, 62}
{51, 60, 63} {51, 60, 64} {51, 60, 65} {51, 60, 66} {51, 61, 62} {51, 61, 63} {51, 61, 64} {51, 61, 65} {51, 61, 66}
{51, 62, 63} {51, 62, 64} {51, 62, 65} {51, 62, 66} {51, 63, 64} {51, 63, 65} {51, 63, 66} {51, 64, 65} {51, 64, 66}
{51, 65, 66} {52, 53, 54} {52, 53, 55} {52, 53, 56} {52, 53, 57} {52, 53, 58} {52, 53, 59} {52, 53, 60} {52, 53, 61}
{52, 53, 62} {52, 53, 63} {52, 53, 64} {52, 53, 65} {52, 53, 66} {52, 54, 55} {52, 54, 56} {52, 54, 57} {52, 54, 58}
{52, 54, 59} {52, 54, 60} {52, 54, 61} {52, 54, 62} {52, 54, 63} {52, 54, 64} {52, 54, 65} {52, 54, 66} {52, 55, 56}
{52, 55, 57} {52, 55, 58} {52, 55, 59} {52, 55, 60} {52, 55, 61} {52, 55, 62} {52, 55, 63} {52, 55, 64} {52, 55, 65}
{52, 55, 66} {52, 56, 57} {52, 56, 58} {52, 56, 59} {52, 56, 60} {52, 56, 61} {52, 56, 62} {52, 56, 63} {52, 56, 64}
{52, 56, 65} {52, 56, 66} {52, 57, 58} {52, 57, 59} {52, 57, 60} {52, 57, 61} {52, 57, 62} {52, 57, 63} {52, 57, 64}
{52, 57, 65} {52, 57, 66} {52, 58, 59} {52, 58, 60} {52, 58, 61} {52, 58, 62} {52, 58, 63} {52, 58, 64} {52, 58, 65}
{52, 58, 66} {52, 59, 60} {52, 59, 61} {52, 59, 62} {52, 59, 63} {52, 59, 64} {52, 59, 65} {52, 59, 66} {52, 60, 61}
{52, 60, 62} {52, 60, 63} {52, 60, 64} {52, 60, 65} {52, 60, 66} {52, 61, 62} {52, 61, 63} {52, 61, 64} {52, 61, 65}
{52, 61, 66} {52, 62, 63} {52, 62, 64} {52, 62, 65} {52, 62, 66} {52, 63, 64} {52, 63, 65} {52, 63, 66} {52, 64, 65}
{52, 64, 66} {52, 65, 66} {53, 54, 55} {53, 54, 56} {53, 54, 57} {53, 54, 58} {53, 54, 59} {53, 54, 60} {53, 54, 61}
{53, 54, 62} {53, 54, 63} {53, 54, 64} {53, 54, 65} {53, 54, 66} {53, 55, 56} {53, 55, 57} {53, 55, 58} {53, 55, 59}
{53, 55, 60} {53, 55, 61} {53, 55, 62} {53, 55, 63} {53, 55, 64} {53, 55, 65} {53, 55, 66} {53, 56, 57} {53, 56, 58}
{53, 56, 59} {53, 56, 60} {53, 56, 61} {53, 56, 62} {53, 56, 63} {53, 56, 64} {53, 56, 65} {53, 56, 66} {53, 57, 58}
{53, 57, 59} {53, 57, 60} {53, 57, 61} {53, 57, 62} {53, 57, 63} {53, 57, 64} {53, 57, 65} {53, 57, 66} {53, 58, 59}
{53, 58, 60} {53, 58, 61} {53, 58, 62} {53, 58, 63} {53, 58, 64} {53, 58, 65} {53, 58, 66} {53, 59, 60} {53, 59, 61}
{53, 59, 62} {53, 59, 63} {53, 59, 64} {53, 59, 65} {53, 59, 66} {53, 60, 61} {53, 60, 62} {53, 60, 63} {53, 60, 64}
{53, 60, 65} {53, 60, 66} {53, 61, 62} {53, 61, 63} {53, 61, 64} {53, 61, 65} {53, 61, 66} {53, 62, 63} {53, 62, 64}
{53, 62, 65} {53, 62, 66} {53, 63, 64} {53, 63, 65} {53, 63, 66} {53, 64, 65} {53, 64, 66} {53, 65, 66} {54, 55, 56}
{54, 55, 57} {54, 55, 58} {54, 55, 59} {54, 55, 60} {54, 55, 61} {54, 55, 62} {54, 55, 63} {54, 55, 64} {54, 55, 65}
{54, 55, 66} {54, 56, 57} {54, 56, 58} {54, 56, 59} {54, 56, 60} {54, 56, 61} {54, 56, 62} {54, 56, 63} {54, 56, 64}
{54, 56, 65} {54, 56, 66} {54, 57, 58} {54, 57, 59} {54, 57, 60} {54, 57, 61} {54, 57, 62} {54, 57, 63} {54, 57, 64}
{54, 57, 65} {54, 57, 66} {54, 58, 59} {54, 58, 60} {54, 58, 61} {54, 58, 62} {54, 58, 63} {54, 58, 64} {54, 58, 65}
{54, 58, 66} {54, 59, 60} {54, 59, 61} {54, 59, 62} {54, 59, 63} {54, 59, 64} {54, 59, 65} {54, 59, 66} {54, 60, 61}
{54, 60, 62} {54, 60, 63} {54, 60, 64} {54, 60, 65} {54, 60, 66} {54, 61, 62} {54, 61, 63} {54, 61, 64} {54, 61, 65}
{54, 61, 66} {54, 62, 63} {54, 62, 64} {54, 62, 65} {54, 62, 66} {54, 63, 64} {54, 63, 65} {54, 63, 66} {54, 64, 65}
{54, 64, 66} {54, 65, 66} {55, 56, 57} {55, 56, 58} {55, 56, 59} {55, 56, 60} {55, 56, 61} {55, 56, 62} {55, 56, 63}
{55, 56, 64} {55, 56, 65} {55, 56, 66} {55, 57, 58} {55, 57, 59} {55, 57, 60} {55, 57, 61} {55, 57, 62} {55, 57, 63}
{55, 57, 64} {55, 57, 65} {55, 57, 66} {55, 58, 59} {55, 58, 60} {55, 58, 61} {55, 58, 62} {55, 58, 63} {55, 58, 64}
{55, 58, 65} {55, 58, 66} {55, 59, 60} {55, 59, 61} {55, 59, 62} {55, 59, 63} {55, 59, 64} {55, 59, 65} {55, 59, 66}
{55, 60, 61} {55, 60, 62} {55, 60, 63} {55, 60, 64} {55, 60, 65} {55, 60, 66} {55, 61, 62} {55, 61, 63} {55, 61, 64}

TABLE 3A-continued

{55, 61, 65} {55, 61, 66} {55, 62, 63} {55, 62, 64} {55, 62, 65} {55, 62, 66} {55, 63, 64} {55, 63, 65} {55, 63, 66}
{55, 64, 65} {55, 64, 66} {55, 65, 66} {56, 57, 58} {56, 57, 59} {56, 57, 60} {56, 57, 61} {56, 57, 62} {56, 57, 63}
{56, 57, 64} {56, 57, 65} {56, 57, 66} {56, 58, 59} {56, 58, 60} {56, 58, 61} {56, 58, 62} {56, 58, 63} {56, 58, 64}
{56, 58, 65} {56, 58, 66} {56, 59, 60} {56, 59, 61} {56, 59, 62} {56, 59, 63} {56, 59, 64} {56, 59, 65} {56, 59, 66}
{56, 60, 61} {56, 60, 62} {56, 60, 63} {56, 60, 64} {56, 60, 65} {56, 60, 66} {56, 61, 62} {56, 61, 63} {56, 61, 64}
{56, 61, 65} {56, 61, 66} {56, 62, 63} {56, 62, 64} {56, 62, 65} {56, 62, 66} {56, 63, 64} {56, 63, 65} {56, 63, 66}
{56, 64, 65} {56, 64, 66} {56, 65, 66} {57, 58, 59} {57, 58, 60} {57, 58, 61} {57, 58, 62} {57, 58, 63} {57, 58, 64}
{57, 58, 65} {57, 58, 66} {57, 59, 60} {57, 59, 61} {57, 59, 62} {57, 59, 63} {57, 59, 64} {57, 59, 65} {57, 59, 66}
{57, 60, 61} {57, 60, 62} {57, 60, 63} {57, 60, 64} {57, 60, 65} {57, 60, 66} {57, 61, 62} {57, 61, 63} {57, 61, 64}
{57, 61, 65} {57, 61, 66} {57, 62, 63} {57, 62, 64} {57, 62, 65} {57, 62, 66} {57, 63, 64} {57, 63, 65} {57, 63, 66}
{57, 64, 65} {57, 64, 66} {57, 65, 66} {58, 59, 60} {58, 59, 61} {58, 59, 62} {58, 59, 63} {58, 59, 64} {58, 59, 65}
{58, 59, 66} {58, 60, 61} {58, 60, 62} {58, 60, 63} {58, 60, 64} {58, 60, 65} {58, 60, 66} {58, 61, 62} {58, 61, 63}
{58, 61, 64} {58, 61, 65} {58, 61, 66} {58, 62, 63} {58, 62, 64} {58, 62, 65} {58, 62, 66} {58, 63, 64} {58, 63, 65}
{58, 63, 66} {58, 64, 65} {58, 64, 66} {58, 65, 66} {59, 60, 61} {59, 60, 62} {59, 60, 63} {59, 60, 64} {59, 60, 65}
{59, 60, 66} {59, 61, 62} {59, 61, 63} {59, 61, 64} {59, 61, 65} {59, 61, 66} {59, 62, 63} {59, 62, 64} {59, 62, 65}
{59, 62, 66} {59, 63, 64} {59, 63, 65} {59, 63, 66} {59, 64, 65} {59, 64, 66} {59, 65, 66} {60, 61, 62} {60, 61, 63}
{60, 61, 64} {60, 61, 65} {60, 61, 66} {60, 62, 63} {60, 62, 64} {60, 62, 65} {60, 62, 66} {60, 63, 64} {60, 63, 65}
{60, 63, 66} {60, 64, 65} {60, 64, 66} {60, 65, 66} {61, 62, 63} {61, 62, 64} {61, 62, 65} {61, 62, 66} {61, 63, 64}
{61, 63, 65} {61, 63, 66} {61, 64, 65} {61, 64, 66} {61, 65, 66} {62, 63, 64} {62, 63, 65} {62, 63, 66} {62, 64, 65}
{62, 64, 66} {62, 65, 66} {63, 64, 65} {63, 64, 66} {63, 65, 66} {64, 65, 66}

TABLE 3B

{93,96,100} {93,96,106} {93,96,111} {93,96,112} {93,96,113} {93,96,114} {93,96,115} {93,96,116}
{93,96,121} {93,96,122} {93,96,123} {93,96,124} {93,96,125} {93,96,126} {93,96,127} {93,96,128}
{93,96,129} {93,96,130} {93,96,131} {93,96,132} {93,96,133} {93,96,134} {93,96,135} {93,96,136}
{93,96,137} {93,96,138} {93,96,139} {93,100,106} {93,100,111} {93,100,112} {93,100,113} {93,100,114}
{93,100,115} {93,100,116} {93,100,121} {93,100,122} {93,100,123} {93,100,124} {93,100,125}
{93,100,126} {93,100,127} {93,100,128} {93,100,129} {93,100,130} {93,100,131} {93,100,132}
{93,100,133} {93,100,134} {93,100,135} {93,100,136} {93,100,137} {93,100,138} {93,100,139}
{93,106,111} {93,106,112} {93,106,113} {93,106,114} {93,106,115} {93,106,116} {93,106,121}
{93,106,122} {93,106,123} {93,106,124} {93,106,125} {93,106,126} {93,106,127} {93,106,128}
{93,106,129} {93,106,130} {93,106,131} {93,106,132} {93,106,133} {93,106,134} {93,106,135}
{93,106,136} {93,106,137} {93,106,138} {93,106,139} {93,111,112} {93,111,113} {93,111,114}
{93,111,115} {93,111,116} {93,111,121} {93,111,122} {93,111,123} {93,111,124} {93,111,125}
{93,111,126} {93,111,127} {93,111,128} {93,111,129} {93,111,130} {93,111,131} {93,111,132}
{93,111,133} {93,111,134} {93,111,135} {93,111,136} {93,111,137} {93,111,138} {93,111,139}
{93,112,113} {93,112,114} {93,112,115} {93,112,116} {93,112,121} {93,112,122} {93,112,123}
{93,112,124} {93,112,125} {93,112,126} {93,112,127} {93,112,128} {93,112,129} {93,112,130}
{93,112,131} {93,112,132} {93,112,133} {93,112,134} {93,112,135} {93,112,136} {93,112,137}
{93,112,138} {93,112,139} {93,113,114} {93,113,115} {93,113,116} {93,113,121} {93,113,122}
{93,113,123} {93,113,124} {93,113,125} {93,113,126} {93,113,127} {93,113,128} {93,113,129}
{93,113,130} {93,113,131} {93,113,132} {93,113,133} {93,113,134} {93,113,135} {93,113,136}
{93,113,137} {93,113,138} {93,113,139} {93,114,115} {93,114,116} {93,114,121} {93,114,122}
{93,114,123} {93,114,124} {93,114,125} {93,114,126} {93,114,127} {93,114,128} {93,114,129}
{93,114,130} {93,114,131} {93,114,132} {93,114,133} {93,114,134} {93,114,135} {93,114,136}
{93,114,137} {93,114,138} {93,114,139} {93,115,116} {93,115,121} {93,115,122} {93,115,123}
{93,115,124} {93,115,125} {93,115,126} {93,115,127} {93,115,128} {93,115,129} {93,115,130}
{93,115,131} {93,115,132} {93,115,133} {93,115,134} {93,115,135} {93,115,136} {93,115,137}
{93,115,138} {93,115,139} {93,116,121} {93,116,122} {93,116,123} {93,116,124} {93,116,125}
{93,116,126} {93,116,127} {93,116,128} {93,116,129} {93,116,130} {93,116,131} {93,116,132}
{93,116,133} {93,116,134} {93,116,135} {93,116,136} {93,116,139}
{93,121,122} {93,121,123} {93,121,124} {93,121,125} {93,121,126} {93,121,127} {93,121,128}
{93,121,129} {93,121,130} {93,121,131} {93,121,132} {93,121,133} {93,121,134} {93,121,135}
{93,121,136} {93,121,137} {93,121,138} {93,121,139} {93,122,123} {93,122,124} {93,122,125}
{93,122,126} {93,122,127} {93,122,128} {93,122,129} {93,122,130} {93,122,131} {93,122,132}
{93,122,133} {93,122,134} {93,122,135} {93,122,136} {93,122,137} {93,122,138} {93,122,139}
{93,123,124} {93,123,125} {93,123,126} {93,123,127} {93,123,128} {93,123,129} {93,123,130}
{93,123,131} {93,123,132} {93,123,133} {93,123,134} {93,123,135} {93,123,136} {93,123,137}
{93,123,138} {93,123,139} {93,124,125} {93,124,126} {93,124,127} {93,124,128} {93,124,129}
{93,124,130} {93,124,131} {93,124,132} {93,124,133} {93,124,134} {93,124,135} {93,124,136}
{93,124,137} {93,124,138} {93,124,139} {93,125,126} {93,125,127} {93,125,128} {93,125,129}
{93,125,130} {93,125,131} {93,125,132} {93,125,133} {93,125,134} {93,125,135} {93,125,136}
{93,125,137} {93,125,138} {93,125,139} {93,126,127} {93,126,128} {93,126,129} {93,126,130}
{93,126,131} {93,126,132} {93,126,133} {93,126,134} {93,126,135} {93,126,136} {93,126,137}
{93,126,138} {93,126,139} {93,127,128} {93,127,129} {93,127,130} {93,127,131} {93,127,132}
{93,127,133} {93,127,134} {93,127,135} {93,127,136} {93,127,137} {93,127,138} {93,127,139}
{93,128,129} {93,128,130} {93,128,131} {93,128,132} {93,128,133} {93,128,134} {93,128,135}
{93,128,136} {93,128,137} {93,128,138} {93,128,139} {93,129,130} {93,129,131} {93,129,132}
{93,129,133} {93,129,134} {93,129,135} {93,129,136} {93,129,137} {93,129,138} {93,129,139}
{93,130,131} {93,130,132} {93,130,133} {93,130,134} {93,130,135} {93,130,136} {93,130,137}
{93,130,138} {93,130,139} {93,131,132} {93,131,133} {93,131,134} {93,131,135} {93,131,136}
{93,132,137} {93,131,138} {93,131,139} {93,132,133} {93,132,134} {93,132,135} {93,132,136}
{93,132,137} {93,132,138} {93,132,139} {93,133,134} {93,133,135} {93,133,136} {93,133,137}
{93,133,138} {93,133,139} {93,134,135} {93,134,136} {93,134,137} {93,134,138} {93,134,139}
{93,135,136} {93,135,137} {93,135,138} {93,135,139} {93,136,137} {93,136,138} {93,136,139}
{93,137,138} {93,137,139} {93,138,139} {96,100,106} {96,100,111} {96,100,112} {96,100,113}

TABLE 3B-continued

{96,100,114} {96,100,115} {96,100,116} {96,100,121} {96,100,122} {96,100,123} {96,100,124}
{96,100,125} {96,100,126} {96,100,127} {96,100,128} {96,100,129} {96,100,130} {96,100,131}
{96,100,132} {96,100,133} {96,100,134} {96,100,135} {96,100,136} {96,100,137} {96,100,138}
{96,100,139} {96,106,111} {96,106,112} {96,106,113} {96,106,114} {96,106,115} {96,106,116}
{96,106,121} {96,106,122} {96,106,123} {96,106,124} {96,106,125} {96,106,126} {96,106,127}
{96,106,128} {96,106,129} {96,106,130} {96,106,131} {96,106,132} {96,106,133} {96,106,134}
{96,106,135} {96,106,136} {96,106,137} {96,106,138} {96,106,139} {96,111,112} {96,111,113}
{96,111,114} {96,111,115} {96,111,116} {96,111,121} {96,111,122} {96,111,123} {96,111,124}
{96,111,125} {96,111,126} {96,111,127} {96,111,128} {96,111,129} {96,111,130} {96,111,131}
{96,111,132} {96,111,133} {96,111,134} {96,111,135} {96,111,136} {96,111,137} {96,111,138}
{96,111,139} {96,112,113} {96,112,114} {96,112,115} {96,112,116} {96,112,121} {96,112,122}
{96,112,123} {96,112,124} {96,112,125} {96,112,126} {96,112,127} {96,112,128} {96,112,129}
{96,112,130} {96,112,131} {96,112,132} {96,112,133} {96,112,134} {96,112,135} {96,112,136}
{96,112,137} {96,112,138} {96,112,139} {96,113,114} {96,113,115} {96,113,116} {96,113,121}
{96,113,122} {96,113,123} {96,113,124} {96,113,125} {96,113,126} {96,113,127} {96,113,128}
{96,113,129} {96,113,130} {96,113,131} {96,113,132} {96,113,133} {96,113,134} {96,113,135}
{96,113,136} {96,113,137} {96,113,138} {96,113,139} {96,114,116} {96,114,115} {96,114,121}
{96,114,122} {96,114,123} {96,114,124} {96,114,125} {96,114,126} {96,114,127} {96,114,128}
{96,114,129} {96,114,130} {96,114,131} {96,114,132} {96,114,133} {96,114,134} {96,114,135}
{96,114,136} {96,114,137} {96,114,138} {96,114,139} {96,115,116} {96,115,121} {96,115,122}
{96,115,123} {96,115,124} {96,115,125} {96,115,126} {96,115,127} {96,115,128} {96,115,129}
{96,115,130} {96,115,131} {96,115,132} {96,115,133} {96,115,134} {96,115,135} {96,115,136}
{96,115,137} {96,115,138} {96,115,139} {96,116,121} {96,116,122} {96,116,123} {96,116,124}
{96,116,125} {96,116,126} {96,116,127} {96,116,128} {96,116,129} {96,116,130} {96,116,131}
{96,116,132} {96,116,133} {96,116,134} {96,116,135} {96,116,136} {96,116,137} {96,116,138}
{96,116,139} {96,121,122} {96,121,123} {96,121,124} {96,121,125} {96,121,126} {96,121,127}
{96,121,128} {96,121,129} {96,121,130} {96,121,131} {96,121,132} {96,121,133} {96,121,134}
{96,121,135} {96,121,136} {96,121,137} {96,121,138} {96,121,139} {96,122,123} {96,122,124}
{96,122,125} {96,122,126} {96,122,127} {96,122,128} {96,122,129} {96,122,130} {96,122,131}
{96,122,132} {96,122,133} {96,122,134} {96,122,135} {96,122,136} {96,122,137} {96,122,138}
{96,122,139} {96,123,124} {96,123,125} {96,123,126} {96,123,127} {96,123,128} {96,123,129}
{96,123,130} {96,123,131} {96,123,132} {96,123,133} {96,123,134} {96,123,135} {96,123,136}
{96,123,137} {96,123,138} {96,123,139} {96,124,125} {96,124,126} {96,124,127} {96,124,128}
{96,124,129} {96,124,130} {96,124,131} {96,124,132} {96,124,133} {96,124,134} {96,124,135}
{96,124,136} {96,124,137} {96,124,138} {96,124,139} {96,125,126} {96,125,127} {96,125,128}
{96,125,129} {96,125,130} {96,125,131} {96,125,132} {96,125,133} {96,125,134} {96,125,135}
{96,125,136} {96,125,137} {96,125,138} {96,125,139} {96,126,127} {96,126,128} {96,126,129}
{96,126,130} {96,126,131} {96,126,132} {96,126,133} {96,126,134} {96,126,135} {96,126,136}
{96,126,137} {96,126,138} {96,126,139} {96,127,128} {96,127,129} {96,127,130} {96,127,131}
{96,127,132} {96,127,133} {96,127,134} {96,127,135} {96,127,136} {96,127,137} {96,127,138}
{96,127,139} {96,128,129} {96,128,130} {96,128,131} {96,128,132} {96,128,133} {96,128,134}
{96,128,135} {96,128,136} {96,128,137} {96,128,138} {96,128,139} {96,129,130} {96,129,131}
{96,129,132} {96,129,133} {96,129,134} {96,129,135} {96,129,136} {96,129,137} {96,129,138}
{96,129,139} {96,130,131} {96,130,132} {96,130,133} {96,130,134} {96,130,135} {96,130,136}
{96,130,137} {96,130,138} {96,130,139} {96,131,132} {96,131,133} {96,131,134} {96,131,135}
{96,131,136} {96,131,137} {96,131,138} {96,131,139} {96,132,133} {96,132,134} {96,132,135}
{96,132,136} {96,132,137} {96,132,138} {96,132,139} {96,133,134} {96,133,135} {96,133,136}
{96,133,137} {96,133,138} {96,133,139} {96,134,135} {96,134,136} {96,134,137} {96,134,138}
{96,134,139} {96,135,136} {96,135,137} {96,135,138} {96,135,139} {96,136,137} {96,136,138}
{96,136,139} {96,137,138} {96,137,139} {96,138,139} {100,106,111} {100,106,112} {100,106,113}
{100,106,114} {100,106,115} {100,106,116} {100,106,121} {100,106,122} {100,106,123} {100,106,124}
{100,106,125} {100,106,126} {100,106,127} {100,106,128} {100,106,129} {100,106,130} {100,106,131}
{100,106,132} {100,106,133} {100,106,134} {100,106,135} {100,106,136} {100,106,137} {100,106,138}
{100,106,139} {100,111,112} {100,111,113} {100,111,114} {100,111,115} {100,111,116} {100,111,121}
{100,111,122} {100,111,123} {100,111,124} {100,111,125} {100,111,126} {100,111,127} {100,111,128}
{100,111,129} {100,111,130} {100,111,131} {100,111,132} {100,111,133} {100,111,134} {100,111,135}
{100,111,136} {100,111,137} {100,111,138} {100,111,139} {100,112,113} {100,112,114} {100,112,115}
{100,112,116} {100,112,121} {100,112,122} {100,112,123} {100,112,124} {100,112,125} {100,112,126}
{100,112,127} {100,112,128} {100,112,129} {100,112,130} {100,112,131} {100,112,132} {100,112,133}
{100,112,134} {100,112,135} {100,112,136} {100,112,137} {100,112,138} {100,112,139} {100,113,114}
{100,113,115} {100,113,116} {100,113,121} {100,113,122} {100,113,123} {100,113,124} {100,113,125}
{100,113,126} {100,113,127} {100,113,128} {100,113,129} {100,113,130} {100,113,131} {100,113,132}
{100,113,133} {100,113,134} {100,113,135} {100,113,136} {100,113,137} {100,113,138} {100,113,139}
{100,114,115} {100,114,116} {100,114,121} {100,114,122} {100,114,123} {100,114,124} {100,114,125}
{100,114,126} {100,114,127} {100,114,128} {100,114,129} {100,114,130} {100,114,131} {100,114,132}
{100,114,133} {100,114,134} {100,114,135} {100,114,136} {100,114,137} {100,114,138} {100,114,139}
{100,115,116} {100,115,121} {100,115,122} {100,115,123} {100,115,124} {100,115,125} {100,115,126}
{100,115,127} {100,115,128} {100,115,129} {100,115,130} {100,115,131} {100,115,132} {100,115,133}
{100,115,134} {100,115,135} {100,115,136} {100,115,137} {100,115,138} {100,115,139} {100,116,121}
{100,116,122} {100,116,123} {100,116,124} {100,116,125} {100,116,126} {100,116,127} {100,116,128}
{100,116,129} {100,116,130} {100,116,131} {100,116,132} {100,116,133} {100,116,134} {100,116,135}
{100,116,136} {100,116,137} {100,116,138} {100,116,139} {100,121,122} {100,121,123} {100,121,124}
{100,121,125} {100,121,126} {100,121,127} {100,121,128} {100,121,129} {100,121,130} {100,121,131}
{100,121,132} {100,121,133} {100,121,134} {100,121,135} {100,121,136} {100,121,137} {100,121,138}
{100,121,139} {100,122,123} {100,122,124} {100,122,125} {100,122,126} {100,122,127} {100,122,128}
{100,122,129} {100,122,130} {100,122,131} {100,122,132} {100,122,133} {100,122,134} {100,122,135}
{100,122,136} {100,122,137} {100,122,138} {100,122,139} {100,123,124} {100,123,125} {100,123,126}
{100,123,127} {100,123,128} {100,123,129} {100,123,130} {100,123,131} {100,123,132} {100,123,133}
{100,123,134} {100,123,135} {100,123,136} {100,123,137} {100,123,138} {100,123,139} {100,124,125}
{100,124,126} {100,124,127} {100,124,128} {100,124,129} {100,124,130} {100,124,131} {100,124,132}

TABLE 3B-continued

{100,124,133} {100,124,134} {100,124,135} {100,124,136} {100,124,137} {100,124,138} {100,124,139}
{100,125,126} {100,125,127} {100,125,128} {100,125,129} {100,125,130} {100,125,131} {100,125,132}
{100,125,133} {100,125,134} {100,125,135} {100,125,136} {100,125,137} {100,125,138} {100,125,139}
{100,126,127} {100,126,128} {100,126,129} {100,126,130} {100,126,131} {100,126,132} {100,126,133}
{100,126,134} {100,126,135} {100,126,136} {100,126,137} {100,126,138} {100,126,139} {100,127,128}
{100,127,129} {100,127,130} {100,127,131} {100,127,132} {100,127,133} {100,127,134} {100,127,135}
{100,127,136} {100,127,137} {100,127,138} {100,127,139} {100,128,129} {100,128,130} {100,128,131}
{100,128,132} {100,128,133} {100,128,134} {100,128,135} {100,128,136} {100,128,137} {100,128,138}
{100,128,139} {100,129,130} {100,129,131} {100,129,132} {100,129,133} {100,129,134} {100,129,135}
{100,129,136} {100,129,137} {100,129,138} {100,129,139} {100,130,131} {100,130,132} {100,130,133}
{100,130,134} {100,130,135} {100,130,136} {100,130,137} {100,130,138} {100,130,139} {100,131,132}
{100,131,133} {100,131,134} {100,131,135} {100,131,136} {100,131,137} {100,131,138} {100,131,139}
{100,132,133} {100,132,134} {100,132,135} {100,132,136} {100,132,137} {100,132,138} {100,132,139}
{100,133,134} {100,133,135} {100,133,136} {100,133,137} {100,133,138} {100,133,139} {100,134,135}
{100,134,136} {100,134,137} {100,134,138} {100,134,139} {100,135,136} {100,135,137} {100,135,138}
{100,135,139} {100,136,137} {100,136,138} {100,136,139} {100,137,138} {100,137,139} {100,138,139}
{106,111,112} {106,111,113} {106,111,114} {106,111,115} {106,111,116} {106,111,121} {106,111,122}
{106,111,123} {106,111,124} {106,111,125} {106,111,126} {106,111,127} {106,111,128} {106,111,129}
{106,111,130} {106,111,131} {106,111,132} {106,111,133} {106,111,134} {106,111,135} {106,111,136}
{106,111,137} {106,111,138} {106,111,139} {106,112,113} {106,112,114} {106,112,115} {106,112,116}
{106,112,121} {106,112,122} {106,112,123} {106,112,124} {106,112,125} {106,112,126} {106,112,127}
{106,112,128} {106,112,129} {106,112,130} {106,112,131} {106,112,132} {106,112,133} {106,112,134}
{106,112,135} {106,112,136} {106,112,137} {106,112,138} {106,112,139} {106,113,114} {106,113,115}
{106,113,116} {106,113,121} {106,113,122} {106,113,123} {106,113,124} {106,113,125} {106,113,126}
{106,113,127} {106,113,128} {106,113,129} {106,113,130} {106,113,131} {106,113,132} {106,113,133}
{106,113,134} {106,113,135} {106,113,136} {106,113,137} {106,113,138} {106,113,139} {106,114,115}
{106,114,116} {106,114,121} {106,114,122} {106,114,123} {106,114,124} {106,114,125} {106,114,126}
{106,114,127} {106,114,128} {106,114,129} {106,114,130} {106,114,131} {106,114,132} {106,114,133}
{106,114,134} {106,114,135} {106,114,136} {106,114,137} {106,114,138} {106,114,139} {106,115,116}
{106,115,121} {106,115,122} {106,115,123} {106,115,124} {106,115,125} {106,115,126} {106,115,127}
{106,115,128} {106,115,129} {106,115,130} {106,115,131} {106,115,132} {106,115,133} {106,115,134}
{106,115,135} {106,115,136} {106,115,137} {106,115,138} {106,115,139} {106,116,121} {106,116,122}
{106,116,123} {106,116,124} {106,116,125} {106,116,126} {106,116,127} {106,116,128} {106,116,129}
{106,116,130} {106,116,131} {106,116,132} {106,116,133} {106,116,134} {106,116,135} {106,116,136}
{106,116,137} {106,116,138} {106,116,139} {106,121,122} {106,121,123} {106,121,124} {106,121,125}
{106,121,126} {106,121,127} {106,121,128} {106,121,129} {106,121,130} {106,121,131} {106,121,132}
{106,121,133} {106,121,134} {106,121,135} {106,121,136} {106,121,137} {106,121,138} {106,121,139}
{106,122,123} {106,122,124} {106,122,125} {106,122,126} {106,122,127} {106,122,128} {106,122,129}
{106,122,130} {106,122,131} {106,122,132} {106,122,133} {106,122,134} {106,122,135} {106,122,136}
{106,122,137} {106,122,138} {106,122,139} {106,123,124} {106,123,125} {106,123,126} {106,123,127}
{106,123,128} {106,123,129} {106,123,130} {106,123,131} {106,123,132} {106,123,133} {106,123,134}
{106,123,135} {106,123,136} {106,123,137} {106,123,138} {106,123,139} {106,124,125} {106,124,126}
{106,124,127} {106,124,128} {106,124,129} {106,124,130} {106,124,131} {106,124,132} {106,124,133}
{106,124,134} {106,124,135} {106,124,136} {106,124,137} {106,124,138} {106,124,139} {106,125,126}
{106,125,127} {106,125,128} {106,125,129} {106,125,130} {106,125,131} {106,125,132} {106,125,133}
{106,125,134} {106,125,135} {106,125,136} {106,125,137} {106,125,138} {106,125,139} {106,126,127}
{106,126,128} {106,126,129} {106,126,130} {106,126,131} {106,126,132} {106,126,133} {106,126,134}
{106,126,135} {106,126,136} {106,126,137} {106,126,138} {106,126,139} {106,127,128} {106,127,129}
{106,127,130} {106,127,131} {106,127,132} {106,127,133} {106,127,134} {106,127,135} {106,127,136}
{106,127,137} {106,127,138} {106,127,139} {106,128,129} {106,128,130} {106,128,131} {106,128,132}
{106,128,133} {106,128,134} {106,128,135} {106,128,136} {106,128,137} {106,128,138} {106,128,139}
{106,129,130} {106,129,131} {106,129,132} {106,129,133} {106,129,134} {106,129,135} {106,129,136}
{106,129,137} {106,129,138} {106,129,139} {106,130,131} {106,130,132} {106,130,133} {106,130,134}
{106,130,135} {106,130,136} {106,130,137} {106,130,138} {106,130,139} {106,131,132} {106,131,133}
{106,131,134} {106,131,135} {106,131,136} {106,131,137} {106,131,138} {106,131,139} {106,132,133}
{106,132,134} {106,132,135} {106,132,136} {106,132,137} {106,132,138} {106,132,139} {106,133,134}
{106,133,135} {106,133,136} {106,133,137} {106,133,138} {106,133,139} {106,134,135} {106,134,136}
{106,134,137} {106,134,138} {106,134,139} {106,135,136} {106,135,137} {106,135,138} {106,135,139}
{106,136,137} {106,136,138} {106,136,139} {106,137,138} {106,137,139} {106,138,139} {111,112,113}
{111,112,114} {111,112,115} {111,112,116} {111,112,121} {111,112,122} {111,112,123} {111,112,124}
{111,112,125} {111,112,126} {111,112,127} {111,112,128} {111,112,129} {111,112,130} {111,112,131}
{111,112,132} {111,112,133} {111,112,134} {111,112,135} {111,112,136} {111,112,137} {111,112,138}
{111,112,139} {111,113,114} {111,113,115} {111,113,116} {111,113,121} {111,113,122} {111,113,123}
{111,113,124} {111,113,125} {111,113,126} {111,113,127} {111,113,128} {111,113,129} {111,113,130}
{111,113,131} {111,113,132} {111,113,133} {111,113,134} {111,113,135} {111,113,136} {111,113,137}
{111,113,138} {111,113,139} {111,114,115} {111,114,116} {111,114,121} {111,114,122} {111,114,123}
{111,114,124} {111,114,125} {111,114,126} {111,114,127} {111,114,128} {111,114,129} {111,114,130}
{111,114,131} {111,114,132} {111,114,133} {111,114,134} {111,114,135} {111,114,136} {111,114,137}
{111,114,138} {111,114,139} {111,115,116} {111,115,121} {111,115,122} {111,115,123} {111,115,124}
{111,115,125} {111,115,126} {111,115,127} {111,115,128} {111,115,129} {111,115,130} {111,115,131}
{111,115,132} {111,115,133} {111,115,134} {111,115,135} {111,115,136} {111,115,137} {111,115,138}
{111,115,139} {111,116,121} {111,116,122} {111,116,123} {111,116,124} {111,116,125} {111,116,126}
{111,116,127} {111,116,128} {111,116,129} {111,116,130} {111,116,131} {111,116,132} {111,116,133}
{111,116,134} {111,116,135} {111,116,136} {111,116,137} {111,116,138} {111,116,139} {111,121,122}
{111,121,123} {111,121,124} {111,121,125} {111,121,126} {111,121,127} {111,121,128} {111,121,129}
{111,121,130} {111,121,131} {111,121,132} {111,121,133} {111,121,134} {111,121,135} {111,121,136}
{111,121,137} {111,121,138} {111,121,139} {111,122,123} {111,122,124} {111,122,125} {111,122,126}
{111,122,127} {111,122,128} {111,122,129} {111,122,130} {111,122,131} {111,122,132} {111,122,133}
{111,122,134} {111,122,135} {111,122,136} {111,122,137} {111,122,138} {111,122,139} {111,123,124}
{111,123,125} {111,123,126} {111,123,127} {111,123,128} {111,123,129} {111,123,130} {111,123,131}

TABLE 3B-continued

{111,123,132} {111,123,133} {111,123,134} {111,123,135} {111,123,136} {111,123,137} {111,123,138}
{111,123,139} {111,124,125} {111,124,126} {111,124,127} {111,124,128} {111,124,129} {111,124,130}
{111,124,131} {111,124,132} {111,124,133} {111,124,134} {111,124,135} {111,124,136} {111,124,137}
{111,124,138} {111,124,139} {111,125,126} {111,125,127} {111,125,128} {111,125,129} {111,125,130}
{111,125,131} {111,125,132} {111,125,133} {111,125,134} {111,125,135} {111,125,136} {111,125,137}
{111,125,138} {111,125,139} {111,126,127} {111,126,128} {111,126,129} {111,126,130} {111,126,131}
{111,126,132} {111,126,133} {111,126,134} {111,126,135} {111,126,136} {111,126,137} {111,126,138}
{111,126,139} {111,127,128} {111,127,129} {111,127,130} {111,127,131} {111,127,132} {111,127,133}
{111,127,134} {111,127,135} {111,127,136} {111,127,137} {111,127,138} {111,127,139} {111,128,129}
{111,128,130} {111,128,131} {111,128,132} {111,128,133} {111,128,134} {111,128,135} {111,128,136}
{111,128,137} {111,128,138} {111,128,139} {111,129,130} {111,129,131} {111,129,132} {111,129,133}
{111,129,134} {111,129,135} {111,129,136} {111,129,137} {111,129,138} {111,129,139} {111,130,131}
{111,130,132} {111,130,133} {111,130,134} {111,130,135} {111,130,136} {111,130,137} {111,130,138}
{111,130,139} {111,131,132} {111,131,133} {111,131,134} {111,131,135} {111,131,136} {111,131,137}
{111,131,138} {111,131,139} {111,132,133} {111,132,134} {111,132,135} {111,132,136} {111,132,137}
{111,132,138} {111,132,139} {111,133,134} {111,133,135} {111,133,136} {111,133,137} {111,133,138}
{111,133,139} {111,134,135} {111,134,136} {111,134,137} {111,134,138} {111,134,139} {111,135,136}
{111,135,137} {111,135,138} {111,135,139} {111,136,137} {111,136,138} {111,136,139} {111,137,138}
{111,137,139} {111,138,139} {112,113,114} {112,113,115} {112,113,116} {112,113,121} {112,113,122}
{112,113,123} {112,113,124} {112,113,125} {112,113,126} {112,113,127} {112,113,128} {112,113,129}
{112,113,130} {112,113,131} {112,113,132} {112,113,133} {112,113,134} {112,113,135} {112,113,136}
{112,113,137} {112,113,138} {112,113,139} {112,114,115} {112,114,116} {112,114,121} {112,114,122}
{112,114,123} {112,114,124} {112,114,125} {112,114,126} {112,114,127} {112,114,128} {112,114,129}
{112,114,130} {112,114,131} {112,114,132} {112,114,133} {112,114,134} {112,114,135} {112,114,136}
{112,114,137} {112,114,138} {112,114,139} {112,115,116} {112,115,121} {112,115,122} {112,115,123}
{112,115,124} {112,115,125} {112,115,126} {112,115,127} {112,115,128} {112,115,129} {112,115,130}
{112,115,131} {112,115,132} {112,115,133} {112,115,134} {112,115,135} {112,115,136} {112,115,137}
{112,115,138} {112,115,139} {112,116,121} {112,116,122} {112,116,123} {112,116,124} {112,116,125}
{112,116,126} {112,116,127} {112,116,128} {112,116,129} {112,116,130} {112,116,131} {112,116,132}
{112,116,133} {112,116,134} {112,116,135} {112,116,136} {112,116,137} {112,116,138} {112,116,139}
{112,121,122} {112,121,123} {112,121,124} {112,121,125} {112,121,126} {112,121,127} {112,121,128}
{112,121,129} {112,121,130} {112,121,131} {112,121,132} {112,121,133} {112,121,134} {112,121,135}
{112,121,136} {112,121,137} {112,121,138} {112,121,139} {112,122,123} {112,122,124} {112,122,125}
{112,122,126} {112,122,127} {112,122,128} {112,122,129} {112,122,130} {112,122,131} {112,122,132}
{112,122,133} {112,122,134} {112,122,135} {112,122,136} {112,122,137} {112,122,138} {112,122,139}
{112,123,124} {112,123,125} {112,123,126} {112,123,127} {112,123,128} {112,123,129} {112,123,130}
{112,123,131} {112,123,132} {112,123,133} {112,123,134} {112,123,135} {112,123,136} {112,123,137}
{112,123,138} {112,123,139} {112,124,125} {112,124,126} {112,124,127} {112,124,128} {112,124,129}
{112,124,130} {112,124,131} {112,124,132} {112,124,133} {112,124,134} {112,124,135} {112,124,136}
{112,124,137} {112,124,138} {112,124,139} {112,125,126} {112,125,127} {112,125,128} {112,125,129}
{112,125,130} {112,125,131} {112,125,132} {112,125,133} {112,125,134} {112,125,135} {112,125,136}
{112,125,137} {112,125,138} {112,125,139} {112,126,127} {112,126,128} {112,126,129} {112,126,130}
{112,126,131} {112,126,132} {112,126,133} {112,126,134} {112,126,135} {112,126,136} {112,126,137}
{112,126,138} {112,126,139} {112,127,128} {112,127,129} {112,127,130} {112,127,131} {112,127,132}
{112,127,133} {112,127,134} {112,127,135} {112,127,136} {112,127,137} {112,127,138} {112,127,139}
{112,128,129} {112,128,130} {112,128,131} {112,128,132} {112,128,133} {112,128,134} {112,128,135}
{112,128,136} {112,128,137} {112,128,138} {112,128,139} {112,129,130} {112,129,131} {112,129,132}
{112,129,133} {112,129,134} {112,129,135} {112,129,136} {112,129,137} {112,129,138} {112,129,139}
{112,130,131} {112,130,132} {112,130,133} {112,130,134} {112,130,135} {112,130,136} {112,130,137}
{112,130,138} {112,130,139} {112,131,132} {112,131,133} {112,131,134} {112,131,135} {112,131,136}
{112,131,137} {112,131,138} {112,131,139} {112,132,133} {112,132,134} {112,132,135} {112,132,136}
{112,132,137} {112,132,138} {112,132,139} {112,133,134} {112,133,135} {112,133,136} {112,133,137}
{112,133,138} {112,133,139} {112,134,135} {112,134,136} {112,134,137} {112,134,138} {112,134,139}
{112,135,136} {112,135,137} {112,135,138} {112,135,139} {112,136,137} {112,136,138} {112,136,139}
{112,137,138} {112,137,139} {112,138,139} {113,114,115} {113,114,116} {113,114,121} {113,114,122}
{113,114,123} {113,114,124} {113,114,125} {113,114,126} {113,114,127} {113,114,128} {113,114,129}
{113,114,130} {113,114,131} {113,114,132} {113,114,133} {113,114,134} {113,114,135} {113,114,136}
{113,114,137} {113,114,138} {113,114,139} {113,115,116} {113,115,121} {113,115,122} {113,115,123}
{113,115,124} {113,115,125} {113,115,126} {113,115,127} {113,115,128} {113,115,129} {113,115,130}
{113,115,131} {113,115,132} {113,115,133} {113,115,134} {113,115,135} {113,115,136} {113,115,137}
{113,115,138} {113,115,139} {113,116,121} {113,116,122} {113,116,123} {113,116,124} {113,116,125}
{113,116,126} {113,116,127} {113,116,128} {113,116,129} {113,116,130} {113,116,131} {113,116,132}
{113,116,133} {113,116,134} {113,116,135} {113,116,136} {113,116,137} {113,116,138} {113,116,139}
{113,121,122} {113,121,123} {113,121,124} {113,121,125} {113,121,126} {113,121,127} {113,121,128}
{113,121,129} {113,121,130} {113,121,131} {113,121,132} {113,121,133} {113,121,134} {113,121,135}
{113,121,136} {113,121,137} {113,121,138} {113,121,139} {113,122,123} {113,122,124} {113,122,125}
{113,122,126} {113,122,127} {113,122,128} {113,122,129} {113,122,130} {113,122,131} {113,122,132}
{113,122,133} {113,122,134} {113,122,135} {113,122,136} {113,122,137} {113,122,138} {113,122,139}
{113,123,124} {113,123,125} {113,123,126} {113,123,127} {113,123,128} {113,123,129} {113,123,130}
{113,123,131} {113,123,132} {113,123,133} {113,123,134} {113,123,135} {113,123,136} {113,123,137}
{113,123,138} {113,123,139} {113,124,125} {113,124,126} {113,124,127} {113,124,128} {113,124,129}
{113,124,130} {113,124,131} {113,124,132} {113,124,133} {113,124,134} {113,124,135} {113,124,136}
{113,124,137} {113,124,138} {113,124,139} {113,125,126} {113,125,127} {113,125,128} {113,125,129}
{113,125,130} {113,125,131} {113,125,132} {113,125,133} {113,125,134} {113,125,135} {113,125,136}
{113,125,137} {113,125,138} {113,125,139} {113,126,127} {113,126,128} {113,126,129} {113,126,130}
{113,126,131} {113,126,132} {113,126,133} {113,126,134} {113,126,135} {113,126,136} {113,126,137}
{113,126,138} {113,126,139} {113,127,128} {113,127,129} {113,127,130} {113,127,131} {113,127,132}
{113,127,133} {113,127,134} {113,127,135} {113,127,136} {113,127,137} {113,127,138} {113,127,139}
{113,128,129} {113,128,130} {113,128,131} {113,128,132} {113,128,133} {113,128,134} {113,128,135}
{113,128,136} {113,128,137} {113,128,138} {113,128,139} {113,129,130} {113,129,131} {113,129,132}

TABLE 3B-continued

| | | | | | | |
|---|---|---|---|---|---|---|
| {113,129,133} | {113,129,134} | {113,129,135} | {113,129,136} | {113,129,137} | {113,129,138} | {113,129,139} |
| {113,130,131} | {113,130,132} | {113,130,133} | {113,130,134} | {113,130,135} | {113,130,136} | {113,130,137} |
| {113,130,138} | {113,130,139} | {113,131,132} | {113,131,133} | {113,131,134} | {113,131,135} | {113,131,136} |
| {113,131,137} | {113,131,138} | {113,131,139} | {113,132,133} | {113,132,134} | {113,132,135} | {113,132,136} |
| {113,132,137} | {113,132,138} | {113,132,139} | {113,133,134} | {113,133,135} | {113,133,136} | {113,133,137} |
| {113,133,138} | {113,133,139} | {113,134,135} | {113,134,136} | {113,134,137} | {113,134,138} | {113,134,139} |
| {113,135,136} | {113,135,137} | {113,135,138} | {113,135,139} | {113,136,137} | {113,136,138} | {113,136,139} |
| {113,137,138} | {113,137,139} | {113,138,139} | {114,115,116} | {114,115,121} | {114,115,122} | {114,115,123} |
| {114,115,124} | {114,115,125} | {114,115,126} | {114,115,127} | {114,115,128} | {114,115,129} | {114,115,130} |
| {114,115,131} | {114,115,132} | {114,115,133} | {114,115,134} | {114,115,135} | {114,115,136} | {114,115,137} |
| {114,115,138} | {114,115,139} | {114,116,121} | {114,116,122} | {114,116,123} | {114,116,124} | {114,116,125} |
| {114,116,126} | {114,116,127} | {114,116,128} | {114,116,129} | {114,116,130} | {114,116,131} | {114,116,132} |
| {114,116,133} | {114,116,134} | {114,116,135} | {114,116,136} | {114,116,137} | {114,116,138} | {114,116,139} |
| {114,121,122} | {114,121,123} | {114,121,124} | {114,121,125} | {114,121,126} | {114,121,127} | {114,121,128} |
| {114,121,129} | {114,121,130} | {114,121,131} | {114,121,132} | {114,121,133} | {114,121,134} | {114,121,135} |
| {114,121,136} | {114,121,137} | {114,121,138} | {114,121,139} | {114,122,123} | {114,122,124} | {114,122,125} |
| {114,122,126} | {114,122,127} | {114,122,128} | {114,122,129} | {114,122,130} | {114,122,131} | {114,122,132} |
| {114,122,133} | {114,122,134} | {114,122,135} | {114,122,136} | {114,122,137} | {114,122,138} | {114,122,139} |
| {114,123,124} | {114,123,125} | {114,123,126} | {114,123,127} | {114,123,128} | {114,123,129} | {114,123,130} |
| {114,123,131} | {114,123,132} | {114,123,133} | {114,123,134} | {114,123,135} | {114,123,136} | {114,123,137} |
| {114,123,138} | {114,123,139} | {114,124,125} | {114,124,126} | {114,124,127} | {114,124,128} | {114,124,129} |
| {114,124,130} | {114,124,131} | {114,124,132} | {114,124,133} | {114,124,134} | {114,124,135} | {114,124,136} |
| {114,124,137} | {114,124,138} | {114,124,139} | {114,125,126} | {114,125,127} | {114,125,128} | {114,125,129} |
| {114,125,130} | {114,125,131} | {114,125,132} | {114,125,133} | {114,125,134} | {114,125,135} | {114,125,136} |
| {114,125,137} | {114,125,138} | {114,125,139} | {114,126,127} | {114,126,128} | {114,126,129} | {114,126,130} |
| {114,126,131} | {114,126,132} | {114,126,133} | {114,126,134} | {114,126,135} | {114,126,136} | {114,126,137} |
| {114,126,138} | {114,126,139} | {114,127,128} | {114,127,129} | {114,127,130} | {114,127,131} | {114,127,132} |
| {114,127,133} | {114,127,134} | {114,127,135} | {114,127,136} | {114,127,137} | {114,127,138} | {114,127,139} |
| {114,128,129} | {114,128,130} | {114,128,131} | {114,128,132} | {114,128,133} | {114,128,134} | {114,128,135} |
| {114,128,136} | {114,128,137} | {114,128,138} | {114,128,139} | {114,129,130} | {114,129,131} | {114,129,132} |
| {114,129,133} | {114,129,134} | {114,129,135} | {114,129,136} | {114,129,137} | {114,129,138} | {114,129,139} |
| {114,130,131} | {114,130,132} | {114,130,133} | {114,130,134} | {114,130,135} | {114,130,136} | {114,130,137} |
| {114,130,138} | {114,130,139} | {114,131,132} | {114,131,133} | {114,131,134} | {114,131,135} | {114,131,136} |
| {114,131,137} | {114,131,138} | {114,131,139} | {114,132,133} | {114,132,134} | {114,132,135} | {114,132,136} |
| {114,132,137} | {114,132,138} | {114,132,139} | {114,133,134} | {114,133,135} | {114,133,136} | {114,133,137} |
| {114,133,138} | {114,133,139} | {114,134,135} | {114,134,136} | {114,134,137} | {114,134,138} | {114,134,139} |
| {114,135,136} | {114,135,137} | {114,135,138} | {114,135,139} | {114,136,137} | {114,136,138} | {114,136,139} |
| {114,137,138} | {114,137,139} | {114,138,139} | {115,116,121} | {115,116,122} | {115,116,123} | {115,116,124} |
| {115,116,125} | {115,116,126} | {115,116,127} | {115,116,128} | {115,116,129} | {115,116,130} | {115,116,131} |
| {115,116,132} | {115,116,133} | {115,116,134} | {115,116,135} | {115,116,136} | {115,116,137} | {115,116,138} |
| {115,116,139} | {115,121,122} | {115,121,123} | {115,121,124} | {115,121,125} | {115,121,126} | {115,121,127} |
| {115,121,128} | {115,121,129} | {115,121,130} | {115,121,131} | {115,121,132} | {115,121,133} | {115,121,134} |
| {115,121,135} | {115,121,136} | {115,121,137} | {115,121,138} | {115,121,139} | {115,122,123} | {115,122,124} |
| {115,122,125} | {115,122,126} | {115,122,127} | {115,122,128} | {115,122,129} | {115,122,130} | {115,122,131} |
| {115,122,132} | {115,122,133} | {115,122,134} | {115,122,135} | {115,122,136} | {115,122,137} | {115,122,138} |
| {115,122,139} | {115,123,124} | {115,123,125} | {115,123,126} | {115,123,127} | {115,123,128} | {115,123,129} |
| {115,123,130} | {115,123,131} | {115,123,132} | {115,123,133} | {115,123,134} | {115,123,135} | {115,123,136} |
| {115,123,137} | {115,123,138} | {115,123,139} | {115,124,125} | {115,124,126} | {115,124,127} | {115,124,128} |
| {115,124,129} | {115,124,130} | {115,124,131} | {115,124,132} | {115,124,133} | {115,124,134} | {115,124,135} |
| {115,124,136} | {115,124,137} | {115,124,138} | {115,124,139} | {115,125,126} | {115,125,127} | {115,125,128} |
| {115,125,129} | {115,125,130} | {115,125,131} | {115,125,132} | {115,125,133} | {115,125,134} | {115,125,135} |
| {115,125,136} | {115,125,137} | {115,125,138} | {115,125,139} | {115,126,127} | {115,126,128} | {115,126,129} |
| {115,126,130} | {115,126,131} | {115,126,132} | {115,126,133} | {115,126,134} | {115,126,135} | {115,126,136} |
| {115,126,137} | {115,126,138} | {115,126,139} | {115,127,128} | {115,127,129} | {115,127,130} | {115,127,131} |
| {115,127,132} | {115,127,133} | {115,127,134} | {115,127,135} | {115,127,136} | {115,127,137} | {115,127,138} |
| {115,127,139} | {115,128,129} | {115,128,130} | {115,128,131} | {115,128,132} | {115,128,133} | {115,128,134} |
| {115,128,135} | {115,128,136} | {115,128,137} | {115,128,138} | {115,128,139} | {115,129,130} | {115,129,131} |
| {115,129,132} | {115,129,133} | {115,129,134} | {115,129,135} | {115,129,136} | {115,129,137} | {115,129,138} |
| {115,129,139} | {115,130,131} | {115,130,132} | {115,130,133} | {115,130,134} | {115,130,135} | {115,130,136} |
| {115,130,137} | {115,130,138} | {115,130,139} | {115,131,132} | {115,131,133} | {115,131,134} | {115,131,135} |
| {115,131,136} | {115,131,137} | {115,131,138} | {115,131,139} | {115,132,133} | {115,132,134} | {115,132,135} |
| {115,132,136} | {115,132,137} | {115,132,138} | {115,132,139} | {115,133,134} | {115,133,135} | {115,133,136} |
| {115,133,137} | {115,133,138} | {115,133,139} | {115,134,135} | {115,134,136} | {115,134,137} | {115,134,138} |
| {115,134,139} | {115,135,136} | {115,135,137} | {115,135,138} | {115,135,139} | {115,136,137} | {115,136,138} |
| {115,136,139} | {115,137,138} | {115,137,139} | {115,138,139} | {116,121,122} | {116,121,123} | {116,121,124} |
| {116,121,125} | {116,121,126} | {116,121,127} | {116,121,128} | {116,121,129} | {116,121,130} | {116,121,131} |
| {116,121,132} | {116,121,133} | {116,121,134} | {116,121,135} | {116,121,136} | {116,121,137} | {116,121,138} |
| {116,121,139} | {116,122,123} | {116,122,124} | {116,122,125} | {116,122,126} | {116,122,127} | {116,122,128} |
| {116,122,129} | {116,122,130} | {116,122,131} | {116,122,132} | {116,122,133} | {116,122,134} | {116,122,135} |
| {116,122,136} | {116,122,137} | {116,122,138} | {116,122,139} | {116,123,124} | {116,123,125} | {116,123,126} |
| {116,123,127} | {116,123,128} | {116,123,129} | {116,123,130} | {116,123,131} | {116,123,132} | {116,123,133} |
| {116,123,134} | {116,123,135} | {116,123,136} | {116,123,137} | {116,123,138} | {116,123,139} | {116,124,125} |
| {116,124,126} | {116,124,127} | {116,124,128} | {116,124,129} | {116,124,130} | {116,124,131} | {116,124,132} |
| {116,124,133} | {116,124,134} | {116,124,135} | {116,124,136} | {116,124,137} | {116,124,138} | {116,124,139} |
| {116,125,126} | {116,125,127} | {116,125,128} | {116,125,129} | {116,125,130} | {116,125,131} | {116,125,132} |
| {116,125,133} | {116,125,134} | {116,125,135} | {116,125,136} | {116,125,137} | {116,125,138} | {116,125,139} |
| {116,126,127} | {116,126,128} | {116,126,129} | {116,126,130} | {116,126,131} | {116,126,132} | {116,126,133} |
| {116,126,134} | {116,126,135} | {116,126,136} | {116,126,137} | {116,126,138} | {116,126,139} | {116,127,128} |
| {116,127,129} | {116,127,130} | {116,127,131} | {116,127,132} | {116,127,133} | {116,127,134} | {116,127,135} |
| {116,127,136} | {116,127,137} | {116,127,138} | {116,127,139} | {116,128,129} | {116,128,130} | {116,128,131} |

TABLE 3B-continued

{116,128,132} {116,128,133} {116,128,134} {116,128,135} {116,128,136} {116,128,137} {116,128,138}
{116,128,139} {116,129,130} {116,129,131} {116,129,132} {116,129,133} {116,129,134} {116,129,135}
{116,129,136} {116,129,137} {116,129,138} {116,129,139} {116,130,131} {116,130,132} {116,130,133}
{116,130,134} {116,130,135} {116,130,136} {116,130,137} {116,130,138} {116,130,139} {116,131,132}
{116,131,133} {116,131,134} {116,131,135} {116,131,136} {116,131,137} {116,131,138} {116,131,139}
{116,132,133} {116,132,134} {116,132,135} {116,132,136} {116,132,137} {116,132,138} {116,132,139}
{116,133,134} {116,133,135} {116,133,136} {116,133,137} {116,133,138} {116,133,139} {116,134,135}
{116,134,136} {116,134,137} {116,134,138} {116,134,139} {116,135,136} {116,135,137} {116,135,138}
{116,135,139} {116,136,137} {116,136,138} {116,136,139} {116,137,138} {116,137,139} {116,138,139}
{121,122,123} {121,122,124} {121,122,125} {121,122,126} {121,122,127} {121,122,128} {121,122,129}
{121,122,130} {121,122,131} {121,122,132} {121,122,133} {121,122,134} {121,122,135} {121,122,136}
{121,122,137} {121,122,138} {121,122,139} {121,123,124} {121,123,125} {121,123,126} {121,123,127}
{121,123,128} {121,123,129} {121,123,130} {121,123,131} {121,123,132} {121,123,133} {121,123,134}
{121,123,135} {121,123,136} {121,123,137} {121,123,138} {121,123,139} {121,124,125} {121,124,126}
{121,124,127} {121,124,128} {121,124,129} {121,124,130} {121,124,131} {121,124,132} {121,124,133}
{121,124,134} {121,124,135} {121,124,136} {121,124,137} {121,124,138} {121,124,139} {121,125,126}
{121,125,127} {121,125,128} {121,125,129} {121,125,130} {121,125,131} {121,125,132} {121,125,133}
{121,125,134} {121,125,135} {121,125,136} {121,125,137} {121,125,138} {121,125,139} {121,126,127}
{121,126,128} {121,126,129} {121,126,130} {121,126,131} {121,126,132} {121,126,133} {121,126,134}
{121,126,135} {121,126,136} {121,126,137} {121,126,138} {121,126,139} {121,127,128} {121,127,129}
{121,127,130} {121,127,131} {121,127,132} {121,127,133} {121,127,134} {121,127,135} {121,127,136}
{121,127,137} {121,127,138} {121,127,139} {121,128,129} {121,128,130} {121,128,131} {121,128,132}
{121,128,133} {121,128,134} {121,128,135} {121,128,136} {121,128,137} {121,128,138} {121,128,139}
{121,129,130} {121,129,131} {121,129,132} {121,129,133} {121,129,134} {121,129,135} {121,129,136}
{121,129,137} {121,129,138} {121,129,139} {121,130,131} {121,130,132} {121,130,133} {121,130,134}
{121,130,135} {121,130,136} {121,130,137} {121,130,138} {121,130,139} {121,131,132} {121,131,133}
{121,131,134} {121,131,135} {121,131,136} {121,131,137} {121,131,138} {121,131,139} {121,132,133}
{121,132,134} {121,132,135} {121,132,136} {121,132,137} {121,132,138} {121,132,139} {121,133,134}
{121,133,135} {121,133,136} {121,133,137} {121,133,138} {121,133,139} {121,134,135} {121,134,136}
{121,134,137} {121,134,138} {121,134,139} {121,135,136} {121,135,137} {121,135,138} {121,135,139}
{121,136,137} {121,136,138} {121,136,139} {121,137,138} {121,137,139} {121,138,139} {122,123,124}
{122,123,125} {122,123,126} {122,123,127} {122,123,128} {122,123,129} {122,123,130} {122,123,131}
{122,123,132} {122,123,133} {122,123,134} {122,123,135} {122,123,136} {122,123,137} {122,123,138}
{122,123,139} {122,124,125} {122,124,126} {122,124,127} {122,124,128} {122,124,129} {122,124,130}
{122,124,131} {122,124,132} {122,124,133} {122,124,134} {122,124,135} {122,124,136} {122,124,137}
{122,124,138} {122,124,139} {122,125,126} {122,125,127} {122,125,128} {122,125,129} {122,125,130}
{122,125,131} {122,125,132} {122,125,133} {122,125,134} {122,125,135} {122,125,136} {122,125,137}
{122,125,138} {122,125,139} {122,126,127} {122,126,128} {122,126,129} {122,126,130} {122,126,131}
{122,126,132} {122,126,133} {122,126,134} {122,126,135} {122,126,136} {122,126,137} {122,126,138}
{122,126,139} {122,127,128} {122,127,129} {122,127,130} {122,127,131} {122,127,132} {122,127,133}
{122,127,134} {122,127,135} {122,127,136} {122,127,137} {122,127,138} {122,127,139} {122,128,129}
{122,128,130} {122,128,131} {122,128,132} {122,128,133} {122,128,134} {122,128,135} {122,128,136}
{122,128,137} {122,128,138} {122,128,139} {122,129,130} {122,129,131} {122,129,132} {122,129,133}
{122,129,134} {122,129,135} {122,129,136} {122,129,137} {122,129,138} {122,129,139} {122,130,131}
{122,130,132} {122,130,133} {122,130,134} {122,130,135} {122,130,136} {122,130,137} {122,130,138}
{122,130,139} {122,131,132} {122,131,133} {122,131,134} {122,131,135} {122,131,136} {122,131,137}
{122,131,138} {122,131,139} {122,132,133} {122,132,134} {122,132,135} {122,132,136} {122,132,137}
{122,132,138} {122,132,139} {122,133,134} {122,133,135} {122,133,136} {122,133,137} {122,133,138}
{122,133,139} {122,134,135} {122,134,136} {122,134,137} {122,134,138} {122,134,139} {122,135,136}
{122,135,137} {122,135,138} {122,135,139} {122,136,137} {122,136,138} {122,136,139} {122,137,138}
{122,137,139} {122,138,139} {123,124,125} {123,124,126} {123,124,127} {123,124,128} {123,124,129}
{123,124,130} {123,124,131} {123,124,132} {123,124,133} {123,124,134} {123,124,135} {123,124,136}
{123,124,137} {123,124,138} {123,124,139} {123,125,126} {123,125,127} {123,125,128} {123,125,129}
{123,125,130} {123,125,131} {123,125,132} {123,125,133} {123,125,134} {123,125,135} {123,125,136}
{123,125,137} {123,125,138} {123,125,139} {123,126,127} {123,126,128} {123,126,129} {123,126,130}
{123,126,131} {123,126,132} {123,126,133} {123,126,134} {123,126,135} {123,126,136} {123,126,137}
{123,126,138} {123,126,139} {123,127,128} {123,127,129} {123,127,130} {123,127,131} {123,127,132}
{123,127,133} {123,127,134} {123,127,135} {123,127,136} {123,127,137} {123,127,138} {123,127,139}
{123,128,129} {123,128,130} {123,128,131} {123,128,132} {123,128,133} {123,128,134} {123,128,135}
{123,128,136} {123,128,137} {123,128,138} {123,128,139} {123,129,130} {123,129,131} {123,129,132}
{123,129,133} {123,129,134} {123,129,135} {123,129,136} {123,129,137} {123,129,138} {123,129,139}
{123,130,131} {123,130,132} {123,130,133} {123,130,134} {123,130,135} {123,130,136} {123,130,137}
{123,130,138} {123,130,139} {123,131,132} {123,131,133} {123,131,134} {123,131,135} {123,131,136}
{123,131,137} {123,131,138} {123,131,139} {123,132,133} {123,132,134} {123,132,135} {123,132,136}
{123,132,137} {123,132,138} {123,132,139} {123,133,134} {123,133,135} {123,133,136} {123,133,137}
{123,133,138} {123,133,139} {123,134,135} {123,134,136} {123,134,137} {123,134,138} {123,134,139}
{123,135,136} {123,135,137} {123,135,138} {123,135,139} {123,136,137} {123,136,138} {123,136,139}
{123,137,138} {123,137,139} {123,138,139} {124,125,126} {124,125,127} {124,125,128} {124,125,129}
{124,125,130} {124,125,131} {124,125,132} {124,125,133} {124,125,134} {124,125,135} {124,125,136}
{124,125,137} {124,125,138} {124,125,139} {124,126,127} {124,126,128} {124,126,129} {124,126,130}
{124,126,131} {124,126,132} {124,126,133} {124,126,134} {124,126,135} {124,126,136} {124,126,137}
{124,126,138} {124,126,139} {124,127,128} {124,127,129} {124,127,130} {124,127,131} {124,127,132}
{124,127,133} {124,127,134} {124,127,135} {124,127,136} {124,127,137} {124,127,138} {124,127,139}
{124,128,129} {124,128,130} {124,128,131} {124,128,132} {124,128,133} {124,128,134} {124,128,135}
{124,128,136} {124,128,137} {124,128,138} {124,128,139} {124,129,130} {124,129,131} {124,129,132}
{124,129,133} {124,129,134} {124,129,135} {124,129,136} {124,129,137} {124,129,138} {124,129,139}
{124,130,131} {124,130,132} {124,130,133} {124,130,134} {124,130,135} {124,130,136} {124,130,137}
{124,130,138} {124,130,139} {124,131,132} {124,131,133} {124,131,134} {124,131,135} {124,131,136}
{124,131,137} {124,131,138} {124,131,139} {124,132,133} {124,132,134} {124,132,135} {124,132,136}
{124,132,137} {124,132,138} {124,132,139} {124,133,134} {124,133,135} {124,133,136} {124,133,137}

TABLE 3B-continued

{124,133,138} {124,133,139} {124,134,135} {124,134,136} {124,134,137} {124,134,138} {124,134,139}
{124,135,136} {124,135,137} {124,135,138} {124,135,139} {124,136,137} {124,136,138} {124,136,139}
{124,137,138} {124,137,139} {124,138,139} {125,126,127} {125,126,128} {125,126,129} {125,126,130}
{125,126,131} {125,126,132} {125,126,133} {125,126,134} {125,126,135} {125,126,136} {125,126,137}
{125,126,138} {125,126,139} {125,127,128} {125,127,129} {125,127,130} {125,127,131} {125,127,132}
{125,127,133} {125,127,134} {125,127,135} {125,127,136} {125,127,137} {125,127,138} {125,127,139}
{125,128,129} {125,128,130} {125,128,131} {125,128,132} {125,128,133} {125,128,134} {125,128,135}
{125,128,136} {125,128,137} {125,128,138} {125,128,139} {125,129,130} {125,129,131} {125,129,132}
{125,129,133} {125,129,134} {125,129,135} {125,129,136} {125,129,137} {125,129,138} {125,129,139}
{125,130,131} {125,130,132} {125,130,133} {125,130,134} {125,130,135} {125,130,136} {125,130,137}
{125,130,138} {125,130,139} {125,131,132} {125,131,133} {125,131,134} {125,131,135} {125,131,136}
{125,131,137} {125,131,138} {125,131,139} {125,132,133} {125,132,134} {125,132,135} {125,132,136}
{125,132,137} {125,132,138} {125,132,139} {125,133,134} {125,133,135} {125,133,136} {125,133,137}
{125,133,138} {125,133,139} {125,134,135} {125,134,136} {125,134,137} {125,134,138} {125,134,139}
{125,135,136} {125,135,137} {125,135,138} {125,135,139} {125,136,137} {125,136,138} {125,136,139}
{125,137,138} {125,137,139} {125,138,139} {126,127,128} {126,127,129} {126,127,130} {126,127,131}
{126,127,132} {126,127,133} {126,127,134} {126,127,135} {126,127,136} {126,127,137} {126,127,138}
{126,127,139} {126,128,129} {126,128,130} {126,128,131} {126,128,132} {126,128,133} {126,128,134}
{126,128,135} {126,128,136} {126,128,137} {126,128,138} {126,128,139} {126,129,130} {126,129,131}
{126,129,132} {126,129,133} {126,129,134} {126,129,135} {126,129,136} {126,129,137} {126,129,138}
{126,129,139} {126,130,131} {126,130,132} {126,130,133} {126,130,134} {126,130,135} {126,130,136}
{126,130,137} {126,130,138} {126,130,139} {126,131,132} {126,131,133} {126,131,134} {126,131,135}
{126,131,136} {126,131,137} {126,131,138} {126,131,139} {126,132,133} {126,132,134} {126,132,135}
{126,132,136} {126,132,137} {126,132,138} {126,132,139} {126,133,134} {126,133,135} {126,133,136}
{126,133,137} {126,133,138} {126,133,139} {126,134,135} {126,134,136} {126,134,137} {126,134,138}
{126,134,139} {126,135,136} {126,135,137} {126,135,138} {126,135,139} {126,136,137} {126,136,138}
{126,136,139} {126,137,138} {126,137,139} {126,138,139} {127,128,129} {127,128,130} {127,128,131}
{127,128,132} {127,128,133} {127,128,134} {127,128,135} {127,128,136} {127,128,137} {127,128,138}
{127,128,139} {127,129,130} {127,129,131} {127,129,132} {127,129,133} {127,129,134} {127,129,135}
{127,129,136} {127,129,137} {127,129,138} {127,129,139} {127,130,131} {127,130,132} {127,130,133}
{127,130,134} {127,130,135} {127,130,136} {127,130,137} {127,130,138} {127,130,139} {127,131,132}
{127,131,133} {127,131,134} {127,131,135} {127,131,136} {127,131,137} {127,131,138} {127,131,139}
{127,132,133} {127,132,134} {127,132,135} {127,132,136} {127,132,137} {127,132,138} {127,132,139}
{127,133,134} {127,133,135} {127,133,136} {127,133,137} {127,133,138} {127,133,139} {127,134,135}
{127,134,136} {127,134,137} {127,134,138} {127,134,139} {127,135,136} {127,135,137} {127,135,138}
{127,135,139} {127,136,137} {127,136,138} {127,136,139} {127,137,138} {127,137,139} {127,138,139}
{128,129,130} {128,129,131} {128,129,132} {128,129,133} {128,129,134} {128,129,135} {128,129,136}
{128,129,137} {128,129,138} {128,129,139} {128,130,131} {128,130,132} {128,130,133} {128,130,134}
{128,130,135} {128,130,136} {128,130,137} {128,130,138} {128,130,139} {128,131,132} {128,131,133}
{128,131,134} {128,131,135} {128,131,136} {128,131,137} {128,131,138} {128,131,139} {128,132,133}
{128,132,134} {128,132,135} {128,132,136} {128,132,137} {128,132,138} {128,132,139} {128,133,134}
{128,133,135} {128,133,136} {128,133,137} {128,133,138} {128,133,139} {128,134,135} {128,134,136}
{128,134,137} {128,134,138} {128,134,139} {128,135,136} {128,135,137} {128,135,138} {128,135,139}
{128,136,137} {128,136,138} {128,136,139} {128,137,138} {128,137,139} {128,138,139} {129,130,131}
{129,130,132} {129,130,133} {129,130,134} {129,130,135} {129,130,136} {129,130,137} {129,130,138}
{129,130,139} {129,131,132} {129,131,133} {129,131,134} {129,131,135} {129,131,136} {129,131,137}
{129,131,138} {129,131,139} {129,132,133} {129,132,134} {129,132,135} {129,132,136} {129,132,137}
{129,132,138} {129,132,139} {129,133,134} {129,133,135} {129,133,136} {129,133,137} {129,133,138}
{129,133,139} {129,134,135} {129,134,136} {129,134,137} {129,134,138} {129,134,139} {129,135,136}
{129,135,137} {129,135,138} {129,135,139} {129,136,137} {129,136,138} {129,136,139} {129,137,138}
{129,137,139} {129,138,139} {130,131,132} {130,131,133} {130,131,134} {130,131,135} {130,131,136}
{130,131,137} {130,131,138} {130,131,139} {130,132,133} {130,132,134} {130,132,135} {130,132,136}
{130,132,137} {130,132,138} {130,132,139} {130,133,134} {130,133,135} {130,133,136} {130,133,137}
{130,133,138} {130,133,139} {130,134,135} {130,134,136} {130,134,137} {130,134,138} {130,134,139}
{130,135,136} {130,135,137} {130,135,138} {130,135,139} {130,136,137} {130,136,138} {130,136,139}
{130,137,138} {130,137,139} {130,138,139} {131,132,133} {131,132,134} {131,132,135} {131,132,136}
{131,132,137} {131,132,138} {131,132,139} {131,133,134} {131,133,135} {131,133,136} {131,133,137}
{131,133,138} {131,133,139} {131,134,135} {131,134,136} {131,134,137} {131,134,138} {131,134,139}
{131,135,136} {131,135,137} {131,135,138} {131,135,139} {131,136,137} {131,136,138} {131,136,139}
{131,137,138} {131,137,139} {131,138,139} {132,133,134} {132,133,135} {132,133,136} {132,133,137}
{132,133,138} {132,133,139} {132,134,135} {132,134,136} {132,134,137} {132,134,138} {132,134,139}
{132,135,136} {132,135,137} {132,135,138} {132,135,139} {132,136,137} {132,136,138} {132,136,139}
{132,137,138} {132,137,139} {132,138,139} {133,134,135} {133,134,136} {133,134,137} {133,134,138}
{133,134,139} {133,135,136} {133,135,137} {133,135,138} {133,135,139} {133,136,137} {133,136,138}
{133,136,139} {133,137,138} {133,137,139} {133,138,139} {134,135,136} {134,135,137} {134,135,138}
{134,135,139} {134,136,137} {134,136,138} {134,136,139} {134,137,138} {134,137,139} {134,138,139}
{135,136,137} {135,136,138} {135,136,139} {135,137,138} {135,137,139} {135,138,139} {136,137,138}
{136,137,139} {136,138,139} {137,138,139}

In some embodiments, when an ALK polypeptide includes a first sequence and a second sequence, or a first sequence, a second sequence, and a third sequence, as described above, a linker is placed between adjacent sequences. A linker is a linkage or connection between two adjacent sequences in an ALK polypeptide, for which the linker connects the C-terminus of the first sequence to the N-terminus of the second sequence, such that the two sequences are joined to each other in tandem series in an ALK polypeptide. A linker can be a simple covalent bond, e.g., a peptide bond, an amino acid spacer, a synthetic polymer, e.g., a polyethylene glycol (PEG) polymer, or any kind of bond created from a chemical reaction, e.g. chemical conjugation. The peptide bond can be formed from synthetic means through a conventional organic chemistry reaction well-known in the art, or by natural production from a host cell, wherein a polynucleotide sequence encoding the first and second sequences in tandem series in an ALK polypeptide can be directly transcribed and translated into a contiguous polypeptide by the necessary molecular machineries, e.g., DNA polymerase and ribosome, in the host cell. In some embodiments, a linker is an amino acid spacer including 1-200 amino acids. Suitable peptide spacers are known in the art, and include, for example, peptide linkers containing flexible amino acid residues such as glycine and serine. In certain embodiments, a spacer can contain motifs, e.g., multiple or repeating motifs, of GS, GGS, GGGGS (SEQ ID NO: 71), GGSG (SEQ ID NO: 72), or SGGG (SEQ ID NO: 73). In certain embodiments, a spacer can contain 2 to 12 amino acids including motifs of GS, e.g., GS, GSGS (SEQ ID NO: 74), GSGSGS (SEQ ID NO: 75), GSGSGSGS (SEQ ID NO: 76), GSGSGSGSGS (SEQ ID NO: 77), or GSGSGSGSGSGS (SEQ ID NO: 78). In certain other embodiments, a spacer can contain 3 to 12 amino acids including motifs of GGS, e.g., GGS, GGSGGS (SEQ ID NO: 79), GGSGGSGGS (SEQ ID NO: 80), and GGSGGSGGSGGS (SEQ ID NO: 81). In yet other embodiments, a spacer can contain 4 to 12 amino acids including motifs of GGSG (SEQ ID NO: 72), e.g., GGSG (SEQ ID NO: 72), GGSGGGSG (SEQ ID NO: 82), or GGSGGGSGGGSG (SEQ ID NO: 83). In other embodiments, a spacer can contain motifs of GGGGS (SEQ ID NO: 71), e.g., GGGGSGGGGSGGGGS (SEQ ID NO: 84). In other embodiments, a spacer can also contain amino acids other than glycine and serine, e.g., GENLYFQSGG (SEQ ID NO: 85), SACYCELS (SEQ ID NO: 86), RSIAT (SEQ ID NO: 87), RPACKIPNDLKQKVMNH (SEQ ID NO: 88), GGSAGGSGSGSSGGSSGASGTGTAGGTGSGSGTGSG (SEQ ID NO: 89), AAANSSIDLISVPVDSR (SEQ ID NO: 90), or GGSGGGSEGGGSEGGGSEGGGSEGGGSEGGGSGGGS (SEQ ID NO: 91).

In the case that a linker is a synthetic polymer, e.g., a PEG polymer, the polymer can be functionalized with reactive chemical functional groups at each end to react with the terminal amino acids at the connecting ends of the sequences in an ALK polypeptide. In the case that a linker (except peptide bond mentioned above) is made from a chemical reaction, chemical functional groups, e.g., amine, carboxylic acid, ester, azide, or other functional groups commonly used in the art, can be attached synthetically to the C-terminus of one sequence and the N-terminus of another sequence, respectively. The two functional groups can then react to through synthetic chemistry means to form a chemical bond, thus connecting the two sequences together. Such chemical conjugation procedures are routine for those skilled in the art.

In some embodiments, an ALK polypeptide described herein may be covalently linked to one or more moieties or conjugates which enhance the activity, cellular distribution, and/or cellular uptake of the resulting ALK polypeptide. Typical conjugate groups include, but are not limited to, cholesterol moieties, lipid moieties, carbohydrate moieties, peptides, antibodies, biotin, phenazine, folate, phenanthridine, anthraquinone, acridine, and other small molecules.

In some embodiments, an immunogenic composition described herein may further include one or more immunomodulators, adjuvants, and/or anti-cancer agents (e.g., tyrosine kinase inhibitors, e.g., Crizotinib, Ceritinib, Alectinib, or Brigatinib). In some embodiments, an immunogenic composition described herein may be free of immunomodulators, adjuvants, and/or anti-cancer agents.

Interbilayer Crosslinked Multilamellar Lipid Vesicles

In some embodiments, an immunogenic composition includes (a) a multilamellar lipid vesicle having crosslinks between lipid bilayers; and (b) one or more ALK polypeptides described herein. Stabilized multilamellar lipid vesicles having crosslinks between lipid bilayers (i.e., interbilayer-crosslinked multilamellar vesicles or ICMVs) can be used to deliver one or more ALK polypeptides. Multilamellar lipid vesicles are stabilized by linking adjacent (or apposed) lipid bilayers to one another and may include ALK polypeptides covalently conjugated to a lipid in the vesicle. As used herein, a multilamellar vesicle is a nano- or microsphere having a shell that includes two or more concentrically arranged lipid bilayers. As used herein, adjacent or apposed lipid bilayers (or lipid bilayer surfaces) refer to bilayers or surfaces that are in close proximity to each other but that are otherwise distinct and typically physically separate. This term does not typically mean the relationship between the two monolayers of a single bilayer. The present invention also incorporates by reference herein the disclosures of U.S. Pat. No. 8,747,869 (see, e.g., column 1, line 43 through column 5, line 40, and column 8, line 9 through column 35, line 69) and U.S. Pat. No. 9,149,432 (see, e.g., column 11, line 32 through column 35, line 32), which are directed to compositions, methods of synthesis, and methods of use of stabilized multilamellar vesicles.

The ICMVs are formed by crosslinking headgroups of adjacent lipid bilayers within multilamellar vesicles in which one or more ALK polypeptides have been covalently conjugated. In some embodiments, the ALK polypeptides may be conjugated to a lipid in the vesicle, e.g., within the vesicle core, within the vesicle walls, or on an outer surface of the vesicle. The stabilized nature of these vesicles and the covalent conjugation of one or more ALK polypeptides allow them to incorporate higher amounts of the ALK polypeptides and to retain such protein over a longer time period, as compared to simple liposomes or lipid coated nanoparticles or microparticles. Their sustained release kinetics, particularly in the presence of serum, make them useful in in vivo delivery of ALK polypeptides for which a slow, steady and prolonged release is desirable or for which slow release in the extracellular environment but rapid release within cells is desirable. In some embodiments, the ICMVs including one or more conjugated ALK polypeptides also include immunomodulators. The ICMVs exhibit rapid release in the presence of endolysosomal lipases.

The amount of an ALK polypeptide in the vesicles may vary and may depend on the nature of the protein. In some embodiments, 10-500 µg of the ALK polypeptide per mg of lipid may be incorporated into the vesicles of the invention. In some embodiments, the vesicles may include about 10 µg of the ALK polypeptide, or about 20 µg of the ALK polypeptide, or about 50 µg of the ALK polypeptide, or about 100 µg of the ALK polypeptide, or about 150 µg of the ALK polypeptide, or about 200 µg of the ALK polypeptide, or about 250 µg of the ALK polypeptide, or about 300 µg of the ALK polypeptide, or about 325 µg of the ALK polypeptide, or about 350 µg of the ALK polypeptide, or about 375 µg of the ALK polypeptide, or about 400 µg of the ALK polypeptide, or about 500 µg of the ALK polypeptide, per mg of lipid. In other embodiments, the vesicles may include 10-20 µg of the ALK polypeptide per mg of lipid, or 15-60 µg of the ALK polypeptide per mg of lipid, or 50-200 µg of the ALK polypeptide per mg of lipid, or 100-300 µg of the ALK polypeptide per mg of lipid, or 200-400 µg of the ALK polypeptide per mg of lipid, or 300-500 µg of the ALK polypeptide per mg of lipid.

The number of lipid bilayers in the ICMVs may vary from about 2-30 (e.g., 2-15, 5-20, 10-30). Accordingly, in various embodiments, the number of layers may be 2, 3, 4, 5, 6, 7, 8, 9, 10, 11, 12, 13, 14, 15 or more. The bilayers are typically composed of lipids having hydrophilic heads and hydrophobic tails that are arranged in a manner similar to a cell membrane (i.e., with the hydrophilic heads exposed to typically an aqueous environment and the hydrophobic tails buried in the bilayer). The ICMVs are stabilized via crosslinks between their lipid bilayers. As used herein, this means that at least two lipid bilayers in the shell of the vesicle are crosslinked to each other. The crosslinked bilayers are typically those that are apposed or adjacent to each other. Most or all of the lipid bilayers in the shell may be crosslinked to their apposing lipid bilayer in the shell. There may be one or more crosslinks between lipid bilayers. Typically, there will be numerous crosslinks between lipid bilayers. The arrangement and positioning of such crosslinks may be random or non-random. The degree of crosslinks (and thus the resultant stability of the vesicles) will depend upon the proportion of functionalized lipids (or other lipid bilayer components) used to make the vesicles and the crosslinking conditions (including, for example, time of incubation of the vesicles with a crosslinker). It will be understood that the higher the proportion of functionalized lipids (or other lipid bilayer components) in the vesicles, the more crosslinks that will be formed, all other factors and parameters being equal. Similarly, the more favorable the conditions towards crosslinking, the greater degree of crosslinking that will be achieved.

One or more of the lipids used in the synthesis of the vesicles may be functionalized lipids. As used herein, a functionalized lipid is a lipid having a reactive group that can be used to crosslink adjacent bilayers of the multilamellar vesicle (e.g., an ICMV). The bilayer component may be modified to include the reactive group. In some embodiments, the reactive group is one that will react with a crosslinker (or other moiety) to form crosslinks between such functionalized lipids (and thus between lipid bilayers in the vesicle). The reactive group may be located anywhere on the lipid that allows it to contact a crosslinker and be crosslinked to another lipid in an adjacent apposed bilayer. In some embodiments, it is in the head group of the lipid, including for example a phospholipid. An example of a reactive group is a maleimide group. Maleimide groups may be crosslinked to each other in the presence of dithiol crosslinkers such as but not limited to dithiolthrietol (DTT). An example of a functionalized lipid is 1,2-dioleoyl-sn-glycero-3-phosphoethanolamine-N-[4-(p-maleimidophenyl) butyramide, referred to herein as MPB. Another example of a functionalized lipid is 1,2-distearoyl-sn-glycero-3-phosphoethanolamine-N-[maleimide(polyethylene glycol)2000] (also referred to as maleimide-PEG 2k-PE). Another example of a functionalized lipid is dioleoyl-phosphatidylethanolamine 4-(N-maleimidomethyl)-cyclohexane-1-carboxylate (DOPE-mal). It is to be understood that the invention contemplates the use of other functionalized lipids, other functionalized lipid bilayer components, other reactive groups, and other crosslinkers. In addition to the maleimide groups, other examples of reactive groups include, but are not limited, to other thiol reactive groups, amino groups such as primary and secondary amines, carboxyl groups, hydroxyl groups, aldehyde groups, alkyne groups, azide groups, carbonyls, haloacetyl (e.g., iodoacetyl) groups, imidoester groups, N-hydroxysuccinimide esters, sulfhydryl groups, and pyridyl disulfide groups.

The stabilized multilamellar lipid vesicles having crosslinks between lipid bilayers (i.e., interbilayer-crosslinked multilamellar vesicles or ICMVs) include one or more ALK polypeptides conjugated to a lipid of the vesicle. As used herein, "conjugated" refers to covalent attachment or crosslink of the ALK polypeptide to the lipid of the stabilized multilamellar lipid vesicle (e.g., ICMV). The ALK polypeptide may be covalently attached to the lipid by reaction of complementary reactive groups on the ALK polypeptide and the lipid. The ALK polypeptide and/or lipid may be functionalized to contain the complementary reactive groups or the reactive groups may be a group already present in the ALK polypeptide or lipid. For example, the ALK polypeptide may include or be functionalized to include a thiol group and a covalent linkage may be formed by reaction with a lipid functionalized to include a maleimide group. Alternatively, the reactive group on the ALK polypeptide may be an amine or carboxylic acid and the covalent attachment to the lipid could be an amide bond formed by reaction with an amine or carboxylic acid of the lipid. The ALK polypeptide may be conjugated to the lipid prior to vesicle (e.g., ICMV) synthesis, and therefore may be encapsulated within the vesicle, between the lipid bilayers of the vesicle, or present on the outer surface of the vesicle.

Reactive groups to be used to conjugate the ALK polypeptide to the lipid may be the same as those used to crosslink the bilayers, in which case no additional functionalized lipids (or other functionalized components) are required. As an example, if the vesicles (e.g., ICMVs) include maleimide functionalized lipids, then the functionalized ALK polypeptide may be thiol-functionalized ALK polypeptide. Alternatively, the reactive groups used to stabilize the vesicles may be different from those used to conjugate the ALK polypeptide to the lipid. Those of ordinary skill in the art will appreciate that other modified versions of ALK polypeptide may be used depending on the nature of the reactive group in the functionalized lipid (or component) in the lipid bilayer of the vesicles. Suitable reactive groups include without limitation amino groups such as primary and secondary amines, carboxyl groups, sulfhydryl groups, hydroxyl groups, aldehyde groups, azide groups, carbonyls, maleimide groups, haloacetyl (e.g., iodoacetyl) groups, imidoester groups, N-hydroxysuccinimide ester groups, and pyridyl disulfide groups.

An ALK polypeptide may be functionalized or reactive. As used herein, a functionalized ALK polypeptide is an ALK polypeptide that includes a reactive group that can be used to conjugate the ALK polypeptide to a lipid (e.g., a functionalized lipid). The ALK polypeptide may be modified to include the reactive group. An ALK polypeptide used in the synthesis of the stabilized multilamellar lipid vesicles (e.g., ICMVs) including one or more ALK polypeptides may be functionalized ALK polypeptide. In some embodiments, the reactive group in an ALK polypeptide is one that will react to form a covalent attachment to a lipid of the stabilized multilamellar lipid vesicle (e.g., ICMV). The reactive group may be located anywhere on the ALK polypeptide that allows it to be conjugated to a lipid. An example of a reactive group is a thiol group. Other functionalized ALK polypeptides and other reactive groups may also be used. In addition to the thiol group, other examples of reactive groups include, but are not limited to, other thiol reactive groups, amino groups such as primary and secondary amines, carboxyl groups, hydroxyl groups, aldehyde groups, alkyne groups, azide groups, carbonyls, haloacetyl (e.g., iodoacetyl) groups, imidoester groups, N-hydroxysuccinimide ester groups, sulfhydryl groups, and pyridyl disulfide groups.

In some embodiments, an stabilized multilamellar lipid vesicle (e.g., ICMV) is functionalized with a maleimide reactive group, which can react with a cysteine in an ALK polypeptide to form a covalent attachment between the ALK polypeptide and the multilamellar lipid vesicle. In some embodiments, the cysteine in the ALK polypeptide is a naturally occurring cysteine or a non-naturally occurring cysteine (i.e., a cysteine that is introduced into the ALK polypeptide using conventional techniques in the art, e.g., PCR or site-directed mutagenesis). In some embodiments, the cysteine in the ALK polypeptide is a terminal-cysteine. A terminal-cysteine refers to a cysteine that is located near the N- or C-terminus of the ALK polypeptide. In some embodiments, for an ALK polypeptide that is 40-230 amino acids in length, a terminal-cysteine refers to a cysteine that is located within 10 amino acid residues of the amino terminus (i.e., at amino acid positions 1 through 10) and/or within 10 amino acid residues of the carboxy terminus (i.e., at amino acids (n-10) through n, where n represents the number of amino acid residues in the ALK polypeptide). Thus, a terminal-cysteine may occupy positions 1, 2, 3, 4, 5, 6, 7, 8, 9, 10, n-10, n-9, n-8, n-7, n-6, n-5, n-4, n-3, n-2, n-1 and/or n, where 1 represents the residue at the amino terminus and n represents the residue at the carboxy terminus. In some embodiments, for an ALK polypeptide that is 20-39 amino acids in length, a terminal-cysteine refers a cysteine that is located within 5 amino acid residues of the amino terminus (i.e., at amino acid positions 1 through 5) and/or within 5 amino acid residues of the carboxy terminus (i.e., at amino acids (n-5) through n, where n represents the number of amino acid residues in the ALK polypeptide). In some embodiments, for an ALK polypeptide that is 8-19 amino acids in length, a terminal-cysteine refers a cysteine that is located within 2 amino acid residues of the amino terminus (i.e., at amino acid positions 1 or 2) and/or within 2 amino acid residues of the carboxy terminus (i.e., at amino acids (n-2) through n, where n represents the number of amino acid residues in the ALK polypeptide).

An average of 1-2 molecules of added reactive group (e.g., a thiol) per ALK polypeptide molecule is desirable for efficient conjugation of the ALK polypeptide to the lipid. However, for some ALK polypeptides, addition of more reactive groups (e.g., a thiol molecule) per ALK polypeptide molecule may result in increased conjugation. As such, addition of 2, 3, 4, 5, or more reactive groups (e.g., thiols) per ALK polypeptide molecule is encompassed by the invention. As an example, ALK polypeptides may be conjugated to lipids by reacting a thiol-functionalized ALK polypeptide with a maleimide functionalized lipid. Thiol-functionalized ALK polypeptides may be prepared using methods known in the art, e.g., 2-iminothiolane-HCl (Traut's reagent), N-succinimidyl S-acetylthioacetate hydrochloride (SATA), or N-Succinimidyl S-acetyl(thiotetraethylene glycol). For example, treatment of an ALK polypeptide containing a primary amine with 10, 20, 30, 40, 50, 60, 70, 80, or more molar equivalents of Traut's reagent at room temperature (e.g., for 1 hour) provides thiol-functionalized ALK polypeptides. An average of 1-2 molecules of added thiol per ALK polypeptide molecule is desirable for efficient conjugation. However, for some ALK polypeptides, addition of more thiol molecules per ALK polypeptide molecule may result in increased conjugation. As such, addition of 2, 3, 4, 5, or more thiol molecules per ALK polypeptide molecule is encompassed by the invention.

Amphiphilic Conjugates

In some embodiments, an immunogenic composition includes an amphiphilic conjugate. An amphiphilic conjugate refers to a conjugate that includes an ALK polypeptide covalently linked to an albumin-binding domain (e.g., a lipid). In some embodiments, an amphiphilic conjugate includes an ALK polypeptide that is covalently linked to an albumin-binding domain (e.g., a lipid) directly. In some embodiments, an amphiphilic conjugate includes an ALK polypeptide that is covalently linked to an albumin-binding domain (e.g., a lipid) through a linker. For amphiphilic conjugates that include an ALK polypeptide conjugated to an albumin-binding domain either directly or through a linker, the albumin-binding domain binds to endogenous albumin, which prevents the amphiphilic conjugate from rapidly flushing into the bloodstream and instead re-targets them to lymphatics and draining lymph nodes where they accumulate due to filtering of albumin by antigen presenting cells. In some embodiments, an amphiphilic conjugate may spontaneously insert itself into lipid bilayers of a multilamellar lipid vesicle having crosslinks between lipid bilayers (e.g., an ICMV). In some embodiments, an amphiphilic conjugate may be further linked to a targeting agent. A targeting agent may be a therapeutic, prophylactic, or diagnostic agent. For example, a targeting agent may be an antibody, a protein, a peptide, or a small molecule drug that can target the amphiphilic conjugate to a specific cell or tissue. For example, a targeting agent may be a tumor-specific targeting agent (e.g., a tumor-specific antibody or chemotherapeutic agent) that targets the amphiphilic conjugate to a tumor (e.g., a tumor that expresses ALK or a portion thereof (e.g., an ALK+ tumor).

In some embodiments, for amphiphilic conjugates that include an ALK polypeptide conjugated to an albumin-binding domain either directly or through a linker, the albumin-binding domain may be linear, branched, or cyclic. In some embodiments, the albumin-binding domain may be a lipid. In some embodiments, the albumin-binding domain may be a diacyl lipid (e.g., a diacyl lipid including 5-30 carbon units, which may be saturated, unsaturated, or combinations thereof). In some embodiments, the albumin-binding domain may be a fatty acid lipid (e.g., a fatty acid lipid including 5-30 carbon units, which may be saturated, unsaturated, or combinations thereof). In some embodiments, the albumin-binding domain (e.g., a lipid) may be a fatty acid derivative, e.g., a fatty acid ester, a fatty acid amide, a fatty acid thioester, cholesterol, a cholesterol derivative, or a steroid acid. In some embodiments, the albumin-binding domain (e.g., a lipid) contains at least 8 or more carbon units. In some embodiments, the albumin-binding domain is a peptide, e.g., a peptide having the sequence DICLPRWGCLW (SEQ ID NO: 92), which is described in U.S. Pat. No. 7,635,749 and US Patent Publication No. US20050287153.

In some embodiments, for amphiphilic conjugates that include an ALK polypeptide conjugated to an albumin-binding domain (e.g., a lipid) through a linker, the linker may be selected from the group consisting of polymers, a string of amino acids (e.g., a string of hydrophilic amino acids, such as serine, threonine, cysteine, tyrosine, asparagine, glutamine, aspartic acid, glutamic acid, lysine, arginine, histidine, or combinations thereof), nucleic acids (e.g., an oligonucleotide, e.g., an oligonucleotide including "n" guanines, wherein n is 1-10), polysaccharides (e.g., dextran), or a combination thereof. In some embodiments, the linker includes consecutive polyethylene glycol units. In some embodiments, the linker includes "N" consecutive polyethylene glycol units, wherein N is between 20 and 80, between 30 and 80, between 40 and 60, or between 45 and 55 (e.g., 48 polyethylene glycol units).

In some embodiments, an ALK polypeptide in an amphiphilic conjugate includes at least 6 contiguous amino acids from a sequence of any one of SEQ ID NOs: 1-66 and 93-139 and does not include a sequence of any one of SEQ ID NOs: 67-70 and 140-145, In some embodiments, an ALK polypeptide in an amphiphilic conjugate includes a first sequence selected from any one of SEQ ID NOs: 1-66 and a second sequence selected from any one of SEQ ID NOs: 1-66, wherein the first and second sequences are different, wherein the first and second sequences include a pair of sequences of SEQ ID NOs recited in Table 2A, and wherein the ALK polypeptide does not include a sequence of any one of SEQ ID NOs: 67-70 and 140-145. In some embodiments, an ALK polypeptide in an amphiphilic conjugate includes a first sequence selected from any one of SEQ ID NOs: 1-66, a second sequence selected from any one of SEQ ID NOs: 1-66, and a third sequence selected from any one of SEQ ID NOs: 1-66, wherein the first, second, and third sequences are different, wherein the first, second, and third sequences include a set of sequences of SEQ ID NOs recited in Table 3A, and wherein the ALK polypeptide does not include a sequence of any one of SEQ ID NOs: 67-70 and 140-145.

In some embodiments, an ALK polypeptide in an amphiphilic conjugate includes at least 6 contiguous amino acids from a sequence of any one of SEQ ID NOs: 93, 96, 100, 106, 111-116, and 121-139 and does not include a sequence of any one of SEQ ID NOs: 67-70 and 140-145, In some embodiments, an ALK polypeptide in an amphiphilic conjugate includes a first sequence selected from any one of SEQ ID NOs: 93, 96, 100, 106, 111-116, and 121-139 and a second sequence selected from any one of SEQ ID NOs: 93, 96, 100, 106, 111-116, and 121-139, wherein the first and second sequences are different, wherein the first and second sequences include a pair of sequences of SEQ ID NOs recited in Table 2B, and wherein the ALK polypeptide does not include a sequence of any one of SEQ ID NOs: 67-70 and 140-145. In some embodiments, an ALK polypeptide in an amphiphilic conjugate includes a first sequence selected from any one of SEQ ID NOs: 93, 96, 100, 106, 111-116, and 121-139, a second sequence selected from any one of SEQ ID NOs: 93, 96, 100, 106, 111-116, and 121-139, and a third sequence selected from any one of SEQ ID NOs: 93, 96, 100, 106, 111-116, and 121-139, wherein the first, second, and third sequences are different, wherein the first, second, and third sequences include a set of sequences of SEQ ID NOs recited in Table 3B, and wherein the ALK polypeptide does not include a sequence of any one of SEQ ID NOs: 67-70 and 140-145.

Partner Proteins

In some embodiments, an ALK polypeptide described herein may be fused to a partner protein, or a fragment thereof (i.e., an extracellular domain or a fragment thereof). A partner protein refers to a protein that ALK translocates next to in a chromosomal translocation. For example, within anaplastic large cell lymphomas (ALCLs), nearly 70% of the cases carry the t(2;5)(p23;q35) chromosomal translocation that juxtaposes ALK locus to nucleophosmin (NPM) gene locus, generating a fusion protein of NPM and the cytoplasmic domain of ALK. Examples of partner proteins include, but are not limited to, a nucleophosmin (NPM) protein, a tropomyosin 3 (TPM3) protein, a tropomyosin 4 (TPM4) protein, a TRK-fused gene (TFG) protein, a 5-Aminoimidazole-4-carboxamide ribonucleotide formyltransferase/IMP cyclohydrolase (ATIC) protein, a clathrin heavy chain-like 1 (CLTC1) protein, a moesin (MSN) protein, an ALK lymphoma oligomerization partner on chromosome 17 (ALO17) protein, a RAN binding protein 2 (RANBP2), a non-muscle myosin heavy chain (MYH9) protein, a cysteinyl-tRNA synthetase (CARS) protein, a SEC31 homologue A (SEC31 L1) protein, a transforming growth factor (TGF) protein, and an echinoderm microtubule-associated protein-like 4 (EML4) protein, and a fragment thereof, such as an extracellular domain or a fragment of the extracellular domain thereof. A partner protein may be fused to the N- or C-terminus of an ALK polypeptide described herein.

Immunomodulators

In some embodiments, an immunogenic composition described herein may include one or more immunomodulators. An immunomodulator is an agent that stimulates (i.e., an immunostimulator) or inhibits (i.e., an immunoinhibitor) an immune response in a subject to whom it is administered, whether alone or in combination with another agent. In some embodiments, immunomodulators as described herein specifically exclude CureTech's anti-PD-1 antibody CT-011 as described in Patent and Patent Application Publication Nos.: U.S. Pat. No. 8,686,119, WO 2013014668, and WO 2009101611.

Examples of immunomodulators include, but are not limited to, an anti-CTLA-4 antibody, an anti-CD40 antibody, a cyclophosphamide (CPM), an AMD3100, an anti-LAG-3/CD223 antibody, an anti-B7-H5 antibody, an anti-OX40 antibody, an anti-CD28 antibody, an anti-GITR antibody, an anti-4-1 BB/CD137 antibody, a 4-1 BB ligand, an anti-BTLA antibody, an anti-TIM-3/HAVCR2 antibody, an anti-KIR antibody, an anti-Flt3/CD135 antibody, an anti-FasL antibody, an anti-CD25 antibody, an GM-CSF, an anti-GM-CSF-receptor (R) antibody, an IL-2, an anti-IL-2-R antibody, an IL-7, an anti-IL-7-R antibody, an IL-21, an anti-IL-21-R antibody, an IL-12, an anti-IL-12-R antibody, an IL-15, an anti-IL-15-R antibody, an IL-18, an anti-IL-18-R antibody, an anti-IDO antibody, an ipilimumab, a crizotinib, a ceritinib, an alectinib, a brigatinib, a celecoxib, a SOCS-1 inhibitor, a heat shock protein (HSP), a HSP inhibitor, a polyinosinic:polycytidylic acid (poly I:C), and an anti-galectin-1 antibody. In some embodiments, one or more immunomodulators are selected from the group consisting of an anti-CTLA-4 antibody, an anti-CD40 antibody, a cyclophosphamide (CPM), and an AMD3100.

Immunostimulators

As used herein, an immunostimulator is an agent that stimulates an immune response (including enhancing a pre-existing immune response) in a subject to whom it is administered, whether alone or in combination with another agent. Examples include antigens, adjuvants (e.g., TLR ligands such as imiquimod and resiquimod, imidazoquinolines, nucleic acids including an unmethylated CpG dinucleotide, monophosphoryl lipid A (MPLA) or other lipopolysaccharide derivatives, single-stranded or double-stranded RNA, flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), AMD3100, immunostimulatory antibodies (e.g., anti-CD40 antibody, anti-CTLA-4 antibody, anti-CD28 antibody, anti-CD3 antibody, or single chain/antibody fragments of these molecules), and PD-1 inhibitors. The term "PD-1 inhibitor" refers to any agent that inhibits the molecular pathway of PD-1. For example, a PD-1 inhibitor can be an antibody that binds to the PD-1 to block ligand binding to PD-1 (e.g., an anti-PD-1 antibody, nivolumab, and pembrolizumab). A PD-1 inhibitor can also be an antibody that binds to PD-L1 or PD-L2, each of which is a ligand of PD-1, to prevent it from binding to PD-1 (e.g., an anti-PD-L1 antibody (e.g., BMS-936559 and MPDL3280A) and an anti-PD-L2 antibody (see, e.g., Patent Application Publication No.: WO 2010036959 (see, e.g., p. 79, ¶ [0253] through p. 101, ¶ [0296]))).

Examples of anti-PD-1 antibodies include nivolumab, pembrolizumab, as well as antibodies described in the following Patent and Patent Application Publication Nos.: WO 2013173223 (see, e.g., p. 3, lines 19-21, p. 8, line 25 through p. 9, line 30, p. 40, line 9 through p. 50, line 24), U.S. Pat. No. 8,008,449 (see, e.g., column 69, Table 2, column 63, line 55 through column 86, line 15), U.S. Pat. No. 8,552,154 (see, e.g., column 67, Table 4, column 57, line 35 through column 74, line 43), U.S. Pat. No. 8,735,553 (see, e.g., column 35, Table 22, column 31, Table 20, column 13, line 9 through column 36, line 62), WO 2004056875 (see, e.g., p. 37, Table 6, p. 33, ¶ [0106] through p. 43, ¶ [0137]), U.S. Pat. No. 7,488,802 (see, e.g., column 22, Tables 6 and 7, column 19, line 62 through column 25, line 4), US 20140294852 (see, e.g., p. 37, Table 2, p. 34, ¶ [0525] through p. 40, [0585]), U.S. Pat. No. 8,779,105 (see, e.g., column 69, Table 2, column 63, line 55 through column 86, line 11), U.S. Pat. No. 8,741,295 (see, e.g., column 18, line 1 through column 24, line 60), EP 2535354 (see, e.g., p. 23, Table IV, p. 23, line 1 through p. 28, line 35), U.S. Pat. No. 8,168,757 (see, e.g., column 34, line 36 through column 48, line 2), US 20130095098 (see, e.g., p. 12, ¶ [0165] through p. 14, ¶ [0188]), WO 2010029435 (see, e.g., p. 14, Example 1, p. 17, Example 2, pp. 26-28), WO 2014100079 (see, e.g., p. 39, ¶ [00155] through p. 45, ¶ [00174]), U.S. Pat. No. 7,943,743 (see, e.g., column 67, Tables 2 and 3, column 61, line 7 through column 74, line 51), EP 2170959 (see, e.g., p. 26, Table V, p. 16, line 39 through p. 28, line 2), WO 2008156712 (see, e.g., p. 56, Table V, pp. 40-57), and U.S. Pat. No. 8,217,149 (see, e.g., column 99, line 6 through column 118, line 15), each of which is incorporated herein by reference in its entirety. In certain embodiments, the anti-PD-1 antibody has the sequence of nivolumab (see, e.g., FIGS. 4a, 4b, and 9 of Patent No.: U.S. Pat. No. 8,008,449) or pembrolizumab (see, e.g., Patent Application Publication No.: US 2011/0008369). Anti-PD-1 antibodies as described herein specifically exclude CureTech's anti-PD-1 antibody CT-011 as described in Patent and Patent Publication Nos.: U.S. Pat. No. 8,686,119, WO 2013014668, and WO 2009101611.

Examples of anti-PD-L1 antibodies include BMS-936559, MPDL3280A, as well as antibodies described in the following Patent and Patent Application Publication Nos.: U.S. Pat. No. 8,552,154 (see, e.g., column 57, line 35 through column 69, line 16), WO 2014055897 (see, e.g., p. 50, ¶ [00190] through p. 58, ¶ [00219]), WO 2013079174 (see, e.g., p. 48, line 15 through p. 68, line 31), U.S. Pat. No. 8,217,149 (see, e.g., column 99, line 5 through column 118, line 15), U.S. Pat. No. 7,943,743 (see, e.g., column 61, line 9 through column 76, line 45), WO 2014100079 (see, e.g., p. 39, ¶ [00155] through p. 45, ¶ [00175]), U.S. Pat. No. 8,552,154 (see, e.g., column 57, line 35 through column 75, line 13), and U.S. Pat. No. 8,741,295 (see, e.g., column 18, line 32 through column 24, line 60), each of which is incorporated herein by reference in its entirety.

Examples of anti-CD40 antibodies include antibodies described in the following Patent and Patent Application Publication Nos.: US 20030059427 (see, e.g., p. 15, ¶ [0157] through p. 20, ¶ [0212]), WO 2013034904 (see, e.g., p. 58, line 4 through p. 102, line 20), WO 2003029296 (see, e.g., p. 30, line 20 through p. 34, line 16), U.S. Pat. No. 8,637,032 (see, e.g., column 252, line 55 through column 254, line 37), WO 2002028905 (see, e.g., p. 20, line 18 through p. 32, line 30), U.S. Pat. No. 8,778,345 (see, e.g., column 48, line 31 through column 54, line 38), WO 1997031025 (see, e.g., p. 14, line 6 through p. 31, line 26), WO 2012125569 (see, e.g., p. 25, line 33 through p. 27, line 14), WO 2011123489 (see, e.g., p. 93, ¶ [00339] through p. 109, ¶ [00145]), CA 2544949 (see, e.g., p. 78, line 26 through p. 122, line 21), WO 2014070934 (see, e.g., p. 86, line 4 through p. 103, line 4), US 20140093497 (see, e.g., p. 12, ¶ [0112] through p. 13, ¶ [0118]), WO 2010104761 (see, e.g., p. 37, line 3 through p. 66, line 29), U.S. Pat. No. 8,591,900 (see, e.g., column 60, line 14 through column 80, line 29), WO 2007124299 (see, e.g., 68, line 29 through p. p. 88, line 17), U.S. Pat. No. 7,445,780 (see, e.g., column 22, line 29 through column 36, line 39), WO 2006073443 (see, e.g., p. 82, line 6 through p. 89, line 12), WO 2005044294 (see, e.g., p. 137, line 19 through p. 158, line 15), U.S. Pat. No. 5,677,165 (see, e.g., column 11, line 45 through column 18, line 6), WO 2001083755 (see, e.g., p. 39, line 4 through p. 47, line 2), US 20080057070 (see, e.g., p. 26, ¶ [0176] through p. 47, ¶ [0296]), U.S. Pat. No. 7,172,759 (see, e.g., column 9, line 5 through column 12, line 58), WO 2006128103 (see, e.g., p. 75, ¶ [00244] through p. 84, ¶ [000255]), WO 2001016180 (see, e.g., p. 79, line 21 through p. 89, line 14), WO 2003040170 (see, e.g., p. 76, ¶ [0248] through p. 141, ¶ [0239]), U.S. Pat. No. 6,312,693 (see, e.g., column 8, line 51 through column 34, line 45), U.S. Pat. No. 8,492,531 (see, e.g., column 47, line 46 through column 58, line 31), U.S. Pat. No. 8,551,485 (see, e.g., column 78, line 15 through column 85, line 7), U.S. Pat. No. 6,838,261 (see, e.g., column 26, line 10 through column 34, line 26), EP 2243492 (see, e.g., p. 26, ¶ [0144] through p. 37, ¶ [0219]), and EP 2011802 (see, e.g., p. 12, ¶ [0047] through p. 40, ¶ [0127]), each of which is incorporated herein by reference in its entirety.

Examples of anti-CD40 antibodies include antibodies described in the following Patent and Patent Application Publication Nos.: US 20030059427 (see, e.g., p. 15, ¶ [0157] through p. 20, ¶ [0212]), WO 2013034904 (see, e.g., p. 58, line 4 through p. 102, line 20), WO 2003029296 (see, e.g., p. 30, line 20 through p. 34, line 16), U.S. Pat. No. 8,637,032 (see, e.g., column 252, line 55 through column 254, line 37), WO 2002028905 (see, e.g., p. 20, line 18 through p. 32, line 30), U.S. Pat. No. 8,778,345 (see, e.g., column 48, line 31 through column 54, line 38), WO 1997031025 (see, e.g., p. 14, line 6 through p. 31, line 26), WO 2012125569 (see, e.g., p. 25, line 33 through p. 27, line 14), WO 2011123489 (see, e.g., p. 93, ¶ [00339] through p. 109, ¶ [00145]), CA 2544949 (see, e.g., p. 78, line 26 through p. 122, line 21), WO 2014070934 (see, e.g., p. 86, line 4 through p. 103, line 4), US 20140093497 (see, e.g., p. 12, ¶ [0112] through p. 13, ¶ [0118]), WO 2010104761 (see, e.g., p. 37, line 3 through p. 66, line 29), U.S. Pat. No. 8,591,900 (see, e.g., column 60, line 14 through column 80, line 29), WO 2007124299 (see, e.g., 68, line 29 through p. p. 88, line 17), U.S. Pat. No. 7,445,780 (see, e.g., column 22, line 29 through column 36, line 39), WO 2006073443 (see, e.g., p. 82, line 6 through p. 89, line 12), WO 2005044294 (see, e.g., p. 137, line 19 through p. 158, line 15), U.S. Pat. No. 5,677,165 (see, e.g., column 11, line 45 through column 18, line 6), WO 2001083755 (see, e.g., p. 39, line 4 through p. 47, line 2), US 20080057070 (see, e.g., p. 26, ¶ [0176] through p. 47, ¶ [0296]), U.S. Pat. No. 7,172,759 (see, e.g., column 9, line 5 through column 12, line 58), WO 2006128103 (see, e.g., p. 75, ¶ [00244] through p. 84, ¶ [000255]), WO 2001016180 (see, e.g., p. 79, line 21 through p. 89, line 14), WO 2003040170 (see, e.g., p. 76, ¶ [0248] through p. 141, ¶ [0239]), U.S. Pat. No. 6,312,693 (see, e.g., column 8, line 51 through column 34, line 45), U.S. Pat. No. 8,492,531 (see, e.g., column 47, line 46 through column 58, line 31), U.S.

Pat. No. 8,551,485 (see, e.g., column 78, line 15 through column 85, line 7), U.S. Pat. No. 6,838,261 (see, e.g., column 26, line 10 through column 34, line 26), EP 2243492 (see, e.g., p. 26, ¶ [0144] through p. 37, ¶ [0219]), and EP 2011802 (see, e.g., p. 12, ¶ [0047] through p. 40, ¶ [0127]), each of which is incorporated herein by reference in its entirety. Examples of anti-CTLA-4 antibodies include ipilimumab (see, e.g., Patent No.: U.S. Pat. No. 6,682,736 (see, e.g., column 34, line 40 through colum 48, line 6)) and antibodies described in the following Patent and Patent Application Publication Nos.: WO 2012120125 (see, e.g., p. 13, line 1 through p. 27, line 18), U.S. Pat. No. 8,017,114 (see, e.g., column 46, line 40 through column 74, line 12), WO 2001014424 (see, e.g., p. 65, line 21 through p. 96, line 15), and WO 2000037504 (see, e.g., p. 56, line 25 through p. 86, line 31), each of which is incorporated herein by reference in its entirety.

Immunoinhibitors

As used herein, an immunoinhibitor is an agent that inhibits an immune response in a subject to whom it is administered, whether alone or in combination with another agent. Examples include steroids, retinoic acid, dexamethasone, cyclophosphamide, anti-CD3 antibody or antibody fragment, and other immunosuppressants. Examples include immunoinhibitory antibodies (e.g., anti-CD3 antibody, or single chain/antibody fragments of this molecule), steroids, retinoic acid, dexamethasone, cyclophosphamide (CPM) (such as those described in the Patent Nos.: U.S. Pat. No. 4,537,883 (see, e.g., column 9, line 62 through column 13, line 6), U.S. Pat. No. 3,808,297 (see, e.g., column 7, line 5 through colunn 9, line 75), and U.S. Pat. No. 5,036,060 (see, e.g., column 5, line 60 through column 14, line 19), each of which is incorporate herein by reference in its entirety), and other immunosuppressants.

Other immunomodulators include cell-surface makers and antibodies that target cell-surface makers. Examples of immunomodulators such as cell-surface makers and antibodies that target cell-surface makers include anti-LAG-3/CD223 antibodies (such as C9B7W (UniProt ID No. P18627) and those described in the Patent and Patent Application Publication Nos.: WO 2010019570 (see, p. 73, line 4 through e.g., p. 97, line 10), WO 2014008218 (see, e.g., p. 57, line 20 through p. 65, line 17), and WO 2008132601 (see, e.g., p. 15, line 13 through p. 28, line 17)), anti-VISTA/PD-L3 antibodies (such as those described in the Patent and Patent Application Publication Nos.: US 20140105912 (see, e.g., p. 71, ¶ [0601] through p. 87, ¶ [0755]), U.S. Pat. No. 8,236,304 (see, e.g., column 17, line 7 through column 18, line 48), and US 20110027278 (see, e.g., p. 39, ¶ [0302] through p. 43, ¶ [0333])), anti-B7-H5 antibodies (such as those described in the Patent Application Publication No.: US 20080248007 (see, e.g., p. 9, ¶ [0087] through p. 10, ¶ [0094])), anti-OX40 antibodies (such as those described in the Patent Application Publication No.: WO 2013130102 (see, e.g., p. 31, ¶ [0101] through p. 41, ¶ [0124])), anti-CD28 antibodies (such as those described in the Patent Application Publication No.: EP0440373 (see, e.g., p. 4, line 45 through p. 8, line 37)), anti-GITR antibodies (such as those described in the Patent and Patent Application Publication Nos.: WO 2007133822 (see, e.g., p. 48, line 16 through p. 52, line 18), WO 2009009116 (see, e.g., p. 52, line 30 through p. 56, line 6), WO 2004107618 (see, e.g., p. 78, ¶ [0199] through p. 105, ¶ [0261]), WO 2006105021 (see, e.g., p. 70, line 21 through p. 80, line 31), U.S. Pat. No. 7,812,135 (see, e.g., column 55, line 52 through column 66, line 38), and U.S. Pat. No. 8,591,886 (see, e.g., column 41, line 15 through column 44, line 20)), anti-4-1 BB/CD137 antibodies (such as those described in the Patent No: U.S. Pat. No. 8,716,452 (see, e.g., column 13, line 55 through column 20, line 62)), 4-1BB ligands (such as those described in the Patent Application Publication Nos.: WO 1994026290 (see, e.g., 21, line 23 through p. 32, line 33), US 20060110802 (see, e.g., p. 9, ¶ [0098] through p. 16, ¶ [0167]), WO 1999036093 (see, e.g., p. 18, line 5 through p. 56, line 17), WO 2010132389 (see, e.g., p. 30, ¶ [00134] through p. 41, ¶ [00166]), WO 2012145183 (see, e.g., p. 43, line 26 through p. 64, line 12), US 20080008716 (see, e.g., p. 3, ¶ [0042] through p. 7, ¶ [0070]), WO 2004010947 (see, e.g., p. 13, line 12 through p. 23, line 19), and US 20070286860 (see, e.g., p. 27, ¶ [0172] through p. 31, ¶ [200])), anti-BTLA antibodies (such as those described in the Patent and Patent Application Publication Nos.: WO 2010106051 (see, e.g., p. 35, line through p. 35, line 8), WO 2008076560 (see, e.g., p. 85, line 2 through p. 97, line 11), U.S. Pat. No. 8,349,320 (see, e.g., column 47, line 62 through column 72, line 26), and U.S. Pat. No. 8,563,694 (see, e.g., column 56, line 25 through column 65, line 45)), anti-TIM-3/HAVCR2 antibodies (such as those described in the Patent and Patent Application Publication Nos.: U.S. Pat. No. 8,841,418 (see, e.g., column 36, line 45 through column 46, line 47), EP 2417984 (see, e.g., p. 19, ¶ [0137] through p. 28, ¶ [0206]), WO 2014022332 (see, e.g., p. 51, ¶ [00191] through p. 54, ¶ [00202]), and U.S. Pat. No. 8,697,069 (see, e.g., p. 40, line 26 through p. 50, line 37)), anti-KIR antibodies (such as those described in the Patent and Patent Application Publication Nos.: WO 2014066532 (see, e.g., p. 25, line 30 through p. 57, line 17), EP 2446897 (see, e.g., p. 45, ¶ [0294] through p. 47, ¶ [0309]), WO 2014055648 (see, e.g., pp. 24-49), and US 20140302052 (see, e.g., p. 2, ¶ [0021] through p. 4, ¶ [0044])), anti-Flt3/CD135 antibodies (such as those described in the Patent and Patent Application Publication Nos.: U.S. Pat. No. 6,291,661 (see, e.g., column 23, line 36 through column 38, line 23), EP 0754230 (see, e.g., p. 13, ¶ [0099] through p. 20, ¶ [0138]), EP 0992584 (see, e.g., p. 25, line 28 through p. 30, line 45), and WO 2011076922 (see, e.g., p. 95, ¶ [000269] through p. 82, ¶ [000233])), anti-FasL antibodies (such as those described in the Patent and Patent Application Publication Nos.: US 20100266577 (see, e.g., p. 7, ¶ [0089] through p. 10, ¶ [0122]), US 20070142456 (see, e.g., p. 6, ¶ [0054] through p. 8, ¶ [0066]), WO 2011066211 (see, e.g., pp. 38-97), US 20020187534 (see, e.g., p. 5, ¶ [0061] through p. 10, ¶ [0112]), WO 1999036079 (see, e.g., p. 53, line 15 through p. 60, line 19), and WO 1997033617 (see, e.g., p. 18, line 1 through p. 25, line 17)), and anti-CD25 antibodies (such as those described in the Patent and Patent Application Publication Nos.: WO 2006108670 (see, e.g., pp. 4-8), U.S. Pat. No. 8,182,812 (see, e.g., column 43, line 6 through column 54, line 15), and CA 2585776 (see, e.g., p. 31, ¶ [00100] through p. 52, ¶ [00163])).

Other immunomodulators include cytokines or antibodies that target cytokine receptors. Examples of immunomodulators such as cytokines and antibodies that target cytokine receptors include GM-CSF (such as those described in the Patent and Patent Application Publication Nos.: WO 2013074489 (see, e.g., p. 52, line 29 through p. 61, line 26), U.S. Pat. No. 5,891,429 (see, e.g., column 12, line 1 through column 28, line 21), and WO 1989010403 (see, e.g., p. 5, line 35 through p. 13, line 21)), anti-GM-CSF-receptor (R) antibodies (such as those described in the Patent and Patent Application Publication Nos.: WO 1994011404 (see, e.g., pp. 9-28), U.S. Pat. No. 8,263,075 (see, e.g., column 29, line 25 through column 49, line 26), and U.S. Pat. No. 5,932,704 (see, e.g., column 2, line 55 through column 12, line 67)), IL-2 (such as those described in the Patent and Patent Application Publication Nos.: WO 2013130102 (see, e.g., p. 31, ¶ [0101] through p. 41, ¶ [0124]), U.S. Pat. No. 8,349,311 (see, e.g., column 21, line 31 through column 31, line 9), WO 2005007121 (see, e.g., p. 30, line 29 through p. 43, line 31), and WO 1991002000 (see, e.g., pp. 2-7)), anti-IL-2-R antibodies (such as those described in the Patent Application Publication No.: WO 1989009622 (see, e.g., p. 18, line 4 through p. 33, line 12)), IL-7 (such as those described in the Patent and Patent Application Publication Nos.: WO 2012031115 (see, e.g., p. 77, ¶ [00240] through p. 102, ¶ [00347]), WO 2013074489 (see, e.g., p. 52, line 30 through p. 61, line 26), U.S. Pat. No. 7,323,549 (see, e.g., column 12, line 14 through column 24, line 37), and U.S. Pat. No. 8,338,575 (see, e.g., column 11, line 60 through column 24, line 18)), anti-IL-7-R antibodies, IL-21 (as those described in the Patent Application Publication No.: WO 2013169693 (see, e.g., p. 44, line 3 through p. 73, line 15)), anti-IL-21-R antibodies, IL-12 (as those described in the Patent No.: U.S. Pat. No. 8,765,462 (see, e.g., column 27, line 15 through column 50, line 16)), anti-IL-12-R antibodies, IL-15, anti-IL-15-R antibodies, IL-18, anti-IL-8-R antibodies, and anti-IDO antibodies.

Yet other immunomodulators include kinase inhibitors such as crizotinib (see, e.g., Patent Application Publication No.: WO 2013017989 (see, e.g., pp. 54-69)), ceritinib (see, e.g., Patent Application Publication Nos.: WO 2012082972 (see, e.g., p. 11, line 6 through p. 14, line 17) and WO 2008073687 (see, e.g., p. 34, ¶ [0089] through p. 144, ¶ [0151])), alectinib, and brigatinib, COX-2 inhibitors such as celecoxib (such as those described in the Patent and Patent Application Publication Nos.: WO 2000032189 (see, e.g., p. 38, line 17 through p. 61, line 20), U.S. Pat. No. 6,127,545 (see, e.g., column 7, line 30 through column 17, line 67), WO 2002028270 (see, e.g., p. 37, line 27 through p. 45, line 28), U.S. Pat. No. 6,403,630 (see, e.g., column 16, line 29 through column 17, line 7), and U.S. Pat. No. 5,972,986 (see, e.g., column 5, line 9 through column 16, line 44)), SOCS-1 inhibitors (e.g., P13K or Jak inhibitors), heat shock proteins (HSP) (such as those described in the Patent and Patent Application Publication Nos.: U.S. Pat. No. 7,678,803 (see, e.g., column 79, line 20 through column 158, line 55), U.S. Pat. No. 7,608,635 (see, e.g., column 93, line 55 through column 108, line 40), U.S. Pat. No. 8,318,790 (see, e.g., column 158, line 51 through column 196, line 20), and US 20130184336 (see, e.g., p. 5, ¶ [0075] through p. 6, ¶ [0093])), HSP inhibitors (such as those described in the Patent No.: U.S. Pat. No. 7,776,849 (see, e.g., column 32, line 47 through column 50, line 67)), and anti-galectin-1 antibodies (such as those described in the Patent Application Publication Nos.: WO 2012131079 (see, e.g., pp. 24-35), WO 2014070214 (see, e.g., p. 42, line 15 through p. 53, line 13), and WO 2014043708 (see, e.g., p. 27, ¶ [00140] through p. 36, ¶ [00199])).

The disclosures of the aforementioned Patent and Patent Application Publication Nos. are incorporated herein by reference in their entireties.

Adjuvants

In some embodiments, an immunogenic composition described herein may include one or more adjuvants. An adjuvant refers to a substance that causes stimulation of the immune system. In this context, an adjuvant is used to enhance an immune response to one or more antigens (e.g., an ALK polypeptide). An adjuvant may be administered to a subject before, in combination with, or after administration of the antigens (e.g., an ALK polypeptide). In some embodiments, an adjuvant may be conjugated to a lipid in the ICMV.

The adjuvant may be without limitation a lipid (e.g., monophosphoryl lipid A (MPLA)), alum (e.g., aluminum hydroxide, aluminum phosphate); Freund's adjuvant; saponins purified from the bark of the *Q. saponaria* tree such as QS21 (a glycolipid that elutes in the 21st peak with HPLC fractionation; Antigenics, Inc., Worcester, Mass.); poly[di (carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS1312, water-based nanoparticles combined with a soluble immunostimulant, Seppic), and CDNs (cyclic di-nucleotides).

Adjuvants may be toll-like receptor (TLR) ligands. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

Anti-Cancer Agents

In some embodiments, an immunogenic composition described herein may include one or more anti-cancer agents. An anti-cancer agent is an agent that at least partially inhibits the development or progression of a cancer, including inhibiting in whole or in part symptoms associated with the cancer even if only for the short term. Several anti-cancer agents can be categorized as DNA damaging agents and these include topoisomerase inhibitors (e.g., etoposide, ramptothecin, topotecan, teniposide, mitoxantrone), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), anthracyclines, vinca alkaloids, or epipodophyllotoxins.

Examples of anti-cancer agents include without limitation Acivicin; Aclarubicin; Acodazole Hydrochloride; Acronine;

Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE); Brequinar Sodium; Bropirimine; Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE); Doxorubicin; Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA), Esorubicin; Estramustine; Etanidazole; Etoposide; Etoprine; Fadrozole; Fazarabine; Fenretinide; Floxuridine; Fludarabine; 5-Fluorouracil; Fluorocitabine; Fosquidone; Fostriecin; Gefitinib (IRESSA), Gemcitabine; Hydroxyurea; Idarubicin; Ifosfamide; Ilmofosine; Imatinib mesylate (GLEEVAC); Interferon alpha-2a; Interferon alpha-2b; Interferon alpha-n1; Interferon alpha-n3; Interferon beta-I a; Interferon gamma-I b; Iproplatin; Irinotecan; Lanreotide; Lenalidomide (REVLIMID, REVIMID); Letrozole; Leuprolide; Liarozole; Lometerxol; Lomustine; Losoxantrone; Masoprocol; Maytansine; Mechlorethamine; Megestrol; Melengestrol; Melphalan; Menogaril; Mercaptopurine; Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemeterxed (ALIMTA), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR); Teniposide; Teroxirone; Testolactone; Thalidomide (THALOMID) and derivatives thereof; Thiamiprine; Thioguanine; Thiotepa; Tiazofurin; Tirapazamine; Topotecan; Toremifene; Trestolone; Triciribine; Trimeterxate; Triptorelin; Tubulozole; Uracil Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

The anti-cancer agent may be an enzyme inhibitor including without limitation a tyrosine kinase inhibitor, a cyclin-dependent kinase (CDK) inhibitor, a mitogen-activated protein (MAP) kinase inhibitor, or an epidermal growth factor receptor (EGFR) inhibitor. The tyrosine kinase inhibitor may be without limitation Genistein (4',5,7-trihydroxyisoflavone), Tyrphostin 25 (3,4,5-trihydroxyphenyl), methylene]-propanedinitrile, Herbimycin A, Daidzein (4',7-dihydroxyisoflavone), AG-126, trans-1-(3'-carboxy-4'-hydroxyphenyl)-2-(2",5"-dihydroxy-phenyl)ethane, or HDBA (2-Hydroxy-5-(2,5-Dihydroxybenzylamino)-2-hydroxybenzoic acid. The CDK inhibitor may be without limitation p21, p27, p57, p15, p16, p18, or p19. The MAP kinase inhibitor may be without limitation KY12420 (C.sub.23H.sub.240.sub.8), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA), gefitinib (IRESSA), WH1-P97 (quinazoline derivative), LFM-Al2 (leflunomide metabolite analog), ABX-EGF, lapatinib, canertinib, ZD-6474 (ZACTIMA), AEE788, and AG1458.

The anti-cancer agent may be a vascular endothelial growth factor (VEGF) inhibitor including without limitation bevacizumab (AVASTIN), ranibizumab (LUCENTIS), pegaptanib (MACUGEN), sorafenib, sunitinib (SUTENT), vatalanib, ZD-6474 (ZACTIMA), anecortave (RETAANE), squalamine lactate, and semaphorin.

The anti-cancer agent may be an antibody or an antibody fragment including without limitation an antibody or an antibody fragment including but not limited to bevacizumab (AVASTIN), trastuzumab (HERCEPTIN), alemtuzumab (CAMPATH, indicated for B cell chronic lymphocytic leukemia), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), IOR-05, IOR-T6 (anti-CD1), IOR EGF/R3, celogovab (ONCOSCINT OV103), epratuzumab (LYMPHOCIDE), pemtumomab (THERAGYN), and Gliomab-H (indicated for brain cancer, melanoma).

Methods of Constructing a Library of ALK Polypeptides

Figure 2A:
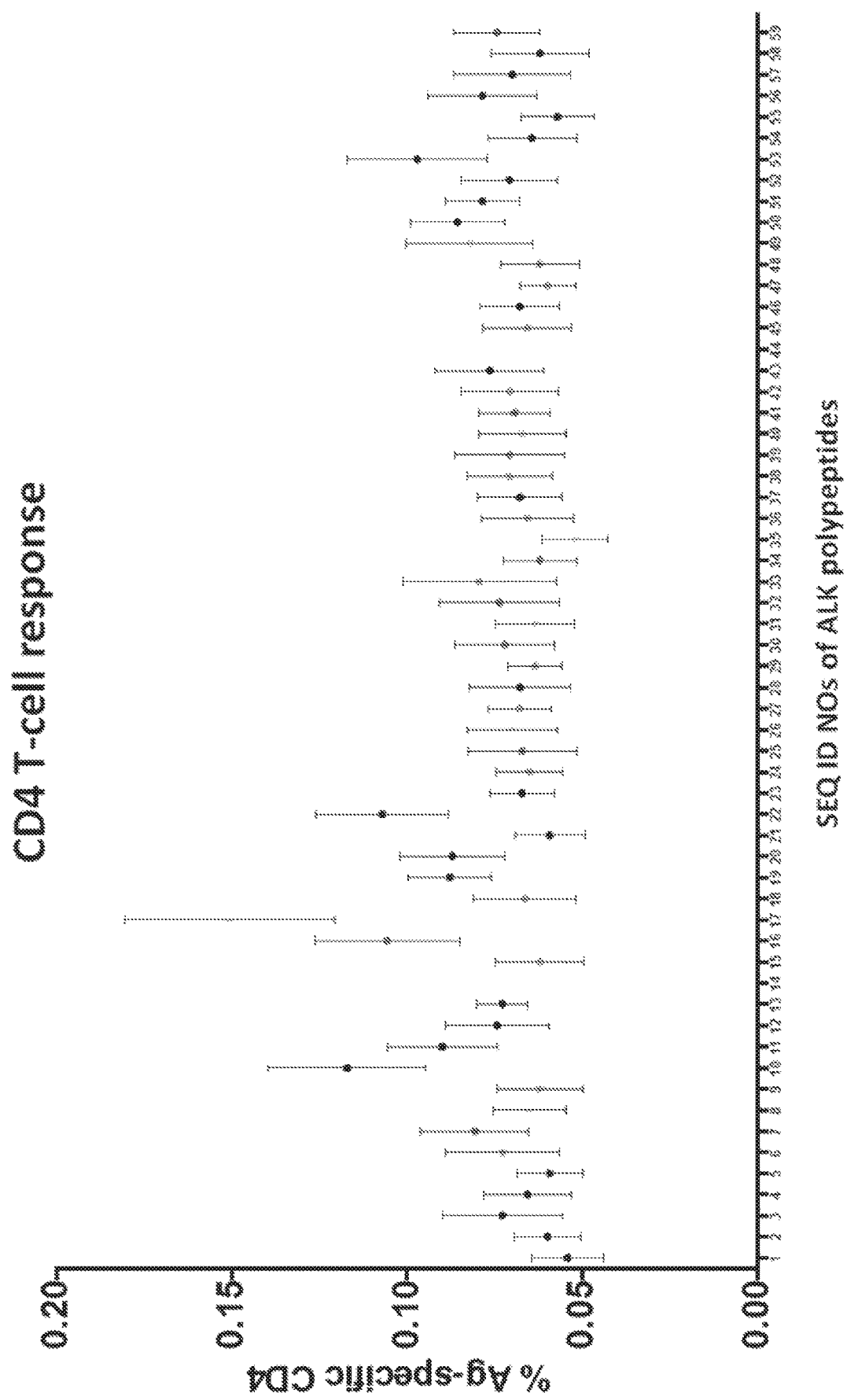
FIGS. 2A and 2B show the CD4 T-cell response stimulated by ALK polypeptides each having the sequence of any one of SEQ ID NOs: 1-59 listed in Table 1A.
Figure 2B:
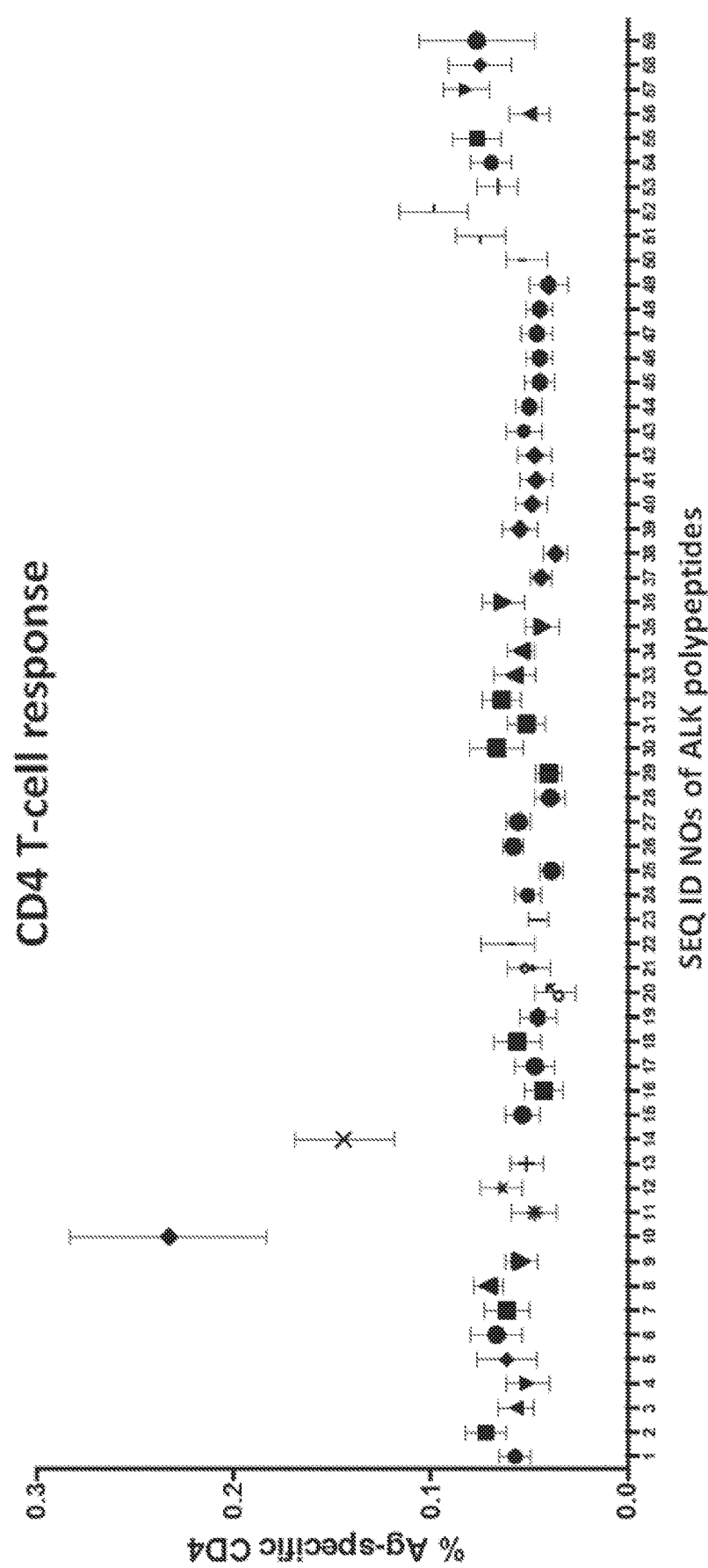
Figure 2D:
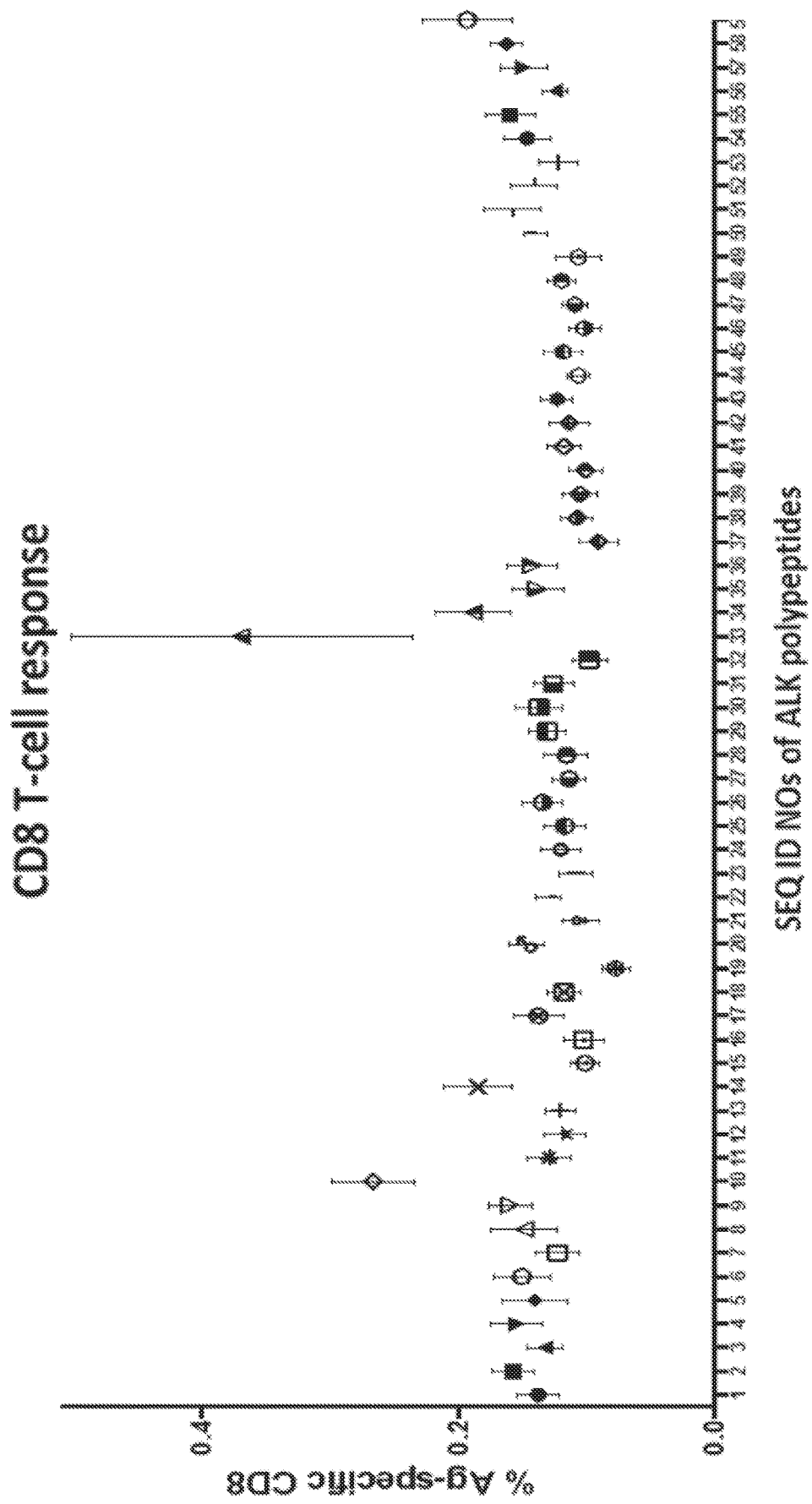

A library of ALK polypeptides may be constructed in a random or semi-random fashion. For example, ALK polypeptides each having 15 amino acids (e.g., SEQ ID NOs: 1-58) may be constructed from the sequence of any one of SEQ ID NOs: 67-70 (e.g., SEQ ID NO: 70). The 15-mer ALK polypeptides (e.g., SEQ ID NOs: 1-58) overlap each other by 10 amino acids. After initial screening of the 15-mer ALK polypeptides, ALK polypeptides that demonstrate desirable immunogenic properties may be selected for further screening. For example, intracellular cytokine staining (ICS) results in FIGS. 2A and 2B show that the strongest CD4 T-cell responses were found in cells re-stimulated with ALK polypeptides having the sequences of SEQ ID NOs: 10, 14, 17, 22, 52, and 53, and ICS results in FIGS. 2C and 2D show that the strongest CD8 T-cell response was found in cells re-stimulated with ALK polypeptide having the sequence of SEQ ID NOs: 10, 14, and 33. Thus, ALK polypeptides having sequences of SEQ ID NOs: 10, 14, 17, 22, 33, 52, and 53 may be further tested. Other ALK polypeptides may be constructed from ALK polypeptides having sequences of SEQ ID NOs: 10, 14, 17, 22, 33, 52, and 53. For example, 9-mer ALK polypeptides may be constructed from the sequence of any one of SEQ ID NOs: 10, 14, 17, 22, 33, 52, and 53. ALK polypeptides each having 9 amino acids (e.g., SEQ ID NOs: 60-66) are constructed from the sequence of SEQ ID NO: 33. The 9-mer ALK polypeptides having sequences of SEQ ID NOs: 60-66 overlap each other by one amino acid and cover the entire sequence of SEQ ID NO: 33.

In another example, ALK polypeptides each having 31 amino acids (e.g., SEQ ID NOs: 93-121) may be constructed from the sequence of any one of SEQ ID NOs: 67-70 (e.g., SEQ ID NO: 70). The 31-mer ALK polypeptides (e.g., SEQ ID NOs: 93-121) overlap each other by 12 amino acids.

In some embodiments, a Cys in an ALK polypeptide described herein (e.g., any one of the ALK polypeptides in Tables 1 A and 1B) may be replaced by an Ala. In some embodiments, a Cys in an ALK polypeptide of any one of SEQ ID NOs: 94, 95, 97-99, 101-105, 107-110, and 117-120 may be replaced with an Ala, generating the ALK polypeptides of SEQ ID NOs:122-139 in Table 10.

A library of ALK polypeptides may also be constructed using computer-aided design. Computer programs that help to design polypeptides are available in the art and are described in, e.g., U.S. Pat. Nos. 8,575,070 and 8,275,595, US Patent Publication No. 2015/0205911, and International Patent Publication No.

WO 2001047541. Computer programs may combine methods used in biological sequence analysis and bioinformatics data mining. In some embodiments, computer programs may scan ALK polypeptides and identify the motifs or specific amino acids that may be important in conferring the immunogenic properties of potentially active ALK polypeptides. In some embodiments, computer programs may select and combine certain fragments from individual ALK polypeptides and construct new ALK polypeptides based on the most active ALK polypeptides. Examples of computer programs that may be used to construct a library of ALK polypeptides include, but are not limited to, Rosetta and Panorama.

Depending on how much is known about the immunogenic property of the potentially active ALK polypeptides, certain residues in the library may be kept constant, while other positions varied. For example, if certain properties of the ALK polypeptides are known (e.g., having a positively charged amino acid, such as lysine or arginine at or near a particular position), the variable positions can be built around the pre-determined residue position.

In some embodiments, one or more amino acid substitutions in an ALK polypeptide may improve its immunogenic property. In some embodiments, an amino acid in a wild-type ALK may be replaced by a different amino acid (e.g., a naturally occurring amino acid (e.g., Ala, Arg, Asn, Asp, Cys, Gln, Glu, Gly, His, Ile, Leu, Lys, Met, Phe, Pro, Ser, Thr, Trp, Tyr, or Val) or a non-naturally occurring amino acid). In some embodiments, a Cys in an ALK polypeptide described herein (e.g., any one of the ALK polypeptides in Tables 1 A and 1B) may be replaced by an Ala. A "non-naturally occurring amino acid" is an amino acid which is not naturally produced or found in a mammal. Examples of non-naturally occurring amino acids include D-amino acids; an amino acid having an acetylaminomethyl group attached to a sulfur atom of a cysteine; a pegylated amino acid; the omega amino acids of the formula $NH_2(CH_2)_n COOH$ where n is 2-6, neutral nonpolar amino acids, such as sarcosine, t-butyl alanine, t-butyl glycine, N-methyl isoleucine, and norleucine; oxymethionine; phenylglycine; citrulline; methionine sulfoxide; cysteic acid; ornithine; diaminobutyric acid; diaminopropionic acid; and hydroxyproline. Other amino acids are α-aminobutyric acid, α-amino-α-methylbutyrate, am inocyclopropane-carboxylate, aminoisobutyric acid, aminonorbornyl-carboxylate, L-cyclohexylalanine, cyclopentylalanine, L-N-methylleucine, L-N-methylmethionine, L-N-methylnorvaline, L-N-methylphenylalanine, L-N-methylproline, L-N-methylserine, L-N-methyltryptophan, D-ornithine, L-N-methylethylglycine, L-norleucine, α-methyl-aminoisobutyrate, α-methylcyclohexylalanine, D-α-methylalanine, D-α-methylarginine, D-α-methylasparagine, D-α-methylaspartate, D-α-methylcysteine, D-α-methylglutamine, D-α-methylhistidine, D-α-methylisoleucine, D-α-methylleucine, D-α-methyllysine, D-α-methylmethionine, D-α-methylornithine, D-α-methylphenylalanine, D-α-methylproline, D-α-methylserine, D-N-methylserine, D-α-methylthreonine, D-α-methyltryptophan, D-α-methyltyrosine, D-α-methylvaline, D-N-methylalanine, D-N-methylarginine, D-N-methylasparagine, D-N-methylaspartate, D-N-methylcysteine, D-N-methylglutamine, D-N-methylglutamate, D-N-methylhistidine, D-N-methylisoleucine, D-N-methylleucine, D-N-methyllysine, N-methylcyclohexylalanine, D-N-methylornithine, N-methylglycine, N-methylaminoisobutyrate, N-(1-methylpropyl) glycine, N-(2-methylpropyl)glycine, D-N-methyltryptophan, D-N-methyltyrosine, D-N-methylvaline, γ-aminobutyric acid, L-t-butylglycine, L-ethylglycine, L-homophenylalanine, L-α-methylarginine, L-α-methylaspartate, L-α-methylcysteine, L-α-methylglutamine, L-α-methylhistidine, L-α-methylisoleucine, L-α-methylleucine, L-α-methylmethionine, L-α-methylnorvaline, L-α-methylphenylalanine, L-α-methylserine, L-α-methyltryptophan, L-α-methylvaline, N—(N-(2,2-diphenylethyl) carbamylmethylglycine, 1-carboxy-1-(2,2-diphenyl-ethylamino) cyclopropane, 4-hydroxyproline, ornithine, 2-aminobenzoyl (anthraniloyl), D-cyclohexylalanine, 4-phenyl-phenylalanine, L-citrulline, α-cyclohexylglycine, L-1,2,3,4-tetrahydroisoquinoline-3-carboxylic acid, L-thiazolidine-4-carboxylic acid, L-homotyrosine, L-2-furylalanine, L-histidine (3-methyl), N-(3-guanidinopropyl)glycine, O-methyl-L-tyrosine, 0-glycan-serine, meta-tyrosine, nor-tyrosine, L-N,N', N"-trimethyllysine, homolysine, norlysine, N-glycan asparagine, 7-hydroxy-1,2,3,4-tetrahydro-4-fluorophenylalanine, 4-methylphenylalanine, bis-(2-picolyl)amine, pentafluorophenylalanine, indoline-2-carboxylic acid, 2-aminobenzoic acid, 3-amino-2-naphthoic acid, asymmetric dimethylarginine, L-tetrahydroisoquinoline-1-carboxylic acid, D-tetrahydroisoquinoline-1-carboxylic acid, 1-aminocyclohexane acetic acid, D/L-allylglycine, 4-aminobenzoic acid, 1-amino-cyclobutane carboxylic acid, 2 or 3 or 4-aminocyclohexane carboxylic acid, 1-amino-1-cyclopentane carboxylic acid, 1-aminoindane-1-carboxylic acid, 4-aminopyrrolidine-2-carboxylic acid, 2-aminotetraline-2-carboxylic acid, azetidine-3-carboxylic acid, 4-benzyl-pyrolidine-2-carboxylic acid, tert-butylglycine, b-(benzothiazolyl-2-yl)-alanine, b-cyclopropyl alanine, 5,5-dimethyl-1,3-thiazolidine-4-carboxylic acid, (2R,4S)-4-hydroxypiperidine-2-carboxylic acid, (2S,4S) and (2S,4R)-4-(2-naphthylmethoxy)-pyrolidine-2-carboxylic acid, (2S, 4S) and (2S,4R)4-phenoxy-pyrrolidine-2-carboxylic acid, (2R,5S) and (2S,5R)-5-phenyl-pyrrolidine-2-carboxylic acid, (2S,4S)-4-amino-1-benzoyl-pyrrolidine-2-carboxylic acid, t-butylalanine, (2S,5R)-5-phenyl-pyrrolidine-2-carboxylic acid, 1-aminomethyl-cyclohexane-acetic acid, 3,5-bis-(2-amino)ethoxy-benzoic acid, 3,5-diamino-benzoic acid, 2-methylamino-benzoic acid, N-methylanthranylic acid, L-N-methylalanine, L-N-methylarginine, L-N-methylasparagine, L-N-methylaspartic acid, L-N-methylcysteine, L-N-methylglutamine, L-N-methylglutamic acid, L-N-methylhistidine, L-N-methylisoleucine, L-N-methyllysine, L-N-methylnorleucine, L-N-methylornithine, L-N-methylthreonine, L-N-methyltyrosine, L-N-methylvaline, L-N-methyl-t-butylglycine, L-norvaline, α-methyl-γ-aminobutyrate, 4,4'-biphenylalanine, α-methylcylcopentylalanine, α-methyl-α-naphthylalanine, α-methylpenicillamine, N-(4-aminobutyl)glycine, N-(2-aminoethyl)glycine, N-(3-aminopropyl)glycine, N-amino-α-methylbutyrate, α-napthylalanine, N-benzylglycine, N-(2-carbamylethyl)glycine, N-(carbamylmethyl)glycine, N-(2-carboxyethyl)glycine, N-(carboxymethyl)glycine, N-cyclobutylglycine, N-cyclodecylglycine, N-cycloheptylglycine, N-cyclohexylglycine, N-cyclodecylglycine, N-cylcododecylglycine, N-cyclooctylglycine, N-cyclopropylglycine, N-cycloundecylglycine, N-(2,2-diphenylethyl)glycine, N-(3,3-diphenylpropyl)glycine, N-(3-guanidinopropyl)glycine, N-(1-hydroxyethyl) glycine, N-(hydroxyethyl))glycine, N-(imidazolylethyl)) glycine, N-(3-indolylyethyl)glycine, N-methyl-γ-aminobutyrate, D-N-methylmethionine, N-methylcyclopentylalanine, D-N-methylphenylalanine, D-N-methylproline, D-N-methylthreonine, N-(1-methylethyl)glycine, N-methyl-napthylalanine, N-methylpenicillamine, N-(p-hydroxyphenyl)glycine, N-(thiomethyl)glycine, penicillamine, L-α-methylalanine, L-α-methylasparagine, L-α-methyl-t-butylglycine, L-methylethylglycine, L-α-methylglutamate, L-α-methylhomophenylalanine, N-(2-methylthioethyl)glycine, L-α-methyllysine, L-α-methylnorleucine, L-α-methylornithine, L-α-methylproline, L-α-methylthreonine, L-α-methyltyrosine, L-N-methyl-homophenylalanine, N—(N-(3,3-diphenylpropyl) carbamylmethylglycine, L-pyroglutamic acid, D-pyroglutamic acid, O-methyl-L-serine, O-methyl-L-homoserine, 5-hydroxylysine, α-carboxyglutamate, phenylglycine, L-pipecolic acid (homoproline), L-homoleucine, L-lysine (dimethyl), L-2-naphthylalanine, L-dimethyldopa or L-dimethoxy-phenylalanine, L-3-pyridylalanine, L-histidine (benzoyloxymethyl), N-cycloheptylglycine, L-diphenylalanine, O-methyl-L-homotyrosine, Lβ-homolysine, O-glycan-threoine, Ortho-tyrosine, L-N,N'-dimethyllysine, L-homoarginine, neotryptophan, 3-benzothienylalanine, isoquinoline-3-carboxylic acid, diaminopropionic acid, homocysteine, 3,4-dimethoxyphenylalanine, 4-chlorophenylalanine, L-1,2,3,4-tetrahydronorharman-3-carboxylic acid, adamantylalanine, symmetrical dimethylarginine, 3-carboxythiomorpholine, D-1,2,3,4-tetrahydronorharman-3-carboxylic acid, 3-aminobenzoic acid, 3-amino-1-carboxymethyl-pyridin-2-one, 1-amino-1-cyclohexane carboxylic acid, 2-aminocyclopentane carboxylic acid, 1-amino-1-cyclopropane carboxylic acid, 2-aminoindane-2-carboxylic acid, 4-amino-tetrahydrothiopyran-4-carboxylic acid, azetidine-2-carboxylic acid, b-(benzothiazol-2-yl)-alanine, neopentylglycine, 2-carboxymethyl piperidine, b-cyclobutyl alanine, allylglycine, diaminopropionic acid, homo-cyclo-hexyl alanine, (2S,4R)-4-hydroxypiperidine-2-carboxylic acid, octahydroindole-2-carboxylic acid, (2S,4R) and (2S, 4R)-4-(2-naphthyl), pyrrolidine-2-carboxylic acid, nipecotic acid, (2S,4R) and (2S,4S)-4-(4-phenylbenzyl) pyrrolidine-2-carboxylic acid, (3S)-1-pyrrolidine-3-carboxylic acid, (2S,4S)-4-tritylmercapto-pyrrolidine-2-carboxylic acid, (2S, 4S)-4-mercaptoproline, t-butylglycine, N,N-bis(3-aminopropyl)glycine, 1-amino-cyclohexane-1-carboxylic acid, N-mercaptoethylglycine, and selenocysteine.

Methods of Producing ALK Polypeptides

ALK polypeptides described herein can be produced from a host cell. A host cell refers to a vehicle that includes the necessary cellular components, e.g., organelles, needed to express the polypeptides and constructs described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, etc). The choice of nucleic acid vectors depends in part on the host cells to be used. Generally, preferred host cells are of either prokaryotic (e.g., bacterial) or eukaryotic (e.g., mammalian) origin. ALK polypeptides described herein can be also produced by the solid phase method of Merrifield (J. Am. Chem. Soc. 85:2149-2154, 1963) or other well-known procedures using conventional automated peptide synthesizers.

Nucleic Acid Vector Construction and Host Cells A polynucleotide sequence encoding the amino acid sequence of an ALK polypeptide described herein may be prepared by a variety of methods known in the art. These methods include, but are not limited to, oligonucleotide-mediated (or site-directed) mutagenesis and PCR mutagenesis. A polynucleotide molecule encoding an ALK polypeptide described herein may be obtained using standard techniques, e.g., gene synthesis. Alternatively, a polynucleotide molecule encoding a wild-type ALK may be mutated to contain specific substitutions using standard techniques in the art, e.g., QuikChange™ mutagenesis. Polynucleotides can be synthesized using nucleotide synthesizer or PCR techniques.

Polynucleotide sequences encoding ALK polypeptides described herein may be inserted into a vector capable of replicating and expressing the polynucleotides in prokaryotic or eukaryotic host cells. Many vectors are available in the art and can be used for the purpose of the invention. Each vector may contain various components that may be adjusted and optimized for compatibility with the particular host cell. For example, the vector components may include, but are not limited to, an origin of replication, a selection marker gene, a promoter, a ribosome binding site, a signal sequence, a polynucleotide sequence encoding an ALK polypeptide described herein, and a transcription termination sequence. In some embodiments, a vector can include internal ribosome entry site (IRES) that allows the expression of multiple ALK polypeptides. Some examples of bacterial expression vectors include, but are not limited to, pGEX series of vectors (e.g., pGEX-2T, pGEX-3X, pGEX-4T, pGEX-5X, pGEX-6P), pET series of vectors (e.g., pET-21, pET-21a, pET-21b, pET-23, pET-24), pACYC series of vectors (e.g., pACYDuet-1), pDEST series of vectors (e.g., pDEST14, pDEST15, pDEST24, pDEST42), and pBR322 and its derivatives (see, e.g., U.S. Pat. No. 5,648,237). Some examples of mammalian expression vectors include, but are not limited to, pCDNA3, pCDNA4, pNICE, pSELECT, and pFLAG-CMV. Other types of nucleic acid vectors include viral vectors for expressing a protein in a cell (e.g., a cell of a subject). Such viral vectors include, but are not limited to, retroviral vectors, adenoviral vectors, poxviral vectors (e.g., vaccinia viral vectors, such as Modified Vaccinia Ankara (MVA)), adeno-associated viral vectors, and alphaviral vectors.

In some embodiments, E. coli cells are used as host cells for the invention. Examples of E. coli strains include, but are not limited to, E. coli 294 (ATCC® 31,446), E. coli A 1776 (ATCC® 31,537, E. coli BL21 (DE3) (ATCC® BAA-1025), and E. coli RV308 (ATCC® 31,608). In other embodiments, mammalian cells are used as host cells for the invention. Examples of mammalian cell types include, but are not limited to, human embryonic kidney (HEK) cells, Chinese hamster ovary (CHO) cells, HeLa cells, PC3 cells, Vero cells, and MC3T3 cells. Different host cells have characteristic and specific mechanisms for the posttranslational processing and modification of protein products. Appropriate cell lines or host systems may be chosen to ensure the correct modification and processing of the protein expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences.

Protein Production, Recovery, and Purification

Host cells used to produce the ALK polypeptides described herein may be grown in media known in the art and suitable for culturing of the selected host cells. Examples of suitable media for bacterial host cells include Luria broth (LB) plus necessary supplements, such as a selection agent, e.g., ampicillin. Examples of suitable media for mammalian host cells include Minimal Essential Medium (MEM), Dulbecco's Modified Eagle's Medium (DMEM), DMEM with supplemented fetal bovine serum (FBS), and RPMI-1640. Host cells are cultured at suitable temperatures, such as from about 20° C. to about 39° C., e.g., from 25° C. to about 37° C. The pH of the medium is generally from about 6.8 to 7.4, e.g., 7.0, depending mainly on the host organism. If an inducible promoter is used in the expression vector of the invention, protein expression is induced under conditions suitable for the activation of the promoter.

Protein recovery typically involves disrupting the host cell, generally by such means as osmotic shock, sonication, or lysis. Once the cells are disrupted, cell debris may be removed by centrifugation or filtration. The proteins may be further purified, for example, by affinity resin chromatography. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin, SDS-PAGE, and gel filtration.

Alternatively, ALK polypeptides described herein can be produced by the cells of a subject (e.g., a human), e.g., in the context of therapy, by administrating a vector (e.g., a retroviral vector, adenoviral vector, poxviral vector (e.g., vaccinia viral vector, such as Modified Vaccinia Ankara (MVA)), adeno-associated viral vector, and alphaviral vector) containing a nucleic acid molecule encoding the ALK polypeptide described herein. The vector, once inside a cell of the subject (e.g., by transformation, transfection, electroporation, calcium phosphate precipitation, direct microinjection, infection, etc) will promote expression of the ALK polypeptide described herein, which is then secreted from the cell.

Pharmaceutical Compositions and Preparations

In some embodiments, pharmaceutical compositions of the invention may contain one or more ALK polypeptides described herein as the therapeutic proteins. In addition to a therapeutic amount of the protein, the pharmaceutical compositions may contain a pharmaceutically acceptable carrier or excipient, which can be formulated by methods known to those skilled in the art. In other embodiments, pharmaceutical compositions of the invention may contain nucleic acid molecules encoding one or more ALK polypeptides described herein (e.g., in a vector, such as a viral vector). The nucleic acid molecule encoding an ALK polypeptide described herein may be cloned into an appropriate expression vector, which may be delivered via well-known methods in gene therapy.

Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. Pharmaceutical compositions of the invention can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium).

The pharmaceutical compositions of the invention may be prepared in microcapsules, such as hydroxylmethylcellulose or gelatin-microcapsule and poly-(methylmethacrylate) microcapsule. The pharmaceutical compositions of the invention may also be prepared in other drug delivery systems such as liposomes, albumin microspheres, microemulsions, nano-particles, and nanocapsules. Such techniques are described in Remington: The Science and Practice of Pharmacy $22^{nd}$ edition (2012). The pharmaceutical compositions to be used for in vivo administration must be sterile. This is readily accomplished by filtration through sterile filtration membranes.

The pharmaceutical compositions of the invention may also be prepared as a sustained-release formulation. Suitable examples of sustained-release preparations include semipermeable matrices of solid hydrophobic polymers containing the ALK polypeptides described herein. Examples of sustained release matrices include polyesters, hydrogels, polyactides (U.S. Pat. No. 3,773,919), copolymers of L-glutamic acid and γ ethyl-L-glutamate, non-degradable ethylene-vinyl acetate, degradable lactic acid-glycolic acid copolymers such as LUPRON DEPOT™, and poly-D-(-)-3-hydroxybutyric acid. Some sustained-release formulations enable release of molecules over a few months, e.g., one to six months, while other formulations release pharmaceutical compositions of the invention for shorter time periods, e.g., days to weeks.

The pharmaceutical composition may be formed in a unit dose form as needed. The amount of an active component, e.g., an ALK polypeptide of the invention, included in the pharmaceutical preparations is such that a suitable dose within the designated range is provided (e.g., a dose within the range of 0.01-100 mg/kg of body weight).

The pharmaceutical composition for gene therapy can be in an acceptable diluent, or can include a slow release matrix in which the gene delivery vehicle is imbedded. Vectors that may be used as in vivo gene delivery vehicle include, but are not limited to, retroviral vectors, adenoviral vectors, poxviral vectors (e.g., vaccinia viral vectors, such as Modified Vaccinia Ankara (MVA)), adeno-associated viral vectors, and alphaviral vectors. In some embodiments, a vector can include internal ribosome entry site (IRES) that allows the expression of multiple ALK polypeptides described herein. Other vehicles and methods for gene delivery are described in U.S. Pat. Nos. 5,972,707, 5,697,901, and 6,261,554, each of which is incorporated by reference herein in its entirety.

Other methods of producing pharmaceutical compositions are described in, e.g., U.S. Pat. Nos. 5,478,925, 8,603,778, 7,662,367, and 7,892,558, all of which are incorporated by reference herein in their entireties.

Routes, Dosage, and Timing of Administration Pharmaceutical compositions of the invention that contain one or more ALK polypeptides described herein as the therapeutic proteins may be formulated for parenteral administration, subcutaneous administration, intravenous administration, intramuscular administration, intra-arterial administration, intrathecal administration, or intraperitoneal administration. The pharmaceutical composition may also be formulated for, or administered via, nasal, spray, oral, aerosol, rectal, or vaginal administration. Methods of administering therapeutic proteins are known in the art. See, for example, U.S. Pat. Nos. 6,174,529, 6,613,332, 8,518,869, 7,402,155, and 6,591,129, and US Patent Application Publication Nos. US20140051634, WO1993000077, and US20110184145, the disclosures of which are incorporated by reference in their entireties. One or more of these methods may be used to administer a pharmaceutical composition of the invention that contains one or more ALK polypeptides described herein. For injectable formulations, various effective pharmaceutical carriers are known in the art. See, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986).

The dosage of the pharmaceutical compositions of the invention depends on factors including the route of administration, the disease to be treated, and physical characteristics, e.g., age, weight, general health, of the subject. Typically, the amount of an ALK polypeptide described herein contained within a single dose may be an amount that effectively treats the disease without inducing significant toxicity. A pharmaceutical composition of the invention may include a dosage of an ALK polypeptide described herein ranging from 0.001 to 500 mg (e.g., 0.05, 0.01, 0.1, 0.2, 0.3, 0.5, 0.7, 0.8, 1 mg, 2 mg, 3 mg, 4 mg, 5 mg, 10 mg, 15 mg, 20 mg, 30 mg, 50 mg, 100 mg, 250 mg, or 500 mg) and, in a more specific embodiment, about 0.1 to about 100 mg and, in a more specific embodiment, about 0.2 to about 20 mg. The dosage may be adapted by the clinician in accordance with conventional factors such as the extent of the disease and different parameters of the subject.

A pharmaceutical composition of the invention can be administered in an amount from about 0.001 mg up to about 500 mg/kg/day (e.g., 0.05, 0.01, 0.1, 0.2, 0.3, 0.5, 0.7, 0.8, 1 mg, 2 mg, 3 mg, 4 mg, 5 mg, 10 mg, 15 mg, 20 mg, 30 mg, 50 mg, 100 mg, 250 mg, or 500 mg/kg/day). Pharmaceutical compositions of the invention that contain an ALK polypeptide described herein may be administered to a subject in need thereof, for example, one or more times (e.g., 1-10 times or more) daily, weekly, monthly, biannually, annually, or as medically necessary. Dosages may be provided in either a single or multiple dosage regimens. For example, in some embodiments, the effective amount is a dose that ranges from about 0.1 to about 100 mg/kg/day, from about 0.2 mg to about 20 mg of the ALK polypeptide described herein per day, about 1 mg to about 10 mg of the ALK polypeptide described herein per day, from about 0.7 mg to about 210 mg of the ALK polypeptide described herein per week, 1.4 mg to about 140 mg of the ALK polypeptide described herein per week, about 0.3 mg to about 300 mg of the ALK polypeptide described herein every three days, about 0.4 mg to about 40 mg of the ALK polypeptide described herein every other day, and about 2 mg to about 20 mg of the ALK polypeptide described herein every other day. The timing between administrations may decrease as the medical condition improves or increase as the health of the patient declines.

Methods of Treatment

The invention provides methods of treating a disease associated with ALK in a subject (e.g., a mammal, e.g., a human) by administering to the subject a therapeutically effective amount of an immunogenic composition or pharmaceutical composition described herein. In some embodiments, the immunogenic composition or pharmaceutical composition includes one or more ALK polypeptides described herein, as well as one or more immunomodulators, adjuvants, and/or anti-cancer agents. In some embodiments, the immunogenic composition or pharmaceutical composition is administered without an immunomodulator, an adjuvant, and/or an anti-cancer agent.

In some embodiments, the method includes administering to the subject 1) a therapeutically effective amount of an immunogenic composition or pharmaceutical composition described herein, and 2) one or more immunomodulators.

In some embodiments, the method includes administering to the subject 1) a therapeutically effective amount of an immunogenic composition or pharmaceutical composition described herein, and 2) one or more tyrosine kinase inhibitors.

In some embodiments, 1) and 2) are administered substantially simultaneously (e.g., in two separate pharmaceutical compositions administered at the same time). In some embodiments, 1) and 2) are administered separately (e.g., in two separate pharmaceutical compositions administered at different times). In some embodiments, 1) is administered first, followed by administering of 2). In some embodiments, 2) is administered first, followed by administering of 1).

In some embodiments, the methods described herein are used in combination with a radiation therapy. Radiation therapy uses high-energy particles or waves, such as x-rays, gamma rays, electron beams, or protons, to destroy or damage cancer cells. For example, a subject may be treated with radiation therapy before or after being administered a therapeutically effective amount of an immunogenic composition or pharmaceutical composition described herein. In some embodiments, a subject may be treated with radiation therapy before or after being administered a therapeutically effective amount of an immunogenic composition or pharmaceutical composition described herein and one or more immunomodulators. In some embodiments, a subject may be treated with radiation therapy before or after being administered a therapeutically effective amount of an immunogenic composition or pharmaceutical composition described herein and one or more tyrosine kinase inhibitors.

In some embodiments, the immunomodulator used in the methods of the invention is selected from the group consisting of a PD-1 inhibitor, an anti-CTLA-4 antibody, an anti-CD40 antibody, a cyclophosphamide (CPM), an AMD3100, an anti-LAG-3/CD223 antibody, an anti-B7-H5 antibody, an anti-OX40 antibody, an anti-CD28 antibody, an anti-GITR antibody, an anti-4-1 BB/CD137 antibody, a 4-1 BB ligand, an anti-BTLA antibody, an anti-TIM-3/HAVCR2 antibody, an anti-KIR antibody, an anti-Flt3/CD135 antibody, an anti-FasL antibody, an anti-CD25 antibody, an GM-CSF, an anti-GM-CSF-receptor (R) antibody, an IL-2, an anti-IL-2-R antibody, an IL-7, an anti-IL-7-R antibody, an IL-21, an anti-IL-21-R antibody, an IL-12, an anti-IL-12-R antibody, an IL-15, an anti-IL-15-R antibody, an IL-18, an anti-IL-18-R antibody, an anti-IDO antibody, an ipilimumab, a crizotinib, a ceritinib, an alectinib, a brigatinib, a celecoxib, a SOCS-1 inhibitor, a heat shock protein (HSP), a HSP inhibitor, and an anti-galectin-1 antibody.

In some embodiments, the tyrosine kinase inhibitor used in the methods of the invention is Crizotinib. In some embodiments, the tyrosine kinase inhibitor is Ceritinib. In some embodiments, the tyrosine kinase inhibitor is Alectinib. In some embodiments, the tyrosine kinase inhibitor is Brigatinib.

In some embodiments, a disease associated with ALK that can be treated by methods of the invention is cancer, such as a solid tumor cancer or an ALK+ cancer. In some embodiments, an immunogenic composition or pharmaceutical composition described herein is administered before or after surgery to remove at least some of a solid tumor in the solid tumor cancer. In some embodiments, the cancer is anaplastic large cell lymphoma, non-small-cell lung cancer, neuroblastoma, rhabdomyosarcoma, neuroectodermal cancer, glioblastoma, breast carcinoma, melanoma, inflammatory myofibroblastic tumor, soft tissue tumor, ALK expressing lymphoma, or ALK expressing lung, colon, or prostate carcinoma.

Other cancers that may be treated with methods of the invention include, but are not limited to, bladder cancer, pancreatic cancer, lung cancer, liver cancer, ovarian cancer, colon cancer, stomach cancer, breast cancer, prostate cancer, renal cancer, testicular cancer, thyroid cancer, uterine cancer, rectal cancer, a cancer of the respiratory system, a cancer of the urinary system, oral cavity cancer, skin cancer, leukemia, sarcoma, carcinoma, basal cell carcinoma, non-Hodgkin's lymphoma, acute myeloid leukemia (AML), chronic lymphocytic leukemia (CLL), B-cells chronic lymphocytic leukemia (B-CLL), multiple myeloma (MM), erythroleukemia, renal cell carcinoma, astrocytoma, oligoastrocytoma, biliary tract cancer, choriocarcinoma, CNS cancer, larynx cancer, small cell lung cancer, adenocarcinoma, giant (or oat) cell carcinoma, and squamous cell carcinoma.

EXAMPLES

Example 1—Overall T-Cell Response Stimulated by ALK Polypeptides Having the Sequences of SEQ ID NOs: 1-59 in Table 1A To identify the immunodominant ALK polypeptides, mice were immunized with ALK polypeptides having the sequences of SEQ ID NOs: 1-59 listed in Table 1A mixed with Freund's adjuvant. Spleens and lymph nodes were removed from immunized mice and assayed by Enzyme-Linked ImmunoSpot (ELISPOT). Cells were separately re-stimulated with ALK polypeptide pools each containing five ALK polypeptides. For example, as shown in FIG. 1, "1-5" indicates an ALK polypeptide pool containing five ALK polypeptides having the sequences of SEQ ID NOs: 1-5 (Table 1A). ELISPOT results in FIG. 1 show that the strongest T cell responses were found in cells re-stimulated with ALK polypeptide pools 6-10, 26-20, and 31-35.

Example 2—CD4 and CD8 T-Cell Responses Stimulated by ALK Polypeptides

To identify the immunodominant ALK polypeptides, mice were immunized with ALK polypeptides having the sequences of SEQ ID NOs: 1-59 listed in Table 1A mixed with Freund's adjuvant. Spleens and lymph nodes were then removed from immunized mice and assayed by intracellular cytokine staining (ICS). Cells were re-stimulated with individual ALK polypeptides listed in Table 1A. ICS results in FIGS. 2A and 2B show that the strongest CD4 T-cell responses were found in cells re-stimulated with ALK polypeptides having the sequences of SEQ ID NOs: 10, 14, 17, 22, 52, and 53. Similarly, ICS results in FIGS. 2C and 2D show that the strongest CD8 T-cell response was found in cells re-stimulated with ALK polypeptide having sequence of SEQ ID NOs: 10, 14, and 33.

Example 3—Overall T-Cell Response Stimulated by ALK Polypeptides Having the Sequences of SEQ ID NOs: 60-66 in Table 1A To identify the immunodominant ALK polypeptides, mice were immunized with ALK polypeptides having the sequences of SEQ ID NOs: 60-66 listed in Table 1 A (10 µg) mixed with polyinosinic:polycytidylic acid (poly I:C) (50 µg). Three doses were administered on Day 0, 25, and 56. One week after immunization, 170 µl of blood was collected from each mouse for detection of T-cell response using ELISPOT. An ALK polypeptide pool containing 7 overlapping 9-mer ALK polypeptides (SEQ ID NOs: 60-66; see Table 1A) covering the sequence LTCPGPGRVAKIGDF (SEQ ID NO: 33) was incubated with the cells. The sequence LTCPGPGRVAKIGDF (SEQ ID NO: 33) was previously identified as a CD8 T-cell (CD8) stimulating sequence in Example 2. As shown in FIG. 3, T-cell response were detected in cells re-stimulated with the ALK polypeptide pool containing the 7 overlapping 9-mer ALK polypeptides.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Other embodiments are described in the following claims:

1. An amphiphilic conjugate comprising:
   (a) an albumin-binding domain;
   (b) an ALK polypeptide; and
   (c) an optional linker,
   wherein the ALK polypeptide is 9 to 40 amino acids in length, comprises at least 6 contiguous amino acids from a sequence of SEQ ID NO: 3, and does not comprise a sequence of any one of SEQ ID NOs: 67-70 and 140-145, and
   wherein the ALK polypeptide is conjugated directly to the albumin-binding domain or is conjugated to the albumin-binding domain through the linker.

2. The amphiphilic conjugate of claim 1, wherein the albumin-binding domain is a lipid.

3. The amphiphilic conjugate of claim 1, wherein the linker is selected from the group consisting of polymers, a string of amino acids, nucleic acids, polysaccharides, or a combination thereof.

4. An immunogenic composition comprising an amphiphilic conjugate of claim 1.

5. A pharmaceutical composition comprising a therapeutically effective amount of an immunogenic composition of claim 4 and one or more pharmaceutically acceptable carriers or excipients.

* * * * *

SEQUENCE LISTING

<160> NUMBER OF SEQ ID NOS: 145

<210> SEQ ID NO 1
<211> LENGTH: 15
<212> TYPE: PRT
<213> ORGANISM: Artificial Sequence
<220> FEATURE:
<223> OTHER INFORMATION: synthetic construct

```
<400> SEQUENCE: 1

Cys Phe Ala Gly Lys Thr Ser Ser Ile Ser Asp Leu Lys Glu Val
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: synthetic construct

<400> SEQUENCE: 2

Thr Ser Ser Ile Ser Asp Leu Lys Glu Val Pro Arg Lys Asn Ile
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: synthetic construct

<400> SEQUENCE: 3

Asp Leu Lys Glu Val Pro Arg Lys Asn Ile Thr Leu Ile Arg Gly
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: synthetic construct

<400> SEQUENCE: 4

Pro Arg Lys Asn Ile Thr Leu Ile Arg Gly Leu Gly His Gly Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: synthetic construct

<400> SEQUENCE: 5

Thr Leu Ile Arg Gly Leu Gly His Gly Ala Phe Gly Glu Val Tyr
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetic construct

<400> SEQUENCE: 6

Leu Gly His Gly Ala Phe Gly Glu Val Tyr Glu Gly Gln Val Ser
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: synthetic construct
```

<400> SEQUENCE: 7

Phe Gly Glu Val Tyr Glu Gly Gln Val Ser Gly Met Pro Asn Asp
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: synthetic construct

<400> SEQUENCE: 8

Glu Gly Gln Val Ser Gly Met Pro Asn Asp Pro Ser Pro Leu Gln
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: synthetic construct

<400> SEQUENCE: 9

Gly Met Pro Asn Asp Pro Ser Pro Leu Gln Val Ala Val Arg Thr
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: synthetic construct

<400> SEQUENCE: 10

Pro Ser Pro Leu Gln Val Ala Val Arg Thr Leu Pro Glu Val Cys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: synthetic construct

<400> SEQUENCE: 11

Val Ala Val Arg Thr Leu Pro Glu Val Cys Ser Glu Gln Asp Glu
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: synthetic construct

<400> SEQUENCE: 12

Leu Pro Glu Val Cys Ser Glu Gln Asp Glu Leu Asp Phe Leu Met
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: synthetic construct

```
<400> SEQUENCE: 13

Ser Glu Gln Asp Glu Leu Asp Phe Leu Met Glu Ala Leu Ile Ile
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: synthetic construct

<400> SEQUENCE: 14

Leu Asp Phe Leu Met Glu Ala Leu Ile Ile Ser Lys Phe Asn His
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: synthetic construct

<400> SEQUENCE: 15

Glu Ala Leu Ile Ile Ser Lys Phe Asn His Gln Asn Ile Val Arg
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: synthetic construct

<400> SEQUENCE: 16

Ser Lys Phe Asn His Gln Asn Ile Val Arg Cys Ile Gly Val Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: synthetic construct

<400> SEQUENCE: 17

Gln Asn Ile Val Arg Cys Ile Gly Val Ser Leu Gln Ser Leu Pro
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: synthetic construct

<400> SEQUENCE: 18

Cys Ile Gly Val Ser Leu Gln Ser Leu Pro Arg Phe Ile Leu Leu
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: synthetic construct
```

```
<400> SEQUENCE: 19

Leu Gln Ser Leu Pro Arg Phe Ile Leu Leu Glu Leu Met Ala Gly
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: synthetic construct

<400> SEQUENCE: 20

Arg Phe Ile Leu Leu Glu Leu Met Ala Gly Gly Asp Leu Lys Ser
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: synthetic construct

<400> SEQUENCE: 21

Glu Leu Met Ala Gly Gly Asp Leu Lys Ser Phe Leu Arg Glu Thr
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: synthetic construct

<400> SEQUENCE: 22

Gly Asp Leu Lys Ser Phe Leu Arg Glu Thr Arg Pro Arg Pro Ser
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: synthetic construct

<400> SEQUENCE: 23

Phe Leu Arg Glu Thr Arg Pro Arg Pro Ser Gln Pro Ser Ser Leu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: synthetic construct

<400> SEQUENCE: 24

Arg Pro Arg Pro Ser Gln Pro Ser Ser Leu Ala Met Leu Asp Leu
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: synthetic construct
```

```
<400> SEQUENCE: 25

Gln Pro Ser Ser Leu Ala Met Leu Asp Leu Leu His Val Ala Arg
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: synthetic construct

<400> SEQUENCE: 26

Ala Met Leu Asp Leu Leu His Val Ala Arg Asp Ile Ala Cys Gly
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: synthetic construct

<400> SEQUENCE: 27

Leu His Val Ala Arg Asp Ile Ala Cys Gly Cys Gln Tyr Leu Glu
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: synthetic construct

<400> SEQUENCE: 28

Asp Ile Ala Cys Gly Cys Gln Tyr Leu Glu Glu Asn His Phe Ile
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: synthetic construct

<400> SEQUENCE: 29

Cys Gln Tyr Leu Glu Glu Asn His Phe Ile His Arg Asp Ile Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: synthetic construct

<400> SEQUENCE: 30

Glu Asn His Phe Ile His Arg Asp Ile Ala Ala Arg Asn Cys Leu
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: synthetic construct
```

```
<400> SEQUENCE: 31

His Arg Asp Ile Ala Ala Arg Asn Cys Leu Leu Thr Cys Pro Gly
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: synthetic construct

<400> SEQUENCE: 32

Ala Arg Asn Cys Leu Leu Thr Cys Pro Gly Pro Gly Arg Val Ala
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: synthetic construct

<400> SEQUENCE: 33

Leu Thr Cys Pro Gly Pro Gly Arg Val Ala Lys Ile Gly Asp Phe
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: synthetic construct

<400> SEQUENCE: 34

Pro Gly Arg Val Ala Lys Ile Gly Asp Phe Gly Met Ala Arg Asp
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: synthetic construct

<400> SEQUENCE: 35

Lys Ile Gly Asp Phe Gly Met Ala Arg Asp Ile Tyr Arg Ala Ser
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: synthetic construct

<400> SEQUENCE: 36

Gly Met Ala Arg Asp Ile Tyr Arg Ala Ser Tyr Tyr Arg Lys Gly
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: synthetic construct
```

```
<400> SEQUENCE: 37

Ile Tyr Arg Ala Ser Tyr Tyr Arg Lys Gly Gly Cys Ala Met Leu
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: synthetic construct

<400> SEQUENCE: 38

Tyr Tyr Arg Lys Gly Gly Cys Ala Met Leu Pro Val Lys Trp Met
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: synthetic construct

<400> SEQUENCE: 39

Gly Cys Ala Met Leu Pro Val Lys Trp Met Pro Pro Glu Ala Phe
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: synthetic construct

<400> SEQUENCE: 40

Pro Val Lys Trp Met Pro Pro Glu Ala Phe Met Glu Gly Ile Phe
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: synthetic construct

<400> SEQUENCE: 41

Pro Pro Glu Ala Phe Met Glu Gly Ile Phe Thr Ser Lys Thr Asp
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: synthetic construct

<400> SEQUENCE: 42

Met Glu Gly Ile Phe Thr Ser Lys Thr Asp Thr Trp Ser Phe Gly
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: synthetic construct
```

<400> SEQUENCE: 43

Thr Ser Lys Thr Asp Thr Trp Ser Phe Gly Val Leu Leu Trp Glu
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: synthetic construct

<400> SEQUENCE: 44

Thr Trp Ser Phe Gly Val Leu Leu Trp Glu Ile Phe Ser Leu Gly
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: synthetic construct

<400> SEQUENCE: 45

Val Leu Leu Trp Glu Ile Phe Ser Leu Gly Tyr Met Pro Tyr Pro
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: synthetic construct

<400> SEQUENCE: 46

Ile Phe Ser Leu Gly Tyr Met Pro Tyr Pro Ser Lys Ser Asn Gln
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: synthetic construct

<400> SEQUENCE: 47

Tyr Met Pro Tyr Pro Ser Lys Ser Asn Gln Glu Val Leu Glu Phe
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: synthetic construct

<400> SEQUENCE: 48

Ser Lys Ser Asn Gln Glu Val Leu Glu Phe Val Thr Ser Gly Gly
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: synthetic construct

<400> SEQUENCE: 49

Glu Val Leu Glu Phe Val Thr Ser Gly Gly Arg Met Asp Pro Pro
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: synthetic construct

<400> SEQUENCE: 50

Val Thr Ser Gly Gly Arg Met Asp Pro Pro Lys Asn Cys Pro Gly
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: synthetic construct

<400> SEQUENCE: 51

Arg Met Asp Pro Pro Lys Asn Cys Pro Gly Pro Val Tyr Arg Ile
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: synthetic construct

<400> SEQUENCE: 52

Lys Asn Cys Pro Gly Pro Val Tyr Arg Ile Met Thr Gln Cys Trp
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: synthetic construct

<400> SEQUENCE: 53

Pro Val Tyr Arg Ile Met Thr Gln Cys Trp Gln His Gln Pro Glu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: synthetic construct

<400> SEQUENCE: 54

Met Thr Gln Cys Trp Gln His Gln Pro Glu Asp Arg Pro Asn Phe
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: synthetic construct

```
<400> SEQUENCE: 55

Gln His Gln Pro Glu Asp Arg Pro Asn Phe Ala Ile Ile Leu Glu
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: synthetic construct

<400> SEQUENCE: 56

Asp Arg Pro Asn Phe Ala Ile Ile Leu Glu Arg Ile Glu Tyr Cys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: synthetic construct

<400> SEQUENCE: 57

Ala Ile Ile Leu Glu Arg Ile Glu Tyr Cys Thr Gln Asp Pro Asp
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: synthetic construct

<400> SEQUENCE: 58

Arg Ile Glu Tyr Cys Thr Gln Asp Pro Asp Val Ile Asn Thr Ala
1               5                   10                  15

<210> SEQ ID NO 59
<211> LENGTH: 12
<212> TYPE: PRT
<213> ORGANISM: Artificial Sequence
<220> FEATURE:
<223> OTHER INFORMATION: synthetic construct

<400> SEQUENCE: 59

Thr Gln Asp Pro Asp Val Ile Asn Thr Ala Leu Pro
1               5                   10

<210> SEQ ID NO 60
<211> LENGTH: 9
<212> TYPE: PRT
<213> ORGANISM: Artificial Sequence
<220> FEATURE:
<223> OTHER INFORMATION: synthetic construct

<400> SEQUENCE: 60

Leu Thr Cys Pro Gly Pro Gly Arg Val
1               5

<210> SEQ ID NO 61
<211> LENGTH: 9
<212> TYPE: PRT
<213> ORGANISM: Artificial Sequence
<220> FEATURE:
<223> OTHER INFORMATION: synthetic construct
```

```
<400> SEQUENCE: 61

Thr Cys Pro Gly Pro Gly Arg Val Ala
1               5

<210> SEQ ID NO 62
<211> LENGTH: 9
<212> TYPE: PRT
<213> ORGANISM: Artificial Sequence
<220> FEATURE:
<223> OTHER INFORMATION: synthetic construct

<400> SEQUENCE: 62

Cys Pro Gly Pro Gly Arg Val Ala Lys
1               5

<210> SEQ ID NO 63
<211> LENGTH: 9
<212> TYPE: PRT
<213> ORGANISM: Artificial Sequence
<220> FEATURE:
<223> OTHER INFORMATION: synthetic construct

<400> SEQUENCE: 63

Pro Gly Pro Gly Arg Val Ala Lys Ile
1               5

<210> SEQ ID NO 64
<211> LENGTH: 9
<212> TYPE: PRT
<213> ORGANISM: Artificial Sequence
<220> FEATURE:
<223> OTHER INFORMATION: synthetic construct

<400> SEQUENCE: 64

Gly Pro Gly Arg Val Ala Lys Ile Gly
1               5

<210> SEQ ID NO 65
<211> LENGTH: 9
<212> TYPE: PRT
<213> ORGANISM: Artificial Sequence
<220> FEATURE:
<223> OTHER INFORMATION: synthetic construct

<400> SEQUENCE: 65

Pro Gly Arg Val Ala Lys Ile Gly Asp
1               5

<210> SEQ ID NO 66
<211> LENGTH: 9
<212> TYPE: PRT
<213> ORGANISM: Artificial Sequence
<220> FEATURE:
<223> OTHER INFORMATION: synthetic construct

<400> SEQUENCE: 66

Gly Arg Val Ala Lys Ile Gly Asp Phe
1               5

<210> SEQ ID NO 67
<211> LENGTH: 1620
<212> TYPE: PRT
<213> ORGANISM: Homo sapiens
```

<400> SEQUENCE: 67

Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Pro Ser Leu Phe
    50                  55                  60

Arg Val Tyr Ala Arg Asp Leu Leu Pro Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
                100                 105                 110

Gly Ser Pro Ala Pro Ala Glu Ala Arg Thr Leu Ser Arg Val Leu Lys
                115                 120                 125

Gly Gly Ser Val Arg Lys Leu Arg Arg Ala Lys Gln Leu Val Leu Glu
            130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
                180                 185                 190

Lys Lys Ala Ser Glu Val Gly Arg Glu Gly Arg Leu Ser Ala Ala Ile
                195                 200                 205

Arg Ala Ser Gln Pro Arg Leu Leu Phe Gln Ile Phe Gly Thr Gly His
            210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
                260                 265                 270

Glu Leu Glu Tyr Ser Pro Pro Leu His Asp Leu Arg Asn Gln Ser Trp
                275                 280                 285

Ser Trp Arg Arg Ile Pro Ser Glu Glu Ala Ser Gln Met Asp Leu Leu
            290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Glu His Cys Thr Leu Ala Val Ser Val His
                340                 345                 350

Arg His Leu Gln Pro Ser Gly Arg Tyr Ile Ala Gln Leu Leu Pro His
                355                 360                 365

Asn Glu Ala Ala Arg Glu Ile Leu Leu Met Pro Thr Pro Gly Lys His
            370                 375                 380

Gly Trp Thr Val Leu Gln Gly Arg Ile Gly Arg Pro Asp Asn Pro Phe
385                 390                 395                 400

-continued

```
Arg Val Ala Leu Glu Tyr Ile Ser Ser Gly Asn Arg Ser Leu Ser Ala
                405                 410                 415
Val Asp Phe Phe Ala Leu Lys Asn Cys Ser Glu Gly Thr Ser Pro Gly
        420                 425                 430
Ser Lys Met Ala Leu Gln Ser Ser Phe Thr Cys Trp Asn Gly Thr Val
        435                 440                 445
Leu Gln Leu Gly Gln Ala Cys Asp Phe His Gln Asp Cys Ala Gln Gly
        450                 455                 460
Glu Asp Glu Ser Gln Met Cys Arg Lys Leu Pro Val Gly Phe Tyr Cys
465                 470                 475                 480
Asn Phe Glu Asp Gly Phe Cys Gly Trp Thr Gln Gly Thr Leu Ser Pro
                485                 490                 495
His Thr Pro Gln Trp Gln Val Arg Thr Leu Lys Asp Ala Arg Phe Gln
                500                 505                 510
Asp His Gln Asp His Ala Leu Leu Ser Thr Thr Asp Val Pro Ala
        515                 520                 525
Ser Glu Ser Ala Thr Val Thr Ser Ala Thr Phe Pro Ala Pro Ile Lys
        530                 535                 540
Ser Ser Pro Cys Glu Leu Arg Met Ser Trp Leu Ile Arg Gly Val Leu
545                 550                 555                 560
Arg Gly Asn Val Ser Leu Val Leu Val Glu Asn Lys Thr Gly Lys Glu
                565                 570                 575
Gln Gly Arg Met Val Trp His Val Ala Ala Tyr Glu Gly Leu Ser Leu
                580                 585                 590
Trp Gln Trp Met Val Leu Pro Leu Leu Asp Val Ser Asp Arg Phe Trp
                595                 600                 605
Leu Gln Met Val Ala Trp Trp Gly Gln Gly Ser Arg Ala Ile Val Ala
        610                 615                 620
Phe Asp Asn Ile Ser Ile Ser Leu Asp Cys Tyr Leu Thr Ile Ser Gly
625                 630                 635                 640
Glu Asp Lys Ile Leu Gln Asn Thr Ala Pro Lys Ser Arg Asn Leu Phe
                645                 650                 655
Glu Arg Asn Pro Asn Lys Glu Leu Lys Pro Gly Glu Asn Ser Pro Arg
                660                 665                 670
Gln Thr Pro Ile Phe Asp Pro Thr Val His Trp Leu Phe Thr Thr Cys
                675                 680                 685
Gly Ala Ser Gly Pro His Gly Pro Thr Gln Ala Gln Cys Asn Asn Ala
        690                 695                 700
Tyr Gln Asn Ser Asn Leu Ser Val Glu Val Gly Ser Glu Gly Pro Leu
705                 710                 715                 720
Lys Gly Ile Gln Ile Trp Lys Val Pro Ala Thr Asp Thr Tyr Ser Ile
                725                 730                 735
Ser Gly Tyr Gly Ala Ala Gly Gly Lys Gly Gly Lys Asn Thr Met Met
                740                 745                 750
Arg Ser His Gly Val Ser Val Leu Gly Ile Phe Asn Leu Glu Lys Asp
        755                 760                 765
Asp Met Leu Tyr Ile Leu Val Gly Gln Gln Gly Glu Asp Ala Cys Pro
        770                 775                 780
Ser Thr Asn Gln Leu Ile Gln Lys Val Cys Ile Gly Glu Asn Asn Val
785                 790                 795                 800
Ile Glu Glu Glu Ile Arg Val Asn Arg Ser Val His Glu Trp Ala Gly
                805                 810                 815
```

-continued

Gly Gly Gly Gly Gly Gly Ala Thr Tyr Val Phe Lys Met Lys Asp
                820             825             830

Gly Val Pro Val Pro Leu Ile Ile Ala Ala Gly Gly Gly Arg Ala
            835             840             845

Tyr Gly Ala Lys Thr Asp Thr Phe His Pro Glu Arg Leu Glu Asn Asn
            850             855             860

Ser Ser Val Leu Gly Leu Asn Gly Asn Ser Gly Ala Ala Gly Gly
865             870             875             880

Gly Gly Trp Asn Asp Asn Thr Ser Leu Leu Trp Ala Gly Lys Ser Leu
            885             890             895

Gln Glu Gly Ala Thr Gly Gly His Ser Cys Pro Gln Ala Met Lys Lys
            900             905             910

Trp Gly Trp Glu Thr Arg Gly Gly Phe Gly Gly Gly Gly Gly Cys
            915             920             925

Ser Ser Gly Gly Gly Gly Gly Tyr Ile Gly Gly Asn Ala Ala Ser
930             935             940

Asn Asn Asp Pro Glu Met Asp Gly Glu Asp Gly Val Ser Phe Ile Ser
945             950             955             960

Pro Leu Gly Ile Leu Tyr Thr Pro Ala Leu Lys Val Met Glu Gly His
            965             970             975

Gly Glu Val Asn Ile Lys His Tyr Leu Asn Cys Ser His Cys Glu Val
            980             985             990

Asp Glu Cys His Met Asp Pro Glu Ser His Lys Val Ile Cys Phe Cys
            995             1000            1005

Asp His Gly Thr Val Leu Ala Glu Asp Gly Val Ser Cys Ile Val
    1010            1015            1020

Ser Pro Thr Pro Glu Pro His Leu Pro Leu Ser Leu Ile Leu Ser
    1025            1030            1035

Val Val Thr Ser Ala Leu Val Ala Ala Leu Val Leu Ala Phe Ser
    1040            1045            1050

Gly Ile Met Ile Val Tyr Arg Arg Lys His Gln Glu Leu Gln Ala
    1055            1060            1065

Met Gln Met Glu Leu Gln Ser Pro Glu Tyr Lys Leu Ser Lys Leu
    1070            1075            1080

Arg Thr Ser Ile Ile Met Thr Asp Tyr Asn Pro Asn Tyr Cys Phe
    1085            1090            1095

Ala Gly Lys Thr Ser Ser Ile Ser Asp Leu Lys Glu Val Pro Arg
    1100            1105            1110

Lys Asn Ile Thr Leu Ile Arg Gly Leu Gly His Gly Ala Phe Gly
    1115            1120            1125

Glu Val Tyr Glu Gly Gln Val Ser Gly Met Pro Asn Asp Pro Ser
    1130            1135            1140

Pro Leu Gln Val Ala Val Lys Thr Leu Pro Glu Val Cys Ser Glu
    1145            1150            1155

Gln Asp Glu Leu Asp Phe Leu Met Glu Ala Leu Ile Ile Ser Lys
    1160            1165            1170

Phe Asn His Gln Asn Ile Val Arg Cys Ile Gly Val Ser Leu Gln
    1175            1180            1185

Ser Leu Pro Arg Phe Ile Leu Leu Glu Leu Met Ala Gly Gly Asp
    1190            1195            1200

Leu Lys Ser Phe Leu Arg Glu Thr Arg Pro Arg Pro Ser Gln Pro
    1205            1210            1215

-continued

```
Ser Ser Leu Ala Met Leu Asp Leu Leu His Val Ala Arg Asp Ile
1220                1225                1230

Ala Cys Gly Cys Gln Tyr Leu Glu Glu Asn His Phe Ile His Arg
1235                1240                1245

Asp Ile Ala Ala Arg Asn Cys Leu Leu Thr Cys Pro Gly Pro Gly
1250                1255                1260

Arg Val Ala Lys Ile Gly Asp Phe Gly Met Ala Arg Asp Ile Tyr
1265                1270                1275

Arg Ala Ser Tyr Tyr Arg Lys Gly Gly Cys Ala Met Leu Pro Val
1280                1285                1290

Lys Trp Met Pro Pro Glu Ala Phe Met Glu Gly Ile Phe Thr Ser
1295                1300                1305

Lys Thr Asp Thr Trp Ser Phe Gly Val Leu Leu Trp Glu Ile Phe
1310                1315                1320

Ser Leu Gly Tyr Met Pro Tyr Pro Ser Lys Ser Asn Gln Glu Val
1325                1330                1335

Leu Glu Phe Val Thr Ser Gly Gly Arg Met Asp Pro Pro Lys Asn
1340                1345                1350

Cys Pro Gly Pro Val Tyr Arg Ile Met Thr Gln Cys Trp Gln His
1355                1360                1365

Gln Pro Glu Asp Arg Pro Asn Phe Ala Ile Ile Leu Glu Arg Ile
1370                1375                1380

Glu Tyr Cys Thr Gln Asp Pro Asp Val Ile Asn Thr Ala Leu Pro
1385                1390                1395

Ile Glu Tyr Gly Pro Leu Val Glu Glu Glu Glu Lys Val Pro Val
1400                1405                1410

Arg Pro Lys Asp Pro Glu Gly Val Pro Pro Leu Leu Val Ser Gln
1415                1420                1425

Gln Ala Lys Arg Glu Glu Glu Arg Ser Pro Ala Ala Pro Pro Pro
1430                1435                1440

Leu Pro Thr Thr Ser Ser Gly Lys Ala Ala Lys Lys Pro Thr Ala
1445                1450                1455

Ala Glu Ile Ser Val Arg Val Pro Arg Gly Pro Ala Val Glu Gly
1460                1465                1470

Gly His Val Asn Met Ala Phe Ser Gln Ser Asn Pro Pro Ser Glu
1475                1480                1485

Leu His Lys Val His Gly Ser Arg Asn Lys Pro Thr Ser Leu Trp
1490                1495                1500

Asn Pro Thr Tyr Gly Ser Trp Phe Thr Glu Lys Pro Thr Lys Lys
1505                1510                1515

Asn Asn Pro Ile Ala Lys Lys Glu Pro His Asp Arg Gly Asn Leu
1520                1525                1530

Gly Leu Glu Gly Ser Cys Thr Val Pro Pro Asn Val Ala Thr Gly
1535                1540                1545

Arg Leu Pro Gly Ala Ser Leu Leu Leu Glu Pro Ser Ser Leu Thr
1550                1555                1560

Ala Asn Met Lys Glu Val Pro Leu Phe Arg Leu Arg His Phe Pro
1565                1570                1575

Cys Gly Asn Val Asn Tyr Gly Tyr Gln Gln Gln Gly Leu Pro Leu
1580                1585                1590

Glu Ala Ala Thr Ala Pro Gly Ala Gly His Tyr Glu Asp Thr Ile
1595                1600                1605
```

Leu Lys Ser Lys Asn Ser Met Asn Gln Pro Gly Pro
    1610                1615                1620

<210> SEQ ID NO 68
<211> LENGTH: 1620
<212> TYPE: PRT
<213> ORGANISM: Artificial Sequence
<220> FEATURE:
<223> OTHER INFORMATION: synthetic construct

<400> SEQUENCE: 68

Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Pro Ser Leu Phe
50                  55                  60

Arg Val Tyr Ala Arg Asp Leu Leu Leu Pro Pro Ser Ser Ser Glu Leu
65              70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Arg Ala Lys Gln Leu Val Leu Glu
130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
            340                 345                 350

Arg His Leu Gln Pro Ser Gly Arg Tyr Ile Ala Gln Leu Pro His
                355                 360                 365

Asn Glu Ala Ala Arg Glu Ile Leu Leu Met Pro Thr Pro Gly Lys His
    370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
                420                 425                 430

Ser Lys Met Ala Leu Gln Ser Ser Phe Thr Cys Trp Asn Gly Thr Val
435                 440                 445

Leu Gln Leu Gly Gln Ala Cys Asp Phe His Gln Asp Cys Ala Gln Gly
            450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
        515                 520                 525

Ser Glu Ser Ala Thr Val Thr Ser Ala Thr Phe Pro Ala Pro Ile Lys
    530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
                580                 585                 590

Trp Gln Trp Met Val Leu Pro Leu Leu Asp Val Ser Asp Arg Phe Trp
            595                 600                 605

Leu Gln Met Val Ala Trp Trp Gly Gln Gly Ser Arg Ala Ile Val Ala
        610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
                660                 665                 670

Gln Thr Pro Ile Phe Asp Pro Thr Val His Trp Leu Phe Thr Thr Cys
            675                 680                 685

Gly Ala Ser Gly Pro His Gly Pro Thr Gln Ala Gln Cys Asn Asn Ala
        690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
                725                 730                 735

Ser Gly Tyr Gly Ala Ala Gly Gly Lys Gly Gly Lys Asn Thr Met Met
                740                 745                 750

Arg Ser His Gly Val Ser Val Leu Gly Ile Phe Asn Leu Glu Lys Asp
        755                 760                 765

-continued

```
Asp Met Leu Tyr Ile Leu Val Gly Gln Gln Gly Glu Asp Ala Cys Pro
770                 775                 780
Ser Thr Asn Gln Leu Ile Gln Lys Val Cys Ile Gly Glu Asn Asn Val
785                 790                 795                 800
Ile Glu Glu Glu Ile Arg Val Asn Arg Ser Val His Glu Trp Ala Gly
                805                 810                 815
Gly Gly Gly Gly Gly Gly Ala Thr Tyr Val Phe Lys Met Lys Asp
                820                 825                 830
Gly Val Pro Val Pro Leu Ile Ile Ala Ala Gly Gly Gly Arg Ala
                835                 840                 845
Tyr Gly Ala Lys Thr Asp Thr Phe His Pro Glu Arg Leu Glu Asn Asn
850                 855                 860
Ser Ser Val Leu Gly Leu Asn Gly Asn Ser Gly Ala Ala Gly Gly Gly
865                 870                 875                 880
Gly Gly Trp Asn Asp Asn Thr Ser Leu Leu Trp Ala Gly Lys Ser Leu
                885                 890                 895
Gln Glu Gly Ala Thr Gly Gly His Ser Cys Pro Gln Ala Met Lys Lys
                900                 905                 910
Trp Gly Trp Glu Thr Arg Gly Gly Phe Gly Gly Gly Gly Gly Cys
                915                 920                 925
Ser Ser Gly Gly Gly Gly Gly Tyr Ile Gly Gly Asn Ala Ala Ser
930                 935                 940
Asn Asn Asp Pro Glu Met Asp Gly Glu Asp Gly Val Ser Phe Ile Ser
945                 950                 955                 960
Pro Leu Gly Ile Leu Tyr Thr Pro Ala Leu Lys Val Met Glu Gly His
                965                 970                 975
Gly Glu Val Asn Ile Lys His Tyr Leu Asn Cys Ser His Cys Glu Val
                980                 985                 990
Asp Glu Cys His Met Asp Pro Glu Ser His Lys Val Ile Cys Phe Cys
                995                 1000                1005
Asp His Gly Thr Val Leu Ala Glu Asp Gly Val Ser Cys Ile Val
        1010                1015                1020
Ser Pro Thr Pro Glu Pro His Leu Pro Leu Ser Leu Ile Leu Ser
        1025                1030                1035
Val Val Thr Ser Ala Leu Val Ala Ala Leu Val Leu Ala Phe Ser
        1040                1045                1050
Gly Ile Met Ile Val Tyr Arg Arg Lys His Gln Glu Leu Gln Ala
        1055                1060                1065
Met Gln Met Glu Leu Gln Ser Pro Glu Tyr Lys Leu Ser Lys Leu
        1070                1075                1080
Arg Thr Ser Ile Ile Met Thr Asp Tyr Asn Pro Asn Tyr Cys Phe
        1085                1090                1095
Ala Gly Lys Thr Ser Ser Ile Ser Asp Leu Lys Glu Val Pro Arg
        1100                1105                1110
Lys Asn Ile Thr Leu Ile Arg Gly Leu Gly His Gly Ala Phe Gly
        1115                1120                1125
Glu Val Tyr Glu Gly Gln Val Ser Gly Met Pro Asn Asp Pro Ser
        1130                1135                1140
Pro Leu Gln Val Ala Val Arg Thr Leu Pro Glu Val Cys Ser Glu
        1145                1150                1155
Gln Asp Glu Leu Asp Phe Leu Met Glu Ala Leu Ile Ile Ser Lys
        1160                1165                1170
```

```
Phe Asn His Gln Asn Ile Val Arg Cys Ile Gly Val Ser Leu Gln
1175                1180                1185

Ser Leu Pro Arg Phe Ile Leu Leu Glu Leu Met Ala Gly Gly Asp
1190                1195                1200

Leu Lys Ser Phe Leu Arg Glu Thr Arg Pro Arg Pro Ser Gln Pro
1205                1210                1215

Ser Ser Leu Ala Met Leu Asp Leu Leu His Val Ala Arg Asp Ile
1220                1225                1230

Ala Cys Gly Cys Gln Tyr Leu Glu Glu Asn His Phe Ile His Arg
1235                1240                1245

Asp Ile Ala Ala Arg Asn Cys Leu Leu Thr Cys Pro Gly Pro Gly
1250                1255                1260

Arg Val Ala Lys Ile Gly Asp Phe Gly Met Ala Arg Asp Ile Tyr
1265                1270                1275

Arg Ala Ser Tyr Tyr Arg Lys Gly Gly Cys Ala Met Leu Pro Val
1280                1285                1290

Lys Trp Met Pro Pro Glu Ala Phe Met Glu Gly Ile Phe Thr Ser
1295                1300                1305

Lys Thr Asp Thr Trp Ser Phe Gly Val Leu Leu Trp Glu Ile Phe
1310                1315                1320

Ser Leu Gly Tyr Met Pro Tyr Pro Ser Lys Ser Asn Gln Glu Val
1325                1330                1335

Leu Glu Phe Val Thr Ser Gly Gly Arg Met Asp Pro Pro Lys Asn
1340                1345                1350

Cys Pro Gly Pro Val Tyr Arg Ile Met Thr Gln Cys Trp Gln His
1355                1360                1365

Gln Pro Glu Asp Arg Pro Asn Phe Ala Ile Ile Leu Glu Arg Ile
1370                1375                1380

Glu Tyr Cys Thr Gln Asp Pro Asp Val Ile Asn Thr Ala Leu Pro
1385                1390                1395

Ile Glu Tyr Gly Pro Leu Val Glu Glu Glu Lys Val Pro Val
1400                1405                1410

Arg Pro Lys Asp Pro Glu Gly Val Pro Pro Leu Leu Val Ser Gln
1415                1420                1425

Gln Ala Lys Arg Glu Glu Glu Arg Ser Pro Ala Ala Pro Pro Pro
1430                1435                1440

Leu Pro Thr Thr Ser Ser Gly Lys Ala Ala Lys Lys Pro Thr Ala
1445                1450                1455

Ala Glu Ile Ser Val Arg Val Pro Arg Gly Pro Ala Val Glu Gly
1460                1465                1470

Gly His Val Asn Met Ala Phe Ser Gln Ser Asn Pro Pro Ser Glu
1475                1480                1485

Leu His Lys Val His Gly Ser Arg Asn Lys Pro Thr Ser Leu Trp
1490                1495                1500

Asn Pro Thr Tyr Gly Ser Trp Phe Thr Glu Lys Pro Thr Lys Lys
1505                1510                1515

Asn Asn Pro Ile Ala Lys Lys Glu Pro His Asp Arg Gly Asn Leu
1520                1525                1530

Gly Leu Glu Gly Ser Cys Thr Val Pro Pro Asn Val Ala Thr Gly
1535                1540                1545

Arg Leu Pro Gly Ala Ser Leu Leu Leu Glu Pro Ser Ser Leu Thr
1550                1555                1560
```

```
Ala Asn Met Lys Glu Val Pro Leu Phe Arg Leu Arg His Phe Pro
1565                1570                1575

Cys Gly Asn Val Asn Tyr Gly Tyr Gln Gln Gln Gly Leu Pro Leu
1580                1585                1590

Glu Ala Ala Thr Ala Pro Gly Ala Gly His Tyr Glu Asp Thr Ile
1595                1600                1605

Leu Lys Ser Lys Asn Ser Met Asn Gln Pro Gly Pro
1610                1615                1620

<210> SEQ ID NO 69
<211> LENGTH: 563
<212> TYPE: PRT
<213> ORGANISM: Homo sapiens

<400> SEQUENCE: 69

Val Tyr Arg Arg Lys His Gln Glu Leu Gln Ala Met Gln Met Glu Leu
1               5                   10                  15

Gln Ser Pro Glu Tyr Lys Leu Ser Lys Leu Arg Thr Ser Thr Ile Met
                20                  25                  30

Thr Asp Tyr Asn Pro Asn Tyr Cys Phe Ala Gly Lys Thr Ser Ser Ile
            35                  40                  45

Ser Asp Leu Lys Glu Val Pro Arg Lys Asn Ile Thr Leu Ile Arg Gly
    50                  55                  60

Leu Gly His Gly Ala Phe Gly Glu Val Tyr Glu Gly Gln Val Ser Gly
65                  70                  75                  80

Met Pro Asn Asp Pro Ser Pro Leu Gln Val Ala Val Lys Thr Leu Pro
                85                  90                  95

Glu Val Cys Ser Glu Gln Asp Glu Leu Asp Phe Leu Met Glu Ala Leu
            100                 105                 110

Ile Ile Ser Lys Phe Asn His Gln Asn Ile Val Arg Cys Ile Gly Val
        115                 120                 125

Ser Leu Gln Ser Leu Pro Arg Phe Ile Leu Leu Glu Leu Met Ala Gly
    130                 135                 140

Gly Asp Leu Lys Ser Phe Leu Arg Glu Thr Arg Pro Arg Pro Ser Gln
145                 150                 155                 160

Pro Ser Ser Leu Ala Met Leu Asp Leu Leu His Val Ala Arg Asp Ile
                165                 170                 175

Ala Cys Gly Cys Gln Tyr Leu Glu Glu Asn His Phe Ile His Arg Asp
            180                 185                 190

Ile Ala Ala Arg Asn Cys Leu Leu Thr Cys Pro Gly Pro Gly Arg Val
        195                 200                 205

Ala Lys Ile Gly Asp Phe Gly Met Ala Arg Asp Ile Tyr Arg Ala Ser
    210                 215                 220

Tyr Tyr Arg Lys Gly Gly Cys Ala Met Leu Pro Val Lys Trp Met Pro
225                 230                 235                 240

Pro Glu Ala Phe Met Glu Gly Ile Phe Thr Ser Lys Thr Asp Thr Trp
                245                 250                 255

Ser Phe Gly Val Leu Leu Trp Glu Ile Phe Ser Leu Gly Tyr Met Pro
            260                 265                 270

Tyr Pro Ser Lys Ser Asn Gln Glu Val Leu Glu Phe Val Thr Ser Gly
        275                 280                 285

Gly Arg Met Asp Pro Pro Lys Asn Cys Pro Gly Pro Val Tyr Arg Ile
    290                 295                 300
```

Met Thr Gln Cys Trp Gln His Gln Pro Glu Asp Arg Pro Asn Phe Ala
305                 310                 315                 320

Ile Ile Leu Glu Arg Ile Glu Tyr Cys Thr Gln Asp Pro Asp Val Ile
                325                 330                 335

Asn Thr Ala Leu Pro Ile Glu Tyr Gly Pro Leu Val Glu Glu Glu Glu
            340                 345                 350

Lys Val Pro Val Arg Pro Lys Asp Pro Glu Gly Val Pro Pro Leu Leu
        355                 360                 365

Val Ser Gln Gln Ala Lys Arg Glu Glu Arg Ser Pro Ala Ala Pro
370                 375                 380

Pro Pro Leu Pro Thr Thr Ser Ser Gly Lys Ala Ala Lys Lys Pro Thr
385                 390                 395                 400

Ala Ala Glu Val Ser Val Arg Val Pro Arg Gly Pro Ala Val Glu Gly
                405                 410                 415

Gly His Val Asn Met Ala Phe Ser Gln Ser Asn Pro Pro Ser Glu Leu
            420                 425                 430

His Arg Val His Gly Ser Arg Asn Lys Pro Thr Ser Leu Trp Asn Pro
        435                 440                 445

Thr Tyr Gly Ser Trp Phe Thr Glu Lys Pro Thr Lys Lys Asn Asn Pro
450                 455                 460

Ile Ala Lys Lys Glu Pro His Glu Arg Gly Asn Leu Gly Leu Glu Gly
465                 470                 475                 480

Ser Cys Thr Val Pro Pro Asn Val Ala Thr Gly Arg Leu Pro Gly Ala
                485                 490                 495

Ser Leu Leu Leu Glu Pro Ser Ser Leu Thr Ala Asn Met Lys Glu Val
            500                 505                 510

Pro Leu Phe Arg Leu Arg His Phe Pro Cys Gly Asn Val Asn Tyr Gly
        515                 520                 525

Tyr Gln Gln Gln Gly Leu Pro Leu Glu Ala Ala Thr Ala Pro Gly Ala
530                 535                 540

Gly His Tyr Glu Asp Thr Ile Leu Lys Ser Lys Asn Ser Met Asn Gln
545                 550                 555                 560

Pro Gly Pro

<210> SEQ ID NO 70
<211> LENGTH: 563
<212> TYPE: PRT
<213> ORGANISM: Artificial Sequence
<220> FEATURE:
<223> OTHER INFORMATION: synthetic construct

<400> SEQUENCE: 70

Val Tyr Arg Arg Lys His Gln Glu Leu Gln Ala Met Gln Met Glu Leu
1               5                   10                  15

Gln Ser Pro Glu Tyr Lys Leu Ser Lys Leu Arg Thr Ser Thr Ile Met
            20                  25                  30

Thr Asp Tyr Asn Pro Asn Tyr Cys Phe Ala Gly Lys Thr Ser Ser Ile
        35                  40                  45

Ser Asp Leu Lys Glu Val Pro Arg Lys Asn Ile Thr Leu Ile Arg Gly
    50                  55                  60

Leu Gly His Gly Ala Phe Gly Glu Val Tyr Glu Gly Gln Val Ser Gly
65                  70                  75                  80

Met Pro Asn Asp Pro Ser Pro Leu Gln Val Ala Val Arg Thr Leu Pro
                85                  90                  95

```
Glu Val Cys Ser Glu Gln Asp Glu Leu Asp Phe Leu Met Glu Ala Leu
            100                 105                 110

Ile Ile Ser Lys Phe Asn His Gln Asn Ile Val Arg Cys Ile Gly Val
            115                 120                 125

Ser Leu Gln Ser Leu Pro Arg Phe Ile Leu Leu Glu Leu Met Ala Gly
            130                 135                 140

Gly Asp Leu Lys Ser Phe Leu Arg Glu Thr Arg Pro Arg Pro Ser Gln
145                 150                 155                 160

Pro Ser Ser Leu Ala Met Leu Asp Leu Leu His Val Ala Arg Asp Ile
                165                 170                 175

Ala Cys Gly Cys Gln Tyr Leu Glu Glu Asn His Phe Ile His Arg Asp
                180                 185                 190

Ile Ala Ala Arg Asn Cys Leu Leu Thr Cys Pro Gly Pro Gly Arg Val
                195                 200                 205

Ala Lys Ile Gly Asp Phe Gly Met Ala Arg Asp Ile Tyr Arg Ala Ser
            210                 215                 220

Tyr Tyr Arg Lys Gly Gly Cys Ala Met Leu Pro Val Lys Trp Met Pro
225                 230                 235                 240

Pro Glu Ala Phe Met Glu Gly Ile Phe Thr Ser Lys Thr Asp Thr Trp
                245                 250                 255

Ser Phe Gly Val Leu Leu Trp Glu Ile Phe Ser Leu Gly Tyr Met Pro
                260                 265                 270

Tyr Pro Ser Lys Ser Asn Gln Glu Val Leu Glu Phe Val Thr Ser Gly
            275                 280                 285

Gly Arg Met Asp Pro Pro Lys Asn Cys Pro Gly Pro Val Tyr Arg Ile
            290                 295                 300

Met Thr Gln Cys Trp Gln His Gln Pro Glu Asp Arg Pro Asn Phe Ala
305                 310                 315                 320

Ile Ile Leu Glu Arg Ile Glu Tyr Cys Thr Gln Asp Pro Asp Val Ile
                325                 330                 335

Asn Thr Ala Leu Pro Ile Glu Tyr Gly Pro Leu Val Glu Glu Glu Glu
                340                 345                 350

Lys Val Pro Val Arg Pro Lys Asp Pro Glu Gly Val Pro Pro Leu Leu
                355                 360                 365

Val Ser Gln Gln Ala Lys Arg Glu Glu Glu Arg Ser Pro Ala Ala Pro
            370                 375                 380

Pro Pro Leu Pro Thr Thr Ser Ser Gly Lys Ala Ala Lys Lys Pro Thr
385                 390                 395                 400

Ala Ala Glu Val Ser Val Arg Val Pro Arg Gly Pro Ala Val Glu Gly
                405                 410                 415

Gly His Val Asn Met Ala Phe Ser Gln Ser Asn Pro Pro Ser Glu Leu
                420                 425                 430

His Arg Val His Gly Ser Arg Asn Lys Pro Thr Ser Leu Trp Asn Pro
            435                 440                 445

Thr Tyr Gly Ser Trp Phe Thr Glu Lys Pro Thr Lys Lys Asn Asn Pro
            450                 455                 460

Ile Ala Lys Lys Glu Pro His Glu Arg Gly Asn Leu Gly Leu Glu Gly
465                 470                 475                 480

Ser Cys Thr Val Pro Pro Asn Val Ala Thr Gly Arg Leu Pro Gly Ala
                485                 490                 495

Ser Leu Leu Leu Glu Pro Ser Ser Leu Thr Ala Asn Met Lys Glu Val
                500                 505                 510
```

```
Pro Leu Phe Arg Leu Arg His Phe Pro Cys Gly Asn Val Asn Tyr Gly
        515                 520                 525

Tyr Gln Gln Gln Gly Leu Pro Leu Glu Ala Ala Thr Ala Pro Gly Ala
    530                 535                 540

Gly His Tyr Glu Asp Thr Ile Leu Lys Ser Lys Asn Ser Met Asn Gln
545                 550                 555                 560

Pro Gly Pro

<210> SEQ ID NO 71
<211> LENGTH: 5
<212> TYPE: PRT
<213> ORGANISM: Artificial Sequence
<220> FEATURE:
<223> OTHER INFORMATION: synthetic construct

<400> SEQUENCE: 71

Gly Gly Gly Gly Ser
1               5

<210> SEQ ID NO 72
<211> LENGTH: 4
<212> TYPE: PRT
<213> ORGANISM: Artificial Sequence
<220> FEATURE:
<223> OTHER INFORMATION: synthetic construct

<400> SEQUENCE: 72

Gly Gly Ser Gly
1

<210> SEQ ID NO 73
<211> LENGTH: 4
<212> TYPE: PRT
<213> ORGANISM: Artificial Sequence
<220> FEATURE:
<223> OTHER INFORMATION: synthetic construct

<400> SEQUENCE: 73

Ser Gly Gly Gly
1

<210> SEQ ID NO 74
<211> LENGTH: 4
<212> TYPE: PRT
<213> ORGANISM: Artificial Sequence
<220> FEATURE:
<223> OTHER INFORMATION: synthetic construct

<400> SEQUENCE: 74

Gly Ser Gly Ser
1

<210> SEQ ID NO 75
<211> LENGTH: 6
<212> TYPE: PRT
<213> ORGANISM: Artificial Sequence
<220> FEATURE:
<223> OTHER INFORMATION: synthetic construct

<400> SEQUENCE: 75

Gly Ser Gly Ser Gly Ser
1               5

<210> SEQ ID NO 76
```

```
<211> LENGTH: 8
<212> TYPE: PRT
<213> ORGANISM: Artificial Sequence
<220> FEATURE:
<223> OTHER INFORMATION: synthetic construct

<400> SEQUENCE: 76

Gly Ser Gly Ser Gly Ser Gly Ser
1               5

<210> SEQ ID NO 77
<211> LENGTH: 10
<212> TYPE: PRT
<213> ORGANISM: Artificial Sequence
<220> FEATURE:
<223> OTHER INFORMATION: synthetic construct

<400> SEQUENCE: 77

Gly Ser Gly Ser Gly Ser Gly Ser Gly Ser
1               5                   10

<210> SEQ ID NO 78
<211> LENGTH: 12
<212> TYPE: PRT
<213> ORGANISM: Artificial Sequence
<220> FEATURE:
<223> OTHER INFORMATION: synthetic construct

<400> SEQUENCE: 78

Gly Ser Gly Ser Gly Ser Gly Ser Gly Ser Gly Ser
1               5                   10

<210> SEQ ID NO 79
<211> LENGTH: 6
<212> TYPE: PRT
<213> ORGANISM: Artificial Sequence
<220> FEATURE:
<223> OTHER INFORMATION: synthetic construct

<400> SEQUENCE: 79

Gly Gly Ser Gly Gly Ser
1               5

<210> SEQ ID NO 80
<211> LENGTH: 9
<212> TYPE: PRT
<213> ORGANISM: Artificial Sequence
<220> FEATURE:
<223> OTHER INFORMATION: synthetic construct

<400> SEQUENCE: 80

Gly Gly Ser Gly Gly Ser Gly Gly Ser
1               5

<210> SEQ ID NO 81
<211> LENGTH: 12
<212> TYPE: PRT
<213> ORGANISM: Artificial Sequence
<220> FEATURE:
<223> OTHER INFORMATION: synthetic construct

<400> SEQUENCE: 81

Gly Gly Ser Gly Gly Ser Gly Gly Ser Gly Gly Ser
1               5                   10

<210> SEQ ID NO 82
<211> LENGTH: 8
```

```
<212> TYPE: PRT
<213> ORGANISM: Artificial Sequence
<220> FEATURE:
<223> OTHER INFORMATION: synthetic construct

<400> SEQUENCE: 82

Gly Gly Ser Gly Gly Ser Gly
1               5

<210> SEQ ID NO 83
<211> LENGTH: 12
<212> TYPE: PRT
<213> ORGANISM: Artificial Sequence
<220> FEATURE:
<223> OTHER INFORMATION: synthetic construct

<400> SEQUENCE: 83

Gly Gly Ser Gly Gly Ser Gly Gly Gly Ser Gly
1               5                   10

<210> SEQ ID NO 84
<211> LENGTH: 15
<212> TYPE: PRT
<213> ORGANISM: Artificial Sequence
<220> FEATURE:
<223> OTHER INFORMATION: synthetic construct

<400> SEQUENCE: 84

Gly Gly Gly Gly Ser Gly Gly Gly Gly Ser Gly Gly Gly Gly Ser
1               5                   10                  15

<210> SEQ ID NO 85
<211> LENGTH: 10
<212> TYPE: PRT
<213> ORGANISM: Artificial Sequence
<220> FEATURE:
<223> OTHER INFORMATION: synthetic construct

<400> SEQUENCE: 85

Gly Glu Asn Leu Tyr Phe Gln Ser Gly Gly
1               5                   10

<210> SEQ ID NO 86
<211> LENGTH: 8
<212> TYPE: PRT
<213> ORGANISM: Artificial Sequence
<220> FEATURE:
<223> OTHER INFORMATION: synthetic construct

<400> SEQUENCE: 86

Ser Ala Cys Tyr Cys Glu Leu Ser
1               5

<210> SEQ ID NO 87
<211> LENGTH: 5
<212> TYPE: PRT
<213> ORGANISM: Artificial Sequence
<220> FEATURE:
<223> OTHER INFORMATION: synthetic construct

<400> SEQUENCE: 87

Arg Ser Ile Ala Thr
1               5

<210> SEQ ID NO 88
<211> LENGTH: 17
<212> TYPE: PRT
```

<213> ORGANISM: Artificial Sequence
<220> FEATURE:
<223> OTHER INFORMATION: synthetic construct

<400> SEQUENCE: 88

Arg Pro Ala Cys Lys Ile Pro Asn Asp Leu Lys Gln Lys Val Met Asn
1               5                   10                  15
His

<210> SEQ ID NO 89
<211> LENGTH: 36
<212> TYPE: PRT
<213> ORGANISM: Artificial Sequence
<220> FEATURE:
<223> OTHER INFORMATION: synthetic construct

<400> SEQUENCE: 89

Gly Gly Ser Ala Gly Gly Ser Gly Ser Gly Ser Ser Gly Gly Ser Ser
1               5                   10                  15

Gly Ala Ser Gly Thr Gly Thr Ala Gly Gly Thr Gly Ser Gly Ser Gly
            20                  25                  30

Thr Gly Ser Gly
        35

<210> SEQ ID NO 90
<211> LENGTH: 17
<212> TYPE: PRT
<213> ORGANISM: Artificial Sequence
<220> FEATURE:
<223> OTHER INFORMATION: synthetic construct

<400> SEQUENCE: 90

Ala Ala Ala Asn Ser Ser Ile Asp Leu Ile Ser Val Pro Val Asp Ser
1               5                   10                  15
Arg

<210> SEQ ID NO 91
<211> LENGTH: 36
<212> TYPE: PRT
<213> ORGANISM: Artificial Sequence
<220> FEATURE:
<223> OTHER INFORMATION: synthetic construct

<400> SEQUENCE: 91

Gly Gly Ser Gly Gly Gly Ser Glu Gly Gly Ser Glu Gly Gly Gly Gly
1               5                   10                  15

Ser Glu Gly Gly Gly Ser Glu Gly Gly Ser Glu Gly Gly Gly Gly Ser
            20                  25                  30

Gly Gly Gly Ser
        35

<210> SEQ ID NO 92
<211> LENGTH: 11
<212> TYPE: PRT
<213> ORGANISM: Artificial Sequence
<220> FEATURE:
<223> OTHER INFORMATION: synthetic construct

<400> SEQUENCE: 92

Asp Ile Cys Leu Pro Arg Trp Gly Cys Leu Trp
1               5                   10

<210> SEQ ID NO 93

```
<211> LENGTH: 31
<212> TYPE: PRT
<213> ORGANISM: Artificial Sequence
<220> FEATURE:
<223> OTHER INFORMATION: synthetic construct

<400> SEQUENCE: 93

Val Tyr Arg Arg Lys His Gln Glu Leu Gln Ala Met Gln Met Glu Leu
1               5                   10                  15

Gln Ser Pro Glu Tyr Lys Leu Ser Lys Leu Arg Thr Ser Thr Ile
            20                  25                  30

<210> SEQ ID NO 94
<211> LENGTH: 31
<212> TYPE: PRT
<213> ORGANISM: Artificial Sequence
<220> FEATURE:
<223> OTHER INFORMATION: synthetic construct

<400> SEQUENCE: 94

Glu Tyr Lys Leu Ser Lys Leu Arg Thr Ser Thr Ile Met Thr Asp Tyr
1               5                   10                  15

Asn Pro Asn Tyr Cys Phe Ala Gly Lys Thr Ser Ser Ile Ser Asp
            20                  25                  30

<210> SEQ ID NO 95
<211> LENGTH: 31
<212> TYPE: PRT
<213> ORGANISM: Artificial Sequence
<220> FEATURE:
<223> OTHER INFORMATION: synthetic construct

<400> SEQUENCE: 95

Tyr Cys Phe Ala Gly Lys Thr Ser Ser Ile Ser Asp Leu Lys Glu Val
1               5                   10                  15

Pro Arg Lys Asn Ile Thr Leu Ile Arg Gly Leu Gly His Gly Ala
            20                  25                  30

<210> SEQ ID NO 96
<211> LENGTH: 31
<212> TYPE: PRT
<213> ORGANISM: Artificial Sequence
<220> FEATURE:
<223> OTHER INFORMATION: synthetic construct

<400> SEQUENCE: 96

Asn Ile Thr Leu Ile Arg Gly Leu Gly His Gly Ala Phe Gly Glu Val
1               5                   10                  15

Tyr Glu Gly Gln Val Ser Gly Met Pro Asn Asp Pro Ser Pro Leu
            20                  25                  30

<210> SEQ ID NO 97
<211> LENGTH: 31
<212> TYPE: PRT
<213> ORGANISM: Artificial Sequence
<220> FEATURE:
<223> OTHER INFORMATION: synthetic construct

<400> SEQUENCE: 97

Gln Val Ser Gly Met Pro Asn Asp Pro Ser Pro Leu Gln Val Ala Val
1               5                   10                  15

Lys Thr Leu Pro Glu Val Cys Ser Glu Gln Asp Glu Leu Asp Phe
            20                  25                  30
```

-continued

```
<210> SEQ ID NO 98
<211> LENGTH: 31
<212> TYPE: PRT
<213> ORGANISM: Artificial Sequence
<220> FEATURE:
<223> OTHER INFORMATION: synthetic construct

<400> SEQUENCE: 98

Pro Glu Val Cys Ser Glu Gln Asp Glu Leu Asp Phe Leu Met Glu Ala
1               5                   10                  15

Leu Ile Ile Ser Lys Phe Asn His Gln Asn Ile Val Arg Cys Ile
            20                  25                  30

<210> SEQ ID NO 99
<211> LENGTH: 31
<212> TYPE: PRT
<213> ORGANISM: Artificial Sequence
<220> FEATURE:
<223> OTHER INFORMATION: synthetic construct

<400> SEQUENCE: 99

Ser Lys Phe Asn His Gln Asn Ile Val Arg Cys Ile Gly Val Ser Leu
1               5                   10                  15

Gln Ser Leu Pro Arg Phe Ile Leu Leu Glu Leu Met Ala Gly Gly
            20                  25                  30

<210> SEQ ID NO 100
<211> LENGTH: 31
<212> TYPE: PRT
<213> ORGANISM: Artificial Sequence
<220> FEATURE:
<223> OTHER INFORMATION: synthetic construct

<400> SEQUENCE: 100

Pro Arg Phe Ile Leu Leu Glu Leu Met Ala Gly Gly Asp Leu Lys Ser
1               5                   10                  15

Phe Leu Arg Glu Thr Arg Pro Arg Pro Ser Gln Pro Ser Leu
            20                  25                  30

<210> SEQ ID NO 101
<211> LENGTH: 31
<212> TYPE: PRT
<213> ORGANISM: Artificial Sequence
<220> FEATURE:
<223> OTHER INFORMATION: synthetic construct

<400> SEQUENCE: 101

Glu Thr Arg Pro Arg Pro Ser Gln Pro Ser Ser Leu Ala Met Leu Asp
1               5                   10                  15

Leu Leu His Val Ala Arg Asp Ile Ala Cys Gly Cys Gln Tyr Leu
            20                  25                  30

<210> SEQ ID NO 102
<211> LENGTH: 31
<212> TYPE: PRT
<213> ORGANISM: Artificial Sequence
<220> FEATURE:
<223> OTHER INFORMATION: synthetic construct

<400> SEQUENCE: 102

Val Ala Arg Asp Ile Ala Cys Gly Cys Gln Tyr Leu Glu Glu Asn His
1               5                   10                  15

Phe Ile His Arg Asp Ile Ala Ala Arg Asn Cys Leu Leu Thr Cys
            20                  25                  30
```

<210> SEQ ID NO 103
<211> LENGTH: 31
<212> TYPE: PRT
<213> ORGANISM: Artificial Sequence
<220> FEATURE:
<223> OTHER INFORMATION: synthetic construct

<400> SEQUENCE: 103

```
Arg Asp Ile Ala Ala Arg Asn Cys Leu Leu Thr Cys Pro Gly Pro
1               5                   10                  15

Arg Val Ala Lys Ile Gly Asp Phe Gly Met Ala Arg Asp Ile Tyr
            20                  25                  30
```

<210> SEQ ID NO 104
<211> LENGTH: 31
<212> TYPE: PRT
<213> ORGANISM: Artificial Sequence
<220> FEATURE:
<223> OTHER INFORMATION: synthetic construct

<400> SEQUENCE: 104

```
Lys Ile Gly Asp Phe Gly Met Ala Arg Asp Ile Tyr Arg Ala Ser Tyr
1               5                   10                  15

Tyr Arg Lys Gly Gly Cys Ala Met Leu Pro Val Lys Trp Met Pro
            20                  25                  30
```

<210> SEQ ID NO 105
<211> LENGTH: 31
<212> TYPE: PRT
<213> ORGANISM: Artificial Sequence
<220> FEATURE:
<223> OTHER INFORMATION: synthetic construct

<400> SEQUENCE: 105

```
Gly Gly Cys Ala Met Leu Pro Val Lys Trp Met Pro Glu Ala Phe
1               5                   10                  15

Met Glu Gly Ile Phe Thr Ser Lys Thr Asp Thr Trp Ser Phe Gly
            20                  25                  30
```

<210> SEQ ID NO 106
<211> LENGTH: 31
<212> TYPE: PRT
<213> ORGANISM: Artificial Sequence
<220> FEATURE:
<223> OTHER INFORMATION: synthetic construct

<400> SEQUENCE: 106

```
Ile Phe Thr Ser Lys Thr Asp Thr Trp Ser Phe Gly Val Leu Leu Trp
1               5                   10                  15

Glu Ile Phe Ser Leu Gly Tyr Met Pro Tyr Pro Ser Lys Ser Asn
            20                  25                  30
```

<210> SEQ ID NO 107
<211> LENGTH: 31
<212> TYPE: PRT
<213> ORGANISM: Artificial Sequence
<220> FEATURE:
<223> OTHER INFORMATION: synthetic construct

<400> SEQUENCE: 107

```
Ser Leu Gly Tyr Met Pro Tyr Pro Ser Lys Ser Asn Gln Glu Val Leu
1               5                   10                  15

Glu Phe Val Thr Ser Gly Gly Arg Met Asp Pro Pro Lys Asn Cys
            20                  25                  30
```

<210> SEQ ID NO 108
<211> LENGTH: 31
<212> TYPE: PRT
<213> ORGANISM: Artificial Sequence
<220> FEATURE:
<223> OTHER INFORMATION: synthetic construct

<400> SEQUENCE: 108

Thr Ser Gly Gly Arg Met Asp Pro Pro Lys Asn Cys Pro Gly Val
1               5                   10                  15

Tyr Arg Ile Met Thr Gln Cys Trp Gln His Gln Pro Glu Asp Arg
            20                  25                  30

<210> SEQ ID NO 109
<211> LENGTH: 31
<212> TYPE: PRT
<213> ORGANISM: Artificial Sequence
<220> FEATURE:
<223> OTHER INFORMATION: synthetic construct

<400> SEQUENCE: 109

Met Thr Gln Cys Trp Gln His Gln Pro Glu Asp Arg Pro Asn Phe Ala
1               5                   10                  15

Ile Ile Leu Glu Arg Ile Glu Tyr Cys Thr Gln Asp Pro Asp Val
            20                  25                  30

<210> SEQ ID NO 110
<211> LENGTH: 31
<212> TYPE: PRT
<213> ORGANISM: Artificial Sequence
<220> FEATURE:
<223> OTHER INFORMATION: synthetic construct

<400> SEQUENCE: 110

Glu Arg Ile Glu Tyr Cys Thr Gln Asp Pro Asp Val Ile Asn Thr Ala
1               5                   10                  15

Leu Pro Ile Glu Tyr Gly Pro Leu Val Glu Glu Glu Lys Val
            20                  25                  30

<210> SEQ ID NO 111
<211> LENGTH: 31
<212> TYPE: PRT
<213> ORGANISM: Artificial Sequence
<220> FEATURE:
<223> OTHER INFORMATION: synthetic construct

<400> SEQUENCE: 111

Glu Tyr Gly Pro Leu Val Glu Glu Glu Lys Val Pro Val Arg Pro
1               5                   10                  15

Lys Asp Pro Glu Gly Val Pro Pro Leu Leu Val Ser Gln Gln Ala
            20                  25                  30

<210> SEQ ID NO 112
<211> LENGTH: 31
<212> TYPE: PRT
<213> ORGANISM: Artificial Sequence
<220> FEATURE:
<223> OTHER INFORMATION: synthetic construct

<400> SEQUENCE: 112

Glu Gly Val Pro Pro Leu Leu Val Ser Gln Gln Ala Lys Arg Glu Glu
1               5                   10                  15

```
Glu Arg Ser Pro Ala Ala Pro Pro Leu Pro Thr Thr Ser Ser
            20                  25                  30
```

<210> SEQ ID NO 113
<211> LENGTH: 31
<212> TYPE: PRT
<213> ORGANISM: Artificial Sequence
<220> FEATURE:
<223> OTHER INFORMATION: synthetic construct

<400> SEQUENCE: 113

```
Pro Ala Ala Pro Pro Leu Pro Thr Thr Ser Ser Gly Lys Ala Ala
1               5                   10                  15

Lys Lys Pro Thr Ala Ala Glu Ile Ser Val Arg Val Pro Arg Gly
            20                  25                  30
```

<210> SEQ ID NO 114
<211> LENGTH: 31
<212> TYPE: PRT
<213> ORGANISM: Artificial Sequence
<220> FEATURE:
<223> OTHER INFORMATION: synthetic construct

<400> SEQUENCE: 114

```
Thr Ala Ala Glu Ile Ser Val Arg Val Pro Arg Gly Pro Ala Val Glu
1               5                   10                  15

Gly Gly His Val Asn Met Ala Phe Ser Gln Ser Asn Pro Pro Ser
            20                  25                  30
```

<210> SEQ ID NO 115
<211> LENGTH: 31
<212> TYPE: PRT
<213> ORGANISM: Artificial Sequence
<220> FEATURE:
<223> OTHER INFORMATION: synthetic construct

<400> SEQUENCE: 115

```
Val Asn Met Ala Phe Ser Gln Ser Asn Pro Pro Ser Glu Leu His Lys
1               5                   10                  15

Val His Gly Ser Arg Asn Lys Pro Thr Ser Leu Trp Asn Pro Thr
            20                  25                  30
```

<210> SEQ ID NO 116
<211> LENGTH: 31
<212> TYPE: PRT
<213> ORGANISM: Artificial Sequence
<220> FEATURE:
<223> OTHER INFORMATION: synthetic construct

<400> SEQUENCE: 116

```
Ser Arg Asn Lys Pro Thr Ser Leu Trp Asn Pro Thr Tyr Gly Ser Trp
1               5                   10                  15

Phe Thr Glu Lys Pro Thr Lys Lys Asn Asn Pro Ile Ala Lys Lys
            20                  25                  30
```

<210> SEQ ID NO 117
<211> LENGTH: 31
<212> TYPE: PRT
<213> ORGANISM: Artificial Sequence
<220> FEATURE:
<223> OTHER INFORMATION: synthetic construct

```
<400> SEQUENCE: 117

Lys Pro Thr Lys Asn Asn Pro Ile Ala Lys Glu Pro His Asp
1               5                   10                  15

Arg Gly Asn Leu Gly Leu Glu Gly Ser Cys Thr Val Pro Pro Asn
            20                  25                  30

<210> SEQ ID NO 118
<211> LENGTH: 31
<212> TYPE: PRT
<213> ORGANISM: Artificial Sequence
<220> FEATURE:
<223> OTHER INFORMATION: synthetic construct

<400> SEQUENCE: 118

Leu Gly Leu Glu Gly Ser Cys Thr Val Pro Pro Asn Val Ala Thr Gly
1               5                   10                  15

Arg Leu Pro Gly Ala Ser Leu Leu Glu Pro Ser Ser Leu Thr
            20                  25                  30

<210> SEQ ID NO 119
<211> LENGTH: 31
<212> TYPE: PRT
<213> ORGANISM: Artificial Sequence
<220> FEATURE:
<223> OTHER INFORMATION: synthetic construct

<400> SEQUENCE: 119

Gly Ala Ser Leu Leu Glu Pro Ser Ser Leu Thr Ala Asn Met Lys
1               5                   10                  15

Glu Val Pro Leu Phe Arg Leu Arg His Phe Pro Cys Gly Asn Val
            20                  25                  30

<210> SEQ ID NO 120
<211> LENGTH: 31
<212> TYPE: PRT
<213> ORGANISM: Artificial Sequence
<220> FEATURE:
<223> OTHER INFORMATION: synthetic construct

<400> SEQUENCE: 120

Leu Phe Arg Leu Arg His Phe Pro Cys Gly Asn Val Asn Tyr Gly Tyr
1               5                   10                  15

Gln Gln Gln Gly Leu Pro Leu Glu Ala Ala Thr Ala Pro Gly Ala
            20                  25                  30

<210> SEQ ID NO 121
<211> LENGTH: 31
<212> TYPE: PRT
<213> ORGANISM: Artificial Sequence
<220> FEATURE:
<223> OTHER INFORMATION: synthetic construct

<400> SEQUENCE: 121

Gly Leu Pro Leu Glu Ala Ala Thr Ala Pro Gly Ala Gly His Tyr Glu
1               5                   10                  15

Asp Thr Ile Leu Lys Ser Lys Asn Ser Met Asn Gln Pro Gly Pro
            20                  25                  30

<210> SEQ ID NO 122
<211> LENGTH: 31
<212> TYPE: PRT
<213> ORGANISM: Artificial Sequence
<220> FEATURE:
```

<223> OTHER INFORMATION: synthetic construct

<400> SEQUENCE: 122

Glu Tyr Lys Leu Ser Lys Leu Arg Thr Ser Thr Ile Met Thr Asp Tyr
1               5                   10                  15
Asn Pro Asn Tyr Ala Phe Ala Gly Lys Thr Ser Ser Ile Ser Asp
            20                  25                  30

<210> SEQ ID NO 123
<211> LENGTH: 31
<212> TYPE: PRT
<213> ORGANISM: Artificial Sequence
<220> FEATURE:
<223> OTHER INFORMATION: synthetic construct

<400> SEQUENCE: 123

Tyr Ala Phe Ala Gly Lys Thr Ser Ser Ile Ser Asp Leu Lys Glu Val
1               5                   10                  15
Pro Arg Lys Asn Ile Thr Leu Ile Arg Gly Leu Gly His Gly Ala
            20                  25                  30

<210> SEQ ID NO 124
<211> LENGTH: 31
<212> TYPE: PRT
<213> ORGANISM: Artificial Sequence
<220> FEATURE:
<223> OTHER INFORMATION: synthetic construct

<400> SEQUENCE: 124

Gln Val Ser Gly Met Pro Asn Asp Pro Ser Pro Leu Gln Val Ala Val
1               5                   10                  15
Lys Thr Leu Pro Glu Val Ala Ser Glu Gln Asp Glu Leu Asp Phe
            20                  25                  30

<210> SEQ ID NO 125
<211> LENGTH: 31
<212> TYPE: PRT
<213> ORGANISM: Artificial Sequence
<220> FEATURE:
<223> OTHER INFORMATION: synthetic construct

<400> SEQUENCE: 125

Pro Glu Val Ala Ser Glu Gln Asp Glu Leu Asp Phe Leu Met Glu Ala
1               5                   10                  15
Leu Ile Ile Ser Lys Phe Asn His Gln Asn Ile Val Arg Ala Ile
            20                  25                  30

<210> SEQ ID NO 126
<211> LENGTH: 31
<212> TYPE: PRT
<213> ORGANISM: Artificial Sequence
<220> FEATURE:
<223> OTHER INFORMATION: synthetic construct

<400> SEQUENCE: 126

Ser Lys Phe Asn His Gln Asn Ile Val Arg Ala Ile Gly Val Ser Leu
1               5                   10                  15
Gln Ser Leu Pro Arg Phe Ile Leu Leu Glu Leu Met Ala Gly Gly
            20                  25                  30

<210> SEQ ID NO 127
<211> LENGTH: 31
<212> TYPE: PRT
<213> ORGANISM: Artificial Sequence

```
<220> FEATURE:
<223> OTHER INFORMATION: synthetic construct

<400> SEQUENCE: 127

Glu Thr Arg Pro Arg Pro Ser Gln Pro Ser Ser Leu Ala Met Leu Asp
1               5                   10                  15

Leu Leu His Val Ala Arg Asp Ile Ala Ala Gly Ala Gln Tyr Leu
            20                  25                  30

<210> SEQ ID NO 128
<211> LENGTH: 31
<212> TYPE: PRT
<213> ORGANISM: Artificial Sequence
<220> FEATURE:
<223> OTHER INFORMATION: synthetic construct

<400> SEQUENCE: 128

Val Ala Arg Asp Ile Ala Ala Gly Ala Gln Tyr Leu Glu Glu Asn His
1               5                   10                  15

Phe Ile His Arg Asp Ile Ala Ala Arg Asn Ala Leu Leu Thr Ala
            20                  25                  30

<210> SEQ ID NO 129
<211> LENGTH: 31
<212> TYPE: PRT
<213> ORGANISM: Artificial Sequence
<220> FEATURE:
<223> OTHER INFORMATION: synthetic construct

<400> SEQUENCE: 129

Arg Asp Ile Ala Ala Arg Asn Ala Leu Leu Thr Ala Pro Gly Pro Gly
1               5                   10                  15

Arg Val Ala Lys Ile Gly Asp Phe Gly Met Ala Arg Asp Ile Tyr
            20                  25                  30

<210> SEQ ID NO 130
<211> LENGTH: 31
<212> TYPE: PRT
<213> ORGANISM: Artificial Sequence
<220> FEATURE:
<223> OTHER INFORMATION: synthetic construct

<400> SEQUENCE: 130

Lys Ile Gly Asp Phe Gly Met Ala Arg Asp Ile Tyr Arg Ala Ser Tyr
1               5                   10                  15

Tyr Arg Lys Gly Gly Ala Ala Met Leu Pro Val Lys Trp Met Pro
            20                  25                  30

<210> SEQ ID NO 131
<211> LENGTH: 31
<212> TYPE: PRT
<213> ORGANISM: Artificial Sequence
<220> FEATURE:
<223> OTHER INFORMATION: synthetic construct

<400> SEQUENCE: 131

Gly Gly Ala Ala Met Leu Pro Val Lys Trp Met Pro Glu Ala Phe
1               5                   10                  15

Met Glu Gly Ile Phe Thr Ser Lys Thr Asp Thr Trp Ser Phe Gly
            20                  25                  30

<210> SEQ ID NO 132
<211> LENGTH: 31
<212> TYPE: PRT
```

```
<213> ORGANISM: Artificial Sequence
<220> FEATURE:
<223> OTHER INFORMATION: synthetic construct

<400> SEQUENCE: 132

Ser Leu Gly Tyr Met Pro Tyr Pro Ser Lys Ser Asn Gln Glu Val Leu
1               5                   10                  15

Glu Phe Val Thr Ser Gly Gly Arg Met Asp Pro Pro Lys Asn Ala
            20                  25                  30

<210> SEQ ID NO 133
<211> LENGTH: 31
<212> TYPE: PRT
<213> ORGANISM: Artificial Sequence
<220> FEATURE:
<223> OTHER INFORMATION: synthetic construct

<400> SEQUENCE: 133

Thr Ser Gly Gly Arg Met Asp Pro Pro Lys Asn Ala Pro Gly Pro Val
1               5                   10                  15

Tyr Arg Ile Met Thr Gln Ala Trp Gln His Gln Pro Glu Asp Arg
            20                  25                  30

<210> SEQ ID NO 134
<211> LENGTH: 31
<212> TYPE: PRT
<213> ORGANISM: Artificial Sequence
<220> FEATURE:
<223> OTHER INFORMATION: synthetic construct

<400> SEQUENCE: 134

Met Thr Gln Ala Trp Gln His Gln Pro Glu Asp Arg Pro Asn Phe Ala
1               5                   10                  15

Ile Ile Leu Glu Arg Ile Glu Tyr Ala Thr Gln Asp Pro Asp Val
            20                  25                  30

<210> SEQ ID NO 135
<211> LENGTH: 31
<212> TYPE: PRT
<213> ORGANISM: Artificial Sequence
<220> FEATURE:
<223> OTHER INFORMATION: synthetic construct

<400> SEQUENCE: 135

Glu Arg Ile Glu Tyr Ala Thr Gln Asp Pro Asp Val Ile Asn Thr Ala
1               5                   10                  15

Leu Pro Ile Glu Tyr Gly Pro Leu Val Glu Glu Glu Lys Val
            20                  25                  30

<210> SEQ ID NO 136
<211> LENGTH: 31
<212> TYPE: PRT
<213> ORGANISM: Artificial Sequence
<220> FEATURE:
<223> OTHER INFORMATION: synthetic construct

<400> SEQUENCE: 136

Lys Pro Thr Lys Lys Asn Asn Pro Ile Ala Lys Lys Glu Pro His Asp
1               5                   10                  15

Arg Gly Asn Leu Gly Leu Glu Gly Ser Ala Thr Val Pro Pro Asn
            20                  25                  30

<210> SEQ ID NO 137
<211> LENGTH: 31
```

```
<212> TYPE: PRT
<213> ORGANISM: Artificial Sequence
<220> FEATURE:
<223> OTHER INFORMATION: synthetic construct

<400> SEQUENCE: 137

Leu Gly Leu Glu Gly Ser Ala Thr Val Pro Pro Asn Val Ala Thr Gly
1               5                   10                  15
Arg Leu Pro Gly Ala Ser Leu Leu Glu Pro Ser Ser Leu Thr
            20                  25                  30

<210> SEQ ID NO 138
<211> LENGTH: 31
<212> TYPE: PRT
<213> ORGANISM: Artificial Sequence
<220> FEATURE:
<223> OTHER INFORMATION: synthetic construct

<400> SEQUENCE: 138

Gly Ala Ser Leu Leu Glu Pro Ser Ser Leu Thr Ala Asn Met Lys
1               5                   10                  15
Glu Val Pro Leu Phe Arg Leu Arg His Phe Pro Ala Gly Asn Val
            20                  25                  30

<210> SEQ ID NO 139
<211> LENGTH: 31
<212> TYPE: PRT
<213> ORGANISM: Artificial Sequence
<220> FEATURE:
<223> OTHER INFORMATION: synthetic construct

<400> SEQUENCE: 139

Leu Phe Arg Leu Arg His Phe Pro Ala Gly Asn Val Asn Tyr Gly Tyr
1               5                   10                  15
Gln Gln Gln Gly Leu Pro Leu Glu Ala Ala Thr Ala Pro Gly Ala
            20                  25                  30

<210> SEQ ID NO 140
<211> LENGTH: 24
<212> TYPE: PRT
<213> ORGANISM: Artificial Sequence
<220> FEATURE:
<223> OTHER INFORMATION: synthetic construct

<400> SEQUENCE: 140

Pro Ser Ser Leu Ala Met Leu Asp Leu Leu His Val Ala Arg Asp Ile
1               5                   10                  15
Ala Cys Gly Cys Gln Tyr Leu Glu
            20

<210> SEQ ID NO 141
<211> LENGTH: 24
<212> TYPE: PRT
<213> ORGANISM: Artificial Sequence
<220> FEATURE:
<223> OTHER INFORMATION: synthetic construct

<400> SEQUENCE: 141

Lys Phe Asn His Gln Asn Ile Val Arg Cys Ile Gly Val Ser Leu Gln
1               5                   10                  15
Ser Leu Pro Arg Phe Ile Leu Leu
            20

<210> SEQ ID NO 142
```

```
<211> LENGTH: 24
<212> TYPE: PRT
<213> ORGANISM: Artificial Sequence
<220> FEATURE:
<223> OTHER INFORMATION: synthetic construct

<400> SEQUENCE: 142

Pro Lys Asn Cys Pro Gly Pro Val Tyr Arg Ile Met Thr Gln Cys Trp
1               5                   10                  15

Gln His Gln Pro Glu Asp Arg Pro
            20

<210> SEQ ID NO 143
<211> LENGTH: 10
<212> TYPE: PRT
<213> ORGANISM: Artificial Sequence
<220> FEATURE:
<223> OTHER INFORMATION: synthetic construct

<400> SEQUENCE: 143

Ser Leu Ala Met Leu Asp Leu Leu His Val
1               5                   10

<210> SEQ ID NO 144
<211> LENGTH: 9
<212> TYPE: PRT
<213> ORGANISM: Artificial Sequence
<220> FEATURE:
<223> OTHER INFORMATION: synthetic construct

<400> SEQUENCE: 144

Ala Met Leu Asp Leu Leu His Val Ala
1               5

<210> SEQ ID NO 145
<211> LENGTH: 9
<212> TYPE: PRT
<213> ORGANISM: Artificial Sequence
<220> FEATURE:
<223> OTHER INFORMATION: synthetic construct

<400> SEQUENCE: 145

Cys Ile Gly Val Ser Leu Gln Ser Leu
1               5
```